US012653828B2

(12) United States Patent
Barlaam et al.

(10) Patent No.: US 12,653,828 B2
(45) Date of Patent: Jun. 16, 2026

(54) POLQ INHIBITORS

(71) Applicant: ASTRAZENECA AB, Sodertalje (SE)

(72) Inventors: Bernard Barlaam, Cambridge (GB); Michael Bodnarchuk, Cambridge (GB); Gail Wrigley, Cambridge (GB); Jon Winter-Holt, Cambridge (GB); Oliver Turner, Cambridge (GB); Ariamala Gopalsamy, Wilmington, DE (US); Jason Shields, Wilmington, DE (US); Sofia Ferrer Cabrera, Cambridge (GB); Helen Elizabeth Jones, Cambridge (GB)

(73) Assignee: ASTRAZENECA AB, Södertälje (SE)

( * ) Notice: Subject to any disclaimer, the term of this patent is extended or adjusted under 35 U.S.C. 154(b) by 372 days.

(21) Appl. No.: 18/529,426

(22) Filed: Dec. 5, 2023

(65) Prior Publication Data

US 2024/0366615 A1 Nov. 7, 2024

Related U.S. Application Data

(60) Provisional application No. 63/386,263, filed on Dec. 6, 2022, provisional application No. 63/497,847, filed on Apr. 24, 2023.

(51) Int. Cl.
*A61K 31/52* (2006.01)
*C07D 473/30* (2006.01)

(52) U.S. Cl.
CPC ............ *A61K 31/52* (2013.01); *C07D 473/30* (2013.01)

(58) Field of Classification Search
CPC .............................. C07D 473/30; A61K 31/52
See application file for complete search history.

(56) References Cited

FOREIGN PATENT DOCUMENTS

WO 2019079297 A1 4/2019

OTHER PUBLICATIONS

International Search Report and Written Opinion for International Application No. PCT/IB2023/062262, mailed Feb. 9, 2024, 9 Pages.

*Primary Examiner* — Rebecca L Anderson

(57) ABSTRACT

The specification generally relates to compounds of Formula (I):

(I)

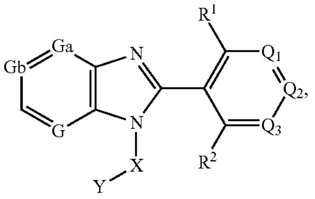

or a stereoisomer or pharmaceutically salt thereof, wherein G, $G_a$, $G_b$, X, Y, $R^1$, $R^2$, $Q^1$, $Q^2$, and $Q^3$ have any of the meanings defined herein, together with compositions containing them and their use in therapy. The compounds are inhibitors of the polymerase, DNA polymerase theta (Polθ or POLQ), and are thereby particularly useful in the treatment of cancer.

24 Claims, No Drawings

POLQ INHIBITORS

This application claims priority to U.S. Provisional Applications 63/386,263, filed Dec. 6, 2022, and 63/497,847, filed Apr. 24, 2023, each of which is incorporated by reference herein in its entirety for all purposes.

BACKGROUND

DNA polymerase theta (Polθ) is a specialized polymerase encoded in the human genome by the POLQ gene and hence it is also simply known as POLQ. It belongs to the A family, a group of DNA polymerases regarded as error prone due to their lack of proofreading activity. It is the only human DNA polymerase that also contains an active DNA helicase domain (Loeb and Monnat, 2008; Ramsden et al., 2022). POLQ has been involved in genome maintenance processes through its roles in translesion synthesis (TLS), a DNA-damage tolerance mechanism, and alternative DNA-end joining (alt-EJ), a DNA repair mechanism involved in the resolution of DNA double-strand breaks (DSBs) (Ramsden et al., 2022; Yoon et al., 2019).

DNA DSBs are the most cytotoxic lesion faced by cells and several DNA-damage signalling and repair mechanisms have evolved to deal with them. In human cells, DSB repair is mostly performed by the non-homologous end joining (NHEJ) and homologous recombination repair (HRR) pathways, with a third pathway, named alt-EJ, generally regarded as a less frequently used option. The first steps of the HRR and alt-EJ pathways are shared, where the ends of the DNA DSB will be processed (resected) to generate regions of single-stranded DNA (ssDNA). While during HRR resection is relatively extensive, it is kept to shorter stretches during alt-EJ through a mechanism that remained elusive. In addition, alt-EJ has been linked to the use of sequence microhomologies (2-6 base pairs) surrounding the DSB site for repair by direct annealing, processing of the DNA flaps and ligation, which explains its error-prone nature. As such, alt-EJ is also referred to as microhomology-mediated end joining (MMEJ) (Ciccia and Elledge, 2010).

HRR is a form of DNA repair that, once a DSB has occurred on a chromosome's chromatid, uses the sister chromatid as template for repair. As such, HRR is regarded as error-free and can only take place once a sister chromatid is available, namely during the DNA replication (synthesis) phase (S phase) and gap phase 2 (G2 phase) of the cell cycle. HRR deficiency (HRD) is well described in tumours and is genetically associated with mutations in the breast cancer susceptibility genes BRCA1 and BRCA2 (BRCA genes), among others (Pellegrino et al., 2019). HRD is also associated with increasing levels of genomic instability, highlighted by the presence of specific mutational signatures involving single-base substitutions (SBS), insertions-deletions (INDEL) and rearrangements (Nik-Zainal et al., 2016). Interestingly, the SBS signature associated with HRD (SBS3), is also associated with an INDEL signature (ID6) that is characterised by extensive microhomology usage at the break point (Alexandrov et al., 2020), suggesting that MMEJ could be an important DNA repair pathway in the absence of HRR. In agreement with this, signatures of MMEJ-mediated repair events have been identified in secondary (reversion) mutations restoring the open-reading frame of BRCA and other HRR-related genes in tumours from patients progressing on treatment, strongly suggesting that these reversion events are mediated by MMEJ repair and driving therapy resistance in these clinical cases (Pettitt et al., 2020; Tobalina et al., 2021).

Recently, POLQ has been involved in MMEJ repair while not playing a significant role in HRR, making it the only MMEJ-specific protein known to date (Wyatt et al., 2016; Yousefzadeh et al., 2014). Interestingly, reports have highlighted a synthetic lethal genetic dependency between inactivating mutations in genes involved in HRR (BRCA1, BRCA2, FANCD2, ATM) and lack of POLQ activity (Ceccaldi et al., 2015; Mateos-Gomez et al., 2015; Shima et al., 2004), being that activity either polymerase or helicase (Mateos-Gomez et al., 2017). As such, there is an increasing interest in developing POLQ inhibitors for the treatment of HRD tumours, both as single agents or in combination with poly(ADP-ribose) polymerase (PARP) inhibitors (Zatreanu et al., 2021; Zhou et al., 2021). Importantly, it has also been shown that POLQ-deficient cells are sensitive to DNA damaging agents including ionising radiation (Higgins et al., 2010; Yousefzadeh et al., 2014), which could open the possibility of combinations of POLQ inhibitors with chemo- or radiotherapy (Higgins and Boulton, 2018).

Accordingly, there is a need for POLQ inhibitors that are selective, demonstrate good bioavailability and are suitable for dosing.

SUMMARY

One embodiment disclosed herein provides a compound of formula (I):

(I)

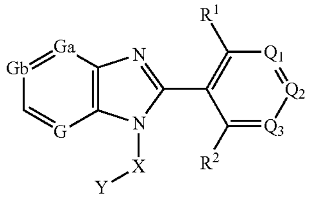

or any stereoisomer thereof or pharmaceutically acceptable salt thereof;

wherein, $R^1$ and $R^2$ are each, independently, H, halo, $C_1$-$C_3$ alkyl, $C_1$-$C_3$ alkoxy, $C_1$-$C_3$ haloalkyl, $C_1$-$C_3$ hydroxyalkyl, —CN, $C_2$-$C_4$ alkyne, or $C_2$-$C_6$ alkoxyalkyl;

$Q^1$, $Q^2$, and $Q^3$ are, independently N, C-L-R, or $CR^x$, wherein no more than one of $Q^1$, $Q^2$, and $Q^3$ is C-L-R;

L is a bond, —O—; —C(O)—; —$O(CH_2)_pC(O)$—; —$C(O)NR^y$—; —$O(CH_2)_pC(O)NR^y$—; —$O(CH_2)_p NR^y$; —$NR^y$—; —$(CH_2)_p$—; —$(CH_2)_pNR^y$—; —$(CH_2)_pO$—; —$(CH_2)_pC(O)$—; —$(CH_2)_pC(O)O$—; or, —$O(CH_2)_p$—;

p is, independently, 1, 2, or 3

R is H, $R^a$, $R^b$, $R^c$, or $R^d$;

$R^a$ is a 3-10 membered heterocycle optionally substituted with 1 to 4 substituents independently selected from amino, carboxy, halo, hydroxy, oxo, —CN, —$S(O)_2OH$, $C_1$-$C_4$ alkylamino, $C_1$-$C_5$alkoxy, $C_2$-$C_5$ alkoxyalkyl, 4-6 membered heterocycle, and $C_1$-$C_7$ alkyl, wherein the $C_1$-$C_7$ alkyl is optionally substituted with 1 to 4 substituents independently selected from amino, carboxy, halo, hydroxy, oxo, —CN, $C_2$-$C_8$ ester, and $C_1$-$C_5$ alkoxy;

$R^b$ is a $C_1$-$C_7$ alkyl, wherein one or two methylene groups from the $C_1$-$C_7$ alkyl are optionally independently replaced with $NR^e$ or O and one or two single bonds in a $C_2$-$C_7$ alkyl chain are optionally independently replaced with a double or triple bond(s), wherein the $C_1$-$C_7$ alkyl is optionally substituted with 1 to 4 substituents independently selected from: halo, oxo, hydroxy, carboxyl, amino, —CN, $C_2$-$C_4$ alkynyl, $C_2$-$C_6$ carbamate, $C_1$-$C_8$ amide, $C_1$-$C_4$ sulfonyl, $C_1$-$C_4$ sulfonamide, $C_1$-$C_4$ alkylamino, $C_1$-$C_5$ alkoxy, $C_3$-$C_6$ carbocycle, and 3-10 membered heterocycle, wherein the $C_3$-$C_6$ carbocycle is optionally substituted with 1 to 4 substituents independently selected from hydroxy, halo, and carboxy;

wherein the 3-10 membered heterocycle is optionally substituted with 1 to 4 substituents independently selected from amino, carboxy, halo, hydroxy, oxo, —CN, —$S(O)_2OH$, $C_1$-$C_4$ alkylamino, $C_1$-$C_5$ alkoxy, $C_2$-$C_5$ alkoxyalkyl, 4-6 membered heterocycle, and $C_1$-$C_7$ alkyl, wherein the $C_1$-$C_7$ alkyl is optionally substituted with 1 to 4 substituents independently selected from amino, carboxy, halo, hydroxy, oxo, —CN, $C_2$-$C_8$ ester, and $C_1$-$C_5$ alkoxy;

$R^c$ is a $C_3$-$C_6$ carbocycle optionally substituted with 1 to 4 substituents independently selected from hydroxy halo, and carboxy;

$R^d$ is $C_1$-$C_4$ sulfonyl or $C_1$-$C_4$ sulfonamide;

$R^y$ is H, $C_1$-$C_3$ alkyl, or $C_{1-3}$ haloalkyl;

$R^x$ is H, halo, hydroxy, —CN, —$NH_2$, $C_1$-$C_3$ alkoxy, $C_1$-$C_3$ alkyl, or $C_{1-3}$ haloalkyl;

$R^e$ is H, halo, $C_1$-$C_8$ alkyl, or $C_1$-$C_8$ haloalkyl;

X is a $C_1$-$C_4$ alkylene;

Y is a phenyl or 5-6 membered heteroaryl, wherein the phenyl or heteroaryl is optionally substituted with 1-3 substituents independently selected from halo, $C_1$-$C_3$ alkyl, $C_1$-$C_3$ alkoxy, —CN, $C_1$-$C_3$ haloalkyl, and cyclopropyl;

G is N or CH;

$G_a$ and $G_b$ are N, CH, or $CR^5$ wherein one, and only one, of $G_a$ and $G_b$ is N or CH and one, and only one, of $G_a$ and $G_b$ is $CR^5$;

$R^5$ is

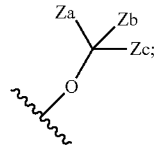

$Z_a$ and $Z_b$ are, independently, $C_1$-$C_3$ alkyl or $C_1$-$C_3$ haloalkyl, or $Z_a$ and $Z_b$ form a 3-6 membered carbocycle or heterocycle; and $Z_c$ is H, —CN, $C_1$-$C_3$ alkyl, $C_1$-$C_3$ haloalkyl, or $C_2$-$C_4$ alkyne.

DETAILED DESCRIPTION

This detailed description and its specific examples, while indicating embodiments, are intended for purposes of illustration only. Therefore, there is no limitation to the illustrative embodiments described in this specification. In addition, it is to be appreciated that various features that are, for clarity reasons, described in the context of separate embodiments, also may be combined to form a single embodiment. Conversely, various features that are, for brevity reasons, described in the context of a single embodiment, also may be combined to form sub-combinations thereof.

Listed below are definitions of various terms used in the specification and claims.

The term "alkoxy" refers to an alkyl group attached to the rest of the molecule via an oxygen atom. Representative alkoxy groups include, but are not limited to, methoxy, ethoxy, propoxy, tert-butoxy and the like.

The term "alkoxyalkyl" refers to an alkyl group attached to an alkoxy group, where in the group is attached to the rest of the molecule via a carbon on the alkyl group, i.e. a group having a structure of —R—O—R' wherein R and R' are the same or different alkyl groups.

The term "alkyl" or "alkane" refers to straight chained or branched non-aromatic hydrocarbon which is completely saturated. Examples of straight chained and branched alkyl groups include methyl, ethyl, n-propyl, iso-propyl, n-butyl, sec-butyl, tert-butyl, pentyl, hexyl, pentyl and octyl.

The term "alkylamino" refers to an amino group substituted with at least one alkyl group, i.e. a group having a structure of —NRR', NHR, NRR'H', or $NH_2R_+$ wherein R and R' are the same or different alkyl groups.

The term "alkyne" or "alkynyl" is a non-aromatic hydrocarbon comprising at least one carbon-carbon triple bond. Examples of alkyne groups include acetylene, propyne, and butyne.

The term "amide" refers to a group with the general formula of $RC(=O)NR^1R^2$, or

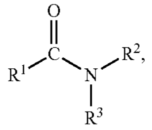

where $R^1$, $R^2$, and $R^3$ are either hydrogen or the same or different alkyl groups, provided at least one is an alkyl group.

The term "carbamate" refers to a group with the general formula of R1OC(O)NR2R3 or

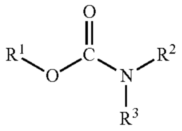

wherein $R^1$, $R^2$, and $R^3$ are either hydrogen or the same or different alkyl groups, provided at least one is an alkyl group. The carbamate is connected to the rest of the molecule via a carbon on any of the alkyl groups.

The term "carbocycle" refers to a partially or completely saturated non-aromatic hydrocarbon ring system, including cycloalkyls, cycloalkenyls, and cycloalkynyls. Cycloalkyls include cyclopropane, cyclobutane, cyclopentane, cyclohexane, cyclopropene, cyclobutene, cyclopentene, and cyclohexene.

The term "ester" refers to a group having the structure $R^1$—C(O)—$OR^2$, or

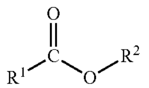

wherein $R^1$ and $R^2$ are the same or different alkyl groups. The ester is connected to the rest of the molecule via a carbon on either alkyl group.

The term "halo" means fluoro, chloro, bromo, and iodo. In some embodiments, halo is fluoro or chloro. In other embodiments, halo is fluoro. In still other embodiments, halo is chloro.

The term "haloalkyl" means an alkyl group in which one or more hydrogens has been substituted with a halo.

The term "hydroxyalkyl" means an alkyl group in which one or more hydrogens has been substituted with a hydroxy group.

The term "heterocycle" "heterocyclic" or "heterocyclyl" refers to a partially or completely saturated hydrocarbon ring system wherein at least one of the ring carbon atoms is replaced with a heteroatom independently selected from nitrogen, oxygen and sulphur. Heterocyclic groups can be attached to the rest of the molecule via a carbon or nitrogen ring-member atoms. Heterocycles include monocyclic heterocycles as well as spiro, fused and/or bridged polycyclic heterocycles such as bicyclic heterocycles. Examples of monocyclic heterocycles include, but are not limited to, tetrahydropyran, tetrahydrofuran, morpholine, azetidine, pyrrolidine, piperidine, piperazine, azepane, diazepane, oxetane, and isoxazolidine. Examples of polycyclic heterocycles include 2-azaspiro[3.3]heptane, 2,6-diazaspiro[3.3]heptane, 1,6-diazaspiro[3.3]heptane, 2-thia-6-azaspiro[3.3]heptane, 3,6-diazabicyclo[3.1.1]heptane, 2,6-diazaspiro[3.4]octane, 3,8-diazabicyclo[3.2.1]octane, and 4,7-diazaspiro[2.5]octane.

The term "sulfonyl" refers to a group having the general formula $R^1S(O)_2R^2$, or

wherein $R^1$ and $R^2$ are either hydrogen or the same or different alkyl groups, provided at least one is an alkyl group. The sulfonyl is connected to the rest of the molecule via a carbon on either alkyl group.

In this specification the prefix $C_{x-y}$ as used in terms such as "$C_{x-y}$ alkyl" and the like where x and y are integers, indicates the numerical range of carbon atoms that are present in the group. Examples of suitable $C_{1-3}$ alkyl groups include, but are not limited to, methyl, ethyl, n-propyl, and i-propyl. Examples of suitable $C_{1-4}$ alkyl groups include, but are not limited to, methyl, ethyl, n-propyl, and i-propyl, n-butyl, i-butyl, s-butyl and t-butyl. In some cases, a group will have two sections comprising carbon, which case the prefix indicates the numerical range of total carbons in the group, e.g., $C_{2-6}$ alkoxyalkyl, refers to an alkoxyalkyl group wherein the alkyl group and the alkoxy group together have 2 to 6 carbons.

A "patient" refers to an animal in which the one or more active agents as described herein will have a therapeutic effect. In some embodiments, the patient is a human being.

As used herein, unless otherwise stated, the term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, unless otherwise stated, the phrase "effective amount" means an amount of a compound or composition which is sufficient to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

The term "treating", as used herein, unless otherwise indicated, means reversing, alleviating, inhibiting the progress of, or slowing or delaying the progression of, the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. The term "treating" also includes the reduction or inhibition of the growth of a tumor or proliferation of cancerous cells in a subject.

The language "pharmaceutically acceptable salt" includes acid addition or base addition salts that retain the biological effectiveness and properties of the compounds disclosed herein. In many cases, the compounds disclosed herein capable of forming acid and/or base salts by virtue of the presence of basic and/or carboxyl groups or groups similar thereto.

Compounds

One embodiment disclosed herein provides a compound of formula (I):

(I)

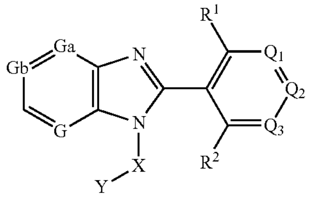

or any stereoisomer thereof or pharmaceutically acceptable salt thereof;

wherein, $R^1$ and $R^2$ are each, independently, H, halo, $C_1$-$C_3$ alkyl, $C_1$-$C_3$ alkoxy, $C_1$-$C_3$ haloalkyl, $C_1$-$C_3$ hydroxyalkyl, —CN, $C_2$-$C_4$ alkyne, or $C_2$-$C_6$ alkoxyalkyl;

$Q^1$, $Q^2$, and $Q^3$ are, independently N, C-L-R, or $CR^x$, wherein no more than one of $Q^1$, $Q^2$, and $Q^3$ is C-L-R;

L is a bond, —O—; —C(O)—; —$O(CH_2)_pC(O)$—; —$C(O)NR^y$—; —$O(CH_2)_pC(O)NR^y$—; —$O(CH_2)_pNR^y$; —$NR^y$—; —$(CH_2)_p$—; —$(CH_2)_pNR^y$—; —$(CH_2)_pO$—; —$(CH_2)_pC(O)$—; —$(CH_2)_pC(O)O$—; —$O(CH_2)_p$—;

p is, independently, 1, 2, or 3

R is H, $R^a$, $R^b$, $R^c$, or $R^d$;

$R^a$ is a 3-10 membered heterocycle optionally substituted with 1 to 4 substituents independently selected from amino, carboxy, halo, hydroxy, oxo, —CN, —$S(O)_2OH$, C1-C4 alkylamino, C1-C5 alkoxy, $C_2$-$C_5$ alkoxyalkyl, 4-6 membered heterocycle, and $C_1$-$C_7$ alkyl, wherein the C1-C7 alkyl is optionally substituted with 1 to 4 substituents independently selected from amino, carboxy, halo, hydroxy, oxo, —CN, $C_2$-$C_8$ ester, and $C_1$-$C_5$ alkoxy;

$R^b$ is a $C_1$-$C_7$ alkyl, wherein one or two methylene groups from the $C_1$-$C_7$ alkyl are optionally independently replaced with $NR^e$ or O and one or two single bonds in a $C_2$-$C_7$ alkyl chain are optionally independently replaced with a double or triple bond(s), wherein the $C_1$-$C_7$ alkyl is optionally substituted with 1 to 4 substituents independently selected from: halo, oxo, hydroxy, carboxyl, amino, —CN, $C_2$-$C_4$ alkynyl, $C_2$-$C_6$ carbamate, $C_1$-$C_8$ amide, $C_1$-$C_4$ sulfonyl, $C_1$-$C_4$ sulfonamide, $C_1$-$C_4$ alkylamino, $C_1$-$C_5$ alkoxy, $C_3$-$C_6$ carbocycle, and 3-10 membered heterocycle, wherein the $C_3$-$C_6$ carbocycle is optionally substituted with 1 to 4 substituents independently selected from hydroxy, halo, and carboxy, wherein the 3-10 membered heterocycle is optionally substituted with 1 to 4 substituents independently selected from amino, carboxy, halo, hydroxy, oxo, —CN, —$S(O)_2OH$, $C_1$-$C_4$ alkylamino, $C_1$-$C_5$ alkoxy, $C_2$-$C_5$ alkoxyalkyl, 4-6 membered heterocycle, and $C_1$-$C_7$ alkyl, wherein the $C_1$-$C_7$ alkyl is optionally substituted with 1 to 4 substituents independently selected from amino, carboxy, halo, hydroxy, oxo, —CN, $C_2$-$C_8$ ester, and $C_1$-$C_5$ alkoxy;

$R^c$ is a $C_3$-$C_6$ carbocycle optionally substituted with 1 to 4 substituents independently selected from hydroxy, halo, and carboxy;

$R^d$ is $C_1$-$C_4$ sulfonyl or $C_1$-$C_4$ sulfonamide;

$R^y$ is H, $C_1$-$C_3$ alkyl, or $C_{1-3}$ haloalkyl;

$R^x$ is H, halo, hydroxy, —CN, —$NH_2$, $C_1$-$C_3$ alkoxy, $C_1$-$C_3$ alkyl, or $C_{1-3}$ haloalkyl;

$R^e$ is H, halo, $C_1$-$C_8$ alkyl, or $C_1$-$C_8$ haloalkyl;

X is a $C_1$-$C_4$ alkylene;

Y is a phenyl or 5-6 membered heteroaryl, wherein the phenyl or heteroaryl is optionally substituted with 1-3 substituents independently selected from halo, $C_1$-$C_3$ alkyl, $C_1$-$C_3$ alkoxy, —CN, $C_1$-$C_3$ haloalkyl, and cyclopropyl;

G is N or CH;

$G_a$ and $G_b$ are N, CH, or $CR^5$ wherein one, and only one, of $G_a$ and $G_b$ is N or CH and one, and only one, of $G_a$ and $G_b$ is $CR^5$;

$R^5$ is

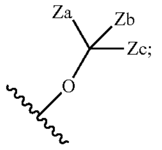

$Z_a$ and $Z_b$ are, independently, $C_1$-$C_3$ alkyl or $C_1$-$C_3$ haloalkyl, or $Z_a$ and $Z_b$ form a 3-6 membered carbocycle or heterocycle; and $Z_c$ is H, —CN, $C_1$-$C_3$ alkyl, $C_1$-$C_3$ haloalkyl, or $C_2$-$C_4$ alkyne.

Some embodiments disclosed herein provide a compound of formula (I), or any stereoisomer thereof or pharmaceutically acceptable salt thereof, wherein G is N.

Some embodiments disclosed herein provide a compound of formula (I), or any stereoisomer thereof or pharmaceutically acceptable salt thereof, wherein G is CH.

Some embodiments disclosed herein provide a compound of formula (I), or any stereoisomer thereof or pharmaceutically acceptable salt thereof, wherein $G_a$ is $CR_5$.

Some embodiments disclosed herein provide a compound of formula (I), or any stereoisomer thereof or pharmaceutically acceptable salt thereof, wherein $G_b$ is $CR_5$.

Some embodiments disclosed herein provide a compound of formula (I), or any stereoisomer thereof or pharmaceutically acceptable salt thereof, wherein $G_b$ is N.

Some embodiments disclosed herein provide a compound of formula (I), or any stereoisomer thereof or pharmaceutically acceptable salt thereof, wherein $G_b$ is CH.

Some embodiments disclosed herein provide a compound of formula (I), or any stereoisomer thereof or pharmaceutically acceptable salt thereof, wherein $G_b$ is N.

Some embodiments disclosed herein provide a compound of formula (I), or any stereoisomer thereof or pharmaceutically acceptable salt thereof, wherein $G_b$ is CH.

Some embodiments disclosed herein provide a compound of formula (I), or any stereoisomer thereof or pharmaceutically acceptable salt thereof, wherein $Z_a$ and $Z_b$, are independently, $C_1$-$C_3$ alkyl.

Some embodiments disclosed herein provide a compound of formula (I), or any stereoisomer thereof or pharmaceutically acceptable salt thereof, wherein $Z_a$ and $Z_b$ are —$CH_3$.

Some embodiments disclosed herein provide a compound of formula (I), or any stereoisomer thereof or pharmaceutically acceptable salt thereof, wherein $G_a$ or $G_b$ is $CR_5$ and $R^5$ is

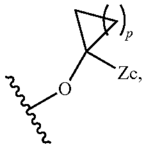

wherein p is 1-4.

Some embodiments disclosed herein provide a compound of formula (I), or any stereoisomer thereof or pharmaceutically acceptable salt thereof, wherein $G_a$ or $G_b$ is $CR_5$ and $R^5$ is

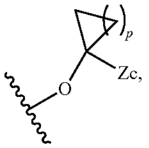

wherein p is 2.

Some embodiments disclosed herein provide a compound of formula (I), or any stereoisomer thereof or pharmaceutically acceptable salt thereof, wherein $G_a$ or $G_b$ is $CR_5$ and $R^5$ is

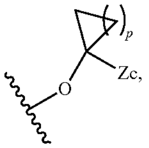

wherein p is 1.

Some embodiments disclosed herein provide a compound of formula (I), or any stereoisomer thereof or pharmaceutically acceptable salt thereof, wherein $Z_c$ is —$CH_3$.

Some embodiments disclosed herein provide a compound of formula (I), or any stereoisomer thereof or pharmaceutically acceptable salt thereof, wherein $Z_c$ is —CN.

Some embodiments disclosed herein provide a compound of formula (I), or any stereoisomer thereof or pharmaceutically acceptable salt thereof, wherein G is N, $G_b$ is N, $G_a$ is $CR_5$ and $R^5$ is

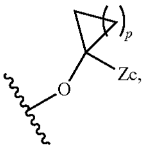

wherein p is 1-4.

Some embodiments disclosed herein provide a compound of formula (I), or any stereoisomer thereof or pharmaceutically acceptable salt thereof, wherein G is N, $G_b$ is N, $G_a$ is $CR_5$ and $R^5$ is

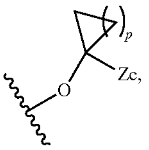

wherein p is 1.

Some embodiments disclosed herein provide a compound of formula (I), or any stereoisomer thereof or pharmaceutically acceptable salt thereof, wherein G is N, $G_b$ is N, $G_a$ is $CR_5$ and $R^5$ is

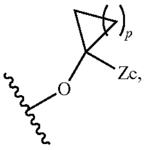

wherein p is 2.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

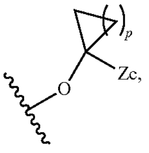

wherein p is 1-4, and $Z_c$ is $C_1$-$C_3$ alkyl

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

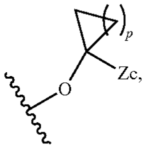

wherein p is 1-4, and $Z_c$ is —$CH_3$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

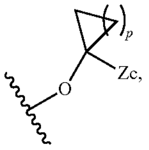

wherein p is 1, and $Z_c$ is $C_1$-$C_3$ alkyl.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

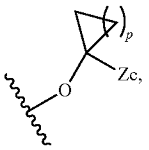

wherein p is 1, and $Z_c$ is —$CH_3$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

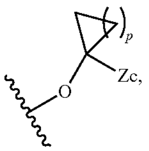

wherein p is 2, and $Z_c$ is —$CH_3$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

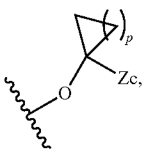

wherein p is 1-4, and $Z_c$ is —CN.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

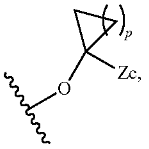

wherein p is 1, and $Z_c$ is —CN.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

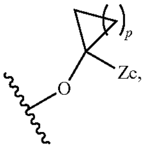

wherein p is 2, and $Z_c$ is —CN.

Some embodiments disclosed herein provide a compound of formula (I), or any stereoisomer thereof or pharmaceutically acceptable salt thereof, wherein Y is phenyl.

Some embodiments disclosed herein provide a compound of formula (I), or any stereoisomer thereof or pharmaceutically acceptable salt thereof, wherein Y is a N-heteroaryl.

Some embodiments disclosed herein provide a compound of formula (I), or any stereoisomer thereof or pharmaceutically acceptable salt thereof, wherein Y is a pyridine.

Some embodiments disclosed herein provide a compound of formula (I), or any stereoisomer thereof or pharmaceutically acceptable salt thereof, wherein Y is substituted.

Some embodiments disclosed herein provide a compound of formula (I), or any stereoisomer thereof or pharmaceutically acceptable salt thereof, wherein Y is substituted with 1-3 substituents independently selected from halo, $C_1$-$C_3$ alkyl, $C_1$-$C_3$ alkoxy, —CN, $C_1$-$C_3$ and haloalkyl.

Some embodiments disclosed herein provide a compound of formula (I), or any stereoisomer thereof or pharmaceutically acceptable salt thereof, wherein Y is substituted with —Cl.

Some embodiments disclosed herein provide a compound of formula (I), or any stereoisomer thereof or pharmaceutically acceptable salt thereof, wherein Y is substituted with —$CH_3$.

Some embodiments disclosed herein provide a compound of formula (I), or any stereoisomer thereof or pharmaceutically acceptable salt thereof, wherein Y is substituted with cyclopropyl.

Some embodiments disclosed herein provide a compound of formula (I), or any stereoisomer thereof or pharmaceutically acceptable salt thereof, wherein Y is not substituted.

Some embodiments disclosed herein provide a compound of formula (I), or any stereoisomer thereof or pharmaceutically acceptable salt thereof, wherein Y is phenyl, substituted with 1 substituent selected from halo, $C_1$-$C_3$ alkyl, $C_1$-$C_3$ alkoxy, —CN, $C_1$-$C_3$ haloalkyl, and cyclopropyl.

Some embodiments disclosed herein provide a compound of formula (I), or any stereoisomer thereof or pharmaceutically acceptable salt thereof, wherein Y is pyridine, substituted with 1 substituent selected from halo, $C_1$-$C_3$ alkyl, $C_1$-$C_3$ alkoxy, —CN, $C_1$-$C_3$ haloalkyl, and cyclopropyl.

Some embodiments disclosed herein provide a compound of formula (I), or any stereoisomer thereof or pharmaceutically acceptable salt thereof, wherein Y is phenyl, substituted with 1 substituent selected from halo and $C_1$-$C_3$ alkyl.

Some embodiments disclosed herein provide a compound of formula (I), or any stereoisomer thereof or pharmaceutically acceptable salt thereof, wherein Y is pyridine, substituted with 1 substituent selected from halo and $C_1$-$C_3$ alkyl.

Some embodiments disclosed herein provide a compound of formula (I), or any stereoisomer thereof or pharmaceutically acceptable salt thereof, wherein Y is phenyl, substituted with 1 substituent selected from —Cl and —$CH_3$.

Some embodiments disclosed herein provide a compound of formula (I), or any stereoisomer thereof or pharmaceutically acceptable salt thereof, wherein Y is pyridine, substituted with 1 substituent selected from —Cl and —$CH_3$.

Some embodiments disclosed herein provide a compound of formula (I), or any stereoisomer thereof or pharmaceutically acceptable salt thereof, wherein $R^1$ and $R^2$ are each, independently, H, halo, $C_1$-$C_3$ alkyl, $C_1$-$C_3$ alkoxy, $C_1$-$C_3$ hydroxyalkyl, —CN, or $C_2$-$C_4$ alkyne.

Some embodiments disclosed herein provide a compound of formula (I), or any stereoisomer thereof or pharmaceutically acceptable salt thereof, wherein $R^1$ and $R^2$ are each, independently, H, halo, —$CH_3$, —$OCH_3$, $CH_2OH$, —CN, or —C—CH.

Some embodiments disclosed herein provide a compound of formula (I), or any stereoisomer thereof or pharmaceutically acceptable salt thereof, wherein $R^1$ and $R^2$ are each, independently, H, halo, or $C_1$-$C_3$ alkyl.

Some embodiments disclosed herein provide a compound of formula (I), or any stereoisomer thereof or pharmaceutically acceptable salt thereof, wherein $R^1$ and $R^2$ are each, independently, H, halo, or —$CH_3$.

Some embodiments disclosed herein provide a compound of formula (I), or any stereoisomer thereof or pharmaceutically acceptable salt thereof, wherein $R^1$ and $R^2$ are each, independently, H, —Cl, —F, or —$CH_3$.

Some embodiments disclosed herein provide a compound of formula (I), or any stereoisomer thereof or pharmaceutically acceptable salt thereof, wherein $R^1$ and $R^2$ are —H.

Some embodiments disclosed herein provide a compound of formula (I), or any stereoisomer thereof or pharmaceutically acceptable salt thereof, wherein $R^1$ is halo.

Some embodiments disclosed herein provide a compound of formula (I), or any stereoisomer thereof or pharmaceutically acceptable salt thereof, wherein $R^1$ is —Cl.

Some embodiments disclosed herein provide a compound of formula (I), or any stereoisomer thereof or pharmaceutically acceptable salt thereof, wherein $R^1$ is —F.

Some embodiments disclosed herein provide a compound of formula (I), or any stereoisomer thereof or pharmaceutically acceptable salt thereof, wherein $R^1$ is —$CH_3$. Some embodiments disclosed herein provide a compound of formula (I), or any stereoisomer thereof or pharmaceutically acceptable salt thereof, wherein $R^2$ is —H.

Some embodiments disclosed herein provide a compound of formula (I), or any stereoisomer thereof or pharmaceutically acceptable salt thereof, wherein $R^1$ is halo and $R^2$ is —H.

Some embodiments disclosed herein provide a compound of formula (I), or any stereoisomer thereof or pharmaceutically acceptable salt thereof, wherein $R^1$ is —Cl and $R^2$ is —H.

Some embodiments disclosed herein provide a compound of formula (I), or any stereoisomer thereof or pharmaceutically acceptable salt thereof, wherein $R^1$ is —F and $R^2$ is —H.

Some embodiments disclosed herein provide a compound of formula (I), or any stereoisomer thereof or pharmaceutically acceptable salt thereof, wherein $R^1$ is —$CH_3$ and $R^2$ is —H.

Some embodiments disclosed herein provide a compound of formula (I), or any stereoisomer thereof or pharmaceutically acceptable salt thereof, wherein $R^2$ is halo.

Some embodiments disclosed herein provide a compound of formula (I), or any stereoisomer thereof or pharmaceutically acceptable salt thereof, wherein $R^2$ is —Cl.

Some embodiments disclosed herein provide a compound of formula (I), or any stereoisomer thereof or pharmaceutically acceptable salt thereof, wherein $R^2$ is —F.

Some embodiments disclosed herein provide a compound of formula (I), or any stereoisomer thereof or pharmaceutically acceptable salt thereof, wherein $R^2$ is —$CH_3$.

Some embodiments disclosed herein provide a compound of formula (I), or any stereoisomer thereof or pharmaceutically acceptable salt thereof, wherein $R^1$ is —H.

Some embodiments disclosed herein provide a compound of formula (I), or any stereoisomer thereof or pharmaceutically acceptable salt thereof, wherein $R^1$ is —H and $R^2$ is halo.

Some embodiments disclosed herein provide a compound of formula (I), or any stereoisomer thereof or pharmaceutically acceptable salt thereof, wherein $R^1$ is —H and $R^2$ is —Cl.

Some embodiments disclosed herein provide a compound of formula (I), or any stereoisomer thereof or pharmaceutically acceptable salt thereof, wherein $R^1$ is —H and $R^2$ is —F.

Some embodiments disclosed herein provide a compound of formula (I), or any stereoisomer thereof or pharmaceutically acceptable salt thereof, wherein $R^1$ is —H and $R^2$ is —$CH_3$.

Some embodiments disclosed herein provide a compound of formula (I), or any stereoisomer thereof or pharmaceutically acceptable salt thereof, wherein $Q^1$, $Q^2$, or $Q^3$ is C-L-R.

Some embodiments disclosed herein provide a compound of formula (I), or any stereoisomer thereof or pharmaceutically acceptable salt thereof, wherein $Q^1$ is C-L-R.

Some embodiments disclosed herein provide a compound of formula (I), or any stereoisomer thereof or pharmaceutically acceptable salt thereof, wherein $Q^2$ is C-L-R.

Some embodiments disclosed herein provide a compound of formula (I), or any stereoisomer thereof or pharmaceutically acceptable salt thereof, wherein $Q^3$ is C-L-R.

Some embodiments disclosed herein provide a compound of formula (I), or any stereoisomer thereof or pharmaceutically acceptable salt thereof, wherein $Q^1$, $Q^2$, or $Q^3$ is C-L-R and L is a bond, —O—, —$(CH_2)_p$O— or —O$(CH_2)_p$—.

Some embodiments disclosed herein provide a compound of formula (I), or any stereoisomer thereof or pharmaceutically acceptable salt thereof, wherein $Q^1$ is C-L-R and L is a bond, —O—, —$(CH_2)_p$O— or —O$(CH_2)_p$—.

Some embodiments disclosed herein provide a compound of formula (I), or any stereoisomer thereof or pharmaceutically acceptable salt thereof, wherein $Q^2$ is C-L-R and L is a bond, —O—, —$(CH_2)_p$O— or —O$(CH_2)_p$—.

Some embodiments disclosed herein provide a compound of formula (I), or any stereoisomer thereof or pharmaceutically acceptable salt thereof, wherein $Q^3$ is C-L-R and L is a bond, —O—, —$(CH_2)_p$O— or —O$(CH_2)_p$—.

Some embodiments disclosed herein provide a compound of formula (I), or any stereoisomer thereof or pharmaceutically acceptable salt thereof, wherein $Q^1$, $Q^2$, or $Q^3$ is C-L-R and L is a bond.

Some embodiments disclosed herein provide a compound of formula (I), or any stereoisomer thereof or pharmaceutically acceptable salt thereof, wherein $Q^1$ is C-L-R and L is a bond.

Some embodiments disclosed herein provide a compound of formula (I), or any stereoisomer thereof or pharmaceutically acceptable salt thereof, wherein $Q^2$ is C-L-R and L is a bond.

Some embodiments disclosed herein provide a compound of formula (I), or any stereoisomer thereof or pharmaceutically acceptable salt thereof, wherein $Q^3$ is C-L-R and L is a bond.

Some embodiments disclosed herein provide a compound of formula (I), or any stereoisomer thereof or pharmaceutically acceptable salt thereof, wherein $Q^1$, $Q^2$, or $Q^3$ is C-L-R and L is —O—.

Some embodiments disclosed herein provide a compound of formula (I), or any stereoisomer thereof or pharmaceutically acceptable salt thereof, wherein $Q^1$ is C-L-R and L is —O—.

Some embodiments disclosed herein provide a compound of formula (I), or any stereoisomer thereof or pharmaceutically acceptable salt thereof, wherein $Q^2$ is C-L-R and L is —O—.

Some embodiments disclosed herein provide a compound of formula (I), or any stereoisomer thereof or pharmaceutically acceptable salt thereof, wherein $Q^3$ is C-L-R and L is —O—.

Some embodiments disclosed herein provide a compound of formula (I), or any stereoisomer thereof or pharmaceutically acceptable salt thereof, wherein $Q^1$, $Q^2$, or $Q^3$ is C-L-R and L is —$(CH_2)_p$O.

Some embodiments disclosed herein provide a compound of formula (I), or any stereoisomer thereof or pharmaceutically acceptable salt thereof, wherein $Q^1$ is C-L-R and L is —$(CH_2)_p$O.

Some embodiments disclosed herein provide a compound of formula (I), or any stereoisomer thereof or pharmaceutically acceptable salt thereof, wherein $Q^2$ is C-L-R and L is —$(CH_2)_p$O.

Some embodiments disclosed herein provide a compound of formula (I), or any stereoisomer thereof or pharmaceutically acceptable salt thereof, wherein $Q^3$ is C-L-R and L is —$(CH_2)_p$O.

Some embodiments disclosed herein provide a compound of formula (I), or any stereoisomer thereof or pharmaceutically acceptable salt thereof, wherein $Q^1$, $Q^2$, or $Q^3$ is C-L-R and L is —O$(CH_2)_p$—.

Some embodiments disclosed herein provide a compound of formula (I), or any stereoisomer thereof or pharmaceutically acceptable salt thereof, wherein $Q^1$ is C-L-R and L is —O$(CH_2)_p$—.

Some embodiments disclosed herein provide a compound of formula (I), or any stereoisomer thereof or pharmaceutically acceptable salt thereof, wherein $Q^2$ is C-L-R and L is —O$(CH_2)_p$—.

Some embodiments disclosed herein provide a compound of formula (I), or any stereoisomer thereof or pharmaceutically acceptable salt thereof, wherein $Q^3$ is C-L-R and L is —O$(CH_2)_p$—.

Some embodiments disclosed herein provide a compound of formula (I), or any stereoisomer thereof or pharmaceutically acceptable salt thereof, wherein $Q^1$, $Q^2$, or $Q^3$ is C-L-R and L is —$O(CH_2)_2$—.

Some embodiments disclosed herein provide a compound of formula (I), or any stereoisomer thereof or pharmaceutically acceptable salt thereof, wherein $Q^1$ is C-L-R and L is —$O(CH_2)_2$—.

Some embodiments disclosed herein provide a compound of formula (I), or any stereoisomer thereof or pharmaceutically acceptable salt thereof, wherein $Q^2$ is C-L-R and L is —$O(CH_2)_2$—.

Some embodiments disclosed herein provide a compound of formula (I), or any stereoisomer thereof or pharmaceutically acceptable salt thereof, wherein $Q^3$ is C-L-R and L is —$O(CH_2)_2$—.

Some embodiments disclosed herein provide a compound of formula (I), or any stereoisomer thereof or pharmaceutically acceptable salt thereof, wherein $Q^1$, $Q^2$, or $Q^3$ is C-L-R and L is —C(O)—; —$O(CH_2)_pC(O)$—; —$C(O)NR^y$—; —$O(CH_2)_pC(O)NR^y$—; —$(CH_2)_pC(O)$—; or —$(CH_2)_pC(O)O$—.

Some embodiments disclosed herein provide a compound of formula (I), or any stereoisomer thereof or pharmaceutically acceptable salt thereof, wherein $Q^1$ is C-L-R and L is —C(O)—; —$O(CH_2)_pC(O)$—; —$C(O)NR^y$—; —$O(CH_2)_pC(O)NR^y$—; —$(CH_2)_pC(O)$—; or —$(CH_2)_pC(O)O$—.

Some embodiments disclosed herein provide a compound of formula (I), or any stereoisomer thereof or pharmaceutically acceptable salt thereof, wherein $Q^2$ is C-L-R and L is —C(O)—; —$O(CH_2)_pC(O)$—; —$C(O)NR^y$—; —$O(CH_2)_pC(O)NR^y$—; —$(CH_2)_pC(O)$—; or —$(CH_2)_pC(O)O$—.

Some embodiments disclosed herein provide a compound of formula (I), or any stereoisomer thereof or pharmaceutically acceptable salt thereof, wherein $Q^3$ is C-L-R and L is —C(O)—; —$O(CH_2)_pC(O)$—; —$C(O)NR^y$—; —$O(CH_2)_pC(O)NR^y$—; —$(CH_2)_pC(O)$—; or —$(CH_2)_pC(O)O$—.

Some embodiments disclosed herein provide a compound of formula (I), or any stereoisomer thereof or pharmaceutically acceptable salt thereof, wherein $Q^1$, $Q^2$, or $Q^3$ is C-L-R and R is H, $R^a$ or $R^b$.

Some embodiments disclosed herein provide a compound of formula (I), or any stereoisomer thereof or pharmaceutically acceptable salt thereof, wherein $Q^1$ is C-L-R and R is H, $R^a$ or $R^b$.

Some embodiments disclosed herein provide a compound of formula (I), or any stereoisomer thereof or pharmaceutically acceptable salt thereof, wherein $Q^2$ is C-L-R and R is H, $R^a$ or $R^b$.

Some embodiments disclosed herein provide a compound of formula (I), or any stereoisomer thereof or pharmaceutically acceptable salt thereof, wherein $Q^3$ is C-L-R and R is H, $R^a$ or $R^b$.

Some embodiments disclosed herein provide a compound of formula (I), or any stereoisomer thereof or pharmaceutically acceptable salt thereof, wherein $Q^1$, $Q^2$, or $Q^3$ is C-L-R and R is $R^a$.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is a 3-10 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is a 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is a 6 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is piperidine, 1,2-diazinane, 1,3-diazinane, 1,4-diazinane, 1,2-oxazinane, 1,3-oxazinane, or 1,4-oxazinane.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is substituted with 1 to 4 substituents independently selected from amino, carboxy, halo, hydroxy, oxo, —CN, —$S(O)_2OH$, $C_1$-$C_4$ alkylamino, $C_1$-$C_5$ alkoxy, $C_2$-$C_5$ alkoxyalkyl, 4-6 membered heterocycle, and $C_1$-$C_7$ alkyl, wherein the $C_1$-$C_7$ alkyl is optionally substituted with 1 to 4 substituents independently selected from amino, carboxy, halo, hydroxy, oxo, —CN, $C_2$-$C_8$ ester, and $C_1$-$C_5$ alkoxy.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is substituted with $C_1$-$C_7$ alkyl, wherein the $C_1$-$C_7$ alkyl is optionally substituted with 1 to 4 substituents independently selected from amino, carboxy, halo, hydroxy, oxo, —CN, $C_2$-$C_8$ ester, and $C_1$-$C_5$ alkoxy.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is substituted with $C_1$-$C_7$ alkyl substituted with oxo.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is substituted with $C_1$-$C_7$ alkyl substituted with a $C_1$-$C_5$ alkoxy.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and $R^a$ is substituted with methyl.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_p$— and $R^a$ is an optionally substituted 3-10 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_p$— and $R^a$ is an optionally substituted 3-10 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_2$— and $R^a$ is an optionally substituted 3-10 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_2$— and $R^a$ is an optionally substituted 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_2$— and $R^a$ is an unsubstituted 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_2$— and $R^a$ is a 4-7 membered N-heterocycle substituted with hydroxy, methyl, or amino.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_3$— and $R^a$ is an optionally substituted 3-10 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_3$— and $R^a$ is a 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_3$— and $R^a$ is an unsubstituted 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —$O(CH_2)_3$— and $R^a$ is a 4-7 membered N-heterocycle substituted with hydroxy, methyl, or amino.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is a bond and $R^a$ is an optionally substituted 3-10 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is a bond and $R^a$ is a 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is a bond and $R^a$ is an unsubstituted 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is a bond and $R^a$ is a 4-7 membered N-heterocycle substituted with hydroxy, methyl, or amino.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —O— and $R^a$ is an optionally substituted 3-10 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —O— and $R^a$ is a 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —O— and $R^a$ is an unsubstituted 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^a$ and L is —O— and $R^a$ is a 4-7 membered N-heterocycle substituted with hydroxy, methyl, or amino.

Some embodiments disclosed herein provide a compound of formula (I), or any stereoisomer thereof or pharmaceutically acceptable salt thereof, wherein $Q^1$, $Q^2$, or $Q^3$ is C-L-R and R is $R^b$.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with 1 to 4 substituents independently selected from: halo, oxo, hydroxy, carboxyl, amino, —CN, $C_2$-$C_4$ alkynyl, $C_2$-$C_6$ carbamate, $C_1$-$C_8$ amide, $C_1$-$C_4$ sulfonyl, $C_1$-$C_4$ sulfonamide, $C_1$-$C_4$ alkylamino, $C_1$-$C_5$ alkoxy, $C_3$-$C_6$ carbocycle, and 3-10 membered heterocycle, wherein the $C_3$-$C_6$ carbocycle is optionally substituted with 1 to 4 substituents independently selected from hydroxy, halo, and carboxy, and wherein the 3-10 membered heterocycle is optionally substituted with 1 to 4 substituents independently selected from amino, carboxy, halo, hydroxy, oxo, —CN, —$S(O)_2OH$, $C_1$-$C_4$ alkylamino, $C_1$-$C_5$ alkoxy, $C_2$-$C_5$ alkoxyalkyl, 4-6 membered heterocycle, and $C_1$-$C_7$ alkyl, wherein the $C_1$-$C_7$ alkyl is optionally substituted with 1 to 4 substituents independently selected from amino, carboxy, halo, hydroxy, oxo, —CN, $C_2$-$C_8$ ester, and $C_1$-$C_5$ alkoxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with at least one $C_3$-$C_6$ carbocycle, wherein the $C_3$-$C_6$ carbocycle is substituted with 1 to 4 substituents independently selected from hydroxy, halo, and carboxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with at least one $C_3$-$C_6$ carbocycle, wherein the $C_3$-$C_6$ carbocycle is substituted with 1 to 4 substituents independently selected from hydroxy and halo.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with hydroxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with a 3-10 membered heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with a N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with a 4-7 membered N-heterocycle.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with a 3-10 membered heterocycle, such as, but not limited to a N-heterocycle, such as, but not limited to a 4-7 membered N-heterocycle, wherein the heterocycle is substituted with 1 to 4 substituents independently selected from amino, carboxy, halo, hydroxy, oxo, —CN, —$S(O)_2OH$, C1-C4 alkylamino, C1-C5 alkoxy, $C_2$-$C_5$ alkoxyalkyl, 4-6 membered heterocycle, and $C_1$-$C_7$ alkyl, wherein the $C_1$-$C_7$ alkyl is optionally substituted with 1 to 4 substituents independently selected from amino, carboxy, halo, hydroxy, oxo, —CN, $C_2$-$C_8$ ester, and $C_1$-$C_5$ alkoxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with a 3-10 membered heterocycle, such as, but not limited to a N-heterocycle, such as, but not limited to a 4-7 membered N-heterocycle, wherein the heterocycle is substituted with C1-C7 alkyl, oxo, and/or halo.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with amino, $C_1$-$C_8$ amide, and/or $C_1$-$C_4$ alkylamino.

Some embodiments disclosed herein provide a compound of formula (I), or any stereoisomer thereof or pharmaceutically acceptable salt thereof, wherein $Q^1$, $Q^2$, or $Q^3$ is C-L-$R^b$ and $R^b$ is substituted with oxo, hydroxy, and/or carboxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an optionally substituted $C_1$-$C_5$ alkyl.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an optionally substituted $C_1$-$C_3$ alkyl.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an $C_1$-$C_5$ alkyl substituted with 1 to 4 substituents independently selected from amino, carboxy, oxy, and hydroxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an $C_1$-$C_3$ alkyl substituted with 1 to 4 substituents independently selected from amino, carboxy, oxy, and hydroxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an $C_1$-$C_5$ alkyl substituted with 1 to 4 substituents independently selected from —CN, $C_2$-$C_4$ alkynyl, $C_2$-$C_6$ carbamate, and $C_1$-$C_8$ amide.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an $C_1$-$C_3$ alkyl substituted with 1 to 4 substituents independently selected from —CN, $C_2$-$C_4$ alkynyl, $C_2$-$C_6$ carbamate, and $C_1$-$C_8$ amide.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an unsubstituted $C_1$-$C_5$ alkyl.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an unsubstituted $C_1$-$C_3$ alkyl.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an optionally substituted $C_1$-$C_7$ alkyl, wherein one or two methylene groups from the $C_1$-$C_7$ alkyl is independently replaced with $NR^e$ or O.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an optionally substituted $C_1$-$C_7$ alkyl, wherein one methylene group from the $C_1$-$C_7$ alkyl is replaced with NH.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is —O—, and $R^b$ is an optionally substituted $C_1$-$C_7$ alkyl, wherein one methylene group from the $C_1$-$C_7$ alkyl is replaced with $NCH_3$.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an optionally substituted $C_1$-$C_5$ alkyl.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an optionally substituted $C_1$-$C_3$ alkyl.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an $C_1$-$C_5$ alkyl substituted with 1 to 4 substituents independently selected from amino, carboxy, oxy, and hydroxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an $C_1$-$C_3$ alkyl substituted with 1 to 4 substituents independently selected from amino, carboxy, oxy, and hydroxy.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an $C_1$-$C_5$ alkyl substituted with 1 to 4 substituents independently selected from —CN, $C_2$-$C_4$ alkynyl, $C_2$-$C_6$ carbamate, and $C_1$-$C_8$ amide.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an $C_1$-$C_3$ alkyl substituted with 1 to 4 substituents independently selected from —CN, $C_2$-$C_4$ alkynyl, $C_2$-$C_6$ carbamate, and $C_1$-$C_8$ amide.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an unsubstituted $C_1$-$C_5$ alkyl.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an unsubstituted $C_1$-$C_3$ alkyl.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an optionally substituted $C_1$-$C_7$ alkyl, wherein one or two methylene groups from the $C_1$-$C_7$ alkyl is independently replaced with $NR^e$ or O.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an optionally substituted $C_1$-$C_7$ alkyl, wherein one methylene group from the $C_1$-$C_7$ alkyl is replaced with NH.

Some embodiments disclosed herein provide a compound of formula (I), or any stereoisomer thereof or pharmaceutically acceptable salt thereof, wherein $Q^1$, $Q^2$, or $Q^3$ is C-L-$R^b$, L is a bond, and $R^b$ is an optionally substituted $C_1$-$C_7$ alkyl, wherein one methylene group from the $C_1$-$C_7$ alkyl is replaced with $NCH_3$.

Some embodiments disclosed herein provide a compound of formula (I), or any stereoisomer thereof or pharmaceutically acceptable salt thereof, wherein $Q^1$, $Q^2$, or $Q^3$ is C-L-$R^c$.

Some embodiments disclosed herein provide a compound of formula (I), or any stereoisomer thereof or pharmaceutically acceptable salt thereof, wherein $Q^1$, $Q^2$, or $Q^3$ is C-L-$R^c$ and $R^c$ is substituted with 1 to 4 substituents independently selected from hydroxy, halo, and carboxy.

Some embodiments disclosed herein provide a compound of formula (I), or any stereoisomer thereof or pharmaceutically acceptable salt thereof, wherein $Q^1$, $Q^2$, or $Q^3$ is C-L-$R^c$ and $R^c$ is substituted with 1 to 4 substituents independently selected from hydroxy and halo.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

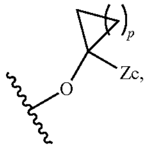

wherein p is 1-4, $Z_c$ is $C_1$-$C_3$ alkyl, Y is an N-heteroaryl with 1 substituent selected from halo, $C_1$-$C_3$ alkyl, $C_1$-$C_3$ alkoxy, —CN, $C_1$-$C_3$ haloalkyl, and cyclopropyl, $R^1$ and $R^2$ are each, independently, H, —Cl, —F, or —$CH_3$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

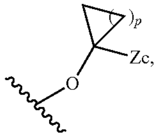

wherein p is 1 or 2, $Z_c$ is —$CH_3$, Y is phenyl with 1 substituent selected from halo, $C_1$-$C_3$ alkyl, $C_1$-$C_3$ alkoxy, —CN, $C_1$-$C_3$ haloalkyl, and cyclopropyl, $R^1$ and $R^2$ are each, independently, H, —Cl, —F, or —$CH_3$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

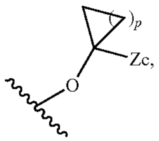

wherein p is 1 or 2, $Z_c$ is —$CH_3$, Y is an N-heteroaryl with 1 substituent selected from halo, $C_1$-$C_3$ alkyl, $C_1$-$C_3$ alkoxy, —CN, $C_1$-$C_3$ haloalkyl, and cyclopropyl, $R^1$ and $R^2$ are each, independently, H, —Cl, —F, or —$CH_3$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

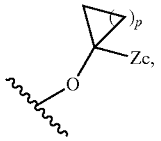

p is 1-4, and $Z_c$ is $C_1$-$C_3$ alkyl;

Y is phenyl with 1 substituent selected from halo, $C_1$-$C_3$ alkyl, $C_1$-$C_3$ alkoxy, —CN, $C_1$-$C_3$ haloalkyl, and cyclopropyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^a$ or $R^b$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

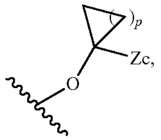

p is 1-4, and $Z_c$ is $C_1$-$C_3$ alkyl;

Y is N-heteroaryl with 1 substituent selected from halo, $C_1$-$C_3$ alkyl, $C_1$-$C_3$ alkoxy, —CN, $C_1$-$C_3$ haloalkyl, and cyclopropyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^a$ or $R^b$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

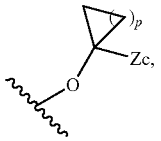

p is 1 or 2, and $Z_c$ is —$CH_3$;

Y is phenyl with 1 substituent selected from halo, $C_1$-$C_3$ alkyl, $C_1$-$C_3$ alkoxy, —CN, $C_1$-$C_3$ haloalkyl, and cyclopropyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^a$ or $R^b$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

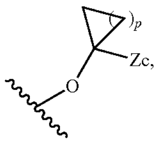

p is 1 or 2, and $Z_c$ is —$CH_3$;

Y is N-heteroaryl with 1 substituent selected from halo, $C_1$-$C_3$ alkyl, $C_1$-$C_3$ alkoxy, —CN, $C_1$-$C_3$ haloalkyl, and cyclopropyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^a$ or $R^b$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

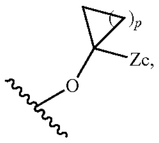

p is 1-4, and $Z_c$ is $C_1$-$C_3$ alkyl;

Y is phenyl with 1 substituent selected from halo and $C_1$-$C_3$ alkyl $R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^a$ or $R^b$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

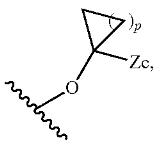

p is 1-4, and $Z_c$ is $C_1$-$C_3$ alkyl;

Y is N-heteroaryl with 1 substituent selected from halo and $C_1$-$C_3$ alkyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^a$ or $R^b$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

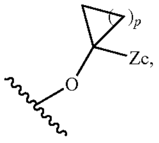

p is 1-4, and $Z_c$ is $C_1$-$C_3$ alkyl;

Y is phenyl with 1 substituent selected from halo, $C_1$-$C_3$ alkyl, $C_1$-$C_3$ alkoxy, —CN, $C_1$-$C_3$ haloalkyl, and cyclopropyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^a$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

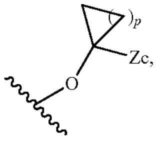

p is 1-4, and $Z_c$ is $C_1$-$C_3$ alkyl;

Y is N-heteroaryl with 1 substituent selected from halo, $C_1$-$C_3$ alkyl, $C_1$-$C_3$ alkoxy, —CN, $C_1$-$C_3$ haloalkyl, and cyclopropyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^a$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

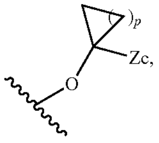

p is 1-4, and $Z_c$ is $C_1$-$C_3$ alkyl;

Y is phenyl with 1 substituent selected from halo, $C_1$-$C_3$ alkyl, $C_1$-$C_3$ alkoxy, —CN, $C_1$-$C_3$ haloalkyl, and cyclopropyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_p$O— or —O$(CH_2)_p$—, and R is $R^b$.

Some embodiments disclosed herein provide a compound of formula (I), or any stereoisomer thereof or pharmaceutically acceptable salt thereof, wherein G is N, $G_b$ is N, $G_a$ is $CR_5$, $R^5$ is

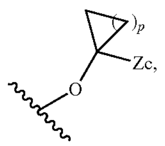

p is 1-4, and $Z_c$ is $C_1$-$C_3$ alkyl;

Y is N-heteroaryl with 1 substituent selected from halo, $C_1$-$C_3$ alkyl, $C_1$-$C_3$ alkoxy, —CN, $C_1$-$C_3$ haloalkyl, and cyclopropyl;

$R^1$ and $R^2$ are each, independently, H, halo, or $C_1$-$C_3$ alkyl;

$Q^1$, $Q^2$, and $Q^3$ are C-L-R or CH wherein one, and only one, of $Q^1$, $Q^2$, and $Q^3$ is C-L-R, L is a bond, —O—, —$(CH_2)_pO$— or —$O(CH_2)_p$—, and R is $R^b$.

Some embodiments disclosed herein provide compounds of formula (I) having the structure of formula (I-A)

(I-A)

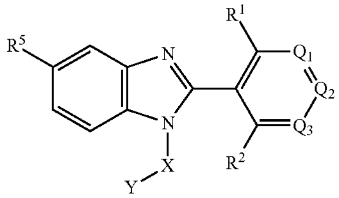

or any stereoisomer thereof or pharmaceutically acceptable salt thereof; wherein, $R^1$, $R^2$, $R^5$, $Q^1$, $Q^2$, $Q^3$, and X and Y are as defined in formula (I).

Other embodiments disclosed herein provide compounds of formula (I-A), or any stereoisomer thereof or pharmaceutically acceptable salt thereof, wherein X is —$CH_2$—.

Still other embodiments disclosed herein provide compounds of formula (I-A), or any stereoisomer thereof or pharmaceutically acceptable salt thereof, wherein Y is phenyl.

Yet other embodiments disclosed herein provide compounds of formula (I-A), or any stereoisomer thereof or pharmaceutically acceptable salt thereof, wherein Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-A), or any stereoisomer thereof or pharmaceutically acceptable salt thereof, wherein Y is phenyl substituted with one or two substituents independently selected from halo, $C_1$-$C_3$ alkyl, $C_1$-$C_3$ alkoxy, —CN, $C_1$-$C_3$ haloalkyl, and cyclopropyl. In further embodiments of the invention, Y is phenyl substituted with one or two substituents independently selected from halo and $C_1$-$C_3$ alkyl.

Other embodiments disclosed herein provide compounds of formula (I-A), or any stereoisomer thereof or pharmaceutically acceptable salt thereof, wherein X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Other embodiments disclosed herein provide compounds of formula (I-A), or any stereoisomer thereof or pharmaceutically acceptable salt thereof, wherein $Z_a$ and $Z_b$ are independently $C_1$-$C_3$ alkyl and $Z_c$ is H. In still further embodiments, $Z_a$ and $Z_b$ are —$CH_3$ and $Z_c$ is H.

Other embodiments disclosed herein provide compounds of formula (I-A), or any stereoisomer thereof or pharmaceutically acceptable salt thereof, wherein X is —$CH_2$—, Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, $Z_a$ and $Z_b$ are independently $C_1$-$C_3$ alkyl and $Z_c$ is H.

In still other embodiments X is —$CH_2$—, Y is phenyl substituted with one or two substituents independently selected from halo and $C_1$-$C_3$ alkyl, $Z_a$ and $Z_b$ are —$CH_3$ and $Z_c$ is H. In further embodiments Y is phenyl, $Z_a$ and $Z_b$ are —$CH_3$ and $Z_c$ is H.

Some embodiments disclosed herein provide compounds of formula (I) having the structure of formula (I-B):

(I-B)

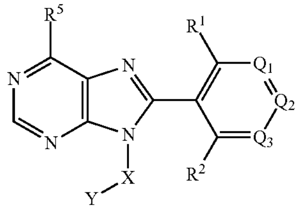

or any stereoisomer thereof or pharmaceutically acceptable salt thereof; wherein, $R^1$, $R^2$, $R^5$, $Q^1$, $Q^2$, $Q^3$, and X and Y are as defined in formula (I).

Other embodiments disclosed herein provide compounds of formula (I-B), or any stereoisomer thereof or pharmaceutically acceptable salt thereof, wherein X is —$CH_2$—.

Still other embodiments disclosed herein provide compounds of formula (I-B), or any stereoisomer thereof or pharmaceutically acceptable salt thereof, wherein Y is phenyl.

Yet other embodiments disclosed herein provide compounds of formula (I-B), or any stereoisomer thereof or pharmaceutically acceptable salt thereof, wherein Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-B), or any stereoisomer thereof or pharmaceutically acceptable salt thereof, wherein Y is phenyl substituted with one or two substituents independently selected from halo, $C_1$-$C_3$ alkyl, $C_1$-$C_3$ alkoxy, —CN, $C_1$-$C_3$ haloalkyl, and cyclopropyl. In further embodiments of the invention, Y is phenyl substituted with one or two substituents independently selected from halo and $C_1$-$C_3$ alkyl.

Other embodiments disclosed herein provide compounds of formula (I-B), or any stereoisomer thereof or pharmaceutically acceptable salt thereof, wherein X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Other embodiments disclosed herein provide compounds of formula (I-B), or any stereoisomer thereof or pharmaceutically acceptable salt thereof, wherein $Z_a$ and $Z_b$ are independently $C_1$-$C_3$ alkyl and $Z_c$ is H. In still further embodiments, $Z_a$ and $Z_b$ are —$CH_3$ and $Z_c$ is H.

Other embodiments disclosed herein provide compounds of formula (I-B), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN. In still further embodiments, $Z_a$ and $Z_b$ form a 3 membered carbocycle and $Z_c$ is H or $C_1$-$C_3$ alkyl. In other further embodiments, $Z_a$ and $Z_b$ form a 4 membered carbocycle and Z is H or $C_1$-$C_3$ alkyl.

Some embodiments disclosed herein provide compounds of formula (I) having the structure of formula (I-C)

(I-C)

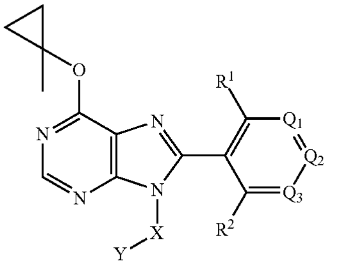

or any stereoisomer thereof or pharmaceutically acceptable salt thereof; wherein, $R^1$, $R^2$, $R^5$, $Q^1$, $Q^2$, $Q^3$, and X and Y are as defined in formula (I).

Other embodiments disclosed herein provide compounds of formula (I-C), or any stereoisomer thereof or pharmaceutically acceptable salt thereof, wherein X is —$CH_2$—.

Still other embodiments disclosed herein provide compounds of formula (I-C), or any stereoisomer thereof or pharmaceutically acceptable salt thereof, wherein Y is phenyl.

Yet other embodiments disclosed herein provide compounds of formula (I-C), or any stereoisomer thereof or pharmaceutically acceptable salt thereof, wherein Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-C), or any stereoisomer thereof or pharmaceutically acceptable salt thereof, wherein Y is phenyl substituted with one or two substituents independently selected from halo, $C_1$-$C_3$ alkyl, $C_1$-$C_3$ alkoxy, —CN, $C_1$-$C_3$ haloalkyl, and cyclopropyl. In further embodiments of the invention, Y is phenyl substituted with one or two substituents independently selected from halo and $C_1$-$C_3$ alkyl. In yet further embodiments of the invention, Y is phenyl substituted with halo. In still further embodiments of the invention, Y is phenyl substituted with Cl.

Still other embodiments disclosed herein provide compounds of formula (I-C), or any stereoisomer thereof or pharmaceutically acceptable salt thereof, wherein Y is a 5-6 membered heteroaryl. In further embodiments, Y is pyridine.

Yet other embodiments disclosed herein provide compounds of formula (I-C), or any stereoisomer thereof or pharmaceutically acceptable salt thereof, wherein Y is a 5-6 membered heteroaryl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Other embodiments disclosed herein provide compounds of formula (I-C), or any stereoisomer thereof or pharmaceutically acceptable salt thereof, wherein X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-C), or any stereoisomer thereof or pharmaceutically acceptable salt thereof, wherein X is —$CH_2$— and Y is phenyl optionally substituted with 1-3 substituents independently selected from halo and $C_1$-$C_3$ alkyl.

Some embodiments disclosed herein provide compounds of formula (I) having the structure of formula (I-D):

(I-D)

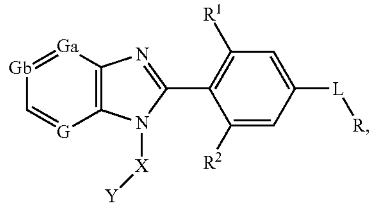

or any stereoisomer thereof or pharmaceutically acceptable salt thereof; wherein, G, $G_a$, $G_b$, X, Y, $R^1$, $R^2$, L and R are as defined in formula (I).

Other embodiments herein provide compounds of formula (I-D), or any stereoisomer thereof or pharmaceutically acceptable salt thereof, wherein L is a bond, —O—, —$(CH_2)_p$O—, or O$(CH_2)_p$—.

Yet other embodiments herein provide compounds of formula (I-D), or any stereoisomer thereof or pharmaceutically acceptable salt thereof, wherein L is a bond, —O—, —$(CH_2)_p$O—, or O$(CH_2)_p$— and R is $R^a$ or $R^b$.

Still other embodiments herein provide compound of formula (I-D), or any stereoisomer thereof or pharmaceutically acceptable salt thereof, wherein L is a bond and R is $R^a$ or $R^b$.

Other embodiments herein provide compound of formula (I-D), or any stereoisomer thereof or pharmaceutically acceptable salt thereof, wherein L is a bond and R is $R^a$ or $R^b$.

Still other embodiments herein provide compound of formula (I-D), or any stereoisomer thereof or pharmaceutically acceptable salt thereof, wherein L is —O— and R is $R^a$ or $R^b$.

Yet other embodiments herein provide compounds of formula (I-D), or any stereoisomer thereof or pharmaceutically acceptable salt thereof, wherein L is —$(CH_2)_p$O— and R is $R^a$ or $R^b$.

Other embodiments herein provide compounds of formula (I-D), or any stereoisomer thereof or pharmaceutically acceptable salt thereof, wherein L is a O$(CH_2)_p$— and R is $R^a$ or $R^b$.

Other embodiments herein provide compound of formula (I-D), or any stereoisomer thereof or pharmaceutically acceptable salt thereof, wherein L is a bond and R is $R^a$.

Still other embodiments herein provide compound of formula (I-D), or any stereoisomer thereof or pharmaceutically acceptable salt thereof, wherein L is —O— and R is $R^a$.

Yet other embodiments herein provide compounds of formula (I-D), or any stereoisomer thereof or pharmaceutically acceptable salt thereof, wherein L is $(CH_2)_p$O— and R is $R^a$.

Other embodiments herein provide compounds of formula (I-D), or any stereoisomer thereof or pharmaceutically acceptable salt thereof, wherein L is a O$(CH_2)_p$— and R is $R^a$.

Other embodiments herein provide compound of formula (I-D), or any stereoisomer thereof or pharmaceutically acceptable salt thereof, wherein L is a bond and R is $R^b$.

Still other embodiments herein provide compound of formula (I-D), or any stereoisomer thereof or pharmaceutically acceptable salt thereof, wherein L is —O— and R is $R^b$.

Yet other embodiments herein provide compounds of formula (I-D), or any stereoisomer thereof or pharmaceutically acceptable salt thereof, wherein L is —$(CH_2)_pO$— and R is $R^b$.

Other embodiments herein provide compounds of formula (I-D), or any stereoisomer thereof or pharmaceutically acceptable salt thereof, wherein L is a $O(CH_2)_p$— and R is $R^b$.

Some embodiments disclosed herein provide compounds of formula (I) having the structure of formula (I-E)

(I-E)

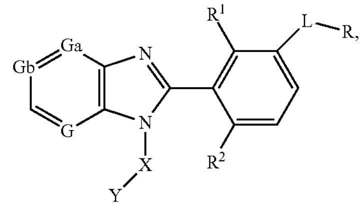

or any stereoisomer thereof or pharmaceutically acceptable salt thereof; wherein, G, $G_a$, $G_b$, X, Y, $R^1$, $R^2$, L and R are as defined in formula (I).

Other embodiments herein provide compounds of formula (I-E), or any stereoisomer thereof or pharmaceutically acceptable salt thereof, wherein formula (I-E), or any stereoisomer thereof or pharmaceutically acceptable salt thereof, wherein L is a bond, —O—, —$(CH_2)_pO$—, or $O(CH_2)_p$—.

Yet other embodiments herein provide compounds of formula (I-E), or any stereoisomer thereof or pharmaceutically acceptable salt thereof, wherein L is a bond, —O—, —$(CH_2)_pO$—, or $O(CH_2)_p$— and R is $R^a$ or $R^b$.

Still other embodiments herein provide compound of formula (I-E), or any stereoisomer thereof or pharmaceutically acceptable salt thereof, wherein L is a bond and R is $R^a$ or $R^b$.

Other embodiments herein provide compound of formula (I-E), or any stereoisomer thereof or pharmaceutically acceptable salt thereof, wherein L is a bond and R is $R^a$ or $R^b$.

Still other embodiments herein provide compound of formula (I-E), or any stereoisomer thereof or pharmaceutically acceptable salt thereof, wherein L is —O— and R is $R^a$ or $R^b$.

Yet other embodiments herein provide compounds of formula (I-E), or any stereoisomer thereof or pharmaceutically acceptable salt thereof, wherein L is —$(CH_2)_pO$— and R is $R^a$ or $R^b$.

Other embodiments herein provide compounds of formula (I-E), or any stereoisomer thereof or pharmaceutically acceptable salt thereof, wherein L is a $O(CH_2)_p$— and R is $R^a$ or $R^b$.

Other embodiments herein provide compound of formula (I-E), or any stereoisomer thereof or pharmaceutically acceptable salt thereof, wherein L is a bond and R is $R^a$.

Still other embodiments herein provide compound of formula (I-E), or any stereoisomer thereof or pharmaceutically acceptable salt thereof, wherein L is —O— and R is $R^a$.

Yet other embodiments herein provide compounds of formula (I-E), or any stereoisomer thereof or pharmaceutically acceptable salt thereof, wherein L is $(CH_2)_pO$— and R is $R^a$.

Other embodiments herein provide compounds of formula (I-E), or any stereoisomer thereof or pharmaceutically acceptable salt thereof, wherein L is a $O(CH_2)_p$— and R is $R^a$.

Other embodiments herein provide compound of formula (I-E), or any stereoisomer thereof or pharmaceutically acceptable salt thereof, wherein L is a bond and R is $R^b$.

Still other embodiments herein provide compound of formula (I-E), or any stereoisomer thereof or pharmaceutically acceptable salt thereof, wherein L is —O— and R is $R^b$.

Yet other embodiments herein provide compounds of formula (I-E), or any stereoisomer thereof or pharmaceutically acceptable salt thereof, wherein L is —$(CH_2)_pO$— and R is $R^b$.

Other embodiments herein provide compounds of formula (I-E), or any stereoisomer thereof or pharmaceutically acceptable salt thereof, wherein L is a $O(CH_2)_p$— and R is $R^b$.

Some embodiments disclosed herein provide compounds of formula (I) having the structure of formula (I-F):

(I-F)

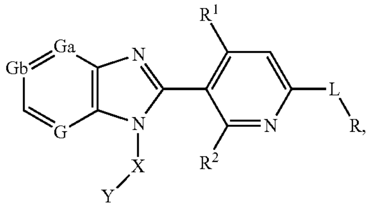

or any stereoisomer thereof or pharmaceutically acceptable salt thereof; wherein, G, $G_a$, $G_b$, X, Y, $R^1$ $R^2$, L and R are as defined in formula (I).

Other embodiments herein provide compounds of formula (I-F), or any stereoisomer thereof or pharmaceutically acceptable salt thereof, wherein L is a bond, —O—, —$(CH_2)_pO$—, or $O(CH_2)_p$—.

Yet other embodiments herein provide compounds of formula (I-F), or any stereoisomer thereof or pharmaceutically acceptable salt thereof, wherein L is a bond, —O—, —$(CH_2)_pO$—, or $O(CH_2)_p$— and R is $R^a$ or $R^b$.

Still other embodiments herein provide compound of formula (I-F), or any stereoisomer thereof or pharmaceutically acceptable salt thereof, wherein L is a bond and R is $R^a$ or $R^b$.

Other embodiments herein provide compound of formula (I-F), or any stereoisomer thereof or pharmaceutically acceptable salt thereof, wherein L is a bond and R is $R^a$ or $R^b$.

Still other embodiments herein provide compound of formula (I-F), or any stereoisomer thereof or pharmaceutically acceptable salt thereof, wherein L is —O— and R is $R^a$ or $R^b$.

Yet other embodiments herein provide compounds of formula (I-F), or any stereoisomer thereof or pharmaceutically acceptable salt thereof, wherein L is $(CH_2)_pO$— and R is $R^a$ or $R^b$.

Other embodiments herein provide compounds of formula (I-F), or any stereoisomer thereof or pharmaceutically acceptable salt thereof, wherein L is a $O(CH_2)_p$— and R is $R^a$ or $R^b$.

Other embodiments herein provide compound of formula (I-F), or any stereoisomer thereof or pharmaceutically acceptable salt thereof, wherein L is a bond and R is $R^a$.

Still other embodiments herein provide compound of formula (I-F), or any stereoisomer thereof or pharmaceutically acceptable salt thereof, wherein L is —O— and R is $R^a$.

Yet other embodiments herein provide compounds of formula (I-F), or any stereoisomer thereof or pharmaceutically acceptable salt thereof, wherein L is —$(CH_2)_pO$— and R is $R^a$.

Other embodiments herein provide compounds of formula (I-F), or any stereoisomer thereof or pharmaceutically acceptable salt thereof, wherein L is a $O(CH_2)_p$— and R is $R^a$.

Other embodiments herein provide compound of formula (I-F), or any stereoisomer thereof or pharmaceutically acceptable salt thereof, wherein L is a bond and R is $R^b$.

Still other embodiments herein provide compound of formula (I-F), or any stereoisomer thereof or pharmaceutically acceptable salt thereof, wherein L is —O— and R is $R^b$.

Yet other embodiments herein provide compounds of formula (I-F), or any stereoisomer thereof or pharmaceutically acceptable salt thereof, wherein L is —$(CH_2)_pO$— and R is $R^b$.

Other embodiments herein provide compounds of formula (I-F), or any stereoisomer thereof or pharmaceutically acceptable salt thereof, wherein L is a $O(CH_2)_p$— and R is $R^b$.

Some embodiments disclosed herein provide compounds of formula (I) having the structure of formula (I-G):

(I-G)

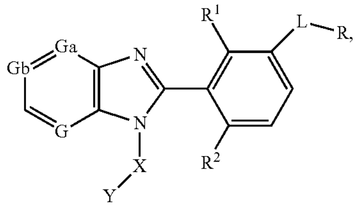

or any stereoisomer thereof or pharmaceutically acceptable salt thereof; wherein, G, $G_a$, $G_b$, X, Y, $R^1$ $R^2$, L and R are as defined in formula (I).

Other embodiments herein provide compounds of formula (I-G), or any stereoisomer thereof or pharmaceutically acceptable salt thereof, wherein L is a bond, —O—, —$(CH_2)_pO$—, or $O(CH_2)_p$—.

Yet other embodiments herein provide compounds of formula (I-G), or any stereoisomer thereof or pharmaceutically acceptable salt thereof, wherein L is a bond, —O—, —$(CH_2)_pO$—, or $O(CH_2)_p$— and R is $R^a$ or $R^b$.

Still other embodiments herein provide compound of formula (I-G), or any stereoisomer thereof or pharmaceutically acceptable salt thereof, wherein L is a bond and R is $R^a$ or $R^b$.

Other embodiments herein provide compound of formula (I-G), or any stereoisomer thereof or pharmaceutically acceptable salt thereof, wherein L is a bond and R is $R^a$ or $R^b$.

Still other embodiments herein provide compound of formula (I-G), or any stereoisomer thereof or pharmaceutically acceptable salt thereof, wherein L is —O— and R is $R^a$ or $R^b$.

Yet other embodiments herein provide compounds of formula (I-G), or any stereoisomer thereof or pharmaceutically acceptable salt thereof, wherein L is $(CH_2)_pO$— and R is $R^a$ or $R^b$.

Other embodiments herein provide compounds of formula (I-G), or any stereoisomer thereof or pharmaceutically acceptable salt thereof, wherein L is a $O(CH_2)_p$— and R is $R^a$ or $R^b$.

Other embodiments herein provide compound of formula (I-G), or any stereoisomer thereof or pharmaceutically acceptable salt thereof, wherein L is a bond and R is $R^a$.

Still other embodiments herein provide compound of formula (I-G), or any stereoisomer thereof or pharmaceutically acceptable salt thereof, wherein L is —O— and R is $R^a$.

Yet other embodiments herein provide compounds of formula (I-G), or any stereoisomer thereof or pharmaceutically acceptable salt thereof, wherein L is —$(CH_2)_pO$— and R is $R^a$.

Other embodiments herein provide compounds of formula (I-G), or any stereoisomer thereof or pharmaceutically acceptable salt thereof, wherein L is a $O(CH_2)_p$— and R is $R^a$.

Other embodiments herein provide compound of formula (I-G), or any stereoisomer thereof or pharmaceutically acceptable salt thereof, wherein L is a bond and R is $R^b$.

Still other embodiments herein provide compound of formula (I-G), or any stereoisomer thereof or pharmaceutically acceptable salt thereof, wherein L is —O— and R is $R^b$.

Yet other embodiments herein provide compounds of formula (I-G), or any stereoisomer thereof or pharmaceutically acceptable salt thereof, wherein L is —$(CH_2)_pO$— and R is $R^b$.

Other embodiments herein provide compounds of formula (I-G), or any stereoisomer thereof or pharmaceutically acceptable salt thereof, wherein L is a $O(CH_2)_p$— and R is $R^b$.

Some embodiments disclosed herein provide compounds of formula (I) having the structure of formula (I-H)

(I-H)

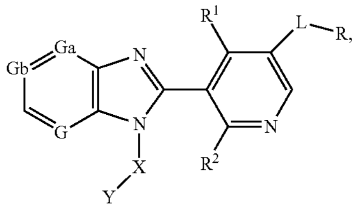

or any stereoisomer thereof or pharmaceutically acceptable salt thereof; wherein, G, $G_a$, $G_b$, X, Y, $R^1$ $R^2$, L and R are as defined in formula (I).

Other embodiments herein provide compounds of formula (I-H), or any stereoisomer thereof or pharmaceutically acceptable salt thereof, wherein L is a bond, —O—, —$(CH_2)_pO$—, or $O(CH_2)_p$—.

Yet other embodiments herein provide compounds of formula (I-H), or any stereoisomer thereof or pharmaceutically acceptable salt thereof, wherein L is a bond, —O—, —$(CH_2)_pO$—, or $O(CH_2)_p$— and R is $R^a$ or $R^b$.

Still other embodiments herein provide compound of formula (I-H), or any stereoisomer thereof or pharmaceutically acceptable salt thereof, wherein L is a bond and R is $R^a$ or $R^b$.

Other embodiments herein provide compound of formula (I-H), or any stereoisomer thereof or pharmaceutically acceptable salt thereof, wherein L is a bond and R is $R^a$ or $R^b$.

Still other embodiments herein provide compound of formula (I-H), or any stereoisomer thereof or pharmaceutically acceptable salt thereof, wherein L is —O— and R is $R^a$ or $R^b$.

Yet other embodiments herein provide compounds of formula (I-H), or any stereoisomer thereof or pharmaceutically acceptable salt thereof, wherein L is —$(CH_2)_pO$— and R is $R^a$ or $R^b$.

Other embodiments herein provide compounds of formula (I-H), or any stereoisomer thereof or pharmaceutically acceptable salt thereof, wherein L is a $O(CH_2)_p$— and R is $R^a$ or $R^b$.

Other embodiments herein provide compound of formula (I-H), or any stereoisomer thereof or pharmaceutically acceptable salt thereof, wherein L is a bond and R is $R^a$.

Still other embodiments herein provide compound of formula (I-H), or any stereoisomer thereof or pharmaceutically acceptable salt thereof, wherein L is —O— and R is $R^a$.

Yet other embodiments herein provide compounds of formula (I-H), or any stereoisomer thereof or pharmaceutically acceptable salt thereof, wherein L is $(CH_2)_pO$— and R is $R^a$.

Other embodiments herein provide compounds of formula (I-H), or any stereoisomer thereof or pharmaceutically acceptable salt thereof, wherein L is a $O(CH_2)_p$— and R is $R^a$.

Other embodiments herein provide compound of formula (I-H), or any stereoisomer thereof or pharmaceutically acceptable salt thereof, wherein L is a bond and R is $R^b$.

Still other embodiments herein provide compound of formula (I-H), or any stereoisomer thereof or pharmaceutically acceptable salt thereof, wherein L is —O— and R is $R^b$.

Yet other embodiments herein provide compounds of formula (I-H), or any stereoisomer thereof or pharmaceutically acceptable salt thereof, wherein L is —$(CH_2)_pO$— and R is $R^b$.

Other embodiments herein provide compounds of formula (I-H), or any stereoisomer thereof or pharmaceutically acceptable salt thereof, wherein L is a $O(CH_2)_p$— and R is $R^b$.

Some embodiments disclosed herein provide compounds of formula (I) having the structure of formula (I-I):

(I-I)

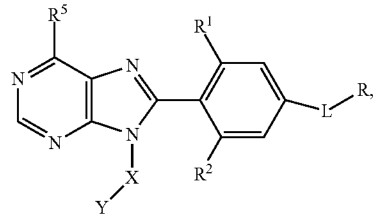

or any stereoisomer thereof or pharmaceutically acceptable salt thereof, wherein, X, Y, $R^1$ $R^2$, $R^5$, L and R are as defined in formula (I).

Other embodiments disclosed herein provide compounds of formula (I-I), or any stereoisomer thereof or pharmaceutically acceptable salt thereof, wherein X is —$CH_2$—.

Still other embodiments disclosed herein provide compounds of formula (I-I), or any stereoisomer thereof or pharmaceutically acceptable salt thereof, wherein Y is phenyl.

Yet other embodiments disclosed herein provide compounds of formula (I-I), or any stereoisomer thereof or pharmaceutically acceptable salt thereof, wherein Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-I), or any stereoisomer thereof or pharmaceutically acceptable salt thereof, wherein Y is phenyl substituted with one or two substituents independently selected from halo, $C_1$-$C_3$ alkyl, $C_1$-$C_3$ alkoxy, —CN, $C_1$-$C_3$ haloalkyl, and cyclopropyl. In further embodiments of the invention, Y is phenyl substituted with one or two substituents independently selected from halo and $C_1$-$C_3$ alkyl.

Other embodiments disclosed herein provide compounds of formula (I-I), or any stereoisomer thereof or pharmaceutically acceptable salt thereof, wherein X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Other embodiments disclosed herein provide compounds of formula (I-I), or any stereoisomer thereof or pharmaceutically acceptable salt thereof, wherein $Z_a$ and $Z_b$ are independently $C_1$-$C_3$ alkyl and Z is H. In still further embodiments, $Z_a$ and $Z_b$ are —$CH_3$ and $Z_c$ is H.

Other embodiments disclosed herein provide compounds of formula (I-I), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN. In still further embodiments, $Z_a$ and $Z_b$ form a 3 membered carbocycle and $Z_c$ is H or $C_1$-$C_3$ alkyl. In other further embodiments, $Z_a$ and $Z_b$ form a 4 membered carbocycle and $Z_c$ is H or $C_1$-$C_3$ alkyl.

Other embodiments herein provide compounds of formula (I-I), or any stereoisomer thereof or pharmaceutically acceptable salt thereof, wherein L is a bond, —O—, —$(CH_2)_pO$—, or $O(CH_2)_p$—.

Yet other embodiments herein provide compounds of formula (I-I), or any stereoisomer thereof or pharmaceutically acceptable salt thereof, wherein L is a bond, —O—, —$(CH_2)_pO$—, or $O(CH_2)_p$— and R is $R^a$ or $R^b$.

Still other embodiments herein provide compound of formula (I-I), or any stereoisomer thereof or pharmaceutically acceptable salt thereof, wherein L is a bond and R is $R^a$ or $R^b$.

Other embodiments herein provide compound of formula (I-I), or any stereoisomer thereof or pharmaceutically acceptable salt thereof, wherein L is a bond and R is $R^a$ or $R^b$.

Still other embodiments herein provide compound of formula (I-I), or any stereoisomer thereof or pharmaceutically acceptable salt thereof, wherein L is —O— and R is $R^a$ or $R^b$.

Yet other embodiments herein provide compounds of formula (I-I), or any stereoisomer thereof or pharmaceutically acceptable salt thereof, wherein L is —$(CH_2)_p$O— and R is $R^a$ or $R^b$.

Other embodiments herein provide compounds of formula (I-I), or any stereoisomer thereof or pharmaceutically acceptable salt thereof, wherein L is a O$(CH_2)_p$— and R is $R^a$ or $R^b$.

Other embodiments herein provide compound of formula (I-I), or any stereoisomer thereof or pharmaceutically acceptable salt thereof, wherein L is a bond and R is $R^a$.

Still other embodiments herein provide compound of formula (I-I), or any stereoisomer thereof or pharmaceutically acceptable salt thereof, wherein L is —O— and R is $R^a$.

Yet other embodiments herein provide compounds of formula (I-I), or any stereoisomer thereof or pharmaceutically acceptable salt thereof, wherein L is —$(CH_2)_p$O— and R is $R^a$.

Other embodiments herein provide compounds of formula (I-I), or any stereoisomer thereof or pharmaceutically acceptable salt thereof, wherein L is a O$(CH_2)_p$— and R is $R^a$.

Other embodiments herein provide compound of formula (I-I), or any stereoisomer thereof or pharmaceutically acceptable salt thereof, wherein L is a bond and R is $R^b$.

Still other embodiments herein provide compound of formula (I-I), or any stereoisomer thereof or pharmaceutically acceptable salt thereof, wherein L is —O— and R is $R^b$.

Yet other embodiments herein provide compounds of formula (I-I), or any stereoisomer thereof or pharmaceutically acceptable salt thereof, wherein L is —$(CH_2)_p$O— and R is $R^b$.

Other embodiments herein provide compounds of formula (I-I), or any stereoisomer thereof or pharmaceutically acceptable salt thereof, wherein L is a O$(CH_2)_p$— and R is $R^b$.

Other embodiments disclosed herein provide compounds of formula (I-I), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, and L is a bond, —O—, —$(CH_2)_p$O—, or O$(CH_2)_p$— and R is $R^a$ or $R^b$.

Other embodiments disclosed herein provide compounds of formula (I-I), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, $R^1$ and $R^2$ are each, independently, H, halo, or —$CH_3$, and L is a bond, —O—, —$(CH_2)_p$O—, or O$(CH_2)_p$— and R is $R^a$ or $R^b$.

Some embodiments disclosed herein provide compounds of formula (I) having the structure of formula (I-J)

(I-J)

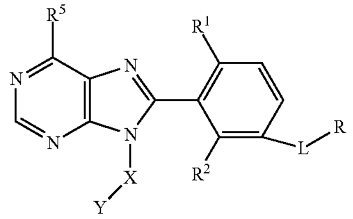

or any stereoisomer thereof or pharmaceutically acceptable salt thereof; wherein, X, Y, $R^1$ $R^2$, $R^5$, L and R are as defined in formula (I).

Other embodiments disclosed herein provide compounds of formula (I-J), or any stereoisomer thereof or pharmaceutically acceptable salt thereof, wherein X is —$CH_2$—.

Still other embodiments disclosed herein provide compounds of formula (I-J), or any stereoisomer thereof or pharmaceutically acceptable salt thereof, wherein Y is phenyl.

Yet other embodiments disclosed herein provide compounds of formula (I-J), or any stereoisomer thereof or pharmaceutically acceptable salt thereof, wherein Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-J), or any stereoisomer thereof or pharmaceutically acceptable salt thereof, wherein Y is phenyl substituted with one or two substituents independently selected from halo, $C_1$-$C_3$ alkyl, $C_1$-$C_3$ alkoxy, —CN, $C_1$-$C_3$ haloalkyl, and cyclopropyl. In further embodiments of the invention, Y is phenyl substituted with one or two substituents independently selected from halo and $C_1$-$C_3$ alkyl.

Other embodiments disclosed herein provide compounds of formula (I-J), or any stereoisomer thereof or pharmaceutically acceptable salt thereof, wherein X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Other embodiments disclosed herein provide compounds of formula (I-J), or any stereoisomer thereof or pharmaceutically acceptable salt thereof, wherein $Z_a$ and $Z_b$ are independently $C_1$-$C_3$ alkyl and $Z_c$ is H. In still further embodiments, $Z_a$ and $Z_b$ are —$CH_3$ and $Z_c$ is H.

Other embodiments disclosed herein provide compounds of formula (I-J), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN. In still further embodiments, $Z_a$ and $Z_b$ form a 3 membered carbocycle and $Z_c$ is H or $C_1$-$C_3$ alkyl. In other further embodiments, $Z_a$ and $Z_b$ form a 4 membered carbocycle and $Z_c$ is H or $C_1$-$C_3$ alkyl.

Other embodiments herein provide compounds of formula (I-J), or any stereoisomer thereof or pharmaceutically acceptable salt thereof, wherein L is a bond, —O—, —$(CH_2)_p$O—, or O$(CH_2)_p$—.

Yet other embodiments herein provide compounds of formula (I-J), or any stereoisomer thereof or pharmaceutically acceptable salt thereof, wherein L is a bond, —O—, —$(CH_2)_p$O—, or O$(CH_2)_p$— and R is $R^a$ or $R^b$.

Still other embodiments herein provide compound of formula (I-J), or any stereoisomer thereof or pharmaceutically acceptable salt thereof, wherein L is a bond and R is $R^a$ or $R^b$.

Other embodiments herein provide compound of formula (I-J), or any stereoisomer thereof or pharmaceutically acceptable salt thereof, wherein L is a bond and R is $R^a$ or $R^b$.

Still other embodiments herein provide compound of formula (I-J), or any stereoisomer thereof or pharmaceutically acceptable salt thereof, wherein L is —O— and R is $R^a$ or $R^b$.

Yet other embodiments herein provide compounds of formula (I-J), or any stereoisomer thereof or pharmaceutically acceptable salt thereof, wherein L is $—(CH_2)_pO—$ and R is $R^a$ or $R^b$.

Other embodiments herein provide compounds of formula (I-J), or any stereoisomer thereof or pharmaceutically acceptable salt thereof, wherein L is a $O(CH_2)_p—$ and R is $R^a$ or $R^b$.

Other embodiments herein provide compound of formula (I-J), or any stereoisomer thereof or pharmaceutically acceptable salt thereof, wherein L is a bond and R is $R^a$.

Still other embodiments herein provide compound of formula (I-J), or any stereoisomer thereof or pharmaceutically acceptable salt thereof, wherein L is —O— and R is $R^a$.

Yet other embodiments herein provide compounds of formula (I-J), or any stereoisomer thereof or pharmaceutically acceptable salt thereof, wherein L is $—(CH_2)_pO—$ and R is $R^a$.

Other embodiments herein provide compounds of formula (I-J), or any stereoisomer thereof or pharmaceutically acceptable salt thereof, wherein L is a $O(CH_2)_p—$ and R is $R^a$.

Other embodiments herein provide compound of formula (I-J), or any stereoisomer thereof or pharmaceutically acceptable salt thereof, wherein L is a bond and R is $R^b$.

Still other embodiments herein provide compound of formula (I-J), or any stereoisomer thereof or pharmaceutically acceptable salt thereof, wherein L is —O— and R is $R^b$.

Yet other embodiments herein provide compounds of formula (I-J), or any stereoisomer thereof or pharmaceutically acceptable salt thereof, wherein L is $(CH_2)_pO—$ and R is $R^b$.

Other embodiments herein provide compounds of formula (I-J), or any stereoisomer thereof or pharmaceutically acceptable salt thereof, wherein L is a $O(CH_2)_p—$ and R is $R^b$.

Other embodiments disclosed herein provide compounds of formula (I-J), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is $—CH_2—$ and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, and L is a bond, —O—, $—(CH_2)_pO—$, or $O(CH_2)_p—$ and R is $R^a$ or $R^b$.

Other embodiments disclosed herein provide compounds of formula (I-J), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is $—CH_2—$ and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, $R^1$ and $R^2$ are each, independently, H, halo, or $—CH_3$, and L is a bond, —O—, $—(CH_2)_pO—$, or $O(CH_2)_p—$ and R is $R^a$ or $R^b$.

Some embodiments disclosed herein provide compounds of formula (I) having the structure of formula (I-K)

(I-K)

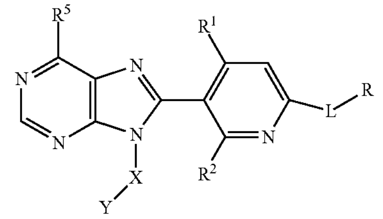

or any stereoisomer thereof or pharmaceutically acceptable salt thereof; wherein, X, Y, $R^1$ $R^2$, $R^5$, L and R are as defined in formula (I).

Other embodiments disclosed herein provide compounds of formula (I-K), or any stereoisomer thereof or pharmaceutically acceptable salt thereof, wherein X is $—CH_2—$.

Still other embodiments disclosed herein provide compounds of formula (I-K), or any stereoisomer thereof or pharmaceutically acceptable salt thereof, wherein Y is phenyl.

Yet other embodiments disclosed herein provide compounds of formula (I-K), or any stereoisomer thereof or pharmaceutically acceptable salt thereof, wherein Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-K), or any stereoisomer thereof or pharmaceutically acceptable salt thereof, wherein Y is phenyl substituted with one or two substituents independently selected from halo, $C_1$-$C_3$ alkyl, $C_1$-$C_3$ alkoxy, —CN, $C_1$-$C_3$ haloalkyl, and cyclopropyl. In further embodiments of the invention, Y is phenyl substituted with one or two substituents independently selected from halo and $C_1$-$C_3$ alkyl.

Other embodiments disclosed herein provide compounds of formula (I-K), or any stereoisomer thereof or pharmaceutically acceptable salt thereof, wherein X is $—CH_2—$ and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Other embodiments disclosed herein provide compounds of formula (I-K), or any stereoisomer thereof or pharmaceutically acceptable salt thereof, wherein $Z_a$ and $Z_b$ are independently $C_1$-$C_3$ alkyl and $Z_c$ is H. In still further embodiments, $Z_a$ and $Z_b$ are $—CH_3$ and $Z_c$ is H.

Other embodiments disclosed herein provide compounds of formula (I-K), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN. In still further embodiments, $Z_a$ and $Z_b$ form a 3 membered carbocycle and $Z_c$ is H or $C_1$-$C_3$ alkyl. In other further embodiments, $Z_a$ and $Z_b$ form a 4 membered carbocycle and $Z_c$ is H or $C_1$-$C_3$ alkyl.

Other embodiments herein provide compounds of formula (I-K), or any stereoisomer thereof or pharmaceutically acceptable salt thereof, wherein L is a bond, —O—, $—(CH_2)_pO—$, or $O(CH_2)_p—$.

Yet other embodiments herein provide compounds of formula (I-K), or any stereoisomer thereof or pharmaceutically acceptable salt thereof, wherein L is a bond, —O—, $—(CH_2)_pO—$, or $O(CH_2)_p—$ and R is $R^a$ or $R^b$.

Still other embodiments herein provide compound of formula (I-K), or any stereoisomer thereof or pharmaceutically acceptable salt thereof, wherein L is a bond and R is $R^a$ or $R^b$.

Other embodiments herein provide compound of formula (I-K), or any stereoisomer thereof or pharmaceutically acceptable salt thereof, wherein L is a bond and R is $R^a$ or $R^b$.

Still other embodiments herein provide compound of formula (I-K), or any stereoisomer thereof or pharmaceutically acceptable salt thereof, wherein L is —O— and R is $R^a$ or $R^b$.

Yet other embodiments herein provide compounds of formula (I-K), or any stereoisomer thereof or pharmaceutically acceptable salt thereof, wherein L is $(CH_2)_pO$— and R is $R^a$ or $R^b$.

Other embodiments herein provide compounds of formula (I-K), or any stereoisomer thereof or pharmaceutically acceptable salt thereof, wherein L is a $O(CH_2)_p$— and R is $R^a$ or $R^b$.

Other embodiments herein provide compound of formula (I-K), or any stereoisomer thereof or pharmaceutically acceptable salt thereof, wherein L is a bond and R is $R^a$.

Still other embodiments herein provide compound of formula (I-K), or any stereoisomer thereof or pharmaceutically acceptable salt thereof, wherein L is —O— and R is $R^a$.

Yet other embodiments herein provide compounds of formula (I-K), or any stereoisomer thereof or pharmaceutically acceptable salt thereof, wherein L is —$(CH_2)_pO$— and R is $R^a$.

Other embodiments herein provide compounds of formula (I-K), or any stereoisomer thereof or pharmaceutically acceptable salt thereof, wherein L is a $O(CH_2)_p$— and R is $R^a$.

Other embodiments herein provide compound of formula (I-K), or any stereoisomer thereof or pharmaceutically acceptable salt thereof, wherein L is a bond and R is $R^b$.

Still other embodiments herein provide compound of formula (I-K), or any stereoisomer thereof or pharmaceutically acceptable salt thereof, wherein L is —O— and R is $R^b$.

Yet other embodiments herein provide compounds of formula (I-K), or any stereoisomer thereof or pharmaceutically acceptable salt thereof, wherein L is —$(CH_2)_pO$— and R is $R^b$.

Other embodiments herein provide compounds of formula (I-K), or any stereoisomer thereof or pharmaceutically acceptable salt thereof, wherein L is a $O(CH_2)_p$— and R is $R^b$.

Other embodiments disclosed herein provide compounds of formula (I-K), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, and L is a bond, —O—, —$(CH_2)_pO$—, or $O(CH_2)_p$— and R is $R^a$ or $R^b$.

Other embodiments disclosed herein provide compounds of formula (I-K), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, $R^1$ and $R^2$ are each, independently, H, halo, or —$CH_3$, and L is a bond, —O—, —$(CH_2)_pO$—, or $O(CH_2)_p$— and R is $R^a$ or $R^b$.

Some embodiments disclosed herein provide compounds of formula (I) having the structure of formula (I-L)

(I-L)

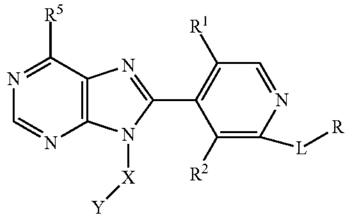

or any stereoisomer thereof or pharmaceutically acceptable salt thereof; wherein, X, Y, $R^1$ $R^2$, $R^5$, L and R are as defined in formula (I).

Other embodiments disclosed herein provide compounds of formula (I-L), or any stereoisomer thereof or pharmaceutically acceptable salt thereof, wherein X is —$CH_2$—.

Still other embodiments disclosed herein provide compounds of formula (I-L), or any stereoisomer thereof or pharmaceutically acceptable salt thereof, wherein Y is phenyl.

Yet other embodiments disclosed herein provide compounds of formula (I-L), or any stereoisomer thereof or pharmaceutically acceptable salt thereof, wherein Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-L), or any stereoisomer thereof or pharmaceutically acceptable salt thereof, wherein Y is phenyl substituted with one or two substituents independently selected from halo, $C_1$-$C_3$ alkyl, $C_1$-$C_3$ alkoxy, —CN, $C_1$-$C_3$ haloalkyl, and cyclopropyl. In further embodiments of the invention, Y is phenyl substituted with one or two substituents independently selected from halo and $C_1$-$C_3$ alkyl.

Other embodiments disclosed herein provide compounds of formula (I-L), or any stereoisomer thereof or pharmaceutically acceptable salt thereof, wherein X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Other embodiments disclosed herein provide compounds of formula (I-L), or any stereoisomer thereof or pharmaceutically acceptable salt thereof, wherein $Z_a$ and $Z_b$ are independently $C_1$-$C_3$ alkyl and $Z_c$ is H. In still further embodiments, $Z_a$ and $Z_b$ are —$CH_3$ and $Z_c$ is H.

Other embodiments disclosed herein provide compounds of formula (I-L), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN. In still further embodiments, $Z_a$ and $Z_b$ form a 3 membered carbocycle and $Z_c$ is H or $C_1$-$C_3$ alkyl. In other further embodiments, $Z_a$ and $Z_b$ form a 4 membered carbocycle and $Z_c$ is H or $C_1$-$C_3$ alkyl.

Other embodiments herein provide compounds of formula (I-L), or any stereoisomer thereof or pharmaceutically acceptable salt thereof, wherein L is a bond, —O—, —$(CH_2)_pO$—, or $O(CH_2)_p$—.

Yet other embodiments herein provide compounds of formula (I-L), or any stereoisomer thereof or pharmaceutically acceptable salt thereof, wherein L is a bond, —O—, —$(CH_2)_pO$—, or $O(CH_2)_p$— and R is $R^a$ or $R^b$.

Still other embodiments herein provide compound of formula (I-L), or any stereoisomer thereof or pharmaceutically acceptable salt thereof, wherein L is a bond and R is $R^a$ or $R^b$.

Other embodiments herein provide compound of formula (I-L), or any stereoisomer thereof or pharmaceutically acceptable salt thereof, wherein L is a bond and R is $R^a$ or $R^b$.

Still other embodiments herein provide compound of formula (I-L), or any stereoisomer thereof or pharmaceutically acceptable salt thereof, wherein L is —O— and R is $R^a$ or $R^b$.

Yet other embodiments herein provide compounds of formula (I-L), or any stereoisomer thereof or pharmaceutically acceptable salt thereof, wherein L is $—(CH_2)_pO—$ and R is $R^a$ or $R^b$.

Other embodiments herein provide compounds of formula (I-L), or any stereoisomer thereof or pharmaceutically acceptable salt thereof, wherein L is a $O(CH_2)_p—$ and R is $R^a$ or $R^b$.

Other embodiments herein provide compound of formula (I-L), or any stereoisomer thereof or pharmaceutically acceptable salt thereof, wherein L is a bond and R is $R^a$.

Still other embodiments herein provide compound of formula (I-L), or any stereoisomer thereof or pharmaceutically acceptable salt thereof, wherein L is —O— and R is $R^a$.

Yet other embodiments herein provide compounds of formula (I-L), or any stereoisomer thereof or pharmaceutically acceptable salt thereof, wherein L is $—(CH_2)_pO—$ and R is $R^a$.

Other embodiments herein provide compounds of formula (I-L), or any stereoisomer thereof or pharmaceutically acceptable salt thereof, wherein L is a $O(CH_2)_p—$ and R is $R^a$.

Other embodiments herein provide compound of formula (I-L), or any stereoisomer thereof or pharmaceutically acceptable salt thereof, wherein L is a bond and R is $R^b$.

Still other embodiments herein provide compound of formula (I-L), or any stereoisomer thereof or pharmaceutically acceptable salt thereof, wherein L is —O— and R is $R^b$.

Yet other embodiments herein provide compounds of formula (I-L), or any stereoisomer thereof or pharmaceutically acceptable salt thereof, wherein L is $—(CH_2)_pO—$ and R is $R^b$.

Other embodiments herein provide compounds of formula (I-L), or any stereoisomer thereof or pharmaceutically acceptable salt thereof, wherein L is a $O(CH_2)_p—$ and R is $R^b$.

Other embodiments disclosed herein provide compounds of formula (I-L), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is $—CH_2—$ and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, and L is a bond, —O—, $—(CH_2)_pO—$, or $O(CH_2)_p—$ and R is $R^a$ or $R^b$.

Other embodiments disclosed herein provide compounds of formula (I-L), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is $—CH_2—$ and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, $R^1$ and $R^2$ are each, independently, H, halo, or $—CH_3$, and L is a bond, —O—, $—(CH_2)_pO—$, or $O(CH_2)_p—$ and R is $R^a$ or $R^b$.

Some embodiments disclosed herein provide compounds of formula (I) having the structure of formula (I-M)

(I-M)

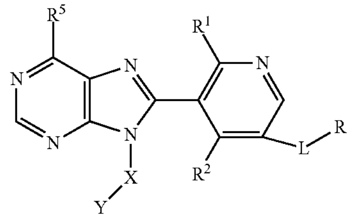

or any stereoisomer thereof or pharmaceutically acceptable salt thereof;

wherein,

X, Y, $R^1$ $R^2$, $R^5$, L and R are as defined in formula (I).

Other embodiments disclosed herein provide compounds of formula (I-M), or any stereoisomer thereof or pharmaceutically acceptable salt thereof, wherein X is $—CH_2—$.

Still other embodiments disclosed herein provide compounds of formula (I-M), or any stereoisomer thereof or pharmaceutically acceptable salt thereof, wherein Y is phenyl.

Yet other embodiments disclosed herein provide compounds of formula (I-M), or any stereoisomer thereof or pharmaceutically acceptable salt thereof, wherein Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Still other embodiments disclosed herein provide compounds of formula (I-M), or any stereoisomer thereof or pharmaceutically acceptable salt thereof, wherein Y is phenyl substituted with one or two substituents independently selected from halo, $C_1$-$C_3$ alkyl, $C_1$-$C_3$ alkoxy, —CN, $C_1$-$C_3$ haloalkyl, and cyclopropyl. In further embodiments of the invention, Y is phenyl substituted with one or two substituents independently selected from halo and $C_1$-$C_3$ alkyl.

Other embodiments disclosed herein provide compounds of formula (I-M), or any stereoisomer thereof or pharmaceutically acceptable salt thereof, wherein X is $—CH_2—$ and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl.

Other embodiments disclosed herein provide compounds of formula (I-M), or any stereoisomer thereof or pharmaceutically acceptable salt thereof, wherein $Z_a$ and $Z_b$ are independently $C_1$-$C_3$ alkyl and $Z_c$ is H. In still further embodiments, $Z_a$ and $Z_b$ are $—CH_3$ and $Z_c$ is H.

Other embodiments disclosed herein provide compounds of formula (I-M), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN. In still further embodiments, $Z_a$ and $Z_b$ form a 3 membered carbocycle and $Z_c$ is H or $C_1$-$C_3$ alkyl. In other further embodiments, $Z_a$ and $Z_b$ form a 4 membered carbocycle and $Z_c$ is H or $C_1$-$C_3$ alkyl.

Other embodiments herein provide compounds of formula (I-M), or any stereoisomer thereof or pharmaceutically acceptable salt thereof, wherein L is a bond, —O—, $—(CH_2)_pO—$, or $O(CH_2)_p—$.

Yet other embodiments herein provide compounds of formula (I-M), or any stereoisomer thereof or pharmaceutically acceptable salt thereof, wherein L is a bond, —O—, $—(CH_2)_pO—$, or $O(CH_2)_p—$ and R is $R^a$ or $R^b$.

Still other embodiments herein provide compound of formula (I-M), or any stereoisomer thereof or pharmaceutically acceptable salt thereof, wherein L is a bond and R is $R^a$ or $R^b$.

Other embodiments herein provide compound of formula (I-M), or any stereoisomer thereof or pharmaceutically acceptable salt thereof, wherein L is a bond and R is $R^a$ or $R^b$.

Still other embodiments herein provide compound of formula (I-M), or any stereoisomer thereof or pharmaceutically acceptable salt thereof, wherein L is —O— and R is $R^a$ or $R^b$.

Yet other embodiments herein provide compounds of formula (I-M), or any stereoisomer thereof or pharmaceutically acceptable salt thereof, wherein L is $(CH_2)_pO$— and R is $R^a$ or $R^b$.

Other embodiments herein provide compounds of formula (I-M), or any stereoisomer thereof or pharmaceutically acceptable salt thereof, wherein L is a $O(CH_2)_p$— and R is $R^a$ or $R^b$.

Other embodiments herein provide compound of formula (I-M), or any stereoisomer thereof or pharmaceutically acceptable salt thereof, wherein L is a bond and R is $R^a$.

Still other embodiments herein provide compound of formula (I-M), or any stereoisomer thereof or pharmaceutically acceptable salt thereof, wherein L is —O— and R is $R^a$.

Yet other embodiments herein provide compounds of formula (I-M), or any stereoisomer thereof or pharmaceutically acceptable salt thereof, wherein L is —$(CH_2)_pO$— and R is $R^a$.

Other embodiments herein provide compounds of formula (I-M), or any stereoisomer thereof or pharmaceutically acceptable salt thereof, wherein L is a $O(CH_2)_p$— and R is $R^a$.

Other embodiments herein provide compound of formula (I-M), or any stereoisomer thereof or pharmaceutically acceptable salt thereof, wherein L is a bond and R is $R^b$.

Still other embodiments herein provide compound of formula (I-M), or any stereoisomer thereof or pharmaceutically acceptable salt thereof, wherein L is —O— and R is $R^b$.

Yet other embodiments herein provide compounds of formula (I-M), or any stereoisomer thereof or pharmaceutically acceptable salt thereof, wherein L is $(CH_2)_pO$— and R is $R^b$.

Other embodiments herein provide compounds of formula (I-M), or any stereoisomer thereof or pharmaceutically acceptable salt thereof, wherein L is a $O(CH_2)_p$— and R is $R^b$.

Other embodiments disclosed herein provide compounds of formula (I-M), or any stereoisomer thereof or pharmaceutically acceptable salt thereof, wherein $Z_a$ and $Z_b$ form a 3-6 membered carbocycle and Z is H, $C_1$-$C_3$ alkyl, or CN; X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, and L is a bond, —O—, —$(CH_2)_pO$—, or $O(CH_2)_p$— and R is $R^a$ or $R^b$.

Other embodiments disclosed herein provide compounds of formula (I-M), or any stereoisomer thereof or pharmaceutically acceptable salt thereof, wherein $Z_a$ and $Z_b$ form a 3-6 membered carbocycle and $Z_c$ is H, $C_1$-$C_3$ alkyl, or CN; X is —$CH_2$— and Y is phenyl optionally substituted with 1-3 substituents independently selected from halo, $C_1$-$C_3$ alkyl, $C_1$-$C_3$ alkoxy, —CN, $C_1$-$C_3$ haloalkyl, and cyclopropyl, $R^1$ and $R^2$ are each, independently, H, halo, or —$CH_3$, and L is a bond, —O—, —$(CH_2)_pO$—, or $O(CH_2)_p$— and R is $R^a$ or $R^b$.

Some embodiments disclosed herein provide a compound selected from:

4-(1-benzyl-5-isopropoxy-1H-benzo[d]imidazol-2-yl)-3-chlorophenol, tert-butyl (3-(4-(1-benzyl-5-isopropoxy-1H-benzo[d]imidazol-2-yl)-3-chlorophenoxy)propyl)carbamate, N-(3-(4-(1-benzyl-5-isopropoxy-1H-benzo[d]imidazol-2-yl)-3-chlorophenoxy)propyl)acetamide, N-(3-(4-(1-benzyl-5-isopropoxy-1H-benzo[d]imidazol-2-yl)-3-chlorophenoxy)propyl)heptanamide, 1-(4-chlorobenzyl)-5-isopropoxy-2-(4-methyl-6-(2-(4-methylpiperazin-1-yl)ethoxy)pyridin-3-yl)-1H-benzo[d]imidazole, 2-(2-chloro-4-(2-(4-methylpiperazin-1-yl)ethoxy)phenyl)-1-(2-chloro-6-fluoro-3-methylbenzyl)-5-isopropoxy-1H-benzo[d]imidazole, 1-(3-chlorobenzyl)-5-isopropoxy-2-(4-methyl-6-(2-(4-methylpiperazin-1-yl)ethoxy)pyridin-3-yl)-1H-benzo[d]imidazole, 1-benzyl-2-(2-chloro-4-(2-(1-methylpyrrolidin-2-yl)ethoxy)phenyl)-5-isopropoxy-1H-benzo[d]imidazole (Isomer 1), 1-benzyl-2-(2-chloro-4-(2-(1-methylpyrrolidin-2-yl)ethoxy)phenyl)-5-isopropoxy-1H-benzo[d]imidazole (Isomer 2), (R)-1-benzyl-2-(2-chloro-4-(2-(1-methylpyrrolidin-2-yl)ethoxy)phenyl)-5-isopropoxy-1H-benzo[d]imidazole, (S)-1-benzyl-2-(2-chloro-4-(2-(1-methylpyrrolidin-2-yl)ethoxy)phenyl)-5-isopropoxy-1H-benzo[d]imidazole, 1-benzyl-2-(2-chloro-4-((1-methylazepan-4-yl)oxy)phenyl)-5-isopropoxy-1H-benzo[d]imidazole (Isomer 1), 1-benzyl-2-(2-chloro-4-((1-methylazepan-4-yl)oxy)phenyl)-5-isopropoxy-1H-benzo[d]imidazole (Isomer 2), (R)-1-benzyl-2-(2-chloro-4-((1-methylazepan-4-yl)oxy)phenyl)-5-isopropoxy-1H-benzo[d]imidazole, (S)-1-benzyl-2-(2-chloro-4-((1-methylazepan-4-yl)oxy)phenyl)-5-isopropoxy-1H-benzo[d]imidazole, 1-benzyl-2-(2-chloro-4-methoxyphenyl)-5-isopropoxy-1H-benzo[d]imidazole, 9-benzyl-6-isopropoxy-8-(4-(2-(4-methylpiperazin-1-yl)ethoxy)phenyl)-9H-purine, 9-benzyl-6-isopropoxy-8-(2-methyl-4-(2-(piperazin-1-yl)ethoxy)phenyl)-9H-purine, tert-butyl 4-(2-(4-(9-benzyl-6-isopropoxy-9H-purin-8-yl)-3-methylphenoxy)ethyl)piperazine-1-carboxylate, 1-(4-(2-(4-(9-benzyl-6-isopropoxy-9H-purin-8-yl)-3-methylphenoxy)ethyl)piperazin-1-yl)ethan-1-one, 1-(4-(2-(4-(9-benzyl-6-isopropoxy-9H-purin-8-yl)-3-methylphenoxy)ethyl)piperazin-1-yl)hexan-1-one, 9-benzyl-8-(2-methyl-4-(2-(4-methylpiperazin-1-yl)ethoxy)phenyl)-6-(1-methylcyclopropoxy)-9H-purine, 1-(4-(5-(9-benzyl-6-(1-methylcyclopropoxy)-9H-purin-8-yl)-4-methylpyridin-2-yl)piperazin-1-yl)ethan-1-one, 9-benzyl-8-(4-methyl-6-(2-(4-methylpiperazin-1-yl)ethoxy)pyridin-3-yl)-6-(1-methylcyclopropoxy)-9H-purine, (R)-1-(4-(9-benzyl-6-(1-methylcyclopropoxy)-9H-purin-8-yl)-3-chlorophenyl)-N,N-dimethylpyrrolidin-3-amine, 9-benzyl-8-(4-methyl-6-(piperazin-1-yl)pyridin-3-yl)-6-(1-methylcyclopropoxy)-9H-purine, 9-benzyl-8-(2-chloro-3-methoxyphenyl)-6-(1-methylcyclopropoxy)-9H-purine, 9-benzyl-8-(2-chloro-4-(piperazin-1-yl)phenyl)-6-(1-methylcyclopropoxy)-9H-purine, 2-(4-(9-benzyl-6-(1-methylcyclopropoxy)-9H-purin-8-yl)-3-chlorophenoxy)-1-(piperazin-1-yl)ethan-1-one, 2-(4-(9-benzyl-6-(1-methylcyclopropoxy)-9H-purin-8-yl)-3-chlorophenoxy)-1-(4-methylpiperazin-1-yl)ethan-1-one, 1-(4-((4-(9-benzyl-6-(1-methylcyclopropoxy)-9H-purin-8-yl)-3-chlorophenoxy)methyl)piperidin-1-yl)ethan-1-one, 9-benzyl-8-(2-chloro-4-(2-(1-methylpyrrolidin-2-yl)ethoxy)phenyl)-6-(1-methylcyclopropoxy)-9H-purine,
9-benzyl-8-(2-chloro-4-(2-(1-methylpyrrolidin-2-yl)ethoxy)phenyl)-6-(1-methylcyclopropoxy)-9H-purine (Isomer 2),
9-benzyl-8-(2-chloro-4-(2-(1-methylpyrrolidin-2-yl)ethoxy)phenyl)-6-(1-methylcyclopropoxy)-9H-purine (Isomer 1),
(R)-9-benzyl-8-(2-chloro-4-(2-(1-methylpyrrolidin-2-yl)ethoxy)phenyl)-6-(1-methylcyclopropoxy)-9H-purine,
(S)-9-benzyl-8-(2-chloro-4-(2-(1-methylpyrrolidin-2-yl)ethoxy)phenyl)-6-(1-methylcyclopropoxy)-9H-purine,
1-(4-(2-(4-(9-benzyl-6-(1-methylcyclopropoxy)-9H-purin-8-yl)-3-chlorophenoxy)ethyl)piperazin-1-yl)ethan-1-one,
3-(4-(9-benzyl-6-(1-methylcyclopropoxy)-9H-purin-8-yl)-3-chlorophenoxy)propan-1-amine,
N-(3-(4-(9-benzyl-6-(1-methylcyclopropoxy)-9H-purin-8-yl)-3-chlorophenoxy)propyl)acetamide,
1-(4-(2-(3-(9-benzyl-6-(1-methylcyclopropoxy)-9H-purin-8-yl)-2-chlorophenoxy)ethyl)piperazin-1-yl)ethan-1-one,
9-benzyl-8-(2-chloro-3-((1-methylpiperidin-4-yl)oxy)phenyl)-6-(1-methylcyclopropoxy)-9H-purine,
9-benzyl-8-(2-chloro-3-(2-(piperazin-1-yl)ethoxy)phenyl)-6-(1-methylcyclopropoxy)-9H-purine,
9-benzyl-8-(2-chloro-3-(piperidin-4-yloxy)phenyl)-6-(1-methylcyclopropoxy)-9H-purine,
9-benzyl-8-(2-chloro-3-(2-(4-methylpiperazin-1-yl)ethoxy)phenyl)-6-(1-methylcyclopropoxy)-9H-purine,
9-benzyl-8-(2-chloro-4-((1-methylazepan-4-yl)oxy)phenyl)-6-(1-methylcyclopropoxy)-9H-purine (Isomer 1),
9-benzyl-8-(2-chloro-4-((1-methylazepan-4-yl)oxy)phenyl)-6-(1-methylcyclopropoxy)-9H-purine (Isomer 2),
(R)-9-benzyl-8-(2-chloro-4-((1-methylazepan-4-yl)oxy)phenyl)-6-(1-methylcyclopropoxy)-9H-purine,
(S)-9-benzyl-8-(2-chloro-4-((1-methylazepan-4-yl)oxy)phenyl)-6-(1-methylcyclopropoxy)-9H-purine,
4-(2-(4-(9-benzyl-6-(1-methylcyclopropoxy)-9H-purin-8-yl)-3-chlorophenoxy)ethyl)piperazin-2-one,
(R)-8-(4-(azetidin-2-ylmethoxy)-2-chlorophenyl)-9-benzyl-6-(1-methylcyclopropoxy)-9H-purine,
(S)-9-benzyl-8-(2-chloro-4-(pyrrolidin-3-yloxy)phenyl)-6-(1-methylcyclopropoxy)-9H-purine
9-benzyl-8-(2-chloro-4-(3-(piperazin-1-yl)propoxy)phenyl)-6-(1-methylcyclopropoxy)-9H-purine,
9-benzyl-8-(2-chloro-4-((3-fluoroazetidin-3-yl)methoxy)phenyl)-6-(1-methylcyclopropoxy)-9H-purine,
2-(4-(9-benzyl-6-(1-methylcyclopropoxy)-9H-purin-8-yl)-3-chlorophenoxy)-N,N-dimethylacetamide,
2-(4-(9-benzyl-6-(1-methylcyclopropoxy)-9H-purin-8-yl)-3-chlorophenoxy)-N-methylacetamide,
1-(4-(3-(4-(9-benzyl-6-(1-methylcyclopropoxy)-9H-purin-8-yl)-3-chlorophenoxy)propyl)piperazin-1-yl)ethan-1-one,
2-(4-(9-benzyl-6-(1-methylcyclopropoxy)-9H-purin-8-yl)-3-chlorophenoxy)ethan-1-amine,
2-(4-(9-benzyl-6-(1-methylcyclopropoxy)-9H-purin-8-yl)-3-chlorophenoxy)acetic acid,
(R)-9-benzyl-8-(2-chloro-4-(pyrrolidin-2-ylmethoxy)phenyl)-6-(1-methylcyclopropoxy)-9H-purine,
N-(2-(4-(9-benzyl-6-(1-methylcyclopropoxy)-9H-purin-8-yl)-3-chlorophenoxy)ethyl)-2-hydroxyacetamide,
2-(4-(9-benzyl-6-(1-methylcyclopropoxy)-9H-purin-8-yl)-3-chlorophenoxy)acetamide,
2-(4-(9-benzyl-6-(1-methylcyclopropoxy)-9H-purin-8-yl)-3-chlorophenoxy)-N-(2-hydroxyethyl)acetamide,
(2-(4-(9-benzyl-6-(1-methylcyclopropoxy)-9H-purin-8-yl)-3-chlorophenoxy)ethyl)glycine,
N-(2-(4-(9-benzyl-6-(1-methylcyclopropoxy)-9H-purin-8-yl)-3-chlorophenoxy)ethyl)-N-methylglycine,
9-benzyl-8-(2-chloro-4-(((3S,4R)-4-fluoropyrrolidin-3-yl)oxy)phenyl)-6-(1-methylcyclopropoxy)-9H-purine,
(R)-9-benzyl-8-(2-chloro-4-(piperidin-3-yloxy)phenyl)-6-(1-methylcyclopropoxy)-9H-purine,
9-benzyl-8-(2-chloro-4-(piperidin-4-yloxy)phenyl)-6-(1-methylcyclopropoxy)-9H-purine,
8-(4-((2-azaspiro[3.3]heptan-6-yl)oxy)-2-chlorophenyl)-9-benzyl-6-(1-methylcyclopropoxy)-9H-purine,
8-(4-(azetidin-3-yloxy)-2-chlorophenyl)-9-benzyl-6-(1-methylcyclopropoxy)-9H-purine,
8-(2-chloro-4-(2-(4-methylpiperazin-1-yl)ethoxy)phenyl)-9-(2-chlorobenzyl)-6-(1-methylcyclopropoxy)-9H-purine,
8-(2-chloro-4-(2-(4-methylpiperazin-1-yl)ethoxy)phenyl)-9-(3-chlorobenzyl)-6-(1-methylcyclopropoxy)-9H-purine,
8-(2-chloro-4-(2-(4-methylpiperazin-1-yl)ethoxy)phenyl)-9-(2,3-difluorobenzyl)-6-(1-methylcyclopropoxy)-9H-purine,
8-(2-chloro-4-(2-(4-methylpiperazin-1-yl)ethoxy)phenyl)-6-(1-methylcyclopropoxy)-9-phenethyl-9H-purine,
8-(2-chloro-4-(2-(4-methylpiperazin-1-yl)ethoxy)phenyl)-6-(1-methylcyclopropoxy)-9-(pyridin-2-ylmethyl)-9H-purine,
8-(2-chloro-4-(2-(4-methylpiperazin-1-yl)ethoxy)phenyl)-6-(1-methylcyclopropoxy)-9-(pyrimidin-2-ylmethyl)-9H-purine,
8-(2-chloro-4-(2-(piperazin-1-yl)ethoxy)phenyl)-6-(1-methylcyclopropoxy)-9-(pyridin-2-ylmethyl)-9H-purine,
1-(5-(9-benzyl-6-(1-methylcyclopropoxy)-9H-purin-8-yl)-4-methylpyridin-2-yl)piperidin-4-amine,
1-(5-(9-benzyl-6-(1-methylcyclopropoxy)-9H-purin-8-yl)-4-methylpyridin-2-yl)-N,N-dimethylazetidin-3-amine,
1-(5-(9-benzyl-6-(1-methylcyclopropoxy)-9H-purin-8-yl)-4-methylpyridin-2-yl)-N,N-dimethylpiperidin-4-amine,
9-benzyl-8-(4-methyl-6-(3-(piperazin-1-yl)propoxy)pyridin-3-yl)-6-(1-methylcyclopropoxy)-9H-purine,
3-((5-(9-benzyl-6-(1-methylcyclopropoxy)-9H-purin-8-yl)-4-methylpyridin-2-yl)oxy)-N,N-dimethylpropan-1-amine,
1-(4-(3-((5-(9-benzyl-6-(1-methylcyclopropoxy)-9H-purin-8-yl)-4-methylpyridin-2-yl)oxy)propyl)piperazin-1-yl)ethan-1-one,
1-(4-(2-((5-(9-benzyl-6-(1-methylcyclopropoxy)-9H-purin-8-yl)-4-methylpyridin-2-yl)oxy)ethyl)piperazin-1-yl)ethan-1-one,
9-benzyl-8-(4-methyl-6-(3-(pyrrolidin-1-yl)propoxy)pyridin-3-yl)-6-(1-methylcyclopropoxy)-9H-purine,
9-benzyl-8-(4-methyl-6-(2-(piperazin-1-yl)ethoxy)pyridin-3-yl)-6-(1-methylcyclopropoxy)-9H-purine,
4-(3-((5-(9-benzyl-6-(1-methylcyclopropoxy)-9H-purin-8-yl)-4-methylpyridin-2-yl)oxy)propyl)morpholine,
2-((5-(9-benzyl-6-(1-methylcyclopropoxy)-9H-purin-8-yl)-4-methylpyridin-2-yl)oxy)ethan-1-amine,
3-((5-(9-benzyl-6-(1-methylcyclopropoxy)-9H-purin-8-yl)-4-methylpyridin-2-yl)oxy)propan-1-amine,
1-(3-((5-(9-benzyl-6-(1-methylcyclopropoxy)-9H-purin-8-yl)-4-methylpyridin-2-yl)oxy)azetidin-1-yl)ethan-1-one,
(S)-9-benzyl-8-(4-methyl-6-(pyrrolidin-3-yloxy)pyridin-3-yl)-6-(1-methylcyclopropoxy)-9H-purine,
2-((5-(9-benzyl-6-(1-methylcyclopropoxy)-9H-purin-8-yl)-4-methylpyridin-2-yl)oxy)-N,N-dimethylethan-1-amine,
(S)-9-benzyl-8-(4-methyl-6-(piperidin-3-yloxy)pyridin-3-yl)-6-(1-methylcyclopropoxy)-9H-purine, 9-benzyl-8-(3-methyl-2-(2-(piperazin-1-yl)ethoxy)pyridin-4-yl)-6-(1-methylcyclopropoxy)-9H-purine,
(R)-2-(((5-(9-benzyl-6-(1-methylcyclopropoxy)-9H-purin-8-yl)-4-methylpyridin-2-yl)oxy)methyl)morpholine,
(R)-3-(((5-(9-benzyl-6-(1-methylcyclopropoxy)-9H-purin-8-yl)-4-methylpyridin-2-yl)oxy)methyl)morpholine,
8-{6-[(azetidin-3-yl)oxy]-4-methylpyridin-3-yl}-9-benzyl-6-[(1-methylcyclopropyl)oxy]-9H-purine,
9-benzyl-8-(2,6-difluoro-4-(2-(4-methylpiperazin-1-yl)ethoxy)phenyl)-6-(1-methylcyclopropoxy)-9H-purine,
9-benzyl-8-(2-fluoro-4-(2-(4-methylpiperazin-1-yl)ethoxy)phenyl)-6-(1-methylcyclopropoxy)-9H-purine,
9-benzyl-8-(2-methoxy-4-(2-(4-methylpiperazin-1-yl)ethoxy)phenyl)-6-(1-methylcyclopropoxy)-9H-purine,
9-benzyl-8-(2,6-dimethyl-4-(2-(4-methylpiperazin-1-yl)ethoxy)phenyl)-6-(1-methylcyclopropoxy)-9H-purine,
9-benzyl-8-(2,3-difluoro-4-(2-(4-methylpiperazin-1-yl)ethoxy)phenyl)-6-(1-methylcyclopropoxy)-9H-purine,
9-benzyl-8-(2-bromo-4-(2-(4-methylpiperazin-1-yl)ethoxy)phenyl)-6-(1-methylcyclopropoxy)-9H-purine,
8-(2-chloro-4-(2-(4-methylpiperazin-1-yl)ethoxy)phenyl)-6-(1-methylcyclopropoxy)-9-(pyridin-3-ylmethyl)-9H-purine,
2-(9-benzyl-6-(1-methylcyclopropoxy)-9H-purin-8-yl)-5-(2-(4-methylpiperazin-1-yl)ethoxy)benzonitrile,
9-benzyl-8-(2-ethynyl-4-(2-(4-methylpiperazin-1-yl)ethoxy)phenyl)-6-(1-methylcyclopropoxy)-9H-purine,
(2-(9-benzyl-6-(1-methylcyclopropoxy)-9H-purin-8-yl)-5-(2-(4-methylpiperazin-1-yl)ethoxy)phenyl)methanol,
3-(4-(9-benzyl-6-(1-methylcyclopropoxy)-9H-purin-8-yl)-3-chlorophenoxy)propanoic acid,
(2-(4-(9-benzyl-6-(1-methylcyclopropoxy)-9H-purin-8-yl)-3-chlorophenoxy)ethyl)-L-proline,
(R)-1-(2-(4-(9-benzyl-6-(1-methylcyclopropoxy)-9H-purin-8-yl)-3-chlorophenoxy)ethyl)pyrrolidin-3-ol,
1-(2-(4-(9-benzyl-6-(1-methylcyclopropoxy)-9H-purin-8-yl)-3-chlorophenoxy)ethyl)azetidin-3-ol,
1-(2-(4-(9-benzyl-6-(1-methylcyclopropoxy)-9H-purin-8-yl)-3-chlorophenoxy)ethyl)piperidin-4-ol
2-(2-(4-(9-benzyl-6-(1-methylcyclopropoxy)-9H-purin-8-yl)-3)-2-azaspiro[3.3]heptan-6-ol,
1-(3-(4-(9-benzyl-6-(1-methylcyclopropoxy)-9H-purin-8-yl)-3-chlorophenoxy)propyl)azetidin-3-ol,
8-(4-(2-(1,6-diazaspiro[3.3]heptan-6-yl)ethoxy)-2-chlorophenyl)-9-benzyl-6-(1-methylcyclopropoxy)-9H-purine,
(S)-4-(2-(4-(9-benzyl-6-(1-methylcyclopropoxy)-9H-purin-8-yl)-3-chlorophenoxy)ethyl)-3-methylpiperazin-2-one,
6-(2-(4-(9-benzyl-6-(1-methylcyclopropoxy)-9H-purin-8-yl)-3-chlorophenoxy)ethyl)-2-thia-6-azaspiro[3.3]heptane 2,2-dioxide,
1-(2-(4-(9-benzyl-6-(1-methylcyclopropoxy)-9H-purin-8-yl)-3-chlorophenoxy)ethyl)-1,4-diazepan-5-one,
(R)-4-(2-(4-(9-benzyl-6-(1-methylcyclopropoxy)-9H-purin-8-yl)-3-chlorophenoxy)ethyl)-3-methylpiperazin-2-one,
6-(2-(4-(9-benzyl-6-(1-methylcyclopropoxy)-9H-purin-8-yl)-3-chlorophenoxy)ethyl)-2-thia-6-azaspiro[3.3]heptane,
9-benzyl-8-(2,3-dichloro-4-(2-(piperazin-1-yl)ethoxy)phenyl)-6-(1-methylcyclopropoxy)-9H-purine,
9-benzyl-8-(2-chloro-5-methoxy-4-(2-(piperazin-1-yl)ethoxy)phenyl)-6-(1-methylcyclopropoxy)-9H-purine,
9-benzyl-8-(2-chloro-3-methoxy-4-(2-(piperazin-1-yl)ethoxy)phenyl)-6-(1-methylcyclopropoxy)-9H-purine,
9-benzyl-8-(2,5-dichloro-4-(2-(piperazin-1-yl)ethoxy)phenyl)-6-(1-methylcyclopropoxy)-9H-purine,
9-(2-chlorobenzyl)-8-(4-methyl-6-(2-(piperazin-1-yl)ethoxy)pyridin-3-yl)-6-(1-methylcyclopropoxy)-9H-purine,
9-(3-chlorobenzyl)-8-(4-methyl-6-(2-(piperazin-1-yl)ethoxy)pyridin-3-yl)-6-(1-methylcyclopropoxy)-9H-purine,
8-(2-chloro-4-(2-(piperazin-1-yl)ethoxy)phenyl)-6-(1-methylcyclobutoxy)-9-(pyridin-2-ylmethyl)-9H-purine,
8-(2-chloro-4-(2-(piperazin-1-yl)ethoxy)phenyl)-6-(1-methylcyclopropoxy)-9-(2-(pyridin-3-yl)ethyl)-9H-purine,
(S)-8-(2-chloro-4-(2-(piperazin-1-yl)ethoxy)phenyl)-6-(1-methylcyclopropoxy)-9-(2-phenylpropyl)-9H-purine,
(R)-8-(2-chloro-4-(2-(piperazin-1-yl)ethoxy)phenyl)-6-(1-methylcyclopropoxy)-9-(2-phenylpropyl)-9H-purine,
8-(2-chloro-4-(2-(piperazin-1-yl)ethoxy)phenyl)-6-(1-methylcyclopropoxy)-9-(2-(pyridin-2-yl)ethyl)-9H-purine,
8-(2-chloro-4-(2-(piperazin-1-yl)ethoxy)phenyl)-6-(1-methylcyclopropoxy)-9-phenethyl-9H-purine,
8-(2-chloro-4-(2-(piperazin-1-yl)ethoxy)phenyl)-9-(3-chlorobenzyl)-6-(1-methylcyclopropoxy)-9H-purine,
8-(2-chloro-4-(2-(4-methylpiperazin-1-yl)ethoxy)phenyl)-6-(1-methylcyclopropoxy)-9-(pyridin-4-ylmethyl)-9H-purine,
4-((8-(2-chloro-4-(2-(piperazin-1-yl)ethoxy)phenyl)-6-(1-methylcyclopropoxy)-9H-purin-9-yl)methyl)thiazole,
8-(2-chloro-4-(2-(piperazin-1-yl)ethoxy)phenyl)-9-((5-chloropyridin-2-yl)methyl)-6-(1-methylcyclopropoxy)-9H-purine,
2-((8-(2-chloro-4-(2-(piperazin-1-yl)ethoxy)phenyl)-6-(1-methylcyclopropoxy)-9H-purin-9-yl)methyl)thiazole,
8-(2-chloro-4-(2-(piperazin-1-yl)ethoxy)phenyl)-9-((3-chloropyridin-2-yl)methyl)-6-(1-methylcyclopropoxy)-9H-purine,
4-((8-(2-chloro-4-(2-(piperazin-1-yl)ethoxy)phenyl)-6-(1-methylcyclopropoxy)-9H-purin-9-yl)methyl)-2-methylthiazole,
8-(2-chloro-4-(2-(piperazin-1-yl)ethoxy)phenyl)-6-(1-methylcyclopropoxy)-9-((6-methylpyridin-2-yl)methyl)-9H-purine,
8-(2-chloro-4-(2-(piperazin-1-yl)ethoxy)phenyl)-6-(1-methylcyclopropoxy)-9-((4-(trifluoromethyl)pyridin-2-yl)methyl)-9H-purine,
6-((8-(2-chloro-4-(2-(piperazin-1-yl)ethoxy)phenyl)-6-(1-methylcyclopropoxy)-9H-purin-9-yl)methyl)picolinonitrile,
8-(2-chloro-4-(2-(piperazin-1-yl)ethoxy)phenyl)-9-((6-methoxypyridin-2-yl)methyl)-6-(1-methylcyclopropoxy)-9H-purine,
2-((8-(2-chloro-4-(2-(piperazin-1-yl)ethoxy)phenyl)-6-(1-methylcyclopropoxy)-9H-purin-9-yl)methyl)nicotinonitrile,
4-((8-(2-chloro-4-(2-(piperazin-1-yl)ethoxy)phenyl)-6-(1-methylcyclopropoxy)-9H-purin-9-yl)methyl)-5-methylthiazole,
8-(2-chloro-4-(2-(piperazin-1-yl)ethoxy)phenyl)-6-(1-methylcyclopropoxy)-9-(2-(pyridin-4-yl)ethyl)-9H-purine,
8-(2-chloro-4-(2-(piperazin-1-yl)ethoxy)phenyl)-6-(1-methylcyclopropoxy)-9-((4-methylpyridin-2-yl)methyl)-9H-purine,
2-((8-(2-chloro-4-(2-(piperazin-1-yl)ethoxy)phenyl)-6-(1-methylcyclopropoxy)-9H-purin-9-yl)methyl)-5-methylthiazole,
2-((8-(2-chloro-4-(2-(piperazin-1-yl)ethoxy)phenyl)-6-(1-methylcyclopropoxy)-9H-purin-9-yl)methyl)isonicotinonitrile, 8-(2-chloro-4-(2-(piperazin-1-yl)ethoxy)phenyl)-9-((4-methoxypyridin-2-yl)methyl)-6-(1-methylcyclopropoxy)-9H-purine, 5-chloro-2-((8-(2-chloro-4-(2-(piperazin-1-yl)ethoxy)phenyl)-6-(1-methylcyclopropoxy)-9H-purin-9-yl)methyl)thiazole, 2-chloro-4-((8-(2-chloro-4-(2-(piperazin-1-yl)ethoxy)phenyl)-6-(1-methylcyclopropoxy)-9H-purin-9-yl)methyl)thiazole, 8-(2-chloro-4-(2-(piperazin-1-yl)ethoxy)phenyl)-6-(1-methylcyclopropoxy)-9-((5-methylpyridin-2-yl)methyl)-9H-purine, 8-(2-chloro-4-(2-(piperazin-1-yl)ethoxy)phenyl)-6-(1-methylcyclopropoxy)-9-((3-methylpyridin-2-yl)methyl)-9H-purine, 8-(2-chloro-4-(2-(piperazin-1-yl)ethoxy)phenyl)-9-((3-methoxypyridin-2-yl)methyl)-6-(1-methylcyclopropoxy)-9H-purine, 1-(4-(9-benzyl-6-(1-methylcyclopropoxy)-9H-purin-8-yl)-3-chlorophenyl)azetidin-3-amine, 1-(4-(9-benzyl-6-(1-methylcyclopropoxy)-9H-purin-8-yl)-3-chlorophenyl)piperidin-4-amine, 4-(4-(9-benzyl-6-(1-methylcyclopropoxy)-9H-purin-8-yl)-3-chlorophenyl)piperazin-2-one, (E)-3-(4-(9-benzyl-6-(1-methylcyclopropoxy)-9H-purin-8-yl)-3-chlorophenyl)acrylic acid, 1-(2-(4-(9-benzyl-6-(1-methylcyclopropoxy)-9H-purin-8-yl)-3-chlorophenoxy)ethyl)piperazin-2-one, 4-(9-benzyl-6-(1-methylcyclopropoxy)-9H-purin-8-yl)-3-chloro-N,N-dimethylbenzamide, 4-(9-benzyl-6-(1-methylcyclopropoxy)-9H-purin-8-yl)-3-chloro-N-methylbenzamide, (4-(9-benzyl-6-(1-methylcyclopropoxy)-9H-purin-8-yl)-3-chlorophenyl)(piperazin-1-yl)methanone, 4-(9-benzyl-6-(1-methylcyclopropoxy)-9H-purin-8-yl)-3-chlorobenzamide, 9-benzyl-8-(2-chloro-4-(pyrrolidin-1-ylmethyl)phenyl)-6-(1-methylcyclopropoxy)-9H-purine, 9-benzyl-8-(2-chloro-4-(piperazin-1-ylmethyl)phenyl)-6-(1-methylcyclopropoxy)-9H-purine, (4-(9-benzyl-6-(1-methylcyclopropoxy)-9H-purin-8-yl)-3-chlorophenyl)methanamine, 9-benzyl-8-(2-chloro-4-methoxyphenyl)-6-(1-methylcyclopropoxy)-9H-purine, 9-benzyl-8-(2-methoxypyridin-3-yl)-6-(1-methylcyclopropoxy)-9H-purine, 2-(2-chloro-4-(2-(piperazin-1-yl)ethoxy)phenyl)-4-(1-methylcyclobutoxy)-1-(pyridin-2-ylmethyl)-1H-benzo[d]imidazole, 1-benzyl-2-(2-chloro-4-(2-(piperazin-1-yl)ethoxy)phenyl)-4-(1-methylcyclobutoxy)-1H-benzo[d]imidazole, 2-(2-chloro-4-(2-(piperazin-1-yl)ethoxy)phenyl)-7-(1-methylcyclobutoxy)-3-(pyridin-2-ylmethyl)-3H-imidazo[4,5-b]pyridine, 3-benzyl-2-(2-chloro-4-(2-(piperazin-1-yl)ethoxy)phenyl)-7-(1-methylcyclobutoxy)-3H-imidazo[4,5-b]pyridine, 9-benzyl-8-(2-chloro-4-(2-(piperazin-1-yl)ethoxy)phenyl)-6-(1-ethynylcyclopropoxy)-9H-purine, 9-benzyl-8-(2-chloro-4-(2-(piperazin-1-yl)ethoxy)phenyl)-6-(1-ethylcyclopropoxy)-9H-purine, 9-benzyl-8-(2-chloro-4-(2-(piperazin-1-yl)ethoxy)phenyl)-6-(1-ethynylcyclobutoxy)-9H-purine, 8-(2-chloro-4-(2-(piperazin-1-yl)ethoxy)phenyl)-9-(3-chlorobenzyl)-6-cyclopropoxy-9H-purine, 1-((8-(2-chloro-4-(2-(piperazin-1-yl)ethoxy)phenyl)-9-(3-chlorobenzyl)-9H-purin-6-yl)oxy)cyclopropane-1-carbonitrile, 2-(2-(3-chloro-4-(9-((4-chloropyridin-2-yl)methyl)-6-(1-methylcyclopropoxy)-9H-purin-8-yl)phenoxy)ethyl)-2-azaspiro[3.3]heptan-6-ol, (R)-1-(2-(3-chloro-4-(9-((4-chloropyridin-2-yl)methyl)-6-(1-methylcyclopropoxy)-9H-purin-8-yl)phenoxy)ethyl)pyrrolidin-3-ol, (S)-9-benzyl-8-(2-chloro-4-(2-(3-methylpiperazin-1-yl)ethoxy)phenyl)-6-(1-methylcyclopropoxy)-9H-purine, 8-(4-(2-(3,8-diazabicyclo[3.2.1]octan-3-yl)ethoxy)-2-chlorophenyl)-9-benzyl-6-(1-methylcyclopropoxy)-9H-purine, 3-(2-(4-(9-benzyl-6-(1-methylcyclopropoxy)-9H-purin-8-yl)-3-chlorophenoxy)ethyl)-3,6-diazabicyclo[3.1.1]heptane, (R)-9-benzyl-8-(2-chloro-4-(2-(3-methylpiperazin-1-yl)ethoxy)phenyl)-6-(1-methylcyclopropoxy)-9H-purine, (R)-1-(2-(4-(9-benzyl-6-(1-methylcyclopropoxy)-9H-purin-8-yl)-3-chlorophenoxy)ethyl)piperidin-3-ol, 2-(2-(4-(9-benzyl-6-(1-methylcyclopropoxy)-9H-purin-8-yl)-3-chlorophenoxy)ethyl)-2,6-diazaspiro[3.4]octan-7-one, (cis)-9-benzyl-8-(2-chloro-4-(2-(3,5-dimethylpiperazin-1-yl)ethoxy)phenyl)-6-(1-methylcyclopropoxy)-9H-purine, (S)-9-benzyl-8-(2-chloro-4-(2-(2-methylpiperazin-1-yl)ethoxy)phenyl)-6-(1-methylcyclopropoxy)-9H-purine, (R)-9-benzyl-8-(2-chloro-4-(2-(2-methylpiperazin-1-yl)ethoxy)phenyl)-6-(1-methylcyclopropoxy)-9H-purine, 1-(2-(4-(9-benzyl-6-(1-methylcyclopropoxy)-9H-purin-8-yl)-3-chlorophenoxy)ethyl)-1,4-diazepan-2-one, 1-(2-(4-(9-benzyl-6-(1-methylcyclopropoxy)-9H-purin-8-yl)-3-chlorophenoxy)ethyl)-3-methylpiperazin-2-one (Isomer 1), 1-(2-(4-(9-benzyl-6-(1-methylcyclopropoxy)-9H-purin-8-yl)-3-chlorophenoxy)ethyl)-3-methylpiperazin-2-one (Isomer 2), (R)-1-(2-(4-(9-benzyl-6-(1-methylcyclopropoxy)-9H-purin-8-yl)-3-chlorophenoxy)ethyl)-3-methylpiperazin-2-one, (S)-1-(2-(4-(9-benzyl-6-(1-methylcyclopropoxy)-9H-purin-8-yl)-3-chlorophenoxy)ethyl)-3-methylpiperazin-2-one, 6-(2-(4-(9-benzyl-6-(1-methylcyclopropoxy)-9H-purin-8-yl)-3-chlorophenoxy)ethyl)-3,6-diazabicyclo[3.1.1]heptane, 1-(2-(4-(9-benzyl-6-(1-methylcyclopropoxy)-9H-purin-8-yl)-3-chlorophenoxy)ethyl)-3,3-dimethylpiperazin-2-one, 8-(4-(2-(4,7-diazaspiro[2.5]octan-7-yl)ethoxy)-2-chlorophenyl)-9-benzyl-6-(1-methylcyclopropoxy)-9H-purine, (R)-(4-(2-(4-(9-benzyl-6-(1-methylcyclopropoxy)-9H-purin-8-yl)-3-chlorophenoxy)ethyl)piperazin-2-yl)methanol, 8-(4-(2-((1S,4S)-2,5-diazabicyclo[2.2.1]heptan-2-yl)ethoxy)-2-chlorophenyl)-9-benzyl-6-(1-methylcyclopropoxy)-9H-purine, 8-(4-(2-((1R,4R)-2,5-diazabicyclo[2.2.1]heptan-2-yl)ethoxy)-2-chlorophenyl)-9-benzyl-6-(1-methylcyclopropoxy)-9H-purine, (1S,4S)-2-(2-(4-(9-benzyl-6-(1-methylcyclopropoxy)-9H-purin-8-yl)-3-chlorophenoxy)ethyl)-2,5-diazabicyclo[2.2.2]octane, 8-(4-(2-(4,7-diazaspiro[2.5]octan-4-yl)ethoxy)-2-chlorophenyl)-9-benzyl-6-(1-methylcyclopropoxy)-9H-purine, (S)-2-(4-(2-(4-(9-benzyl-6-(1-methylcyclopropoxy)-9H-purin-8-yl)-3-chlorophenoxy)ethyl)piperazin-2-yl)acetonitrile, 1-(3-(4-(9-benzyl-6-(1-methylcyclopropoxy)-9H-purin-8-yl)-3-chlorophenoxy)propyl)piperazin-2-one, 4-(3-(4-(9-benzyl-6-(1-methylcyclopropoxy)-9H-purin-8-yl)-3-chlorophenoxy)propyl)piperazin-2-one, 8-(2-chloro-4-(2-(piperazin-1-yl)ethoxy)phenyl)-9-((4-cyclopropylpyridin-2-yl)methyl)-6-(1-methylcyclopropoxy)-9H-purine, 8-(2-chloro-4-(2-(piperazin-1-yl)ethoxy)phenyl)-9-((4-ethylpyridin-2-yl)methyl)-6-(1-methylcyclopropoxy)-9H-purine, 8-(2-chloro-4-(2-(piperazin-1-yl)ethoxy)phenyl)-9-(1-(4-chloropyridin-2-yl)ethyl)-6-(1-methylcyclopropoxy)-9H-purine (Isomer 2), 8-(2-chloro-4-(2-(piperazin-1-yl)ethoxy)phenyl)-9-(1-(4-chloropyridin-2-yl)ethyl)-6-(1-methylcyclopropoxy)-9H-purine (Isomer 1), (R)-8-(2-chloro-4-(2-(piperazin-1-yl)ethoxy)phenyl)-9-(1-(4-chloropyridin-2-yl)ethyl)-6-(1-methylcyclopropoxy)-9H-purine, (S)-8-(2-chloro-4-(2-(piperazin-1-yl)ethoxy)phenyl)-9-(1-(4-chloropyridin-2-yl)ethyl)-6-(1-methylcyclopropoxy)-9H-purine, 8-(2-chloro-4-(2-(piperazin-1-yl)ethoxy)phenyl)-6-(1-methylcyclopropoxy)-9-(1-(pyridin-2-yl)propan-2-yl)-9H-purine (Isomer 2), 8-(2-chloro-4-(2-(piperazin-1-yl)ethoxy)phenyl)-6-(1-methylcyclopropoxy)-9-(1-(pyridin-2-yl)propan-2-yl)-9H-purine (Isomer 1), (R)-8-(2-chloro-4-(2-(piperazin-1-yl)ethoxy)phenyl)-6-(1-methylcyclopropoxy)-9-(1-(pyridin-2-yl)propan-2-yl)-9H-purine, (S)-8-(2-chloro-4-(2-(piperazin-1-yl)ethoxy)phenyl)-6-(1-methylcyclopropoxy)-9-(1-(pyridin-2-yl)propan-2-yl)-9H-purine, 2-(3-Chloro-4-(6-(1-methylcyclopropoxy)-9-((4-methylpyridin-2-yl)methyl)-9H-purin-8-yl)phenyl)acetamide, (E)-3-(3-Chloro-4-(9-(3-chlorobenzyl)-6-(1-methylcyclopropoxy)-9H-purin-8-yl)phenyl)acrylic acid, 3-(3-Chloro-4-(9-(3-chlorobenzyl)-6-(1-methylcyclopropoxy)-9H-purin-8-yl)phenoxy)-2,2-dimethylpropanoic acid, 2-(3-Chloro-4-(6-(1-methylcyclopropoxy)-9-((4-methylpyridin-2-yl)methyl)-9H-purin-8-yl)phenoxy)ethan-1-ol, 4-(3-Chloro-4-(9-(3-chlorobenzyl)-6-(1-methylcyclopropoxy)-9H-purin-8-yl)phenoxy)-2-methylbutanoic acid, 4-(3-Chloro-4-(9-(3-chlorobenzyl)-6-(1-methylcyclopropoxy)-9H-purin-8-yl)phenoxy)-2-methylbutanoic acid (Isomer 1), 4-(3-Chloro-4-(9-(3-chlorobenzyl)-6-(1-methylcyclopropoxy)-9H-purin-8-yl)phenoxy)-2-methylbutanoic acid (Isomer 2), (R)-4-(3-Chloro-4-(9-(3-chlorobenzyl)-6-(1-methylcyclopropoxy)-9H-purin-8-yl)phenoxy)-2-methylbutanoic acid, (S)-4-(3-Chloro-4-(9-(3-chlorobenzyl)-6-(1-methylcyclopropoxy)-9H-purin-8-yl)phenoxy)-2-methylbutanoic acid, (S)-1-(3-Chloro-4-(6-(1-methylcyclopropoxy)-9-((4-methylpyridin-2-yl)methyl)-9H-purin-8-yl)phenoxy)propan-2-ol, (R)-1-(3-Chloro-4-(6-(1-methylcyclopropoxy)-9-((4-methylpyridin-2-yl)methyl)-9H-purin-8-yl)phenoxy)propan-2-ol, 1-(3-Chloro-4-(6-(1-methylcyclopropoxy)-9-((4-methylpyridin-2-yl)methyl)-9H-purin-8-yl)phenoxy)propan-2-ol, 2-(3-Chloro-4-(9-((4-chloropyridin-2-yl)methyl)-6-(1-methylcyclopropoxy)-9H-purin-8-yl)phenyl)acetamide, 1-(3-(3-Chloro-4-(6-(1-methylcyclopropoxy)-9-((4-methylpyridin-2-yl)methyl)-9H-purin-8-yl)phenoxy)azetidin-1-yl)-2-hydroxyethan-1-one, 1-(3-(3-Chloro-4-(6-(1-methylcyclopropoxy)-9-((4-methylpyridin-2-yl)methyl)-9H-purin-8-yl)phenoxy)azetidin-1-yl)ethan-1-one, (S)-5-(3-Chloro-4-(6-(1-methylcyclopropoxy)-9-((4-methylpyridin-2-yl)methyl)-9H-purin-8-yl)phenoxy)piperidin-2-one, 5-(3-Chloro-4-(6-(1-methylcyclopropoxy)-9-((4-methylpyridin-2-yl)methyl)-9H-purin-8-yl)phenoxy)tetrahydropyrimidin-2(1H)-one, 5-(3-Chloro-4-(9-(3-chlorobenzyl)-6-(1-methylcyclopropoxy)-9H-purin-8-yl)phenoxy)pentanoic acid, 4-(3-Chloro-4-(9-(3-chlorobenzyl)-6-(1-methylcyclopropoxy)-9H-purin-8-yl)phenoxy)butanoic acid, 1-(3-Chloro-4-(6-(1-methylcyclopropoxy)-9-((4-methylpyridin-2-yl)methyl)-9H-purin-8-yl)phenoxy)-2-methylpropan-2-ol, 2-(2-(3-Chloro-4-(9-(3-chlorobenzyl)-6-(1-methylcyclopropoxy)-9H-purin-8-yl)phenoxy)ethoxy)acetic acid.

(R)-4-(3-chloro-4-(9-(5-chloro-2-methoxybenzyl)-6-(1-methylcyclopropoxy)-9H-purin-8-yl)phenoxy)-2-methylbutanoic acid, (S)-4-(3-chloro-4-(9-(5-chloro-2-methoxybenzyl)-6-(1-methylcyclopropoxy)-9H-purin-8-yl)phenoxy)-2-methylbutanoic acid, 3-(2-Chloro-3-(9-(5-chloro-2-methoxybenzyl)-6-(1-methylcyclopropoxy)-9H-purin-8-yl)phenoxy)propanoic acid, (R)-4-(2-chloro-3-(9-(5-chloro-2-methoxybenzyl)-6-(1-methylcyclopropoxy)-9H-purin-8-yl)phenoxy)-3-methylbutanoic acid, (S)-4-(2-chloro-3-(9-(5-chloro-2-methoxybenzyl)-6-(1-methylcyclopropoxy)-9H-purin-8-yl)phenoxy)-3-methylbutanoic acid, (1s,3s)-3-(2-chloro-3-(9-(5-chloro-2-methoxybenzyl)-6-(1-methylcyclopropoxy)-9H-purin-8-yl)phenoxy)cyclobutane-1-carboxylic acid, (R)-4-(2-Chloro-3-(9-(5-chloro-2-cyanobenzyl)-6-(1-methylcyclopropoxy)-9H-purin-8-yl)phenoxy)-2-methylbutanoic acid, (S)-4-(2-Chloro-3-(9-(5-chloro-2-cyanobenzyl)-6-(1-methylcyclopropoxy)-9H-purin-8-yl)phenoxy)-2-methylbutanoic acid, and pharmaceutically acceptable salts thereof.

It is to be understood that any of definitions, claims, aspects or embodiments of the variable groups of the formulae disclosed herein, may be combined with any other definitions, claims, aspects or embodiments herein (unless the context does not permit) to provide further embodiments of the specification.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulfate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, sulfate/hydrogensulfate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic acid, sulfosalicylic acid, and the like.

Pharmaceutically acceptable base addition salts can be formed with inorganic and organic bases. Inorganic bases from which salts can be derived include, for example, ammonia and salts of ammonium and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the compounds disclosed herein can be synthesized from a basic or acidic moiety, by conventional chemical methods. Generally, such salts can be prepared by reacting free acid forms of these compounds with a stoichiometric amount of the appropriate base (such as $Na^+$, $Ca^{2+}$, $Mg^{2+}$, or $K^+$ hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); Berge et al., "J. Pharm. Sci., 1977, 66, 1-19 and in "Handbook of Pharmaceutical Salts: Properties, Selection, and Use" by Stahl and Wermuth (Wiley-VCH, Weinheim, Germany, 2002).

It is also to be understood that certain compounds disclosed herein, and pharmaceutically salts thereof, can exist in solvated as well as unsolvated forms such as, for example, hydrated and anhydrous forms. It is to be understood that the compounds herein encompass all such solvated forms. For the sake of clarity, this includes both solvated (e.g., hydrated) forms of the free form of the compound, as well as solvated (e.g., hydrated) forms of the salt of the compound.

Any formula given herein is also intended to represent unlabeled forms as well as isotopically labeled forms for the compounds disclosed herein. Isotopically labeled compounds have structures depicted by the formulas given herein except that one or more atoms are replaced by an atom of the same element but with differing mass number. Examples of isotopes that can be incorporated into the compounds disclosed herein and their pharmaceutically acceptable salts include isotopes of hydrogen, carbon, nitrogen, oxygen, phosphorous, sulfur, fluorine, chlorine and iodine, such as $^2H$, $^3H$, $^{11}C$, $^{13}C$, $^{14}C$, $^{15}N$, $^{35}S$, $^{36}Cl$ and $^{125}I$. Isotopically labeled compounds disclosed herein can generally be prepared by conventional techniques known to those skilled in the art or by processes analogous to those described in the accompanying Examples using appropriate isotopically labeled reagents in place of the non-labeled reagents previously employed.

The compounds disclosed herein may have different isomeric forms. The language "optical isomer," "stereoisomer" "enantiomer" or "diastereoisomer" refers to any of the various stereoisomeric configurations which may exist for a given compound disclosed herein. It is understood that a substituent may be attached at a chiral center of a carbon atom and, therefore, the disclosed compounds include enantiomers, diastereomers and racemates. The term "enantiomer" includes pairs of stereoisomers that are non-superimposable mirror images of each other. A 1:1 mixture of a pair of enantiomers is a racemic mixture. The (+/−) term is used to designate a racemic mixture where appropriate. The terms "diastereomers" or "diastereoisomers" include stereoisomers that have at least two asymmetric atoms, but which are not mirror images of each other. The absolute stereochemistry is specified according to the Cahn-Ingold-Prelog R—S system. When a compound is a pure enantiomer, the stereochemistry at each chiral center may be specified by either R or S. Resolved compounds whose absolute configuration is unknown can be designated (+) or (−) depending on the direction (dextro- or levorotatory) which they rotate plane polarized light at the wavelength of the sodium D line. Certain compounds disclosed herein have been isolated or prepared as a single enantiomer, but have unknown absolute configuration. In some instances, these compounds are labelled as (Isomer 1) or (Isomer 2). In the case of a single enantiomer so labelled, is to be understood that it could be either the R or S enantiomer. For example, 8-(2-chloro-4-(2-(piperazin-1-yl)ethoxy)phenyl)-6-(1-methylcyclopropoxy)-9-(1-(pyridin-2-yl)propan-2-yl)-9H-purine (Isomer 1) (Example S8), could be (R)-8-(2-chloro-4-(2-(piperazin-1-yl)ethoxy)phenyl)-6-(1-methylcyclopropoxy)-9-(1-(pyridin-2-yl)propan-2-yl)-9H-purine or (S)-8-(2-chloro-4-(2-(piperazin-1-yl)ethoxy)phenyl)-6-(1-methylcyclopropoxy)-9-(1-(pyridin-2-yl)propan-2-yl)-9H-purine and 8-(2-chloro-4-(2-(piperazin-1-yl)ethoxy)phenyl)-6-(1-methylcyclopropoxy)-9-(1-(pyridin-2-yl)propan-2-yl)-9H-purine (Isomer 2) (Example S7), could be (S)-8-(2-chloro-4-(2-(piperazin-1-yl)ethoxy)phenyl)-6-(1-methylcyclopropoxy)-9-(1-(pyridin-2-yl)propan-2-yl)-9H-purine or (R)-8-(2-chloro-4-(2-(piperazin-1-yl)ethoxy)phenyl)-6-(1-methylcyclopropoxy)-9-(1-(pyridin-2-yl)propan-2-yl)-9H-purine.

It is understood that one of skill in the art could determine optical rotation and/or absolute stereochemistry. It is understood that such a disclosure includes other stereoisomeric forms of the same compound, as well as stereoisomeric mixtures. Certain of the compounds disclosed herein contain one or more asymmetric centers or axes and may thus give rise to enantiomers, diastereomers or other stereoisomeric forms that may be defined, in terms of absolute stereochemistry, as (R)- or (S)-. The present disclosure is meant to include all such possible isomers, including racemic mixtures, optically pure forms and intermediate mixtures. Optically active (R)- and (S)-isomers may be prepared using chiral synthons or chiral reagents, or resolved using conventional techniques well known in the art, such as chiral HPLC.

Pharmaceutical Compositions

In some embodiments, disclosed are pharmaceutical compositions comprising a compound disclosed herein and a pharmaceutically acceptable carrier.

The language "pharmaceutically acceptable carrier" includes compounds, materials, compositions, and/or dosage forms which are, within the scope of sound medical judgment, suitable for use in contact with the tissues of human beings and animals without excessive toxicity, irritation, allergic response, or other problem or complication, as ascertained by one of skill in the art.

The disclosed compositions may be in a form suitable for oral use (for example, as tablets, lozenges, hard or soft capsules, aqueous or oily suspensions, emulsions, dispersible powders or granules, syrups or elixirs), for topical use (for example, as creams, ointments, gels, or aqueous or oily solutions or suspensions), for administration by inhalation (for example, as a finely divided powder or a liquid aerosol), for administration by insufflation (for example, as a finely divided powder) or for parenteral administration (for example, as a sterile aqueous or oily solution for intravenous, subcutaneous, intramuscular or intramuscular dosing or as a suppository for rectal dosing).

The amount of active ingredient that is combined with one or more pharmaceutically acceptable carriers to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The pharmaceutical formulations of the compounds disclosed herein may conveniently be administered in unit dosage form and may be prepared by any of the methods well-known in the pharmaceutical art, for example as described in Remington's Pharmaceutical Sciences, 17th ed., Mack Publishing Company, Easton, PA., (1985).

Pharmaceutical formulations suitable for oral administration may comprise one or more physiologically compatible carriers and/or excipients and may be in solid or liquid form. Tablets and capsules may be prepared with binding agents, fillers, lubricants and/or surfactants, such as sodium lauryl sulfate. Liquid compositions may contain conventional additives such as suspending agents, emulsifying agents and/or preservatives. Liquid compositions may be encapsulated in, for example, gelatin to provide a unit dosage form. Solid oral dosage forms include tablets, two-piece hard shell capsules and soft elastic gelatin (SEG) capsules. Such two-piece hard shell capsules may be made for example by filling a compound of Formula (I) into a gelatin or hydroxypropyl methylcellulose (HPMC) shell.

Therapeutic Utilities

The term "subject" includes warm blooded mammals, for example, primates, dogs, cats, rabbits, rats, and mice. In some embodiments, the subject is a primate, for example, a human. In some embodiments, the subject is suffering from cancer. In some embodiments, the subject is in need of treatment (e. g., the subject would benefit biologically or medically from treatment). In some embodiments, the subject is suffering from cancer.

The language "treat," "treating" and "treatment," as well as "alleviating" or "to alleviate" both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, this includes amelioration of one or more symptoms of a cancer, or the slowing or delaying of progression of cancer in a subject. The language "treat," "treating," "treatment," "alleviating," and "to alleviate" also includes the reduction or inhibition of the growth of a tumor or proliferation of cancerous cells in a subject. In certain aspects, a subject is successfully "treated" for cancer according to the methods of the present disclosure if the patient shows, e. g., total, partial, or transient remission of a certain type of cancer.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof. In certain embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer exhibits homologous recombination repair deficiency (HRD).

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is a solid cancer, such as breast, ovarian, pancreatic, or prostate cancer. In certain embodiments, the cancer is a breast, ovarian, pancreatic, or prostate cancer comprising a BRCA1 and/or BRCA2 mutation. In other embodiments, the cancer is a breast, ovarian, pancreatic, or prostate cancer comprising a BRCA1 mutation. In still other embodiments, the cancer is a breast, ovarian, pancreatic, or prostate cancer comprising a BRCA2 mutation.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is breast cancer. In further embodiments, the cancer is BRCA1 and/or BRCA2-positive breast cancer. In other embodiments, the cancer is BRCA1-positive breast cancer. In still other embodiments, the cancer is BRCA2-positive breast cancer.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is ovarian cancer. In further embodiments, the cancer is BRCA1 and/or BRCA2-positive ovarian cancer. In other embodiments, the cancer is BRCA1-positive ovarian cancer. In still other embodiments, the cancer is BRCA2-positive ovarian cancer.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is pancreatic cancer. In further embodiments, the cancer is BRCA1 and/or BRCA2-positive pancreatic cancer. In other embodiments, the cancer is BRCA1-positive pancreatic cancer. In still other embodiments, the cancer is BRCA2-positive pancreatic cancer.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is prostate cancer. In further embodiments, the cancer is BRCA1 and/or BRCA2-positive prostate cancer. In other embodiments, the cancer is BRCA1-positive prostate cancer. In still other embodiments, the cancer is BRCA2-positive prostate cancer.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is PARP inhibitor (PARPi) resistant. In some embodiments, the PARPi resistant cancer is PARPi-resistant ovarian cancer. In some embodiments, the PARPi resistant cancer is PARPi-resistant breast cancer. In some embodiments, the PARPi resistant cancer is PARPi-resistant prostate cancer. In some embodiments, the PARPi resistant cancer is PARPi-resistant pancreatic cancer.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the method comprises treating a subject with primary and secondary solid tumors. In still other embodiments, the method comprises treating subjects with primary solid tumors. In yet other embodiments, the method comprises treating subjects with secondary solid tumors.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is Ataxia Telangiectasia Mutated (ATM) mutation-positive. In certain embodiments, the ATM mutation-positive cancer is a hematological cancer, such as leukemia or lymphoma. In certain embodiments, the ATM mutation-positive cancer is acute leukemia, chronic lymphocytic leukemia (CLL), acute myeloid leukemia (AML) or myelodysplastic syndrome (MDS). In other embodiments, the ATM mutation-positive cancer is a solid cancer. In certain embodiments, the ATM mutation-positive cancer is lung cancer, gastric cancer, stomach cancer, breast cancer, ovarian cancer, colorectal cancer, melanoma, or sarcoma.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is positive for a mutation in genes coding for Fanconi anemia (FA) proteins or FA-like genes, including FANCA, FANCB, FANCC, FANCD1 (BRCA2), FANCD2, FANCE, FANCF, FANCG, FANCI, FANJ (BRIP1), FANCL, FANCM, FANCN (PALB2), FANCP (SLX4), and FANCS (BRCA1).

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is positive for a mutation in genes coding for DNA repair proteins, including RAD50, RAD51, RAD51B, RAD51C, RAD51D, RAD51L1, RAD51L2, RAD51L3, XRCC2, XRCC3, RAD52, RAD54, RAD54L, RAD54B, MRE11, NBS1, DMC1, CTIP (CTBP-interacting Protein), PALB2 (Partner and Localizer of BRCA2), RECQL4 (RecQ Protein-like 4), BLM (Bloom syndrome, RecQ helicase-like), WRN (Werner syndrome, RecQ helicase-like), NBS1 (Nibrin), and EMSY.

In some embodiments, there is provided a method of treating cancer in a subject in need thereof comprising administering a therapeutically effective amount of a compound of Formula (I), a compound disclosed herein, a stereoisomer thereof, or a pharmaceutically acceptable salt thereof, wherein the cancer is positive for a mutation in one or more genes associated with the double strand break (DSB) repair pathway, including AICDA, ALKBH3, APOBEC2, APOBEC4, APTX, ATF2, ATM, AURKA, BARD1, BRCA2, BRIP1, CBX3, CCNH, CDC16, CDC25A, CDC25B, CDC45, CDKN1A, CDKN2A, CHEK2, CLK2, CLSPN, CUL4A, CUL5, DCLRE1A, DCLRE1C, DDB1, DKC1, DNMT3A, DNMT3B, DUT, EME2, ENDOV, EP300, ERCC4, ERCC5, FAN1, FANCG, FANCL, FBXO18, FEN1, GADD45A, GINS1, GTF2H2, GTF2H3, GTF2H4, HDAC2, HDAC3, HDAC4, HELQ, INIP, INO80C, KDM4B, LIG3, LMO4, MAD2L2, MBD4, MGMT, MLH1, MNAT1, MPG, MRE11A, MSH2, MSH6, MTBP, MUTYH, NABP1, NBN, NEIL1, NEIL2, NEIL3, NEK1, NHEJ1, NTHL1, ORC6, PALB2, PARP2, PARP3, PAXIP1, PIF1, PMS2, POLB, POLE, POLK, POLL, POLM, POLN, PPP1CA, PRKDC, PRMT2, PROKR1, RAD21, RAD23B, RAD51, RAD51AP1, RAD52, RAD9A, RAD9B, RB1, RECQL4, RECQL5, REV1, RIF1, RINT1, RMI1, RNASEH1, RNASEH2A, RPA1, RPA2, RTEL1, SHPRH, SIRT6, SLX4, SMC5, SMG1, SMUG1, SPO11, SUMO1, SUMO2, SUV39H1, SUV420H2, SWI5, TDG, TELO2, THOC1, TICRR, TNKS, TNKS2, TOP1, TOP2A, TOP3A, TOP3B, TREX2, TRP53BP1, UBE2N, UNG, UVSSA, WRN, XAB2, XRCC2, XRCC3, and/or, XRCC5.

In some embodiments, there is provided a compound of Formula (I), a compound disclosed herein, a stereoisomer thereof, or a pharmaceutically acceptable salt thereof for use in treating cancer in a subject in need thereof. In some embodiments, there is provided a compound of Formula (I), a compound disclosed herein, a stereoisomer thereof, or a pharmaceutically acceptable salt thereof for use in treating cancer in a subject in need thereof wherein the cancer exhibits homologous recombination repair deficiency (HRD).

In some embodiments, there is provided compound of Formula (I), a compound disclosed herein, a stereoisomer thereof, or a pharmaceutically acceptable salt thereof for use in of treating cancer in a subject in need thereof, wherein the cancer is a solid cancer, such as breast, ovarian, pancreatic, or prostate cancer. In certain embodiments, the cancer is a breast, ovarian, pancreatic, or prostate cancer comprising a BRCA1 and/or BRCA2 mutation. In other embodiments, the cancer is a breast, ovarian, pancreatic, or prostate cancer comprising a BRCA1 mutation. In still other embodiments, the cancer is a breast, ovarian, pancreatic, or prostate cancer comprising a BRCA2 mutation.

In some embodiments, there is provided a compound of Formula (I), a compound disclosed herein, a stereoisomer thereof, or a pharmaceutically acceptable salt thereof for use in treating cancer in a subject in need thereof, wherein the cancer is breast cancer. In further embodiments, the cancer is BRCA1 and/or BRCA2-positive breast cancer. In other embodiments, the cancer is BRCA1-positive breast cancer. In still other embodiments, the cancer is BRCA2-positive breast cancer.

In some embodiments, there is provided a compound of Formula (I), a compound disclosed herein, a stereoisomer thereof, or a pharmaceutically acceptable salt thereof for use in treating cancer in a subject in need thereof, wherein the cancer is ovarian cancer. In further embodiments, the cancer is BRCA1 and/or BRCA2-positive ovarian cancer. In other embodiments, the cancer is BRCA1-positive ovarian cancer. In still other embodiments, the cancer is BRCA2-positive ovarian cancer.

In some embodiments, there is provided a compound of Formula (I), a compound disclosed herein, a stereoisomer thereof, or a pharmaceutically acceptable salt thereof for use in treating cancer in a subject in need thereof, wherein the cancer is pancreatic cancer. In further embodiments, the cancer is BRCA1 and/or BRCA2-positive pancreatic cancer. In other embodiments, the cancer is BRCA1-positive pancreatic cancer. In still other embodiments, the cancer is BRCA2-positive pancreatic cancer.

In some embodiments, there is provided a compound of Formula (I), a compound disclosed herein, a stereoisomer thereof, or a pharmaceutically acceptable salt thereof for use in treating cancer in a subject in need thereof, wherein the cancer is prostate cancer. In further embodiments, the cancer is BRCA1 and/or BRCA2-positive prostate cancer. In other embodiments, the cancer is BRCA1-positive prostate cancer. In still other embodiments, the cancer is BRCA2-positive prostate cancer.

In some embodiments, there is provided a compound of Formula (I), a compound disclosed herein, a stereoisomer thereof, or a pharmaceutically acceptable salt thereof for use in treating cancer in a subject in need thereof, wherein the cancer is a PARP inhibitor (PARPi) resistant cancer. In some embodiments, the PARPi resistant cancer is PARPi-resistant ovarian cancer. In some embodiments, the PARPi resistant cancer is PARPi-resistant breast cancer. In some embodiments, the PARPi resistant cancer is PARPi-resistant prostate cancer. In some embodiments, the PARPi resistant cancer is PARPi-resistant pancreatic cancer.

In some embodiments, there is provided a compound of Formula (I), a compound disclosed herein, a stereoisomer thereof, or a pharmaceutically acceptable salt thereof for use in treating cancer in a subject in need thereof, wherein the method comprises treating a subject with primary and secondary solid tumors. In still other embodiments, the method comprises treating subjects with primary solid tumors. In yet other embodiments, the method comprises treating subjects with secondary solid tumors.

In some embodiments, there is provided a compound of Formula (I), a compound disclosed herein, a stereoisomer thereof, or a pharmaceutically acceptable salt thereof for use in treating cancer in a subject in need thereof, wherein the cancer is Ataxia Telangiectasia Mutated (ATM) mutation-positive. In certain embodiments, the ATM mutation-positive cancer is a hematological cancer, such as leukemia or lymphoma. In certain embodiments, the ATM mutation-positive cancer is acute leukemia, chronic lymphocytic leukemia (CLL), acute myeloid leukemia (AML) or myelodysplastic syndrome (MDS). In other embodiments, the ATM mutation-positive cancer is a solid cancer. In certain embodiments, the ATM mutation-positive cancer is lung cancer, gastric cancer, stomach cancer, breast cancer, ovarian cancer, colorectal cancer, melanoma, or sarcoma.

In some embodiments, there is provided a compound of Formula (I), a compound disclosed herein, a stereoisomer thereof, or a pharmaceutically acceptable salt thereof for use in treating cancer in a subject in need thereof, wherein the cancer is positive for a mutation in genes coding for Fanconi anemia (FA) proteins or FA-like genes, including FANCA, FANCB, FANCC, FANCD1 (BRCA2), FANCD2, FANCE, FANCF, FANCG, FANCI, FANJ (BRIP1), FANCL, FANCM, FANCN (RALB2), FANCP (SLX4), and FANCS (BRCA1).

In some embodiments, there is provided a compound of Formula (I), a compound disclosed herein, a stereoisomer thereof, or a pharmaceutically acceptable salt thereof for use in treating cancer in a subject in need thereof, wherein the cancer is positive for a mutation in genes coding for DNA repair proteins, including RAD50, RAD51, RAD51B, RAD51C, RAD51D, RAD51L1, RAD51L2, RAD51L3, XRCC2, XRCC3, RAD52, RAD54, RAD54L, RAD54B, MRE11, NBS1, DMC1, CTIP (CTBP-interacting Protein), PALB2 (Partner and Localizer of BRCA2), RECQL4 (RecQ Protein-like 4), BLM (Bloom syndrome, RecQ helicase-like), WRN (Werner syndrome, RecQ helicase-like), NBS1 (Nibrin), and EMSY.

In some embodiments, there is provided a compound of Formula (I), a compound disclosed herein, a stereoisomer thereof, or a pharmaceutically acceptable salt thereof for use in treating cancer in a subject in need thereof wherein the cancer is positive for a mutation in one or more genes associated with the double strand break (DSB) repair pathway, including AICDA, ALKBH3, APOBEC2, APOBEC4, APTX, ATF2, ATM, AURKA, BARD1, BRCA2, BRIP1, CBX3, CCNH, CDC16, CDC25A, CDC25B, CDC45, CDKN1A, CDKN2A, CHEK2, CLK2, CLSPN, CUL4A, CUL5, DCLRE1A, DCLRE1C, DDB1, DKC1, DNMT3A, DNMT3B, DUT, EME2, ENDOV, EP300, ERCC4, ERCC5, FAN1, FANCG, FANCL, FBXO18, FEN1, GADD45A, GINS1, GTF2H2, GTF2H3, GTF2H4, HDAC2, HDAC3, HDAC4, HELQ, INIP, INO80C, KDM4B, LIG3, LMO4, MAD2L2, MBD4, MGMT, MLH1, MNAT1, MPG, MRE11A, MSH2, MSH6, MTBP, MUTYH, NABP1, NBN, NEIL1, NEIL2, NEIL3, NEK1, NHEJ1, NTHL1, ORC6, PALB2, PARP2, PARP3, PAXIP1, PIF1, PMS2, POLB, POLE, POLK, POLL, POLM, POLN, PPP1CA, PRKDC, PRMT2, PROKR1, RAD21, RAD23B, RAD51, RAD51AP1, RAD52, RAD9A, RAD9B, RB1, RECQL4, RECQL5, REV1, RIF1, RINT1, RMI1, RNASEH1, RNASEH2A, RPA1, RPA2, RTEL1, SHPRH, SIRT6, SLX4, SMC5, SMG1, SMUG1, SPO11, SUMO1, SUMO2, SUV39H1, SUV420H2, SWI5, TDG, TELO2, THOC1, TICRR, TNKS, TNKS2, TOP1, TOP2A, TOP3A, TOP3B, TREX2, TRP53BP1, UBE2N, UNG, UVSSA, WRN, XAB2, XRCC2, XRCC3, and/or, XRCC5.

Combination Therapy

The compounds of Formula (I), a compound disclosed herein, a stereoisomer thereof, or a pharmaceutically acceptable salt thereof, may also be administered in conjunction with other compounds used for the treatment of the above conditions.

In some embodiments, there is provided a method of treating cancer in a subject in need thereof comprising administering a combination of a therapeutically effective amount of a compound of Formula (I), a compound disclosed herein, a stereoisomer thereof, or a pharmaceutically acceptable salt thereof and a second active ingredient, wherein the compound and second active ingredient are administered concurrently, sequentially or in admixture.

In some embodiments, there is provided a method of treating cancer in a subject in need thereof comprising administering a combination of a therapeutically effective amount of a compound of Formula (I), a compound disclosed herein, a stereoisomer thereof, or a pharmaceutically acceptable salt thereof and a PARP inhibitor, wherein the compound and second active ingredient are administered concurrently, sequentially or in admixture. In certain embodiments, the PARP inhibitor is olaparib, AZD9574 (WO 2021/260092), AZD5305 (WO 2021/013735), talazoparib, niraparib, or rucaparib. In other embodiments, the PARP inhibitor is olaparib, AZD9674, or AZD5305. In particular embodiments, the cancer is breast, ovarian, pancreatic, or prostate cancer. In certain embodiments, the PARP inhibitor is olaparib and the cancer is breast, ovarian, pancreatic, or prostate cancer. In other embodiments, the PARP inhibitor is niraparib and the cancer is ovarian cancer. In other embodiments, the PARP inhibitor is rucaparib and the cancer is ovarian cancer or prostate cancer. In other embodiments, the PARP inhibitor is talazoparib and the cancer is breast cancer or prostate cancer.

In some embodiments, there is provided a method of treating cancer in a subject in need thereof comprising administering a combination of a therapeutically effective amount of a compound of Formula (I), a compound disclosed herein, a stereoisomer thereof, or a pharmaceutically acceptable salt thereof and an ATR inhibitor, wherein the compound and second active ingredient are administered concurrently, sequentially or in admixture. In certain embodiments, the ATR inhibitor is AZD6738 (WO 2011/154737).

In some embodiments, there is provided a method of treating cancer in a subject in need thereof comprising administering a combination of a therapeutically effective amount of a compound of Formula (I), a compound disclosed herein, a stereoisomer thereof, or a pharmaceutically acceptable salt thereof and an DNA-PK inhibitor, wherein the compound and second active ingredient are administered concurrently, sequentially or in admixture. In certain embodiments, the DNA-PK inhibitor is AZD7648 (WO 2018/114999).

In some embodiments, there is provided a method of treating cancer in a subject in need thereof comprising administering a combination of a therapeutically effective amount of a compound of Formula (I), a compound disclosed herein, a stereoisomer thereof, or a pharmaceutically acceptable salt thereof and an antibody drug conjugate, wherein the compound and antibody drug conjugate are administered concurrently, sequentially or in admixture. In certain embodiments, the antibody drug conjugate is trastuzumab deruxtecan (T-DXd) In certain embodiments, the antibody drug conjugate is a TOPOisomerase antibody drug conjugate. In particular embodiments, the cancer is breast cancer, gastric cancer or non-small cell lung cancer (NSCLC).

In some embodiments, there is provided a method of treating cancer in a subject in need thereof comprising administering a combination of a therapeutically effective amount of a compound of Formula (I), a compound disclosed herein, a stereoisomer thereof, or a pharmaceutically acceptable salt thereof and a platinum-based anti-cancer drug, wherein the compound and platinum-based anti-cancer drug are administered concurrently, sequentially or in admixture. In certain embodiments, the platinum-based anti-cancer drug is cisplatin, carboplatin, oxaliplatin, nedaplatin, lobaplatin, triplatin tetranitrate, triplatin tetranitrate, picoplatin, or satraplatin.

In some embodiments, there is provided a method of treating cancer in a subject in need thereof comprising administering a combination of a therapeutically effective amount of a compound of Formula (I), a compound disclosed herein, a stereoisomer thereof, or a pharmaceutically acceptable salt thereof and a taxane, wherein the compound and platinum-based anti-cancer drug are administered concurrently, sequentially or in admixture. In certain embodiments, the taxane is docetaxel.

In some embodiments, there is provided a method of treating cancer in a subject in need thereof comprising administering a combination of a therapeutically effective amount of a compound of Formula (I), a compound disclosed herein, a stereoisomer thereof, or a pharmaceutically acceptable salt thereof in combination with immunotherapy, wherein the compound and immunotherapy are administered concurrently, sequentially or in admixture. In certain embodiments, the immunotherapy is an antibody, such as durvalumab. In particular embodiments, the immunotherapy is durvalumab and the cancer is non-small cell lung cancer (NSCLC).

In some embodiments, there is provided a compound of Formula (I), a compound disclosed herein, a stereoisomer thereof, or a pharmaceutically acceptable salt thereof for use in treating cancer in a subject in need thereof in combination with a second active ingredient, wherein the compound and second active ingredient are administered concurrently, sequentially or in admixture.

In some embodiments, there is provided a compound of Formula (I), a compound disclosed herein, a stereoisomer thereof, or a pharmaceutically acceptable salt thereof for use in treating cancer in a subject in need thereof in combination with a PARP inhibitor, wherein the compound and second active ingredient are administered concurrently, sequentially or in admixture. In certain embodiments, the PARP inhibitor is olaparib, AZD9574 (WO 2021/260092), AZD5305 (WO 2021/013735), talazoparib, niraparib, or rucaparib. In other embodiments, the PARP inhibitor is olaparib, AZD9674, or AZD5305. In certain embodiments, the PARP inhibitor is olaparib and the cancer is breast, ovarian, pancreatic, or prostate cancer. In other embodiments, the PARP inhibitor is niraparib and the cancer is ovarian cancer. In other embodiments, the PARP inhibitor is rucaparib and the cancer is ovarian cancer or prostate cancer. In other embodiments, the PARP inhibitor is talazoparib and the cancer is breast cancer or prostate cancer.

In some embodiments, there is provided a compound of Formula (I), a compound disclosed herein, a stereoisomer thereof, or a pharmaceutically acceptable salt thereof for use in treating cancer in a subject in need thereof in combination with an ATR inhibitor, wherein the compound and second active ingredient are administered concurrently, sequentially or in admixture. In certain embodiments, the ATR inhibitor is AZD6738 (WO 2011/154737).

In some embodiments, there is provided a compound of Formula (I), a compound disclosed herein, a stereoisomer thereof, or a pharmaceutically acceptable salt thereof for use in treating cancer in a subject in need thereof in combination with an DNA-PK inhibitor, wherein the compound and second active ingredient are administered concurrently, sequentially or in admixture. In certain embodiments, the DNA-PK inhibitor is AZD7648 (WO 2018/114999).

In some embodiments, there is provided a compound of Formula (I), a compound disclosed herein, a stereoisomer thereof, or a pharmaceutically acceptable salt thereof for use in treating cancer in a subject in need thereof in combination with an antibody drug conjugate, wherein the compound and antibody drug conjugate are administered concurrently, sequentially or in admixture. In certain embodiments, the antibody drug conjugate is trastuzumab deruxtecan (T-DXd) In certain embodiments, the antibody drug conjugate is a TOPOisomerase antibody drug conjugate. In particular embodiments, the cancer is breast cancer, gastric cancer or non-small cell lung cancer (NSCLC).

In some embodiments, there is provided a compound of Formula (I), a compound disclosed herein, a stereoisomer thereof, or a pharmaceutically acceptable salt thereof for use in treating cancer in a subject in need thereof in combination with a platinum-based anti-cancer drug, wherein the compound and platinum-based anti-cancer drug are administered concurrently, sequentially or in admixture. In certain embodiments, the platinum-based anti-cancer drug is cisplatin, carboplatin, oxaliplatin, nedaplatin, lobaplatin, triplatin tetranitrate, triplatin tetranitrate, picoplatin, or satraplatin. In particular embodiments, the platinum-based anti-cancer drug is carboplatin.

In some embodiments, there is provided a compound of Formula (I), a compound disclosed herein, a stereoisomer thereof, or a pharmaceutically acceptable salt thereof for use in treating cancer in a subject in need thereof in combination with a taxane, wherein the compound and platinum-based anti-cancer drug are administered concurrently, sequentially or in admixture. In certain embodiments, the taxane is docetaxel.

In some embodiments, there is provided compound of Formula (I), a compound disclosed herein, a stereoisomer thereof, or a pharmaceutically acceptable salt thereof for use in of treating cancer in a subject in need thereof in combination with immunotherapy, wherein the compound and immunotherapy are administered concurrently, sequentially or in admixture. In certain embodiments, the immunotherapy is an antibody, such as durvalumab. In particular embodiments, the immunotherapy is durvalumab and the cancer is non-small cell lung cancer (NSCLC).

Another aspect of the present specification provides a process for preparing a compound of the Formula (I), or a pharmaceutically acceptable salt thereof. A suitable process is illustrated by the following representative process variants in which, unless otherwise stated, G, $G_a$, $G_b$, $Q^1$, $Q^2$, $Q^3$ and $R^1$, $R^2$, $R^a$, $R^b$, $R^c$, $R^d$, X, Y $Z_a/Z_{aa}$, $Z_b/Z_{bb}$, $Z_c/Z_{cc}$ have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

(I)

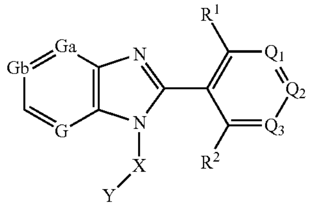

Compounds of Formula (I) may be made by, for example:

a) 1. by reaction of another compound of formula (I) where $Q^1$, $Q^2$ or $Q^3$ is C—OH with a primary or secondary alcohol under conditions known in the art as suitable for Mitsunobu reaction (e. g. Example 1);

or by reaction with a primary or secondary halide under typical conditions for nucleophilic substitution, e. g. a suitable solvent such as DMA or DMF in the presence of a suitable base, for example potassium carbonate or cesium carbonate at a suitable temperature (0-120° C.) with or without a protecting group for other functionalities.

2. by reaction of another compound of formula (I) where $Q^1$, $Q^2$ or $Q^3$ is C-LG, LG being a leaving group such as halogen, with an suitable amine (e. g. Example 19) under conditions known in the art, optionally catalysed by metal complexes such as palladium catalysts suitable for Buchwald-Hartwig amination reactions.

3. by reaction of another compound of formula (I) where $Q^1$, $Q^2$ or $Q^3$ is C-LG, LG being a leaving group such as halogen, with a suitable alcohol (e. g. Example 20) under conditions known in the art (e. g. reaction in the presence of a strong base such sodium hydride to form the alkoxide), optionally catalysed by metal complexes such as palladium catalysts (e. g. RockPhos Pd G3) suitable for ether formation reactions.

More generally, a compound of Formula (I) can be made from a compound of Formula (I) (e. g. amide coupling in Example N1, reductive amination in Example N6).

Compound of formula (I) where $Q^1$, $Q^2$ or $Q^3$ is C—OH or where $Q^1$, $Q^2$ or $Q^3$ is C-LG can be made by methods illustrated thereafter b) When $G_a$ is $CR^5$ and $R^5$ is

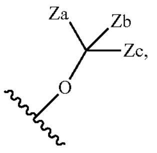

by reaction of another compound of formula (II) with a compound of formula (III), where LG is a leaving group known to the art, for example halide such as F, Cl or Br, or trifluoromethanesulfonate (triflate). Conditions for the reaction may use a suitable solvent (for example THF) in the presence of a suitable base (for example sodium hydride or LHMDS) and a suitable temperature (such as from 0° C. to ambient temperature), with or without a protecting group for other functionalities.

(II)

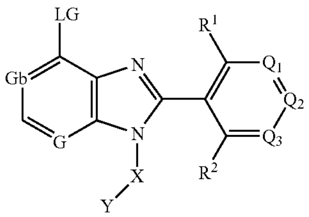

(III)

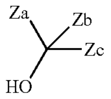

Compound of formula (II) can be made by reaction of compound of formula (IV) with compound of formula (V). Conditions for the reaction involved a one-step procedure as described in paragraph (d). The reaction can be converted in a two-step procedure with the isolation of intermediate compound of formula (VI). Conditions for the reaction are described in paragraph (d).

Alternatively, compound of formula (II) can be made by reaction of compound of formula (IVa) with compound of formula (V). Conditions for the reaction are described in paragraph (d).

(IV)

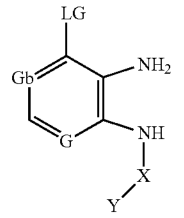

(V)

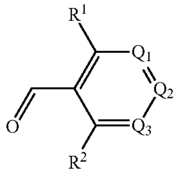

(VI)

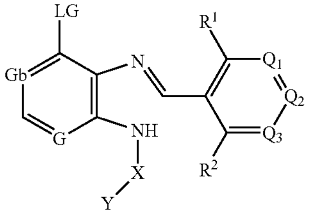

Alternatively, compound of formula (IV) can be made by reaction of formulae (IVa) by reduction of the nitro group to the amino group, as described in paragraph (d)

(IVa)

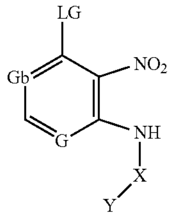

When X=$CH_2$, compound of formula (IVa) can be made from reaction between compound of formula (VII) and compound of formula (VIIIa) under conditions known in the art as suitable for reductive amination.

Alternatively compound of formula (IVa) can be made from reaction between compound of formula (VIIa) and compound of formula (VIII). Conditions for the reaction may use an inert solvent (for example DMF) in the presence of a base (such as triethylamine) and a suitable temperature (e. g. room temperature).

(VII)

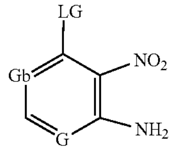

-continued (VIIa)

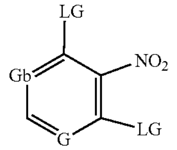

(VIII)

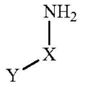

(VIIIa)

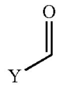

Alternatively compounds (II) can be obtained from reaction between compound of formula (IIa) and compound of formula (VIIIb) under conditions known in the art as suitable for nucleophilic substitution or from reaction between compound of formula (IIa) and compound of formula (VIIIc) under conditions known in the art as suitable for Mitsunobu reactions.

(IIa)

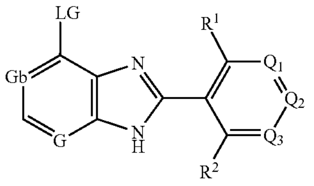

(VIIIb)

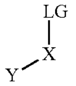

(VIIIc)

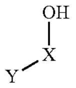

c) When $G_b$ is $CR^5$ and $R^5$ is

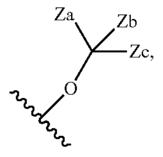

by reaction of another compound of formula (IX) with a compound of formula (X) under conditions known in the art as suitable for Mitsunobu reaction, or by reaction nucleophilic substitution reaction of another compound of formula (IX) with a compound of formula (Xa), where LG is a leaving group known to the art, for example halide such as Cl, Br or I). Conditions for the nucleophilic substitution reaction may use a suitable solvent (for example acetonitrile, DMF or DMA) in the presence of a suitable base (for example potassium carbonate) and a suitable temperature (between 0-120° C.) with or without a protecting group for other functionalities.

(IX)

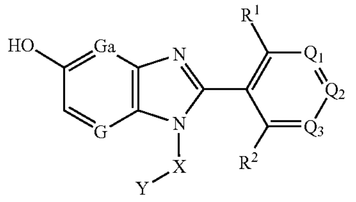

(X)

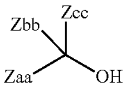

(Xa)

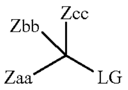

Compound of formula (IX) can be made by reaction of compound of formula (XI) with compound of formula (V), with or without a protecting group for the hydroxy group.

Compound of formula (IX) can also be made by reaction of compound of formula (XIa) with compound of formula (V), with or without a protecting group for the hydroxy group.

Alternatively compound of formula (XI) can be made from compound of formula (XIa) by reduction of the nitro group to the amino group.

Conditions for the above reactions are illustrated in paragraph (d).

(XI)

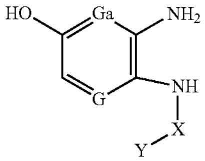

(XIa)

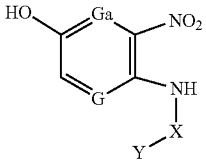

Compound of formula (XIa) can be made by reaction of compound of formula (XII) with compound of formula (VIII) where LG is a leaving group known to the art, for example halide (such as F or Cl) or trifluoromethanesulfonate (triflate); with or without a protecting group for the hydroxy group.

(XII)

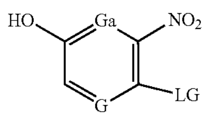

(VIII)

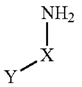

d) by reaction of compound of formula (XIII) with compound of formula (V). Conditions for the reaction involved one step procedure and may use a suitable solvent (for example EtOH, isopropanol, dioxane or DMSO) and a suitable temperature (60-120° C.), optionally in the presence of a mild oxidant (such as iron(III) chloride and/or atmospheric oxygen) and/or an acid (e. g. p-toluenesulfonic acid, acetic acid) and/or a catalyst (e. g. copper(II) acetate in Example 8). The reaction can be converted in a two-step procedure with the isolation of intermediate compound of formula (XIV), where a mild oxidant (e. g. iron(III) chloride and/or oxygen) is added for the second step.

Alternatively by reaction of compound of formula (XIIIa) with compound of formula (V) for the reaction may use a suitable solvent (for example NMP and water) in the presence of a mild reducing agent such as sodium dithionate (also known as sodium hydrosulfite) at a suitable temperature (e. g. 80-120° C.).

Alternatively compound of formula (XIII) can be made from compound of formula (XIIIa) by reduction of the nitro group to the amino group (e. g. in the presence of iron with a suitable solvent such as ethanol)

(XIII)

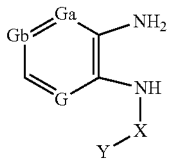

(XIIIa)

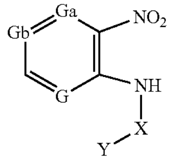

(XIV)

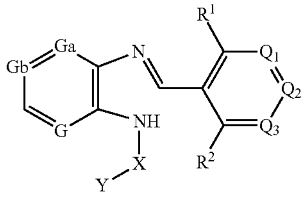

Compound of formula (XIIIa) can be made by reaction of compound of formula (XV) and another compound of formula (VIII) where LG is a leaving group known to the art, for example halide (such as F or Cl) or trifluoromethanesulfonate (triflate) or methanesulfonyl.

(XV)

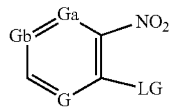

When $G_a$ is $CR^5$ and $R^5$ is

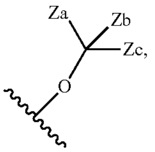

compound of formula (XIIIa) can be made by reaction of compound of formula (IVa) with compound of formula (III). Conditions for the reaction may use a suitable solvent (for example THF) in the presence of a suitable base (for example sodium hydride or LHMDS) and a suitable temperature (such around ambient temperature) with or without a protecting group for other functionalities (IVa)

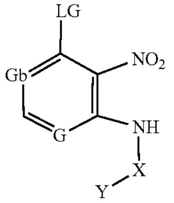

(III)

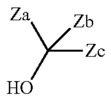

When $G_a$ is $CR^5$ and $R^5$ is

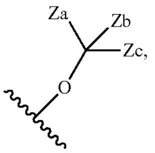

compound of formula (XIIIa) can also be made by reaction of another compound of formula (XVI) with a compound of formula (III) under conditions known in the art as suitable for Mitsunobu reaction, or by reaction (nucleophilic substitution) of another compound of formula (XVI) with a compound of formula (IIIa), where LG is a leaving group known to the art, for example halide such as Cl, Br or I). Conditions for the nucleophilic substitution reaction may use a suitable solvent (for example acetonitrile, DMF or DMA) in the presence of a suitable base (for example potassium carbonate) and a suitable temperature (between 0-120° C.) with or without a protecting group for other functionalities (XVI)

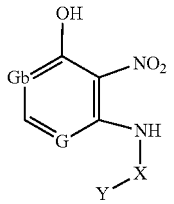

-continued (IIIa)

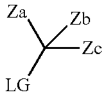

Compound of formula (XVI) can be made by reaction of another compound of formula (XVII) and another compound of formula (VIII) with or without a protecting group for the hydroxyl and other functionalities (XVII)

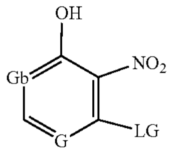

(e) by reaction of compound of formula (XVIII), when LG is a leaving group known to the art for example halide such as Cl, Br or I, with compound of formula (XIX) when FG is a functional group suitable for cross-couplings reactions (e. g. Suzuki reaction) such as a boronate ester or boronic acid. Conditions of the reaction are illustrated in Example 5.

(XVIII)

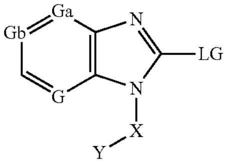

(XIX)

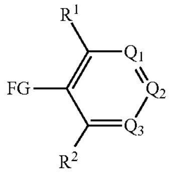

Compound of formula (XVIII) can be made from compound of formula (XX), for example by bromination (when LG is Br) as described in Example 5.

(XX)

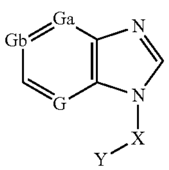

(f) from reaction between compound of formula (XXI) and compound of formula (VIIIb) under conditions known in the art as suitable for nucleophilic substitution (e. g. Example 23).

or from reaction between compound of formula (XXI) and compound of formula (VIIIc) under conditions known in the art as suitable for Mitsunobu reactions.

(XXI)

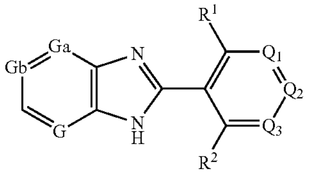

(VIIIb)

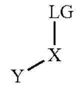

(VIIIc)

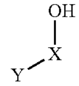

It is understood that compound of formula (XXI), by analogy with compound of formula (I), may be made by reaction already illustrated in the paragraphs (a) to (e).

EXAMPLES

The compounds described in this specification are further illustrated in the following Examples. These Examples are given by way of illustration only and are non-limiting. In general:

General Experimental Conditions and Abbreviations

The compounds described in this specification are further illustrated in the following Examples. The compounds were named using Chemdraw version 20.0.2.51. These Examples are given by way of illustration only and are non-limiting. In general:

Reagents and solvents (all anhydrous HPLC-grade) were obtained from commercial suppliers and used without any further purification unless otherwise stated. All reagents were weighed and handled in air unless otherwise stated. Brine refers to a saturated solution of NaCl. Concentration under reduced pressure refers to the use of a rotary evaporator.

Operations were carried out at ambient temperature, i. e. in the range 17 to 25° C. and under an atmosphere of an inert gas such as nitrogen unless otherwise stated.

Evaporations were carried out by rotary evaporation under reduced pressure utilising a warm or hot water bath or utilising Genevac equipment or Biotage v10 evaporator in vacuo and work up procedures were carried out after removal of residual solids by filtration.

Flash chromatographic purifications were performed on an automated Teledyne Isco CombiFlash® Rf, Teledyne Isco CombiFlash® Companion® or CHEETAH® MP200 system with integrated UV detection using prepacked silica gel columns (40-60 μm) or C18 spherical (20-35 μm) using the chromatographic conditions as detailed in corresponding experimental data.

Preparative reverse phase HPLC was performed on an Agilent 1290 Infinity II Preparative system equipped with a SQ MS detector (Multimode ESI/APCI source), with a Waters CSH C18 OBD column (5 microns silica, 30 mm diameter, 100 mm length); Waters MassLynx system with integrated MS detection, with a XBridge or Xselect CSH Prep C18 OBD column (5 μm silica, 30 mm diameter, 150 mm length); Gilson GX-281 with integrated UV detection, with either XBridge (10 μm, 19 mm diameter, 150 mm length) or Sunfire C18 columns (10 μm, 19 mm diameter, 250 mm length) using decreasingly polar mixtures of water (containing 0.1-0.3% aqueous ammonium), water (containing 0.05% aqueous ammonia and 10 mmol $NH_4HCO_3$), water (containing 0.1% formic acid) or water (containing 0.05% TFA) and acetonitrile or methanol as eluents.

Preparative SFC purification was performed on either a Sepiatec P100 SFC system or Waters Prep 100 SFC system equipped with QDa MS detector, using the chromatographic conditions as detailed in corresponding experimental data.

Preparative chiral HPLC was performed with a Gilson GX-281 system with integrated UV detection and equipped with one of Chiralpak AS, AD, Chiralcel OD, OJ Chiralpak IA, IB, IC, ID, IE, IF, IG, IH columns (Daicel Chemical Industries, Ltd.) (R,R)-Whelk-O1, (S,S)-Whelk-O1 columns (Regis technologies, Inc.) CHIRAL Cellulose-SB, SC, SA columns (YMC Co., Ltd.) at different column size (250×20 mm, 250×30 mm) with noted percentage of either ethanol in hexane (% Et/Hex) or isopropanol in hexane (% IPA/Hex) as isocratic solvent systems.

Yields, where present, are not necessarily the maximum attainable.

In general, the structures of end-products of the Formula I were confirmed by nuclear magnetic resonance (NMR) spectroscopy; $^1H$-NMR chemical shift values were measured on the delta scale and are quoted in ppm with measurement against TMS or residual solvent peaks as internal standards; proton magnetic resonance spectra were determined using a Bruker Avance 500 spectrometer at a proton frequency of 500 MHz, Bruker Avance 400, Bruker Avance III HD or Bruker Avance Neo spectrometers at a proton frequency of 400 MHz or Bruker Avance III, Avance III HD or Avance III NEO spectrometers at a proton frequency of 300 MHz; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; br s, broad signal; hept, heptet.

In general, end products of the Formula I were also characterized by mass spectrometry following liquid chromatography (LCMS or UPLC); reverse-phase C18 silica was used with a flow rate of 1 mL/min and detection was by Electrospray Mass Spectrometry and by UV/vis absorbance recording a wavelength range of 220-320 nm. Analytical UPLC was performed using a Waters Acquity UPLC CSH C18 column with dimensions 2.1×50 mm and particle size 1.7 micron) Gradient analysis was employed using decreasingly polar mixtures as eluent, for example decreasingly polar mixtures of water (containing 0.1% v/v formic acid or 0.3% ammonia v/v) as solvent A and acetonitrile as solvent B. A typical 1.7 minute analytical UPLC method would employ a solvent gradient over 1.3 min, at 1 mL/min, from a 97:3 mixture of solvents A and B respectively to a 3:97 mixture of solvents A and B. Also, LCMS was performed using a Shimadzu LCMS-2020 with electrospray ionization in positive ion detection mode with 20ADXR pump, SIL-20ACXR autosampler, CTO-20AC column oven, M20A PDA Detector and LCMS 2020 MS detector. LC was run in two set ups: 1) Halo C18 column (2.0 μm 3.0×30 mm) in combination with a gradient (5-100% B in 1.2 minutes) of water and formic acid-FA (0.1%) (A) and $CH_3CN$ and FA (0.1%) (B) at a flow rate of 1.5 mL/min; 2) Poroshell HPH C18 column (2.7 μm 3.0×50 mm) in combination with a gradient (5-95% B in 2 minutes) of aqueous 46 mM ammonium carbonate/ammonia buffer at pH 10 (A) and MeCN (B) at a flow rate of 1.2 mL/min; 3) Halo C18 column (2.0 μm 3.0×30 mm) in combination with a gradient (5-95% B in 2 minutes) of water and TFA (0.05%) (A) and $CH_3CN$ and TFA (0.05%) at a flow rate of 1.5 mL/min (B). The Column Oven (CTO-20AC) temperature was 40.0° C. The injection volume was 1 μL. PDA (SPD-M20A) detection was in the range 190-400 nm. The MS detector, which was configured with electrospray ionization as ionizable source; Acquisition mode: Scan; Nebulizing Gas Flow: 1.5 L/min; Drying Gas Flow: 15 L/min; Detector Voltage: Tuning Voltage±0.2 kv; DL Temperature: 250° C.; Heat Block Temperature: 250° C.; Scan Range: 90.00-900.00 m/z. It is understood that, unless otherwise specified, the reported molecular ion corresponds to the [M+H]+, rounded to the lower unit. Typically, unless otherwise specified; for molecules with multiple isotopic patterns (e. g. $^{35}Cl$, $^{79}Br$, $^{12}C$) only the lower most common isotope is reported.

Ion exchange purification was generally performed using a SCX-2 (Biotage, Propylsulfonic acid functionalized silica. Manufactured using a trifunctional silane. Non end-capped) cartridge.

Intermediate purity was assessed by thin layer chromatographic, mass spectral, HPLC (high performance liquid chromatography) and/or NMR analysis.

The following abbreviations have been used $Ac_2O$ acetic anhydride
AcOH acetic acid
aq. aqueous
BINAP 2,2'-bis(diphenylphosphino)-1,1'-binaphthalene
BOC tert-butyloxycarbonyl
Cbz benzyloxycarbonyl
DCM dichloromethane
DEA diethylamine
DIAD diisopropyl azodicarboxylate
DIEA diisopropylethylamine
DMA N,N-dimethylacetamide
DMF N,N-dimethylformamide
DMSO dimethyl sulphoxide
$Et_2O$ diethyl ether
EtOAc ethyl acetate
EtOH ethanol
h hour(s)
HATU 1-[Bis(dimethylamino)methylene]-1H-1,2,3-triazolo[4,5-b]pyridinium 3-oxid hexafluorophosphate
HOBt 1-hydroxybenzotriazole
HPLC high performance liquid chromatography
IPA or iPrOH isopropanol
LCMS liquid chromatography-mass spectrometry
LHMDS lithium bis(trimethylsilyl)amide
MeCN acetonitrile
MeI methyl iodide
MeOH methanol
min minute(s)
$Ms_2O$ methanesulfonic anhydride
MTBE methyl tert-butyl ether
NMP 1-methyl-2-pyrrolidone
m/z mass to charge ratio
NMR nuclear magnetic resonance
PDA photo-diode array
$Pd_2(dba)_3$ tris(dibenzylideneacetone) dipalladium(0)
$PdCl_2(dppf)$ [1,1'-bis(diphenylphosphino)ferrocene]dichloropalladium(II)
$PdCl_2(PPh_3)_2$ bis(triphenylphosphine)palladium(II) dichloride
$Pd(PPh_3)_4$ palladium-tetrakis(triphenylphosphine)
$PPh_3$ triphenyl phosphine
RockPhos Pd G3 [(2-di-tert-butylphosphino-3-methoxy-6-methyl-2',4',6'-triisopropyl-1,1'-biphenyl)-2-(2-aminobiphenyl)]palladium(II) methanesulfonate
rac racemic
rac-BINAP Pd see CAS Number: 2151915-22-7
G3
rt/RT room temperature
$scCO_2$ supercritical carbon dioxide
SCX strong cation exchanger
SFC supercritical fluid chromatography
T3P Propylphosphonic anhydride
TBAF Tetra-N-butylammonium fluoride
TBDPS tert-butyldiphenylsilyl
TEA triethylamine
tert tertiary
TFA trifluoroacetic acid
THF tetrahydrofuran
TLC thin layer chromatography
TMS tetramethylsilane
UPLC ultra performance liquid chromatography
UV ultraviolet

Example 1

9-Benzyl-6-isopropoxy-8-(2-methyl-4-(2-(4-methylpiperazin-1-yl)ethoxy)phenyl)-9H-purine

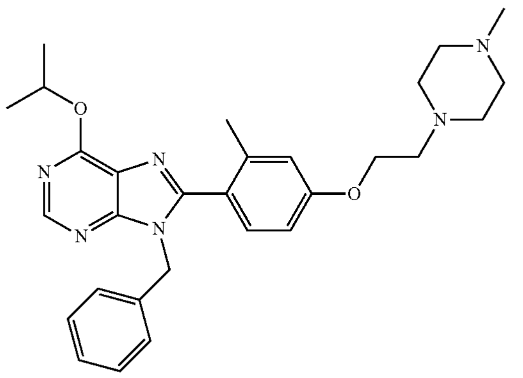 [SMILES: Cc1cc(OCCN2CCN(C)CC2)ccc1-c1nc2c(OC(C)C)ncnc2n1Cc1ccccc1]

DIAD (0.260 mL, 1.34 mmol) was added dropwise to 4-(9-benzyl-6-isopropoxy-9H-purin-8-yl)-3-methylphenol (200 mg, 0.53 mmol), 2-(4-methylpiperazin-1-yl)ethan-1-ol (116 mg, 0.80 mmol) and $PPh_3$ (392 mg, 1.50 mmol) in THF (20 mL) at 0° C. under nitrogen. The resulting mixture was stirred at rt for 16 hours. The residue was purified by preparative TLC (EtOAc) and then further purified by preparative HPLC (XBridge Shield RP18 OBD column, 5 μm silica, 30 mm diameter, 150 mm length), using decreasingly polar mixtures of water (containing 0.05% aq. $NH_3$) and MeCN as eluents. Fractions containing the desired compound were evaporated to dryness to afford 9-benzyl-6-isopropoxy-8-(2-methyl-4-(2-(4-methylpiperazin-1-yl)ethoxy)phenyl)-9H-purine (76 mg, 28%) as a yellow oil. $^1H$ NMR (300 MHz, DMSO-$d_6$): 1.42 (6H, d), 1.95 (3H, s), 2.16 (3H, s), 2.33 (8H, m), 2.70 (2H, t), 4.13 (2H, t), 5.26 (2H, s), 5.62 (1H, p), 6.84-6.94 (4H, m), 7.18-7.31 (4H, m), 8.55 (1H, s). m/z: ES+ [M+H]+ 501.

4-(9-Benzyl-6-isopropoxy-9H-purin-8-yl)-3-methylphenol used as starting material was made as follows:

N4-Benzyl-6-chloropyrimidine-4,5-diamine

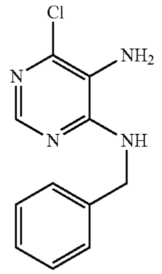 [SMILES: Nc1c(Cl)ncnc1NCc1ccccc1]

A mixture of phenylmethanamine (47.0 g, 439 mmol) and triethylamine (74.0 g, 732 mmol) was added dropwise to 4,6-dichloropyrimidin-5-amine (60 g, 366 mmol) in DMA (400 mL) at 100° C. over a period of 20 minutes under air. The resulting solution was stirred at 100° C. for 8 hours. The reaction mixture was then poured into water (1000 mL) under stirring. The resulting precipitate was collected by filtration, washed with water (500 mL) and dried at 60° C. to afford N4-benzyl-6-chloropyrimidine-4,5-diamine (60.0 g, 70%) as a pale yellow solid.

$^1$H NMR (300 MHz, DMSO-$d_6$): 4.65 (2H, d), 5.11 (2H, s), 7.19-7.29 (1H, m), 7.29-7.45 (5H, m), 7.76 (1H, s). m/z: ES+ [M+H]+ 235.

4-(9-Benzyl-6-chloro-9H-purin-8-yl)-3-methylphenol

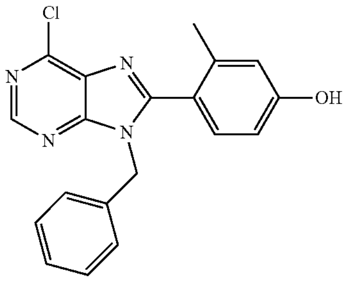 [SMILES: Cc1cc(O)ccc1-c1nc2c(Cl)ncnc2n1Cc1ccccc1]

4-Hydroxy-2-methylbenzaldehyde (580 mg, 4.26 mmol) was added to N4-benzyl-6-chloropyrimidine-4,5-diamine (500 mg, 2.13 mmol) and iron(III) chloride supported on silica gel (6.91 g, 6.39 mmol) in 1,4-dioxane (40 mL). The resulting mixture was stirred at 100° C. for 3 days. The solvent was removed under reduced pressure. The filtrate was collected by filtration, the precipitate was washed with EtOAc (100 mL) and dried under vacuum to afford a crude product. The crude product was purified by flash C18-flash chromatography, elution gradient 5 to 80% MeCN in water (containing 0.05% $NH_4HCO_3$). Pure fractions were evaporated to dryness to afford 4-(9-benzyl-6-chloro-9H-purin-8-yl)-3-methylphenol (230 mg, 31%) as a yellow solid. $^1$H NMR (400 MHz, DMSO-$d_6$): 1.94 (3H, s), 5.34 (2H, s), 6.70-6.75 (2H, m), 6.87-6.92 (2H, m), 7.19-7.26 (4H, m), 8.81 (1H, s), 9.94 (1H, s). m/z: ES+ [M+H]+ 351.

4-(9-Benzyl-6-isopropoxy-9H-purin-8-yl)-3-methylphenol

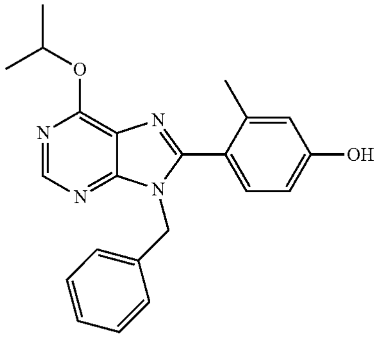 [SMILES: Cc1cc(O)ccc1-c1nc2c(OC(C)C)ncnc2n1Cc1ccccc1]

NaH (50.2 mg, 1.25 mmol) was added portionwise to 4-(9-benzyl-6-chloro-9H-purin-8-yl)-3-methylphenol (220 mg, 0.63 mmol) and IPA (0.097 mL, 1.25 mmol) in THF (10 mL). The resulting mixture was stirred at rt for 2 hours. The reaction mixture was quenched with saturated $NaHCO_3$ (50 mL) and extracted with EtOAc (3×20 mL). The organic layer was dried over $Na_2SO_4$, filtered and evaporated to afford 4-(9-benzyl-6-isopropoxy-9H-purin-8-yl)-3-methylphenol (210 mg, 89%) as a yellow solid. $^1$H NMR (300 MHz, DMSO-$d_6$): 1.41 (6H, d), 1.90 (3H, s), 5.26 (2H, s), 5.61 (1H, p), 6.68-6.75 (2H, m), 6.84-6.90 (2H, m), 7.13-7.25 (4H, m), 8.54 (1H, s), 9.85 (1H, s). m/z: ES+ [M+H]+ 375.

Example 2

2-(2-Chloro-4-(2-(4-methylpiperazin-1-yl)ethoxy)phenyl)-1-(3-chlorobenzyl)-5-isopropoxy-1H-benzo[d]imidazole

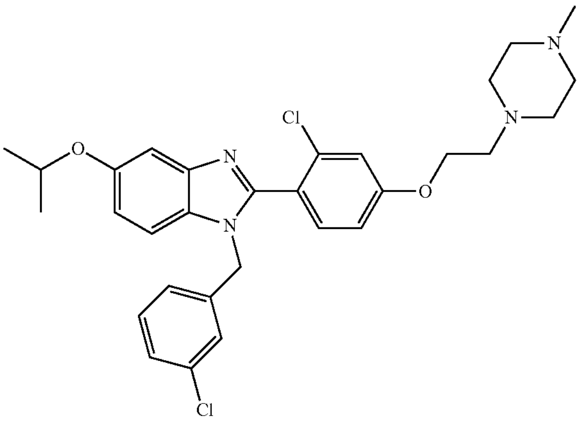 [SMILES: CC(C)Oc1ccc2c(c1)nc(-c1ccc(OCCN3CCN(C)CC3)cc1Cl)n2Cc1cccc(Cl)c1]

2-(2-Chloro-4-(2-(4-methylpiperazin-1-yl)ethoxy)phenyl)-1-(3-chlorobenzyl)-1H-benzo[d]imidazol-5-ol (125 mg, 0.24 mmol), 2-bromopropane (0.046 mL, 0.49 mmol) and potassium carbonate (169 mg, 1.22 mmol) were suspended in acetonitrile (5 mL) and sealed into a microwave tube. The reaction was heated to 100° C. for 12 hours in the microwave reactor and cooled to room temperature. The solid was removed by filtration and the filtrate evaporated to dryness. The crude product was purified by preparative HPLC (Waters CSH C18 OBD column, 5 μm silica, 30 mm diameter, 100 mm length), using decreasingly polar mixtures of water (containing 1% aqueous ammonia) and MeCN as eluents. Fractions containing the desired compound were evaporated to dryness to afford 2-(2-chloro-4-(2-(4-methylpiperazin-1-yl)ethoxy)phenyl)-1-(3-chlorobenzyl)-5-isopropoxy-1H-benzo[d]imidazole (14 mg, 10%). $^1$H NMR (500 MHz, $CD_3OD$): 1.32 (3H, s), 1.33 (3H, s), 2.27 (3H, s), 2.43-2.72 (6H, m), 2.84 (2H, t), 3.30 (2H, p), 4.19 (2H, d), 4.55-4.64 (1H, m), 5.26 (2H, s), 6.86 (1H, dt), 6.93 (2H, dd), 7.01 (1H, dd), 7.15-7.23 (4H, m), 7.31 (1H, d), 7.35 (1H, d). m/z: ES+ [M+H]+ 553.

2-(2-Chloro-4-(2-(4-methylpiperazin-1-yl)ethoxy)phenyl)-1-(3-chlorobenzyl)-1H-benzo[d]imidazol-5-ol used as starting material was made as follows:

2-(2-Chloro-4-(2-(4-methylpiperazin-1-yl)ethoxy)phenyl)-1-(3-chlorobenzyl)-5-methoxy-1H-benzo[d]imidazole

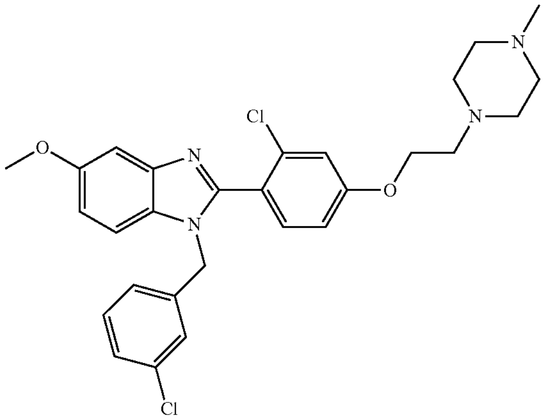

A solution of crude 2-chloro-4-(2-(4-methylpiperazin-1-yl)ethoxy)benzaldehyde (578 mg, 1.02 mmol) in NMP (3 mL) was added in one portion to a stirred suspension of N-(3-chlorobenzyl)-4-methoxy-2-nitroaniline (299 mg, 1.02 mmol, commercially available from Princeton BiolMolecular Research Inc., ACD Identifier: MFCD12564576) and sodium dithionite (628 mg, 3.07 mmol) in water (1 mL). The resulting solution was stirred at reflux for 18 hours. The reaction mixture was diluted with EtOAc (50 mL), and washed sequentially with saturated $NaHCO_3$ (50 mL), water (50 mL), and saturated brine (5 mL). The organic layer was dried with $MgSO_4$, filtered and evaporated onto silica gel (1 g). The resulting powder was purified by flash silica chromatography, elution gradient 0 to 20% MeOH in DCM with ammonia as modifier. Pure fractions were evaporated to dryness to afford 2-(2-chloro-4-(2-(4-methylpiperazin-1-yl)ethoxy)phenyl)-1-(3-chlorobenzyl)-5-methoxy-1H-benzo[d]imidazole (213 mg, 40%) as a white solid. Impure fractions were combined, concentrated in vacuo and repurified by preparative HPLC (Waters CSH C18 OBD column, 5 μm silica, 30 mm diameter, 100 mm length), using decreasingly polar mixtures of water (containing 1% aq. $NH_3$) and MeCN as eluents. Fractions containing the desired compound were evaporated to dryness to afford 2-(2-chloro-4-(2-(4-methylpiperazin-1-yl)ethoxy)phenyl)-1-(3-chlorobenzyl)-5-methoxy-1H-benzo[d]imidazole (92 mg, 17%) as a white solid. $^1$H NMR (500 MHz, $CDCl_3$): 2.30 (3H, s), 2.48 (4H, s), 2.63 (4H, s), 2.84 (2H, t), 3.87 (3H, s), 4.14 (2H, t), 5.17 (2H, s), 6.82 (1H, d), 6.88 (1H, dd), 6.91 (1H, dd), 6.95 (1H, s), 7.04-7.1 (2H, m), 7.15 (1H, t), 7.18-7.22 (1H, m), 7.35 (2H, s). m/z: ES+ 525 [M+H]+ 525.

2-(2-Chloro-4-(2-(4-methylpiperazin-1-yl)ethoxy)phenyl)-1-(3-chlorobenzyl)-1H-benzo[d]imidazol-5-ol

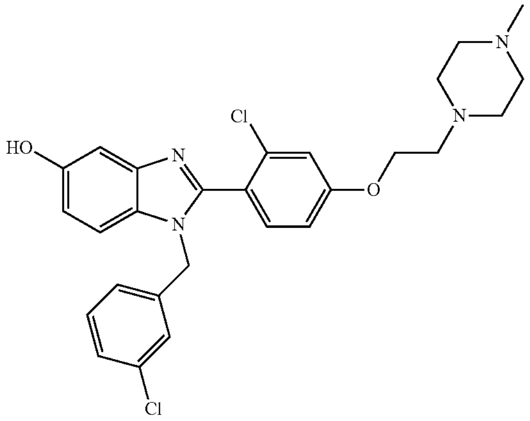 [SMILES: CN1CCN(CCOc2ccc(-c3nc4cc(O)ccc4n3Cc3cccc(Cl)c3)c(Cl)c2)CC1]

A solution of boron tribromide in dichloromethane (1.52 mL, 1.52 mmol) was added dropwise to a stirred solution of 2-(2-chloro-4-(2-(4-methylpiperazin-1-yl)ethoxy)phenyl)-1-(3-chlorobenzyl)-5-methoxy-1H-benzo[d]imidazole (0.20 g, 0.38 mmol) in anhydrous dichloromethane (1 mL) at 0° C. over a period of 2 minutes under nitrogen. The resulting suspension was stirred at room temperature for 35 minutes. The reaction mixture was quenched with 2M HCl (5 mL) and evaporated to remove the DCM. DMSO (2 mL) was added and the resulting solution was purified by flash reverse phase silica chromatography, elution gradient 5 to 95% MeCN in water with 0.1% formic acid as modifier. Pure fractions were evaporated to dryness to afford 2-(2-chloro-4-(2-(4-methylpiperazin-1-yl)ethoxy)phenyl)-1-(3-chlorobenzyl)-1H-benzo[d]imidazol-5-ol (150 mg, 77%) as a white solid. $^1$H NMR (500 MHz, $CDCl_3$): 2.64 (3H, s), 2.81-2.96 (6H, m), 3.06 (4H, s), 4.11 (2H, t), 5.15 (2H, s), 6.83 (2H, td), 6.87 (1H, dd), 6.93 (1H, s), 7-7.06 (2H, m), 7.12-7.22 (2H, m), 7.29-7.35 (2H, m), 8.38 (1H, s). m/z: ES+ [M+H]+ 511.

2-Chloro-4-(2-(4-methylpiperazin-1-yl)ethoxy)benzaldehyde used as starting material is described in Example 4.

Example 3

3-(4-(1-Benzyl-5-isopropoxy-1H-benzo[d]imidazol-2-yl)-3-chlorophenoxy)propan-1-amine

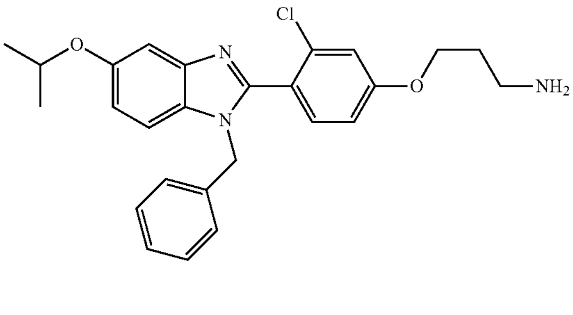 [SMILES: CC(C)Oc1ccc2c(c1)nc(-c1ccc(OCCCN)cc1Cl)n2Cc1ccccc1]

TFA (2 mL, 25.96 mmol) was added slowly to tert-butyl (3-(4-(1-benzyl-5-isopropoxy-1H-benzo[d]imidazol-2-yl)-3-chlorophenoxy)propyl)carbamate (100 mg, 0.18 mmol) in DCM (5 mL) at 0° C. The resulting mixture was stirred at rt for 2 hours. The reaction mixture was evaporated to a crude oil. The crude product was purified by preparative HPLC (XBridge Shield RP18 OBD column, 5 μm silica, 30 mm diameter, 150 mm length), using decreasingly polar mixtures of water (containing 0.05% aq. $NH_3$) and MeCN as eluents. Fractions containing the desired compound were evaporated to dryness to afford 3-(4-(1-benzyl-5-isopropoxy-1H-benzo[d]imidazol-2-yl)-3-chlorophenoxy)propan-1-amine (27 mg, 33%) as a yellow oil which solidified on standing. $^1H$ NMR (400 MHz, $CDCl_3$): 1.39 (6H, d), 1.97-2.07 (2H, m), 2.99 (2H, t), 4.13 (2H, t), 4.58 (1H, p), 5.23 (2H, s), 6.88 (2H, dt), 6.97-7.03 (2H, m), 7.06-7.13 (2H, m), 7.25 (3H, dd), 7.33-7.41 (2H, m). 2H not observed. m/z: ES+ [M+H]+ 450.

Tert-butyl (3-(4-(1-benzyl-5-isopropoxy-1H-benzo[d]imidazol-2-yl)-3-chlorophenoxy) propyl)carbamate used as starting material was made as follows:

N-Benzyl-4-isopropoxy-2-nitroaniline

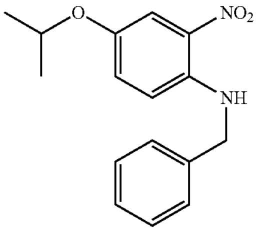 [SMILES: CC(C)Oc1ccc(NCc2ccccc2)c([N+](=O)[O-])c1]

Phenylmethanamine (2.37 g, 22.1 mmol) was added slowly to DIEA (7.02 mL, 40.2 mmol) and 1-fluoro-4-isopropoxy-2-nitrobenzene (4 g, 20.1 mmol, commercially available) in DMA (10 mL) at rt. The resulting mixture was stirred at 100° C. for 18 hours. and cooled to rt. The reaction mixture was poured into water (50 mL) and extracted with EtOAc (3×50 mL). The organic layer was washed sequentially with saturated $NH_4Cl$ (20 mL×1), saturated $NaHCO_3$ (20 mL×1), and saturated brine (20 mL×1). The organic layer was dried over $Na_2SO_4$, filtered and evaporated to afford crude material. The residue was purified by preparative TLC (petroleum ether:EtOAc=1:6), to afford N-benzyl-4-isopropoxy-2-nitroaniline (4.50 g, 78%) as a red oil which solidified on standing. $^1H$ NMR (400 MHz, DMSO-$d_6$): 1.22 (6H, d), 4.47 (1H, hept), 4.60 (2H, d), 6.88 (1H, d), 7.18 (1H, dd), 7.25 (1H, ddd), 7.29-7.39 (4H, m), 7.51 (1H, d), 8.51 (1H, t). m/z (ES+), [M+H]+=287.

4-(1-Benzyl-5-isopropoxy-1H-benzo[d]imidazol-2-yl)-3-chlorophenol—Example A1

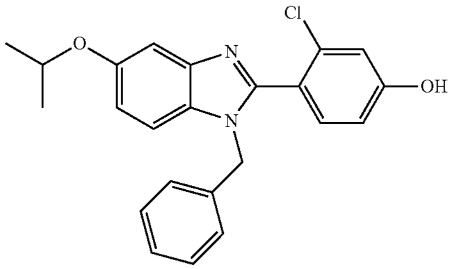 [SMILES: CC(C)Oc1ccc2c(c1)nc(-c1ccc(O)cc1Cl)n2Cc1ccccc1]

A solution of sodium dithionite (7.30 g, 41.9 mmol) in water (5.00 mL) was added dropwise to a stirred mixture of N-benzyl-4-isopropoxy-2-nitroaniline (3 g, 10.5 mmol) and 2-chloro-4-hydroxybenzaldehyde (1.80 g, 11.5 mmol) in NMP (20 mL) at rt. The resulting mixture was stirred at 100° C. for 18 hours. The reaction mixture was poured into saturated brine (75 mL) and extracted with EtOAc (3×100 mL). The organic layer was dried over $Na_2SO_4$, filtered and evaporated to afford a yellow gum. The crude product was purified by flash silica chromatography, elution gradient 0 to 100% petroleum ether in EtOAc. Pure fractions were evaporated to dryness to afford 4-(1-benzyl-5-isopropoxy-1H-benzo[d]imidazol-2-yl)-3-chlorophenol (2.30 g, 56%) as a yellow oil which solidified on standing. $^1H$ NMR (300 MHz, DMSO-$d_6$): 1.27 (6H, d), 4.60 (1H, p), 5.25 (2H, s), 6.85 (2H, td), 6.93-7.04 (3H, m), 7.15-7.30 (4H, m), 7.30 (1H, t), 7.37 (1H, d), 10.41 (1H, s). m/z: ES+ [M+H]+ 393.

Tert-butyl (3-(4-(1-benzyl-5-isopropoxy-1H-benzo[d]imidazol-2-yl)-3-chlorophenoxy) propyl)carbamate—Example A2

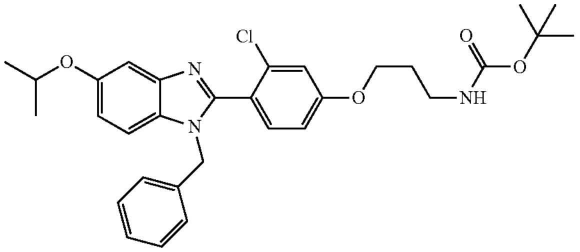 [SMILES: CC(C)Oc1ccc2c(c1)nc(-c1ccc(OCCCNC(=O)OC(C)(C)C)cc1Cl)n2Cc1ccccc1]

DIAD (1.00 g, 4.96 mmol) was added dropwise to 4-(1-benzyl-5-isopropoxy-1H-benzo[d]imidazol-2-yl)-3-chlorophenol (1.5 g, 3.82 mmol), tert-butyl (3-hydroxypropyl) carbamate (0.803 g, 4.58 mmol) and $Ph_3P$ (1.50 g, 5.73 mmol) in THF (20 mL) at 0° C. under nitrogen. The resulting mixture was stirred at rt for 16 hours. The solvent was removed under reduced pressure. The reaction mixture was diluted with EtOAc:petroleum ether (200 mL, 1:5). The solid was filtered out and the organic layer washed sequentially with saturated $NH_4Cl$ (30 mL), saturated $NaHCO_3$ (30 mL), and saturated brine (30 mL×2). The organic layer was dried over $Na_2SO_4$, filtered and evaporated to afford a crude product. The crude product was purified by flash silica chromatography, elution gradient 0 to 30% EtOAc in petroleum ether. Pure fractions were evaporated to dryness to afford tert-butyl (3-(4-(1-benzyl-5-isopropoxy-1H-benzo[d]imidazol-2-yl)-3-chlorophenoxy)propyl)carbamate (900 mg, 43%) as a yellow gum. $^1$H NMR (400 MHz, $CDCl_3$): 1.38 (6H, d), 1.46 (9H, s), 2.03 (2H, q), 3.35 (2H, q), 4.07 (2H, t), 4.58 (1H, hept), 4.74 (1H, s), 5.22 (2H, s), 6.87 (2H, ddd), 6.95-7.02 (2H, m), 7.06 (1H, d), 7.09 (1H, d), 7.25 (3H, dd), 7.35 (1H, d), 7.39 (1H, d). m/z: ES+ [M+H]+ 550.

Example 4

9-Benzyl-8-(2-chloro-4-(2-(4-methylpiperazin-1-yl)ethoxy)phenyl)-6-(1-methylcyclopropoxy)-9H-purine

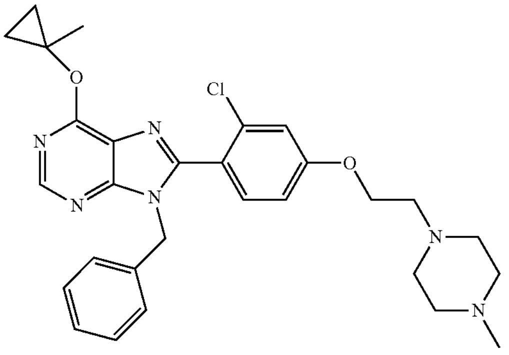 [SMILES: CN1CCN(CCOc2ccc(-c3nc4c(OC5(C)CC5)ncnc4n3Cc3ccccc3)c(Cl)c2)CC1]

To a stirred solution of (E)-N-benzyl-5-((2-chloro-4-(2-(4-methylpiperazin-1-yl)ethoxy)benzylidene)amino)-6-(1-methylcyclopropoxy)pyrimidin-4-amine (82 g crude, calculated as 129 mmol, 1.00 equiv) in IPA (820 mL) was added $FeCl_3$ (32 g, 193 mmol, 1.50 equiv) under nitrogen atmosphere at room temperature. The reaction mixture was stirred at 80° C. for 1.5 h. The resulting mixture was concentrated under vacuum. The reaction mixture was diluted with 500 ml $H_2O$, the aqueous layer was adjusted to pH=10 with NaOH and extracted with DCM/IPA (6:1). The combined organic layers were washed with saturated $NaHCO_3$ and brine (1000 mL×5), dried with $Na_2SO_4$ and concentrated. The residue was applied onto a silica gel column, eluting with DCM/ammonia solution (3.5M in MeOH) (1:0-1:20). The resulting mixture was further purified by SFC (OptiChiral-C9-5 column, 5 μm silica, 30 mm diameter, 250 mm length) eluting with 50% $scCO_2$, and MeOH (containing 0.1% 2M $NH_3$-MeOH) and concentrated under vacuum below 40° C. to afford a yellow solid, which was slurried in $Et_2O$ (10V) for 2 h. The resulting mixture was filtered and the filtrate cake was dried under vacuum to afford 9-benzyl-8-(2-chloro-4-(2-(4-methylpiperazin-1-yl)ethoxy)phenyl)-6-(1-methylcyclopropoxy)-9H-purine (32.4 g, 45%) as a light yellow solid. $^1$H NMR (400 MHz, $CDCl_3$): 0.76-0.88 (2H, m), 1.01-1.26 (2H, m), 1.80 (3H, s), 2.31 (3H, s), 2.37-2.57 (4H, m), 2.64 (4H, br s), 2.85 (2H, t), 4.15 (2H, t), 5.34 (2H, s), 6.82 (1H, dd), 6.93 (2H, dd), 7.06 (1H, d), 7.13-7.21 (2H, m), 7.14-7.19 (2H, m), 8.67 (1H, s). m/z: ES+ [M+H]+ 533.

(E)-N-benzyl-5-((2-chloro-4-(2-(4-methylpiperazin-1-yl)ethoxy)benzylidene)amino)-6-(1-methylcyclopropoxy)pyrimidin-4-amine used as starting material was made as follows:

N-Benzyl-6-chloro-5-nitropyrimidin-4-amine

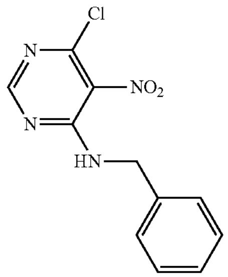 [SMILES: O=[N+]([O-])c1c(Cl)ncnc1NCc1ccccc1]

To a stirred solution of 4,6-dichloro-5-nitropyrimidine (400 g, 2.01 mol, 1.00 equiv) in DCM (4000 mL) was added TEA (228 g, 2.26 mol, 1.1 equiv) under nitrogen atmosphere at room temperature. Phenylmethanamine (243.1 g, 2.26 mol, 1.1 equiv) was charged at 0° C. The reaction mixture was stirred at rt for 30 min. The resulting mixture was washed with brine (1000 mL×5), dried over anhydrous $Na_2SO_4$ and concentrated. The residue was applied onto a silica gel column with petroleum ether/ethyl acetate (2:1-1:1). This afforded N-benzyl-6-chloro-5-nitropyrimidin-4-amine (327 g, 60%) as a yellow solid. $^1$H NMR (300 MHz, $CDCl_3$): 4.82 (2H, d), 7.28-7.47 (5H, m), 7.82 (1H, s), 8.43 (1H, s). m/z: ES+ [M+H]+ 265.

N-Benzyl-6-(1-methylcyclopropoxy)-5-nitropyrimidin-4-amine

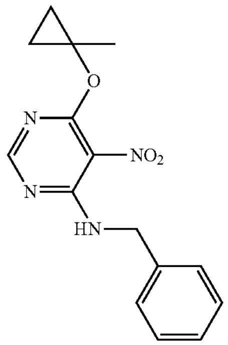 [SMILES: CC1(Oc2ncnc(NCc3ccccc3)c2[N+](=O)[O-])CC1]

To a stirred solution of N-benzyl-6-chloro-5-nitropyrimidin-4-amine (210 g, 0.79 mol, 1.00 equiv) in THF (2100 mL) was added 1-methylcyclopropan-1-ol (114.3 g, 1.59 mmol, 2.00 equiv) under nitrogen atmosphere at room temperature. LHMDS (1980 mL, 1.98 mol, 2.50 equiv) was charged at 0° C. The reaction mixture was stirred at rt for 18 h. The reaction mixture was diluted with 1000 ml $NH_4Cl$, extracted with ethyl acetate (1500 mL×3). The combined organic layers were washed with brine (2000 mL×2), dried with $Na_2SO_4$ and concentrated. The residue was applied onto a silica gel column with petroleum ether/ethyl acetate (1:50-1:20). This afforded N-benzyl-6-(1-methylcyclopropoxy)-5-nitropyrimidin-4-amine (108 g, 45%) as yellow oil. $^1$H NMR (400 MHz, DMSO-$d_6$): 0.76 (2H, t), 0.92 (2H, t), 1.62 (3H, s), 4.70 (2H, d), 7.17-7.26 (1H, m), 7.26-7.39 (4H, m), 8.33 (1H, s), 8.86 (1H, t). m/z: ES+ [M+H]+ 301.

N4-Benzyl-6-(1-methylcyclopropoxy)pyrimidine-4,5-diamine

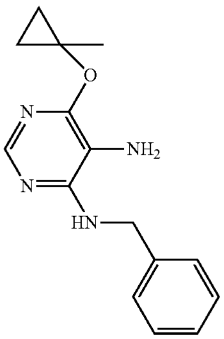 [SMILES: CC1(Oc2ncnc(NCc3ccccc3)c2N)CC1]

To a stirred solution of N-benzyl-6-(1-methylcyclopropoxy)-5-nitropyrimidin-4-amine (108 g, 360 mmol, 1.00 equiv) in EtOH (1080 mL) was added iron powder (201 g, 3.60 mol, 10 equiv) and $NH_4Cl$ (23.2 g, 432 mmol, 1.2 equiv) under nitrogen atmosphere at room temperature. The reaction mixture was stirred at 80° C. for 18 h. The resulting mixture was filtered through celite, eluting with EtOH. The filtrate was concentrated to give crude material. The crude product was purified by flash silica chromatography, eluted with petroleum ether:ethyl acetate 10:1 to 1:3, to afford N4-benzyl-6-(1-methylcyclopropoxy)pyrimidine-4,5-diamine (77 g, 79%) as an off-white solid. $^1H$ NMR (300 MHz, DMSO-$d_6$): 0.68 (2H, t), 0.85 (2H, t), 1.60 (3H, s), 4.12 (2H, s), 4.59 (2H, d), 6.69 (1H, t), 7.05-7.41 (5H, m), 7.72 (1H, s). m/z: ES+ [M+H]+ 271.

(E)-N-benzyl-5-((2-chloro-4-(2-(4-methylpiperazin-1-yl)ethoxy)benzylidene)amino)-6-(1-methylcyclopropoxy)pyrimidin-4-amine

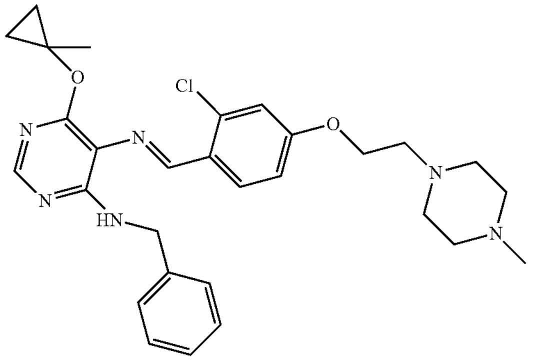 [SMILES: CN1CCN(CCOc2ccc(/C=N/c3c(NCc4ccccc4)ncnc3OC3(C)CC3)c(Cl)c2)CC1]

To a stirred solution of N4-benzyl-6-(1-methylcyclopropoxy)pyrimidine-4,5-diamine (35 g, 129 mmol, 1.00 equiv) in MeOH/AcOH (20V/1V) was added 2-chloro-4-(2-(4-methylpiperazin-1-yl)ethoxy)benzaldehyde (47.6 g, 168 mmol, 1.30 equiv) under nitrogen atmosphere at room temperature. The reaction mixture was stirred at rt for 15 h. The resulting mixture was concentrated under vacuum to afford (E)-N-benzyl-5-((2-chloro-4-(2-(4-methylpiperazin-1-yl)ethoxy)benzylidene)amino)-6-(1-methylcyclopropoxy)pyrimidin-4-amine (82 g, crude) as a yellow oil, which was used directly with no further purification. $^1H$ NMR (300 MHz, $CDCl_3$): 0.69-0.81 (2H, m), 0.98-1.10 (2H, m), 1.70 (3H, s), 2.55 (3H, s), 2.73-3.10 (10H, m), 4.08-4.20 (2H, m), 4.75 (2H, d), 6.38-6.49 (1H, m), 6.77-6.88 (1H, m), 6.88-6.97 (1H, m), 7.24-7.38 (5H, m), 8.00 (1H, d), 8.23 (1H, s), 9.40 (1H, s). m/z: ES+ [M+H]+ 535.

2-Chloro-4-(2-(4-methylpiperazin-1-yl)ethoxy)benzaldehyde used as starting material was made as follows:

Tert-butyl 4-(2-(3-chloro-4-formylphenoxy)ethyl) piperazine-1-carboxylate

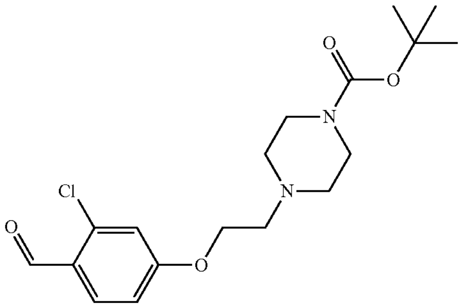 [SMILES: CC(C)(C)OC(=O)N1CCN(CCOc2ccc(C=O)c(Cl)c2)CC1]

To a stirred solution of 2-chloro-4-hydroxybenzaldehyde (300 g, 1.92 mol, 1.00 equiv) in DMF (3000 mL) were added tert-butyl 4-(2-chloroethyl)piperazine-1-carboxylate (643.4 g, 2.59 mol, 1.35 equiv), $K_2CO_3$ (528.8 g, 3.84 mol, 2.00 equiv) and KI (63.6 g, 0.38 mol, 0.20 equiv) under nitrogen atmosphere. The reaction mixture was stirred at 80° C. for 14 h. The resulting mixture was diluted with 2 L water. The resulting mixture was filtered and the filtrate cake was washed with $H_2O$. Then the filtrate cake was dried under vacuum to afford tert-butyl 4-(2-(3-chloro-4-formylphenoxy)ethyl)piperazine-1-carboxylate (390 g, 55%) as a yellow solid, which was used in the next step without further purification. $^1H$ NMR (400 MHz, DMSO-$d_6$): 1.39 (9H, s), 2.43 (4H, t), 2.73 (2H, t), 3.30 (4H, m), 4.23 (2H, t), 7.08 (1H, dd), 7.20 (1H, d), 7.81 (1H, d), 10.19 (1H, s). m/z: ES+ [M+H]+ 369.

2-Chloro-4-(2-(4-methylpiperazin-1-yl)ethoxy)benzaldehyde

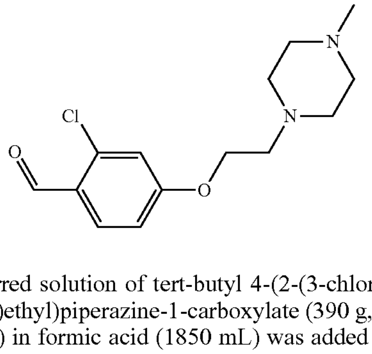

To a stirred solution of tert-butyl 4-(2-(3-chloro-4-formylphenoxy)ethyl)piperazine-1-carboxylate (390 g, 1.06 mol, 1.00 equiv) in formic acid (1850 mL) was added formaldehyde (48.5 g, 1.28 mol, 1.20 equiv) under nitrogen atmosphere. The reaction mixture was stirred at 70° C. for 14 h. The reaction mixture was diluted with 1000 ml H2O, extracted with MTBE (1500 mL×3). The aqueous layer was adjusted to pH=10 with NaOH and extracted with DCM (1000 mL×3). The combined organic layers were washed with saturated and brine (1000 mL×5), dried with $Na_2SO_4$ and concentrated. The residue was purified by flash silica chromatography, eluting with DCM/ammonia solution (3.5M in MeOH) (1:100-1:30). This afforded 2-chloro-4-(2-(4-methylpiperazin-1-yl)ethoxy)benzaldehyde 176 g (42%) as yellow oil. $^1H$ NMR (300 MHz, DMSO-$d_6$): 2.14 (3H, s), 2.39 (8H, d), 2.70 (2H, t), 4.22 (2H, t), 7.10 (1H, dd), 7.22 (1H, d), 7.82 (1H, d), 10.20 (1H, d). m/z: ES+ [M+H]+ 283.

Example 5

9-Benzyl-8-(2-chloro-4-((1-methylpiperidin-4-yl)methoxy)phenyl)-6-(1-methylcyclopropoxy)-9H-purine

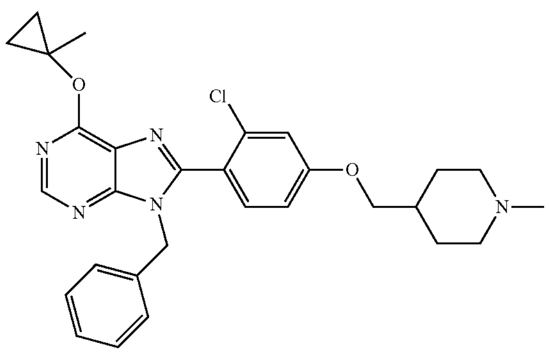 [SMILES: CN1CCC(COc2ccc(-c3nc4c(OC5(C)CC5)ncnc4n3Cc3ccccc3)c(Cl)c2)CC1]

DIAD (143 μL, 0.74 mmol) was added dropwise to 4-(9-benzyl-6-(1-methylcyclopropoxy)-9H-purin-8-yl)-3-chlorophenol (150 mg, 0.37 mmol), (1-methylpiperidin-4-yl)methanol (95 mg, 0.74 mmol) and $Ph_3P$ (193 mg, 0.74 mmol) in THF (5 mL) at 0° C. under nitrogen. The resulting mixture was stirred at rt for 18 hours. The reaction mixture was concentrated and diluted with EtOAc (50 mL) and washed sequentially with saturated $NH_4Cl$ (2×15 mL) and saturated brine (2×15 mL). The organic layer was dried over $Na_2SO_4$, filtered and evaporated to afford crude product. The residue was purified by preparative TLC (EtOAc), to afford the crude product as a yellow gum. The crude product was purified by preparative HPLC (XBridge Shield RP18 OBD column, 5 μm silica, 30 mm diameter, 150 mm length), using decreasingly polar mixtures of water (containing 0.05% aq. $NH_3$) and MeCN as eluents. Fractions containing the desired compound were evaporated to dryness to afford 9-benzyl-8-(2-chloro-4-((1-methylpiperidin-4-yl)methoxy)phenyl)-6-(1-methylcyclopropoxy)-9H-purine (5.0 mg, 2.6%) as a white solid. $^1H$ NMR (400 MHz, DMSO-$d_6$): 0.80-0.88 (2H, m), 0.98-1.06 (2H, m), 1.21-1.37 (2H, m), 1.64-1.78 (6H, m), 1.80-1.95 (2H, m), 2.17 (3H, s), 2.79 (2H, dd), 3.94 (2H, d), 5.29 (2H, s), 6.86-6.95 (2H, m), 7.00-7.06 (1H, m), 7.16-7.25 (4H, m), 7.40 (1H, d), 8.61 (1H, s). m/z: ES+ [M+H]+ 518.

4-(9-Benzyl-6-(1-methylcyclopropoxy)-9H-purin-8-yl)-3-chlorophenol used as starting material was made as follows:

9-Benzyl-6-chloro-9H-purine

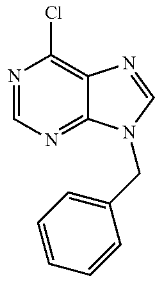 [SMILES: Clc1ncnc2c1ncn2Cc1ccccc1]

(Bromomethyl)benzene (12.2 g, 71.2 mmol) was added dropwise to 6-chloro-9H-purine (10 g, 64.70 mmol), potassium carbonate (10.73 g, 77.64 mmol) in acetonitrile (300 mL) at 25° C. over a period of 10 minutes. The resulting suspension was stirred at 25° C. for 16 hours. The reaction mixture was filtered through celite and the filtrate was concentrated. The crude product was purified by flash silica chromatography, elution gradient 0 to 50% EtOAc in petroleum ether. Pure fractions were evaporated to dryness to afford 9-benzyl-6-chloro-9H-purine (9.00 g, 57%) as a white solid. $^1H$ NMR (400 MHz, $CDCl_3$): 5.48 (2H, s), 7.29-7.47 (5H, m), 8.13 (1H, s), 8.81 (1H, s). m/z: ES+ [M+H]+ 245.

9-Benzyl-6-(1-methylcyclopropoxy)-9H-purine

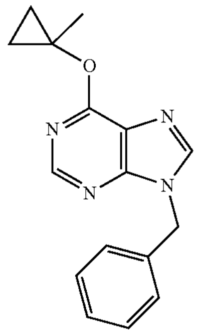 [SMILES: CC1(Oc2ncnc3c2ncn3Cc2ccccc2)CC1]

1-Methylcyclopropan-1-ol (6.52 g, 90.4 mmol) was added to 9-benzyl-6-chloro-9H-purine (8.81 g, 36.0 mmol) in THF (72 mL) was added. The reaction mixture was stirred at 0° C. and then sodium hydride (60% in mineral oil, 3.62 g, 90.5 mmol) was added slowly to the mixture. The reaction was stirred at room temperature for 17 hours. Water (50 mL) was added slowly and the reaction mixture was extracted with DCM (3×50 mL). The organics were combined and concentrated in vacuo. The crude material was purified by column chromatography on silica gel (330 g, 0-50% EtOAc in heptanes) to yield 9-benzyl-6-(1-methylcyclopropoxy)-9H-purine (7.18 g, 71%) as a yellow gum. $^1H$ NMR (500 MHz, $CDCl_3$): 0.8-0.86 (2H, m), 1.1-1.17 (2H, m), 1.78 (3H, s), 5.41 (2H, s), 7.26-7.39 (5H, m), 7.88 (1H, s), 8.64 (1H, s). m/z: ES+ [M+H]+ 281.

9-Benzyl-8-bromo-6-(1-methylcyclopropoxy)-9H-purine

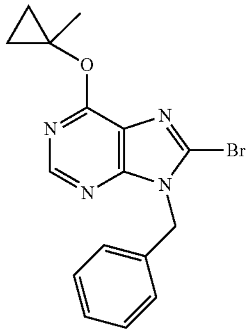 [SMILES: CC1(Oc2ncnc3c2nc(Br)n3Cc2ccccc2)CC1]

Lithium bis(trimethylsilyl)amide (28.6 mL, 28.6 mmol) was added to 9-benzyl-6-(1-methylcyclopropoxy)-9H-purine (5 g, 17.84 mmol) and 1,2-dibromotetrachloroethane (8.72 g, 26.8 mmol) in THF (29 mL) at 0° C. under nitrogen. The resulting mixture was stirred at 25° C. for 16 hours. The reaction mixture was quenched with water (50 mL) and extracted EtOAc (3×100 mL), and saturated brine (1×100 mL). The organic layer was dried over $Na_2SO_4$, filtered and evaporated to afford crude product. The crude product was purified by flash silica chromatography, elution gradient 0 to 30% EtOAc in petroleum ether. Pure fractions were evaporated to dryness to afford 9-benzyl-8-bromo-6-(1-methylcyclopropoxy)-9H-purine (5.70 g, 89%) as a yellow gum. $^1$H NMR (300 MHz, $CDCl_3$): 0.76-0.87 (2H, m), 1.06-1.16 (2H, m), 1.76 (3H, s), 5.44 (2H, s), 7.27-7.37 (5H, m), 8.60 (1H, s); m/z: ES+ [M+H]+ 359.

4-(9-Benzyl-6-(1-methylcyclopropoxy)-9H-purin-8-yl)-3-chlorophenol

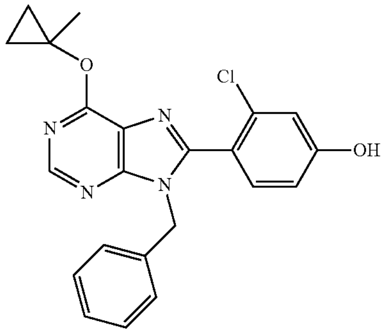 [SMILES: CC1(Oc2ncnc3c2nc(-c2ccc(O)cc2Cl)n3Cc2ccccc2)CC1]

Dichloro[1,1'-bis(diphenylphosphino)ferrocene]palladium(II) (907 mg, 1.39 mmol) was added to 9-benzyl-8-bromo-6-(1-methylcyclopropoxy)-9H-purine (5 g, 13.9 mmol), 3-chloro-4-(4,4,5,5-tetramethyl-1,3,2-dioxaborolan-2-yl)phenol (7.09 g, 27.8 mmol) and cesium carbonate (9.07 g, 27.8 mmol) in 1,4-dioxane (20 mL) and water (2 mL) at 25° C. under nitrogen. The resulting mixture was stirred at 90° C. for 3 hours. The reaction mixture was diluted with EtOAc (50 mL) and washed sequentially with water (3×50 mL). The organic layer was dried over $Na_2SO_4$, filtered and evaporated to afford a crude product. The crude product was purified by flash silica chromatography, elution gradient 0 to 100% EtOAc in petroleum ether. Pure fractions were evaporated to dryness to afford 4-(9-benzyl-6-(1-methylcyclopropoxy)-9H-purin-8-yl)-3-chlorophenol (5.60 g, 99%) as a yellow solid. $^1$H NMR (400 MHz, DMSO-$d_6$): 0.83 (2H, t), 1.02 (2H, t), 1.73 (3H, s), 5.29 (2H, s), 6.83 (1H, dd), 6.88-6.92 (2H, m), 6.99 (1H, d), 7.18-7.22 (3H, m), 7.29 (1H, d), 8.61 (1H, s)—one H non observed. m/z: ES− [M−H]− 405.

Example 6

9-Benzyl-8-(2-chloro-4-(2-(piperazin-1-yl)ethoxy)phenyl)-6-(1-methylcyclopropoxy)-9H-purine

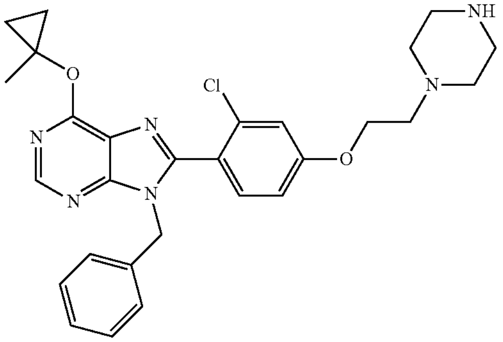 [SMILES: CC1(Oc2ncnc3c2nc(-c2ccc(OCCN4CCNCC4)cc2Cl)n3Cc2ccccc2)CC1]

tert-Butyldimethylsilyltrifluoromethanesulfonate (12.05 mL, 52.5 mmol) was added to tert-butyl 4-(2-(4-(9-benzyl-6-(1-methylcyclopropoxy)-9H-purin-8-yl)-3-chlorophenoxy)ethyl)piperazine-1-carboxylate (6.5 g, 10.50 mmol) in DCM (130 mL). The resulting solution was stirred at rt for 10 minutes. The solvent was removed under reduced pressure. The crude product was purified by flash C18-flash chromatography, elution gradient 30 to 90% MeOH in water (containing 0.1% $NH_4HCO_3$). Pure fractions were evaporated to dryness to afford 9-benzyl-8-(2-chloro-4-(2-(piperazin-1-yl)ethoxy)phenyl)-6-(1-methylcyclopropoxy)-9H-purine (3.10 g, 57%) as a white foam. $^1$H NMR (400 MHz, DMSO-$d_6$): 0.72-0.9 (2H, m), 0.95-1.12 (2H, m), 1.73 (3H, s), 2.25-2.49 (4H, m), 2.59-2.92 (6H, m), 4.19 (2H, t), 5.30 (2H, s), 6.91 (2H, dd), 7.04 (1H, dd), 7.13-7.29 (4H, m), 7.41 (1H, d), 8.63 (1H, s)—one proton not observed. m/z: ES+ [M+H]+ 519.

Tert-butyl 4-(2-(4-(9-benzyl-6-(1-methylcyclopropoxy)-9H-purin-8-yl)-3-chlorophenoxy)ethyl)piperazine-1-carboxylate used as starting material was made as follows:

tert-Butyl 4-(2-(4-(9-benzyl-6-chloro-9H-purin-8-yl)-3-chlorophenoxy)ethyl)piperazine-1-carboxylate

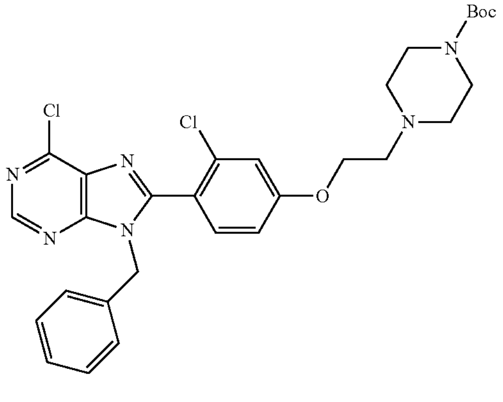 [SMILES: CC(C)(C)OC(=O)N1CCN(CCOc2ccc(-c3nc4c(Cl)ncnc4n3Cc3ccccc3)c(Cl)c2)CC1]

Iron(III) chloride solution (20.73 g, 128 mmol) was added to N4-benzyl-6-chloropyrimidine-4,5-diamine (30 g, 128 mmol, Example 1) and tert-butyl 4-(2-(3-chloro-4-formylphenoxy)ethyl)piperazine-1-carboxylate (51.9 g, 141 mmol) in EtOH (500 mL). The resulting mixture was stirred at 60° C. for 2 days. The reaction mixture was evaporated to dryness, redissolved in EtOAc (100 mL) and washed with water (3×100 mL). The organic layer was dried over $Na_2SO_4$, filtered and evaporated to afford a crude product. The crude product was purified by flash C18 chromatography, elution gradient 40 to 70% MeCN in water. Pure fractions were evaporated to dryness to afford tert-butyl 4-(2-(4-(9-benzyl-6-chloro-9H-purin-8-yl)-3-chlorophenoxy)ethyl)piperazine-1-carboxylate (12.00 g, 16%) as a yellow solid.

$^1$H NMR (300 MHz, DMSO-$d_6$): 1.17 (2H, t), 1.40 (9H, s), 1.99 (2H, s), 2.45 (4H, t), 2.74 (2H, t), 4.22 (2H, t), 5.38 (2H, s), 6.89-6.99 (2H, m), 7.09 (1H, dd), 7.17-7.25 (3H, m), 7.29 (1H, d), 7.51 (1H, d), 8.86 (1H, s). m/z: ES+ [M+H]+ 583.

tert-Butyl 4-(2-(4-(9-benzyl-6-(1-methylcyclopropoxy)-9H-purin-8-yl)-3-chlorophenoxy)ethyl)piperazine-1-carboxylate

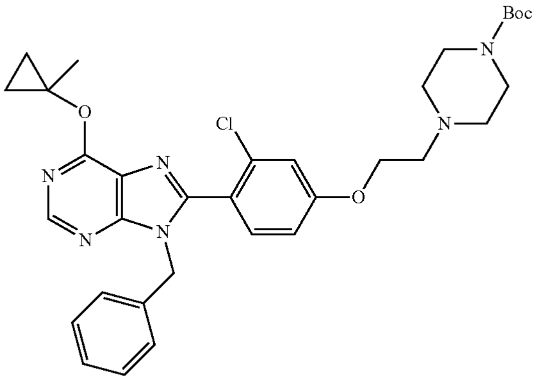 [SMILES: CC(C)(C)OC(=O)N1CCN(CCOc2ccc(-c3nc4c(OC5(C)CC5)ncnc4n3Cc3ccccc3)c(Cl)c2)CC1]

Sodium hydride (6.17 g, 257 mmol) was added to 1-methylcyclopropan-1-ol (5.56 g, 77.12 mmol) and tert-butyl 4-(2-(4-(9-benzyl-6-chloro-9H-purin-8-yl)-3-chlorophenoxy)ethyl)piperazine-1-carboxylate (30 g, 51.4 mmol) in THF (200 mL) at 0° C. under nitrogen. The resulting mixture was stirred at rt for 1 hour. The reaction mixture was poured into ice water. The reaction mixture was evaporated, diluted with EtOAc (250 mL) and washed sequentially with water (3×200 mL) and saturated brine (2×200 mL). The organic layer was dried over $Na_2SO_4$, filtered and evaporated to afford the crude product. The crude product was purified by flash C18-flash chromatography, elution gradient 30 to 80% MeCN in water (containing 0.1% $NH_4HCO_3$). Pure fractions were evaporated to dryness to afford tert-butyl 4-(2-(4-(9-benzyl-6-(1-methylcyclopropoxy)-9H-purin-8-yl)-3-chlorophenoxy)ethyl)piperazine-1-carboxylate (13.00 g, 41%) as a yellow solid. $^1$H NMR (300 MHz, DMSO-$d_6$): 0.8-0.88 (2H, m), 0.98-1.06 (2H, m), 1.40 (9H, s), 1.74 (3H, s), 2.39-2.48 (4H, m), 2.69-2.82 (2H, m), 3.33 (4H, s), 4.20 (2H, t), 5.30 (2H, s), 6.85-6.96 (2H, m), 7.05 (1H, d), 7.14-7.29 (4H, m), 7.42 (1H, d), 8.62 (1H, s). m/z: ES+ [M+H]+ 619.

Tert-butyl 4-(2-(3-chloro-4-formylphenoxy)ethyl)piperazine-1-carboxylate used as starting material was made as described in Example 4.

Example 7

4-((8-(2-Chloro-4-(2-(4-methylpiperazin-1-yl)ethoxy)phenyl)-6-(1-methylcyclopropoxy)-9H-purin-9-yl)methyl)-2-methylthiazole

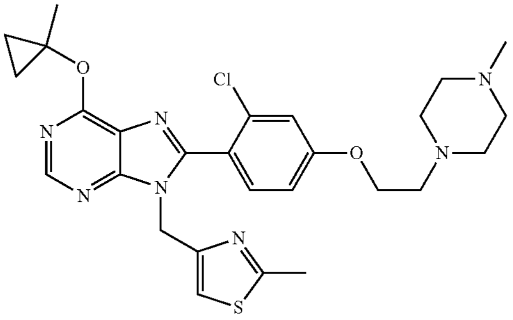 [SMILES: Cc1nc(Cn2c(-c3ccc(OCCN4CCN(C)CC4)cc3Cl)nc3c(OC4(C)CC4)ncnc32)cs1]

A solution of sodium hydrosulfite (282 mg, 1.62 mmol) in water (1 mL) was added to a stirred mixture of 6-(1-methylcyclopropoxy)-N-((2-methylthiazol-4-yl)methyl)-5-nitropyrimidin-4-amine (130 mg, 0.40 mmol) and 2-chloro-4-(2-(4-methylpiperazin-1-yl)ethoxy)benzaldehyde (137 mg, 0.49 mmol, Example 4 starting material) in NMP (3 mL). The resulting mixture was stirred at 100° C. for 16 hours then at 110° C. for a further 16 hours. The crude product was purified by flash C18-flash chromatography, elution gradient 5 to 40% MeCN in water (containing 5% TFA). Fractions were evaporated to dryness to afford the crude product. The crude product was further purified by preparative HPLC (XBridge Prep OBD C18 column, 5 μm silica, 30 mm diameter, 150 mm length), using decreasingly polar mixtures of water (containing 0.1% aq. $NH_3$ and 10 mmol/L $NH_4HCO_3$) and MeCN as eluents. Fractions containing the desired compound were evaporated to dryness to afford 4-((8-(2-chloro-4-(2-(4-methylpiperazin-1-yl)ethoxy)phenyl)-6-(1-methylcyclopropoxy)-9H-purin-9-yl)methyl)-2-methylthiazole (55 mg, 24%) as a white solid.

$^1$H NMR (400 MHz, DMSO-$d_6$): 0.81-0.88 (2H, m), 1.01 (2H, d), 1.73 (3H, s), 2.15 (3H, s), 2.33 (4H, s), 2.49 (3H, s), 2.52 (4H, s), 2.69 (2H, t), 4.17 (2H, t), 5.30 (2H, s), 6.96 (1H, s), 7.02 (1H, dd), 7.22 (1H, d), 7.43 (1H, d), 8.60 (1H, s). m/z: ES+ [M+H]+ 554.

6-(1-Methylcyclopropoxy)-N-((2-methylthiazol-4-yl)methyl)-5-nitropyrimidin-4-amine used as starting material was made as follows:

6-Chloro-N-((2-methylthiazol-4-yl)methyl)-5-nitropyrimidin-4-amine

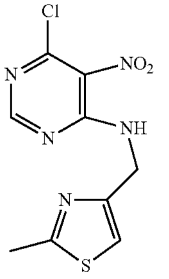 [SMILES: Cc1nc(CNc2ncnc(Cl)c2[N+](=O)[O-])cs1]

A solution of (2-methylthiazol-4-yl)methanamine (330 mg, 2.58 mmol) in DCM (10 mL) was added to a stirred mixture of 4,6-dichloro-5-nitropyrimidine (500 mg, 2.58 mmol) and N,N-diisopropylethylamine (1.35 mL, 7.73 mmol) in DCM (10 mL) at 0° C. The resulting mixture was stirred at rt for 1 hour. The reaction mixture was diluted with water (25 mL), extracted with DCM (3×20 mL). The organic layer was dried over $Na_2SO_4$, filtered and evaporated to give 6-chloro-N-((2-methylthiazol-4-yl)methyl)-5-nitropyrimidin-4-amine (0.4 g) as a yellow gum. The product was used in the next step directly without further purification.

6-(1-methylcyclopropoxy)-N-((2-methylthiazol-4-yl)methyl)-5-nitropyrimidin-4-amine

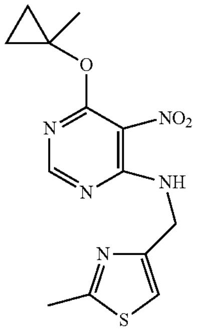 [SMILES: Cc1nc(CNc2ncnc(OC3(C)CC3)c2[N+](=O)[O-])cs1]

LHMDS (2.66 mL, 2.66 mmol) was added to 6-chloro-N-((2-methylthiazol-4-yl)methyl)-5-nitropyrimidin-4-amine (0.38 g, 1.33 mmol) and 1-methylcyclopropan-1-ol (0.192 g, 2.66 mmol) in THF (20 mL) at 0° C. The resulting mixture was stirred at rt for 16 hours. The reaction mixture was quenched with saturated $NH_4Cl$ (25 mL), then the THF solvent was removed under reduced pressure. The reaction mixture was extracted with EtOAc (3×20 mL), the organic layer was dried over $Na_2SO_4$, filtered and evaporated to afford a yellow gum. The crude product was purified by flash C18-flash chromatography, elution gradient 5 to 100% MeCN in water. Pure fractions were evaporated to dryness to afford 6-(1-methylcyclopropoxy)-N-((2-methylthiazol-4-yl)methyl)-5-nitropyrimidin-4-amine (0.150 g, 35%) as a yellow solid. $^1$H NMR (300 MHz, DMSO-$d_6$): 0.76 (2H, dd), 0.88-0.96 (2H, m), 1.61 (3H, s), 2.61 (3H, s), 4.71 (2H, dd), 7.18 (1H, d), 8.33 (1H, s), 8.80 (1H, t). m/z: ES+ [M+H]+ 322.

Example 8

1-Benzyl-2-(2-chloro-4-(2-(piperazin-1-yl)ethoxy)phenyl)-5-isopropoxy-1H-imidazo[4,5-b]pyridine

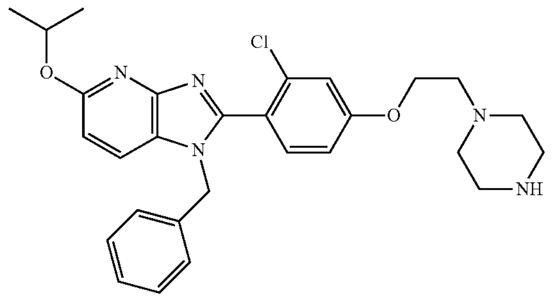 [SMILES: CC(C)Oc1ccc2c(n1)nc(-c1ccc(OCCN3CCNCC3)cc1Cl)n2Cc1ccccc1]

Tert-butyl 4-(2-(4-(1-benzyl-5-isopropoxy-1H-imidazo[4,5-b]pyridin-2-yl)-3-chlorophenoxy)ethyl)piperazine-1-carboxylate (44 mg, 0.07 mmol) was added to trifluoroacetic acid (0.5 ml, 6.49 mmol) in dichloromethane (2 mL). The resulting solution was stirred at rt for 1 hour after which the solvent was removed under reduced pressure. The crude product was purified by flash C18-flash chromatography, elution gradient 30 to 80% MeOH in water (0.1% $NH_4HCO_3$). Pure fractions were evaporated to dryness to afford 1-benzyl-2-(2-chloro-4-(2-(piperazin-1-yl)ethoxy)phenyl)-5-isopropoxy-1H-imidazo[4,5-b]pyridine (0.026 g, 71%) as a white solid. $^1$H NMR (300 MHz, DMSO-$d_6$): 1.32 (6H, d), 2.40 (4H, t), 2.64-2.72 (6H, m), 4.18 (2H, t), 5.24-5.34 (3H, m), 6.63 (1H, d), 6.94-6.99 (2H, m), 7.07 (1H, dd), 7.21-7.29 (4H, m), 7.49 (1H, d), 7.80 (1H, d)—one proton not observed. m/z: ES+ [M+H]+ 506.

Tert-butyl 4-(2-(4-(1-benzyl-5-isopropoxy-1H-imidazo[4,5-b]pyridin-2-yl)-3-chlorophenoxy)ethyl)piperazine-1-carboxylate used as starting material was made as follows:

6-Amino-5-nitropyridin-2(1H)-one

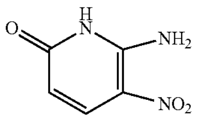 [SMILES: Nc1[nH]c(=O)ccc1[N+](=O)[O-]]

6-Chloro-3-nitropyridin-2-amine (10 g, 57.62 mmol) was added to NaOH (23.1 g, 57.6 mmol) in EtOH (50 mL) and water (16.6 mL). The resulting solution was stirred at 80° C. for 30 minutes. The reaction mixture was acidified with conc. HCl and the precipitate formed was filtered to afford 6-amino-5-nitropyridin-2(1H)-one (8.00 g, 90%) as a yellow solid. The product was used in the next step directly without further purification. $^1$H NMR (300 MHz, DMSO-$d_6$): 11.51 (s, 1H), 8.53 (s, 2H), 7.98 (d, 1H), 5.66 (d, 1H). m/z: ES− [M−H]− 154.

6-Isopropoxy-3-nitropyridin-2-amine

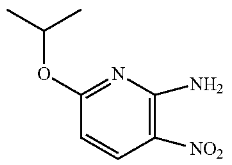

6-Amino-5-nitropyridin-2(1H)-one (4 g, 25.8 mmol) was added to potassium carbonate (10.7 g, 77.4 mmol) and 2-iodopropane (13.1 g, 77.4 mmol) in DMF (80 mL) at 80° C. The resulting solution was stirred at 80° C. overnight. After cooling of the reaction mixture, the solvent was removed under reduced pressure. The crude product was purified by flash silica chromatography, elution gradient 0 to 20% EtOAc in petroleum ether. Pure fractions were evaporated to dryness to afford 6-isopropoxy-3-nitropyridin-2-amine (3.20 g, 63%) as a yellow solid. $^{1}$H NMR (300 MHz, DMSO-$d_6$): 1.18 (6H, d), 5.12-5.24 (1H, m), 5.95 (1H, d), 7.97 (2H, s), 8.10 (1H, d). m/z: ES+ [M+H]+ 198.

6-Isopropoxypyridine-2,3-diamine

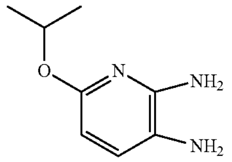

6-Isopropoxy-3-nitropyridin-2-amine (3.1 g, 15.72 mmol) and palladium on carbon (310 mg, 0.29 mmol) in MeOH (60 mL) were stirred under an atmosphere of hydrogen at rt for 2 hours. The reaction mixture was filtered through filter paper to afford 6-isopropoxypyridine-2,3-diamine (2.60 g, 99%) as a purple oil. The product was used in the next step directly without further purification. $^{1}$H NMR (300 MHz, DMSO-$d_6$): 1.18 (6H, d), 3.92-4.69 (2H, m), 4.9-4.97 (1H, m), 4.97-5.51 (2H, m), 5.73 (1H, d), 6.73 (1H, d). m/z: ES+ [M+H]+ 168.

N3-benzyl-6-isopropoxypyridine-2,3-diamine

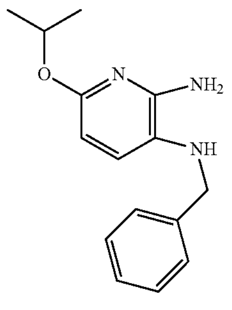 [SMILES: CC(C)Oc1ccc(NCc2ccccc2)c(N)n1]

6-Isopropoxypyridine-2,3-diamine (1.5 g, 8.97 mmol) was added to benzaldehyde (0.909 ml, 8.97 mmol) and acetic acid (0.051 ml, 0.90 mmol) in dichloromethane (30 mL). The reaction was stirred for 5 hours at rt. Sodium triacetoxyborohydride (5.70 g, 26.91 mmol) was then added to the reaction mixture. The resulting solution was stirred for a further 16 hours at rt. The reaction mixture was concentrated under reduced pressure. The crude product was purified by flash silica chromatography, elution gradient 0 to 20% EtOAc in petroleum ether. Pure fractions were evaporated to dryness to afford N3-benzyl-6-isopropoxypyridine-2,3-diamine (1.10 g, 48%) as a purple oil. $^{1}$H NMR (300 MHz, DMSO-$d_6$): 1.17 (6H, d), 4.20 (2H, s), 4.94 (1H, p), 5.45 (2H, s), 5.73 (1H, d), 6.57 (1H, d), 7.12-7.25 (1H, m), 7.25-7.46 (4H, m)—one proton not observed. m/z: ES+ [M+H]+ 258.

Tert-butyl 4-(2-(4-(1-benzyl-5-isopropoxy-1H-imidazo[4,5-b]pyridin-2-yl)-3-chlorophenoxy)ethyl) piperazine-1-carboxylate

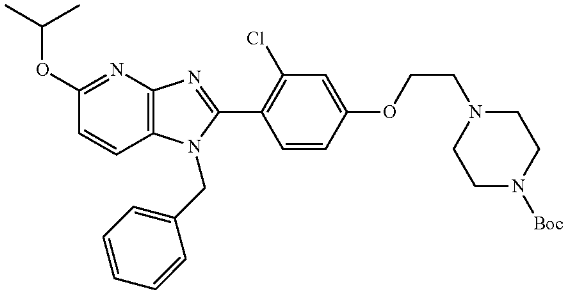 [SMILES: CC(C)Oc1ccc2c(n1)nc(-c1ccc(OCCN3CCN(C(=O)OC(C)(C)C)CC3)cc1Cl)n2Cc1ccccc1]

N3-benzyl-6-isopropoxypyridine-2,3-diamine (50 mg, 0.19 mmol) was added to tert-butyl 4-(2-(3-chloro-4-formylphenoxy)ethyl)piperazine-1-carboxylate (86 mg, 0.23 mmol, Example 6 starting material) and copper(II) acetate monohydrate (7.76 mg, 0.04 mmol) in acetic acid (2 mL). The resulting solution was stirred at 100° C. for 1 hour. The solvent was removed under reduced pressure. The crude product was purified by flash silica chromatography, elution gradient 0 to 10% MeOH in dichloromethane. Pure fractions were evaporated to dryness to afford tert-butyl 4-(2-(4-(1-benzyl-5-isopropoxy-1H-imidazo[4,5-b]pyridin-2-yl)-3-chlorophenoxy)ethyl)piperazine-1-carboxylate (118 mg, 100%) as a yellow solid. $^{1}$H NMR (300 MHz, DMSO-$d_6$): 1.2-1.35 (6H, m), 1.39 (9H, d), 2.44 (4H, s), 2.73 (2H, s), 3.17 (8H, d), 4.08 (3H, q), 4.19 (1H, d), 5.30 (1H, d), 6.82 (1H, t), 6.97 (1H, d), 7.07 (1H, d), 7.2-7.25 (1H, m), 7.27 (1H, d), 7.46-7.56 (1H, m). m/z: ES+ [M+H]+ 606.

Example 9

2-(2-Chloro-4-(2-(4-methylpiperazin-1-yl)ethoxy)phenyl)-1-(3-chlorobenzyl)-1H-benzo[d]imidazol-5-ol

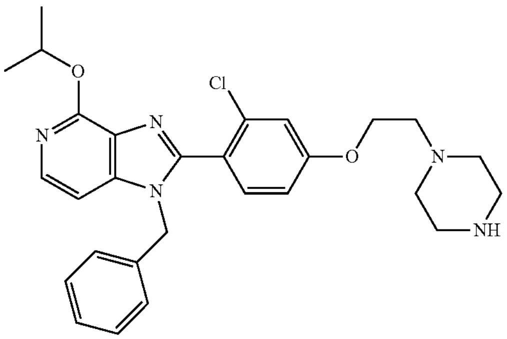 [SMILES: CC(C)Oc1nccc2c1nc(-c1ccc(OCCN3CCNCC3)cc1Cl)n2Cc1ccccc1]

Tert-butyl 4-(2-(4-(1-benzyl-4-isopropoxy-1H-imidazo[4,5-c]pyridin-2-yl)-3-chlorophenoxy)ethyl)piperazine-1-carboxylate (90 mg, 0.15 mmol) was added to trifluoroacetic acid (1 mL, 12.98 mmol) in dichloromethane (4 mL). The resulting solution was stirred at rt for 1 hour. The solvent was removed under reduced pressure. The crude product was purified by flash C18-flash chromatography, elution gradient 30 to 80% MeOH in water (0.1% $NH_4HCO_3$). Pure fractions were evaporated to dryness to afford 1-benzyl-2-(2-chloro-4-(2-(piperazin-1-yl)ethoxy)phenyl)-4-isopropoxy-1H-imidazo[4,5-c]pyridine (0.029 g, 38%) as a white solid. $^1H$ NMR (400 MHz, DMSO-$d_6$): 1.37 (6H, d), 2.36-2.44 (4H, m), 2.64-2.72 (6H, m), 4.18 (2H, t), 5.28 (2H, s), 5.44-5.55 (1H, m), 6.92-6.96 (2H, m), 7.05 (1H, dd), 7.12 (1H, d), 7.21-7.28 (4H, m), 7.47 (1H, d), 7.85 (1H, d)—one proton not observed. m/z: ES+ [M+H]+ 506.

Tert-butyl 4-(2-(4-(1-benzyl-4-isopropoxy-1H-imidazo[4,5-c]pyridin-2-yl)-3-chlorophenoxy)ethyl)piperazine-1-carboxylate used as starting material was made as follows:

4-Chloro-2-isopropoxy-3-nitropyridine

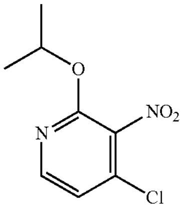

4-Chloro-3-nitropyridin-2(1H)-one (5.0 g, 28.6 mmol) was added to sodium hydride (2.06 g, 85.9 mmol) in DMF (100 mL) at 0° C. The reaction was warmed to rt over 30 minutes and then 2-iodopropane (24.3 g, 143.2 mmol) was added. The resulting solution was stirred at rt for a further 12 hours. The reaction mixture was quenched with saturated $NH_4Cl$ (50 mL), extracted with EtOAc (3×100 mL), the organic layer was dried over $Na_2SO_4$, filtered and evaporated to afford crude product. The crude product was purified by flash C18-flash chromatography, elution gradient 5 to 80% MeOH in water (0.1% $NH_4HCO_3$). Pure fractions were evaporated to dryness to afford 4-chloro-2-isopropoxy-3-nitropyridine (2.10 g, 34%) as a yellow oil. $^1H$ NMR (300 MHz, DMSO-$d_6$): 1.30 (6H, d), 5.29-5.44 (1H, m), 7.43 (1H, d), 8.37 (1H, d).

N-Benzyl-2-isopropoxy-3-nitropyridin-4-amine

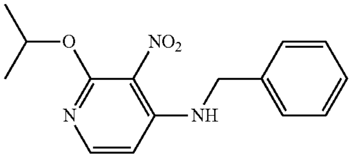 [SMILES: CC(C)Oc1nccc(NCc2ccccc2)c1[N+](=O)[O-]]

4-Chloro-2-isopropoxy-3-nitropyridine (1.0 g, 4.62 mmol) was added to benzylamine (0.504 mL, 4.62 mmol) and TEA (6.43 mL, 46.2 mmol) in DMSO (20 mL). The resulting solution was stirred at 90° C. for 5 hours. The solvent was removed under reduced pressure. The crude product was purified by flash silica chromatography, elution gradient 0 to 10% EtOAc in petroleum ether. Pure fractions were evaporated to dryness to afford N-benzyl-2-isopropoxy-3-nitropyridin-4-amine (1.20 g, 90%) as a yellow solid. $^1H$ NMR (300 MHz, DMSO-$d_6$): 1.25 (6H, d), 4.49 (2H, d), 5.21-5.35 (1H, m), 6.39 (1H, d), 7.21-7.28 (1H, m), 7.3-7.35 (4H, m), 7.75 (1H, d), 7.87 (1H, t). m/z: ES− [M−H]− 286.

N4-Benzyl-2-isopropoxypyridine-3,4-diamine

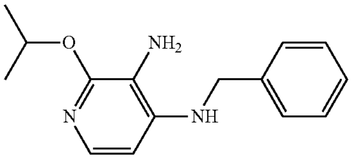 [SMILES: CC(C)Oc1nccc(NCc2ccccc2)c1N]

N-benzyl-2-isopropoxy-3-nitropyridin-4-amine (1 g, 3.48 mmol) was added to iron (0.972 g, 17.40 mmol) and ammonium chloride (1.862 g, 34.80 mmol) in EtOH (16 mL) and water (1.6 mL). The resulting solution was stirred at 80° C. for 12 hours. The reaction mixture was filtered through filter paper then the solvents were removed under reduced pressure. The crude product was purified by flash silica chromatography, elution gradient 0 to 20% EtOAc in petroleum ether. Pure fractions were evaporated to dryness to afford N4-benzyl-2-isopropoxypyridine-3,4-diamine (0.518 g, 58%) as a yellow solid. $^1H$ NMR (300 MHz, DMSO-$d_6$): 1.25 (6H, d), 4.04 (2H, s), 4.35 (2H, d), 5.09-5.19 (1H, m), 5.91 (1H, t), 6.10 (1H, d), 7.18 (1H, d), 7.2-7.25 (1H, m), 7.28-7.32 (1H, m), 7.32-7.37 (3H, m). m/z: ES+ [M+H]+ 258.

Tert-butyl 4-(2-(4-(1-benzyl-4-isopropoxy-1H-imidazo[4,5-c]pyridin-2-yl)-3-chlorophenoxy)ethyl) piperazine-1-carboxylate

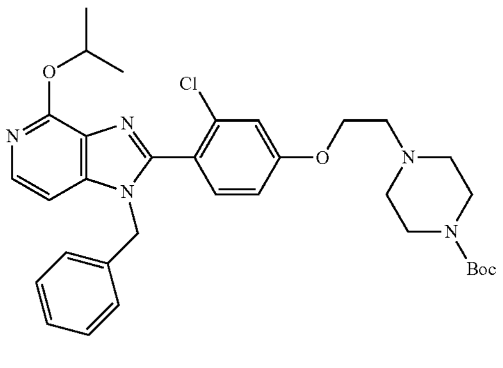 [SMILES: CC(C)Oc1nccc2c1nc(-c1ccc(OCCN3CCN(C(=O)OC(C)(C)C)CC3)cc1Cl)n2Cc1ccccc1]

N4-benzyl-2-isopropoxypyridine-3,4-diamine (50 mg, 0.19 mmol) was added to tert-butyl 4-(2-(3-chloro-4-formylphenoxy)ethyl)piperazine-1-carboxylate (86 mg, 0.23 mmol) and copper(II) acetate monohydrate (7.8 mg, 0.04 mmol) in AcOH (2 mL). The resulting solution was stirred at 100° C. for 1 hour. The solvent was removed under reduced pressure. The crude product was purified by flash C18-flash chromatography, elution gradient 10 to 80% MeOH in water (0.1% $NH_4HCO_3$). Pure fractions were evaporated to dryness to afford tert-butyl 4-(2-(4-(1-benzyl-4-isopropoxy-1H-imidazo[4,5-c]pyridin-2-yl)-3-chlorophenoxy)ethyl)piperazine-1-carboxylate (95 mg, 81%) as a yellow solid. $^1H$ NMR (400 MHz, DMSO-$d_6$): 1.37 (6H, d), 1.39 (9H, s), 2.44 (4H, t), 2.74 (2H, t), 3.28-3.3 (2H, m), 3.32-3.34 (2H, m), 4.20 (2H, t), 5.28 (2H, s), 5.47-5.53 (1H, m), 6.92-6.96 (2H, m), 7.05 (1H, dd), 7.12 (1H, d), 7.21-7.24 (3H, m), 7.27 (1H, d), 7.47 (1H, d), 7.85 (1H, d). m/z: ES+ [M+H]+ 606.

Example 10

8-(2-Chloro-4-(2-(piperazin-1-yl)ethoxy)phenyl)-9-((4-chloropyridin-2-yl)methyl)-6-(1-methylcyclopropoxy)-9H-purine

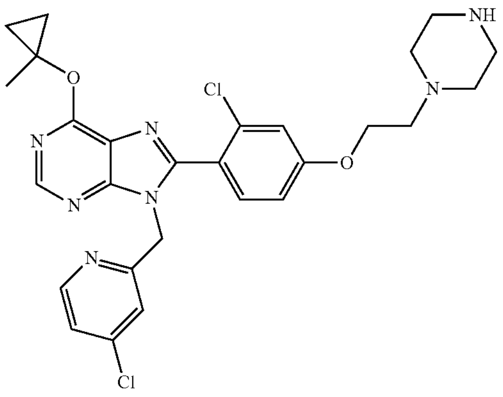 [SMILES: CC1(Oc2ncnc3c2nc(-c2ccc(OCCN4CCNCC4)cc2Cl)n3Cc2cc(Cl)ccn2)CC1]

A solution of tert-butyl 4-(2-(3-chloro-4-(9-((4-chloropyridin-2-yl)methyl)-6-(1-methylcyclopropoxy)-9H-purin-8-yl)phenoxy)ethyl)piperazine-1-carboxylate (2.07 g, 3.16 mmol) in acetonitrile was cooled to 0° C. with an ice/water bath. Hydrogen chloride 4.0 M in dioxane (8.0 mL, 32.0 mmol) was added and the ice bath removed. Stirring was continued at rt for 1 h before additional hydrogen chloride 4.0 M in dioxane (8.0 mL, 32.0 mmol) was added and stirring continued for a further 30 min. The reaction mixture was evaporated to give the crude product as a yellow solid. The crude product was purified by ion exchange chromatography, using an SCX column. The desired product was eluted from the column using 1M $NH_3$/MeOH to dryness to afford the crude free base. The crude free base was purified by flash deactivated alumina chromatography, elution gradient 0 to 10% MeOH in DCM to afford 8-(2-chloro-4-(2-(piperazin-1-yl)ethoxy)phenyl)-9-((4-chloropyridin-2-yl)methyl)-6-(1-methylcyclopropoxy)-9H-purine (1.50 g, 86%) as a yellow foam.

$^1H$ NMR (500 MHz, $CDCl_3$): 0.8-0.87 (2H, m), 1.14-1.2 (2H, m), 1.81 (3H, s), 2.55 (4H, s), 2.80 (2H, t), 2.92 (4H, t), 4.12 (2H, t), 5.44 (2H, s), 6.80 (1H, dd), 6.88 (1H, dd), 7.02 (1H, d), 7.12 (1H, dd), 7.25 (1H, d), 8.30 (1H, dd), 8.64 (1H, s). $^1H$ not observed. m/z: ES+ [M+H]+ 554.

Tert-butyl 4-(2-(3-chloro-4-(9-((4-chloropyridin-2-yl)methyl)-6-(1-methylcyclopropoxy)-9H-purin-8-yl)phenoxy)ethyl)piperazine-1-carboxylate used as starting material was made as follows:

Tert-butyl 4-(2-(3-chloro-4-(6-chloro-9H-purin-8-yl)phenoxy)ethyl)piperazine-1-carboxylate

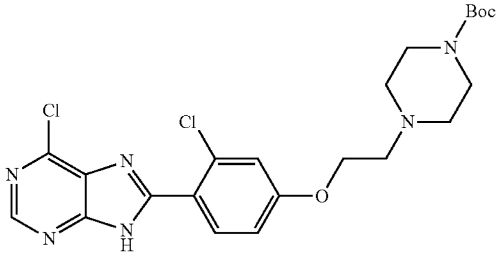 [SMILES: CC(C)(C)OC(=O)N1CCN(CCOc2ccc(-c3nc4c(Cl)ncnc4[nH]3)c(Cl)c2)CC1]

Tert-butyl 4-(2-(3-chloro-4-formylphenoxy)ethyl)piperazine-1-carboxylate (1 g, 2.71 mmol) and 6-chloropyrimidine-4,5-diamine (0.431 g, 2.98 mmol) were dissolved in IPA (38.7 mL). Iron(III) chloride (0.088 g, 0.54 mmol) was added and the reaction stirred at 80° C. under air for 2.5 days. The reaction was cooled to rt, diluted with DCM (50 mL) and water (50 mL) was added. The mixture was filtered through a small plug of celite to aid separation, washing the celite with DCM (50 mL). The mixture was then extracted with DCM (50 mL×3) and the combined organics were washed with saturated $NaHCO_3$ (20 mL), separated, dried over $MgSO_4$, filtered and evaporated to afford crude product. The crude product was purified by flash silica chromatography, elution gradient 0 to 100% EtOAc in heptane then 3:1 EtOAc/EtOH in EtOAc to elute product. Pure fractions were evaporated to dryness to afford tert-butyl 4-(2-(3-chloro-4-(6-chloro-9H-purin-8-yl)phenoxy)ethyl)piperazine-1-carboxylate (1.050 g, 78%) as a pale yellow solid. $^1H$ NMR (500 MHz, DMSO-$d_6$): 1.40 (9H, s), 2.44-2.48 (4H, m), 2.76 (2H, t), 3.26-3.38 (4H, m), 4.23 (2H, t), 7.15 (1H, dd), 7.30 (1H, d), 7.81 (1H, d), 8.75 (1H, s). 1H not observed. m/z: ES+ [M+H]+ 493.

Tert-butyl 4-(2-(3-chloro-4-formylphenoxy)ethyl)piperazine-1-carboxylate used as starting material was made as described in Example 4.

Tert-butyl 4-(2-(3-chloro-4-(6-chloro-9-((4-chloropyridin-2-yl)methyl)-9H-purin-8-yl)phenoxy)ethyl)piperazine-1-carboxylate

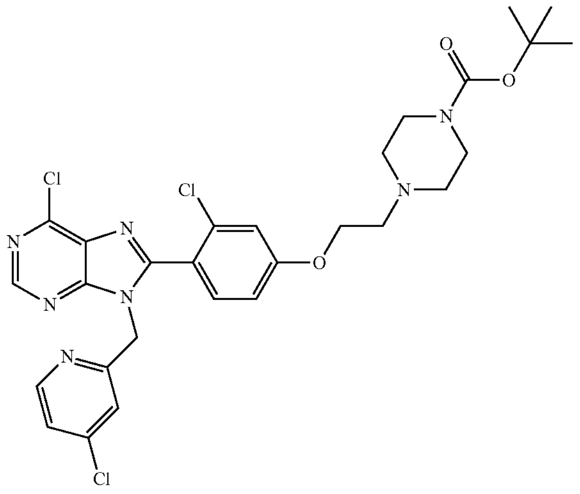 [SMILES: CC(C)(C)OC(=O)N1CCN(CCOc2ccc(-c3nc4c(Cl)ncnc4n3Cc3cc(Cl)ccn3)c(Cl)c2)CC1]

To a solution of tert-butyl 4-(2-(3-chloro-4-(6-chloro-9H-purin-8-yl)phenoxy)ethyl)piperazine-1-carboxylate (1.62 g, 3.28 mmol) and 4-chloro-2-(chloromethyl)pyridine hydrochloride (0.977 g, 4.93 mmol) in anhydrous DMF (16.4 mL) was added cesium carbonate (3.21 g, 9.85 mmol). The reaction was inerted by the application of three cycles of vacuum and nitrogen backfill and then the reaction was stirred at 60° C. under nitrogen for 19 h. The reaction was quenched with ice-water (20 mL), and ethyl acetate (20 mL) was added. The organic layer was removed and the aqueous layer was further extracted with ethyl acetate (10 mL×6). The combined organic layers were washed with a LiCl saturated aqueous solution (10 mL×3), filtered through an isolute phase separation cartridge and evaporated to afford crude product as a brown foam. The crude product was purified by flash silica chromatography, elution gradient 0 to 35% then to 70% 3:1 EtOAc:EtOH in n-heptane. Pure fractions were evaporated to dryness to afford tert-butyl 4-(2-(3-chloro-4-(6-chloro-9-((4-chloropyridin-2-yl)methyl)-9H-purin-8-yl)phenoxy)ethyl)piperazine-1-carboxylate (1.13 g, 56%) as a pale brown foam. $^{1}H$ NMR (500 MHz, $CDCl_3$): 1.47 (9H, s), 2.5-2.54 (4H, m), 2.83 (2H, t), 3.44-3.48 (4H, m), 4.14 (2H, t), 5.47 (2H, s), 6.84 (1H, dd), 6.98 (1H, d), 7.05 (1H, d), 7.14 (1H, dd), 7.31 (1H, d), 8.28 (1H, d), 8.77 (1H, s). m/z: ES+ [M+H]+ 618.

Tert-butyl 4-(2-(3-chloro-4-(9-((4-chloropyridin-2-yl)methyl)-6-(1-methylcyclopropoxy)-9H-purin-8-yl)phenoxy)ethyl)piperazine-1-carboxylate

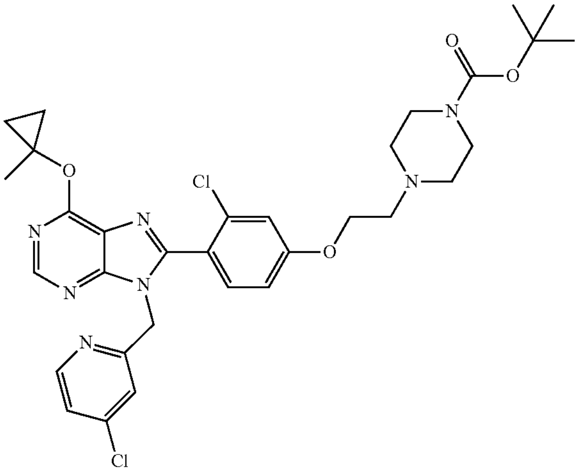 [SMILES: CC(C)(C)OC(=O)N1CCN(CCOc2ccc(-c3nc4c(OC5(C)CC5)ncnc4n3Cc3cc(Cl)ccn3)c(Cl)c2)CC1]

To a suspension of sodium hydride (0.889 g, 22.2 mmol) in tetrahydrofuran (15 mL) cooled to 0° C. under nitrogen was added a solution of 1-methylcyclopropan-1-ol (0.802 g, 11.1 mmol) and tert-butyl 4-(2-(3-chloro-4-(6-chloro-9-((4-chloropyridin-2-yl)methyl)-9H-purin-8-yl)phenoxy)ethyl)piperazine-1-carboxylate (3.44 g, 5.56 mmol) in tetrahydrofuran (30 mL) as a steady stream. The reaction mixture was stirred at 0° C. for 20 min and then the ice bath removed and the reaction was stirred at room temperature under nitrogen for 19 h. The reaction mixture was cooled with an ice/water bath and carefully quenched with saturated ammonium chloride solution (15 mL). After gas evolution had subsided, the mixture was diluted with water (150 mL) and EtOAc (150 mL). The aqueous phase was extracted with EtOAc (150 mL). The combined organic phases were washed with brine, dried and evaporated. The crude product was purified by flash silica chromatography, elution gradient 0 to 100% 3:1 EtOAc/EtOH in heptane to afford tert-butyl 4-(2-(3-chloro-4-(9-((4-chloropyridin-2-yl)methyl)-6-(1-methylcyclopropoxy)-9H-purin-8-yl)phenoxy)ethyl)piperazine-1-carboxylate (2.07 g, 57%) as a pale yellow foam. $^{1}H$ NMR (500 MHz, $CDCl_3$): 0.8-0.87 (2H, m), 1.14-1.2 (2H, m), 1.47 (9H, s), 1.81 (3H, s), 2.45-2.59 (4H, m), 2.82 (2H, t), 3.38-3.53 (4H, m), 4.12 (2H, t), 5.44 (2H, s), 6.80 (1H, dd), 6.89 (1H, d), 7.01 (1H, d), 7.12 (1H, dd), 7.24-7.28 (1H, m), 8.30 (1H, d), 8.64 (1H, s). m/z: ES+ [M+H]+ 654.

Example 11

9-Benzyl-8-(2-chloro-4-(2-(piperazin-1-yl)ethoxy)phenyl)-6-((1,1,1-trifluoro-2-methylpropan-2-yl)oxy)-9H-purine

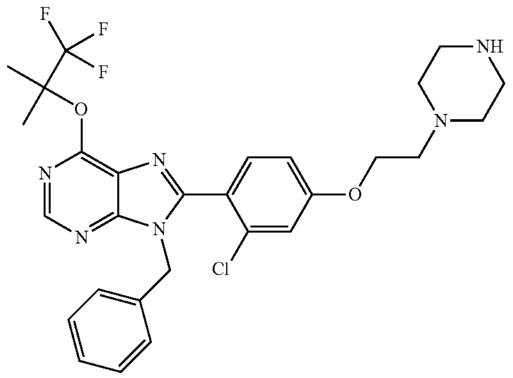 [SMILES: CC(C)(Oc1ncnc2c1nc(-c1ccc(OCCN3CCNCC3)cc1Cl)n2Cc1ccccc1)C(F)(F)F]

Tert-butyl 4-(2-(4-(9-benzyl-6-((1,1,1-trifluoro-2-methylpropan-2-yl)oxy)-9H-purin-8-yl)-3-chlorophenoxy)ethyl)piperazine-1-carboxylate (120 mg, 0.18 mmol) was added to trifluoroacetic acid (0.2 mL, 2.60 mmol) in dichloromethane (2 mL). The resulting solution was stirred at rt for 2 hours. The solvent was removed under reduced pressure. The crude product was purified by flash C18-flash chromatography, elution gradient 50 to 100% MeOH in water (0.1% $NH_4HCO_3$), followed by preparative HPLC (XBridge Prep OBD C18 column, 30*150 mm, 5 μm), using decreasingly polar mixtures of water (containing 10 mmol/L $NH_4HCO_3$) and MeCN as eluents. Fractions containing the desired compound were evaporated to dryness to afford 9-benzyl-8-(2-chloro-4-(2-(piperazin-1-yl)ethoxy)phenyl)-6-((1,1,1-trifluoro-2-methylpropan-2-yl)oxy)-9H-purine (30.0 mg, 29%) as a white solid. $^1H$ NMR (300 MHz, DMSO-$d_6$): 1.95 (6H, s), 2.3-2.45 (4H, m), 2.58-2.79 (6H, m), 4.18 (2H, t), 5.30 (2H, s), 6.91 (2H, dd), 7.04 (1H, dd), 7.15-7.23 (3H, m), 7.27 (1H, d), 7.43 (1H, d), 8.61 (1H, s)-1H not observed. m/z: ES+ [M+H]+ 575.

Tert-butyl 4-(2-(4-(9-benzyl-6-((1,1,1-trifluoro-2-methylpropan-2-yl)oxy)-9H-purin-8-yl)-3-chlorophenoxy)ethyl)piperazine-1-carboxylate used as starting material was made as follows:

N-benzyl-5-nitro-6-((1,1,1-trifluoro-2-methylpropan-2-yl)oxy)pyrimidin-4-amine

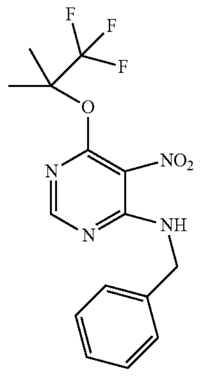 [SMILES: CC(C)(Oc1ncnc(NCc2ccccc2)c1[N+](=O)[O-])C(F)(F)F]

LHMDS (11.3 mL, 11.3 mmol) was added to N-benzyl-6-chloro-5-nitropyrimidin-4-amine (1 g, 3.78 mmol) and 1,1,1-trifluoro-2-methylpropan-2-ol (1.24 mL, 11.3 mmol) in THF (20 mL) under 0° C. The resulting mixture was stirred at 60° C. for 12 hours. The reaction mixture was diluted with EtOAc (100 mL) and washed sequentially with saturated brine (3×100 mL). The organic layer was dried over $Na_2SO_4$, filtered and evaporated to afford crude product. The crude product was purified by flash silica chromatography, elution gradient 0 to 5% EtOAc in petroleum ether. Fractions were evaporated to dryness to afford N-benzyl-5-nitro-6-((1,1,1-trifluoro-2-methylpropan-2-yl)oxy)pyrimidin-4-amine (800 mg, 59%) as a pale yellow oil. $^1H$ NMR (300 MHz, DMSO-$d_6$): 1.81 (6H, s), 4.69 (2H, d), 7.07-7.47 (5H, m), 8.31 (1H, s), 8.90 (1H, t). m/z: ES+ [M+H]+ 357.

N4-benzyl-6-((1,1,1-trifluoro-2-methylpropan-2-yl)oxy)pyrimidine-4,5-diamine

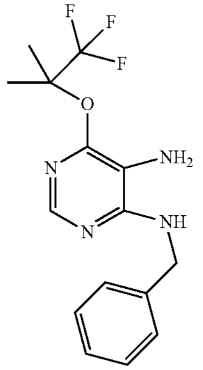 [SMILES: CC(C)(Oc1ncnc(NCc2ccccc2)c1N)C(F)(F)F]

Iron (549 mg, 9.82 mmol) was added to a mixture of N-benzyl-5-nitro-6-((1,1,1-trifluoro-2-methylpropan-2-yl)oxy)pyrimidin-4-amine (700 mg, 1.96 mmol) and ammonium chloride (1.05 g, 19.6 mmol) in ethanol (15 mL). The resulting mixture was stirred at 80° C. for 4 hours. The solvent was then removed under reduced pressure and the crude product was purified by flash silica chromatography, elution gradient 0 to 30% EtOAc in petroleum ether. Pure fractions were evaporated to dryness to afford N4-benzyl-6-((1,1,1-trifluoro-2-methylpropan-2-yl)oxy)pyrimidine-4,5-diamine (400 mg, 63%) as a white solid. $^1H$ NMR (300 MHz, DMSO-$d_6$): 1.72 (6H, s), 4.16 (2H, s), 4.61 (2H, d), 6.95 (1H, t), 7.11-7.46 (5H, m), 7.72 (1H, s). m/z: ES+ [M+H]+ 327.

Tert-butyl 4-(2-(4-(9-benzyl-6-((1,1,1-trifluoro-2-methylpropan-2-yl)oxy)-9H-purin-8-yl)-3-chlorophenoxy)ethyl)piperazine-1-carboxylate

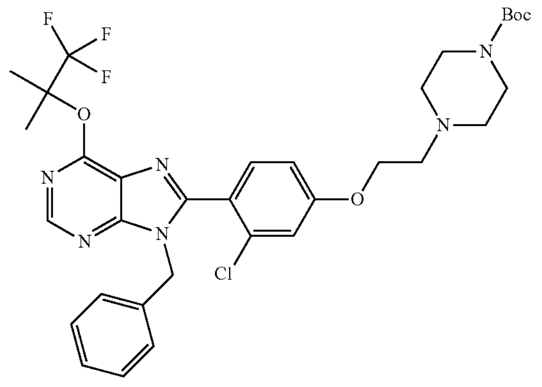 [SMILES: CC(C)(C)OC(=O)N1CCN(CCOc2ccc(-c3nc4c(OC(C)(C)C(F)(F)F)ncnc4n3Cc3ccccc3)c(Cl)c2)CC1]

Iron(III) chloride (49.7 mg, 0.31 mmol) was added to N4-benzyl-6-((1,1,1-trifluoro-2-methylpropan-2-yl)oxy)pyrimidine-4,5-diamine (100 mg, 0.31 mmol), tert-butyl 4-(2-(3-chloro-4-formylphenoxy)ethyl)piperazine-1-carboxylate (124 mg, 0.34 mmol) and AcOH (1.7 μL, 0.03 mmol) in IPA (2 mL). The resulting mixture was stirred at 80° C. for 4 hours. The solvent was then removed under reduced pressure and the crude residue was purified by C18-flash chromatography, elution gradient 40 to 90% MeOH in water (0.1% $NH_4HCO_3$). Pure fractions were evaporated to dryness to afford tert-butyl 4-(2-(4-(9-benzyl-6-((1,1,1-trifluoro-2-methylpropan-2-yl)oxy)-9H-purin-8-yl)-3-chlorophenoxy)ethyl)piperazine-1-carboxylate (140 mg, 68%) as a white foam. $^1H$ NMR (300 MHz, DMSO-$d_6$): 1.38 (9H, s), 1.94 (6H, s), 2.43 (4H, t), 2.72 (2H, t), 3.24-3.32 (4H, m), 4.19 (2H, t), 5.29 (2H, s), 6.90 (2H, dd), 7.03 (1H, dd), 7.12-7.24 (3H, m), 7.26 (1H, d), 7.43 (1H, d), 8.60 (1H, s). m/z: ES+ [M+H]+ 675.

Example 12

9-Benzyl-8-(2-chloro-4-(2-(piperazin-1-yl)ethoxy)phenyl)-6-(1-methylcyclobutoxy)-9H-purine

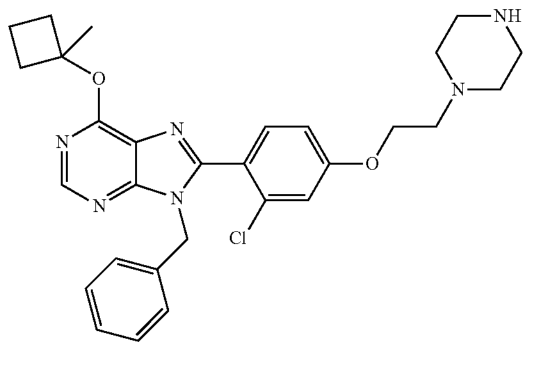 [SMILES: CC1(Oc2ncnc3c2nc(-c2ccc(OCCN4CCNCC4)cc2Cl)n3Cc2ccccc2)CCC1]

$Pd(PPh_3)_4$ (31.0 mg, 0.03 mmol) was added to 9-benzyl-8-bromo-6-(1-methylcyclobutoxy)-9H-purine (100 mg, 0.27 mmol), 1-(2-(3-chloro-4-(4,4,5,5-tetramethyl-1,3,2-dioxaborolan-2-yl)phenoxy)ethyl)piperazine (196 mg, 0.54 mmol) and $Cs_2CO_3$ (262 mg, 0.80 mmol) in 1,4-dioxane (2 mL) and water (0.4 mL) under nitrogen. The resulting solution was stirred at 100° C. for 1 hour. The solvent was removed under reduced pressure. The crude product was purified by flash C18-flash chromatography, elution gradient 50 to 100% MeOH in water (0.1% $NH_4HCO_3$), followed by preparative HPLC (Phenomenex Gemini-NX axia Prep C18 OBD column, 5 μm silica, 19 mm diameter, 100 mm length), using decreasingly polar mixtures of water (containing 0.1% $NH_3$) and MeCN as eluents. Fractions containing the desired compound were evaporated to dryness to afford 9-benzyl-8-(2-chloro-4-(2-(piperazin-1-yl)ethoxy)phenyl)-6-(1-methylcyclobutoxy)-9H-purine (16 mg, 11%) as a white solid. $^1H$ NMR (300 MHz, DMSO-$d_6$): 1.62-1.96 (5H, m), 2.26-2.49 (8H, m), 2.61-2.78 (6H, m), 4.18 (2H, t), 5.28 (2H, s), 6.85-6.95 (2H, m), 6.98-7.11 (1H, m), 7.15-7.25 (3H, m), 7.26 (1H, d), 7.41 (1H, d), 8.51 (1H, s)—one H not observed. m/z: ES+ [M+H]+ 533.

1-(2-(3-Chloro-4-(4,4,5,5-tetramethyl-1,3,2-dioxaborolan-2-yl)phenoxy)ethyl)piperazine used as starting material was made as follows:

Tert-butyl 4-(2-(4-bromo-3-chlorophenoxy)ethyl)piperazine-1-carboxylate

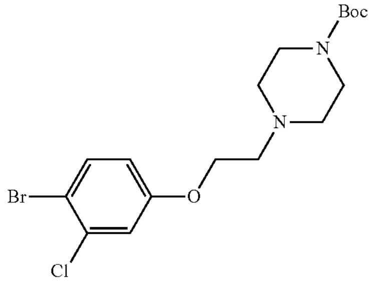 [SMILES: CC(C)(C)OC(=O)N1CCN(CCOc2ccc(Br)c(Cl)c2)CC1]

Potassium carbonate (6.66 g, 48.2 mmol) was added to 4-bromo-3-chlorophenol (5 g, 24.1 mmol), tert-butyl 4-(2-chloroethyl)piperazine-1-carboxylate (7.19 g, 28.92 mmol) in DMF (100 mL) at 25° C. under nitrogen. The resulting suspension was stirred at 80° C. for 3 hours. The reaction mixture was diluted with water (300 mL), and the aqueous layer was extracted with EtOAc (3×100 mL). The organic layer was dried over $Na_2SO_4$, filtered and evaporated to afford the crude product. The crude product was purified by crystallisation from EtOAc/petroleum ether to afford tert-butyl 4-(2-(4-bromo-3-chlorophenoxy)ethyl)piperazine-1-carboxylate (5.50 g, 54%) as a white solid. $^1H$ NMR (300 MHz, $CDCl_3$): 1.46 (9H, s), 2.51 (4H, s), 2.81 (2H, t), 3.45 (4H, t), 4.07 (2H, t), 6.70 (1H, dd), 7.02 (1H, d), 7.47 (1H, d). m/z: ES+ [M+H]+ 419.

Tert-butyl 4-(2-(3-chloro-4-(4,4,5,5-tetramethyl-1,3,2-dioxaborolan-2-yl)phenoxy)ethyl)piperazine-1-carboxylate

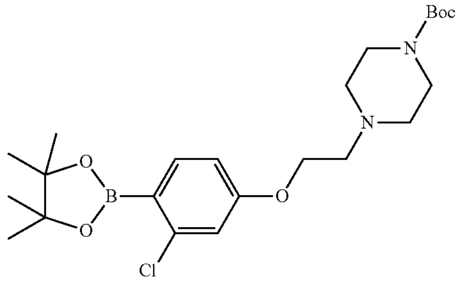 [SMILES: CC(C)(C)OC(=O)N1CCN(CCOc2ccc(B3OC(C)(C)C(C)(C)O3)c(Cl)c2)CC1]

$PdCl_2$(dppf) (0.523 g, 0.71 mmol) was added to tert-butyl 4-(2-(4-bromo-3-chlorophenoxy)ethyl)piperazine-1-carboxylate (3 g, 7.15 mmol), bis(pinacolato)diboron (3.63 g, 14.29 mmol) and potassium acetate (2.10 g, 21.4 mmol) in 1,4-dioxane (60 mL) under nitrogen. The resulting solution was stirred at 100° C. for 2 hours. The reaction mixture was diluted with EtOAc (250 mL), and washed sequentially with water (3×250 mL) and saturated brine (3×250 mL). The organic layer was dried over $Na_2SO_4$, filtered and evaporated to afford the crude product. The crude product was purified by flash silica chromatography, elution gradient 0 to 30% EtOAc in petroleum ether. Pure fractions were evaporated to dryness to afford tert-butyl 4-(2-(3-chloro-4-(4,4,5,5-tetramethyl-1,3,2-dioxaborolan-2-yl)phenoxy)ethyl)piperazine-1-carboxylate (3.00 g, 90%) as a pale yellow gum. $^1$H NMR (300 MHz, DMSO-$d_6$): 1.16 (9H, s), 1.27 (12H, s), 2.42 (4H, m), 2.58 (2H, t), 3.17-3.20 (4H, m), 4.01 (2H, t), 6.79 (1H, dd), 6.88 (1H, d), 7.46 (1H, d). m/z: ES+ [M+H]+ 467.

1-(2-(3-Chloro-4-(4,4,5,5-tetramethyl-1,3,2-dioxaborolan-2-yl)phenoxy)ethyl)piperazine

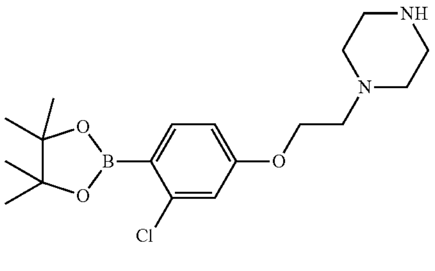 [SMILES: CC1(C)OB(c2ccc(OCCN3CCNCC3)cc2Cl)OC1(C)C]

Trifluoroacetic acid (20 mL) was added to tert-butyl 4-(2-(3-chloro-4-(4,4,5,5-tetramethyl-1,3,2-dioxaborolan-2-yl)phenoxy)ethyl)piperazine-1-carboxylate (2 g, 4.28 mmol) in dichloromethane (20 mL). The resulting solution was stirred at 25° C. for 2 hours and then the solvent was removed under reduced pressure. The crude product was purified by preparative HPLC (XBridge Prep C18 OBD column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 1-(2-(3-chloro-4-(4,4,5,5-tetramethyl-1,3,2-dioxaborolan-2-yl)phenoxy)ethyl)piperazine (1.05 g, 67%) as a white solid. $^1$H NMR (300 MHz, DMSO-$d_6$): 1.29 (12H, s), 3.20 (4H, t), 3.30 (6H, t), 4.30 (2H, t), 6.95 (1H, dd), 7.05 (1H, d), 7.62 (1H, d)—one proton not observed. m/z: ES+ [M+H]+ 367.

9-Benzyl-8-bromo-6-(1-methylcyclobutoxy)-9H-purine used as starting material was made as follows:

9-Benzyl-6-(1-methylcyclobutoxy)-9H-purine

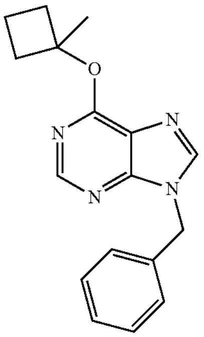 [SMILES: CC1(Oc2ncnc3c2ncn3Cc2ccccc2)CCC1]

Sodium hydride (265 mg, 11.03 mmol) was added portionwise to a mixture of 9-benzyl-6-chloro-9H-purine (900 mg, 3.68 mmol, Example 5 starting material), 1-methylcyclobutan-1-ol (634 mg, 7.36 mmol) in THF (30 mL) at 0° C. over a period of 2 minutes under nitrogen. The resulting suspension was stirred at 25° C. for 4 hours. The reaction mixture was diluted with aqueous $NH_4Cl$ (3 mL) and water (50 mL). The aqueous layer was extracted with EtOAc (3×25 mL). The combined organic layers were dried over $Na_2SO_4$, filtered and evaporated to afford the crude product. The crude product was purified by flash silica chromatography, elution gradient 0 to 40% EtOAc in petroleum ether. Pure fractions were evaporated to dryness to afford 9-benzyl-6-(1-methylcyclobutoxy)-9H-purine (900 mg, 83%) as a colourless solid. $^1$H NMR (300 MHz, $CDCl_3$): 1.64-1.94 (5H, m), 2.29-2.42 (2H, m), 2.52-2.67 (2H, m), 5.41 (2H, s), 7.24-7.38 (5H, m), 7.90 (1H, s), 8.51 (1H, s). m/z: ES+ [M+H]+ 295.

9-Benzyl-8-bromo-6-(1-methylcyclobutoxy)-9H-purine

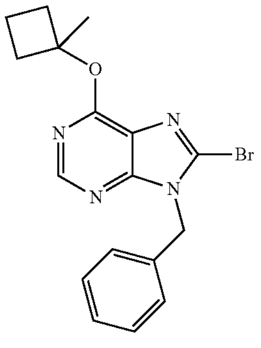 [SMILES: CC1(Oc2ncnc3c2nc(Br)n3Cc2ccccc2)CCC1]

Lithium bis(trimethylsilyl)amide (6.79 mL, 6.79 mmol) was added to a solution of 9-benzyl-6-(1-methylcyclobutoxy)-9H-purine (500 mg, 1.70 mmol) and 1,2-dibromo-1,1,2,2-tetrachloroethane (2.21 g, 6.79 mmol) in THF (30 mL) at 25° C. under nitrogen. The resulting solution was stirred at 25° C. for 5 hours. The reaction mixture was poured into water (150 mL) and extracted with EtOAc (3×100 mL). The organic layer was dried over $Na_2SO_4$, filtered and evaporated to afford the crude product. The crude product was purified by flash silica chromatography, elution gradient 0 to 30% EtOAc in petroleum ether. Pure fractions were evaporated to dryness to afford 9-benzyl-8-bromo-6-(1-methylcyclobutoxy)-9H-purine (400 mg, 63%) as a yellow gum. $^1H$ NMR (300 MHz, DMSO-$d_6$): 1.63 (3H, s), 1.67-1.87 (2H, m), 2.16-2.35 (2H, m), 2.37-2.40 (2H, m), 5.32 (2H, s), 7.11-7.16 (2H, m), 7.12-7.36 (3H, m), 8.37 (1H, s). m/z: ES+ [M+H]+ 373.

Example 13

1-((9-Benzyl-8-(2-chloro-4-(2-(piperazin-1-yl)ethoxy)phenyl)-9H-purin-6-yl)oxy)cyclopropane-1-carbonitrile

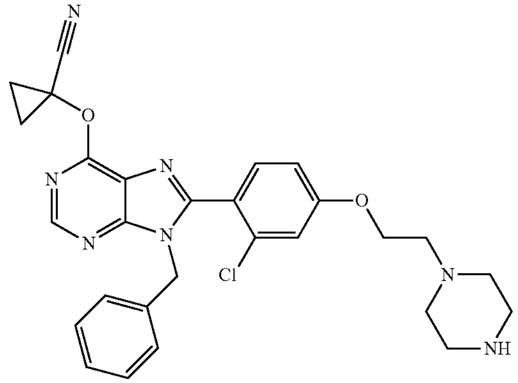 [SMILES: N#CC1(Oc2ncnc3c2nc(-c2ccc(OCCN4CCNCC4)cc2Cl)n3Cc2ccccc2)CC1]

Hydrogen chloride (4M in dioxane) (7.93 µl, 0.03 mmol) was added to a stirred solution of tert-butyl 4-(2-(4-(9-benzyl-6-(1-cyanocyclopropoxy)-9H-purin-8-yl)-3-chlorophenoxy)ethyl)piperazine-1-carboxylate (10 mg, 0.02 mmol) in anhydrous acetonitrile (0.5 mL) cooled to 0° C. After 20 minutes, additional hydrogen chloride (4M in dioxane, 7.9 µL, 0.03 mmol) was added and the reaction was allowed to warm to room temperature. Then the reaction mixture was diluted with methanol and the crude product was purified by ion exchange chromatography, using an SCX column. The desired product was eluted from the column using 1 M $NH_3$/MeOH and pure fractions were evaporated to dryness. The crude product was purified by preparative HPLC (Waters CSH C18 OBD column, 5 µm silica, 30 mm diameter, 100 mm length), using decreasingly polar mixtures of water (containing 1% concentrated aqueous ammonia) and MeCN as eluents. Fractions containing the desired compound were evaporated to dryness to afford 1-((9-benzyl-8-(2-chloro-4-(2-(piperazin-1-yl)ethoxy)phenyl)-9H-purin-6-yl)oxy)cyclopropane-1-carbonitrile (2.6 mg, 31%) as a white solid. $^1H$ NMR (500 MHz, $CDCl_3$): 1.52-1.63 (2H, m), 1.63-1.74 (2H, m), 2.68-2.75 (4H, m), 2.87 (2H, t), 3.02-3.1 (4H, m), 4.15 (2H, t), 5.36 (2H, s), 6.82 (1H, dd), 6.93 (2H, dd), 7.06 (1H, d), 7.14-7.23 (4H, m), 8.74 (1H, s)—one H not observed. m/z: ES+ [M+H]+ 530.

Tert-butyl 4-(2-(4-(9-benzyl-6-(1-cyanocyclopropoxy)-9H-purin-8-yl)-3-chlorophenoxy)ethyl)piperazine-1-carboxylate used as starting material was made as follows:

Tert-butyl 4-(2-(4-(9-benzyl-6-(1-cyanocyclopropoxy)-9H-purin-8-yl)-3-chlorophenoxy)ethyl)piperazine-1-carboxylate

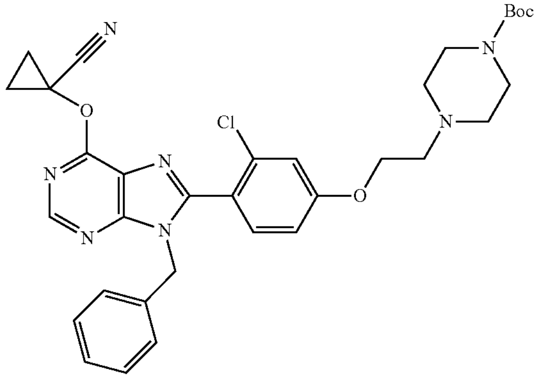 [SMILES: CC(C)(C)OC(=O)N1CCN(CCOc2ccc(-c3nc4c(OC5(C#N)CC5)ncnc4n3Cc3ccccc3)c(Cl)c2)CC1]

Sodium hydride (206 mg, 5.14 mmol) was added to tert-butyl 4-(2-(4-(9-benzyl-6-chloro-9H-purin-8-yl)-3-chlorophenoxy)ethyl)piperazine-1-carboxylate (150 mg, 0.26 mmol, Example 6 starting material) in THF (6 mL) at 0° C. under nitrogen. 1-Hydroxycyclopropane-1-carbonitrile (107 mg, 1.29 mmol) was added after the reaction had been stirred for 15 minutes. The resulting solution was stirred at rt for a further 2 hours. The reaction mixture was poured into saturated $NH_4Cl$ (75 mL) and extracted with EtOAc (3×100 mL). The organic layer was dried over $Na_2SO_4$, filtered and evaporated to afford a brown oil. The crude product was purified by flash silica chromatography, elution gradient 0 to 10% MeOH in DCM. Pure fractions were evaporated to dryness to afford tert-butyl 4-(2-(4-(9-benzyl-6-(1-cyanocyclopropoxy)-9H-purin-8-yl)-3-chlorophenoxy)ethyl)piperazine-1-carboxylate (73.0 mg, 45%) as a green oil. $^1H$ NMR (300 MHz, DMSO-$d_6$): 1.40 (13H, s), 1.64 (2H, t), 1.73-1.82 (2H, m), 2.45 (4H, t), 2.72-2.77 (2H, m), 4.21 (2H, t), 5.35 (2H, s), 6.89-6.94 (2H, m), 7.02-7.11 (1H, m), 7.17-7.24 (4H, m), 7.39-7.46 (1H, m), 8.78 (1H, s). m/z: ES+ [M+H]+ 630.

Example 14

2-(2-Chloro-4-(2-(piperazin-1-yl)ethoxy)phenyl)-3-((4-chloropyridin-2-yl)methyl)-7-(1-methylcyclopropoxy)-3H-imidazo[4,5-b]pyridine

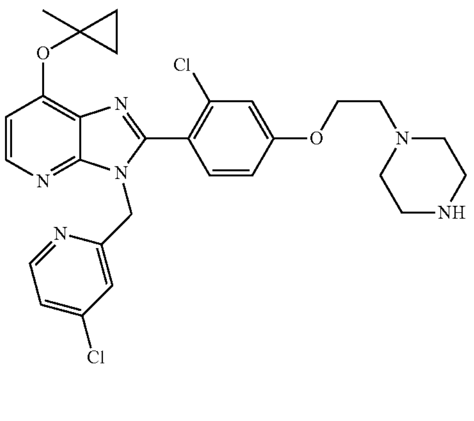 [SMILES: CC1(Oc2ccnc3c2nc(-c2ccc(OCCN4CCNCC4)cc2Cl)n3Cc2cc(Cl)ccn2)CC1]

p-Toluenesulfonic acid monohydrate (94 mg, 0.49 mmol) was added to N2-((4-chloropyridin-2-yl)methyl)-4-(1-methylcyclopropoxy)pyridine-2,3-diamine (100 mg, 0.33 mmol) and 2-chloro-4-(2-(piperazin-1-yl)ethoxy)benzaldehyde (106 mg, 0.39 mmol) in EtOH (5.5 mL) at 25° C. The resulting mixture was stirred at 60° C. for 2 hours. The reaction mixture was quenched with water (15 mL) and extracted with EtOAc (3×50 mL). The organic layer was dried over $Na_2SO_4$, filtered and evaporated to afford a brown oil. 21 Fractions containing the desired compound were evaporated to dryness to afford 2-(2-chloro-4-(2-(piperazin-1-yl)ethoxy)phenyl)-3-((4-chloropyridin-2-yl)methyl)-7-(1-methylcyclopropoxy)-3H-imidazo[4,5-b]pyridine (25 mg, 14%) as a white solid. $^1$H NMR (400 MHz, $CDCl_3$): 0.84 (2H, t), 1.23 (2H, t), 1.72 (3H, s), 2.56-2.61 (4H, m), 2.81 (2H, t), 2.96 (4H, t), 4.12 (2H, t), 5.49 (2H, s), 6.76-6.85 (2H, m), 7.01 (1H, d), 7.06-7.13 (2H, m), 7.30 (1H, d), 8.31 (2H, t)—one proton not observed. m/z: ES+ [M+H]+ 553.

2-Chloro-4-(2-(piperazin-1-yl)ethoxy)benzaldehyde used as starting material was made as follows:

2-Chloro-4-(2-(piperazin-1-yl)ethoxy)benzaldehyde

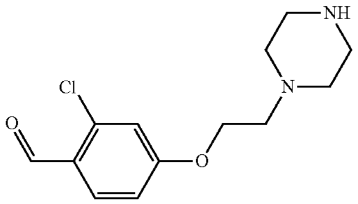 [SMILES: O=Cc1ccc(OCCN2CCNCC2)cc1Cl]

2,2,2-trifluoroacetic acid (3 mL, 2.71 mmol) was added to tert-butyl 4-(2-(3-chloro-4-formylphenoxy)ethyl)piperazine-1-carboxylate (1.0 g, 2.71 mmol, Example 6 starting material) in DCM (5 mL) at 25° C. The resulting mixture was stirred at 25° C. for 1 hour. The reaction mixture was diluted with EtOAc (25 mL) and washed sequentially with water (3×25 mL). The organic layer was dried over $Na_2SO_4$, filtered and evaporated to afford the crude product. The crude product was purified by flash silica chromatography, elution gradient 0 to 50% pentane in EtOAc. Pure fractions were evaporated to dryness to afford 2-chloro-4-(2-(piperazin-1-yl)ethoxy)benzaldehyde (0.700 g, 96%) as a yellow gum. $^1$H NMR (300 MHz, DMSO-$d_6$): 3.22-3.39 (10H, m), 4.41 (2H, t), 7.11 (1H, dd), 7.23 (1H, d), 7.86 (1H, d), 10.20 (1H, d). One H not observed. m/z: ES+ [M+H]+ 269.

N2-((4-Chloropyridin-2-yl)methyl)-4-(1-methylcyclopropoxy)pyridine-2,3-diamine used as starting material was made as follows:

2-Chloro-4-(1-methylcyclopropoxy)-3-nitropyridine

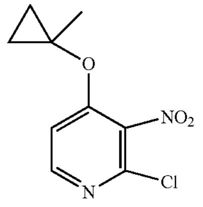

Sodium hydride (0.415 g, 10.4 mmol) was added in one portion to 2,4-dichloro-3-nitropyridine (2 g, 10.4 mmol) and 1-methylcyclopropan-1-ol (0.747 g, 10.4 mmol) in THF (20 mL) at 0° C. under nitrogen. The resulting suspension was stirred at 25° C. for 1 hour. The reaction mixture was quenched with water (20 mL), extracted with EtOAc (3×50 mL). The top layer was dried over $Na_2SO_4$, filtered and evaporated to afford a yellow solid, which was purified by preparative TLC (petroleum ether/EtOAc 3:1), to afford 2-chloro-4-(1-methylcyclopropoxy)-3-nitropyridine (0.900 g, 38%) as a yellow solid. $^1$H NMR (300 MHz, DMSO-$d_6$): 0.85-0.92 (2H, m), 0.98-1.05 (2H, m), 1.57 (3H, s), 7.66 (1H, d), 8.51 (1H, d). m/z: ES+ [M+H]+ 229.

N-((4-chloropyridin-2-yl)methyl)-4-(1-methylcyclopropoxy)-3-nitropyridin-2-amine

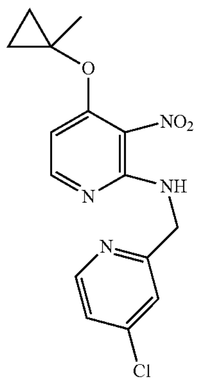 [SMILES: CC1(Oc2ccnc(NCc3cc(Cl)ccn3)c2[N+](=O)[O-])CC1]

BINAP (82 mg, 0.13 mmol) was added to 2-chloro-4-(1-methylcyclopropoxy)-3-nitropyridine (300 mg, 1.31 mmol), (4-chloropyridin-2-yl)methanamine (281 mg, 1.97 mmol), $Cs_2CO_3$ (1283 mg, 3.94 mmol) and $Pd_2(dba)_3$ (120 mg, 0.13 mmol) in dioxane (7 mL) at 25° C. The resulting mixture was stirred at 100° C. for 2 hours. The reaction mixture was quenched with water (20 mL), extracted with EtOAc (3×100 mL) and washed sequentially with water (2×50 mL), saturated brine (2×50 mL). The organic layer was dried over $Na_2SO_4$, filtered and evaporated to afford a yellow oil. This oil was purified by preparative TLC (petroleum ether/EtOAc 2:1), to afford N-((4-chloropyridin-2-yl)methyl)-4-(1-methylcyclopropoxy)-3-nitropyridin-2-amine (275 mg, 63%) as a yellow solid. $^1$H NMR (400 MHz, DMSO-$d_6$): 0.79-0.93 (2H, m), 0.93-1 (2H, m), 1.54 (3H, s), 4.69 (2H, d), 6.74 (1H, d), 7.36 (1H, d), 7.40 (1H, m), 7.87 (1H, t), 8.07 (1H, d), 8.49 (1H, d). m/z: ES+ [M+H]+ 335.

N2-((4-chloropyridin-2-yl)methyl)-4-(1-methylcyclopropoxy)pyridine-2,3-diamine

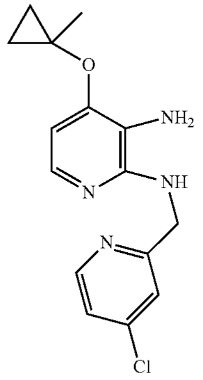 [SMILES: CC1(Oc2ccnc(NCc3cc(Cl)ccn3)c2N)CC1]

Iron (307 mg, 5.50 mmol) was added to N-((4-chloropyridin-2-yl)methyl)-4-(1-methylcyclopropoxy)-3-nitropyridin-2-amine (230 mg, 0.69 mmol) and ammonium chloride (294 mg, 5.50 mmol) in EtOH:$H_2O$ (4:1) (8 mL) at 25° C. The resulting mixture was stirred at 80° C. for 2 hours. The mixture was filtered through a celite pad and the solvent was removed. The reaction mixture was quenched with water (15 mL), extracted with EtOAc (3×50 mL), and washed sequentially with water (2×20 mL) and saturated brine (2×20 mL). The organic layer was dried over $Na_2SO_4$, filtered and evaporated to afford a yellow oil. This oil was purified by preparative TLC (EtOAc) to afford N2-((4-chloropyridin-2-yl)methyl)-4-(1-methylcyclopropoxy)pyridine-2,3-diamine (110 mg, 52%) as a yellow oil. $^1H$ NMR (300 MHz, DMSO-$d_6$): 0.76 (2H, t), 0.81-0.96 (2H, m), 1.50 (3H, s), 4.14 (2H, s), 4.63 (2H, d), 6.25 (1H, t), 6.53 (1H, d), 7.29-7.42 (3H, m), 8.48 (1H, d). m/z: ES+ [M+H]+ 305.

Example 15

2-(2-chloro-4-(2-(piperazin-1-yl)ethoxy)phenyl)-1-((4-chloropyridin-2-yl)methyl)-4-(1-methylcyclopropoxy)-1H-benzo[d]imidazole

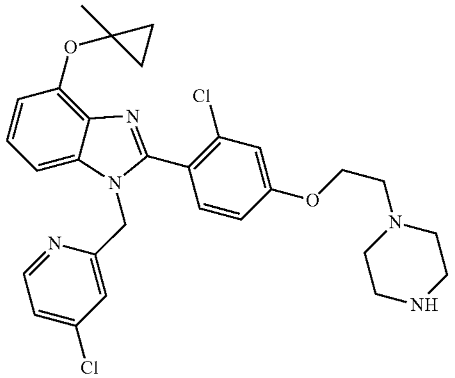 [SMILES: CC1(Oc2cccc3c2nc(-c2ccc(OCCN4CCNCC4)cc2Cl)n3Cc2cc(Cl)ccn2)CC1]

2,2,2-Trifluoroacetic acid (0.3 mL, 3.9 mmol) was added to tert-butyl 4-(2-(3-chloro-4-(1-((4-chloropyridin-2-yl)methyl)-4-(1-methylcyclopropoxy)-1H-benzo[d]imidazol-2-yl)phenoxy)ethyl)piperazine-1-carboxylate (80 mg, 0.12 mmol) in DCM (1 mL) at 25° C. The resulting mixture was stirred at 25° C. for 1 hour. The reaction mixture was diluted with EtOAc (10 mL) and washed sequentially with water (3×10 mL). The organic layer was dried over $Na_2SO_4$, filtered and evaporated to afford the crude product. The crude product was purified by preparative HPLC (XBridge Shield RP18 OBD column, 15*150 mm, 10 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 2-(2-chloro-4-(2-(piperazin-1-yl)ethoxy)phenyl)-1-((4-chloropyridin-2-yl)methyl)-4-(1-methylcyclopropoxy)-1H-benzo[d]imidazole (28 mg, 41%) as a white solid. $^1H$ NMR (400 MHz, DMSO-$d_6$): 0.82 (2H, t), 0.98 (2H, t), 1.59 (3H, s), 2.31-2.45 (4H, m), 2.6-2.76 (6H, m), 4.15 (2H, t), 5.34 (2H, s), 6.95-7.02 (2H, m), 7.06 (1H, d), 7.13-7.19 (2H, m), 7.21 (1H, d), 7.37-7.43 (2H, m), 8.36 (1H, d)—one H not observed. m/z: ES+ [M+H]+ 552.

Tert-butyl 4-(2-(3-chloro-4-(1-((4-chloropyridin-2-yl)methyl)-4-(1-methylcyclopropoxy)-1H-benzo[d]imidazol-2-yl)phenoxy)ethyl)piperazine-1-carboxylate used as starting material was made as follows:

1-Fluoro-3-(1-methylcyclopropoxy)-2-nitrobenzene

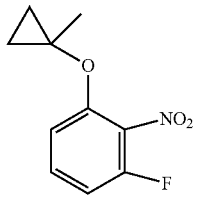

Sodium hydride (78 mg, 3.27 mmol) was added to 1,3-difluoro-2-nitrobenzene (400 mg, 2.51 mmol) and 1-methylcyclopropan-1-ol (181 mg, 2.51 mmol) in THF (3 mL) at 0° C. The resulting mixture was stirred at 25° C. for 2 hours. The reaction mixture was concentrated, diluted with EtOAc (20 mL) and washed sequentially with water (3×5 mL) followed by saturated brine (3×5 mL). The top layer was dried over $Na_2SO_4$, filtered and evaporated to afford the crude product. The crude product was purified by preparative TLC (petroleum ether/EtOAc 2:1), to afford 1-fluoro-3-(1-methylcyclopropoxy)-2-nitrobenzene (440 mg, 83%) as a yellow solid. $^1H$ NMR (300 MHz, DMSO-$d_6$): 0.79-1.01 (4H, m), 1.54 (3H, s), 7.15-7.19 (1H, m), 7.35-7.39 (1H, m), 7.63-7.65 (1H, m). m/z: ES+ [M+H]+ 212.

N-((4-chloropyridin-2-yl)methyl)-3-(1-methylcyclopropoxy)-2-nitroaniline

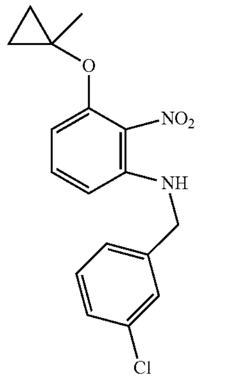 [SMILES: CC1(Oc2cccc(NCc3cccc(Cl)c3)c2[N+](=O)[O-])CC1]

N,N-Diisopropylethylamine (826 mg, 6.39 mmol) was added to 1-fluoro-3-(1-methylcyclopropoxy)-2-nitrobenzene (270 mg, 1.28 mmol) and (4-chloropyridin-2-yl)methanamine (219 mg, 1.53 mmol) in DMSO (5 mL) at 25° C. The resulting mixture was stirred at 130° C. for 2 hours. The reaction mixture was concentrated, diluted with EtOAc (20 mL) and washed sequentially with water (3x5 mL) and saturated brine (3x5 mL). The top layer was dried over $Na_2SO_4$, filtered and evaporated to afford the crude product. The crude product was purified by flash silica chromatography, elution gradient 0 to 5% MeOH in DCM. Pure fractions were evaporated to dryness to afford N-((4-chloropyridin-2-yl)methyl)-3-(1-methylcyclopropoxy)-2-nitroaniline (237 mg, 55%) as a yellow solid. $^1H$ NMR (300 MHz, $CDCl_3$): 0.73 (2H, t), 1.06 (2H, t), 1.58 (3H, s), 4.56 (2H, s), 6.24 (1H, dd), 6.68 (1H, dd), 7.18 (1H, t), 7.23-7.26 (1H, m), 7.27-7.29 (1H, m), 7.36 (1H, d), 8.50 (1H, d). m/z: ES+ [M+H]+ 334.

Tert-butyl 4-(2-(3-chloro-4-(1-((4-chloropyridin-2-yl)methyl)-4-(1-methylcyclopropoxy)-1H-benzo[d]imidazol-2-yl)phenoxy)ethyl)piperazine-1-carboxylate

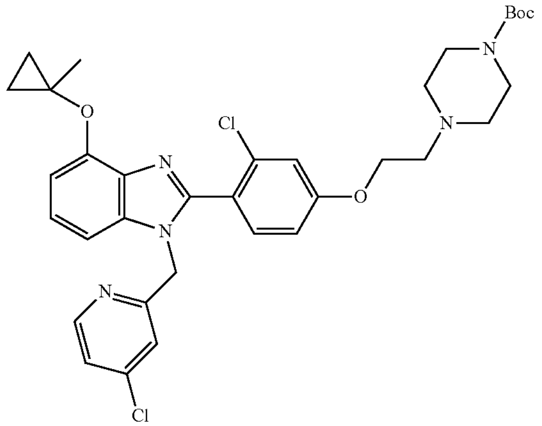 [SMILES: CC(C)(C)OC(=O)N1CCN(CCOc2ccc(-c3nc4c(OC5(C)CC5)cccc4n3Cc3cc(Cl)ccn3)c(Cl)c2)CC1]

Sodium hydrosulfite (730 mg, 4.19 mmol) was added to N-((4-chloropyridin-2-yl)methyl)-3-(1-methylcyclopropoxy)-2-nitroaniline (140 mg, 0.42 mmol) in MeOH (2 mL) and water (2 mL) at 25° C. The mixture was stirred for 16 hours. Then tert-butyl 4-(2-(3-chloro-4-formylphenoxy)ethyl)piperazine-1-carboxylate (201 mg, 0.55 mmol) and 4-methylbenzenesulfonic acid (87 mg, 0.50 mmol) was added. The reaction mixture was stirred at 25° C. for a further 3 hours. The reaction mixture was concentrated and then diluted with EtOAc (15 mL). The crude mixture was then washed sequentially with water (3x15 mL). The organic layer was dried over $Na_2SO_4$, filtered and evaporated to afford the crude product. The crude product was purified by flash silica chromatography, elution gradient 0 to 10% MeOH in DCM. Pure fractions were evaporated to dryness to afford tert-butyl 4-(2-(3-chloro-4-(1-((4-chloropyridin-2-yl)methyl)-4-(1-methylcyclopropoxy)-1H-benzo[d]imidazol-2-yl)phenoxy)ethyl)piperazine-1-carboxylate (90 mg, 33%) as a yellow gum. $^1H$ NMR (300 MHz, DMSO-$d_6$): 0.80 (2H, t), 0.97 (2H, t), 1.38 (9H, s), 1.57 (3H, s), 2.38-2.47 (4H, m), 2.72 (2H, t), 3.25-3.31 (4H, m), 4.16 (2H, t), 5.33 (2H, s), 6.93-7.08 (3H, m), 7.11-7.22 (3H, m), 7.35-7.42 (2H, m), 8.35 (1H, d). m/z: ES+ [M+H]+ 652.

Example 16

2-(2-chloro-4-(2-(piperazin-1-yl)ethoxy)phenyl)-1-((4-chloropyridin-2-yl)methyl)-4-(1-methylcyclopropoxy)-1H-imidazo[4,5-c]pyridine

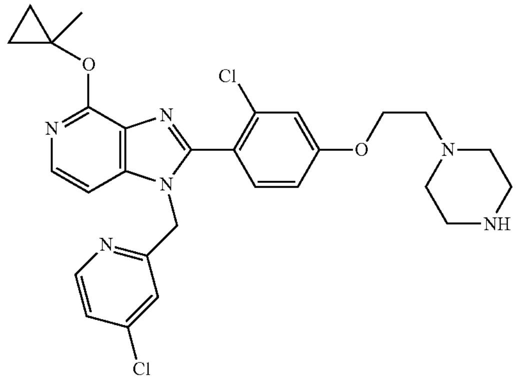 [SMILES: CC1(Oc2nccc3c2nc(-c2ccc(OCCN4CCNCC4)cc2Cl)n3Cc2cc(Cl)ccn2)CC1]

HCl (4M in dioxane, 123 mg, 3.37 mmol) was added to tert-butyl 4-(2-(3-chloro-4-(1-((4-chloropyridin-2-yl)methyl)-4-(1-methylcyclopropoxy)-1H-imidazo[4,5-c]pyridin-2-yl)phenoxy)ethyl)piperazine-1-carboxylate (220 mg, 0.34 mmol) in dichloromethane (1 mL) at rt. The reaction mixture was stirred at rt for 1 hour, then evaporated to dryness, redissolved in DMF (2 mL) and filtered through celite. The residue was purified by preparative HPLC (YMC-Actus Triart C18 ExRS column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 2-(2-chloro-4-(2-(piperazin-1-yl)ethoxy)phenyl)-1-((4-chloropyridin-2-yl)methyl)-4-(1-methylcyclopropoxy)-1H-imidazo[4,5-c]pyridine (67 mg, 36%) as a white solid. $^1H$ NMR (400 MHz, DMSO-$d_6$): 0.78 (2H, t), 0.93 (2H, t), 1.69 (3H, s), 2.34-2.44 (4H, m), 2.59-2.76 (6H, m), 4.15 (2H, t), 5.38 (2H, s), 6.95-7.02 (1H, m), 7.19-7.24 (3H, m), 7.34-7.42 (2H, m), 7.92 (1H, d), 8.34 (1H, d)—one proton not observed. m/z: ES+ [M+H]+ 553

Tert-butyl 4-(2-(3-chloro-4-(1-((4-chloropyridin-2-yl)methyl)-4-(1-methylcyclopropoxy)-1H-imidazo[4,5-c]pyridin-2-yl)phenoxy)ethyl)piperazine-1-carboxylate used as starting material was made as follows:

2-Chloro-4-(methylthio)-3-nitropyridine

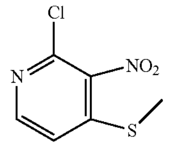

Sodium thiomethoxide (0.872 g, 12.4 mmol) was added to 2,4-dichloro-3-nitropyridine (2 g, 10.4 mmol) in MeOH (10 mL) and the reaction mixture was stirred at rt for 16 hours. The reaction mixture was evaporated to dryness, redissolved in EtOAc (50 mL), and washed sequentially with water (2×15 mL), saturated brine (2×15 mL). The organic layer was dried over $Na_2SO_4$, filtered and evaporated to afford the crude product. The crude product was purified by flash silica chromatography, elution gradient 0 to 30% EtOAc in petroleum ether. Pure fractions were evaporated to dryness to afford 2-chloro-4-(methylthio)-3-nitropyridine (1.40 g, 66%) as a yellow solid. $^1H$ NMR (300 MHz, DMSO-$d_6$): 2.40 (3H, s), 7.54 (1H, d), 8.37 (1H, d). m/z: ES+ [M+H]+ 205.

2-(1-Methylcyclopropoxy)-4-(methylthio)-3-nitropyridine

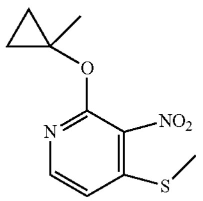 [SMILES: CSc1ccnc(OC2(C)CC2)c1[N+](=O)[O-]]

Sodium hydride (2.06 g, 86.0 mmol) was added in one portion to 2-chloro-4-(methylthio)-3-nitropyridine (2.2 g, 10.7 mmol) and 1-methylcyclopropan-1-ol (1.16 g, 16.1 mmol) in THF (200 mL) at 0° C. under nitrogen. The resulting suspension was stirred at rt for 6 hours. Then the reaction mixture was diluted with EtOAc (100 mL), and washed with saturated brine (2×50 mL). The organic layer was dried over $Na_2SO_4$, filtered and evaporated to afford the crude product. The crude product was purified by flash silica chromatography, elution gradient 10 to 40% EtOAc in petroleum ether. Pure fractions were evaporated to dryness to afford 2-(1-methylcyclopropoxy)-4-(methylthio)-3-nitropyridine (1.30 g, 50%) as a brown solid. $^1H$ NMR (300 MHz, DMSO-$d_6$): 0.76 (2H, t), 0.88 (2H, t), 1.62 (3H, s), 2.59 (3H, s), 7.21 (1H, d), 8.29 (1H, d). m/z: ES+ [M+H]+ 241.

2-(1-Methylcyclopropoxy)-4-(methylsulfonyl)-3-nitropyridine

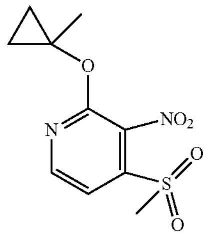 [SMILES: CC1(Oc2nccc(S(C)(=O)=O)c2[N+](=O)[O-])CC1]

m-Chloroperbenzoic acid (2.05 g, 11.9 mmol) was added to 2-(1-methylcyclopropoxy)-4-(methylthio)-3-nitropyridine (1.30 g, 5.41 mmol) in dichloromethane (100 mL) and the reaction was stirred at rt for 6 hours. Then the reaction mixture was evaporated to dryness and redissolved in EtOAc (100 mL) and washed sequentially with water (3×50 mL) and saturated brine (3× 50 mL). The organic layer was dried over $Na_2SO_4$, filtered and evaporated to afford the crude product. The crude product was purified by flash silica chromatography, elution gradient 25 to 50% EtOAc in petroleum ether. Pure fractions were evaporated to dryness to afford 2-(1-methylcyclopropoxy)-4-(methylsulfonyl)-3-nitropyridine (720 mg, 49%) as a yellow solid. $^1H$ NMR (300 MHz, DMSO-$d_6$): 0.80 (2H, t), 0.93 (2H, t), 1.64 (3H, s), 3.46 (3H, s), 7.69 (1H, d), 8.78 (1H, d). m/z: ES+ [M+H]+ 273.

N-((4-chloropyridin-2-yl)methyl)-2-(1-methylcyclopropoxy)-3-nitropyridin-4-amine

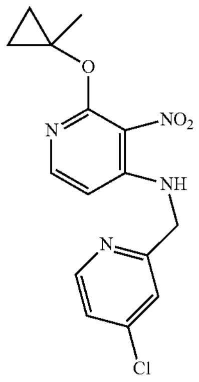 [SMILES: CC1(Oc2nccc(NCc3cc(Cl)ccn3)c2[N+](=O)[O-])CC1]

Triethylamine (0.530 mL, 3.80 mmol) was added to 4-chloro-2-pyridinemethanamine (542 mg, 3.80 mmol) and 2-(1-methylcyclopropoxy)-4-(methylsulfonyl)-3-nitropyridine (690 mg, 2.53 mmol) in DMF (110 mL). The reaction mixture was stirred at 60° C. for 16 hours. Then the reaction mixture was cooled, concentrated and further diluted with EtOAc (100 mL). The organic layer was washed sequentially with water (2×75 mL) and saturated brine (2×75 mL), dried over $Na_2SO_4$, filtered and evaporated. The crude product was purified by flash silica chromatography, elution gradient 30 to 60% EtOAc in petroleum ether. Pure fractions were evaporated to dryness to afford N-((4-chloropyridin-2-yl)methyl)-2-(1-methylcyclopropoxy)-3-nitropyridin-4-amine (260 mg, 31%) as a yellow solid. $^1H$ NMR (300 MHz, DMSO-$d_6$): 0.72 (2H, t), 0.84 (2H, t), 1.60 (3H, s), 4.60 (2H, d), 6.46 (1H, d), 7.4-7.6 (2H, m), 7.86 (1H, d), 7.98 (1H, t), 8.44-8.61 (1H, m). m/z: ES+ [M+H]+ 335.

N4-((4-chloropyridin-2-yl)methyl)-2-(1-methylcyclopropoxy)pyridine-3,4-diamine

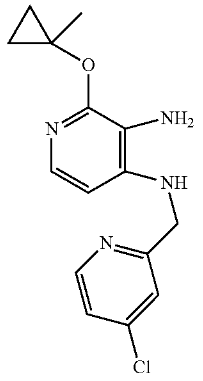 [SMILES: CC1(Oc2nccc(NCc3cc(Cl)ccn3)c2N)CC1]

Iron (417 mg, 7.47 mmol) was added to ammonium chloride (40 mg, 0.75 mmol) and N-((4-chloropyridin-2-yl)methyl)-2-(1-methylcyclopropoxy)-3-nitropyridin-4-amine (250 mg, 0.75 mmol) in ethanol/water (10:1; 1 mL). The reaction mixture was stirred at 60° C. for 3 hours. The reaction mixture then cooled, evaporated to dryness and redissolved in EtOAc (200 mL). The organic layer was washed sequentially with water (2×100 mL) and saturated brine (2×100 mL), dried over $Na_2SO_4$, filtered and evaporated to afford the crude product. The crude product was purified by flash silica chromatography, elution gradient 30 to 60% EtOAc in petroleum ether. Pure fractions were evaporated to dryness to afford N4-((4-chloropyridin-2-yl)methyl)-2-(1-methylcyclopropoxy)pyridine-3,4-diamine (170 mg, 75%) as a yellow solid. $^1$H NMR (300 MHz, DMSO-$d_6$): 0.64 (2H, t), 0.82 (2H, t), 1.58 (3H, s), 3.88-4.16 (2H, m), 4.45 (2H, d), 6.07 (2H, d), 7.23 (1H, d), 7.38-7.53 (2H, m), 8.42-8.66 (1H, m). m/z: ES+ [M+H]+ 305.

Tert-butyl 4-(2-(3-chloro-4-(1-((4-chloropyridin-2-yl)methyl)-4-(1-methylcyclopropoxy)-1H-imidazo[4,5-c]pyridin-2-yl)phenoxy)ethyl)piperazine-1-carboxylate

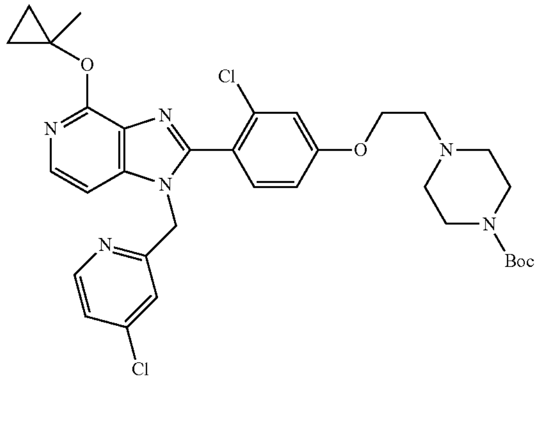 [SMILES: CC(C)(C)OC(=O)N1CCN(CCOc2ccc(-c3nc4c(OC5(C)CC5)nccc4n3Cc3cc(Cl)ccn3)c(Cl)c2)CC1]

Tert-butyl 4-(2-(3-chloro-4-formylphenoxy)ethyl)piperazine-1-carboxylate (203 mg, 0.55 mmol) was added to N4-((4-chloropyridin-2-yl)methyl)-2-(1-methylcyclopropoxy)pyridine-3,4-diamine (140 mg, 0.46 mmol) in MeOH (20 mL) and acetic acid (1 mL) was stirred at rt for 16 hours. The reaction mixture was evaporated to dryness, redissolved in EtOAc (100 mL), and washed sequentially with water (2×50 mL) and saturated brine (2× 50 mL). The organic layer was dried over $Na_2SO_4$, filtered and evaporated to afford the crude product. The crude product was purified by flash silica chromatography, elution gradient 30 to 70% EtOAc in petroleum ether. Pure fractions were evaporated to dryness to afford tert-butyl 4-(2-(3-chloro-4-(1-((4-chloropyridin-2-yl)methyl)-4-(1-methylcyclopropoxy)-1H-imidazo[4,5-c]pyridin-2-yl)phenoxy)ethyl)piperazine-1-carboxylate (230 mg, 77%) as a brown solid. $^1$H NMR (300 MHz, DMSO-$d_6$): 0.78 (2H, t), 0.94 (2H, t), 1.40 (9H, s), 1.70 (3H, s), 2.41-2.47 (4H, m), 2.74 (2H, t), 3.25-3.4 (4H, m), 4.18 (2H, t), 5.39 (2H, s), 6.97-7.04 (1H, m), 7.2-7.25 (3H, m), 7.35-7.43 (2H, m), 7.93 (1H, d), 8.35 (1H, d). m/z: ES+ [M+H]+ 653.

Example 17

3-(3-Chloro-4-(9-((4-chloropyridin-2-yl)methyl)-6-(1-methylcyclopropoxy)-9H-purin-8-yl)phenoxy)-N,N-dimethylpropan-1-amine

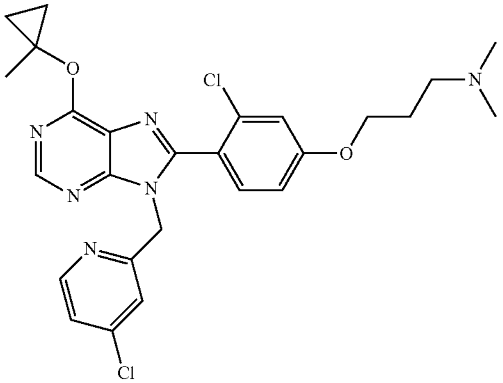

$K_2CO_3$ (56 mg, 0.41 mmol) was added to 3-chloro-4-(9-((4-chloropyridin-2-yl)methyl)-6-(1-methylcyclopropoxy)-9H-purin-8-yl)phenol (60 mg, 0.14 mmol) and 3-bromo-N,N-dimethylpropan-1-amine (45 mg, 0.27 mmol) in DMF (1 mL). The resulting mixture was stirred at 60° C. for 4 hours. The reaction mixture was filtered through celite. The crude filtrate was purified by preparative HPLC (XBridge Shield RP18 OBD column, 30*150 mm, 5 μm), using decreasingly polar mixtures of water (containing 10 mmol/L $NH_4HCO_3$ and 0.1% aqueous ammonia) and MeCN as eluents. The fractions containing the desired compound were evaporated to dryness to afford 3-(3-chloro-4-(9-((4-chloropyridin-2-yl)methyl)-6-(1-methylcyclopropoxy)-9H-purin-8-yl)phenoxy)-N,N-dimethylpropan-1-amine (8.0 mg, 11%) as a yellow solid. $^1$H NMR (400 MHz, DMSO-$d_6$): 0.85 (2H, t), 1.02 (2H, t), 1.73 (3H, s), 1.79-1.91 (2H, m), 2.13 (6H, s), 2.34 (2H, t), 4.07 (2H, t), 5.40 (2H, s), 6.96 (1H, dd), 7.17 (1H, d), 7.26 (1H, d), 7.32-7.44 (2H, m), 8.30 (1H, d), 8.57 (1H, s). m/z: ES+ [M+H]+ 527.

3-Chloro-4-(9-((4-chloropyridin-2-yl)methyl)-6-(1-methylcyclopropoxy)-9H-purin-8-yl)phenol used as starting material was made as follows:

4-((Tert-butyldiphenylsilyl)oxy)-2-chlorobenzaldehyde

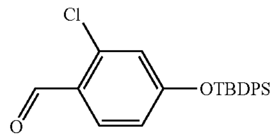

Tert-butylchlorodiphenylsilane (26.3 g, 95.8 mmol) was added to a mixture of 1H-imidazole (4.87 g, 71.5 mmol) and 2-chloro-4-hydroxybenzaldehyde (10 g, 63.9 mmol) in DMF (200 mL) at rt. The mixture was stirred at this temperature for 3 hours. Then the reaction mixture was diluted with EtOAc (500 mL) and washed sequentially with water (3×400 mL) and saturated brine (2×400 mL). The organic layer was dried over $Na_2SO_4$, filtered and evaporated to afford the crude product. The crude product was purified by flash silica chromatography, elution gradient 0 to 30% EtOAc in petroleum ether. Pure fractions were evaporated to dryness to afford 4-((tert-butyldiphenylsilyl)oxy)-2-chlorobenzaldehyde (13.0 g, 51%) as a white solid. $^1$H NMR (300 MHz, DMSO-$d_6$): 1.01 (9H, dd), 6.89-6.95 (1H, m), 7.33-7.56 (7H, m), 7.64-7.72 (5H, m), 10.14 (1H, dd). m/z: ES+ [M+H]+ 395.

8-(4-((Tert-butyldiphenylsilyl)oxy)-2-chlorophenyl)-6-chloro-9H-purine

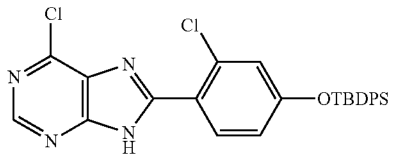

Iron(III) chloride solution (51.3 g, 316 mmol) was added to 6-chloropyrimidine-4,5-diamine (21.96 g, 151.9 mmol) and 4-((tert-butyldiphenylsilyl)oxy)-2-chlorobenzaldehyde (50 g, 126.6 mmol) in IPA (500 mL). The reaction mixture was stirred at 60° C. for 4 hours. The reaction mixture was adjusted to pH 7 with 1 M NaOH. The reaction mixture was poured into water (1.5 L), extracted with EtOAc (3×1.5 L). The organic layer was dried over $Na_2SO_4$, filtered and evaporated to afford the crude product. The crude product was purified by flash silica chromatography, elution gradient 0 to 20% EtOAc in petroleum ether. Pure fractions were evaporated to dryness to afford 8-(4-((tert-butyldiphenylsilyl)oxy)-2-chlorophenyl)-6-chloro-9H-purine (29.0 g, 44%) as a yellow solid. $^1$H NMR (300 MHz, DMSO-$d_6$): 1.08 (9H, s), 6.86 (1H, dd), 7.03 (1H, d), 7.44-7.55 (7H, m), 7.69-7.75 (4H, m), 8.74 (1H, s), 14.06 (1H, s). m/z: ES+ [M+H]+ 519.

8-(4-((Tert-butyldiphenylsilyl)oxy)-2-chlorophenyl)-6-chloro-9-((4-chloropyridin-2-yl)methyl)-9H-purine

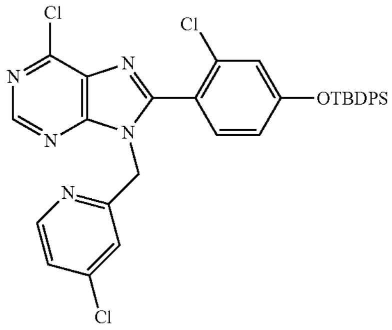

DIAD (9.36 mL, 48.1 mmol) was added to (4-chloropyridin-2-yl)methanol (3.32 g, 23.1 mmol), 8-(4-((tert-butyldiphenylsilyl)oxy)-2-chlorophenyl)-6-chloro-9H-purine (10 g, 19.2 mmol) and triphenylphosphine (12.62 g, 48.1 mmol) in THF (125 mL) at 0° C. over a period of 5 minutes under nitrogen. The resulting mixture was stirred at rt for 2 hours. The reaction mixture was poured into water (750 mL) and extracted with EtOAc (3×750 mL). The organic layer was dried over $Na_2SO_4$, filtered and evaporated to afford a brown oil. The crude product was purified by flash silica chromatography, elution gradient 0 to 30% EtOAc in petroleum ether. Pure fractions were evaporated to dryness to afford 8-(4-((tert-butyldiphenylsilyl)oxy)-2-chlorophenyl)-6-chloro-9-((4-chloropyridin-2-yl)methyl)-9H-purine (12.00 g, 97%) as a beige waxy solid. $^1$H NMR (300 MHz, DMSO-$d_6$): 1.05 (9H, s), 5.45 (2H, s), 6.69 (1H, dd), 6.94 (1H, d), 7.27-7.33 (2H, m), 7.41-7.55 (7H, m), 7.63-7.69 (4H, m), 8.23 (1H, d), 8.79 (1H, s). m/z: ES+ [M+H]+ 644.

3-Chloro-4-(9-((4-chloropyridin-2-yl)methyl)-6-(1-methylcyclopropoxy)-9H-purin-8-yl)phenol

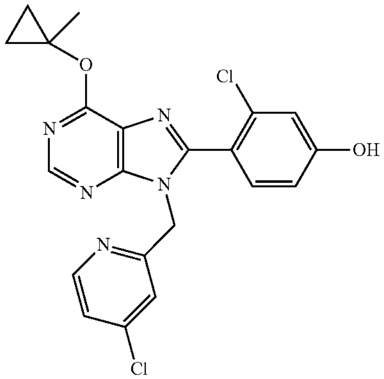 [SMILES: CC1(Oc2ncnc3c2nc(-c2ccc(O)cc2Cl)n3Cc2cc(Cl)ccn2)CC1]

Sodium hydride (2.60 g, 65.1 mmol) was added to solution of 8-(4-((tert-butyldiphenylsilyl)oxy)-2-chlorophenyl)-6-chloro-9-((4-chloropyridin-2-yl)methyl)-9H-purine (12 g, 18.6 mmol) in DMF (12 mL) at 0° C. under nitrogen. The reaction mixture was stirred for 15 minutes and then 1-methylcyclopropan-1-ol (4.19 g, 46.5 mmol) was added at 0° C. The resulting solution was allowed to warm up to rt and stirred for 2 hours. The reaction mixture was then poured into a solution of aqueous saturated $NH_4Cl$ (500 mL) and extracted with EtOAc (3× 500 mL). The organic layer was dried over $Na_2SO_4$, filtered and evaporated to afford the crude product as a brown oil. The crude product was purified by flash silica chromatography, elution gradient 50 to 70% EtOAc in petroleum ether. Pure fractions were evaporated to dryness to afford 3-chloro-4-(9-((4-chloropyridin-2-yl)methyl)-6-(1-methylcyclopropoxy)-9H-purin-8-yl)phenol (3.00 g, 36%) as a white solid. $^1H$ NMR (300 MHz, DMSO-$d_6$): 0.84 (2H, t), 1.02 (2H, t), 1.73 (3H, s), 5.41 (2H, s), 6.78 (1H, dd), 6.94 (1H, d), 7.21-7.32 (2H, m), 7.37 (1H, dd), 8.31 (1H, d), 8.56 (1H, s), 10.43 (1H, s). m/z: ES+ [M+H]+ 442.

Example 18

8-(4-(2-(2,6-Diazaspiro[3.3]heptan-2-yl)ethoxy)-2-chlorophenyl)-9-benzyl-6-(1-methylcyclopropoxy)-9H-purine

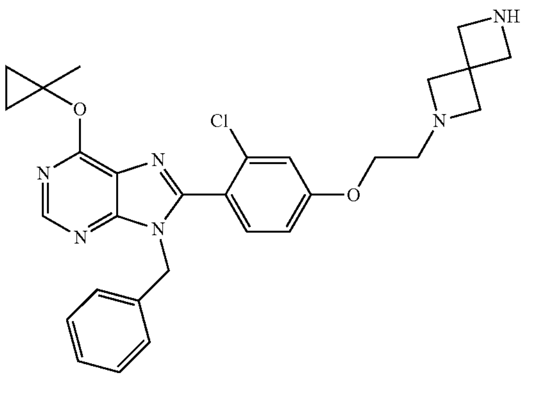 [SMILES: CC1(Oc2ncnc3c2nc(-c2ccc(OCCN4CC5(CNC5)C4)cc2Cl)n3Cc2ccccc2)CC1]

To tert-butyl 6-(2-(4-(9-benzyl-6-(1-methylcyclopropoxy)-9H-purin-8-yl)-3-chlorophenoxy)ethyl)-2,6-diazaspiro[3.3]heptane-2-carboxylate (150 mg, 0.24 mmol) was added TFA (3 mL) at rt. The resulting mixture was stirred at 25° C. for 30 minutes. The reaction mixture was diluted with DCM (50 mL) and neutralised with aqueous saturated $NaHCO_3$. The organic layer was further washed with saturated brine (3×10 mL), dried over $Na_2SO_4$, filtered and evaporated to afford the crude product. The crude product was purified by preparative HPLC (XBridge Prep OBD C18 column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 8-(4-(2-(2,6-diazaspiro[3.3]heptan-2-yl)ethoxy)-2-chlorophenyl)-9-benzyl-6-(1-methylcyclopropoxy)-9H-purine (29.3 mg, 23%) as a yellow solid. $^1H$ NMR (400 MHz, $CDCl_3$): 0.84 (2H, t), 1.16 (2H, t), 1.81 (3H, s), 2.83 (2H, t), 3.36-3.48 (4H, m), 3.83 (4H, s), 4.01 (2H, t), 5.35 (2H, s), 6.80 (1H, dd), 6.91-6.96 (2H, m), 7.04 (1H, d), 7.14-7.21 (4H, m), 8.68 (1H, s)—one H not observed. m/z: ES+ [M+H]+ 531.

Tert-butyl 6-(2-(4-(9-benzyl-6-(1-methylcyclopropoxy)-9H-purin-8-yl)-3-chlorophenoxy)ethyl)-2,6-diazaspiro[3.3]heptane-2-carboxylate used as starting material was made as follows:

4-(2-Bromoethoxy)-2-chlorobenzaldehyde

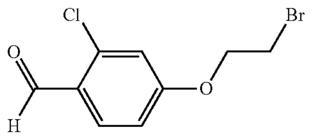 [SMILES: O=Cc1ccc(OCCBr)cc1Cl]

1,2-Dibromoethane (120 g, 639 mmol) was added to 2-chloro-4-hydroxybenzaldehyde (10 g, 63.9 mmol) and $K_2CO_3$ (22.07 g, 160 mmol) in MeCN (50 mL) at 25° C. The resulting mixture was stirred at 60° C. for 8 hours. The reaction mixture was filtered through a filtration paper and concentrated in vacuo. The crude product was purified by flash silica chromatography, elution gradient 0 to 40% EtOAc in petroleum ether. Pure fractions were evaporated to dryness to afford 4-(2-bromoethoxy)-2-chlorobenzaldehyde (13.00 g, 77%) as a white solid. $^1H$ NMR (300 MHz, DMSO-$d_6$): 3.82 (2H, t), 4.48 (2H, t), 7.11 (1H, dd), 7.23 (1H, d), 7.83 (1H, d), 10.19 (1H, s). m/z: ES+ [M+H]+ 265 ($^{35}Cl^{81}Br/^{37}Cl^{79}Br$ peak).

Tert-butyl 6-(2-(3-chloro-4-formylphenoxy)ethyl)-2,6-diazaspiro[3.3]heptane-2-carboxylate

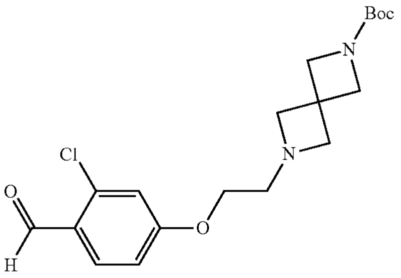 [SMILES: CC(C)(C)OC(=O)N1CC2(CN(CCOc3ccc(C=O)c(Cl)c3)C2)C1]

4-(2-Bromoethoxy)-2-chlorobenzaldehyde (200 mg, 0.76 mmol) was added to tert-butyl 2,6-diazaspiro[3.3]heptane-2-carboxylate (451 mg, 2.28 mmol), potassium carbonate (210 mg, 1.52 mmol) and sodium iodide (11.4 mg, 0.08 mmol) in DMF (5 mL) at RT. The resulting mixture was stirred at 80° C. for 2 hours. The reaction mixture was diluted with EtOAc (100 mL) and washed with saturated brine (3×15 mL). The organic layer was dried over $Na_2SO_4$, filtered and evaporated to afford the crude product. The crude product was purified by flash silica chromatography, elution gradient 0 to 100% EtOAc in petroleum ether. Pure fractions were evaporated to dryness to afford tert-butyl 6-(2-(3-chloro-4-formylphenoxy)ethyl)-2,6-diazaspiro[3.3]heptane-2-carboxylate (150 mg, 52%) as a brown solid. $^1H$ NMR (400 MHz, DMSO-$d_6$): 1.36 (9H, s), 2.7-2.73 (2H, m), 3.31-3.32 (4H, m), 3.81-3.92 (4H, m), 4.03-4.11 (2H, m), 7.03-7.08 (1H, m), 7.13-7.18 (1H, m), 7.79-7.84 (1H, m), 10.19 (1H, s). m/z: ES+ [M+H]+ 381.

Tert-butyl 6-(2-(4-(9-benzyl-6-(1-methylcyclopropoxy)-9H-purin-8-yl)-3-chlorophenoxy)ethyl)-2,6-diazaspiro[3.3]heptane-2-carboxylate

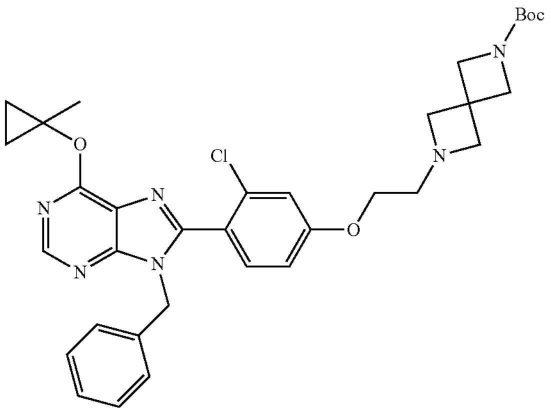 [SMILES: CC(C)(C)OC(=O)N1CC2(CN(CCOc3ccc(-c4nc5c(OC6(C)CC6)ncnc5n4Cc4ccccc4)c(Cl)c3)C2)C1]

Tert-butyl 6-(2-(3-chloro-4-formylphenoxy)ethyl)-2,6-diazaspiro[3.3]heptane-2-carboxylate (140 mg, 0.37 mmol) was added to N4-benzyl-6-(1-methylcyclopropoxy)pyrimidine-4,5-diamine (119 mg, 0.44 mmol) and iron(III) chloride (89 mg, 0.55 mmol) in IPA (5 mL) at rt. The resulting mixture was stirred at 55° C. for 2 hours. The reaction mixture was basified with aqueous 2M NaOH, diluted with EtOAc (100 mL) and washed sequentially with saturated brine (3×20 mL). The organic layer was dried over $Na_2SO_4$, filtered and evaporated to afford the crude product. The crude product was purified by flash silica chromatography, elution gradient 0 to 20% DCM in MeOH. Pure fractions were evaporated to dryness to afford tert-butyl 6-(2-(4-(9-benzyl-6-(1-methylcyclopropoxy)-9H-purin-8-yl)-3-chlorophenoxy)ethyl)-2,6-diazaspiro[3.3]heptane-2-carboxylate (190 mg, 82%) as a brown solid. $^1H$ NMR (400 MHz, DMSO-$d_6$): 0.85 (2H, t), 1.01 (2H, t), 1.36 (9H, s), 1.73 (3H, s), 2.71 (2H, t), 3.30-3.35 (4H, m), 3.81-3.91 (4H, m), 4.00-4.04 (2H, m), 5.21-5.31 (2H, m), 6.87-6.93 (2H, m), 7.00-7.08 (1H, m), 7.18-7.22 (4H, m), 7.40 (1H, d), 8.61 (1H, s). m/z: ES+ [M+H]+ 631.

Example 19

1-(5-(9-Benzyl-6-(1-methylcyclopropoxy)-9H-purin-8-yl)-4-methylpyridin-2-yl)azetidin-3-amine

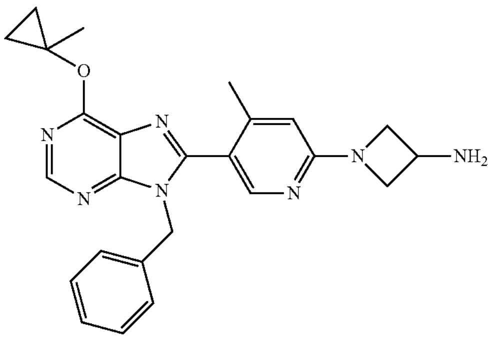 [SMILES: Cc1cc(N2CC(N)C2)ncc1-c1nc2c(OC3(C)CC3)ncnc2n1Cc1ccccc1]

HCl in dioxane (5 mL, 20.00 mmol) was added to tert-butyl (1-(5-(9-benzyl-6-(1-methylcyclopropoxy)-9H-purin-8-yl)-4-methylpyridin-2-yl)azetidin-3-yl)carbamate (200 mg, 0.37 mmol) in EtOAc (1 mL). The resulting mixture was stirred at rt for 2 hours. The solvent was removed under reduced pressure. The crude product was purified by preparative HPLC (XBridge Prep OBD C18 column, 30*150 mm, 5 μm), using decreasingly polar mixtures of water (containing 10 mmol/L NH4HCO3 and 0.1% aqueous ammonia) and MeCN as eluents.

Fractions containing the desired compound were evaporated to dryness to afford 1-(5-(9-benzyl-6-(1-methylcyclopropoxy)-9H-purin-8-yl)-4-methylpyridin-2-yl)azetidin-3-amine (51 mg, 31%) as a light yellow solid. $^1H$ NMR (400 MHz, DMSO-$d_6$): 0.80-0.92 (2H, m), 0.94-1.06 (2H, m), 1.73 (3H, s), 1.94 (3H, s), 3.59 (2H, dd), 3.83 (1H, tt), 4.15 (2H, dd), 5.31 (2H, s), 6.28 (1H, s), 6.85-6.94 (2H, m), 7.17-7.28 (3H, m), 7.97 (1H, s), 8.58 (1H, s). 2H not observed. m/z: ES+ [M+H]+ 442.

Tert-butyl (1-(5-(9-benzyl-6-(1-methylcyclopropoxy)-9H-purin-8-yl)-4-methylpyridin-2-yl)azetidin-3-yl)carbamate used as a starting material was made as follows:

9-Benzyl-8-(6-fluoro-4-methylpyridin-3-yl)-6-(1-methylcyclopropoxy)-9H-purine

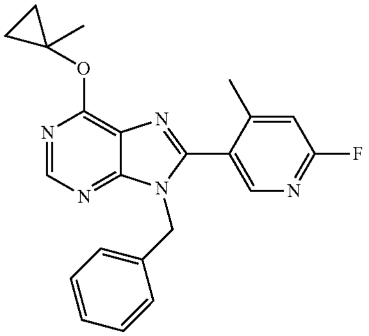 [SMILES: Cc1cc(F)ncc1-c1nc2c(OC3(C)CC3)ncnc2n1Cc1ccccc1]

6-Fluoro-4-methylnicotinaldehyde (1.54 g, 11.10 mmol) was added to N4-benzyl-6-(1-methylcyclopropoxy)pyrimidine-4,5-diamine (2.00 g, 7.40 mmol) in DMSO (30 mL). The resulting mixture was stirred at 100° C. for 16 hours. The reaction mixture was diluted with brine (200 mL) and extracted with EtOAc (4×150 mL). The organic layer was washed with brine (4×150 mL), dried over $Na_2SO_4$, filtered and evaporated to afford crude product. The crude product was purified by flash silica chromatography, elution gradient 0 to 40% EtOAc in pentane. Pure fractions were evaporated to dryness to afford 9-benzyl-8-(6-fluoro-4-methylpyridin-3-yl)-6-(1-methylcyclopropoxy)-9H-purine (1.90 g, 66%) as a yellow solid. $^1H$ NMR (400 MHz, DMSO-$d_6$): 0.84-0.88 (2H, m), 1.02-1.05 (2H, m), 1.75 (3H, s), 1.99 (3H, d), 5.35 (2H, s), 6.89 (2H, t), 7.22 (4H, d), 8.25 (1H, s), 8.68 (1H, s). m/z: ES+ [M+H]+ 390.

Tert-butyl (1-(5-(9-benzyl-6-(1-methylcyclopropoxy)-9H-purin-8-yl)-4-methylpyridin-2-yl)azetidin-3-yl)carbamate

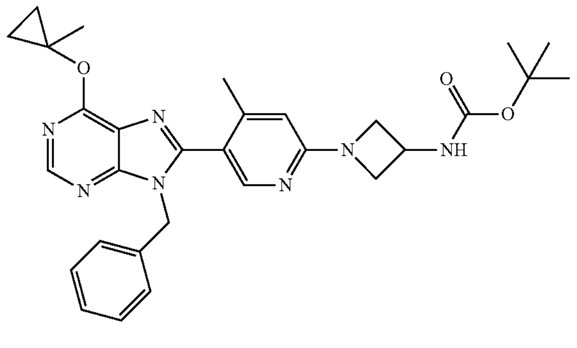 [SMILES: Cc1cc(N2CC(NC(=O)OC(C)(C)C)C2)ncc1-c1nc2c(OC3(C)CC3)ncnc2n1Cc1ccccc1]

Tert-butyl azetidin-3-ylcarbamate, HCl (193 mg, 0.92 mmol) was added to 9-benzyl-8-(6-fluoro-4-methylpyridin-3-yl)-6-(1-methylcyclopropoxy)-9H-purine (180 mg, 0.46 mmol) and DIEA (0.484 ml, 2.77 mmol) in DMSO (1 mL). The resulting mixture was stirred at 100° C. for 1 hour. The reaction mixture was quenched with saturated aq. $NH_4Cl$ (50 mL) and extracted with EtOAc (40 mL×3). The organic layer was washed with brine (3×50 mL), dried over $Na_2SO_4$, filtered and evaporated to afford tert-butyl (1-(5-(9-benzyl-6-(1-methylcyclopropoxy)-9H-purin-8-yl)-4-methylpyridin-2-yl)azetidin-3-yl)carbamate (0.25 g) used in the next step directly without further purification. m/z: ES+ [M+H]+ 542.

Example 20

9-Benzyl-8-(4-chloro-6-(2-(4-methylpiperazin-1-yl)ethoxy)pyridin-3-yl)-6-(1-methylcyclopropoxy)-9H-purine

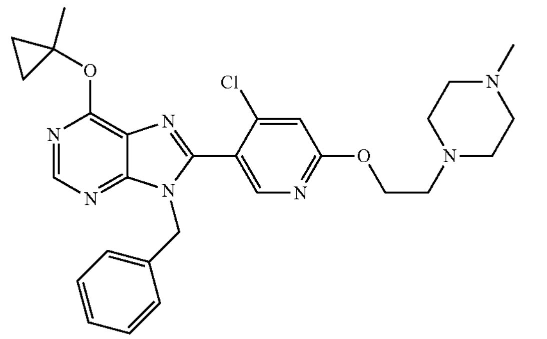 [SMILES: CN1CCN(CCOc2cc(Cl)c(-c3nc4c(OC5(C)CC5)ncnc4n3Cc3ccccc3)cn2)CC1]

RockPhos Pd G3 (18 mg, 0.02 mmol) was added to 9-benzyl-8-(6-bromo-4-chloropyridin-3-yl)-6-(1-methylcyclopropoxy)-9H-purine (100 mg, 0.21 mmol), 2-(4-methylpiperazin-1-yl)ethan-1-ol (30.6 mg, 0.21 mmol) and $Cs_2CO_3$ (208 mg, 0.64 mmol) in toluene (2 mL). The resulting mixture was stirred at 100° C. for 1 hour. The solvent was removed under reduced pressure. The crude product was purified by flash C18-flash chromatography, elution gradient 5 to 100% MeCN in water (0.01% $NH_4HCO_3$). Pure fractions were evaporated to dryness to afford 9-benzyl-8-(4-chloro-6-(2-(4-methylpiperazin-1-yl)ethoxy)pyridin-3-yl)-6-(1-methylcyclopropoxy)-9H-purine (16 mg, 14%) as a white solid. $^1H$ NMR (400 MHz, DMSO-$d_6$): 0.86 (2H, m), 1.03 (2H, m), 1.74 (3H, s), 2.16 (3H, s), 2.25-2.42 (4H, m), 2.52 (4H, m), 2.70 (2H, t), 4.45 (2H, t), 5.35 (2H, s), 6.93 (2H, m), 7.17-7.27 (4H, m), 8.28 (1H, s), 8.65 (1H, s). m/z: ES+ [M+H]+ 534.

9-Benzyl-8-(6-bromo-4-chloropyridin-3-yl)-6-(1-methylcyclopropoxy)-9H-purine used as a starting material was made as follows:

9-Benzyl-8-(6-bromo-4-chloropyridin-3-yl)-6-(1-methylcyclopropoxy)-9H-purine

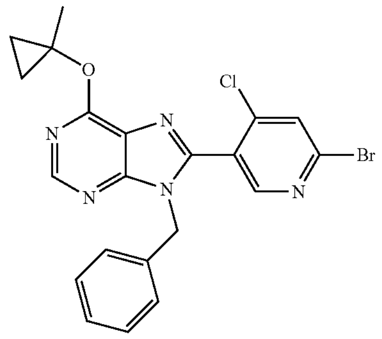 [SMILES: CC1(Oc2ncnc3c2nc(-c2cnc(Br)cc2Cl)n3Cc2ccccc2)CC1]

N4-Benzyl-6-(1-methylcyclopropoxy)pyrimidine-4,5-diamine (180 mg, 0.67 mmol, Example 4 Intermediate) was added to 6-bromo-4-chloronicotinaldehyde (220 mg, 1.00 mmol) in DMSO (2 mL). The resulting mixture was stirred at 80° C. for 1 hour. AcOH (0.38 mL, 6.66 mmol) was added to the mixture and the resulting mixture was stirred at 80° C. for 1 day. The reaction mixture was evaporated to afford crude product. The residue was purified by flash C18-flash chromatography, elution gradient 0 to 100% MeCN in water (containing 0.1% $NH_4HCO_3$). Pure fractions were evaporated to dryness to afford 9-benzyl-8-(6-bromo-4-chloropyridin-3-yl)-6-(1-methylcyclopropoxy)-9H-purine (120 mg, 38%) as a brown solid. $^1H$ NMR (400 MHz, DMSO-$d_6$): 0.86 (2H, t), 1.02 (2H, t), 1.73 (3H, s), 5.38 (2H, s), 6.89-6.99 (2H, m), 7.15-7.30 (3H, m), 8.16 (1H, s), 8.53 (1H, s), 8.68 (1H, s). m/z: ES+ [M+H]+ 470.

Example 21

9-Benzyl-8-(4-methyl-6-(2-(pyrrolidin-1-yl)ethoxy)pyridin-3-yl)-6-(1-methylcyclopropoxy)-9H-purine

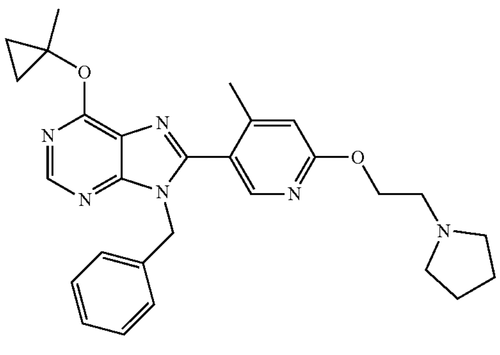 [SMILES: Cc1cc(OCCN2CCCC2)ncc1-c1nc2c(OC3(C)CC3)ncnc2n1Cc1ccccc1]

NaH (23 mg, 0.58 mmol) was added to 2-(pyrrolidin-1-yl)ethan-1-ol (89 mg, 0.77 mmol) in DMF (1 mL). The resulting mixture was stirred at rt for 5 minutes. Then 9-benzyl-8-(6-fluoro-4-methylpyridin-3-yl)-6-(1-methylcyclopropoxy)-9H-purine (150 mg, 0.39 mmol, Example 19 Intermediate) was added to the mixture. The resulting mixture was stirred at rt for 1 hour. The crude product was purified by preparative HPLC (XBridge Shield RP18 OBD column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 9-benzyl-8-(4-methyl-6-(2-(pyrrolidin-1-yl)ethoxy)pyridin-3-yl)-6-(1-methylcyclopropoxy)-9H-purine (47 mg, 25%) as a light yellow solid. $^1$H NMR (400 MHz, DMSO-$d_6$): 0.81-0.88 (2H, m), 1.01-1.03 (2H, m), 1.68 (4H, p), 1.73 (3H, s), 1.92 (3H, s), 2.78 (2H, t), 4.40 (2H, t), 5.33 (2H, s), 6.79 (1H, s), 6.84-6.91 (2H, m), 7.18-7.25 (3H, m), 8.12 (1H, s), 8.63 (1H, s). 4H not observed. m/z: ES+ [M+H]+ 485.

Example 22

9-Benzyl-8-(4-methyl-5-(2-(piperazin-1-yl)ethoxy)pyridin-3-yl)-6-(1-methylcyclopropoxy)-9H-purine

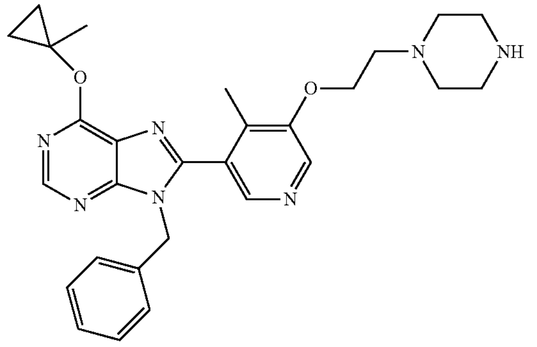 [SMILES: Cc1c(OCCN2CCNCC2)cncc1-c1nc2c(OC3(C)CC3)ncnc2n1Cc1ccccc1]

HCl in dioxane (3 mL, 3.00 mmol) was added to tert-butyl 4-(2-((5-(9-benzyl-6-(1-methylcyclopropoxy)-9H-purin-8-yl)-4-methylpyridin-3-yl)oxy)ethyl)piperazine-1-carboxylate (150 mg, 0.25 mmol) in EtOAc (2 mL). The resulting mixture was stirred at rt for 1 hour. The solvent was removed under reduced pressure. The crude product was purified by preparative HPLC (XBridge Prep OBD C18 column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 9-benzyl-8-(4-methyl-5-(2-(piperazin-1-yl)ethoxy)pyridin-3-yl)-6-(1-methylcyclopropoxy)-9H-purine (73 mg, 58%) as a brown solid. $^1$H NMR (400 MHz, DMSO-$d_6$): 0.82-0.88 (2H, m), 0.99-1.08 (2H, m), 1.74 (3H, s), 1.78 (3H, s), 2.30-2.45 (4H, m), 2.60-2.77 (6H, m), 4.26 (2H, t), 5.30 (2H, s), 6.74-6.94 (2H, m), 7.17-7.21 (3H, m), 8.15 (1H, s), 8.44 (1H, s), 8.65 (1H, s). 1H not observed. m/z: ES+ [M+H]+ 500.

Tert-butyl 4-(2-((5-(9-benzyl-6-(1-methylcyclopropoxy)-9H-purin-8-yl)-4-methylpyridin-3-yl)oxy)ethyl)piperazine-1-carboxylate used as a starting material was made as follows:

Tert-butyl 4-(2-((5-bromo-4-methylpyridin-3-yl)oxy)ethyl)piperazine-1-carboxylate

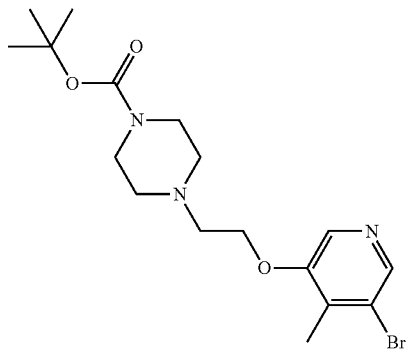 [SMILES: Cc1c(Br)cncc1OCCN1CCN(C(=O)OC(C)(C)C)CC1]

NaH (0.631 g, 15.79 mmol) was added to tert-butyl 4-(2-hydroxyethyl)piperazine-1-carboxylate (5.45 g, 23.68 mmol) in DMF (5 mL) at 0° C. The resulting mixture was stirred at rt for 20 minutes before the addition of 3-bromo-5-fluoro-4-methylpyridine (1.5 g, 7.89 mmol). The resulting mixture was stirred at rt for 1 hour. The reaction mixture was quenched with saturated aq. $NH_4Cl$ (50 mL) and extracted with EtOAc (3x30 mL). The combined organics were dried over $Na_2SO_4$, filtered and evaporated to afford crude product. The crude product was purified by flash C18-flash chromatography, elution gradient 5 to 80% MeCN in water (0.1% $NH_4HCO_3$). Pure fractions were evaporated to dryness to afford tert-butyl 4-(2-((5-bromo-4-methylpyridin-3-yl)oxy)ethyl)piperazine-1-carboxylate (0.840 g, 27%) as a yellow solid. $^1$H NMR (400 MHz, DMSO-$d_6$): 1.39 (9H, s), 2.26 (3H, s), 2.43-2.46 (4H, m), 2.76 (2H, t), 3.28-3.32 (4H, m), 4.24 (2H, t), 8.28 (1H, s), 8.31 (1H, s). m/z: ES+ [M+H]+ 400.

Tert-butyl 4-(2-((5-(methoxycarbonyl)-4-methylpyridin-3-yl)oxy)ethyl)piperazine-1-carboxylate

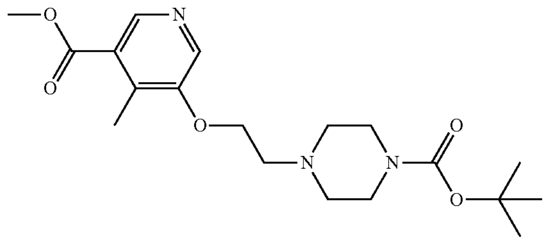 [SMILES: COC(=O)c1cncc(OCCN2CCN(C(=O)OC(C)(C)C)CC2)c1C]

Tert-butyl 4-(2-((5-bromo-4-methylpyridin-3-yl)oxy)ethyl)piperazine-1-carboxylate (80 mg, 2.00 mmol), $PdCl_2$(dppf) (146 mg, 0.20 mmol) and TEA (0.836 ml, 6.00 mmol) in MeOH (20 mL) were stirred under an atmosphere of carbon monoxide at 10 atm and 100° C. for 16 hours. The solvent was removed under reduced pressure. The crude product was purified by flash C18-flash chromatography, elution gradient 5 to 80% MeCN in water (0.1% $NH_4HCO_3$). Pure fractions were evaporated to dryness to afford tert-butyl 4-(2-((5-(methoxycarbonyl)-4-methylpyridin-3-yl)oxy)ethyl)piperazine-1-carboxylate (700 mg, 92%) as a yellow solid. $^1$H NMR (300 MHz, DMSO-$d_6$): 1.37 (9H, s), 2.36 (3H, s), 2.41-2.45 (4H, m), 2.75 (2H, t), 3.26-3.30 (4H, m), 3.84 (3H, s), 4.24 (2H, t), 8.44 (1H, s), 8.51 (1H, s). m/z: ES+ [M+H]+ 380.

Tert-butyl 4-(2-((5-(hydroxymethyl)-4-methylpyridin-3-yl)oxy)ethyl)piperazine-1-carboxylate

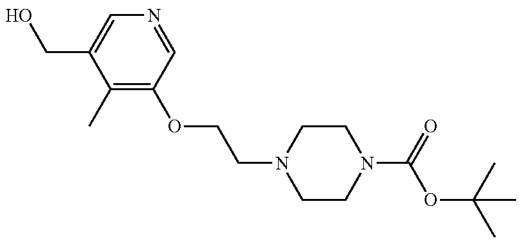 [SMILES: Cc1c(CO)cncc1OCCN1CCN(C(=O)OC(C)(C)C)CC1]

$LiAlH_4$ (1M in THF, 900 μL, 0.90 mmol) was added to tert-butyl 4-(2-((5-(methoxycarbonyl)-4-methylpyridin-3-yl)oxy)ethyl)piperazine-1-carboxylate (680 mg, 1.79 mmol) in THF (15 mL) at 0° C. The resulting mixture was stirred at 0° C. for 1 hour. The reaction mixture was poured into a 15% aqueous solution of NaOH. The organic layer was separated, dried over $Na_2SO_4$, filtered and evaporated to afford tert-butyl 4-(2-((5-(hydroxymethyl)-4-methylpyridin-3-yl)oxy)ethyl)piperazine-1-carboxylate (600 mg, 95%) as a yellow gum. The product was used in the next step directly without further purification. $^1H$ NMR (400 MHz, DMSO-$d_6$): 1.40 (9H, s), 2.14 (3H, s), 2.44-2.47 (4H, m), 2.76 (2H, t), 3.30-3.32 (4H, m), 4.19 (2H, t), 4.51 (2H, d), 5.15 (1H, t), 8.14 (1H, s), 8.19 (1H, s). m/z: ES+ [M+H]+ 352.

Tert-butyl 4-(2-((5-formyl-4-methylpyridin-3-yl)oxy)ethyl)piperazine-1-carboxylate

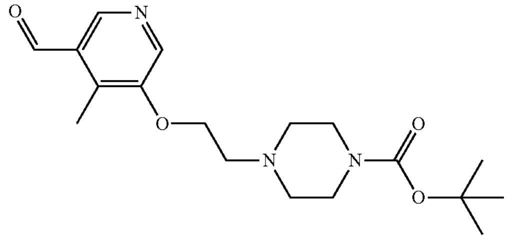 [SMILES: Cc1c(C=O)cncc1OCCN1CCN(C(=O)OC(C)(C)C)CC1]

Manganese(IV) oxide (866 mg, 5.78 mmol) was added to tert-butyl 4-(2-((5-(hydroxymethyl)-4-methylpyridin-3-yl)oxy)ethyl)piperazine-1-carboxylate (580 mg, 1.65 mmol) in EtOAc (10 mL). The resulting mixture was stirred at 80° C. for 16 hours. The mixture was filtered through a Celite pad. The crude product was purified by flash silica chromatography, elution gradient 0 to 10% MeOH in DCM. Pure fractions were evaporated to dryness to afford tert-butyl 4-(2-((5-formyl-4-methylpyridin-3-yl)oxy)ethyl)piperazine-1-carboxylate (0.420 g, 73%) as a yellow solid. $^1H$ NMR (300 MHz, DMSO-$d_6$): 1.37 (9H, s), 2.42-2.49 (7H, m), 2.76 (2H, t), 3.22-3.30 (4H, m), 4.26 (2H, t), 8.51 (1H, s), 8.57 (1H, s), 10.28 (1H, s). m/z: ES+ [M+H]+ 350.

Tert-butyl 4-(2-((5-(9-benzyl-6-(1-methylcyclopropoxy)-9H-purin-8-yl)-4-methylpyridin-3-yl)oxy)ethyl)piperazine-1-carboxylate

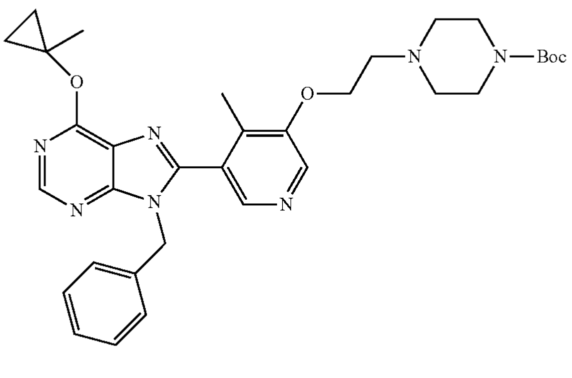 [SMILES: Cc1c(OCCN2CCN(C(=O)OC(C)(C)C)CC2)cncc1-c1nc2c(OC3(C)CC3)ncnc2n1Cc1ccccc1]

N4-Benzyl-6-(1-methylcyclopropoxy)pyrimidine-4,5-diamine (150 mg, 0.55 mmol, Example 4 Intermediate) and tert-butyl 4-(2-((5-formyl-4-methylpyridin-3-yl)oxy)ethyl)piperazine-1-carboxylate (291 mg, 0.83 mmol) in DMSO (3 mL) were stirred at 100° C. for 24 hours. The crude product was purified by flash C18-flash chromatography, elution gradient 5 to 80% MeCN in water (containing 0.1% $NH_4HCO_3$). Pure fractions were evaporated to dryness to afford tert-butyl 4-(2-((5-(9-benzyl-6-(1-methylcyclopropoxy)-9H-purin-8-yl)-4-methylpyridin-3-yl)oxy)ethyl)piperazine-1-carboxylate (170 mg, 51%) as a yellow solid. $^1H$ NMR (300 MHz, DMSO-$d_6$): 0.81-0.85 (2H, m), 0.99-1.06 (2H, m), 1.38 (9H, s), 1.72 (3H, s), 1.76 (3H, s), 2.41-2.45 (4H, m), 2.75 (2H, t), 3.27-3.31 (4H, m), 4.26 (2H, t), 5.28 (2H, s), 6.74-6.89 (2H, m), 7.10-7.27 (3H, m), 8.14 (1H, s), 8.42 (1H, s), 8.64 (1H, s). m/z: ES+ [M+H]+ 600.

Example 23

8-(2-chloro-4-(2-(piperazin-1-yl)ethoxy)phenyl)-9-((6-chloropyridin-2-yl)methyl)-6-(1-methylcyclopropoxy)-9H-purine

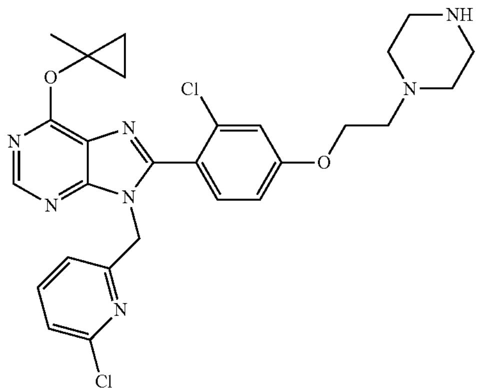 [SMILES: CC1(Oc2ncnc3c2nc(-c2ccc(OCCN4CCNCC4)cc2Cl)n3Cc2cccc(Cl)n2)CC1]

Tert-butyl 4-(2-(3-chloro-4-(6-(1-methylcyclopropoxy)-9H-purin-8-yl)phenoxy)ethyl)piperazine-1-carboxylate (200 mg, 0.38 mmol) was added into DMF (1 mL), followed by $Cs_2CO_3$ (246 mg, 0.76 mmol) and 2-chloro-6-(chloromethyl)pyridine (184 mg, 1.13 mmol). The resulting mixture was stirred at 100° C. for 2 hours.

The reaction mixture was poured into aq. saturated $NaHCO_3$ (100 mL), extracted with ethyl acetate (100 mL×3). The combined organic layers were washed with brine (100 mL), dried over $Na_2SO_4$, filtered and concentrated under reduced pressure to give a residue. To the above residue was added TFA (1 mL) at 25° C., and the mixture was stirred for 0.5 h. The solvent was removed under reduced pressure. The crude product was purified by flash C18-flash chromatography, elution gradient 0 to 100% MeCN in water. Fractions were evaporated to dryness to afford a mixture containing 8-(2-chloro-4-(2-(piperazin-1-yl)ethoxy)phenyl)-9-((6-chloropyridin-2-yl)methyl)-6-(1-methylcyclopropoxy)-9H-purine and 8-(2-chloro-4-(2-(piperazin-1-yl)ethoxy)phenyl)-7-((6-chloropyridin-2-yl) methyl)-6-(1-methylcyclopropoxy)-7H-purine as a pale yellow solid. The mixture was purified by preparative HPLC (YMC-Actus Triart C18 ExRS column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 8-(2-chloro-4-(2-(piperazin-1-yl)ethoxy)phenyl)-9-((6-chloropyridin-2-yl)methyl)-6-(1-methylcyclopropoxy)-9H-purine as a yellow oil (9 mg).

$^1H$ NMR (400 MHz, DMSO-$d_6$): 0.85 (2H, t), 1.01 (2H, t), 1.73 (3H, s), 2.42-2.51 (4H, m), 2.65-2.72 (6H, m), 4.14 (2H, t), 5.37 (2H, s), 7.00 (1H, dd), 7.08 (1H, d), 7.19 (1H, d), 7.34 (1H, d), 7.42 (1H, d), 7.71 (1H, t), 8.57 (1H, s). One proton not observed. m/z: ES+ [M+H]+ 554.

Tert-butyl 4-(2-(3-chloro-4-(6-(1-methylcyclopropoxy)-9H-purin-8-yl)phenoxy)ethyl)piperazine-1-carboxylate used as starting material was made as follows:

6-(1-methylcyclopropoxy)-9-(tetrahydro-2H-pyran-2-yl)-9H-purine

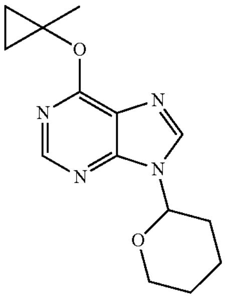 [SMILES: CC1(Oc2ncnc3c2ncn3C2CCCCO2)CC1]

A solution of sodium hydride (60% in mineral oil, 4.1 g, 102 mmol) in dry THF (60 mL) was cooled over ice, then a solution of 1-methylcyclopropan-1-ol (7.21 g, 100 mmol) in THF (20 mL) was added slowly. The reaction mixture stirred for 15 mins, under $N_2$, then a solution of 6-chloro-9-(tetrahydro-2H-pyran-2-yl)-9H-purine (11.94 g, 50.0 mmol) in THF (20 mL) added slowly. The reaction warmed to RT and stirred for 2 h. The reaction mixture was then heated at 60° C. for 2 h. The reaction was quenched with the addition of ice-water/EtOAc and the aqueous phase was extracted (EtOAc×2, 100 mL). The combined organics were passed through a hydrophobic frit and concentrated in vacuo. Purification on silica gel (330 g, 0-50% EtOAc in heptanes) yielded 6-(1-methylcyclopropoxy)-9-(tetrahydro-2H-pyran-2-yl)-9H-purine (7.65 g, 56%) as a yellow gum. $^1H$ NMR (500 MHz, $CDCl_3$): 0.79-0.84 (2H, m), 1.1-1.16 (2H, m), 1.62-1.69 (1H, m), 1.74-1.81 (5H, m), 2.04-2.14 (3H, m), 3.78 (1H, td), 4.13-4.21 (1H, m), 5.75 (1H, dd), 8.12 (1H, s), 8.61 (1H, s). m/z: ES+ [M+H]+ 275.

8-bromo-6-(1-methylcyclopropoxy)-9-(tetrahydro-2H-pyran-2-yl)-9H-purine

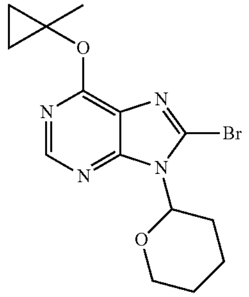 [SMILES: CC1(Oc2ncnc3c2nc(Br)n3C2CCCCO2)CC1]

To a solution of diisopropylamine (5.9 ml, 41.98 mmol) in dry THF (60 ml) under $N_2$ and cooled over dry ice/acetone bath was added butyllithium (2.5M in hexanes) (15.6 mL, 39.0 mmol) slowly. The reaction mixture stirred for 5 mins, then a solution of 6-(1-methylcyclopropoxy)-9-(tetrahydro-2H-pyran-2-yl)-9H-purine (7.65 g, 27.9 mmol) in THF (30 mL) was added slowly. The reaction stirred for 15 mins. Finally, a solution of 1,2-dibromo-1,1,2,2-tetrachloroethane (18.14 g, 55.7 mmol) in THF (30 mL) was added and the reaction mixture was stirred for 3 h. The reaction was then quenched with the addition of 5 mL sat. aq. $NH_4Cl$ and allowed to warm to RT slowly. The reaction mixture was concentrated in vacuo and re-dissolved in EtOAc (150 mL) and water (150 mL). The layers were separated and the aqueous layer was further extracted with EtOAc (150 mL×2). The organics were combined via hydrophobic frit and dried in vacuo. The crude product 8-bromo-6-(1-methylcyclopropoxy)-9-(tetrahydro-2H-pyran-2-yl)-9H-purine was used directly in the next step.

8-bromo-6-(1-methylcyclopropoxy)-9H-purine

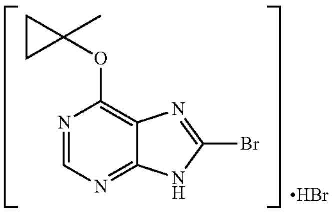

To 8-bromo-6-(1-methylcyclopropoxy)-9-(tetrahydro-2H-pyran-2-yl)-9H-purine (9.54 g, 27 mmol) was added 1,4-dioxane (40 mL) and hydrogen bromide (33% in acetic acid, 15 mL, 82.8 mmol) slowly over ice. The reaction stirred at RT for 5 mins and then the reaction mixture was then diluted with TBME and filtered. The solids washed with TBME and dried under vacuum over the weekend. 8-Bromo-6-(1-methylcyclopropoxy)-9H-purine·HBr salt (9.18 g, 97%) was isolated as a beige solid. $^1H$ NMR (500 MHz, $CD_3OD$): 0.91-0.97 (2H, m), 1.16-1.21 (2H, m), 1.81 (3H, s), 8.91 (1H, s). One proton not observed. m/z: ES+ [M+H]+ 271 ($^{81}Br$ isotope).

Tert-butyl 4-(2-(3-chloro-4-(6-(1-methylcyclopropoxy)-9H-purin-8-yl)phenoxy)ethyl)piperazine-1-carboxylate

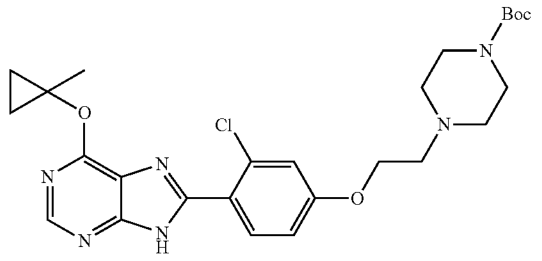 [SMILES: CC(C)(C)OC(=O)N1CCN(CCOc2ccc(-c3nc4c(OC5(C)CC5)ncnc4[nH]3)c(Cl)c2)CC1]

A degassed mixture of dioxane (42 mL) and water (8.4 mL) was added to a multineck flask containing 8-bromo-6-(1-methylcyclopropoxy)-9H-purine·HBr salt (3.50 g, 10.0 mmol), tert-butyl 4-(2-(3-chloro-4-(4,4,5,5-tetramethyl-1,3,2-dioxaborolan-2-yl)phenoxy)ethyl)piperazine-1-carboxylate (6.09 g, 13.05 mmol, Example 5 intermediate), tetrakis (triphenylphosphine) palladium (0) (0.59 g, 0.51 mmol) and cesium carbonate (9.78 g, 30.0 mmol), under nitrogen. The reaction stirred at 120° C. for 3 hrs and then increased to 140° C. Further tetrakis(triphenylphosphine) palladium (0) (0.5 g, 0.43 mmol) was added. The mixture was heated at 140° C. overnight and then cooled to RT. Water (150 mL) was then added and the mixture was extracted with EtOAc (3×150 mL). The organics were combined via a hydrophobic frit and concentrated in vacuo. Purification on silica gel (220 g, 0-100% EtOAc in heptanes and then 0-50% EtOAc/EtOH 3:1 in EtOAc) yielded tert-butyl 4-(2-(3-chloro-4-(6-(1-methylcyclopropoxy)-9H-purin-8-yl)phenoxy)ethyl)piperazine-1-carboxylate (3.61 g, 68%) as a light yellow solid. $^1$H NMR (500 MHz, DMSO-$d_6$): 0.84 (2H, s), 1.01 (2H, s), 1.39 (9H, s), 1.72 (3H, s), 2.43-2.46 (4H, m), 2.74 (2H, t), 3.32 (4H, s), 4.21 (2H, t), 7.10 (1H, dd), 7.25 (1H, d), 7.72 (1H, d), 8.52 (1H, s), 13.53 (1H, s). m/z: ES+ [M+H]+ 529.

Example 24

9-Benzyl-8-(4-methyl-6-(2-(piperazin-1-yl)ethoxy) pyridin-3-yl)-6-(1-methylcyclobutoxy)-9H-purine

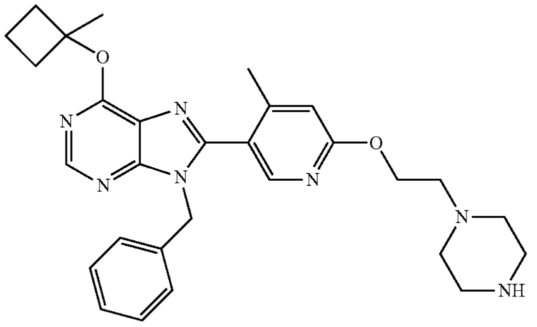 [SMILES: Cc1cc(OCCN2CCNCC2)ncc1-c1nc2c(OC3(C)CCC3)ncnc2n1Cc1ccccc1]

Sodium hydride (36 mg, 1.49 mmol) was added in one portion to 2,2,2-trifluoro-1-(4-(2-hydroxyethyl)piperazin-1-yl)ethan-1-one (81 mg, 0.36 mmol) and 9-benzyl-8-(6-fluoro-4-methylpyridin-3-yl)-6-(1-methylcyclobutoxy)-9H-purine (120 mg, 0.30 mmol) in THF (7 mL) at 0° C. under nitrogen. The resulting solution was stirred at 25° C. for 4 hours. The reaction mixture was quenched with saturated $NH_4Cl$ (2 mL) and the solvent removed under reduced pressure. The crude product was purified by preparative HPLC (Xselect CSH C18 OBD column, 30*150 mm, 5 μm), using decreasingly polar mixtures of water (containing 10 mmol/L $NH_4HCO_3$ and 0.05% aqueous ammonia) and MeCN as eluents. Fractions containing the desired compound were evaporated to dryness to afford 9-benzyl-8-(4-methyl-6-(2-(piperazin-1-yl)ethoxy)pyridin-3-yl)-6-(1-methylcyclobutoxy)-9H-purine (65 mg, 43%) as a white solid. $^1$H NMR (300 MHz, DMSO-$d_6$): 1.63-1.88 (5H, m), 1.92 (3H, s), 2.25-2.49 (8H, m), 2.6-2.8 (6H, m), 4.40 (2H, t), 5.31 (2H, s), 6.79 (1H, s), 6.83-7 (2H, m), 7.11-7.33 (3H, m), 8.12 (1H, s), 8.52 (1H, s). $^1$H not observed. m/z: ES+ [M+H]+ 514.

9-Benzyl-8-(6-fluoro-4-methylpyridin-3-yl)-6-(1-methylcyclobutoxy)-9H-purine used as a starting material was made as follows.

9-Benzyl-8-(6-fluoro-4-methylpyridin-3-yl)-6-(1-methylcyclobutoxy)-9H-purine

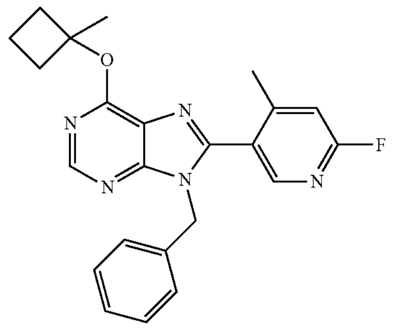 [SMILES: Cc1cc(F)ncc1-c1nc2c(OC3(C)CCC3)ncnc2n1Cc1ccccc1]

$Pd(Ph_3P)_4$ (46 mg, 0.04 mmol) was added in one portion to 9-benzyl-8-bromo-6-(1-methylcyclobutoxy)-9H-purine (150 mg, 0.40 mmol, Example 12 intermediate), (6-fluoro-4-methylpyridin-3-yl)boronic acid (93 mg, 0.60 mmol) and cesium carbonate (262 mg, 0.80 mmol) in 1,4-dioxane (20 mL) and water (5 mL) at 25° C. under nitrogen. The resulting solution was stirred at 100° C. for 4 hours. The reaction mixture was diluted with water. The aqueous layer was extracted with EtOAc (3×20 mL). The organic layer was dried over $Na_2SO_4$, filtered and evaporated to afford crude product. The crude product was purified by flash silica chromatography, elution gradient 0 to 50% EtOAc in petroleum ether. Pure fractions were evaporated to dryness to afford 9-benzyl-8-(6-fluoro-4-methylpyridin-3-yl)-6-(1-methylcyclobutoxy)-9H-purine (150 mg, 93%) as a colourless solid. $^1$H NMR (300 MHz, $CDCl_3$): 1.67-1.95 (5H, m), 2.00 (3H, s), 2.3-2.48 (2H, m), 2.48-2.73 (2H, m), 5.30 (2H, s), 6.75-7.00 (3H, m), 7.12-7.26 (3H, m), 8.06 (1H, s), 8.59 (1H, s). m/z: ES+ [M+H]+ 404.

2,2,2-Trifluoro-1-(4-(2-hydroxyethyl)piperazin-1-yl) ethan-1-one used as a starting material was made as follows:

2,2,2-Trifluoro-1-(4-(2-hydroxyethyl)piperazin-1-yl) ethan-1-one

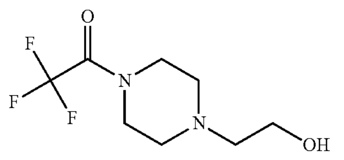 [SMILES: O=C(N1CCN(CCO)CC1)C(F)(F)F]

2,2,2-Trifluoroacetic anhydride (7.74 g, 36.87 mmol) was added dropwise to 2-(piperazin-1-yl)ethan-1-ol (4.00 g, 30.72 mmol) and triethylamine (4.66 g, 46.09 mmol) in DCM (100 mL) at 0° C. under nitrogen. The resulting solution was stirred at 25° C. for 4 hours. The solvent was removed under reduced pressure to get crude product. The crude product was purified by flash silica chromatography, elution gradient 0 to 20% MeOH in DCM. Pure fractions were evaporated to dryness to afford 2,2,2-trifluoro-1-(4-(2-hydroxyethyl)piperazin-1-yl)ethan-1-one (3.80 g, 55%) as a colourless oil. $^1$H NMR (300 MHz, $CDCl_3$): 2.45-2.76 (7H, m), 3.53-3.92 (6H, m). m/z: ES+ [M+H]+ 227.

Example 25

2-(3-Chloro-4-(6-(1-methylcyclopropoxy)-9-((4-methylpyridin-2-yl)methyl)-9H-purin-8-yl)phenoxy)-N,N-dimethylethan-1-amine

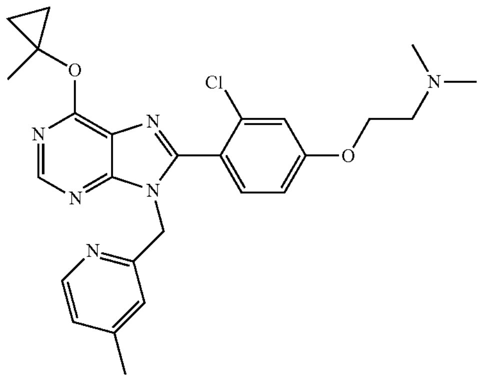

Dimethylamine (0.48 mL, 2.84 mmol) was added to 8-(4-(2-bromoethoxy)-2-chlorophenyl)-6-(1-methylcyclopropoxy)-9-((4-methylpyridin-2-yl)methyl)-9H-purine (150 mg, 0.28 mmol) and potassium carbonate (196 mg, 1.42 mmol) in MeCN (2 mL) under air. The resulting mixture was stirred at 70° C. for 2 hours. The solvent was removed under reduced pressure. The crude product was purified by purified by preparative HPLC (XBridge BEH C18 OBD Prep Column, 5 μm silica, 19 mm diameter, 250 mm length), using decreasingly polar mixtures of water (containing 0.1% aq. $NH_3$ and 10 mmol/L $NH_4HCO_3$) and MeCN as eluents. Fractions containing the desired compound were evaporated to dryness to afford 2-(3-chloro-4-(6-(1-methylcyclopropoxy)-9-((4-methylpyridin-2-yl)methyl)-9H-purin-8-yl)phenoxy)-N,N-dimethylethan-1-amine (30 mg, 21%) as a white solid. $^1$H NMR (400 MHz, DMSO-$d_6$): 0.86 (2H, t), 1.03 (2H, t), 1.74 (3H, s), 2.19 (3H, s), 2.21 (6H, s), 2.62 (2H, t), 4.12 (2H, t), 5.35 (2H, s), 6.86 (1H, s), 6.96 (1H, dd), 7.03 (1H, d), 7.20 (1H, d), 7.37 (1H, d), 8.18 (1H, d), 8.57 (1H, s). m/z: ES+ [M+H]+ 493.

8-(4-(2-Bromoethoxy)-2-chlorophenyl)-6-(1-methylcyclopropoxy)-9-((4-methylpyridin-2-yl)methyl)-9H-purine used as a starting material was made as follows.

8-(4-Bromo-2-chlorophenyl)-6-chloro-9H-purine

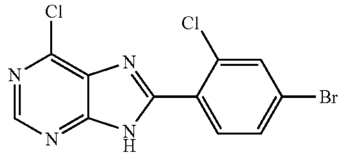 [SMILES: Clc1cc(Br)ccc1-c1nc2c(Cl)ncnc2[nH]1]

Iron(III) chloride (112.0 g, 691.74 mmol) was added to 6-chloropyrimidine-4,5-diamine (20.0 g, 138 mmol) and 4-bromo-2-chlorobenzaldehyde (29.8 g, 136 mmol) in IPA (400 mL) at 25° C. The resulting mixture was stirred at 80° C. for 12 hours. The reaction mixture was concentrated under reduced pressure to remove most of the solvent, then diluted with EtOAc, poured into ice water, and the formed precipitate isolated by filtration. The filter cake was washed with water until the water pH is 7. The solid was dissolved in THF, dried over anhydrous $Na_2SO_4$, filtered, concentrated to dryness to afford 8-(4-bromo-2-chlorophenyl)-6-chloro-9H-purine (32.0 g, 67%) as a yellow solid. $^1$H NMR (300 MHz, DMSO-$d_6$): 7.68-7.78 (1H, m), 7.86-7.97 (2H, m), 8.60 (1H, s). $^1$H not observed. m/z: ES+ [M+H]+ 343.

8-(4-Bromo-2-chlorophenyl)-6-chloro-9-((4-methylpyridin-2-yl)methyl)-9H-purine

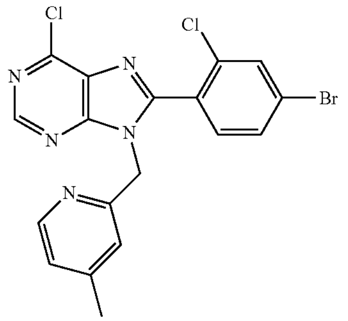 [SMILES: Cc1ccnc(Cn2c(-c3ccc(Br)cc3Cl)nc3c(Cl)ncnc32)c1]

8-(4-Bromo-2-chlorophenyl)-6-chloro-9H-purine (8.00 g, 23.26 mmol) was added to 2-(chloromethyl)-4-methylpyridine (4.94 g, 34.88 mmol) and $K_2CO_3$ (9.64 g, 69.77 mmol) in MeCN (20 mL). The resulting mixture was stirred at 80° C. for 4 hours. The reaction mixture was diluted with EtOAc (75 mL), and washed sequentially with water (25 mL×3). The organic layer was dried over $Na_2SO_4$, filtered and evaporated to afford crude product. The crude product was purified by flash silica chromatography, elution gradient 0 to 60% EtOAc in petroleum ether. Pure fractions were evaporated to dryness to afford 8-(4-bromo-2-chlorophenyl)-6-chloro-9-((4-methylpyridin-2-yl)methyl)-9H-purine (4.90 g, 47%) as a white solid. $^1$H NMR (300 MHz, DMSO-$d_6$): 2.21 (3H, s), 5.47 (2H, s), 6.97 (1H, s), 7.06 (1H, d), 7.53 (1H, d), 7.69 (1H, dd), 7.96 (1H, d), 8.16 (1H, d), 8.85 (1H, s). m/z: ES+ [M+H]+ 448.

8-(4-Bromo-2-chlorophenyl)-6-(1-methylcyclopropoxy)-9-((4-methylpyridin-2-yl)methyl)-9H-purine

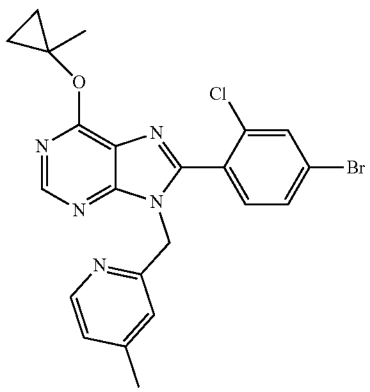 [SMILES: Cc1ccnc(Cn2c(-c3ccc(Br)cc3Cl)nc3c(OC4(C)CC4)ncnc32)c1]

NaH (2.45 g, 61.23 mmol) was added to 8-(4-bromo-2-chlorophenyl)-6-chloro-9-((4-methylpyridin-2-yl)methyl)-9H-purine (5.50 g, 12.2 mmol) and 1-methylcyclopropan-1-ol (2.21 g, 30.6 mmol) in DMF (100 mL) at 0° C. under nitrogen. The resulting mixture was stirred at 25° C. for 2 hours. The reaction mixture was quenched with saturated aq. $NH_4Cl$ (150 mL), extracted with EtOAc (3×100 mL). The organic layer was dried over $Na_2SO_4$, filtered and evaporated under reduced pressure. The crude product was purified by flash silica chromatography, elution gradient 0 to 50% EtOAc in petroleum ether. Pure fractions were evaporated to dryness to afford 8-(4-bromo-2-chlorophenyl)-6-(1-methylcyclopropoxy)-9-((4-methylpyridin-2-yl)methyl)-9H-purine (4.50 g, 76%) as a pale yellow solid. $^1H$ NMR (300 MHz, DMSO-$d_6$): 0.78-0.89 (2H, m), 1.00-1.07 (2H, m), 1.74 (3H, s), 2.20 (3H, s), 5.37 (2H, s), 6.90 (1H, d), 7.04 (1H, dd), 7.45 (1H, d), 7.64 (1H, dd), 7.93 (1H, d), 8.16 (1H, dd), 8.60 (1H, s). m/z: ES+ [M+H]+ 484.

3-Chloro-4-(6-(1-methylcyclopropoxy)-9-((4-methylpyridin-2-yl)methyl)-9H-purin-8-yl)phenol

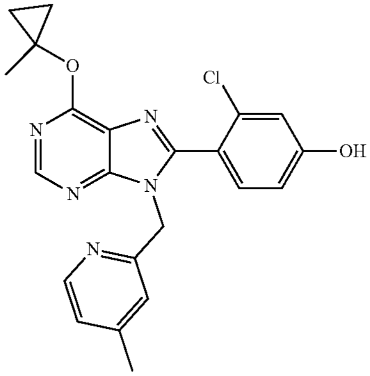 [SMILES: Cc1ccnc(Cn2c(-c3ccc(O)cc3Cl)nc3c(OC4(C)CC4)ncnc32)c1]

1,1'-Bis(diphenylphosphino)ferrocenedichloropalladium (II) dichloromethane adduct (253 mg, 0.31 mmol) was added to 8-(4-bromo-2-chlorophenyl)-6-(1-methylcyclopropoxy)-9-((4-methylpyridin-2-yl)methyl)-9H-purine (1.50 g, 3.09 mmol), 4,4,4',4',5,5,5',5'-octamethyl-2,2'-bi (1,3,2-dioxaborolane) (864 mg, 3.40 mmol) and potassium acetate (607 mg, 6.19 mmol) in 1,4-dioxane (10 mL) at rt under nitrogen. The resulting mixture was stirred at 100° C. for 1 hour. The solvent was removed under reduced pressure. The solid was diluted with THF/water (10 mL). Sodium perborate (1.26 g, 15.47 mmol) was added and the mixture was stirred at RT for a further 30 minutes. The reaction mixture was diluted with EtOAc (150 mL), and washed sequentially with water (50 mL×3). The organic layer was dried over $Na_2SO_4$, filtered and evaporated to afford crude product. The crude product was purified by flash silica chromatography, elution gradient 0 to 20% MeOH in DCM. Pure fractions were evaporated to dryness to afford 3-chloro-4-(6-(1-methylcyclopropoxy)-9-((4-methylpyridin-2-yl)methyl)-9H-purin-8-yl)phenol (1.00 g, 77%) as a white solid. $^1H$ NMR (300 MHz, DMSO-$d_6$): 0.86 (2H, t), 1.02 (2H, t), 1.74 (3H, s), 2.20 (3H, s), 5.34 (2H, s), 6.75 (1H, dd), 6.84 (1H, s), 6.93 (1H, d), 7.04 (1H, d), 7.25 (1H, d), 8.18 (1H, d), 8.56 (1H, s). $^1H$ not observed. m/z: ES+ [M+H]+ 422.

8-(4-(2-Bromoethoxy)-2-chlorophenyl)-6-(1-methylcyclopropoxy)-9-((4-methylpyridin-2-yl)methyl)-9H-purine

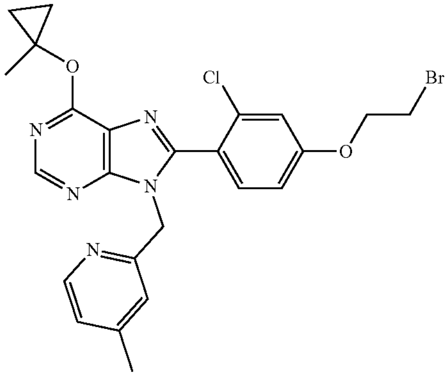 [SMILES: Cc1ccnc(Cn2c(-c3ccc(OCCBr)cc3Cl)nc3c(OC4(C)CC4)ncnc32)c1]

1,2-Dibromoethane (891 mg, 4.74 mmol) was added to $K_2CO_3$ (197 mg, 1.42 mmol) and 3-chloro-4-(6-(1-methylcyclopropoxy)-9-((4-methylpyridin-2-yl)methyl)-9H-purin-8-yl)phenol (400 mg, 0.95 mmol) in MeCN (20 mL) at rt. The resulting mixture was stirred at 60° C. for 18 hours. The reaction mixture was evaporated to dryness and redissolved in EtOAc (150 mL), and washed sequentially with water (125 mL×3) and saturated brine (100 mL×2). The organic layer was dried over $Na_2SO_4$, filtered and evaporated to afford crude product. The crude product was purified by flash silica chromatography, elution gradient 40 to 80% EtOAc in petroleum ether. Pure fractions were evaporated to dryness to afford 8-(4-(2-bromoethoxy)-2-chlorophenyl)-6-(1-methylcyclopropoxy)-9-((4-methylpyridin-2-yl)methyl)-9H-purine (230 mg, 46%) as a white solid. $^1H$ NMR (300 MHz, DMSO-$d_6$): 0.86 (2H, t), 1.03 (2H, t), 1.74 (3H, s), 2.5-2.52 (3H, m), 3.78-3.87 (2H, m), 4.39-4.45 (2H, m), 5.35 (2H, s), 6.87 (1H, d), 6.97-7.06 (2H, m), 7.23 (1H, d), 7.40 (1H, d), 8.18 (1H, d), 8.57 (1H, s). m/z: ES+ [M+H]+ 528.

Example 26

1-(2-(3-Chloro-4-(6-(1-methylcyclopropoxy)-9-((4-methylpyridin-2-yl)methyl)-9H-purin-8-yl)phenoxy)ethyl)azetidin-3-ol

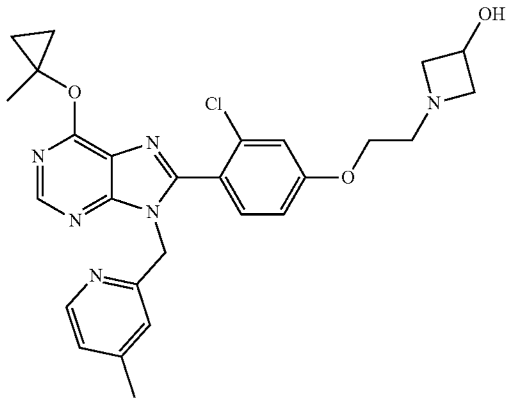 [SMILES: Cc1ccnc(Cn2c(-c3ccc(OCCN4CC(O)C4)cc3Cl)nc3c(OC4(C)CC4)ncnc32)c1]

Azetidin-3-ol (276 mg, 3.78 mmol) was added to 8-(4-(2-bromoethoxy)-2-chlorophenyl)-6-(1-methylcyclopropoxy)-9-((4-methylpyridin-2-yl)methyl)-9H-purine (400 mg, 0.76 mmol, Example 25 intermediate) and $K_2CO_3$ (523 mg, 3.78 mmol) in MeCN (2 mL) under air. The resulting mixture was stirred at 70° C. for 2 hours. The solvent was removed under reduced pressure. The crude product was purified by preparative HPLC (XBridge Prep OBD C18 Column, 5 μm silica, 30 mm diameter, 150 mm length), using decreasingly polar mixtures of water (containing 0.1% aq. $NH_3$ and 10 mmol/L $NH_4HCO_3$) and MeCN as eluents. Fractions containing the desired compound were evaporated to dryness to afford 1-(2-(3-chloro-4-(6-(1-methylcyclopropoxy)-9-((4-methylpyridin-2-yl)methyl)-9H-purin-8-yl)phenoxy)ethyl)azetidin-3-ol (24 mg, 6%) as a white solid. $^1$H NMR (400 MHz, DMSO-$d_6$): 0.86 (2H, t), 1.02 (2H, t), 1.74 (3H, s), 2.20 (3H, s), 2.69-2.84 (4H, m), 3.51-3.59 (2H, m), 4.00 (2H, t), 4.12-4.21 (1H, m), 5.27 (1H, d), 5.34 (2H, s), 6.86 (1H, s), 6.93 (1H, dd), 7.03 (1H, d), 7.16 (1H, d), 7.36 (1H, d), 8.18 (1H, d), 8.57 (1H, s). m/z: ES+ [M+H]+ 521.

Example 27: Further Examples

The following examples in Table A were synthesised as stated in the notes following Table A.

TABLE A

| Ex # | Structure | Name | $^1$H NMR | LCMS [M + H]+ |
|---|---|---|---|---|
| A1 | 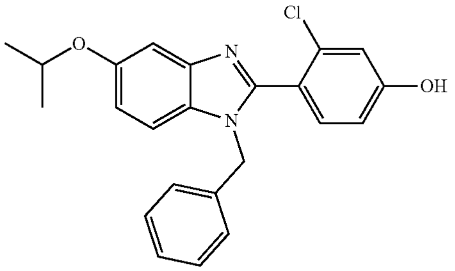 [SMILES: CC(C)Oc1ccc2c(c1)nc(-c1ccc(O)cc1Cl)n2Cc1ccccc1] | 4-(1-benzyl-5-isopropoxy-1H-benzo[d]imidazol-2-yl)-3-chlorophenol | (300 MHz, DMSO-$d_6$): 1.27 (6H, d), 4.60 (1H, p), 5.25 (2H, s), 6.85 (2H, td), 6.93-7.04 (3H, m), 7.15-7.30 (4H, m), 7.30 (1H, t), 7.37 (1H, d), 10.41 (1H, s) | 393 |
| A2 | 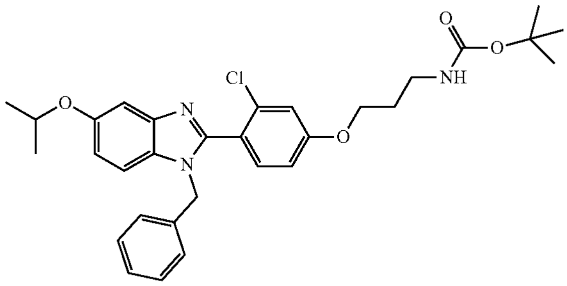 [SMILES: CC(C)Oc1ccc2c(c1)nc(-c1ccc(OCCCNC(=O)OC(C)(C)C)cc1Cl)n2Cc1ccccc1] | tert-butyl (3-(4-(1-benzyl-5-isopropoxy-1H-benzo[d]imidazol-2-yl)-3-chlorophenoxy)propyl)carbamate | (400 MHz, $CDCl_3$): 1.38 (6H, d), 1.46 (9H, s), 2.03 (2H, q), 3.35 (2H, q), 4.07 (2H, t), 4.58 (1H, hept), 4.74 (1H, s), 5.22 (2H, s), 6.87 (2H, ddd), 6.95-7.02 (2H, m), 7.06 (1H, d), 7.09 (1H, d), 7.25 (3H, dd), 7.35 (1H, d), 7.39 (1H, d) | 550 |
| A3 | 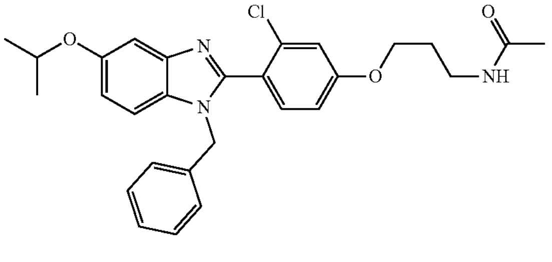 [SMILES: CC(=O)NCCCOc1ccc(-c2nc3cc(OC(C)C)ccc3n2Cc2ccccc2)c(Cl)c1] | N-(3-(4-(1-benzyl-5-isopropoxy-1H-benzo[d]imidazol-2-yl)-3-chlorophenoxy)propyl)acetamide | (300 MHz, $CDCl_3$): 1.36 (6H, d), 1.98 (3H, s), 1.96-2.09 (2H, m), 3.44 (2H, q), 4.04 (2H, t), 4.56 (1H, p), 5.20 (2H, s), 5.99 (1H, s), 6.85 (2H, ddd), 6.92-7.00 (2H, m), 7.02 (1H, d), 7.07 (1H, d), 7.23 (3H, dd), 7.31 (1H, d), 7.36 (1H, d) | 492 |

TABLE A-continued

| Ex # | Structure | Name | $^1$H NMR | LCMS [M + H]+ |
|---|---|---|---|---|
| A4 | 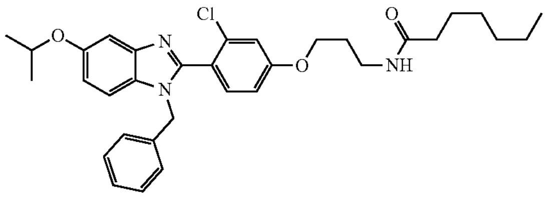 [SMILES: CCCCCCC(=O)NCCCOc1ccc(-c2nc3cc(OC(C)C)ccc3n2Cc2ccccc2)c(Cl)c1] | N-(3-(4-(1-benzyl-5-isopropoxy-1H-benzo[d]imidazol-2-yl)-3-chlorophenoxy)propyl)heptanamide | (300 MHz, $CDCl_3$): 0.81-0.91 (2H, m), 1.28 (6H, d), 1.35 (6H, d), 1.61 (2H, p), 2.01 (2H, p), 2.17 (2H, t), 3.44 (2H, q), 4.03 (2H, t), 4.55 (1H, p), 5.19 (2H, s), 6.01 (1H, t), 6.84 (2H, ddd), 6.96 (2H, dd), 7.00-7.11 (2H, m), 7.22 (3H, dd), 7.28-7.40 (2H, m) One proton not observed. | 562 |
| A5 | 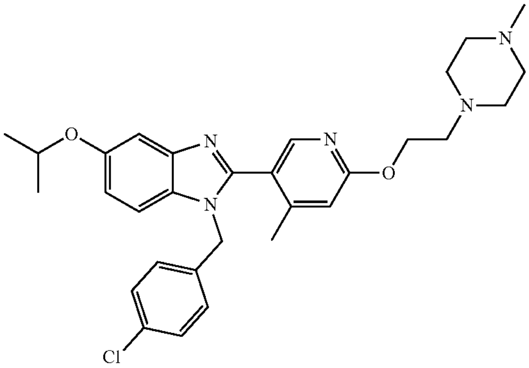 [SMILES: Cc1cc(OCCN2CCN(C)CC2)ncc1-c1nc2cc(OC(C)C)ccc2n1Cc1ccc(Cl)cc1] | 1-(4-chlorobenzyl)-5-isopropoxy-2-(4-methyl-6-(2-(4-methylpiperazin-1-yl)ethoxy)pyridin-3-yl)-1H-benzo[d]imidazole | (400 MHz, DMSO-$d_6$): 1.28 (6H, d), 2.09 (3H, s), 2.13 (3H, s), 2.30 (4H, s), 2.48 (4H, s), 2.68 (2H, t), 4.39 (2H, t), 4.60 (1H, hept), 5.30 (2H, s), 6.81-6.90 (2H, m), 6.93 (2H, d), 7.23 (1H, d), 7.28-7.34 (2H, m), 7.38 (1H, d), 8.12 (1H, s). | 534 |
| A6 | 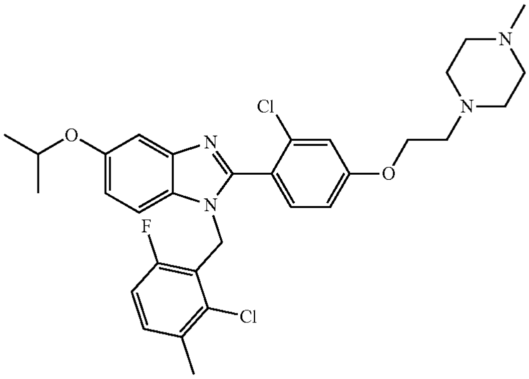 [SMILES: Cc1ccc(F)c(Cn2c(-c3ccc(OCCN4CCN(C)CC4)cc3Cl)nc3cc(OC(C)C)ccc32)c1Cl] | 2-(2-chloro-4-(2-(4-methylpiperazin-1-yl)ethoxy)phenyl)-1-(2-chloro-6-fluoro-3-methylbenzyl)-5-isopropoxy-1H-benzo[d]imidazole | No NMR available | 585 |
| A7 | 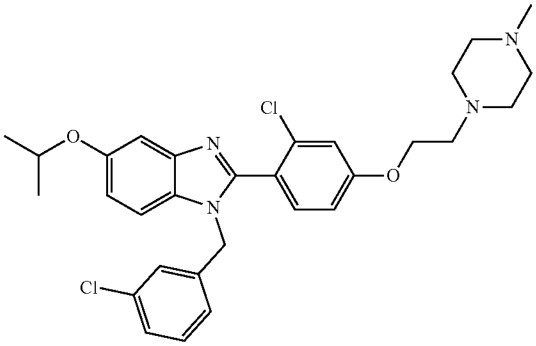 [SMILES: CC(C)Oc1ccc2c(c1)nc(-c1ccc(OCCN3CCN(C)CC3)cc1Cl)n2Cc1cccc(Cl)c1] | 1-(3-chlorobenzyl)-5-isopropoxy-2-(4-methyl-6-(2-(4-methylpiperazin-1-yl)ethoxy)pyridin-3-yl)-1H-benzo[d]imidazole | (300 MHz, DMSO-$d_6$): 1.26 (6H, d), 2.05 (3H, s), 2.10 (3H, s), 2.27 (4H, s), 2.44 (4H, s), 2.65 (2H, t), 4.37 (2H, t), 4.59 (1H, p), 5.30 (2H, s), 6.75-6.89 (3H, m), 6.93 (1H, s), 7.17-7.29 (3H, m), 7.42 (1H, d), 8.10 (1H, s). | 534 |

TABLE A-continued

| Ex # | Structure | Name | $^1$H NMR | LCMS [M + H]+ |
|---|---|---|---|---|
| A8 | 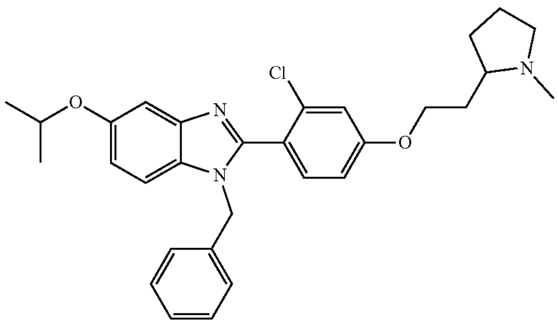 Isomer 1 | 1-benzyl-2-(2-chloro-4-(2-(1-methylpyrrolidin-2-yl)ethoxy)phenyl)-5-isopropoxy-1H-benzo[d]imidazole (Isomer 1) | (500 MHz, $CDCl_3$): 1.36 (6H, d), 1.52-1.84 (3H, m), 1.96-2.04 (2H, m), 2.15-2.22 (2H, m), 2.23-2.3 (1H, m), 2.35 (3H, s), 3.08 (1H, t), 3.96-4.12 (2H, m), 4.55 (1H, p), 5.20 (2H, s), 6.85 (2H, d), 6.94-7 (2H, m), 7.04 (1H, d), 7.06 (1H, d), 7.18-7.25 (3H, m), 7.32 (1H, d), 7.35 (1H, d). | 504 |
| A9 | 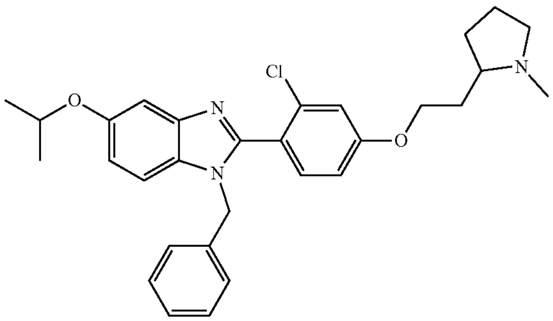 Isomer 2 | 1-benzyl-2-(2-chloro-4-(2-(1-methylpyrrolidin-2-yl)ethoxy)phenyl)-5-isopropoxy-1H-benzo[d]imidazole (Isomer 2) | (500 MHz, $CDCl_3$): 1.36 (6H, d), 1.52-1.65 (1H, m), 1.71-1.83 (3H, m), 1.98-2.04 (1H, m), 2.14-2.21 (2H, m), 2.22-2.29 (1H, m), 2.34 (3H, s), 3-3.13 (1H, m), 3.98-4.12 (2H, m), 4.55 (1H, p), 5.20 (2H, s), 6.85 (2H, d), 6.94-7 (2H, m), 7.04 (1H, d), 7.06 (1H, d), 7.19-7.25 (3H, m), 7.31 (1H, d), 7.35 (1H, d). | 504 |
| A10 | 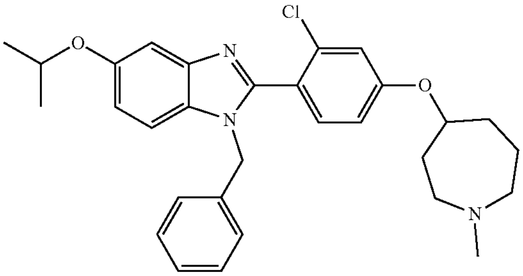 Isomer 1 | 1-benzyl-2-(2-chloro-4-((1-methylazepan-4-yl)oxy)phenyl)-5-isopropoxy-1H-benzo[d]imidazole (Isomer 1) | (500 MHz, $CDCl_3$): 1.36 (6H, d), 1.6-1.7 (1H, m), 1.82-1.93 (2H, m), 1.95-2.03 (1H, m), 2.07-2.25 (2H, m), 2.37 (3H, s), 2.49-2.66 (3H, m), 2.71 (1H, ddd), 4.51-4.65 (2H, m), 5.21 (2H, s), 6.81 (1H, dd), 6.84 (1H, dd), 6.95-6.99 (2H, m), 7.00 (1H, d), 7.05 (1H, d), 7.19-7.25 (3H, m), 7.32 (1H, d), 7.34 (1H, d). | 504 |
| A11 | 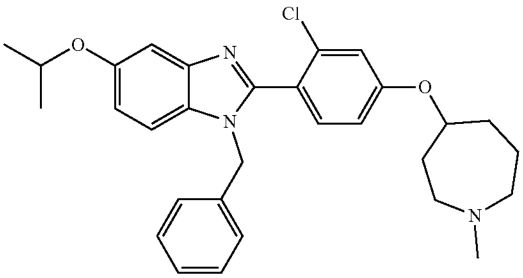 Isomer 2 | 1-benzyl-2-(2-chloro-4-((1-methylazepan-4-yl)oxy)phenyl)-5-isopropoxy-1H-benzo[d]imidazole (Isomer 2) | (500 MHz, $CDCl_3$): 1.36 (6H, d), 1.63-1.69 (1H, m), 1.82-1.93 (2H, m), 1.95-2.03 (1H, m), 2.08-2.24 (2H, m), 2.37 (3H, s), 2.5-2.66 (3H, m), 2.71 (1H, ddd), 4.51-4.62 (2H, m), 5.20 (2H, s), 6.80 (1H, dd), 6.84 (1H, dd), 6.96-6.99 (2H, m), 7.00 (1H, d), 7.05 (1H, d), 7.2-7.25 (3H, m), 7.31 (1H, d), 7.34 (1H, d). | 504 |

TABLE A-continued

| Ex # | Structure | Name | $^1$H NMR | LCMS [M + H]+ |
| --- | --- | --- | --- | --- |
| A12 | 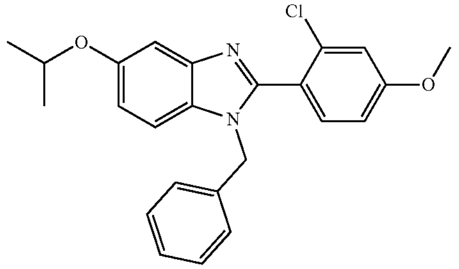 [SMILES: COc1ccc(-c2nc3cc(OC(C)C)ccc3n2Cc2ccccc2)c(Cl)c1] | 1-benzyl-2-(2-chloro-4-methoxyphenyl)-5-isopropoxy-1H-benzo[d]imidazole | (300 MHz, DMSO-$d_6$): 1.28 (6H, d), 3.86 (3H, s), 4.61 (1H, hept), 5.26 (2H, s), 6.84 (1H, dd), 6.97 (2H, dd), 7.06 (1H, dd), 7.15-7.26 (5H, m), 7.32 (1H, d), 7.50 (1H, d). | 407 |

[A1] & [A2] synthesized as described in Example 3, Intermediates

[A3] 3-(4-(1-benzyl-5-isopropoxy-1H-benzo[d]imidazol-2-yl)-3-chlorophenoxy)propan-1-amine (Example 3) was acylated using acetyl chloride and DIEA in DCM.

[A4] 3-(4-(1-benzyl-5-isopropoxy-1H-benzo[d]imidazol-2-yl)-3-chlorophenoxy)propan-1-amine (Example 3) was acylated using heptanoyl chloride and DIEA in DCM.

[A5] made from a similar procedure as 2-(2-chloro-4-(2-(4-methylpiperazin-1-yl)ethoxy)phenyl)-1-(3-chlorobenzyl)-5-methoxy-1H-benzo[d]imidazole (Example 2, intermediate), using N-(4-chlorobenzyl)-4-isopropoxy-2-nitroaniline and 4-methyl-6-(2-(4-methylpiperazin-1-yl)ethoxy)nicotinaldehyde as starting materials. 4-Methyl-6-(2-(4-methylpiperazin-1-yl)ethoxy)nicotinaldehyde was synthesised as follows:

Rockphos G3-Pd (113 mg, 0.12 mmol) was added slowly to 6-bromo-4-methylnicotinaldehyde (500 mg, 2.50 mmol), 2-(4-methylpiperazin-1-yl)ethan-1-ol (433 mg, 3.00 mmol) and $Cs_2CO_3$ (1629 mg, 5.00 mmol) in 1,4-dioxane (20 mL) at 20° C. under nitrogen. The resulting mixture was stirred at 100° C. for 18 hours. The reaction mixture was filtered through celite. The filtrate was concentrated under reduced pressure. The crude product was purified by flash C18-flash chromatography, elution gradient 5 to 80% MeCN in water (0.05% $NH_4HCO_3$). Pure fractions were evaporated to dryness to afford 4-methyl-6-(2-(4-methylpiperazin-1-yl)ethoxy)nicotinaldehyde (160 mg, 24%) as a yellow gum. $^1$H NMR (300 MHz, $CDCl_3$): 2.33 (3H, s), 2.49-2.67 (11H, m), 2.81 (2H, t), 4.53 (2H, t), 6.61 (1H, s), 8.48 (1H, s), 10.05 (1H, s). One proton not observed. m/z: ES+ [M+H]+ 264.

N-(4-chlorobenzyl)-4-isopropoxy-2-nitroaniline was made from a similar procedure to N4-benzyl-6-chloropyrimidine-4,5-diamine (Example 1, intermediate) using 1-fluoro-4-isopropoxy-2-nitrobenzene and (4-chlorophenyl)methanamine. $^1$H NMR (300 MHz, $CDCl_3$): 1.34 (6H, d), 4.47 (1H, q), 4.54 (2H, s), 6.71 (1H, d), 7.08 (1H, dd), 7.34 (3H, t), 7.70 (1H, d), 8.31 (1H, s). One proton not observable. m/z: ES+ [M+H]+ 321.

1-Fluoro-4-isopropoxy-2-nitrobenzene was synthesised as follows:

DIAD (16.1 mL, 82.7 mmol) was added slowly to propan-2-ol (4.97 g, 82.7 mmol), 4-fluoro-3-nitrophenol (10 g, 63.6 mmol) and $Ph_3P$ (25.04 g, 95.5 mmol) in THF (200 mL) at 0° C. under nitrogen. The resulting solution was stirred at rt for 18 hours. The solvent was removed under reduced pressure. The reaction mixture was diluted with EtOAc and petroleum ether (1:20, 100 mL). The solid was filtered out and the organic layer washed sequentially with saturated $NH_4Cl$ (25 mL), saturated $NaHCO_3$ (25 mL) and saturated brine (2×25 mL). The organic layer was dried over $Na_2SO_4$, filtered and evaporated to afford crude product. The residue was purified by silica chromatography 0 to 20% EtOAc in petroleum ether to afford 1-fluoro-4-isopropoxy-2-nitrobenzene (10.00 g, 79%) as a yellow oil. $^1$H NMR (400 MHz, DMSO-$d_6$): 1.27 (6H, d), 4.62-4.76 (1H, m), 7.31-7.39 (1H, m), 7.49 (1H, ddd), 7.57 (1H, dt).

[A6] made from a similar procedure as Example A5, using N-(2-chloro-6-fluoro-3-methylbenzyl)-4-isopropoxy-2-nitroaniline and 2-chloro-4-(2-(4-methylpiperazin-1-yl)ethoxy)benzaldehyde as starting materials.

2-Chloro-4-(2-(4-methylpiperazin-1-yl)ethoxy)benzaldehyde was made following a procedure previous described in Example 4.

N-(2-chloro-6-fluoro-3-methylbenzyl)-4-isopropoxy-2-nitroaniline was made using a similar procedure route as N-(4-chlorobenzyl)-4-isopropoxy-2-nitroaniline in Example A5; using 1-fluoro-4-isopropoxy-2-nitrobenzene and (2-chloro-6-fluoro-3-methylphenyl)methanamine as starting materials. $^1$H NMR (500 MHz, $CDCl_3$): 1.31 (6H, d), 2.36 (3H, s), 4.44 (1H, p), 4.65 (2H, dd), 6.94 (1H, t), 7.06 (1H, d), 7.11-7.21 (2H, m), 7.64 (1H, d), 8.27 (1H, t). m/z: ES+ [M+H]+ 353.

[A7] made from a similar procedure as Example A5, using N-(3-chlorobenzyl)-4-isopropoxy-2-nitroaniline and 4-methyl-6-(2-(4-methylpiperazin-1-yl)ethoxy)nicotinaldehyde as starting materials.

N-(3-chlorobenzyl)-4-isopropoxy-2-nitroaniline was made using a similar procedure route as N-(4-chlorobenzyl)-4-isopropoxy-2-nitroaniline in Example A5; using (3-chlorophenyl)methanamine and 1-fluoro-4-isopropoxy-2-nitrobenzene as starting materials. $^1$H NMR (300 MHz, DMSO-$d_6$): 1.20 (6H, d), 4.47 (1H, hept), 4.60 (2H, d), 6.83 (1H, d), 7.15-7.19 (1H, m), 7.37 (5H, m), 8.53 (1H, t). m/z: ES+ [M+H]+ 321.

[A8] made from a similar procedure as 3-(4-(1-benzyl-5-isopropoxy-1H-benzo[d]imidazol-2-yl)-3-chlorophenoxy)propan-1-amine (Example 3), using as starting materials benzyl-5-isopropoxy-1H-benzo[d]imidazol-2-yl)-3-chlorophenol and (rac)-2-(1-methylpyrrolidin-2-yl)ethan-1-ol, except that the deprotection step with TFA was omitted, to give a crude mixture containing (rac)-1-benzyl-2-(2-chloro-4-(2-(1-methylpyrrolidin-2-yl)ethoxy)phenyl)-5-isopropoxy-1H-benzo[d]imidazole and (rac)-1-benzyl-2-(2-chloro-4-((1-methylazepan-4-yl)oxy)phenyl)-5-isopropoxy-1H-benzo[d]imidazole. Examples A10 and A11 were obtained from purification of this crude mixture by chiral SFC (YMC SJ column, 20*250 mm, 5 micron) eluting with 10% MeOH (containing 0.1% $NH_3$) and 90% $scCO_2$ (60 mL/min, 120 bar, 40° C.) after evaporation of the solvents from pure fractions, to afford 1-benzyl-2-(2-chloro-4-((1-methylazepan-4-yl)oxy)phenyl)-5-isopropoxy-1H-benzo[d]imidazole, isomer 2 (Example A11) (6.9 mg, 19%) and 1-benzyl-2-(2-chloro-4-((1-methylazepan-4-yl)oxy)phenyl)-5-isopropoxy-1H-benzo[d]imidazole, isomer 1 (Example A10) (6.2 mg, 17%). Impure fractions containing a mixture of Examples A8 and A9 were further purified by chiral SFC (ChiralPak IC column, 20*250 mm, 5 micron) eluting with 45% MeOH (containing 0.1% $NH_3$) and 70% $scCO_2$ (60 mL/min, 120 bar, 40° C.) and evaporated to dryness to afford 1-benzyl-2-(2-chloro-4-(2-(1-methylpyrrolidin-2-yl)ethoxy)phenyl)-5-isopropoxy-1H-benzo[d]imidazole, isomer 1 (Example A8) (9.4 mg, 26%) and 1-benzyl-2-(2-chloro-4-(2-(1-methylpyrrolidin-2-yl)ethoxy)phenyl)-5-isopropoxy-1H-benzo[d]imidazole, isomer 2 (Example A9) (13.6 mg, 38%).

[A12] made from a similar procedure as 4-(1-benzyl-5-isopropoxy-1H-benzo[d]imidazol-2-yl)-3-chlorophenol, Example A1, using N-benzyl-4-isopropoxy-2-nitroaniline and 2-chloro-4-methoxybenzaldehyde as starting materials.

The following examples in Table B were synthesised as stated in the notes following Table B.

TABLE B

| Ex # | Structure | Name | $^1H$ NMR | LCMS [M + H]+ |
|---|---|---|---|---|
| B1 | 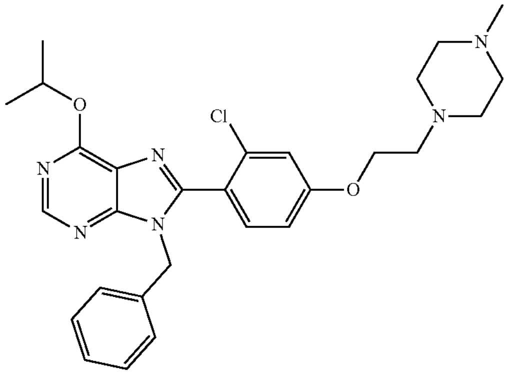 [SMILES: CC(C)Oc1ncnc2c1nc(-c1ccc(OCCN3CCN(C)CC3)cc1Cl)n2Cc1ccccc1] | 9-benzyl-6-isopropoxy-8-(4-(2-(4-methyl-piperazin-1-yl)ethoxy) phenyl)-9H-purine | (400 MHz, DMSO-$d_6$): 1.42 (6H, d), 2.16 (3H, s), 2.35 (8H, m), 2.69 (2H, t), 4.13 (2H, t), 5.56-5.65 (3H, m), 6.97-7.02 (2H, m), 7.03-7.07 (2H, m), 7.21-7.30 (3H, m), 7.64-7.69 (2H, m), 8.50 (1H, s). | 487 |
| B2 | 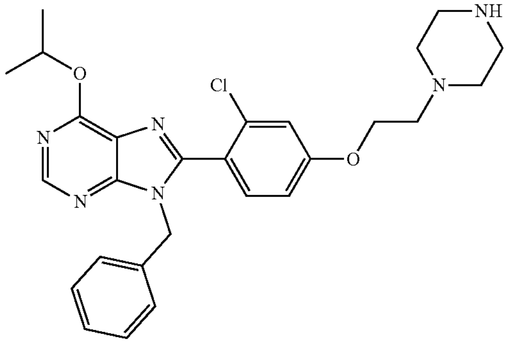 [SMILES: CC(C)Oc1ncnc2c1nc(-c1ccc(OCCN3CCNCC3)cc1Cl)n2Cc1ccccc1] | 9-benzyl-6-isopropoxy-8-(2-methyl-4-(2-(piperazin-1-yl) ethoxy) phenyl)-9H-purine | (500 MHz, $CDCl_3$): 1.49 (6H), d), 1.74 (1H, br s), 1.98 (3H, s), 2.51-2.64 (4H, m), 2.82 (2H, t), 2.88-2.98 (4H, m), 4.15 (2H, t), 5.25 (2H, s), 5.69 (1H, hept), 6.76 (1H, dd), 6.81 (1H, d), 6.94 (2H, dd), 7.12 (1H, d), 7.15-7.24 (3H, m), 8.57 (1H, s). | 487 |
| B3 | 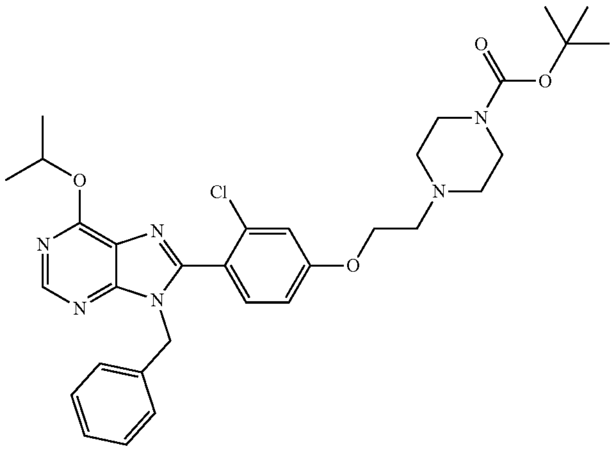 [SMILES: CC(C)Oc1ncnc2c1nc(-c1ccc(OCCN3CCN(C(=O)OC(C)(C)C)CC3)cc1Cl)n2Cc1ccccc1] | tert-butyl 4-(2-(4-(9-benzyl-6-isopropoxy-9H-purin-8-yl)-3-methyl-phenoxy) ethyl) piperazine-1-carboxylate | (300 MHz, $CDCl_3$): 1.46-1.53 (15H, m), 2.00 (3H, s), 2.58 (4H, s), 2.88 (2H, d), 3.50 (4H, s), 4.17 (2H, t), 5.26 (2H, s), 5.70 (1H, p), 6.72-6.85 (2H, m), 6.95 (2H, dd), 7.08-7.24 (4H, m), 8.58 (1H, s). | 587 |

TABLE B-continued

| Ex # | Structure | Name | $^1$H NMR | LCMS [M + H]+ |
|---|---|---|---|---|
| B4 | 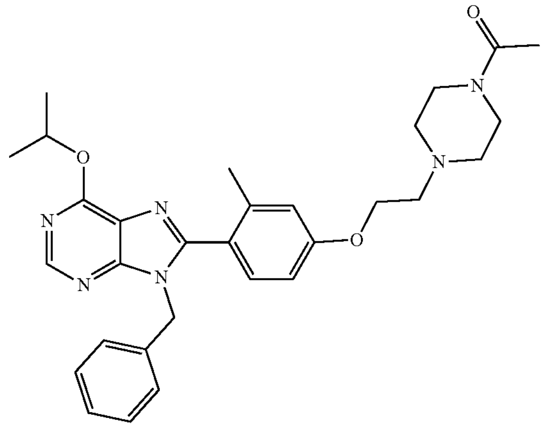 [SMILES: CC(=O)N1CCN(CCOc2ccc(-c3nc4c(OC(C)C)ncnc4n3Cc3ccccc3)c(C)c2)CC1] | 1-(4-(2-(4-(9-benzyl-6-isopropoxy-9H-purin-8-yl)-3-methyl-phenoxy) ethyl) piperazin-1-yl)ethan-1-one | (400 MHz, $CD_3OD$): 1.40-1.52 (6H, m), 1.89 (3H, d), 2.04-2.18 (3H, m), 2.62 (4H, dt), 2.87 (2H, dd), 3.60 (4H, dt), 4.21 (2H, dd), 5.31 (2H, d), 5.70 (1H, ddd), 6.82-6.95 (4H, m), 7.13-7.26 (4H, m), 8.49-8.60 (1H, m). | 529 |
| B5 | 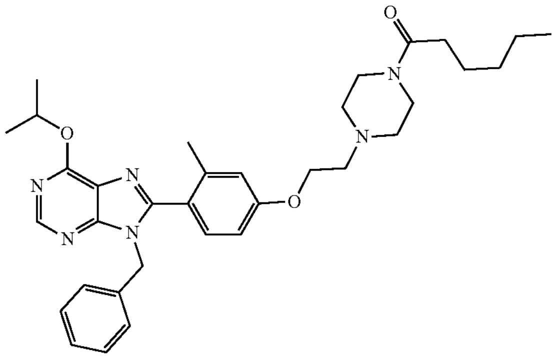 [SMILES: CCCCCC(=O)N1CCN(CCOc2ccc(-c3nc4c(OC(C)C)ncnc4n3Cc3ccccc3)c(C)c2)CC1] | 1-(4-(2-(4-(9-benzyl-6-isopropoxy-9H-purin-8-yl)-3-methyl-phenoxy) ethyl) piperazin-1-yl)hexan-1-one | (300 MHz, $CDCl_3$): 0.84-0.95 (3H, m), 1.33 (4H, dt), 1.49 (6H, d), 1.64 (2H, t), 1.99 (3H, s), 2.25-2.40 (2H, m), 2.59 (4H, s), 2.86 (2H, t), 3.52 (2H, d), 3.68 (2H, s), 4.16 (2H, t), 5.25 (2H, s), 5.70 (1H, h), 6.72-6.83 (2H, m), 6.90-6.98 (2H, m), 7.13 (1H, d), 7.15-7.22 (3H, m), 8.57 (1H, s) | 585 |

[B1] made from a similar procedure as 9-benzyl-6-isopropoxy-8-(2-methyl-4-(2-(4-methylpiperazin-1-yl)ethoxy)phenyl)-9H-purine (Example 1), using 2-(4-methylpiperazin-1-yl)ethan-1-ol and 4-(9-benzyl-6-isopropoxy-9H-purin-8-yl)phenol as starting materials. 4-(9-Benzyl-6-isopropoxy-9H-purin-8-yl)phenol was made using a similar procedure to 4-(9-benzyl-6-isopropoxy-9H-purin-8-yl)-3-methylphenol (Example 1, intermediate) using 4-(9-benzyl-6-chloro-9H-purin-8-yl)phenol as the starting material. $^1$H NMR (400 MHz, DMSO-$d_6$): 1.42 (6H, d), 1.99 (1H, s), 5.56 (2H, s), 6.83-6.88 (2H, m), 6.98-7.02 (2H, m), 7.26 (3H, dddd), 7.54-7.59 (2H, m), 8.48 (1H, s), 10.05 (1H, s). m/z: ES+ [M+H]+ 361.

4-(9-Benzyl-6-chloro-9H-purin-8-yl)phenol was made using a similar procedure to 4-(9-benzyl-6-chloro-9H-purin-8-yl)-3-methylphenol (Example 1, intermediate) using N4-benzyl-6-chloropyrimidine-4,5-diamine and 4-hydroxybenzaldehyde as starting materials. $^1$H NMR (400 MHz, DMSO-$d_6$): 5.64 (2H, s), 6.87-6.92 (2H, m), 7.04-7.07 (2H, m), 7.24-7.31 (3H, m), 7.63-7.67 (2H, m), 8.75 (1H, s), 10.21 (1H, s). m/z: ES+ [M+H]+ 337.

[B2] was made from tert-butyl 4-(2-(4-(9-benzyl-6-isopropoxy-9H-purin-8-yl)-3-methylphenoxy)ethyl)piperazine-1-carboxylate (40 mg, 0.07 mmol) using a similar procedure (BOC deprotection with TFA) as 9-benzyl-8-(2-chloro-4-(2-(piperazin-1-yl)ethoxy)phenyl)-6-((1,1,1-trifluoro-2-methylpropan-2-yl)oxy)-9H-purine (Example 11) to afford 9-benzyl-6-isopropoxy-8-(2-methyl-4-(2-(piperazin-1-yl)ethoxy)phenyl)-9H-purine (18 mg, 53%) as a colourless dry film.

Tert-butyl 4-(2-(4-(9-benzyl-6-isopropoxy-9H-purin-8-yl)-3-methylphenoxy)ethyl)piperazine-1-carboxylate (Example B3) was made using a similar procedure to 4-(1-benzyl-5-isopropoxy-1H-benzo[d]imidazol-2-yl)-3-chlorophenol (Example A1, intermediate in Example 3) using N-benzyl-6-isopropoxy-5-nitropyrimidin-4-amine and tert-butyl 4-(2-(4-formyl-3-methylphenoxy)ethyl)piperazine-1-carboxylate as starting materials.

Tert-butyl 4-(2-(4-formyl-3-methylphenoxy)ethyl)piperazine-1-carboxylate was made as follows:

4-Hydroxy-2-methylbenzaldehyde (2.0 g, 14.7 mmol), tert-butyl 4-(2-chloroethyl)piperazine-1-carboxylate (4.38 g, 17.6 mmol) and potassium carbonate (4.06 g, 29.4 mmol) in MeCN (20 mL) at 25° C. The resulting mixture was stirred at 80° C. for 2 hours. The reaction mixture was diluted with EtOAc (20 mL) and washed sequentially with water (3×20 mL). The organic layer was dried over $Na_2SO_4$, filtered and evaporated to afford crude product. Fractions were evaporated to dryness to afford tert-butyl 4-(2-(4-formyl-3-methylphenoxy)ethyl)piperazine-1-carboxylate (5.00 g, 98%) as a yellow gum. $^1$H NMR (300 MHz, $CDCl_3$): 1.46 (9H, d), 2.60 (4H, d), 2.64 (3H, s), 2.88 (2H, s), 3.43-3.52 (4H, m), 4.21 (2H, s), 6.75 (1H, d), 6.81-6.87 (1H, m), 7.75 (1H, d), 10.12 (1H, s). m/z: ES+ [M+H]+ 349.

N-Benzyl-6-isopropoxy-5-nitropyrimidin-4-amine was made as follows:

Sodium hydride (0.25 g, 6.35 mmol) was added portionwise to propan-2-ol (20 mL, 5.29 mmol) at 0° C. under nitrogen. The resulting solution was stirred at rt for 30 minutes. Then the solution was added dropwise into a solution of N-benzyl-6-chloro-5-nitropyrimidin-4-amine (1.4 g, 5.29 mmol) in propan-2-ol (20 mL, 5.29 mmol) and DMF (5 mL) at rt. The resulting solution was stirred at 60° C. for 18 hours. The reaction mixture was concentrated and diluted with EtOAc (250 mL), and washed sequentially with saturated $NH_4Cl$ (50 mL), saturated $NaHCO_3$ (50 mL), and saturated brine (25 mL×3). The organic layer was dried over $Na_2SO_4$, filtered and evaporated to afford crude product. The crude product was purified by flash silica chromatography, elution gradient 0 to 10% EtOAc in petroleum ether. Pure fractions were evaporated to dryness to afford N-benzyl-6-isopropoxy-5-nitropyrimidin-4-amine (0.750 g, 49.2%) as a yellow oil which solidified on standing. $^1H$ NMR (300 MHz, DMSO-$d_6$): 1.32 (6H, d), 4.71 (2H, d), 5.42 (1H, h), 7.17-7.29 (1H, m), 7.32 (4H, d), 8.28 (1H, s), 8.89 (1H, t). m/z: ES+ [M+H]+ 289.

[B4] 9-benzyl-6-isopropoxy-8-(2-methyl-4-(2-(piperazin-1-yl)ethoxy)phenyl)-9H-purine (Example B2) was acylated using acetyl chloride and DIEA in DCM.

[B5] 9-benzyl-6-isopropoxy-8-(2-methyl-4-(2-(piperazin-1-yl)ethoxy)phenyl)-9H-purine (Example B2) was acylated using heptanoyl chloride and DIEA in DCM.

The following examples in Table C were synthesised using a similar procedure to that described in Example 7, unless stated otherwise in the notes following Table C

TABLE C

| Ex # | Structure | Name | $^1H$ NMR | LCMS [M + H]+ |
|---|---|---|---|---|
| C1 | 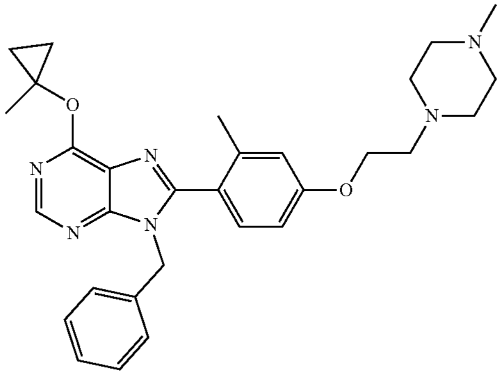 | 9-benzyl-8-(2-methyl-4-(2-(4-methylpiperazin-1-yl)ethoxy)phenyl)-6-(1-methylcyclopropoxy)-9H-purine | (300 MHz, DMSO-$d_6$): 0.79-0.85 (2H, m), 0.97-1.03 (2H, m), 1.71 (3H, s), 1.93 (3H, s), 2.13 (3H, s), 2.30 (4H, s), 2.46 (4H, s), 2.68 (2H, t), 4.10 (2H, t), 5.24 (2H, s), 6.83-6.89 (3H, m), 6.91 (1H, d), 7.17-7.22 (3H, m), 7.25 (1H, d), 8.58 (1H, s) | 513 |
| C2 | 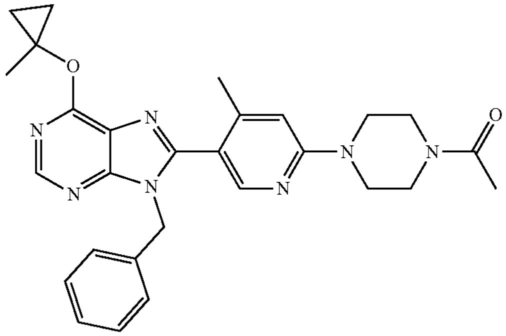 [SMILES: CC(=O)N1CCN(c2cc(C)c(-c3nc4c(OC5(C)CC5)ncnc4n3Cc3ccccc3)cn2)CC1] | 1-(4-(5-(9-benzyl-6-(1-methylcyclopropoxy)-9H-purin-8-yl)-4-methylpyridin-2-yl) piperazin-1-yl)ethan-1-one | (400 MHz, DMSO-$d_6$): 0.82-0.86 (2H, m), 1.00-1.04 (2H, m), 1.73 (3H, s), 1.98 (3H, s), 2.05 (3H, s), 3.50-3.60 (6H, m), 3.60-3.70 (2H, m), 5.33 (2H, s), 6.82 (1H, s), 6.88-6.92 (2H, m), 7.20-7.26 (3H, m), 8.06 (1H, s), 8.59 (1H, s) | 498 |
| C3 | 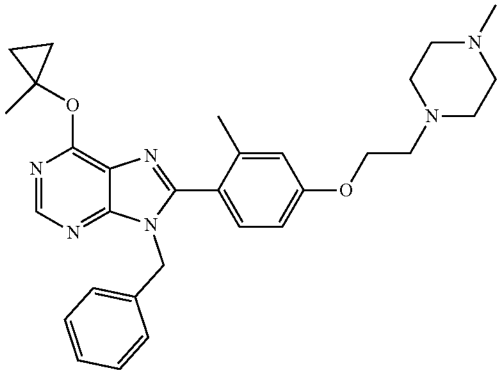 | 9-benzyl-8-(4-methyl-6-(2-(4-methylpiperazin-1-yl) ethoxy)pyridin-3-yl)-6-(1-methylcyclopropoxy)-9H-purine | (300 MHz, DMSO-$d_6$): 0.80-0.86 (2H, m), 0.98-1.03 (2H, m), 1.72 (3H, s), 1.90 (3H, s), 2.13 (3H, s), 2.24-2.36 (4H, m), 2.44 (4H, br s), 2.66 (2H, t), 4.38 (2H, t), 5.31 (2H, s), 6.78 (1H, s), 6.84-6.89 (2H, m), 7.18-7.21 (3H, m), 8.10 (1H, s), 8.61 (1H, s) | 514 |

TABLE C-continued

| Ex # | Structure | Name | $^1$H NMR | LCMS [M + H]+ |
|---|---|---|---|---|
| C4 | 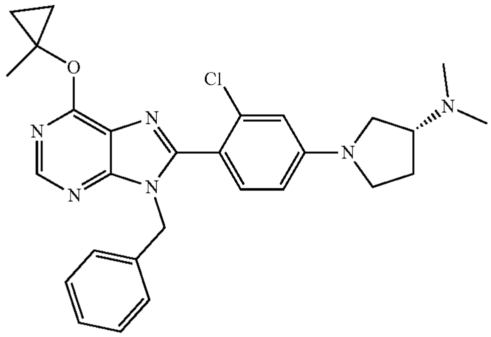 | (R)-1-(4-(9-benzyl-6-(1-methylcyclopropoxy)-9H-purin-8-yl)-3-chlorophenyl)-N,N-dimethylpyrrolidin-3-amine | (300 MHz, DMSO-$d_6$): 0.79-0.85 (2H, m), 0.99 (2H, d), 1.71 (3H, s), 1.83 (1H, q), 2.21 (7H, s), 2.81 (1H, s), 3.08 (1H, t), 3.22-3.29 (1H, m), 3.38-3.55 (2H, m), 5.28 (2H, s), 6.56 (1H, dd), 6.70 (1H, d), 6.87-6.94 (2H, m), 7.16-7.27 (4H, m), 8.55 (1H, s). | 503 |
| C5 | 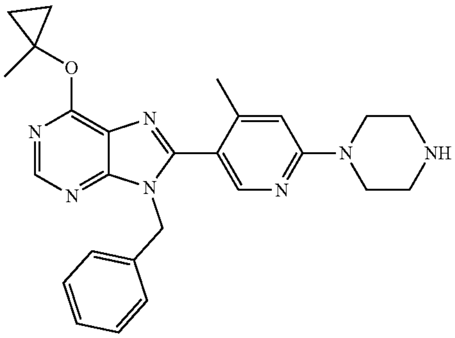 [SMILES: Cc1cc(N2CCNCC2)ncc1-c1nc2c(OC3(C)CC3)ncnc2n1Cc1ccccc1] | 9-benzyl-8-(4-methyl-6-(piperazin-1-yl)pyridin-3-yl)-6-(1-methylcyclopropoxy)-9H-purine | (300 MHz, DMSO-$d_6$): 0.77-0.87 (2H, m), 0.90-1.10 (2H, m), 1.71 (3H, s), 1.95 (3H, s), 2.75 (4H, t), 3.47 (4H, t), 5.31 (2H, s), 6.73 (1H, s), 6.84-6.93 (2H, m), 7.17-7.25 (3H, m), 8.01 (1H, s), 8.56 (1H, s). 1H not observed. | 456 |
| C6 | 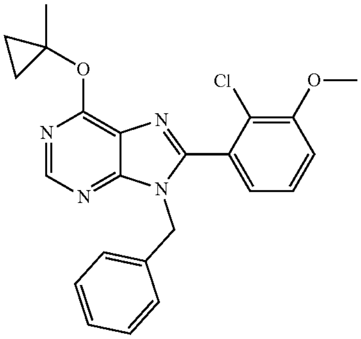 [SMILES: COc1cccc(-c2nc3c(OC4(C)CC4)ncnc3n2Cc2ccccc2)c1Cl] | 9-benzyl-8-(2-chloro-3-methoxyphenyl)-6-(1-methylcyclopropoxy)-9H-purine | (300 MHz, DMSO-$d_6$): 0.83 (2H, t), 1.00 (2H, t), 1.71 (3H, s), 3.91 (3H, s), 5.25 (2H, s), 6.83-6.93 (2H, m), 7.03 (1H, dd), 7.12-7.23 (3H, m), 7.32-7.46 (2H, m), 8.61 (1H, s). | 421 |
| C7 | 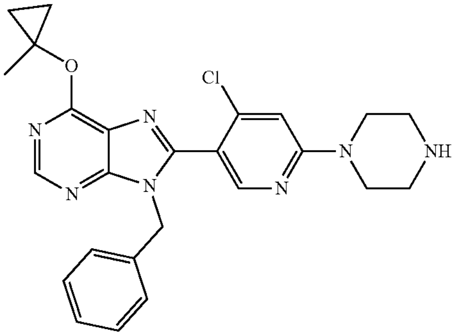 [SMILES: CC1(Oc2ncnc3c2nc(-c2cnc(N4CCNCC4)cc2Cl)n3Cc2ccccc2)CC1] | 9-benzyl-8-(2-chloro-4-(piperazin-1-yl)phenyl)-6-(1-methylcyclopropoxy)-9H-purine | (300 MHz, DMSO-$d_6$): 0.77-0.87 (2H, m), 0.90-1.05 (2H, m), 1.71 (3H, s), 2.80 (4H, t), 3.18 (4H, t), 5.28 (2H, s), 6.85-6.98 (3H, m), 7.06 (1H, d), 7.19 (3H, dd), 7.26 (1H, d), 8.57 (1H, s). 1H not observed. | 475 |

TABLE C-continued

| Ex # | Structure | Name | $^1$H NMR | LCMS [M + H]+ |
|---|---|---|---|---|
| C8 | 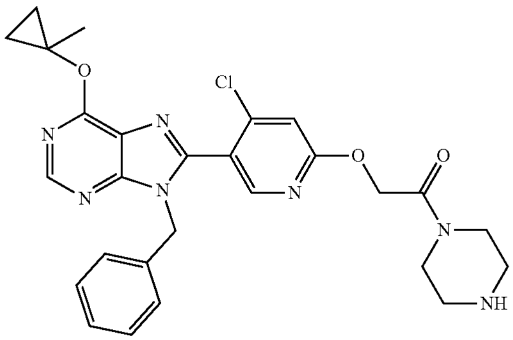 [SMILES: CC1(Oc2ncnc3c2nc(-c2cnc(OCC(=O)N4CCNCC4)cc2Cl)n3Cc2ccccc2)CC1] | 2-(4-(9-benzyl-6-(1-methylcyclopropoxy)-9H-purin-8-yl)-3-chloro-phenoxy)-1-(piperazin-1-yl)ethan-1-one | (400 MHz, DMSO-$d_6$): 0.81-0.89 (2H, m), 0.99-1.06 (2H, m), 1.73 (3H, s), 2.65 (2H, d), 2.71 (2H, s), 3.37 (4H, s), 4.97 (2H, s), 5.28 (2H, s), 6.85-6.93 (2H, m), 7.01 (1H, dd), 7.15-7.28 (4H, m), 7.41 (1H, d), 8.61 (1H, s). 1H not observed. | 533 |
| C9 | 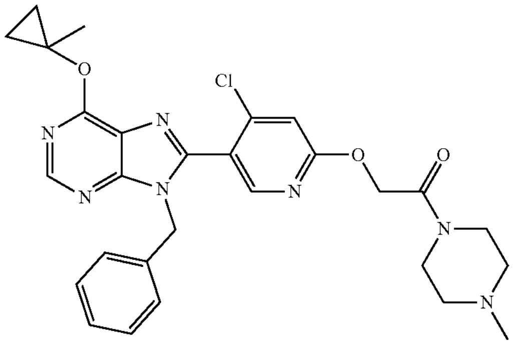 [SMILES: CN1CCN(C(=O)COc2cc(Cl)c(-c3nc4c(OC5(C)CC5)ncnc4n3Cc3ccccc3)cn2)CC1] | 2-(4-(9-benzyl-6-(1-methylcyclopropoxy)-9H-purin-8-yl)-3-chloro-phenoxy)-1-(4-methyl-piperazin-1-yl)ethan-1-one | (400 MHz, DMSO-$d_6$): 0.80-0.88 (2H, m), 0.98-1.06 (2H, m), 1.73 (3H, s), 2.19 (3H, s), 2.27 (2H, t), 2.34 (2H, s), 3.45 (4H, s), 4.99 (2H, s), 5.28 (2H, s), 6.85-6.94 (2H, m), 7.01 (1H, dd), 7.16-7.26 (4H, m), 7.41 (1H, d), 8.61 (1H, s). | 547 |

[C1] made from a similar procedure as 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using 2-methyl-4-(2-(4-methylpiperazin-1-yl)ethoxy)benzaldehyde and N-benzyl-6-(1-methylcyclopropoxy)-5-nitropyrimidin-4-amine (Example 4, intermediate) as starting materials. Product obtained as a white solid (23 mg, 13%).

2-Methyl-4-(2-(4-methylpiperazin-1-yl)ethoxy)benzaldehyde was made by a similar procedure as 9-benzyl-8-(2-chloro-4-((1-methylpiperidin-4-yl)methoxy)phenyl)-6-(1-methylcyclopropoxy)-9H-purine (Example 5), using 4-hydroxy-2-methylbenzaldehyde and 2-(4-methylpiperazin-1-yl)ethan-1-ol as starting materials. Product obtained as a yellow gum, (0.23 g, 30%). $^1$H NMR (300 MHz, DMSO-$d_6$): 2.12 (3H, s), 2.23-2.45 (8H, m), 2.56 (3H, s), 2.67 (2H, t), 4.15 (2H, t), 6.89 (1H, d), 6.94 (1H, dd), 7.75 (1H, d), 10.05 (1H, s). m/z: ES+ [M+H]+ 263.

[C2] made in a similar manner to that described in Example 7 using benzyl-6-(1-methylcyclopropoxy)-5-nitropyrimidin-4-amine (150 mg, 0.50 mmol) and 6-(4-acetylpiperazin-1-yl)-4-methylnicotinaldehyde (247 mg, 1.00 mmol) to afford 1-(4-(5-(9-benzyl-6-(1-methylcyclopropoxy)-9H-purin-8-yl)-4-methylpyridin-2-yl)piperazin-1-yl)ethan-1-one (42 mg, 17%) as a light yellow solid.

6-(4-Acetylpiperazin-1-yl)-4-methylnicotinaldehyde used as starting material was made as follows:

6-(4-Acetylpiperazin-1-yl)-4-methylnicotinaldehyde

6-Chloro-4-methylnicotinaldehyde (0.50 g, 3.21 mmol), 1-(piperazin-1-yl)ethan-1-one (0.824 g, 6.43 mmol) and $K_2CO_3$ (1.33 g, 9.64 mmol) in DMA (5 mL) were stirred under an atmosphere of nitrogen at 100° C. for 3 hours. The reaction mixture was diluted with saturated $NH_4Cl$ (50 mL) and extracted with EtOAc (50 mL×3). The organic layer was washed with brine (50 mL×3), dried over $Na_2SO_4$, filtered and evaporated to afford 6-(4-acetylpiperazin-1-yl)-4-methylnicotinaldehyde (0.45 g, 57%) as a yellow gum. The product was used in the next step directly without further purification. $^1$H NMR (300 MHz, DMSO-$d_6$): 2.03 (3H, s), 2.45 (3H, s), 3.49-3.56 (4H, m), 3.72 (4H, ddd), 6.73 (1H, s), 8.46 (1H, s), 9.84 (1H, s). m/z: ES+ [M+H]+ 248.

[C3] made in a similar manner to that described in Example 7 using N-benzyl-6-(1-methylcyclopropoxy)-5-nitropyrimidin-4-amine (120 mg, 0.40 mmol) and 4-methyl-6-(2-(4-methylpiperazin-1-yl)ethoxy)nicotinaldehyde (210 mg, 0.80 mmol) to afford benzyl-8-(4-methyl-6-(2-(4-methylpiperazin-1-yl)ethoxy)pyridin-3-yl)-6-(1-methylcyclopropoxy)-9H-purine (32 mg, 16%) as a light yellow solid.

[C4] made via a similar method to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using N-benzyl-6-(1-methylcyclopropoxy)-5-nitropyrimidin-4-amine (intermediate in Example 4) and (R)-2-chloro-4-(3-(dimethylamino)pyrrolidin-1-yl)benzaldehyde.

(R)-2-chloro-4-(3-(dimethylamino)pyrrolidin-1-yl)benzaldehyde was obtained as follows: 2-chloro-4-fluorobenzaldehyde (0.3 g, 1.89 mmol), (R)—N,N-dimethylpyrrolidin-3-amine (0.432 g, 3.78 mmol) and $K_2CO_3$ (0.784 g, 5.68 mmol) in DMA (5 mL) were stirred under an atmosphere of nitrogen at 100° C. for 16 hours. The reaction mixture was filtered. The reaction mixture was diluted with saturated $NH_4Cl$ (50 mL) and extracted with EtOAc (3×50 mL). The organic layer was washed with brine (3×50 mL), dried over $Na_2SO_4$, filtered and evaporated to afford a yellow solid. The product was used in the next step directly without further purification. m/z: ES+ [M+H]+ 253

[C5] made in a similar manner to that described in Example 7 using N-benzyl-6-(1-methylcyclopropoxy)-5-nitropyrimidin-4-amine (150 mg, 0.50 mmol) and tert-butyl 4-(5-formyl-4-methylpyridin-2-yl)piperazine-1-carboxylate (305 mg, 1.00 mmol) to afford 9-benzyl-8-(4-methyl-6-(piperazin-1-yl)pyridin-3-yl)-6-(1-methylcyclopropoxy)-9H-purine (31 mg, 14%) as a light yellow solid.

Tert-butyl 4-(5-formyl-4-methylpyridin-2-yl)piperazine-1-carboxylate used as a starting material was made as follows:

Tert-butyl 4-(5-formyl-4-methylpyridin-2-yl)piperazine-1-carboxylate

6-Chloro-4-methylnicotinaldehyde (0.5 g, 3.21 mmol), tert-butyl piperazine-1-carboxylate (1.20 g, 6.43 mmol) and $K_2CO_3$ (1.33 g, 9.64 mmol) in DMA (5 mL) were stirred under an atmosphere of nitrogen at 100° C. for 16 hours. The reaction mixture was diluted with saturated aq. $NH_4Cl$ (50 mL) and extracted with EtOAc (50 mL×3). The organic layer was washed with brine (50 mL×3), dried over $Na_2SO_4$, filtered and evaporated to afford tert-butyl 4-(5-formyl-4-methylpyridin-2-yl)piperazine-1-carboxylate (0.60 g, 61%) as a black gum. The product was used in the next step directly without further purification. $^1H$ NMR (300 MHz, DMSO-$d_6$): 1.43 (9H, s), 1.96 (3H, s), 2.36 (2H, t), 3.30 (2H, t), 3.41-3.44 (2H, m), 3.70-3.73 (2H, m), 6.74 (1H, s), 8.47 (1H, s), 9.85 (1H, s). m/z: ES+ [M+H]+ 306.

[C6] made in a similar manner to that described in Example 7 using N-benzyl-6-(1-methylcyclopropoxy)-5-nitropyrimidin-4-amine (150 mg, 0.50 mmol) and 2-chloro-3-methoxybenzaldehyde (256 mg, 1.50 mmol) to afford 9-benzyl-8-(2-chloro-3-methoxyphenyl)-6-(1-methylcyclopropoxy)-9H-purine (43 mg, 20%) as a light yellow solid.

[C7] was made using a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using N-benzyl-6-(1-methylcyclopropoxy)-5-nitropyrimidin-4-amine (Intermediate in Example 4) and tert-butyl 4-(3-chloro-4-formylphenyl)piperazine-1-carboxylate.

Tert-butyl 4-(3-chloro-4-formylphenyl)piperazine-1-carboxylate was obtained as follows:

2-Chloro-4-fluorobenzaldehyde (0.5 g, 3.15 mmol), tert-butyl piperazine-1-carboxylate (0.587 g, 3.15 mmol) and $K_2CO_3$ (1.31 g, 9.46 mmol) in acetonitrile (10 mL) were stirred under an atmosphere of nitrogen at 100° C. for 16 hours. The solvent was then removed under reduced pressure. The reaction mixture was diluted with saturated $NH_4Cl$ (50 mL) and extracted with EtOAc (3×50 mL). The organic layers were washed with brine (100 mL), dried over $Na_2SO_4$, filtered and evaporated to afford tert-butyl 4-(3-chloro-4-formylphenyl)piperazine-1-carboxylate (0.80 g, 78%) as a yellow gum. The product was used in the next step directly without further purification. m/z: ES+ [M+H]+ 325

[C8] was made using a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using N-benzyl-6-(1-methylcyclopropoxy)-5-nitropyrimidin-4-amine (Intermediate in Example 4) and tert-butyl 4-(2-(3-chloro-4-formylphenoxy)acetyl)piperazine-1-carboxylate.

Tert-butyl 4-(2-(3-chloro-4-formylphenoxy)acetyl)piperazine-1-carboxylate was obtained as follows:

$K_2CO_3$ (0.883 g, 6.39 mmol) was added to tert-butyl 4-(2-chloroacetyl)piperazine-1-carboxylate (1.01 g, 3.83 mmol) and 2-chloro-4-hydroxybenzaldehyde (0.5 g, 3.19 mmol) in DMF (5 mL). The resulting mixture was stirred at 80° C. for 1 hour. The reaction mixture was diluted with saturated brine (50 mL) and extracted with EtOAc (3×50 mL). The organic layers were dried over $Na_2SO_4$, filtered and evaporated to afford crude tert-butyl 4-(2-(3-chloro-4-formylphenoxy)acetyl)piperazine-1-carboxylate (1.2 g, 98%) as a yellow solid. The product was used in the next step directly without further purification. m/z: ES+ [M−tBu]+327

[C9] Sodium triacetoxyborohydride (238.5 mg, 1.13 mmol) was added to 2-(4-(9-benzyl-6-(1-methylcyclopropoxy)-9H-purin-8-yl)-3-chlorophenoxy)-1-(piperazin-1-yl)ethan-1-one (Example C8, 150 mg, 0.28 mmol) in 37% aqueous formaldehyde solution (2 mL). The resulting mixture was stirred at 25° C. for 1 hour. The solvent was removed under reduced pressure. The crude product was purified by flash C18-flash chromatography, elution gradient 5 to 100% MeCN in water (containing 0.1% $NaHCO_3$). Desired fractions were evaporated to dryness and purified further by preparative HPLC, column: XBridge Prep OBD C18 Column, 30*150 mm, 5 μm; using decreasingly polar mixtures of acetonitrile in water (0.1% aq. $NH_3$ and 10 mmol/L $NH_4HCO_3$). Fractions containing the desired compound were evaporated to dryness to afford 2-(4-(9-benzyl-6-(1-methylcyclopropoxy)-9H-purin-8-yl)-3-chlorophenoxy)-1-(4-methylpiperazin-1-yl)ethan-1-one (41 mg, 27%) as a brown solid.

The following examples in Table D were synthesised as described in the notes following Table D.

TABLE D

| Ex # | Structure | Name | $^1H$ NMR | LCMS [M + H]+ |
|---|---|---|---|---|
| D1 | 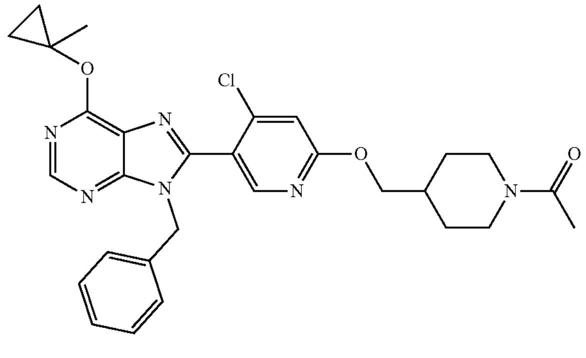 [SMILES: CC(=O)N1CCC(COc2cc(Cl)c(-c3nc4c(OC5(C)CC5)ncnc4n3Cc3ccccc3)cn2)CC1] | 1-(4-((4-(9-benzyl-6-(1-methylcyclopropoxy)-9H-purin-8-yl)-3-chlorophenoxy)methyl)piperidin-1-yl)ethan-1-one | (400 MHz, DMSO-$d_6$): 0.80-0.92 (2H, m), 0.94-1.10 (2H, m), 1.07-1.19 (1H, m), 1.26 (1H, qd), 1.73 (3H, s), 1.79 (2H, td), 1.95-2.05 (4H, m), 2.56 (1H, td), 3.06 (1H, td), 3.85 (1H, d), 3.96 (2H, d), 4.41 (1H, d), 5.29 (2H, s), 6.86-6.95 (2H, m), 7.03 (1H, dd), 7.16-7.26 (4H, m), 7.41 (1H, d), 8.61 (1H, s). | 546 |

TABLE D-continued

| Ex # | Structure | Name | $^1$H NMR | LCMS [M + H]+ |
|---|---|---|---|---|
| D2 | 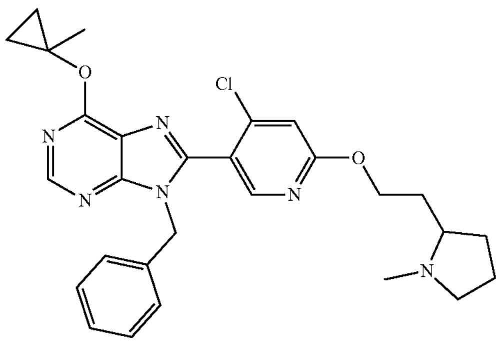 [SMILES: CN1CCCC1CCOc1cc(Cl)c(-c2nc3c(OC4(C)CC4)ncnc3n2Cc2ccccc2)cn1] | 9-benzyl-8-(2-chloro-4-(2-(1-methyl-pyrrolidin-2-yl)ethoxy) phenyl)-6-(1-methylcyclo-propoxy)-9H-purine | (400 MHz, DMSO-$d_6$): 0.80-0.92 (2H, m), 0.94-1.06 (2H, m), 1.49 (1H, dtd), 1.58-1.71 (3H, m), 1.73 (3H, s), 1.86-2.00 (1H, m), 2.01-2.14 (2H, m), 2.20 (1H, dt), 2.24 (3H, s), 2.95 (1H, ddd), 4.12 (2H, t), 5.29 (2H, s), 6.85-6.94 (2H, m), 7.02 (1H, dd), 7.15-7.24 (4H, m), 7.40 (1H, d), 8.16 (1H, s). | 518 |
| D3 | 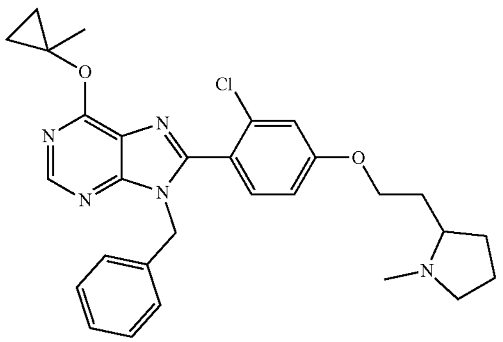 Isomer 2 | 9-benzyl-8-(2-chloro-4-(2-(1-methyl-pyrrolidin-2-yl)ethoxy) phenyl)-6-(1-methylcyclo-propoxy)-9H-purine (Isomer 2) | (500 MHz, DMSO-$d_6$): 0.81-0.86 (2H, m), 1-1.04 (2H, m), 1.45-1.54 (1H, m), 1.59-1.68 (3H, m), 1.73 (3H, s), 1.88-1.96 (1H, m), 2.03-2.1 (2H, m), 2.15-2.21 (1H, m), 2.23 (3H, s), 2.92-2.97 (1H, m), 4.11 (2H, t), 5.29 (2H, s), 6.88-6.91 (2H, m), 7.02 (1H, dd), 7.18-7.23 (4H, m), 7.40 (1H, d), 8.61 (1H, s). | 518 |
| D4 | 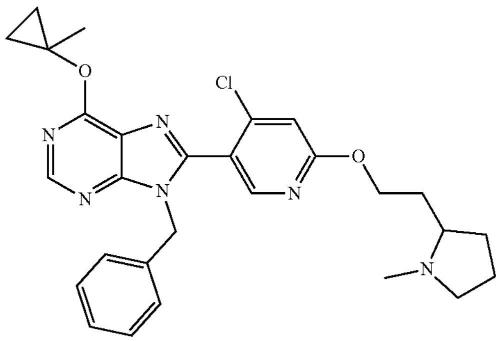 Isomer 1 | 9-benzyl-8-(2-chloro-4-(2-(1-methyl-pyrrolidin-2-yl) ethoxy)phenyl)-6-(1-methyl-cyclopropoxy)-9H-purine (Isomer 1) | (500 MHz, DMSO-$d_6$): 0.81-0.86 (2H, m), 0.99-1.05 (2H, m), 1.44-1.53 (1H, m), 1.59-1.67 (3H, m), 1.72 (3H, s), 1.88-1.97 (1H, m), 2.02-2.10 (2H, m), 2.19 (1H, dq), 2.23 (3H, s), 2.9-2.97 (1H, m), 4.11 (2H, t), 5.28 (2H, s), 6.89 (2H, d), 7.01 (1H, dd), 7.16-7.23 (4H, m), 7.39 (1H, d), 8.61 (1H, s). | 518 |

TABLE D-continued

| Ex # | Structure | Name | $^1$H NMR | LCMS [M + H]+ |
|---|---|---|---|---|
| D5 | 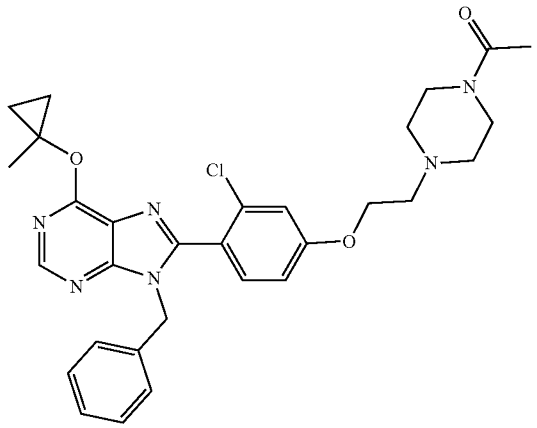 [SMILES: CC(=O)N1CCN(CCOc2ccc(-c3nc4c(OC5(C)CC5)ncnc4n3Cc3ccccc3)c(Cl)c2)CC1] | 1-(4-(2-(4-(9-benzyl-6-(1-methylcyclo-propoxy)-9H-purin-8-yl)-3-chlorophenoxy) ethyl)piperazin-1-yl)ethan-1-one | (400 MHz, DMSO-$d_6$): 0.82-0.87 (2H, t), 1.00-1.05 (2H, t), 1.73 (3H, s), 1.99 (3H, s), 2.44 (2H, t), 2.53 (2H, d), 2.75 (2H, t), 3.43 (4H, q), 4.21 (2H, t), 5.29 (2H, s), 6.88-6.94 (2H, m), 7.05 (1H, dd), 7.18-7.23 (3H, m), 7.27 (1H, d), 7.42 (1H, d), 8.62 (1H, s). | 561 |
| D6 | 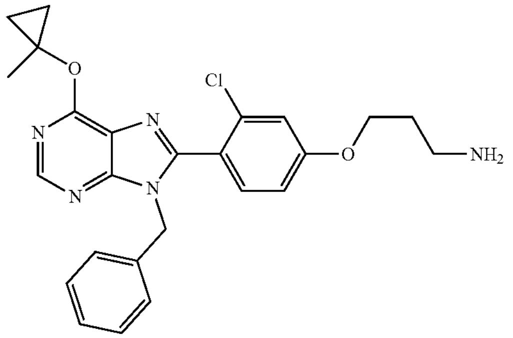 [SMILES: CC1(Oc2ncnc3c2nc(-c2ccc(OCCCN)cc2Cl)n3Cc2ccccc2)CC1] | 3-(4-(9-benzyl-6-(1-methylcyclo-propoxy)-9H-purin-8-yl)-3-chlorophenoxy) propan-1-amine | (300 MHz, DMSO-$d_6$): 0.82-0.87 (2H, t), 1.03 (2H, t), 1.73 (3H, s), 1.81 (2H, m), 1.94 (2H, m), 2.71 (2H, t), 4.14 (2H, t), 5.29 (2H, s), 6.88-6.94 (2H, m), 7.03 (1H, m), 7.21 (4H, m), 7.41 (1H, d), 8.62 (1H, s) | 464 |
| D7 | 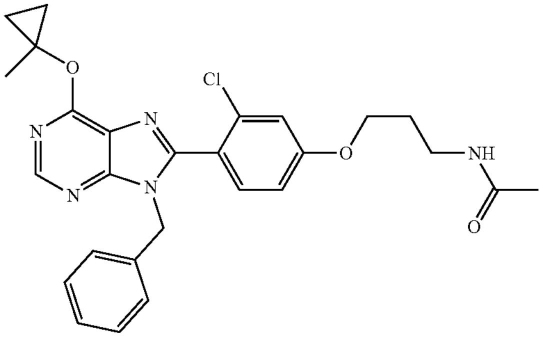 [SMILES: CC(=O)NCCCOc1ccc(-c2nc3c(OC4(C)CC4)ncnc3n2Cc2ccccc2)c(Cl)c1] | N-(3-(4-(9-benzyl-6-(1-methylcyclo-propoxy)-9H-purin-8-yl)-3-chlorophenoxy) propyl)acetamide | (300 MHz, DMSO-$d_6$): 0.80-0.87 (2H, t), 1.02 (2H, t), 1.74 (3H, s), 1.81 (3H, s), 1.87 (2H, m), 3.21 (2H, m), 4.10 (2H, t), 5.30 (2H, s), 6.91 (2H, m), 7.03 (1H, m), 7.21 (4H, m), 7.43 (1H, d), 7.93 (1H, t), 8.62 (1H, s) | 506 |
| D8 | 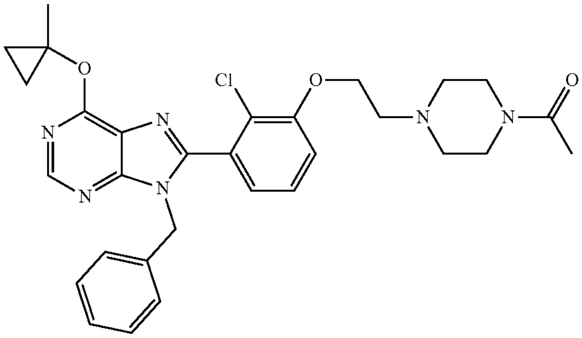 [SMILES: CC(=O)N1CCN(CCOc2cccc(-c3nc4c(OC5(C)CC5)ncnc4n3Cc3ccccc3)c2Cl)CC1] | 1-(4-(2-(3-(9-benzyl-6-(1-methylcyclo-propoxy)-9H-purin-8-yl)-2-chlorophenoxy) ethyl)piperazin-1-yl)ethan-1-one | (300 MHz, DMSO-$d_6$): 0.84 (2H, d), 1.01 (2H, q), 1.71 (3H, s), 1.96 (3H, s), 2.44 (2H, d), 2.53 (2H, d), 2.78 (2H, t), 3.40 (4H, q), 4.25 (2H, t), 5.25 (2H, s), 6.83-6.92 (2H, m), 7.03 (1H, dd), 7.12-7.22 (3H, m), 7.35-7.43 (2H, m), 8.61 (1H, s) | 561 |

TABLE D-continued

| Ex # | Structure | Name | $^1$H NMR | LCMS [M + H]+ |
|---|---|---|---|---|
| D9 | 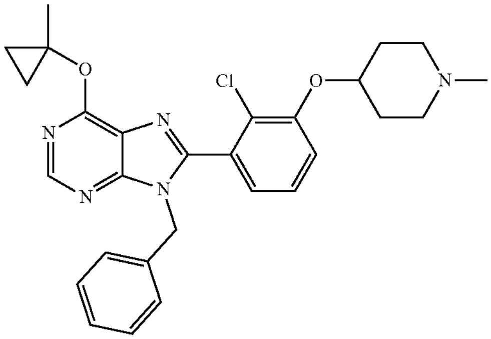 [SMILES: CN1CCC(Oc2cccc(-c3nc4c(OC5(C)CC5)ncnc4n3Cc3ccccc3)c2Cl)CC1] | 9-benzyl-8-(2-chloro-3-((1-methylpiperidin-4-yl)oxy) phenyl)-6-(1-methylcyclo-propoxy)-9H-purine | (300 MHz, DMSO-$d_6$): 0.78-0.87 (2H, m), 1.00 (2H, d), 1.72 (5H, s), 1.91 (2H, s), 2.16 (3H, s), 2.21 (2H, s), 2.59 (2H, s), 4.55 (1H, s), 5.25 (2H, s), 6.86 (2H, dd), 7.02 (1H, dd), 7.17 (3H, dd), 7.32-7.45 (2H, m), 8.61 (1H, s). | 504 |
| D10 | 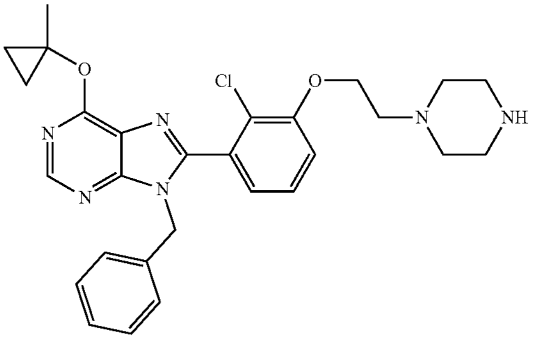 [SMILES: CC1(Oc2ncnc3c2nc(-c2cccc(OCCN4CCNCC4)c2Cl)n3Cc2ccccc2)CC1] | 9-benzyl-8-(2-chloro-3-(2-(piperazin-1-yl)ethoxy) phenyl)-6-(1-methylcyclo-propoxy)-9H-purine | (300 MHz, DMSO-$d_6$): 0.78-0.86 (2H, m), 0.96-1.06 (2H, m), 1.71 (3H, s), 2.41 (4H, s), 2.67 (6H, dd), 4.22 (2H, t), 5.25 (2H, s), 6.84-6.92 (2H, m), 7.02 (1H, dd), 7.14-7.21 (3H, m), 7.38 (2H, d), 8.61 (1H, s). | 519 |
| D11 | 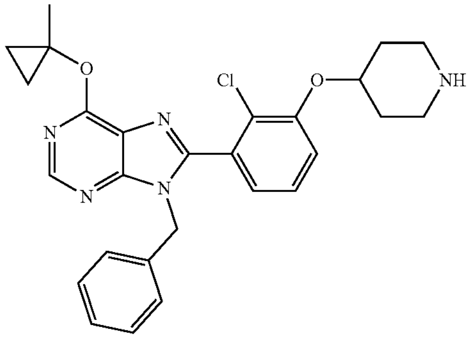 [SMILES: CC1(Oc2ncnc3c2nc(-c2cccc(OC4CCNCC4)c2Cl)n3Cc2ccccc2)CC1] | 9-benzyl-8-(2-chloro-3-(piperidin-4-yloxy)phenyl)-6-(1-methylcyclo-propoxy)-9H-purine | (300 MHz, DMSO-$d_6$): 0.79-0.87 (2H, m), 0.98-1.05 (2H, m), 1.53 (2H, dd), 1.72 (3H, s), 1.88 (2H, s), 2.60 (2H, d), 2.94 (2H, dd), 4.59 (1H, d), 5.26 (2H, s), 6.86 (2H, dd), 7.02 (1H, dd), 7.17 (3H, dd), 7.32-7.46 (2H, m), 8.61 (1H, s). One proton not observed. | 490 |
| D12 | 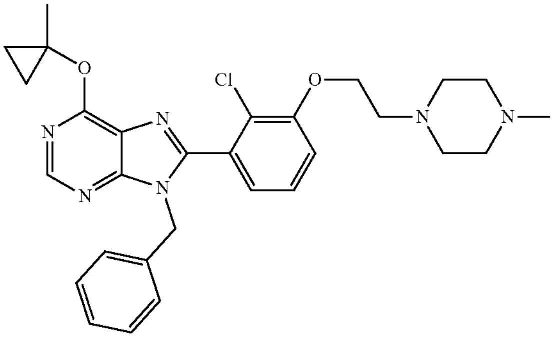 [SMILES: CN1CCN(CCOc2cccc(-c3nc4c(OC5(C)CC5)ncnc4n3Cc3ccccc3)c2Cl)CC1] | 9-benzyl-8-(2-chloro-3-(2-(4-methyl-piperazin-1-yl)ethoxy) phenyl)-6-(1-methylcyclo-propoxy)-9H-purine | (300 MHz, DMSO-$d_6$): 0.78-0.87 (2H, m), 0.97-1.05 (2H, m), 1.71 (3H, s), 2.14 (3H, s), 2.32 (4H, s), 2.52 (4H, d), 2.74 (2H, d), 4.22 (2H, t), 5.25 (2H, s), 6.84-6.91 (2H, m), 7.02 (1H, dd), 7.14-7.21 (3H, m), 7.38 (2H, d), 8.61 (1H, s). | 533 |

TABLE D-continued

| Ex # | Structure | Name | $^1$H NMR | LCMS [M + H]+ |
|---|---|---|---|---|
| D13 | 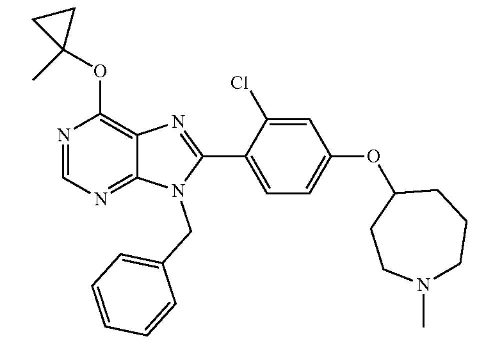 Isomer 1 | 9-benzyl-8-(2-chloro-4-((1-methylazepan-4-yl)oxy)phenyl)-6-(1-methylcyclo-propoxy)-9H-purine (Isomer 1) | (400 MHz, DMSO-$d_6$): 0.81-0.88 (2H, t), 1.02 (2H, t), 1.59 (1H, m), 1.70-1.89 (6H, m), 2.07 (2H, m), 2.26 (3H, s), 2.42-2.49 (2H, m), 2.53-2.65 (2H, m), 4.74 (1H, m), 5.29 (2H, s), 6.90 (2H, m), 6.98 (1H, m), 7.15-7.22 (4H, m), 7.38 (1H, d), 8.62 (1H, s) | 518 |
| D14 | 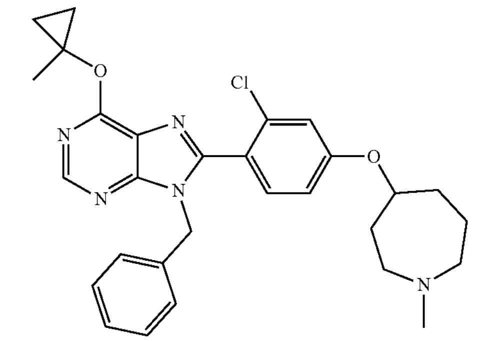 Isomer 2 | 9-benzyl-8-(2-chloro-4-((1-methylazepan-4-yl)oxy)phenyl)-6-(1-methylcyclo-propoxy)-9H-purine (Isomer 2) | (400 MHz, DMSO-$d_6$): 0.81-0.88 (2H, t), 1.02 (2H, t), 1.53-1.64 (1H, m), 1.69-1.90 (6H, m), 2.00-2.14 (2H, m), 2.26 (3H, s), 2.45 (2H, m), 2.53-2.65 (2H, m), 4.75 (1H, m), 5.29 (2H, s), 6.87-6.93 (2H, m), 6.98 (1H, m), 7.16-7.22 (4H, m), 7.38 (1H, d), 8.62 (1H, s) | 518 |
| D15 | 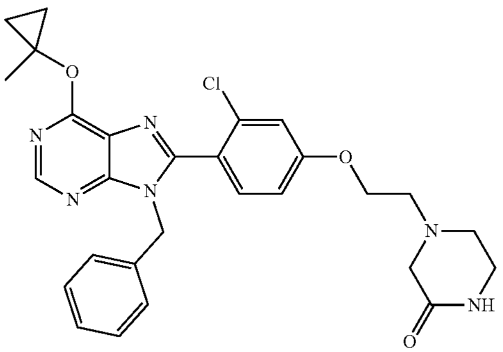 [SMILES: CC1(Oc2ncnc3c2nc(-c2ccc(OCCN4CCNC(=O)C4)cc2Cl)n3Cc2ccccc2)CC1] | 4-(2-(4-(9-benzyl-6-(1-methylcyclo-propoxy)-9H-purin-8-yl)-3-chlorophenoxy) ethyl)piperazin-2-one | (400 MHz, DMSO-$d_6$): 0.78-0.89 (2H, m), 0.97-1.07 (2H, m), 1.73 (3H, s), 2.65-2.73 (2H, m), 2.80 (2H, t), 3.06 (2H, s), 3.11-3.21 (2H, m), 4.22 (2H, t), 5.29 (2H, s), 6.87-6.97 (2H, m), 7.04 (1H, dd), 7.17-7.24 (3H, m), 7.26 (1H, d), 7.41 (1H, d), 7.75 (1H, s), 8.61 (1H, s) | 533 |
| D16 | 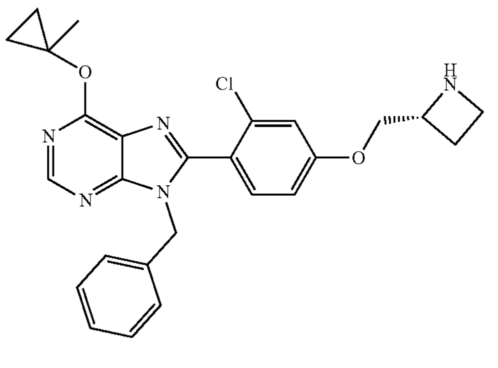 [SMILES: CC1(Oc2ncnc3c2nc(-c2ccc(OC[C@H]4CCN4)cc2Cl)n3Cc2ccccc2)CC1] | (R)-8-(4-(azetidin-2-ylmethoxy)-2-chloro-phenyl)-9-benzyl-6-(1-methylcyclo-propoxy)-9H-purine | (400 MHz, DMSO-$d_6$): 0.78-0.89 (2H, m), 1.01 (2H, d), 1.73 (3H, s), 2.09 (1H, p), 2.21-2.34 (1H, m), 3.19-3.30 (1H, m), 3.51 (1H, q), 3.99-4.16 (3H, m), 5.29 (2H, s), 6.91 (2H, dt), 7.03 (1H, dd), 7.18-7.27 (4H, m), 7.40 (1H, d), 8.61 (1H, s). One proton not observed. | 476 |

TABLE D-continued

| Ex # | Structure | Name | $^1$H NMR | LCMS [M + H]+ |
|---|---|---|---|---|
| D17 | 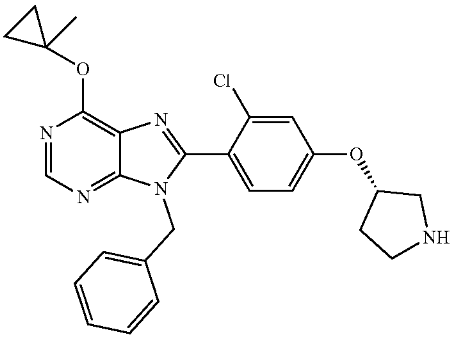 [SMILES: CC1(Oc2ncnc3c2nc(-c2ccc(O[C@H]4CCNC4)cc2Cl)n3Cc2ccccc2)CC1] | (S)-9-benzyl-8-(2-chloro-4-(pyrrolidin-3-yloxy)phenyl)-6-(1-methyl-cyclopropoxy)-9H-purine | (400 MHz, DMSO-$d_6$): 0.81-0.88 (2H, m), 1.01 (2H, d), 1.73 (3H, s), 2.09 (1H, s), 2.20 (1H, s), 3.25 (3H, m), 3.39 (2H, m), 5.22 (1H, m), 5.29 (2H, s), 6.90 (2H, dd), 7.05 (1H, dd), 7.16-7.22 (3H, m), 7.25 (1H, d), 7.45 (1H, d), 8.62 (1H, s). | 476 |
| D18 | 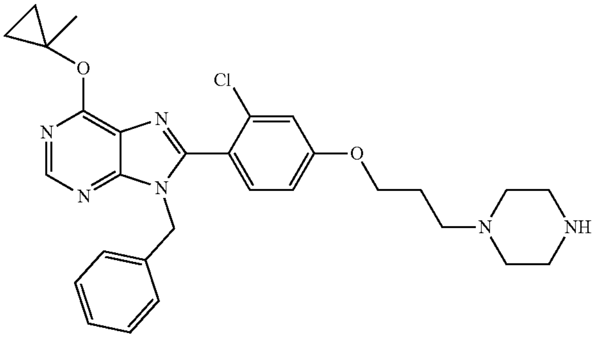 [SMILES: CC1(Oc2ncnc3c2nc(-c2ccc(OCCCN4CCNCC4)cc2Cl)n3Cc2ccccc2)CC1] | 9-benzyl-8-(2-chloro-4-(3-(piperazin-1-yl)propoxy)phenyl)-6-(1-methylcyclo-propoxy)-9H-purine | (400 MHz, DMSO-$d_6$): 0.85 (2H, d), 1.01 (2H, d), 1.73 (3H, s), 1.88 (2H, t), 2.29 (4H, s), 2.38 (2H, t), 2.68 (4H, t), 4.11 (2H, t), 5.29 (2H, s), 6.90 (2H, dd), 7.02 (1H, dd), 7.15-7.25 (4H, m), 7.40 (1H, d), 8.61 (1H, s). One proton not observed. | 533 |
| D19 | 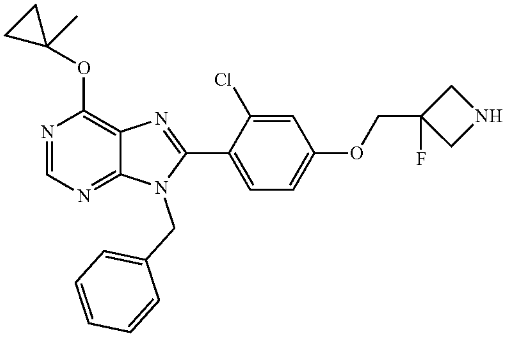 [SMILES: CC1(Oc2ncnc3c2nc(-c2ccc(OCC4(F)CNC4)cc2Cl)n3Cc2ccccc2)CC1] | 9-benzyl-8-(2-chloro-4-((3-fluoroazetidin-3-yl)methoxy)phenyl)-6-(1-methylcyclo-propoxy)-9H-purine | (400 MHz, DMSO-$d_6$): 0.77-0.89 (2H, m), 1.02 (2H, d), 1.73 (3H, s), 3.51 (2H, dd), 3.67 (2H, dd), 4.46 (2H, d), 5.30 (2H, s), 6.91 (2H, dd), 7.10 (1H, dd), 7.20 (3H, p), 7.33 (1H, d), 7.44 (1H, d), 8.62 (1H, s). One proton not observed. | 494 |
| D20 | 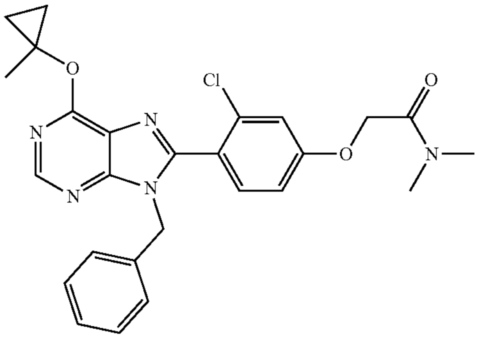 | 2-(4-(9-benzyl-6-(1-methylcyclo-propoxy)-9H-purin-8-yl)-3-chloro-phenoxy)-N,N-dimethyl-acetamide | (400 MHz, DMSO-$d_6$): 0.85 (2H, d), 1.02 (2H, d), 1.73 (3H, s), 2.86 (3H, d), 3.00 (3H, d), 4.98 (2H, s), 5.29 (2H, s), 6.89 (2H, d), 7.01 (1H, dd), 7.15-7.27 (4H, m), 7.41 (1H, dd), 8.61 (1H, d). | 492 |

TABLE D-continued

| Ex # | Structure | Name | $^1H$ NMR | LCMS [M + H]+ |
|---|---|---|---|---|
| D21 | 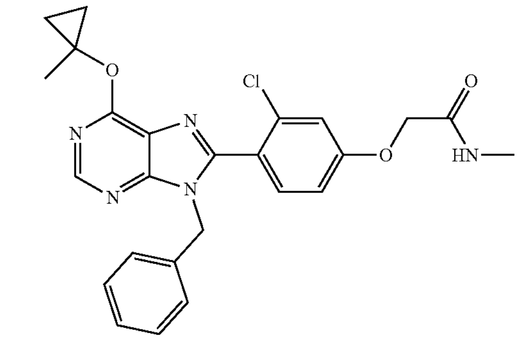 | 2-(4-(9-benzyl-6-(1-methylcyclopropoxy)-9H-purin-8-yl)-3-chlorophenoxy)-N-methylacetamide | (400 MHz, DMSO-$d_6$): 0.85 (2H, d), 1.01 (2H, d), 1.73 (3H, s), 2.68 (3H, d), 4.60 (2H, s), 5.29 (2H, s), 6.90 (2H, dd), 7.06 (1H, dd), 7.15-7.30 (4H, m), 7.45 (1H, d), 8.11 (1H, d), 8.62 (1H, s). | 478 |
| D22 | 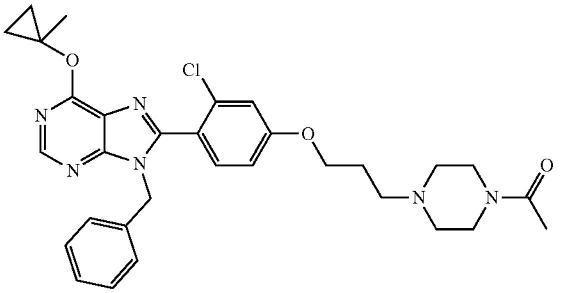 [SMILES: CC(=O)N1CCN(CCCOc2ccc(-c3nc4c(OC5(C)CC5)ncnc4n3Cc3ccccc3)c(Cl)c2)CC1] | 1-(4-(3-(4-(9-benzyl-6-(1-methylcyclopropoxy)-9H-purin-8-yl)-3-chlorophenoxy)propyl)piperazin-1-yl)ethan-1-one | (300 MHz, DMSO-$d_6$): 0.71-0.78 (2H, m), 1.08 (2H, d), 1.72 (3H, d), 1.95 (2H, s), 2.03 (3H, s), 2.45 (6H, d), 3.43 (2H, s), 3.57 (2H, s), 4.02 (2H, t), 5.27 (2H, s), 6.73 (1H, dd), 6.86 (2H, dd), 6.97 (1H, d), 7.00-7.20 (4H, m), 8.59 (1H, s). | 575 |
| D23 | 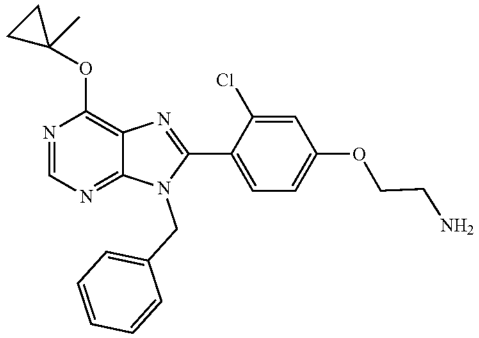 [SMILES: CC1(Oc2ncnc3c2nc(-c2ccc(OCCN)cc2Cl)n3Cc2ccccc2)CC1] | 2-(4-(9-benzyl-6-(1-methylcyclopropoxy)-9H-purin-8-yl)-3-chlorophenoxy)ethan-1-amine | (400 MHz, DMSO-$d_6$): 0.80-0.88 (2H, m), 0.98-1.06 (2H, m), 1.73 (5H, s), 2.89 (2H, t), 4.02 (2H, t), 5.29 (2H, s), 6.87-6.95 (2H, m), 7.04 (1H, dd), 7.16-7.26 (4H, m), 7.41 (1H, d), 8.62 (1H, s). | 450 |
| D24 | 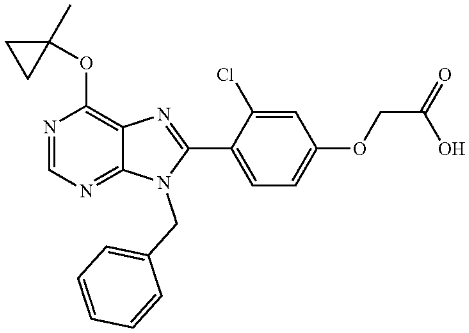 [SMILES: CC1(Oc2ncnc3c2nc(-c2ccc(OCC(=O)O)cc2Cl)n3Cc2ccccc2)CC1] | 2-(4-(9-benzyl-6-(1-methylcyclopropoxy)-9H-purin-8-yl)-3-chlorophenoxy)acetic acid | (400 MHz, DMSO-$d_6$): 0.64-0.9 (2H, m), 0.9-1.09 (2H, m), 1.73 (3H, s), 4.37 (2H, s), 5.28 (2H, s), 6.83-6.94 (3H, m), 7.06 (1H, d), 7.15-7.26 (3H, m), 7.36 (1H, d), 8.60 (1H, s). One proton not observed. | 465 |

TABLE D-continued

| Ex # | Structure | Name | $^1$H NMR | LCMS [M + H]+ |
|---|---|---|---|---|
| D25 | 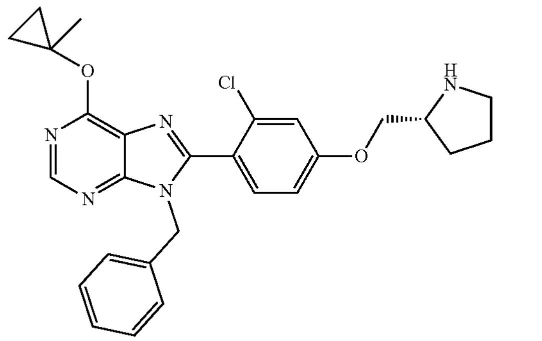 [SMILES: CC1(Oc2ncnc3c2nc(-c2ccc(OC[C@H]4CCCN4)cc2Cl)n3Cc2ccccc2)CC1] | (R)-9-benzyl-8-(2-chloro-4-(pyrrolidin-2-ylmethoxy)phenyl)-6-(1-methylcyclo-propoxy)-9H-purine | (400 MHz, DMSO-$d_6$): 0.78-0.90 (2H, m), 1.01 (2H, d), 1.37-1.51 (1H, m), 1.59-1.76 (5H, m), 1.85 (1H, m), 2.81 (2H, m), 3.41 (1H, m), 3.88-3.93 (2H, m), 5.29 (2H, s), 6.90 (2H, dd), 7.02 (1H, dd), 7.21 (4H, m), 7.40 (1H, d), 8.61 (1H, s). One proton not observed. | 490 |
| D26 | 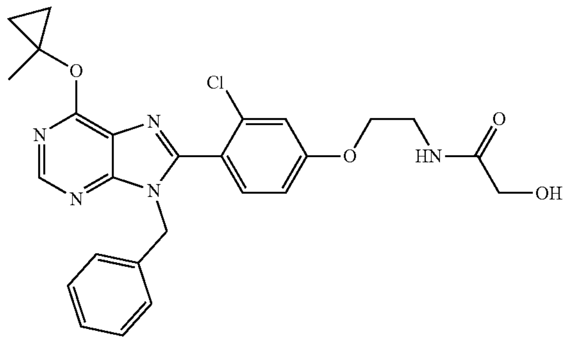 [SMILES: CC1(Oc2ncnc3c2nc(-c2ccc(OCCNC(=O)CO)cc2Cl)n3Cc2ccccc2)CC1] | N-(2-(4-(9-benzyl-6-(1-methylcyclo-propoxy)-9H-purin-8-yl)-3-chlorophenoxy)ethyl)-2-hydroxy-acetamide | (400 MHz, DMSO-$d_6$): 0.78-0.89 (2H, m), 1.01 (2H, d), 1.73 (3H, s), 3.51 (2H, q), 3.83 (2H, d), 4.14 (2H, t), 5.29 (2H, s), 5.55 (1H, t), 6.90 (2H, dd), 7.04 (1H, dd), 7.20 (3H, p), 7.26 (1H, d), 7.42 (1H, d), 7.96 (1H, t), 8.62 (1H, s). | 508 |
| D27 | 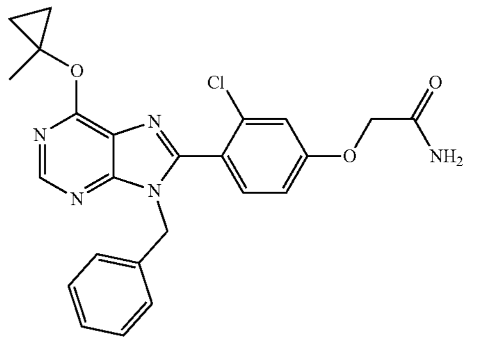 [SMILES: CC1(Oc2ncnc3c2nc(-c2ccc(OCC(N)=O)cc2Cl)n3Cc2ccccc2)CC1] | 2-(4-(9-benzyl-6-(1-methylcyclo-propoxy)-9H-purin-8-yl)-3-chlorophenoxy)acetamide | (400 MHz, DMSO-$d_6$): 0.85 (2H, d), 1.02 (2H, s), 1.73 (3H, s), 4.57 (2H, s), 5.28 (2H, s), 6.86-6.93 (2H, m), 7.05 (1H, dd), 7.16-7.27 (4H, m), 7.41-7.49 (2H, m), 7.63 (1H, s), 8.62 (1H, s). | 464 |
| D28 | 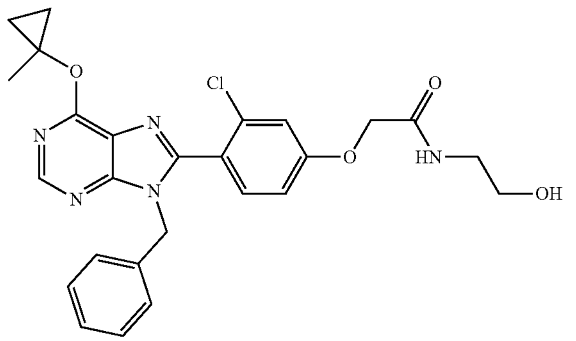 [SMILES: CC1(Oc2ncnc3c2nc(-c2ccc(OCC(=O)NCCO)cc2Cl)n3Cc2ccccc2)CC1] | 2-(4-(9-benzyl-6-(1-methylcyclo-propoxy)-9H-purin-8-yl)-3-chlorophenoxy)-N-(2-hydroxy-ethyl)acetamide | (400 MHz, DMSO-$d_6$): 0.80-0.88 (2H, m), 1.01 (2H, d), 1.73 (3H, s), 3.23 (2H, q), 3.45 (2H, q), 4.62 (2H, s), 4.75 (1H, t), 5.29 (2H, s), 6.90 (2H, dt), 7.06 (1H, dd), 7.21 (3H, dq), 7.27 (1H, d), 7.45 (1H, d), 8.14 (1H, t), 8.62 (1H, s). | 508 |

TABLE D-continued

| Ex # | Structure | Name | $^1$H NMR | LCMS [M + H]+ |
|---|---|---|---|---|
| D29 | 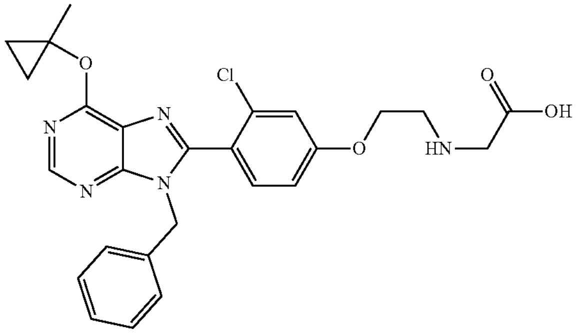 | (2-(4-(9-benzyl-6-(1-methylcyclopropoxy)-9H-purin-8-yl)-3-chlorophenoxy) ethyl)glycine | (400 MHz, DMSO-$d_6$): 0.84 (2H, s), 1.02 (2H, s), 1.73 (3H, s), 3.19 (2H, s), 3.36 (2H, s), 4.27 (2H, t), 5.29 (2H, s), 6.87-6.94 (2H, m), 7.06 (1H, dd), 7.17-7.23 (3H, m), 7.26 (1H, d), 7.45 (1H, d), 8.62 (1H, s). Two protons not observed. | 508 |
| D30 | 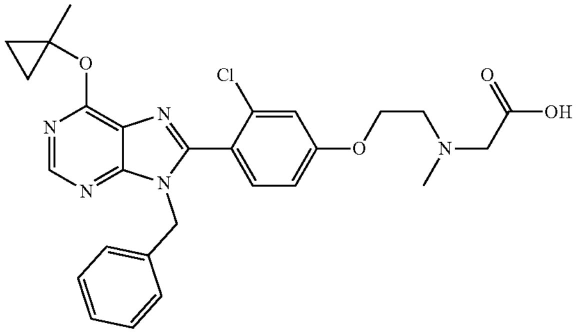 [SMILES: CN(CCOc1ccc(-c2nc3c(OC4(C)CC4)ncnc3n2Cc2ccccc2)c(Cl)c1)CC(=O)O] | N-(2-(4-(9-benzyl-6-(1-methylcyclopropoxy)-9H-purin-8-yl)-3-chlorophenoxy) ethyl)-N-methylglycine | (300 MHz, DMSO-$d_6$): 0.72-0.94 (2H, m), 1-1.13 (2H, m), 1.73 (3H, s), 2.45 (3H, s), 3.00 (2H, t), 3.32 (2H, s), 4.20 (2H, t), 5.29 (2H, s), 6.77-6.98 (2H, m), 6.98-7.13 (1H, m), 7.13-7.3 (4H, m), 7.41 (1H, d), 8.62 (1H, s). One proton not observed. | 522 |
| D31 | 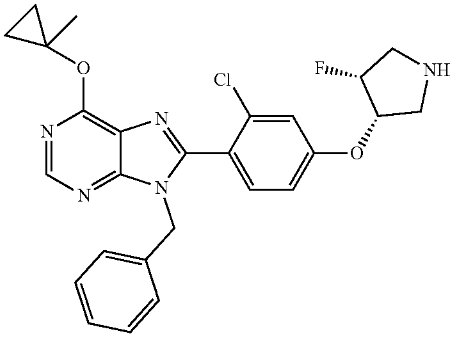 [SMILES: CC1(Oc2ncnc3c2nc(-c2ccc(O[C@H]4CNC[C@H]4F)cc2Cl)n3Cc2ccccc2)CC1] | 9-benzyl-8-(2-chloro-4-(((3S, 4R)-4-fluoro-pyrrolidin-3-yl)oxy)phenyl)-6-(1-methylcyclopropoxy)-9H-purine | (400 MHz, DMSO-$d_6$): 0.78-0.87 (2H, m), 0.99-1.06 (2H, m), 1.73 (3H, s), 2.85 (1H, d), 2.98 (1H, dd), 3.17 (2H, s), 4.88 (1H, m), 5.19-5.38 (3H, m), 6.87-6.93 (2H, m), 7.12 (1H, dd), 7.17-7.23 (3H, m), 7.33 (1H, d), 7.41 (1H, d), 8.62 (1H, s). One proton not observed. | 494 |
| D32 | 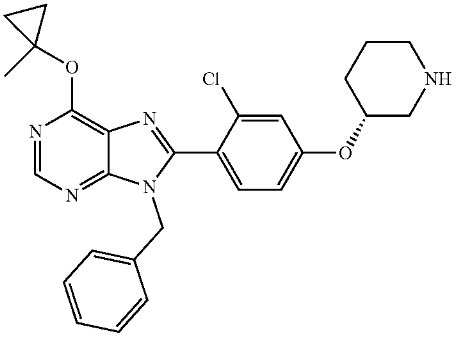 [SMILES: CC1(Oc2ncnc3c2nc(-c2ccc(O[C@@H]4CCCNC4)cc2Cl)n3Cc2ccccc2)CC1] | (R)-9-benzyl-8-(2-chloro-4-(piperidin-3-yloxy)phenyl)-6-(1-methylcyclopropoxy)-9H-purine | (400 MHz, DMSO-$d_6$): 0.84 (2H, t), 1.01 (2H, t), 1.38-1.59 (2H, m), 1.64-1.69 (1H, m), 1.73 (3H, s), 2.02-2.06 (1H, m), 2.43-2.47 (1H, m), 2.50-2.56 (1H, m), 2.68-2.83 (1H, m), 3.06-3.13 (1H, m), 4.26-4.44 (1H, m), 5.29 (2H, s), 6.83-6.95 (2H, m), 7.02-7.04 (1H, m), 7.13-7.26 (4H, m), 7.38 (1H, d), 8.61 (1H, s). One proton not observed. | 490 |

TABLE D-continued

| Ex # | Structure | Name | $^1$H NMR | LCMS [M + H]+ |
|---|---|---|---|---|
| D33 | 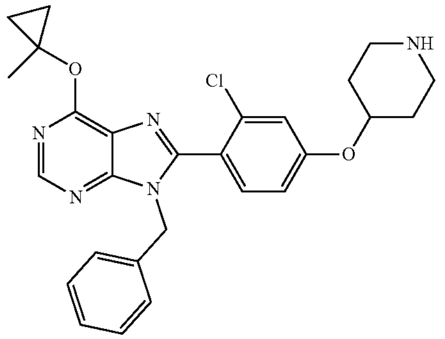 [SMILES: CC1(Oc2ncnc3c2nc(-c2ccc(OC4CCNCC4)cc2Cl)n3Cc2ccccc2)CC1] | 9-benzyl-8-(2-chloro-4-(piperidin-4-yloxy)phenyl)-6-(1-methyl-cyclopropoxy)-9H-purine | (400 MHz, DMSO-$d_6$): 0.80-0.87 (2H, m), 0.97-1.05 (2H, m), 1.38-1.53 (2H, m), 1.73 (3H, s), 1.92-1.96 (2H, m), 2.56-5.62 (2H, m), 2.95 (2H, m), 4.56 (1H, m), 5.29 (2H, s), 6.83-6.92 (2H, m), 7.02-7.05 (1H, m), 7.16-7.26 (4H, m), 7.37 (1H, d), 8.61 (1H, s). One proton not observed. | 490 |
| D34 | 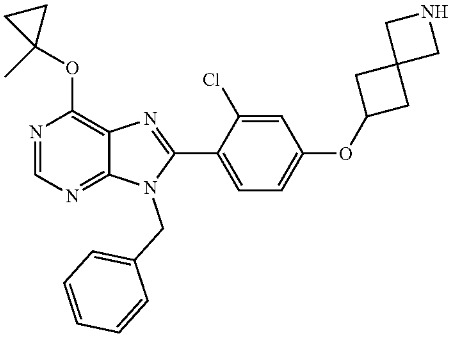 [SMILES: CC1(Oc2ncnc3c2nc(-c2ccc(OC4CC5(CNC5)C4)cc2Cl)n3Cc2ccccc2)CC1] | 8-(4-((2-azaspiro[3.3] heptan-6-yl) oxy)-2-chlorophenyl)-9-benzyl-6-(1-methylcyclo-propoxy)-9H-purine | (400 MHz, DMSO-$d_6$): 0.85 (2H, t), 1.01 (2H, t), 1.73 (3H, s), 2.09-2.22 (2H, m), 2.67-2.76 (2H, m), 3.44-3.56 (3H, m), 3.71-3.9 (2H, m), 4.68-4.74 (1H, m), 5.26 (2H, s), 6.86-6.93 (3H, m), 7.10 (1H, d), 7.16-7.23 (3H, m), 7.38 (1H, d), 8.61 (1H, s). | 502 |
| D35 | 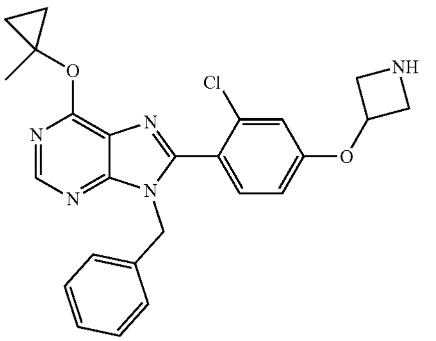 [SMILES: CC1(Oc2ncnc3c2nc(-c2ccc(OC4CNC4)cc2Cl)n3Cc2ccccc2)CC1] | 8-(4-(azetidin-3-yloxy)-2-chlorophenyl)-9-benzyl-6-(1-methylcyclo-propoxy)-9H-purine | (400 MHz, DMSO-$d_6$): 0.84 (2H, t), 1.01 (2H, t), 1.73 (3H, s), 3.52 (2H, t), 3.81 (2H, t), 5.05-5.15 (1H, m), 5.28 (2H, s), 6.75-6.95 (3H, m), 7.07 (1H, d), 7.11-7.26 (3H, m), 7.40 (1H, d), 8.61 (1H, s). | 462 |

[D1] was obtained from 1-(4-(hydroxymethyl)piperidin-1-yl)ethan-1-one and 4-(9-benzyl-6-(1-methylcyclo-propoxy)-9H-purin-8-yl)-3-chlorophenol (Example 5) using a Mitsunobu reaction conducted at rt for 18 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

[D2] was obtained from 2-(1-methylpyrrolidin-2-yl) ethan-1-ol and 4-(9-benzyl-6-(1-methylcyclopropoxy)-9H-purin-8-yl)-3-chlorophenol (Example 5) using a Mitsunobu reaction conducted at rt for 18 hours using a similar procedure used in the synthesis of 9-benzyl-8-(2-chloro-4-((1-methylpiperidin-4-yl)methoxy)phenyl)-6-(1-methylcyclo-propoxy)-9H-purine (Example 5).

[D3] 9-benzyl-8-(2-chloro-4-(2-(1-methylpyrrolidin-2-yl)ethoxy)phenyl)-6-(1-methylcyclopropoxy)-9H-purine (Isomer 2), Example D3 and 9-benzyl-8-(2-chloro-4-(2-(1-methylpyrrolidin-2-yl)ethoxy)phenyl)-6-(1-methylcyclo-propoxy)-9H-purine (Isomer 1), Example D4 were obtained from racemic 9-benzyl-8-(2-chloro-4-(2-(1-methylpyrrolidin-2-yl)ethoxy)phenyl)-6-(1-methylcyclopropoxy)-9H-purine [Example D2] by separation of the two enantiomers by chiral SFC (Phenomenex Lux column iC5, 21.2*250 mm, 5 micron) eluting with 40% MeOH/MeCN (1:1; containing 0.1% $NH_3$) and 60% $scCO_2$ at a flow rate of 60 mL/min, BRP of 120 bar and column temperature of 40° C.; Example D4 eluting first and Example D3 eluting second in the purification

[D5] was obtained from 1-(4-(2-hydroxyethyl)piperazin-1-yl)ethan-1-one and 4-(9-benzyl-6-(1-methylcyclo-propoxy)-9H-purin-8-yl)-3-chlorophenol (see Example 5) using a Mitsunobu reaction conducted at rt for 21 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

[D6] was obtained from tert-butyl (3-hydroxypropyl)carbamate and 4-(9-benzyl-6-(1-methylcyclopropoxy)-9H-purin-8-yl)-3-chlorophenol (see Example 5) using a Mitsunobu reaction conducted at rt for 18 hours using a similar procedure used in the synthesis of 9-benzyl-8-(2-chloro-4-((1- methylpiperidin-4-yl)methoxy)phenyl)-6-(1-methylcyclopropoxy)-9H-purine (Example 5). The BOC group of tert-butyl (3-(4-(9-benzyl-6-(1-methylcyclopropoxy)-9H-purin-8-yl)-3-chlorophenoxy)propyl)carbamate was then removed by reaction of HCl in MeOH.

Tert-butyl (3-(4-(9-benzyl-6-(1-methylcyclopropoxy)-9H-purin-8-yl)-3-chlorophenoxy)propyl)carbamate. m/z: ES+ [M+H]+ 464.

[D7] was obtained from 3-(4-(9-benzyl-6-(1-methylcyclopropoxy)-9H-purin-8-yl)-3-chlorophenoxy)propan-1-amine (Example D6) via an acylation using acetic anhydride and triethylamine.

[D8] was obtained from 1-(4-(2-hydroxyethyl)piperazin-1-yl)ethan-1-one and 3-(9-benzyl-6-(1-methylcyclopropoxy)-9H-purin-8-yl)-2-chlorophenol using a Mitsunobu reaction conducted at rt for 5 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5). 3-(9-Benzyl-6-(1-methylcyclopropoxy)-9H-purin-8-yl)-2-chlorophenol was made from 2-chloro-3-hydroxybenzaldehyde and N-benzyl-6-(1-methylcyclopropoxy)-5-nitropyrimidin-4-amine (Example 4, intermediate) using a similar method previously described in the synthesis of 2-(2-chloro-4-(2-(4-methylpiperazin-1-yl)ethoxy)phenyl)-1-(3-chlorobenzyl)-5-methoxy-1H-benzo[d]imidazole (Example 2, intermediate). $^1$H NMR (300 MHz, $CD_3OD$): 0.71-0.79 (2H, m), 0.96-1.04 (2H, m), 1.69 (3H, s), 5.25 (2H, s), 6.65 (1H, dd), 6.80 (2H, dd), 6.99-7.13 (5H, m), 8.51 (1H, s). One proton not observed. m/z: ES+ [M+H]+ 407.

[D9] was obtained from 1-methylpiperidin-4-ol and 3-(9-benzyl-6-(1-methylcyclopropoxy)-9H-purin-8-yl)-2-chlorophenol (see Example D8, intermediate) using a Mitsunobu reaction conducted at 0° C. for 5 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

[D10] was obtained from tert-butyl 4-(2-hydroxyethyl)piperazine-1-carboxylate and 3-(9-benzyl-6-(1-methylcyclopropoxy)-9H-purin-8-yl)-2-chlorophenol (see Example D8, intermediate) using a Mitsunobu reaction conducted at rt for 16 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5). The BOC group of tert-butyl 4-(2-(3-(9-benzyl-6-(1-methylcyclopropoxy)-9H-purin-8-yl)-2-chlorophenoxy)ethyl)piperazine-1-carboxylate was then removed under HCl in MeOH.

Tert-butyl 4-(2-(3-(9-benzyl-6-(1-methylcyclopropoxy)-9H-purin-8-yl)-2-chlorophenoxy)ethyl)piperazine-1-carboxylate. m/z: ES+ [M+H]+ 619.

[D11] was obtained from tert-butyl 4-hydroxypiperidine-1-carboxylate and 3-(9-benzyl-6-(1-methylcyclopropoxy)-9H-purin-8-yl)-2-chlorophenol (see Example D8, intermediate) using a Mitsunobu reaction conducted at rt for 16 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5). The BOC group of tert-butyl 4-(3-(9-benzyl-6-(1-methylcyclopropoxy)-9H-purin-8-yl)-2-chlorophenoxy)piperidine-1-carboxylate was then removed under HCl in MeOH.

Tert-butyl 4-(3-(9-benzyl-6-(1-methylcyclopropoxy)-9H-purin-8-yl)-2-chlorophenoxy)piperidine-1-carboxylate m/z: ES+ [M+H]+ 590.

[D12] was obtained from 2-(4-methylpiperazin-1-yl)ethan-1-ol and 3-(9-benzyl-6-(1-methylcyclopropoxy)-9H-purin-8-yl)-2-chlorophenol (see Example D8, intermediate) using a Mitsunobu reaction conducted at rt for 3 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

[D13] 9-Benzyl-8-(2-chloro-4-((1-methylazepan-4-yl)oxy)phenyl)-6-(1-methylcyclopropoxy)-9H-purine (Isomer 1), Example D13 and 9-benzyl-8-(2-chloro-4-((1-methylazepan-4-yl)oxy)phenyl)-6-(1-methylcyclopropoxy)-9H-purine (Isomer 2), Example D14 were obtained from the racemic 9-benzyl-8-(2-chloro-4-((1-methylazepan-4-yl)oxy)phenyl)-6-(1-methylcyclopropoxy)-9H-purine, which was prepared using a similar procedure used in the synthesis of 9-benzyl-8-(2-chloro-4-((1-methylpiperidin-4-yl)methoxy)phenyl)-6-(1-methylcyclopropoxy)-9H-purine (Example 5), except the racemate was purified by flash C18-flash chromatography, elution gradient 0 to 100% MeCN in water (0.5% formic acid). The enantiomers were separated by chiral HPLC (CHIRALPAK AD-H column, 2*25 cm, 5 μm eluting with a gradient of EtOH in hexane (containing 0.5% 2M $NH_3$ in MeOH) to afford the first eluting enantiomer [Example D13] and the second eluting enantiomer [Example D14]. The separated enantiomers were further purified by preparative HPLC (XBridge Prep OBD C18 column, 30*150 mm, 5 μm), using decreasingly polar mixtures of water (containing 10 mmol/L $NH_4HCO_3$ and 0.1% aqueous ammonia) and MeCN as eluents.

[D15] was obtained from 2-chloro-4-(2-(3-oxopiperazin-1-yl)ethoxy)benzaldehyde and N4-benzyl-6-(1-methylcyclopropoxy)pyrimidine-4,5-diamine (Example 4, intermediate) by a cyclisation reaction similar to the previously described procedure to form 9-benzyl-8-(2-chloro-4-(2-(4-methylpiperazin-1-yl)ethoxy)phenyl)-6-(1-methylcyclopropoxy)-9H-purine (Example 4). 2-Chloro-4-(2-(3-oxopiperazin-1-yl)ethoxy)benzaldehyde was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purine (Example R3), using piperazin-2-one hydrochloride and 4-(2-bromoethoxy)-2-chlorobenzaldehyde (Example 18, intermediate) as starting material. $^1$H NMR (300 MHz, DMSO-$d_6$): 2.64-2.71 (2H, m), 2.80 (2H, t), 3.05 (2H, s), 3.11-3.19 (2H, m), 4.26 (2H, t), 7.11 (1H, dd), 7.24 (1H, d), 7.75 (1H, s), 7.83 (1H, d), 10.20 (1H, s). m/z: ES+ [M+H]+ 283.

[D16] was obtained from tert-butyl (R)-2-(hydroxymethyl)azetidine-1-carboxylate and 4-(9-benzyl-6-(1-methylcyclopropoxy)-9H-purin-8-yl)-3-chlorophenol (Example 5, intermediate), using a Mitsunobu reaction conducted at rt for 4 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5). The BOC group of tert-butyl (R)-2-((4-(9-benzyl-6-(1-methylcyclopropoxy)-9H-purin-8-yl)-3-chlorophenoxy)methyl)azetidine-1-carboxylate was then removed under HCl in dioxane.

Tert-butyl (R)-2-((4-(9-benzyl-6-(1-methylcyclopropoxy)-9H-purin-8-yl)-3-chlorophenoxy)methyl)azetidine-1-carboxylate. $^1$H NMR (300 MHz, DMSO-$d_6$): 0.79-0.87 (2H, m), 1.01 (2H, d), 1.34 (9H, s), 1.73 (3H, s), 2.15 (1H, q), 2.33 (1H, t), 3.78 (2H, t), 4.18 (1H, dd), 4.32-4.53 (2H, m), 5.29 (2H, s), 6.91 (2H, dd), 7.08 (1H, dd), 7.20 (3H, qd), 7.28 (1H, d), 7.42 (1H, d), 8.62 (1H, s). m/z: ES+ [M+H]+ 576.

[D17] was obtained from tert-butyl (R)-3-hydroxypyrrolidine-1-carboxylate and 4-(9-benzyl-6-(1-methylcyclopropoxy)-9H-purin-8-yl)-3-chlorophenol (Example 5, intermediate), using a Mitsunobu reaction conducted at rt for 1 hour using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

The BOC group of tert-butyl (S)-3-(4-(9-benzyl-6-(1-methylcyclopropoxy)-9H-purin-8-yl)-3-chlorophenoxy)pyrrolidine-1-carboxylate was then removed under HCl in dioxane.

Tert-butyl (S)-3-(4-(9-benzyl-6-(1-methylcyclopropoxy)-9H-purin-8-yl)-3-chlorophenoxy)pyrrolidine-1-carboxylate, $^1$H NMR (300 MHz, DMSO-$d_6$): 0.80-0.87 (m, 2H), 1.01 (d, 2H), 1.41 (d, 9H), 1.73 (s, 3H), 2.13 (d, 2H), 3.35-3.62 (m, 4H), 5.15 (s, 1H), 5.29 (s, 2H), 6.89 (dd, 2H), 7.04 (dd, 1H), 7.15-7.27 (m, 4H), 7.40 (d, 1H), 8.62 (s, 1H). m/z: ES+ [M+H]+ 576.

[D18] was obtained from tert-butyl 4-(3-hydroxypropyl)piperazine-1-carboxylate and 4-(9-benzyl-6-(1-methylcyclopropoxy)-9H-purin-8-yl)-3-chlorophenol (Example 5, intermediate), using a Mitsunobu reaction conducted at rt for 1 hour using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

The BOC group of tert-butyl 4-(3-(4-(9-benzyl-6-(1-methylcyclopropoxy)-9H-purin-8-yl)-3-chlorophenoxy)propyl)piperazine-1-carboxylate was then removed under HCl in dioxane. Tert-butyl 4-(3-(4-(9-benzyl-6-(1-methylcyclopropoxy)-9H-purin-8-yl)-3-chlorophenoxy)propyl)piperazine-1-carboxylate. $^1$H NMR (300 MHz, DMSO-$d_6$): 0.85 (2H, d), 1.01 (2H, d), 1.39 (9H, s), 1.73 (3H, s), 1.90 (2H, dd), 2.33 (4H, t), 2.44 (2H, t), 3.26-3.32 (4H, m), 4.12 (2H, t), 5.29 (2H, s), 6.86-6.95 (2H, m), 7.02 (1H, dd), 7.20 (4H, ddd), 7.40 (1H, d), 8.61 (1H, s). m/z: ES+ [M+H]+ 633.

[D19] was obtained from tert-butyl 3-fluoro-3-(hydroxymethyl)azetidine-1-carboxylate and 4-(9-benzyl-6-(1-methylcyclopropoxy)-9H-purin-8-yl)-3-chlorophenol (Example 5, intermediate), using a Mitsunobu reaction conducted at rt for 4 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

The BOC group of tert-butyl 3-((4-(9-benzyl-6-(1-methylcyclopropoxy)-9H-purin-8-yl)-3-chlorophenoxy)methyl)-3-fluoroazetidine-1-carboxylate was then removed under HCl in dioxane. Tert-butyl 3-((4-(9-benzyl-6-(1-methylcyclopropoxy)-9H-purin-8-yl)-3-chlorophenoxy)methyl)-3-fluoroazetidine-1-carboxylate. $^1$H NMR (300 MHz, DMSO-$d_6$): 0.80-0.88 (2H, m), 1.01 (2H, d), 1.40 (9H, s), 1.73 (3H, s), 3.99 (1H, s), 4.06-4.18 (3H, m), 4.47 (1H, s), 4.55 (1H, s), 5.29 (2H, s), 6.91 (2H, dd), 7.08 (1H, dd), 7.18-7.23 (3H, m), 7.30 (1H, d), 7.45 (1H, d), 8.62 (1H, s). m/z: ES+ [M+H]+ 594.

[D20] was obtained from 2-hydroxy-N-methylacetamide and 4-(9-benzyl-6-(1-methylcyclopropoxy)-9H-purin-8-yl)-3-chlorophenol (Example 5, intermediate), using a Mitsunobu reaction conducted at rt for 1 hour using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

[D21] was obtained from 2-hydroxy-N,N-dimethylacetamide and 4-(9-benzyl-6-(1-methylcyclopropoxy)-9H-purin-8-yl)-3-chlorophenol (Example 5, intermediate), using a Mitsunobu reaction conducted at rt for 1 hour using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

[D22] was obtained from 9-benzyl-8-(2-chloro-4-(3-(piperazin-1-yl)propoxy)phenyl)-6-(1-methylcyclopropoxy)-9H-purine (Example D18) via acylation using acetic anhydride and triethylamine.

[D23] was obtained from tert-butyl (2-hydroxyethyl)carbamate and 4-(9-benzyl-6-(1-methylcyclopropoxy)-9H-purin-8-yl)-3-chlorophenol (Example 5, intermediate), using a Mitsunobu reaction conducted at rt for 3 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

The BOC group of tert-butyl (2-(4-(9-benzyl-6-(1-methylcyclopropoxy)-9H-purin-8-yl)-3-chlorophenoxy)ethyl)carbamate was then removed under HCl in dioxane.

Tert-butyl (2-(4-(9-benzyl-6-(1-methylcyclopropoxy)-9H-purin-8-yl)-3-chlorophenoxy)ethyl)carbamate, $^1$H NMR (300 MHz, DMSO-$d_6$): 0.79-0.86 (2H, m), 1.00 (2H, d), 1.37 (9H, s), 1.71 (3H, s), 3.28 (1H, s), 3.33 (1H, d), 4.03-4.10 (2H, m), 5.27 (2H, s), 6.86-6.93 (2H, m), 7.01 (1H, dd), 7.16-7.22 (4H, m), 7.39 (1H, d), 8.60 (1H, s). One proton not observed. m/z: ES+ [M+H]+ 550.

[D24] obtained from alkylation of 4-(9-benzyl-6-(1-methylcyclopropoxy)-9H-purin-8-yl)-3-chlorophenol (Example 5, intermediate) with ethyl 2-bromoacetate, using similar conditions in the synthesis of 3-(3-chloro-4-formylphenoxy)propanoic acid (Example H11, intermediate). This was followed by ester hydrolysis of ethyl 2-(4-(9-benzyl-6-(1-methylcyclopropoxy)-9H-purin-8-yl)-3-chlorophenoxy)acetate with sodium hydroxide.

Ethyl 2-(4-(9-benzyl-6-(1-methylcyclopropoxy)-9H-purin-8-yl)-3-chlorophenoxy)acetate, 1H NMR (300 MHz, DMSO-$d_6$): 0.85 (2H, d), 1.02 (2H, s), 1.20-1.25 (3H, m), 1.73 (3H, s), 4.16-4.25 (2H, m), 4.95 (2H, s), 5.29 (2H, s), 6.89 (2H, t), 7.05 (1H, dt), 7.17-7.24 (3H, m), 7.27 (1H, t), 7.37-7.49 (1H, m), 8.62 (1H, d). m/z: ES+ [M+H]+ 493.

[D25] was obtained from tert-butyl (R)-2-(hydroxymethyl)pyrrolidine-1-carboxylate and 4-(9-benzyl-6-(1-methylcyclopropoxy)-9H-purin-8-yl)-3-chlorophenol (Example 5, intermediate), using a Mitsunobu reaction conducted at rt for 2 hours using a similar procedure used in the synthesis of 9-benzyl-8-(2-chloro-4-((1-methylpiperidin-4-yl)methoxy)phenyl)-6-(1-methylcyclopropoxy)-9H-purine (Example 5).

The BOC group of tert-butyl (R)-2-((4-(9-benzyl-6-(1-methylcyclopropoxy)-9H-purin-8-yl)-3-chlorophenoxy)methyl)pyrrolidine-1-carboxylate was then removed under HCl in dioxane. Tert-butyl (R)-2-((4-(9-benzyl-6-(1-methylcyclopropoxy)-9H-purin-8-yl)-3-chlorophenoxy)methyl)pyrrolidine-1-carboxylate, $^1$H NMR (300 MHz, DMSO-$d_6$): 0.80-0.87 (2H, m), 1.01 (2H, d), 1.40 (9H, d), 1.76 (6H, d), 1.94 (1H, s), 3.26 (2H, s), 4.13 (1H, t), 4.75-4.80 (2H, m), 5.29 (2H, s), 6.86-6.94 (2H, m), 7.06 (1H, dd), 7.16-7.23 (3H, m), 7.26 (1H, s), 7.41 (1H, d), 8.61 (1H, s). m/z: ES+ [M+H]+ 590.

[D26] was obtained from 2-(4-(9-benzyl-6-(1-methylcyclopropoxy)-9H-purin-8-yl)-3-chlorophenoxy)ethan-1-amine (Example D23) by amide coupling with 2-hydroxyacetic acid as follows:

2-Hydroxyacetic acid (50.7 mg, 0.67 mmol), 1-(3-dimethylaminopropyl)-3-ethylcarbodiimide hydrochloride (63.9 mg, 0.33 mmol), DIEA (194 μL, 1.11 mmol) and HOBt (51.1 mg, 0.33 mmol) in DMF (2 mL) were stirred at rt for 15 minutes. Then 2-(4-(9-benzyl-6-(1-methylcyclopropoxy)-9H-purin-8-yl)-3-chlorophenoxy)ethan-1-amine (100 mg, 0.22 mmol) was added to the mixture. The mixture was stirred at rt for 2 hours. The reaction mixture was diluted with water (25 mL), and extracted with EtOAc (3×20 mL). The organic layer was dried over $Na_2SO_4$, filtered and evaporated. The residue was purified by preparative TLC (DCM:MeOH=10:1, then by preparative chromatography on silica (column: 19*150 mm, 5 μm); eluant: gradient from 5% to 35% EtOH in n-hexane. Fractions containing the desired compound were evaporated to dryness to afford N-(2-(4-(9-benzyl-6-(1-methylcyclopropoxy)-9H-purin-8-yl)-3-chlorophenoxy)ethyl)-2-hydroxyacetamide (19 mg, 17%) as a white solid.

[D27] was obtained from 2-(4-(9-benzyl-6-(1-methylcyclopropoxy)-9H-purin-8-yl)-3-chlorophenoxy)acetic acid (Example D24) by amide coupling with ammonia as follows: 2-(4-(9-Benzyl-6-(1-methylcyclopropoxy)-9H-purin-8-yl)-3-chlorophenoxy)acetic acid (130 mg, 0.28 mmol), HATU (159 mg, 0.42 mmol) and DIEA (0.195 mL, 1.12 mmol) in DMA (3 mL) was stirred at rt for 15 minutes. Then conc. aq. ammonia (1.3 mL, 0.28 mmol) was added to the mixture and stirred at rt for 2 hours. The reaction mixture was concentrated and diluted with water (25 mL), and extracted with EtOAc (3×20 mL). The organic layer was dried over $Na_2SO_4$, filtered and evaporated to afford crude product. The crude product was purified by preparative HPLC (YMC-Actus Triart C18 ExRS column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 2-(4-(9-benzyl-6-(1-methylcyclopropoxy)-9H-purin-8-yl)-3-chlorophenoxy)acetamide (26 mg, 20%) as a white solid.

[D28] was obtained from 2-(4-(9-benzyl-6-(1-methylcyclopropoxy)-9H-purin-8-yl)-3-chlorophenoxy)acetic acid (Example D24) by amide coupling with 2-aminoethan-1-ol following a similar procedure to the synthesis of 2-(4-(9-benzyl-6-(1-methylcyclopropoxy)-9H-purin-8-yl)-3-chlorophenoxy)acetamide (Example D27).

[D29] was obtained from 2-(4-(9-benzyl-6-(1-methylcyclopropoxy)-9H-purin-8-yl)-3-chlorophenoxy)ethan-1-amine (Example D23) as follows:

Sodium hydride (28 mg, 0.70 mmol) was added to 2-(4-(9-benzyl-6-(1-methylcyclopropoxy)-9H-purin-8-yl)-3-chlorophenoxy)ethan-1-amine (210 mg, 0.47 mmol) in DMF (2 mL) at 0° C. The resulting mixture was stirred at rt for 10 minutes. Then ethyl 2-bromoacetate (78 mg, 0.47 mmol) was added to the mixture. The resulting mixture was stirred at rt for 1 hour. Then more sodium hydride (18.7 mg, 0.47 mmol) was added. The mixture was stirred at rt for 10 minutes and then MeI (14.59 μL, 0.23 mmol) was added to the mixture. The resulting mixture was stirred at rt for 1 hour. The reaction mixture was quenched with water (0.1 mL). (2-(4-(9-Benzyl-6-(1-methylcyclopropoxy)-9H-purin-8-yl)-3-chlorophenoxy)ethyl)glycine was isolated as a by-product by purification by preparative HPLC (XSelect CSH Fluoro Phenyl column, 30*150 mm, 5 μm), using decreasingly polar mixtures of water (containing 0.1% formic acid) and MeCN as eluents. Fractions containing the corresponding compound were evaporated to dryness to afford (2-(4-(9-benzyl-6-(1-methylcyclopropoxy)-9H-purin-8-yl)-3-chlorophenoxy)ethyl)glycine (32 mg, 13%) as a pink solid.

[D30] was obtained from the cyclisation of (E)-N-(2-(4-(((4-(benzylamino)-6-(1-methylcyclopropoxy)pyrimidin-5-yl)imino)methyl)-3-chlorophenoxy)ethyl)-N-methylglycine using a similar method to Example 4.

(E)-N-(2-(4-(((4-(Benzylamino)-6-(1-methylcyclopropoxy)pyrimidin-5-yl)imino)methyl)-3-chlorophenoxy)ethyl)-N-methylglycine was made from reaction of N4-benzyl-6-(1-methylcyclopropoxy)pyrimidine-4,5-diamine (Example 4, intermediate) and N-(2-(3-chloro-4-formylphenoxy)ethyl)-N-methylglycine using a similar method to Example 4. m/z: ES+ [M+H]+ 524.

N-(2-(3-Chloro-4-formylphenoxy)ethyl)-N-methylglycine was made from the ester hydrolysis of ethyl N-(2-(3-chloro-4-formylphenoxy)ethyl)-N-methylglycinate under basic LiOH conditions.

$^1H$ NMR (300 MHz, DMSO-$d_6$): 2.44 (3H, s), 3.01 (2H, t), 3.33 (2H, s), 4.24 (2H, t), 7.08 (1H, m), 7.20 (1H, d), 7.83 (1H, d), 8.15 (1H, s), 10.19 (1H, d). m/z: ES+ [M+H]+ 272. Ethyl N-(2-(3-chloro-4-formylphenoxy)ethyl)-N-methylglycinate was made from ethyl 2-bromoacetate and 2-chloro-4-(2-(methylamino) ethoxy)benzaldehyde by N-alkylation as follows: Ethyl 2-bromoacetate (0.504 g, 3.02 mmol) was added in one portion to 2-chloro-4-(2-(methylamino) ethoxy)benzaldehyde (0.43 g, 2.01 mmol) and triethylamine (0.611 g, 6.04 mmol) in THF (20 mL) at 25° C. under air. The resulting solution was stirred at 25° C. for 16 hours. The reaction mixture was diluted with water (200 mL). The aqueous layer was extracted with EtOAc (3×50 mL). The organic layer was dried over $Na_2SO_4$, filtered and evaporated to afford crude product. The crude product was purified by flash silica chromatography, elution gradient 0 to 20% MeOH in DCM. Pure fractions were evaporated to dryness to afford ethyl N-(2-(3-chloro-4-formylphenoxy) ethyl)-N-methylglycinate (0.450 g, 75%) as a pale yellow oil. $^1H$ NMR (300 MHz, DMSO-$d_6$): 1.28 (3H, t), 2.53 (3H, s), 3.04 (2H, t), 3.41 (2H, s), 4.06-4.22 (4H, m), 6.77-7.04 (2H, m), 7.88 (1H, d), 10.33 (1H, t). m/z: ES+ [M+H]+ 300.

2-Chloro-4-(2-(methylamino) ethoxy)benzaldehyde was made by N-alkylation of methanamine with 4-(2-bromoethoxy)-2-chlorobenzaldehyde (Example 18, intermediate) as follows. 4-(2-Bromoethoxy)-2-chlorobenzaldehyde (540 mg, 2.05 mmol) was added in one portion to methanamine (7.97 g, 102.5 mmol) aqueous solution and THF (1 mL) was then added. The resulting solution was stirred at rt for 6 hours. The solvent was removed under reduced pressure to get crude 2-chloro-4-(2-(methylamino) ethoxy)benzaldehyde (0.43 g), which was used directly for next step. m/z: ES+ [M+H]+ 214.

[D31] $K_2CO_3$ (143 mg, 1.03 mmol) was added to 4-(9-benzyl-6-(1-methylcyclopropoxy)-9H-purin-8-yl)-3-chlorophenol (140 mg, 0.34 mmol, Example 5 Intermediate) and tert-butyl (3R,4R)-3-fluoro-4-((methylsulfonyl)oxy)pyrrolidine-1-carboxylate (117 mg, 0.41 mmol) in DMA (4 mL) at rt. The resulting mixture was stirred at 120° C. for 2 days. The reaction mixture was concentrated, diluted with water (25 mL) and extracted with EtOAc (25 mL*3). The combined organic layers were washed with saturated brine (25 mL), dried over $Na_2SO_4$, filtered and evaporated to afford crude tert-butyl (3S,4R)-3-(4-(9-benzyl-6-(1-methylcyclopropoxy)-9H-purin-8-yl)-3-chlorophenoxy)-4-fluoropyrrolidine-1-carboxylate (150 mg, 73%). The product was used in the next step directly without further purification.

m/z: ES+ [M+H]+ 594

HCl in dioxane (0.5 ml, 0.50 mmol) was added to tert-butyl (3S,4R)-3-(4-(9-benzyl-6-(1-methylcyclopropoxy)-9H-purin-8-yl)-3-chlorophenoxy)-4-fluoropyrrolidine-1-carboxylate (130 mg, 0.22 mmol) in EtOAc (1 mL) at rt. The resulting mixture was stirred at RT for 2 hours. The solvent was removed under reduced pressure. The crude product was purified by preparative HPLC Column: XSelect CSH Fluoro Phenyl, 30*150 mm, 5 μm; using decreasingly polar mixtures of acetonitrile in water (0.1% formic acid). Fractions containing the desired compound were evaporated to dryness to afford 9-benzyl-8-(2-chloro-4-(((3S,4R)-4-fluoropyrrolidin-3-yl)oxy)phenyl)-6-(1-methylcyclopropoxy)-9H-purine (13 mg, 12%) as a white solid.

Tert-butyl (3R,4R)-3-fluoro-4-((methylsulfonyl)oxy)pyrrolidine-1-carboxylate was obtained as follows:

Methanesulfonic anhydride (509 mg, 2.92 mmol) was added to tert-butyl (3R,4R)-3-fluoro-4-hydroxypyrrolidine-1-carboxylate (200 mg, 0.97 mmol) in DCM (4 mL) at 0° C. The resulting mixture was stirred at RT for 1 hour. The reaction mixture was evaporated. Water (25 mL) was added. The reaction mixture was extracted sequentially with DCM (20 mL*3). The combined organic layers were washed with saturated brine (20 mL), dried over $Na_2SO_4$, filtered and evaporated to afford crude tert-butyl (3R,4R)-3-fluoro-4-((methylsulfonyl)oxy)pyrrolidine-1-carboxylate (0.150 g, 54%). The product was used in the next step directly without further purification.

[D32] was obtained from tert-butyl (S)-3-hydroxypiperidine-1-carboxylate and 4-(9-benzyl-6-(1-methylcyclopropoxy)-9H-purin-8-yl)-3-chlorophenol (Example 5, intermediate), using a Mitsunobu reaction conducted at 50° C. for 3 hours using a similar procedure used in the synthesis of Example 5, followed by BOC deprotection with HCl in dioxane.

[D33] was obtained from tert-butyl 4-hydroxypiperidine-1-carboxylate and 4-(9-benzyl-6-(1-methylcyclopropoxy)-9H-purin-8-yl)-3-chlorophenol (Example 5, intermediate), using a Mitsunobu reaction conducted at 50° C. for 2 hours using a similar procedure used in the synthesis of Example 5, followed by BOC deprotection with HCl in dioxane.

[D34] was obtained from tert-butyl 6-hydroxy-2-azaspiro[3.3]heptane-2-carboxylate and 4-(9-benzyl-6-(1-methylcyclopropoxy)-9H-purin-8-yl)-3-chlorophenol (Example 5, intermediate), using a Mitsunobu reaction conducted at 50° C. for 2 hours using a similar procedure used in the synthesis of Example 5, followed by BOC deprotection with TFA in DCM.

[D35] was obtained from tert-butyl 3-hydroxyazetidine-1-carboxylate and 4-(9-benzyl-6-(1-methylcyclopropoxy)-9H-purin-8-yl)-3-chlorophenol (Example 5, intermediate), using a Mitsunobu reaction conducted at 70° C. for 6 hours using a similar procedure used in the synthesis of Example 5, followed by BOC deprotection with HCl in dioxane.

The following examples in Table E were synthesised using a similar procedure to 4-(1-benzyl-5-isopropoxy-1H-benzo[d]imidazol-2-yl)-3-chlorophenol (Example 7), unless specified differently in the notes at the end of the Table

TABLE E

| Ex # | Structure | Name | $^1$H NMR | LCMS $[M + H]^+$ |
|---|---|---|---|---|
| | 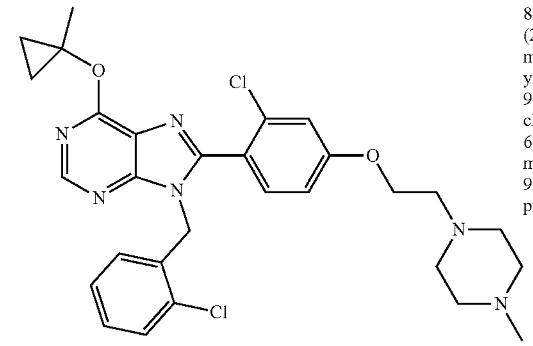 | 8-(2-chloro-4-(2-(4-methylpiperazin-1-yl)ethoxy)phenyl)-9-(2-chlorobenzyl)-6-(1-methylcyclopropoxy)-9H-purine | (300 MHz, DMSO-$d_6$): 0.82 - 0.90 (2H, t), 1.03 (2H, t), 1.74 (3H, s), 2.14 (3H, s), 2.30 (4H, m), 2.50 (4H, m), 2.68 (2H, t), 4.16 (2H, t), 5.40 (2H, s), 6.75 (1H, m), 6.99 (1H, m), 7.14 (1H, m), 7.19 - 7.29 (2H, m), 7.35 - 7.43 (2H, m), 8.61 (1H, s) | 567 |
| E2 | 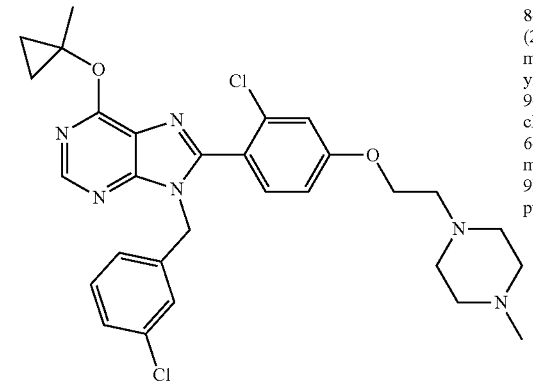 | 8-(2-chloro-4-(2-(4-methylpiperazin-1-yl)ethoxy)phenyl)-9-(3-chlorobenzyl)-6-(1-methylcyclopropoxy)-9H-purine | (300 MHz, DMSO-$d_6$): 0.86 (2H, t), 1.02 (2H, t), 1.74 (3H, s), 2.15 (3H, s), 2.32 (4H, m), 2.42 (4H, m), 2.71 (2H, t), 4.19 (2H, t), 5.30 (2H, s), 6.85 (1H, m), 6.95 (1H, m), 7.05 (1H, m), 7.20 - 7.31 (3H, m), 7.43 (1H, d), 8.64 (1H, s) | 567 |

TABLE E-continued

| Ex # | Structure | Name | $^1$H NMR | LCMS [M + H]$^+$ |
|---|---|---|---|---|
| E3 | 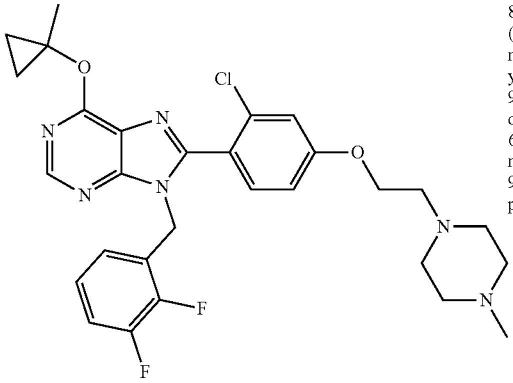 [SMILES: CN1CCN(CCOc2ccc(-c3nc4c(OC5(C)CC5)ncnc4n3Cc3cccc(F)c3F)c(Cl)c2)CC1] | 8-(2-chloro-4-(2-(4-methylpiperazin-1-yl)ethoxy)phenyl)-9-(2,3-difluorobenzyl)-6-(1-methylcyclopropoxy)-9H-purine | (300 MHz, DMSO-$d_6$): 0.86 (2H, t), 0.99 – 1.07 (2H, t), 1.73 (3H, s), 2.15 (3H, s), 2.32 (4H, m), 2.42 (4H, m), 2.71 (2H, t), 4.18 (2H, t), 5.39 (2H, s), 6.74 (1H, m), 7.03 (2H, m), 7.22 (1H, d), 7.30 (1H, m), 7.43 (1H, d), 8.64 (1H, s) | 569 |
| E4 | 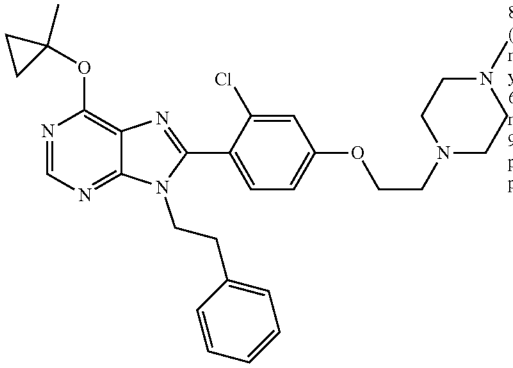 [SMILES: CN1CCN(CCOc2ccc(-c3nc4c(OC5(C)CC5)ncnc4n3CCc3ccccc3)c(Cl)c2)CC1] | 8-(2-chloro-4-(2-(4-methylpiperazin-1-yl)ethoxy)phenyl)-6-(1-methylcyclopropoxy)-9-phenethyl-9H-purine | (400 MHz, DMSO-$d_6$): 0.80 – 0.87 (2H, m), 0.98 – 1.04 (2H, m), 1.73 (3H, s), 2.15 (3H, s), 2.32 (4H, s), 2.54 (4H, s), 2.71 (2H, t), 2.98 (2H, t), 4.19 (2H, t), 4.25 (2H, t), 6.82 (2H, dd), 6.94 – 7.04 (2H, m), 7.16 (3H, dd), 7.26 (1H, d), 8.61 (1H, s) | 547 |
| E5 | 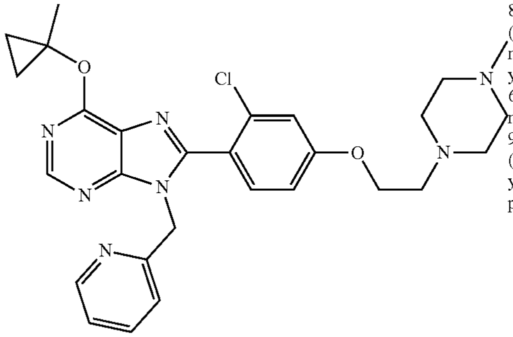 [SMILES: CN1CCN(CCOc2ccc(-c3nc4c(OC5(C)CC5)ncnc4n3Cc3ccccn3)c(Cl)c2)CC1] | 8-(2-chloro-4-(2-(4-methylpiperazin-1-yl)ethoxy)phenyl)-6-(1-methylcyclopropoxy)-9-(pyridin-2-ylmethyl)-9H-purine | (400 MHz, DMSO-$d_6$): 0.75 – 0.88 (2H, m), 0.95 – 1.07 (2H, m), 1.71 (3H, s), 2.11 (3H, s), 2.28 (4H, s), 2.45 (3H, s), 2.51 (1H, t), 2.65 (2H, s),4.12 (2H, t), 5.38 (2H, s), 6.95 (1H, dd), 7.04 (1H, d), 7.15 – 7.22 (2H, m), 7.37 (1H, d), 7.63 (1H, td), 8.31 (1H, dt), 8.54 (1H, s) | 534 |
| E6 | 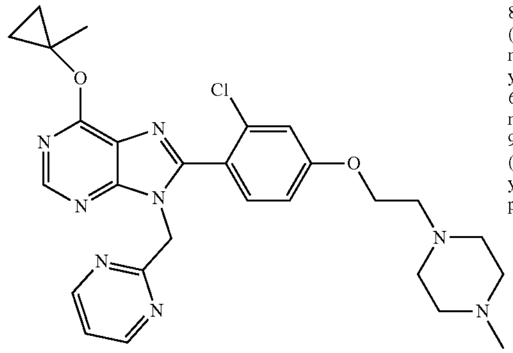 | 8-(2-chloro-4-(2-(4-methylpiperazin-1-yl)ethoxy)phenyl)-6-(1-methylcyclopropoxy)-9-(pyrimidin-2-ylmethyl)-9H-purine | (400 MHz, DMSO-$d_6$): 0.78 – 0.93 (2H, m), 0.96 – 1.12 (2H, m), 1.75 (3H, s), 2.17 (3H, s), 2.28 – 2.41 (4H, m), 2.41 – 2.50 (4H, m), 2.68 (2H, t), 4.14 (2H, t), 5.49 (2H, s), 6.94 (1H, dd), 7.21 (1H, d), 7.33 (1H, d), 7.36 (1H, t), 8.20 (1H, s), 8.55 (1H, s), 8.64 (2H, d). 1H not observed. | 535 |

TABLE E-continued

| Ex # | Structure | Name | $^1$H NMR | LCMS [M + H]$^+$ |
|---|---|---|---|---|
| E7 | 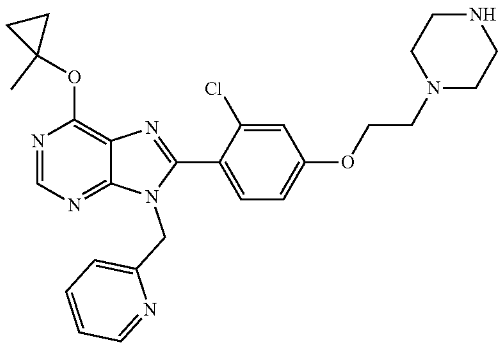 [SMILES: CC1(Oc2ncnc3c2nc(-c2ccc(OCCN4CCNCC4)cc2Cl)n3Cc2ccccn2)CC1] | 8-(2-chloro-4-(2-(piperazin-1-yl)ethoxy)phenyl)-6-(1-methylcyclopropoxy)-9-(pyridin-2-ylmethyl)-9H-purine | (300 MHz, DMSO-$d_6$): 0.79 – 0.89 (2H, m), 1.02 (2H, d), 1.73 (3H, s), 2.42 (4H, s), 2.66 (2H, t), 2.73 (4H, t), 4.14 (2H, t), 5.39 (2H, s), 6.96 (1H, dd), 7.06 (1H, d), 7.17 – 7.23 (2H, m), 7.37 (1H, d), 7.65 (1H, td), 8.31 – 8.35 (1H, m), 8.56 (1H, s). One proton not observed. | 520 |

[E1] was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using N-(2-chlorobenzyl)-6-(1-methylcyclopropoxy)-5-nitropyrimidin-4-amine and 2-chloro-4-(2-(4-methylpiperazin-1-yl)ethoxy)benzaldehyde as starting materials. N-(2-chlorobenzyl)-6-(1-methylcyclopropoxy)-5-nitropyrimidin-4-amine was made following a similar procedure to 6-(1-methylcyclopropoxy)-N-((2-methylthiazol-4-yl)methyl)-5-nitropyrimidin-4-amine (Example 7, intermediate) using 6-chloro-N-(2-chlorobenzyl)-5-nitropyrimidin-4-amine and 1-methylcyclopropan-1-ol as starting material. $^1$H NMR (300 MHz, DMSO-$d_6$): 0.76 (2H, t), 0.91 (2H, t), 1.61 (3H, s), 4.73 (2H, d), 7.22-7.29 (3H, m), 7.39-7.47 (1H, m), 8.29 (1H, s), 8.84 (1H, t). m/z: ES+ [M+H]+ 335.

6-Chloro-N-(2-chlorobenzyl)-5-nitropyrimidin-4-amine was made following a similar procedure to 6-chloro-N-((2-methylthiazol-4-yl)methyl)-5-nitropyrimidin-4-amine (Example 7, intermediate). $^1$H NMR (300 MHz, DMSO-$d_6$): 4.72 (2H, d), 7.23-7.33 (3H, m), 7.40-7.49 (1H, m), 8.42 (1H, s), 9.00 (1H, t). m/z: ES+ [M+H]+ 299.

[E2] was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using N-(3-chlorobenzyl)-6-(1-methylcyclopropoxy)-5-nitropyrimidin-4-amine and 2-chloro-4-(2-(4-methylpiperazin-1-yl)ethoxy)benzaldehyde as starting materials. N-(3-Chlorobenzyl)-6-(1-methylcyclopropoxy)-5-nitropyrimidin-4-amine was made following a similar procedure to 6-(1-methylcyclopropoxy)-N-((2-methylthiazol-4-yl)methyl)-5-nitropyrimidin-4-amine (Example 7, intermediate), using 6-chloro-N-(3-chlorobenzyl)-5-nitropyrimidin-4-amine and 1-methylcyclopropan-1-ol as starting materials. $^1$H NMR (300 MHz, DMSO-$d_6$): 0.73-0.8 (2H, m), 0.93 (2H, t), 1.63 (3H, s), 4.69 (2H, d), 7.26-7.4 (4H, m), 8.34 (1H, s), 8.88 (1H, t). m/z: ES+ [M+H]+ 335.

6-Chloro-N-(3-chlorobenzyl)-5-nitropyrimidin-4-amine was made from (3-chlorophenyl)methanamine and 4,6-dichloro-5-nitropyrimidine following a similar procedure to 6-chloro-N-((2-methylthiazol-4-yl)methyl)-5-nitropyrimidin-4-amine (Example 7, intermediate). $^1$H NMR (300 MHz, DMSO-$d_6$): 4.69 (2H, d), 7.18-7.51 (4H, m), 8.46 (1H, d), 9.02 (1H, t). m/z: ES+ [M+H]+ 299.

[E3] was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using N-(2,3-difluorobenzyl)-6-(1-methylcyclopropoxy)-5-nitropyrimidin-4-amine and 2-chloro-4-(2-(4-methylpiperazin-1-yl)ethoxy)benzaldehyde as starting material. N-(2,3-Difluorobenzyl)-6-(1-methylcyclopropoxy)-5-nitropyrimidin-4-amine was made following a similar procedure to 6-(1-methylcyclopropoxy)-N-((2-methylthiazol-4-yl)methyl)-5-nitropyrimidin-4-amine (Example 7, intermediate), using 6-chloro-N-(2,3-difluorobenzyl)-5-nitropyrimidin-4-amine and 1-methylcyclopropan-1-ol as starting materials. $^1$H NMR (300 MHz, DMSO-$d_6$): 0.75 (2H, t), 0.90 (2H, t), 1.60 (3H, s), 4.75 (2H, d), 7.06-7.19 (2H, m), 7.22-7.34 (1H, m), 8.31 (1H, s), 8.84 (1H, t). m/z: ES+ [M+H]+ 337.

6-Chloro-N-(2,3-difluorobenzyl)-5-nitropyrimidin-4-amine was using a similar procedure to 6-chloro-N-(2-chlorobenzyl)-5-nitropyrimidin-4-amine (Example 7, intermediate), using 4,6-dichloro-5-nitropyrimidine and (2,3-difluorophenyl)methanamine as starting materials. $^1$H NMR (300 MHz, DMSO-$d_6$): 4.73 (2H, d), 6.95-7.22 (2H, m), 7.22-7.42 (1H, m), 8.45 (1H, s), 8.82-9.15 (1H, m). m/z: ES+ [M+H]+ 301.

[E4] was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using 6-(1-methylcyclopropoxy)-5-nitro-N-phenethylpyrimidin-4-amine and 2-chloro-4-(2-(4-methylpiperazin-1-yl)ethoxy)benzaldehyde as starting materials.

6-(1-Methylcyclopropoxy)-5-nitro-N-phenethylpyrimidin-4-amine was made following a similar procedure to 6-(1-methylcyclopropoxy)-N-((2-methylthiazol-4-yl)methyl)-5-nitropyrimidin-4-amine (Example 7, intermediate), using 6-chloro-5-nitro-N-phenethylpyrimidin-4-amine and 1-methylcyclopropan-1-ol as starting materials. $^1$H NMR (300 MHz, DMSO-$d_6$): 0.72-0.80 (2H, m), 0.89-0.96 (2H, m), 1.62 (3H, s), 2.86 (2H, t), 3.71 (2H, dt), 7.17-7.26 (3H, m), 7.26-7.33 (2H, m), 8.36 (1H, s), 8.41 (1H, t). m/z: ES+ [M+H]+ 315.

6-Chloro-5-nitro-N-phenethylpyrimidin-4-amine was made using a similar procedure to 6-chloro-N-(3-chlorobenzyl)-5-nitropyrimidin-4-amine (Example 7, intermediate), using 2-phenylethan-1-amine and 4,6-dichloro-5-nitropyrimidine as starting materials. $^1$H NMR (300 MHz, DMSO-$d_6$): 2.86 (2H, t), 3.67-3.85 (2H, m), 7.13-7.33 (5H, m), 8.07 (1H, s), 9.56 (1H, t). m/z: ES+ [M+H]+ 279.

[E5] was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using 6-(1-methylcyclopropoxy)-5-nitro-N-(pyridin-2-ylmethyl)pyrimidin-4-amine and 2-chloro-4-(2-(4-methylpiperazin-1-yl)ethoxy)benzaldehyde as starting materials.

6-(1-Methylcyclopropoxy)-5-nitro-N-(pyridin-2-ylmethyl)pyrimidin-4-amine was made following a similar procedure to 6-(1-methylcyclopropoxy)-N-((2-methylthiazol-4-yl)methyl)-5-nitropyrimidin-4-amine (Example 7, intermediate), using 6-chloro-5-nitro-N-(pyridin-2-ylmethyl)pyrimidin-4-amine and 1-methylcyclopropan-1-ol as starting material. $^1$H NMR (300 MHz, DMSO-$d_6$): 0.79 (2H, dd), 0.87-1.03 (2H, m), 1.64 (2H, s), 4.82 (2H, d), 7.27-7.43 (2H, m), 7.75-7.85 (1H, m), 8.33 (1H, s), 8.55 (1H, dd), 9.06 (1H, t). One proton not observed. m/z: ES+ [M+H]+ 302.

6-Chloro-5-nitro-N-(pyridin-2-ylmethyl)pyrimidin-4-amine was made using a similar procedure to 6-chloro-N-(3-chlorobenzyl)-5-nitropyrimidin-4-amine (Example 7, intermediate), using 4,6-dichloro-5-nitropyrimidine and pyridin-2-ylmethanamine as starting materials. m/z: ES+ [M+H]+ 266.

[E6] was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using 6-(1-methylcyclopropoxy)-5-nitro-N-(pyrimidin-2-ylmethyl)pyrimidin-4-amine and 2-chloro-4-(2-(4-methylpiperazin-1-yl)ethoxy)benzaldehyde as starting materials and purified by preparative HPLC (Viridis BEH Prep 2-EP OBD column, 30*150 mm, 5 μm), using decreasingly polar mixtures of water (containing formic acid) and MeCN as eluents to isolate the desired compound as the formate salt.

6-(1-Methylcyclopropoxy)-5-nitro-N-(pyrimidin-2-ylmethyl)pyrimidin-4-amine was made following a similar procedure to 6-(1-methylcyclopropoxy)-N-((2-methylthiazol-4-yl)methyl)-5-nitropyrimidin-4-amine (Example 7, intermediate) using 6-chloro-5-nitro-N-(pyrimidin-2-ylmethyl)pyrimidin-4-amine and 1-methylcyclopropan-1-ol as starting materials. $^1$H NMR (300 MHz, DMSO-$d_6$): 0.61-0.69 (2H, m), 0.80-0.87 (2H, m), 1.52 (3H, s), 4.77 (2H, d), 7.30 (1H, t), 8.18 (1H, s), 8.66 (2H, d), 8.90 (1H, s). m/z: ES+ [M+H]+ 303.

6-Chloro-5-nitro-N-(pyrimidin-2-ylmethyl)pyrimidin-4-amine was made using a similar procedure to 6-chloro-N-(2-chlorobenzyl)-5-nitropyrimidin-4-amine (Example 7, intermediate), from 4,6-dichloro-5-nitropyrimidine and pyrimidin-2-ylmethanamine as starting material. $^1$H NMR (300 MHz, DMSO-$d_6$): 4.87 (2H, d), 7.33 (1H, t), 8.70 (2H, d), 10.06 (1H, t), 12.36 (1H, s). m/z: ES+ [M+H]+ 267.

[E7] was made following a similar procedure to 9-benzyl-8-(2-chloro-4-(2-(piperazin-1-yl)ethoxy)phenyl)-6-((1,1,1-trifluoro-2-methylpropan-2-yl)oxy)-9H-purine (Example 11), using tert-butyl 4-(2-(3-chloro-4-(6-(1-methylcyclopropoxy)-9-(pyridin-2-ylmethyl)-9H-purin-8-yl)phenoxy)ethyl)piperazine-1-carboxylate as starting material.

Tert-butyl 4-(2-(3-chloro-4-(6-(1-methylcyclopropoxy)-9-(pyridin-2-ylmethyl)-9H-purin-8-yl)phenoxy)ethyl)piperazine-1-carboxylate was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using 6-(1-methylcyclopropoxy)-5-nitro-N-(pyridin-2-ylmethyl)pyrimidin-4-amine (previously described in Example E5) and tert-butyl 4-(2-(3-chloro-4-formylphenoxy)ethyl)piperazine-1-carboxylate as starting materials.

The following examples in Table F were made in a similar manner to Example 19, except stated otherwise in the notes at the bottom of the Table

TABLE F

| Ex # | Structure | Name | $^1$H NMR | LCMS $[M + H]^+$ |
|---|---|---|---|---|
| F1 | 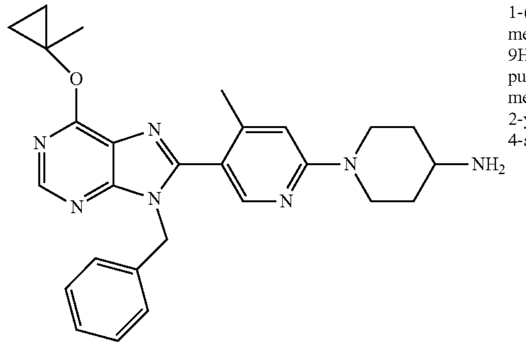 | 1-(5-(9-benzyl-6-(1-methylcyclopropoxy)-9H-purin-8-yl)-4-methylpyridin-2-yl)piperidin-4-amine | (400 MHz, DMSO-$d_6$): 0.80 – 0.87 (2H, m), 1.00 – 1.03 (2H, m), 1.19 – 1.22 (2H, m), 1.73 – 1.78 (5H, m), 1.96 (3H, s), 2.95 (4H, t), 3.51 (1H, s), 4.25 (2H, d), 5.33 (2H, s), 6.78 (1H, s), 6.89 (2H, dd), 7.17 – 7.29 (3H, m), 8.01 (1H, s), 8.58 (1H, s) | 470 |

TABLE F-continued

| Ex # | Structure | Name | $^1$H NMR | LCMS [M + H]$^+$ |
|---|---|---|---|---|
| F2 | 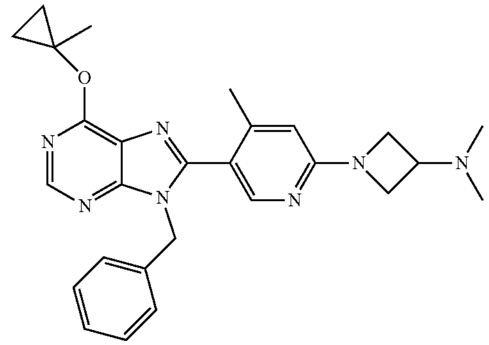 [SMILES: Cc1cc(N2CC(N(C)C)C2)ncc1-c1nc2c(OC3(C)CC3)ncnc2n1Cc1ccccc1] | 1-(5-(9-benzyl-6-(1-methylcyclopropoxy)-9H-purin-8-yl)-4-methylpyridin-2-yl)-N,N-dimethylazetidin-3-amine | (400 MHz, DMSO-$d_6$): 0.81 – 0.87 (2H, m), 0.99 – 1.05 (2H, m), 1.73 (3H, s), 1.93 (3H, s), 2.12 (6H, s), 3.19 (1H, ddd), 3.76 (2H, dd), 4.02 (2H, dd), 5.31 (2H, s), 6.31 (1H, s), 6.89 (2H, dd), 7.22 (3H, dd), 7.98 (1H, s), 8.58 (1H, s) | 470 |
| F3 | 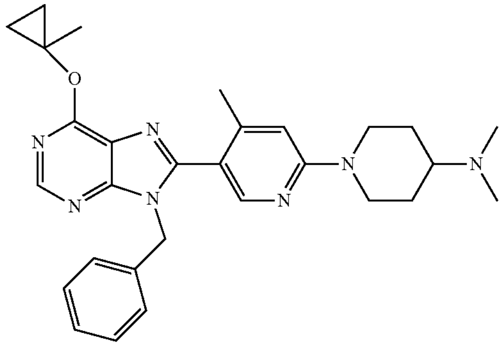 [SMILES: Cc1cc(N2CCC(N(C)C)CC2)ncc1-c1nc2c(OC3(C)CC3)ncnc2n1Cc1ccccc1] | 1-(5-(9-benzyl-6-(1-methylcyclopropoxy)-9H-purin-8-yl)-4-methylpyridin-2-yl)-N,N-dimethylpiperidin-4-amine | (400 MHz, DMSO-$d_6$): 0.81 – 0.87 (2H, m), 0.98 – 1.06 (2H, m), 1.33 (2H, qd), 1.73 (3H, s), 1.80 (2H, d), 1.95 (3H, s), 2.18 (6H, s), 2.26 – 2.39 (1H, m), 2.86 (2H, t), 4.36 (2H, d), 5.33 (2H, s), 6.79 (1H, s), 6.86 – 6.92 (2H, m), 7.22 (3H, dd), 8.01 (1H, s), 8.58 (1H, s) | 498 |

[F1] was made following a similar procedure to 1-(5-(9-benzyl-6-(1-methylcyclopropoxy)-9H-purin-8-yl)-4-methylpyridin-2-yl)azetidin-3-amine (Example 19), using tert-butyl piperidin-4-ylcarbamate (185 mg, 0.92 mmol) and 9-benzyl-8-(6-fluoro-4-methylpyridin-3-yl)-6-(1-methylcyclopropoxy)-9H-purine (180 mg, 0.46 mmol) to afford 1-(5-(9-benzyl-6-(1-methylcyclopropoxy)-9H-purin-8-yl)-4-methylpyridin-2-yl)piperidin-4-amine (22 mg, 13%) as a light yellow solid.

[F2] was made following a similar procedure to 1-(5-(9-benzyl-6-(1-methylcyclopropoxy)-9H-purin-8-yl)-4-methylpyridin-2-yl)azetidin-3-amine (Example 19) using N,N-dimethyl-3-azetidinamine (089 mg, 0.51 mmol) and 9-benzyl-8-(6-fluoro-4-methylpyridin-3-yl)-6-(1-methylcyclopropoxy)-9H-purine (100 g, 0.26 mmol) to afford 1-(5-(9-benzyl-6-(1-methylcyclopropoxy)-9H-purin-8-yl)-4-methylpyridin-2-yl)-N,N-dimethylazetidin-3-amine (37 mg, 31%) as a light yellow solid, except that the BOC deprotection step was omitted.

[F3] was made following a similar procedure to 1-(5-(9-benzyl-6-(1-methylcyclopropoxy)-9H-purin-8-yl)-4-methylpyridin-2-yl)azetidin-3-amine (Example 19) using N,N-dimethylpiperidin-4-amine (66 mg, 0.51 mmol) and 9-benzyl-8-(6-fluoro-4-methylpyridin-3-yl)-6-(1-methylcyclopropoxy)-9H-purine (100 mg, 0.26 mmol) to afford 1-(5-(9-benzyl-6-(1-methylcyclopropoxy)-9H-purin-8-yl)-4-methylpyridin-2-yl)-N,N-dimethylpiperidin-4-amine (33 mg, 26%) as a light yellow solid, except that the BOC deprotection step was omitted Unless stated otherwise, the following examples in Table G were made by a similar method to Example 21. Where BOC deprotection was required, this step was performed by a method similar to that described in Example 19.

TABLE G

| Ex # | Structure | Name | $^1$H NMR | LCMS [M + H]$^+$ |
|---|---|---|---|---|
| G1 | 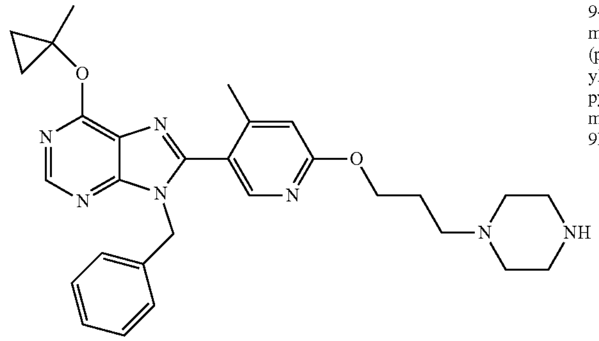 [SMILES: Cc1cc(OCCCN2CCNCC2)ncc1-c1nc2c(OC3(C)CC3)ncnc2n1Cc1ccccc1] | 9-benzyl-8-(4-methyl-6-(3-(piperazin-1-yl)propoxy) pyridin-3-yl)-6-(1-methylcyclopropoxy)-9H-purine | (400 MHz, DMSO-$d_6$): 0.80 – 0.88 (2H, m), 1.01 – 1.04 (2H, m), 1.73 (3H, s), 1.85 (2H, p), 1.92 (3H, s), 2.14 (6H, s), 2.34 (2H, t), 4.31 (2H, t), 5.33 (2H, s), 6.78 (1H, s), 6.88 (2H, dd), 7.21 (3H, p), 8.11 (1H, s), 8.63 (1H, s) | 514 |
| G2 | 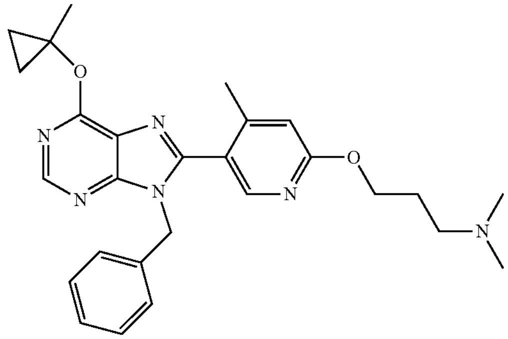 [SMILES: Cc1cc(OCCCN(C)C)ncc1-c1nc2c(OC3(C)CC3)ncnc2n1Cc1ccccc1] | 3-((5-(9-benzyl-6-(1-methylcyclopropoxy)-9H-purin-8-yl)-4-methylpyridin-2-yl)oxy)-N,N-dimethylpropan-1-amine | | 473 |
| G3 | 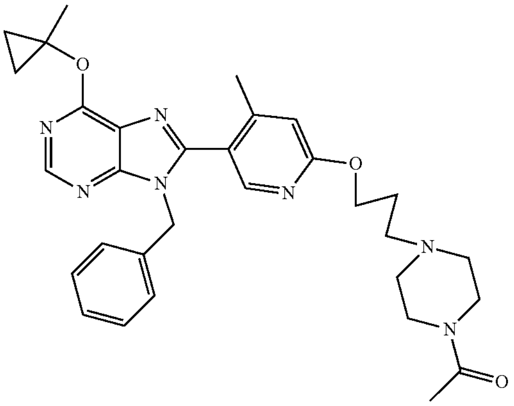 [SMILES: CC(=O)N1CCN(CCCOc2cc(C)c(-c3nc4c(OC5(C)CC5)ncnc4n3Cc3ccccc3)cn2)CC1] | 1-(4-(3-((5-(9-benzyl-6-(1-methylcyclopropoxy)-9H-purin-8-yl)-4-methylpyridin-2-yl)oxy)propyl) piperazin-1-yl)ethan-1-one | (400 MHz, DMSO-$d_6$): 0.81 – 0.89 (2H, m), 0.99 –1.06 (2H, m), 1.73 (3H, s), 1.90 – 1.93 (5H, m), 1.98 (3H, s), 2.31 (2H, br s), 2.38 (2H, br s), 2.43 (2H, t), 3.30 – 3.50 (4H, m), 4.33 (2H, t), 5.33 (2H, s), 6.78 (1H, $), 6.86 – 6.92 (2H, m), 7.20 – 7.22 (3H, m), 8.12 (1H, s), 8.63 (1H, s) | 556 |
| G4 | 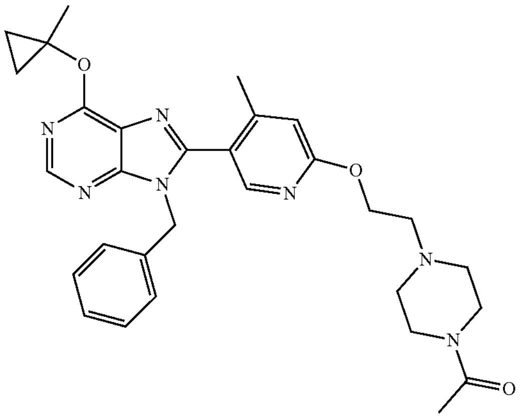 [SMILES: CC(=O)N1CCN(CCOc2cc(C)c(-c3nc4c(OC5(C)CC5)ncnc4n3Cc3ccccc3)cn2)CC1] | 1-(4-(2-((5-(9-benzyl-6-(1-methylcyclopropoxy)-9H-purin-8-yl)-4-methylpyridin-2-yl)oxy)ethyl) piperazin-1-yl)ethan-1-one | (400 MHz, DMSO-$d_6$): 0.79 – 0.89 (2H, m), 0.97 – 1.08 (2H, m), 1.73 (3H, s), 1.93 (3H, s), 1.98 (3H, s), 2.42 (2H, t), 2.48 (2H, d), 2.72 (2H, t), 3.41 (4H, q), 4.43 (2H, t), 5.33 (2H, s), 6.80 (1H, s), 6.88 (2H, dd), 7.15-7.26 (3H, m), 8.12 (1H, s), 8.63 (1H, s) | 542 |

TABLE G-continued

| Ex # | Structure | Name | $^1$H NMR | LCMS [M + H]$^+$ |
|---|---|---|---|---|
| G5 | 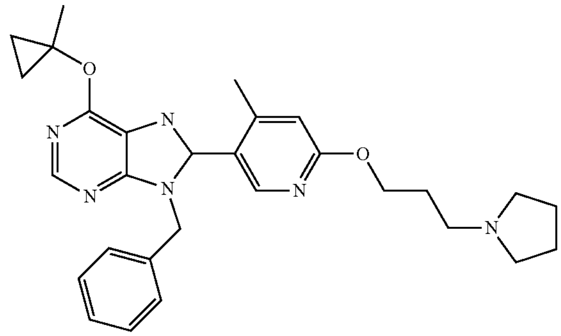 [SMILES: Cc1cc(OCCCN2CCCC2)ncc1C1Nc2c(OC3(C)CC3)ncnc2N1Cc1ccccc1] | 9-benzyl-8-(4-methyl-6-(3-(pyrrolidin-1-yl)propoxy)pyridin-3-yl)-6-(1-methylcyclopropoxy)-9H-purine | (400 MHz, DMSO-$d_6$): 0.79 – 0.89 (2H, m), 0.98 – 1.08 (2H, m), 1.67 (4H, p), 1.73 (3H, s), 1.85 – 1.91 (2H, m), 1.92 (3H, s), 2.41 – 2.44 (4H, m), 4.33 (2H, t), 5.32 (2H, s), 6.78 (1H, s), 6.84 – 6.93 (2H, m), 7.19 – 7.22 (3H, m), 8.11 (1H, s), 8.63 (1H, s). 2H not observed. | 499 |
| G6 | 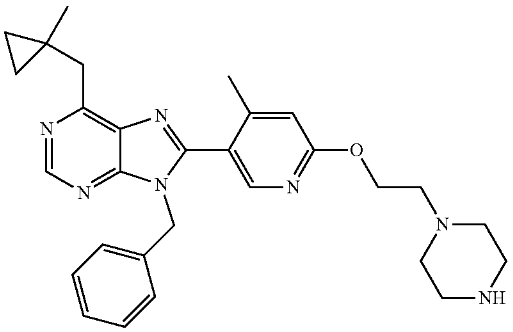 [SMILES: Cc1cc(OCCN2CCNCC2)ncc1-c1nc2c(CC3(C)CC3)ncnc2n1Cc1ccccc1] | 9-benzyl-8-(4-methyl-6-(2-(piperazin-1-yl)ethoxy)pyridin-3-yl)-6-(1-methylcyclopropoxy)-9H-purine | (400 MHz, DMSO-$d_6$): 0.80 – 0.88 (2H, m), 0.98 – 1.06 (2H, m), 1.73 (3H, s), 1.92 (3H, s), 2.39 (4H, t), 2.61 – 2.71 (6H, m), 4.40 (2H, t), 5.32 (2H, s), 6.79 (1H, s), 6.84 – 6.92 (2H, m), 7.17 – 7.25 (3H, m), 8.11 (1H, s), 8.63 (1H, s). 1H not observed. | 500 |
| G7 | 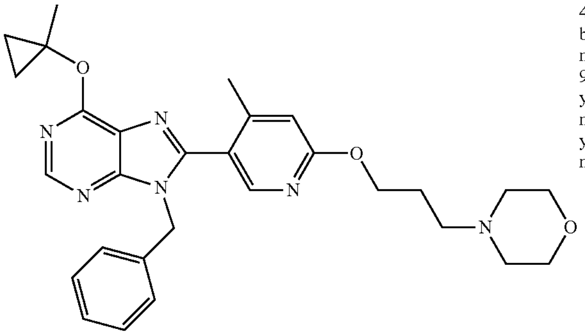 | 4-(3-((5-(9-benzyl-6-(1-methylcyclopropoxy)-9H-purin-8-yl)-4-methylpyridin-2-yl)oxy)propyl) morpholine | (400 MHz, DMSO-$d_6$): 0.80 – 0.88 (2H, m), 1.00 – 1.04 (2H, m), 1.73 (3H, s), 1.85 – 1.96 (5H, m), 2.28 – 2.46 (6H, m), 3.55 – 3.58 (4H, m), 4.33 (2H, t), 5.32 (2H, s), 6.78 (1H, s), 6.88 (2H, dd), 7.20 – 7.22 (3H, m), 8.11 (1H, s), 8.63 (1H, s) | 515 |
| G8 | 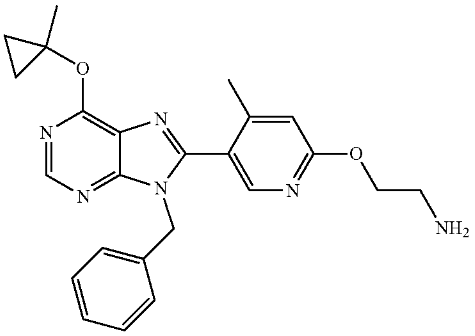 [SMILES: Cc1cc(OCCN)ncc1-c1nc2c(OC3(C)CC3)ncnc2n1Cc1ccccc1] | 2-((5-(9-benzyl-6-(1-methylcyclopropoxy)-9H-purin-8-yl)-4-methylpyridin-2-yl)oxy)ethan-1-amine | (400 MHz, DMSO-$d_6$): 0.80 – 0.89 (2H, m), 0.98 – 1.07 (2H, m), 1.73 (3H, s), 1.80 (2H, br s), 1.93 (3H, s), 2.88 (2H, t), 4.24 (2H, t), 5.33 (2H, s), 6.79 (1H, s), 6.85 – 6.98 (2H, m), 7.14 – 7.30 (3H, m), 8.11 (1H, s), 8.63 (1H, s) | 431 |

TABLE G-continued

| Ex # | Structure | Name | $^1$H NMR | LCMS [M + H]$^+$ |
|---|---|---|---|---|
| G9 | 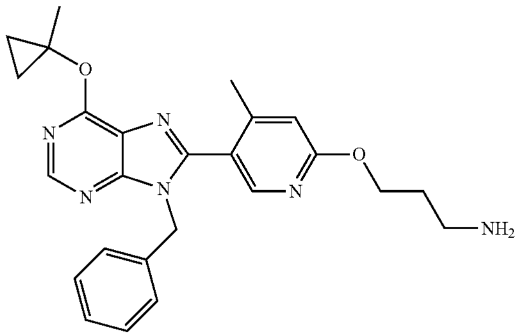 [SMILES: Cc1cc(OCCCN)ncc1-c1nc2c(OC3(C)CC3)ncnc2n1Cc1ccccc1] | 3-((5-(9-benzyl-6-(1-methylcyclopropoxy)-9H-purin-8-yl)-4-methylpyridin-2-yl)oxy)propan-1-amine | (400 MHz, DMSO-$d_6$): 0.80 – 0.88 (2H, m), 0.99 – 1.06 (2H, m), 1.73 (3H, s), 1.79 (2H, p), 1.93 (3H, s), 2.69 (2H, t), 4.35 (2H, t), 5.33 (2H, s), 6.78 (1H, s), 6.84 – 6.93 (2H, m), 7.17 – 7.26 (3H, m), 8.11 (1H, s), 8.62 (1H, s), 2H not observed. | 445 |
| G10 | 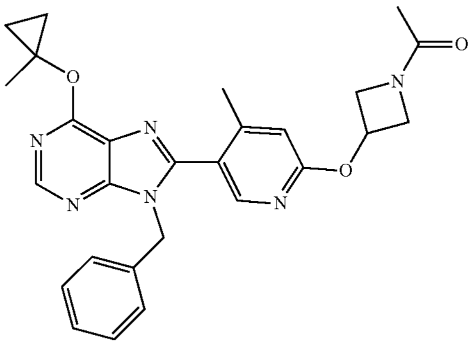 [SMILES: CC(=O)N1CC(Oc2cc(C)c(-c3nc4c(OC5(C)CC5)ncnc4n3Cc3ccccc3)cn2)C1] | 1-(3-((5-(9-benzyl-6-(1-methylcyclopropoxy)-9H-purin-8-yl)-4-methylpyridin-2-yl)oxy)azetidin-1-yl)ethan-1-one | (400 MHz, DMSO-$d_6$): 0.81 –0.93 (2H, m), 1.01 – 1.04 (2H, m), 1.73 (3H, s), 1.80 (3H, s), 1.93 (3H, s), 3.78 – 3.86 (1H, m), 4.07 – 4.15 (1H, m), 4.23 – 4.27 (1H, m), 4.50 – 4.58 (1H, m), 5.32 (2H, s), 5.37 (1H, tt), 6.85 – 6.88 (3H, m), 7.17-7.25 (3H, m), 8.13 (1H, s), 8.63 (1H, s) | 485 |
| G11 | 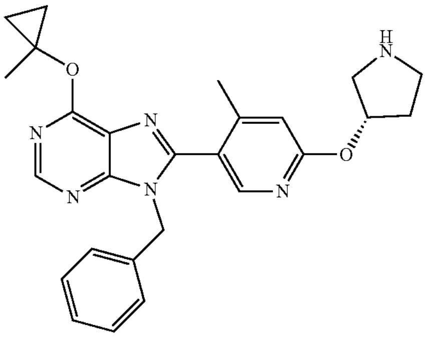 [SMILES: Cc1cc(O[C@H]2CCNC2)ncc1-c1nc2c(OC3(C)CC3)ncnc2n1Cc1ccccc1] | (S)-9-benzyl-8-(4-methyl-6-(pyrrolidin-3-yloxy)pyridin-3-yl)-6-(1-methylcyclopropoxy)-9H-purine | (400 MHz, DMSO-$d_6$): 0.81 – 0.88 (2H, m), 1.01 – 1.04 (2H, m), 1.73 (3H, s), 1.74- 1. 80 (1H, m), 1.92 (3H, s), 2.01 – 2.05 (1H, m), 2.76 – 2.87 (2H, m), 2.88 – 2.93 (1H, m), 3.08 (1H, dd), 5.32 (2H, s), 5.36 – 5.45 (1H, m), 6.74 (1H, s), 6.83 – 6.92 (2H, m), 7.15 –7.26 (3H, m), 8.11 (1H, s), 8.63 (1H, s). 1H not observed. | 457 |
| G12 | 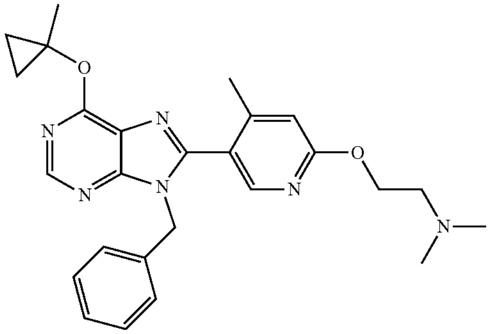 [SMILES: Cc1cc(OCCN(C)C)ncc1-c1nc2c(OC3(C)CC3)ncnc2n1Cc1ccccc1] | 2-((5-(9-benzyl-6-(1-methylcyclopropoxy)-9H-purin-8-yl)-4-methylpyridin-2-yl)oxy)-N,N-dimethylethan-1-amine | (400 MHz, DMSO-$d_6$): 0.80 – 0.88 (2H, m), 1.02 (2H, t), 1.73 (3H, s), 1.92 (3H, s), 2.21 (6H, s), 2.62 (2H, t), 4.38 (2H, t), 5.33 (2H, s), 6.78 (1H, s), 6.88 (2H, dd), 7.21 (3H, q), 8.12 (1H, s), 8.63 (1H, s). | 459 |

TABLE G-continued

| Ex # | Structure | Name | $^1H$ NMR | LCMS [M + H]+ |
|---|---|---|---|---|
| G13 | 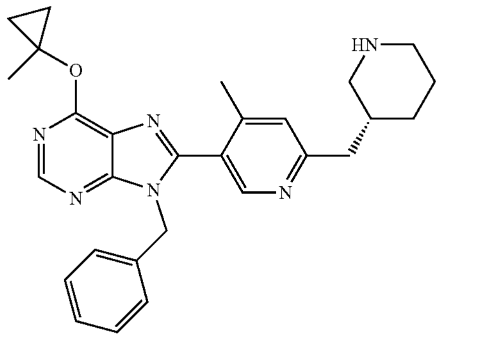 [SMILES: Cc1cc(C[C@H]2CCCNC2)ncc1-c1nc2c(OC3(C)CC3)ncnc2n1Cc1ccccc1] | (S)-9-benzyl-8-(4-methyl-6-(piperidin-3-yloxy)pyridin-3-yl)-6-(1-methylcyclopropoxy)-9H-purine | (400 MHz, DMSO-$d_6$): 0.81 – 0.88 (2H, m), 0.98 – 1.07 (2H, m), 1.37 – 1.61 (2H, m), 1.63 – 1.72 (1H, m), 1.73 (3H, s), 1.93 (3H, s), 2.02 – 2.10 (1H, m), 2.26 (1H, br s), 2.52 – 2.55 (1H, m), 2.67 – 2.77 (1H, m), 3.13 (1H, dd), 4.93 – 4.96 (1H, m), 5.33 (2H, s), 6.73 (1H, s), 6.84 – 6.93 (2H, m), 7.16 – 7.28 (3H, m), 8.09 (1H, s), 8.62 (1H, s). 1H not observed. | 471 |
| G14 | 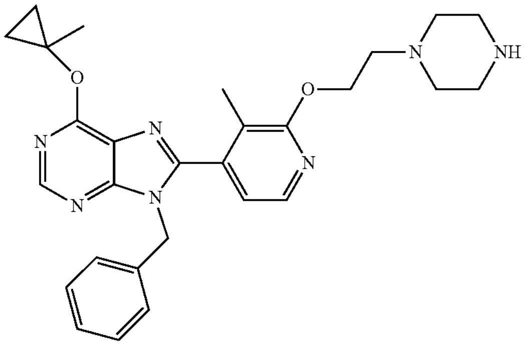 [SMILES: Cc1c(-c2nc3c(OC4(C)CC4)ncnc3n2Cc2ccccc2)ccnc1OCCN1CCNCC1] | 9-benzyl-8-(3-methyl-2-(2-(piperazin-1-yl)ethoxy) pyridin-4-yl)-6-(1-methylcyclopropoxy)-9H-purine | (400 MHz, DMSO-$d_6$): 0.81 – 0.88 (2H, m), 1.02 (2H, m), 1.73 (3H, s), 1.74 (3H, s) 2.39 (4H, br s), 2.65 – 2.68 (6H, m), 4.43 (2H, t), 5.30 (2H, s), 6.83 – 6.90 (2H, m), 6.98 (1H, d), 7.20 (3H, dd), 8.10 (1H, d), 8.65 (1H, s). 1H not observed. | 500 |
| G15 | 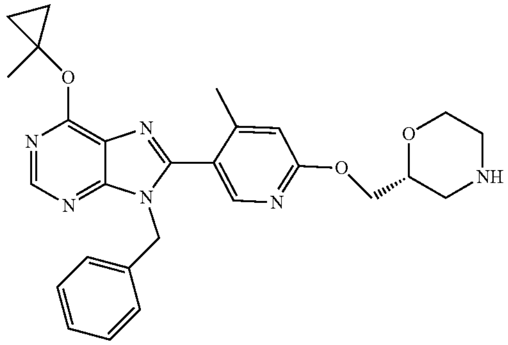 [SMILES: Cc1cc(OC[C@H]2CNCCO2)ncc1-c1nc2c(OC3(C)CC3)ncnc2n1Cc1ccccc1] | (R)-2-(((5-(9-benzyl-6-(1-methylcyclopropoxy)-9H-purin-8-yl)-4-methylpyridin-2-yl)oxy)methyl) morpholine | (400 MHz, DMSO-$d_6$): 0.82 – 0.88 (2H, m), 0.99 – 1.06 (2H, m), 1.73 (3H, s), 1.92 (3H, s), 2.46 – 2.47 (1H, m), 2.65 (2H, dd), 2.84 (1H, dd), 3.45 (1H, td), 3.64 – 3.80 (2H, m), 4.17 – 4.31 (2H, m), 5.32 (2H, s), 6.81 (1H, s), 6.88 (2H, dd), 7.15-7.27 (3H, m), 8.11 (1H, s), 8.63 (1H, s). 1H not observed. | 487 |
| G16 | 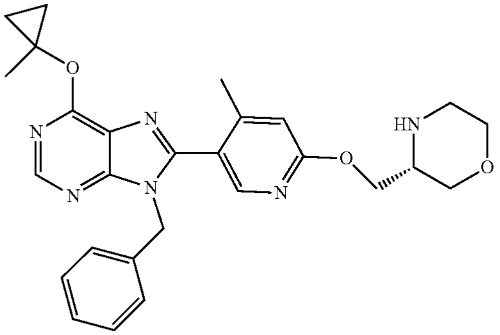 [SMILES: Cc1cc(OC[C@H]2COCCN2)ncc1-c1nc2c(OC3(C)CC3)ncnc2n1Cc1ccccc1] | (R)-3-(((5-(9-benzyl-6-(1-methylcyclopropoxy)-9H-purin-8-yl)-4-methylpyridin-2-yl)oxy)methyl) morpholine | (400 MHz, DMSO-$d_6$): 0.80-0.92 (2H, m), 1.00 – 1.04 (2H, m), 1.73 (3H, s), 1.93 (3H, s), 2.56 (1H, s), 2.69 – 2.83 (2H, m), 3.05 (1H, dtd), 3.22 (1H, dd), 3.38 (1H, td), 3. 66 (1H, dt), 3.79 (1H, dd), 4.09 – 4.24 (2H, m), 5.33 (2H, s), 6.80 (1H, s), 6.84 – 6.92 (2H, m), 7.21 (3H, ddt), 8.11 (1H, s), 8.63 (1H, s) | 487 |

TABLE G-continued

| Ex # | Structure | Name | $^1$H NMR | LCMS [M + H]$^+$ |
| --- | --- | --- | --- | --- |
| G17 | 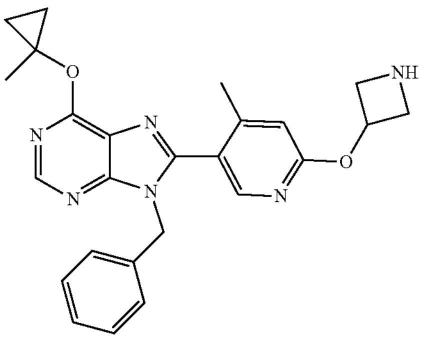 [SMILES: Cc1cc(OC2CNC2)ncc1-c1nc2c(OC3(C)CC3)ncnc2n1Cc1ccccc1] | 8-{6-[(azetidin-3-yl)oxy]-4-methylpyridin-3-yl}-9-benzyl-6-[(1-methylcyclopropyl)oxy]-9H-purine | (400 MHz, DMSO-$d_6$): 0.80-0.88 (2H, m), 0.98 - 1.06 (2H, m), 1.73 (3H, s), 1.91 (3H, s), 3.52 (2H, dd), 3.71 - 3.80 (2H, m), 5.31 (2H, s), 5.37 (1H, p), 6.80 (1H, s), 6.82 - 6.89 (2H, m), 7.15 - 7.25 (3H, m), 8.09 (1H, s), 8.63 (1H, s). 1H not observed. | 443 |

[G1] made by a similar procedure to Example 21 using tert-butyl 4-(3-hydroxypropyl)piperazine-1-carboxylate (94 mg, 0.39 mmol) and 9-benzyl-8-(6-fluoro-4-methylpyridin-3-yl)-6-(1-methylcyclopropoxy)-9H-purine (150 mg, 0.39 mmol), except that the reaction was quenched with saturated aq. $NH_4Cl$ (20 mL), extracted with EtOAc (3×20 mL). The organic layer was dried over $Na_2SO_4$, filtered and evaporated to afford 0.22 g yellow solid which was used in the BOC deprotection step directly without further purification.

[G3] made via acetylation of 9-benzyl-8-(4-methyl-6-(3-(piperazin-1-yl)propoxy)pyridin-3-yl)-6-(1-methylcyclopropoxy)-9H-purine (Example G1)

$Ac_2O$ (24 µL, 0.25 mmol) was added to 9-benzyl-8-(4-methyl-6-(3-(piperazin-1-yl)propoxy)pyridin-3-yl)-6-(1-methylcyclopropoxy)-9H-purine (Example G1, 130 mg, 0.25 mmol) and DIEA (133 µL, 0.76 mmol) in DCM (3 mL). The resulting mixture was stirred at rt for 1 hour. The solvent was removed under reduced pressure. The crude product was purified by preparative HPLC (XBridge Prep OBD column, 30*150 mm, 5 µm), using decreasingly polar mixtures of water (containing 10 mmol/L $NH_4HCO_3$ and 0.1% aqueous ammonia) and MeCN as eluents. Fractions containing the desired compound were evaporated to dryness to afford 1-(4-(3-((5-(9-benzyl-6-(1-methylcyclopropoxy)-9H-purin-8-yl)-4-methylpyridin-2-yl)oxy)propyl)piperazin-1-yl)ethan-1-one (45 mg, 32%) as a light yellow solid.

[G6] made by a similar procedure to Example 21 using tert-butyl 4-(2-hydroxyethyl)piperazine-1-carboxylate (177 mg, 0.77 mmol) and 9-benzyl-8-(6-fluoro-4-methylpyridin-3-yl)-6-(1-methylcyclopropoxy)-9H-purine (150 mg, 0.39 mmol), except that the reaction was quenched with saturated aq. $NH_4Cl$ (20 mL), extracted with EtOAc (3×20 mL), the organic layer was dried over $Na_2SO_4$, filtered and evaporated to afford 0.22 g yellow solid which was used in the BOC deprotection step directly without further purification.

[G8] made by a similar procedure to Example 21 using tert-butyl (2-hydroxyethyl)carbamate (248 mg, 1.54 mmol) and 9-benzyl-8-(6-fluoro-4-methylpyridin-3-yl)-6-(1-methylcyclopropoxy)-9H-purine (300 mg, 0.77 mmol), except that the reaction mixture was quenched with saturated $NH_4Cl$ (20 mL), extracted with EtOAc (3×20 mL), the organic layer was dried over $Na_2SO_4$, filtered and evaporated to afford 0.4 g yellow solid which was used in the BOC deprotection step directly without further purification.

[G9] made by a similar procedure to Example 21 using tert-butyl (3-hydroxypropyl)carbamate (135 mg, 0.77 mmol) and 9-benzyl-8-(6-fluoro-4-methylpyridin-3-yl)-6-(1-methylcyclopropoxy)-9H-purine (150 mg, 0.39 mmol), except that the reaction mixture was quenched with saturated $NH_4Cl$ (20 mL), extracted with EtOAc (3×20 mL), the organic layer was dried over $Na_2SO_4$, filtered and evaporated to afford crude 0.22 g as a yellow solid, which was used in the BOC deprotection step directly without further purification.

[G11] made by a similar procedure to Example 21 tert-butyl (S)-3-hydroxypyrrolidine-1-carboxylate (48.1 mg, 0.26 mmol) and 9-benzyl-8-(6-fluoro-4-methylpyridin-3-yl)-6-(1-methylcyclopropoxy)-9H-purine (100 mg, 0.26 mmol), except that the reaction mixture was quenched with saturated $NH_4Cl$ (20 mL), extracted with EtOAc (3×20 mL), the organic layer was dried over $Na_2SO_4$, filtered and evaporated to afford crude 0.15 g yellow solid, which was used in the BOC deprotection step directly without further purification.

[G12] was made from 2-((5-(9-benzyl-6-(1-methylcyclopropoxy)-9H-purin-8-yl)-4-methylpyridin-2-yl)oxy)ethan-1-amine (Example G8) as follows:

Formaldehyde (4 mL, 0.33 mmol. 37% aqueous solution) was added to 2-((5-(9-benzyl-6-(1-methylcyclopropoxy)-9H-purin-8-yl)-4-methylpyridin-2-yl)oxy)ethan-1-amine (140 mg, 0.33 mmol) in MeOH (2 mL). The resulting mixture was stirred at rt for 20 minutes. Then sodium triacetoxyborohydride (414 mg, 1.95 mmol) was added to the mixture. The resulting mixture was stirred at 60° C. for 16 hours. The solvent was removed under reduced pressure. The crude product was purified by preparative HPLC (XBridge Prep OBD C18 column, 30*150 mm, 5 µm), using decreasingly polar mixtures of water (containing 10 mmol/L $NH_4HCO_3$ and 0.1% aqueous ammonia) and MeCN as eluents. Fractions containing the desired compound were evaporated to dryness to afford 2-((5-(9-benzyl-6-(1-methylcyclopropoxy)-9H-purin-8-yl)-4-methylpyridin-2-yl)oxy)-N,N-dimethylethan-1-amine (31 mg, 21%) as a light yellow solid.

[G13] made by a similar procedure to Example 21 using tert-butyl (S)-3-hydroxypiperidine-1-carboxylate (116 mg, 0.58 mmol) and 9-benzyl-8-(6-fluoro-4-methylpyridin-3-yl)-6-(1-methylcyclopropoxy)-9H-purine (150 mg, 0.39 mmol), except that the reaction mixture was quenched with saturated $NH_4Cl$ (20 mL), extracted with EtOAc (3×20 mL), the organic layer was dried over $Na_2SO_4$, filtered and evaporated to afford crude 0.20 g yellow solid, which was used in the BOC deprotection step directly without further purification.

[G14] made by a similar procedure to Example 21 using tert-butyl 4-(2-hydroxyethyl)piperazine-1-carboxylate (237 mg, 1.03 mmol) and 9-benzyl-8-(2-fluoro-3-methylpyridin-4-yl)-6-(1-methylcyclopropoxy)-9H-purine (200 mg, 0.51 mmol), except that the reaction mixture was quenched with saturated $NH_4Cl$ (20 mL), extracted with EtOAc (3×20 mL), the organic layer was dried over $Na_2SO_4$, filtered and evaporated to afford crude 0.30 g yellow solid, which was used in the BOC deprotection step directly without further purification.

9-Benzyl-8-(2-fluoro-3-methylpyridin-4-yl)-6-(1-methylcyclopropoxy)-9H-purine used as a starting material was obtained from a similar procedure as that described for 9-benzyl-8-(6-fluoro-4-methylpyridin-3-yl)-6-(1-methylcyclopropoxy)-9H-purine (Example 19 intermediate) using N4-benzyl-6-(1-methylcyclopropoxy)pyrimidine-4,5-diamine (200 mg, 0.74 mmol) and 2-fluoro-3-methylisonicotinaldehyde (124 mg, 0.89 mmol) to afford to afford 9-benzyl-8-(2-fluoro-3-methylpyridin-4-yl)-6-(1-methylcyclopropoxy)-9H-purine (0.160 g, 55%) as a brown solid. $^1H$ NMR (400 MHz, DMSO-$d_6$): 0.86 (2H, t), 1.02 (2H, t), 1.73 (3H, s), 1.84 (3H, s), 5.35 (2H, s), 6.87 (2H, dd), 7.20 (3H, dd), 7.43 (1H, d), 8.20 (1H, d), 8.68 (1H, d). m/z: ES+ [M+H]+ 390.

[G15] made by a similar procedure to Example 21 using tert-butyl (R)-2-(hydroxymethyl)morpholine-4-carboxylate (117 mg, 0.54 mmol) and 9-benzyl-8-(6-fluoro-4-methylpyridin-3-yl)-6-(1-methylcyclopropoxy)-9H-purine (150 mg, 0.39 mmol), except that the reaction mixture was quenched with saturated $NH_4Cl$ (20 mL), extracted with EtOAc (3×20 mL), the organic layer was dried over $Na_2SO_4$, filtered and evaporated to afford crude 0.15 g as a yellow solid, which was used in the BOC deprotection step directly without further purification.

[G16] made by a similar procedure to Example 21 using tert-butyl (S)-3-(hydroxymethyl)morpholine-4-carboxylate (669 mg, 3.08 mmol) and 9-benzyl-8-(6-fluoro-4-methylpyridin-3-yl)-6-(1-methylcyclopropoxy)-9H-purine (300 mg, 0.77 mmol) as starting material. After the BOC deprotection step, the compound was purified by flash C18-flash chromatography, elution gradient 5 to 80% MeCN in water (containing 0.1% $NH_4HCO_3$), followed by preparative HPLC (XBridge Prep OBD C18 column, 30*150 mm, 5 μm), using decreasingly polar mixtures of water (containing 10 mmol/L $NH_4HCO_3$ and 0.1% aqueous ammonia) and MeCN as eluents. Fractions containing the BOC deprotected product were evaporated to dryness to afford (R)-3-(((5-(9-benzyl-6-(1-methylcyclopropoxy)-9H-purin-8-yl)-4-methylpyridin-2-yl)oxy)methyl)morpholine (21.0 mg, 5.6%) as a light yellow solid.

[G17] made by a similar procedure to Example 21 using tert-butyl 3-hydroxyazetidine-1-carboxylate (67 mg, 0.39 mmol) and 9-benzyl-8-(6-fluoro-4-methylpyridin-3-yl)-6-(1-methylcyclopropoxy)-9H-purine (100 mg, 0.26 mmol), except that the reaction mixture was quenched with saturated $NH_4Cl$ (20 mL), extracted with EtOAc (3×20 mL). The organic layer was dried over $Na_2SO_4$, filtered and evaporated to afford crude 0.12 g yellow solid, which was used in the BOC deprotection step directly without further purification.

The following examples in Table H were synthesised as stated in the notes at the bottom of the Table.

TABLE H

| Ex # | Structure | Name | $^1H$ NMR | LCMS $[M + H]^+$ |
|---|---|---|---|---|
| H1 | 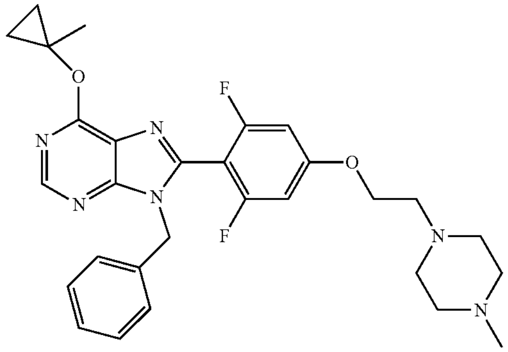 | 9-benzyl-8-(2,6-difluoro-4-(2-(4-methylpiperazin-1-yl)ethoxy)phenyl)-6-(1-methyl-cyclopropoxy)-9H-purine | (400 MHz, DMSO-$d_6$): 0.81 – 0.88 (2H, t), 1.00 – 1.07 (2H, t), 1.73 (3H, s), 2.15 (3H, s), 2.23 – 2.39 (4H, m), 2.49 (4H, m), 2.70 (2H, t), 4.18 (2H, t), 5.33 (2H, s), 6.89 – 7.00 (4H, m), 7.19 – 7.24 (3H, m), 8.64 (1H, s) | 535 |
| H2 | 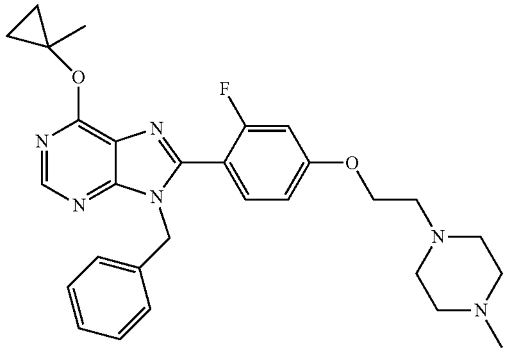 [SMILES: CN1CCN(CCOc2ccc(-c3nc4c(OC5(C)CC5)ncnc4n3Cc3ccccc3)c(F)c2)CC1] | 9-benzyl-8-(2-fluoro-4-(2-(4-methylpiperazin-1-yl)ethoxy)phenyl)-6-(1-methyl-cyclopropoxy)-9H-purine | (400 MHz, DMSO-$d_6$): 0.85 (2H, s), 1.03 (2H, s), 1.73 (3H, s), 2.15 (3H, s), 2.22 – 2.38 (4H, m), 2.42 (4H, m), 2.71 (2H, m), 4.17 (2H, s), 5.38 (2H, s), 6.91 (3H, m), 7.06 (1H, d), 7.21 (3H, s), 7.47 (1H, t), 8.60 (1H, s). | 517 |

TABLE H-continued

| Ex # | Structure | Name | $^1$H NMR | LCMS [M + H]$^+$ |
|---|---|---|---|---|
| H3 | 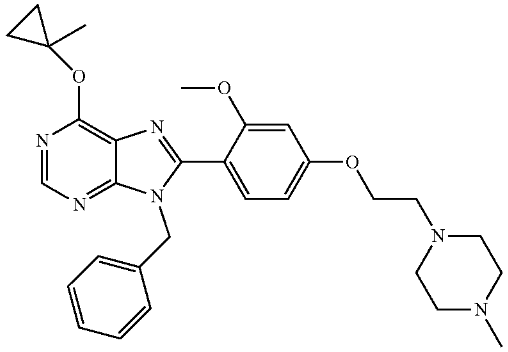 [SMILES: COc1cc(OCCN2CCN(C)CC2)ccc1-c1nc2c(OC3(C)CC3)ncnc2n1Cc1ccccc1] | 9-benzyl-8-(2-methoxy-4-(2-(4-methylpiperazin-1-yl)ethoxy) phenyl)-6-(1-methyl-cyclopropoxy)-9H-purine | (400 MHz, DMSO-$d_6$): 0.84 (2H, s), 1.01 (2H, s), 1.73 (3H, s), 2.16 (3H, s), 2.22 - 2.40 (4H, m), 2.67 - 2.74 (2H, m), 3.67 (3H, s), 4.16 (2H, s), 5.26 (2H, s), 6.62 - 6.67 (1H, d), 6.72 (1H, s), 6.87 - 6.94 (2H, m), 7.20 (3H, m), 7.27 (1H, d), 8.55 (1H, s) 4 H not observed | 529 |
| H4 | 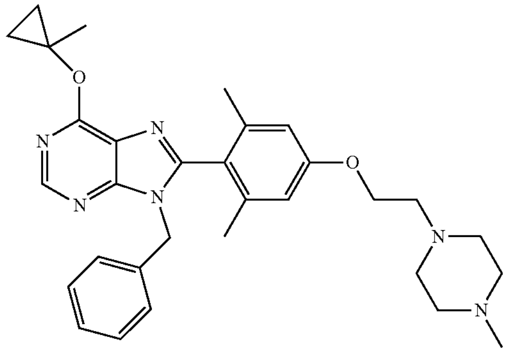 [SMILES: Cc1cc(OCCN2CCN(C)CC2)cc(C)c1-c1nc2c(OC3(C)CC3)ncnc2n1Cc1ccccc1] | 9-benzyl-8-(2,6-dimethyl-4-(2-(4-methylpiperazin-1-yl)ethoxy) phenyl)-6-(1-methyl-cyclopropoxy)-9H-purine | (400 MHz, DMSO-$d_6$): 0.78 - 0.88 (2H, m), 0.98 - 1.08 (2H, m), 1.70 (6H, s), 1.73 (3H, s), 2.15 (3H, s), 2.23 - 2.41 (4H, m), 2.54 (4H, s), 2.70 (2H, t), 4.12 (2H, t), 5.09 (2H, s), 6.75 (2H, s), 6.85 - 6.93 (2H, m), 7.14 - 7.28 (3H, m), 8.65 (1H, s). | 527 |
| H5 | 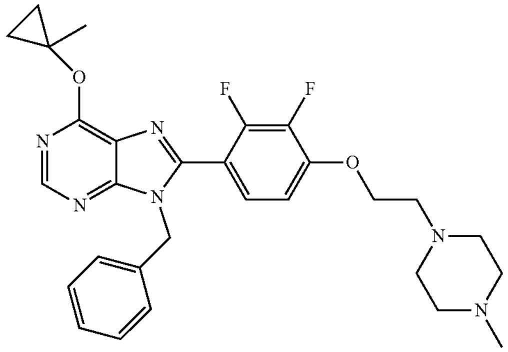 [SMILES: CN1CCN(CCOc2ccc(-c3nc4c(OC5(C)CC5)ncnc4n3Cc3ccccc3)c(F)c2F)CC1] | 9-benzyl-8-(2,3-difluoro-4-(2-(4-methylpiperazin-1-yl)ethoxy) phenyl)-6-(1-methyl-cyclopropoxy)-9H-purine | (400 MHz, DMSO-$d_6$): 0.81 - 0.88 (2H, m), 0.99 - 1.06 (2H, m), 1.73 (3H, s), 2.14 (3H, s), 2.30 (4H, s), 2.47-2.52 (4H, m), 2.73 (2H, t), 4.27 (2H, t), 5.41 (2H, s), 6.88 - 6.95 (2H, m), 7.21 (4H, td), 7.33 (1H, td), 8.62 (1H, s). | 535 |
| H6 | 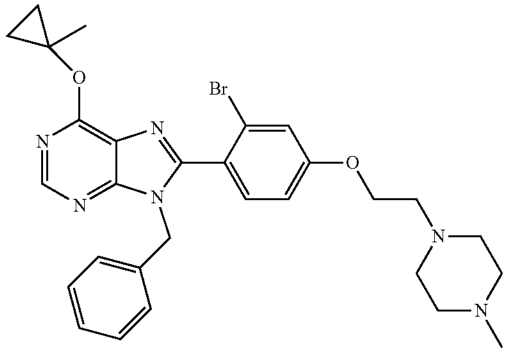 | 9-benzyl-8-(2-bromo-4-(2-(4-methylpiperazin-1-yl)ethoxy)phenyl)-6-(1-methyl-cyclopropoxy)-9H-purine | (400 MHz, DMSO-$d_6$): 0.88 (2H, m), 1.02 (2H, s), 1.73 (3H, s), 2.14 (3H, s), 2.33 (4H, dt), 2.48 (4H, s), 2.70 (2H, t), 4.18 (2H, t), 5.27 (2H, s), 6.91 (2H, dd), 7.06 (1H, dd), 7.20 (3H, ddt), 7.32 - 7.42 (2H, m), 8.61 (1H, s). | 577 |

TABLE H-continued

| Ex # | Structure | Name | $^1$H NMR | LCMS [M + H]$^+$ |
|---|---|---|---|---|
| H7 | 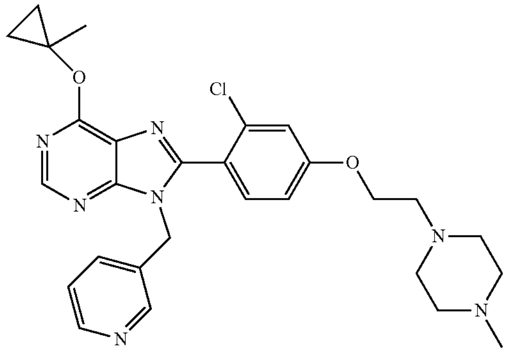 [SMILES: CN1CCN(CCOc2ccc(-c3nc4c(OC5(C)CC5)ncnc4n3Cc3cccnc3)c(Cl)c2)CC1] | 8-(2-chloro-4-(2-(4-methylpiperazin-1-yl)ethoxy)phenyl)-6-(1-methyl-cyclopropoxy)-9-(pyridin-3-ylmethyl)-9H-purine | (400 MHz, DMSO-$d_6$): 0.85 (2H, d), 0.98 – 1.07 (2H, m), 1.73 (3H, s), 2.14 (3H, s), 2.25 – 2.38 (4H, m), 2.45 (4H, d), 2.70 (2H, t), 4.18 (2H, t), 5.32 (2H, s), 7.06 (1H, dd), 7.19 – 7.28 (2H, m), 7.34 (1H, dt), 7.45 (1H, d), 8.16 (1H, d), 8.41 (1H, dd), 8.62 (1H, s) | 534 |
| H8 | 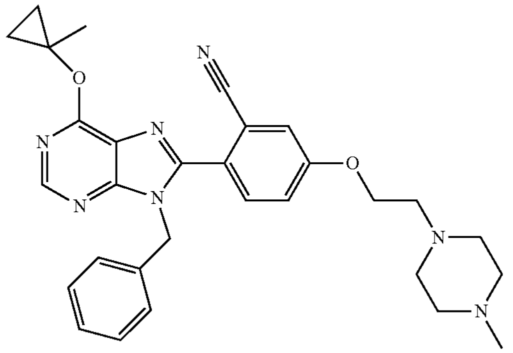 [SMILES: CN1CCN(CCOc2ccc(-c3nc4c(OC5(C)CC5)ncnc4n3Cc3ccccc3)c(C#N)c2)CC1] | 2-(9-benzyl-6-(1-methyl-cyclopropoxy)-9H-purin-8-yl)-5-(2-(4-methylpiperazin-1-yl)ethoxy) benzonitrile | (400 MHz, DMSO-$d_6$): 0.86 (2H, d), 1.03 (2H, d), 1.74 (3H, s), 2.14 (3H, s), 2.23 – 2.37 (4H, m), 2.47 (4H, d), 2.70 (2H, t), 4.22 (2H, t), 5.43 (2H, s), 6.88 (2H, dd), 7.17 – 7.27 (3H, m), 7.39 (1H, dd), 7.62 (1H, d), 7.67 (1H, d), 8.65 (1H, s). | 524 |
| H9 | 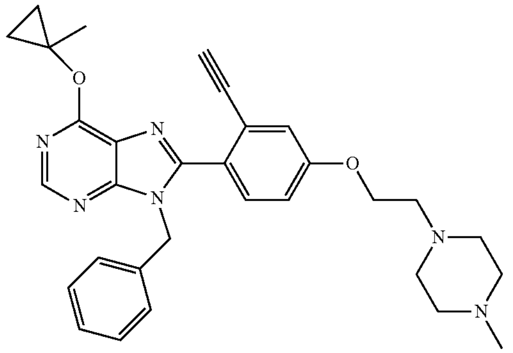 [SMILES: C#Cc1cc(OCCN2CCN(C)CC2)ccc1-c1nc2c(OC3(C)CC3)ncnc2n1Cc1ccccc1] | 9-benzyl-8-(2-ethynyl-4-(2-(4-methylpiperazin-1-yl)ethoxy)phenyl)-6-(1-methyl-cyclopropoxy)-9H-purine | (400 MHz, DMSO-$d_6$): 0.80 – 0.87 (2H, m), 0.98 – 1.05 (2H, m), 1.73 (3H, s), 2.14 (3H, s), 2.31 (4H, s), 2.49 (4H, d), 2.69 (2H, t), 4.17 (2H, t), 4.22 (1H, s), 5.35 (2H, s), 6.85 – 6.90 (2H, m), 7.09 (1H, dd), 7.18 (3H, ddt), 7.24 (1H, d), 7.35 (1H, d), 8.59 (1H, s). | 523 |
| H10 | 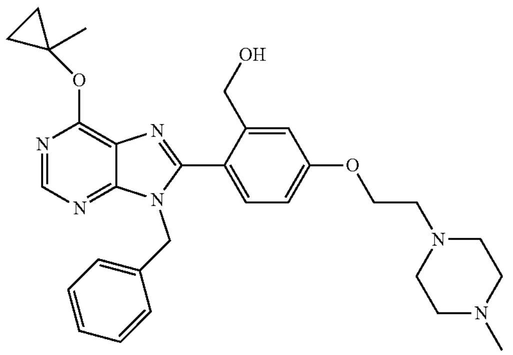 [SMILES: CN1CCN(CCOc2ccc(-c3nc4c(OC5(C)CC5)ncnc4n3Cc3ccccc3)c(CO)c2)CC1] | (2-(9-benzyl-6-(1-methyl-cyclopropoxy)-9H-purin-8-yl)-5-(2-(4-methylpiperazin-1-yl)ethoxy) phenyl) methanol | (400 MHz, DMSO-$d_6$): 0.80 – 0.89 (2H, m), 0.98 – 1.09 (2H, m), 1.73 (3H, s), 2.14 (3H, s), 2.32 (4H, s), 2.47 (4H, d), 2.71 (2H, t), 4.14 (2H, t), 4.26 (2H, s), 5.19 (1H, s), 5.30 (2H, s), 6.86 – 6.97 (3H, m), 7.15 – 7.27 (5H, m), 8.58 (1H, s). | 529 |

TABLE H-continued

| Ex # | Structure | Name | $^1$H NMR | LCMS [M + H]$^+$ |
|---|---|---|---|---|
| H11 | 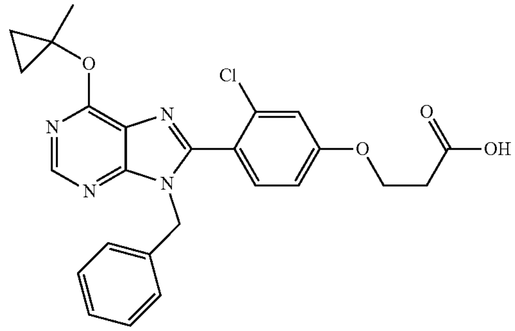 [SMILES: CC1(Oc2ncnc3c2nc(-c2ccc(OCCC(=O)O)cc2Cl)n3Cc2ccccc2)CC1] | 3-(4-(9-benzyl-6-(1-methyl-cyclopropoxy)-9H-purin-8-yl)-3-chlorophenoxy) propanoic acid | (400 MHz, DMSO-d$_6$): 0.80 – 0.92 (2H, m), 1.01 (2H, d), 1.73 (3H, s), 2.68 (2H, t), 4.27 (2H, t), 5.29 (2H, s), 6.90 (2H, dd), 7.02 (1H, dd), 7.16 – 7.25 (4H, m), 7.40 (1H, d), 8.62 (1H, s). One proton not observed. | 479 |
| H12 | 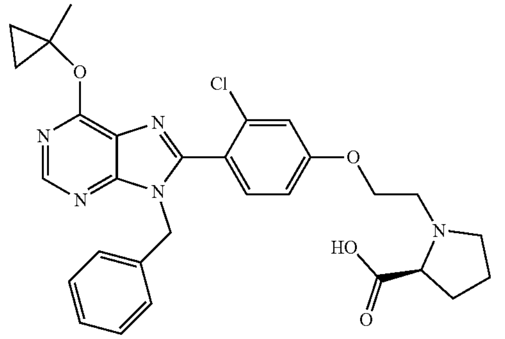 [SMILES: CC1(Oc2ncnc3c2nc(-c2ccc(OCCN4CCC[C@H]4C(=O)O)cc2Cl)n3Cc2ccccc2)CC1] | (2-(4-(9-benzyl-6-(1-methyl-cyclopropoxy)-9H-purin-8-yl)-3-chlorophenoxy) ethyl)-L-proline | (400 MHz, DMSO-d$_6$): 0.73 (2H, t), 0.88 (2H, t), 1.56-1.64 (4H, m), 1.7 – 1.85 (2H, m), 1.98 – 2.1 (1H, m), 2.7 – 2.83 (1H, m), 3.08 – 3.19 (1H, m), 3.24 – 3.34 (2H, m), 3.45 – 3.52 (1H, m), 4.19 (2H, t), 5.17 (2H, s), 6.77 (2H, dd), 6.92 (1H, dd), 7.06 – 7.13 (4H, m), 7.30 (1H, d), 8.48 (1H, s). One proton not observed. | 548 |
| H13 | 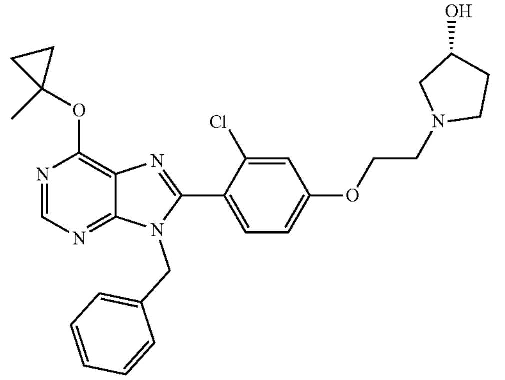 [SMILES: CC1(Oc2ncnc3c2nc(-c2ccc(OCCN4CC[C@@H](O)C4)cc2Cl)n3Cc2ccccc2)CC1] | (R)-1-(2-(4-(9-benzyl-6-(1-methyl-cyclopropoxy)-9H-purin-8-yl)-3-chlorophenoxy) ethyl)pyrrolidin-3-ol | (400 MHz, DMSO-d$_6$): 0.84 (2H, t), 1.01 (2H, t), 1.48 – 1.58 (1H, m), 1.73 (3H, s), 1.91 – 2.03 (1H, m), 2.37 – 2.43 (1H, m), 2.51 – 2.55 (1H, m), 2.61 – 2.7 (1H, m), 2.73 – 2.82 (3H, m), 4.12 – 4.23 (3H, m), 4.69 (1H, d), 5.29 (2H, s), 6.85 – 6.92 (2H, m), 7.03 (1H, dd), 7.18 – 7.22 (3H, m), 7.24 (1H, d), 7.40 (1H, d), 8.61 (1H, s). | 520 |
| H14 | 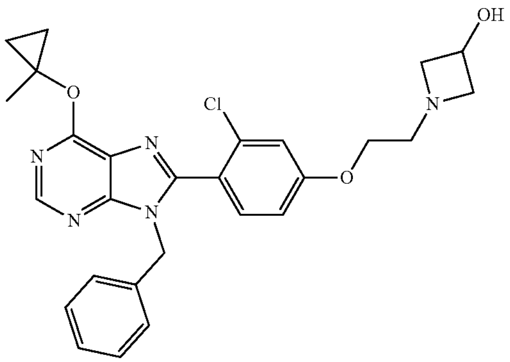 [SMILES: CC1(Oc2ncnc3c2nc(-c2ccc(OCCN4CC(O)C4)cc2Cl)n3Cc2ccccc2)CC1] | 1-(2-(4-(9-benzyl-6-(1-methyl-cyclopropoxy)-9H-purin-8-yl)-3-chlorophenoxy) ethyl)azetidin-3-ol | (400 MHz, DMSO-d$_6$): 0.84 (2H, t), 1.02 (2H, t), 1.73 (3H, s), 2.68 – 2.86 (4H, m), 3.51 – 3.62 (2H, m), 4.03 (2H, t), 4.11 – 4.23 (1H, m), 5.21 – 5.34 (3H, m), 6.86 – 6.94 (2H, m), 6.97 – 7.05 (1H, m), 7.15 – 7.26 (4H, m), 7.40 (1H, d), 8.61 (1H, s). | 506 |

TABLE H-continued

| Ex # | Structure | Name | $^1$H NMR | LCMS [M + H]$^+$ |
| --- | --- | --- | --- | --- |
| H15 | 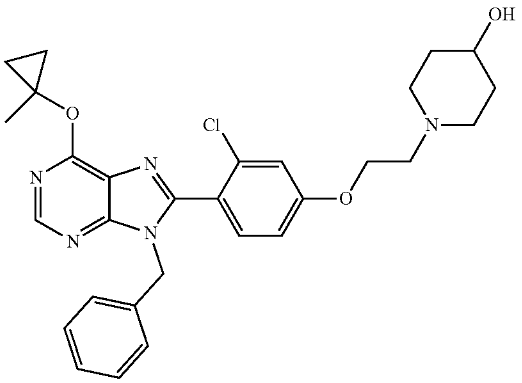 [SMILES: CC1(Oc2ncnc3c2nc(-c2ccc(OCCN4CCC(O)CC4)cc2Cl)n3Cc2ccccc2)CC1] | 1-(2-(4-(9-benzyl-6-(1-methyl-cyclopropoxy)-9H-purin-8-yl)-3-chlorophenoxy)ethyl)piperidin-4-ol | (400 MHz, DMSO-d$_6$): 0.84 (2H, t), 1.01 (2H, t), 1.34 – 1.43 (2H, m), 1.67 – 1.75 (5H, m), 2.08-2.18 (2H, m), 2.68 (2H, t), 2.74 – 2.83 (2H, m), 3.38 – 3.5 (1H, m), 4.16 (2H, t), 4.54 (1H, d), 5.29 (2H, s), 6.89-6.92 (2H, m), 7.03 (1H, dd), 7.18 – 7.22 (3H, m), 7.25 (1H, d), 7.40 (1H, d), 8.61 (1H, s). | 534 |
| H16 | 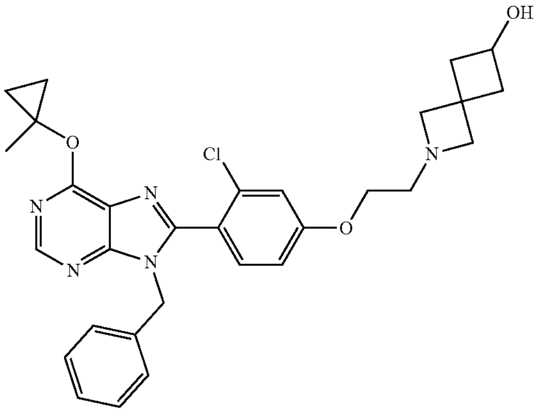 [SMILES: CC1(Oc2ncnc3c2nc(-c2ccc(OCCN4CC5(CC(O)C5)C4)cc2Cl)n3Cc2ccccc2)CC1] | 2-(2-(4-(9-benzyl-6-(1-methyl-cyclopropoxy)-9H-purin-8-yl)-3-chlorophenoxy)ethyl)-2-azaspiro[3.3]heptan-6-ol | (400 MHz, DMSO-d$_6$): 0.85 (2H, t), 1.01 (2H, t), 1.73 (3H, s), 1.81 – 1.91 (2H, m), 2.27 – 2.35 (2H, m), 2.69 (2H, t), 3.09 – 3.17 (4H, m), 3.89 – 3.95 (1H, m), 4.00 (2H, t), 4.92 (1H, t), 5.28 (2H, s), 6.85 – 6.93 (2H, m), 6.99 (1H, dd), 7.17 – 7.22 (4H, m), 7.39 (1H, d), 8.61 (1H, s). | 546 |
| H17 | 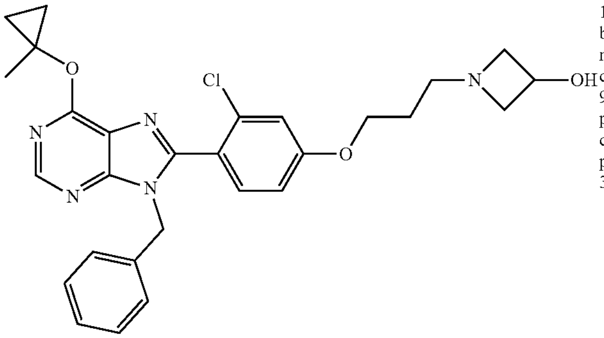 [SMILES: CC1(Oc2ncnc3c2nc(-c2ccc(OCCCN4CC(O)C4)cc2Cl)n3Cc2ccccc2)CC1] | 1-(3-(4-(9-benzyl-6-(1-methyl-cyclopropoxy)-9H-purin-8-yl)-3-chlorophenoxy)propyl)azetidin-3-ol | (400 MHz, DMSO-d$_6$): 0.84 (2H, t), 1.01 (2H, t), 1.70 – 1.77 (5H, m), 2.46 – 2.5 (2H, m), 2.59 – 2.73 (2H, m), 3.43 – 3.56 (2H, m), 4.07 (2H, t), 4.10 – 4.21 (1H, m), 5.12 – 5.39 (3H, m), 6.86 – 6.92 (2H, m), 7.00 – 7.08 (1H, m), 7.16 – 7.23 (4H, m), 7.39 (1H, d), 8.61 (1H, s). | 520 |
| H18 | 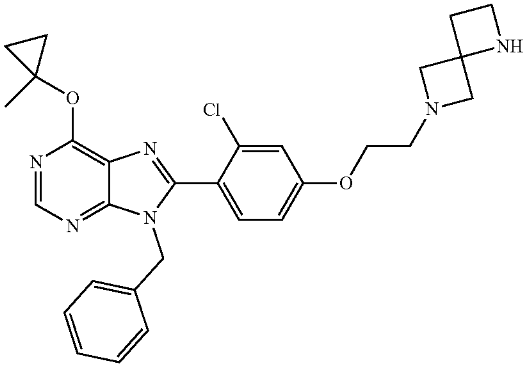 [SMILES: CC1(Oc2ncnc3c2nc(-c2ccc(OCCN4CC5(CCN5)C4)cc2Cl)n3Cc2ccccc2)CC1] | 8-(4-(2-(1,6-diazaspiro[3.3]heptan-6-yl)ethoxy)-2-chlorophenyl)-9-benzyl-6-(1-methyl-cyclopropoxy)-9H-purine | (300 MHz, CD$_3$OD): 0.87 (2H, t), 1.12 (2H, t), 1.81 (3H, s), 2.55 (2H, t), 2.90 (2H, t), 3.33 – 3.36 (2H, m), 3.44 (2H, t), 3.62 – 3.73 (2H, m), 4.10 (2H, t), 5.39 (2H, s), 6.87 – 6.94 (2H, m), 6.91 – 6.99 (1H, m), 7.16 – 7.21 (4H, m), 7.24 (1H, d), 8.62 (1H, s).One proton not observed. | 531 |

TABLE H-continued

| Ex # | Structure | Name | $^1$H NMR | LCMS $[M + H]^+$ |
|---|---|---|---|---|
| H19 | 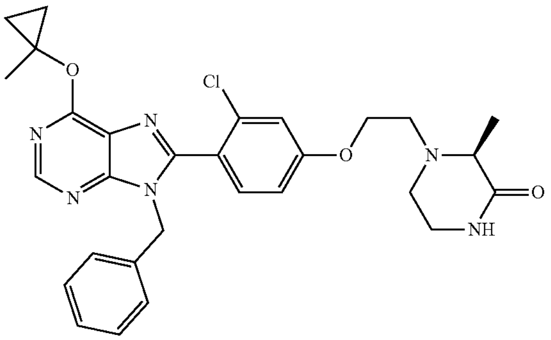 [SMILES: C[C@H]1C(=O)NCCN1CCOc1ccc(-c2nc3c(OC4(C)CC4)ncnc3n2Cc2ccccc2)c(Cl)c1] | (S)-4-(2-(4-(9-benzyl-6-(1-methylcyclopropoxy)-9H-purin-8-yl)-3-chlorophenoxy)ethyl)-3-methylpiperazin-2-one | (300 MHz, DMSO-$d_6$): 0.85 (2H, t), 1.01 (2H, t), 1.24 (3H, d), 1.73 (3H, s), 2.58 – 2.66 (1H, m), 2.77 – 2.83 (1H, m), 2.94 – 3.03 (2H, m), 3.09 – 3.17 (3H, m), 4.18 – 4.23 (2H, m), 5.29 (2H, s), 6.87 – 6.93 (2H, m), 7.04 (1H, dd), 7.19 – 7.22 (3H, m), 7.26 (1H, d), 7.41 (1H, d), 7.69 (1H, s), 8.62 (1H, s). | 547 |
| H20 | 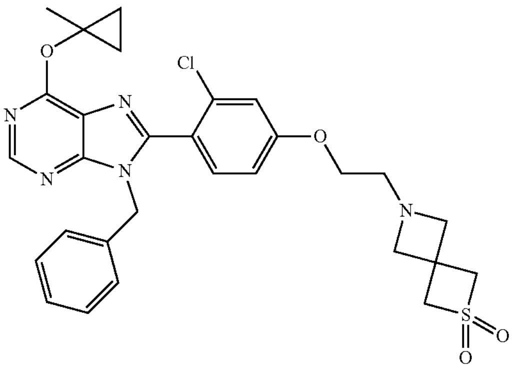 [SMILES: CC1(Oc2ncnc3c2nc(-c2ccc(OCCN4CC5(C4)CS(=O)(=O)C5)cc2Cl)n3Cc2ccccc2)CC1] | 6-(2-(4-(9-benzyl-6-(1-methyl-cyclopropoxy)-9H-purin-8-yl)-3-chlorophenoxy)ethyl)-2-thia-6-azaspiro[3.3]heptane 2,2-dioxide | (400 MHz, DMSO-$d_6$): 0.85 (2H, t), 1.01 (2H, t), 1.73 (3H, s), 2.78 (2H, t), 3.39 – 3.45 (4H, m), 4.05 (2H, t), 4.32 (4H, s), 5.29 (2H, s), 6.88 – 6.92 (2H, m), 6.98 – 7.04 (1H, m), 7.19 – 7.22 (4H, m), 7.41 (1H, d), 8.61 (1H, s). | 580 |
| H21 | 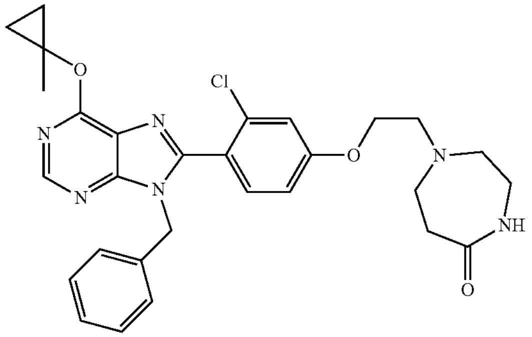 [SMILES: CC1(Oc2ncnc3c2nc(-c2ccc(OCCN4CCNC(=O)CC4)cc2Cl)n3Cc2ccccc2)CC1] | 1-(2-(4-(9-benzyl-6-(1-methyl-cyclopropoxy)-9H-purin-8-yl)-3-chlorophenoxy)ethyl)-1,4-diazepan-5-one | (400 MHz, DMSO-$d_6$): 0.85 (2H, t), 1.01 (2H, t), 1.73 (3H, s), 2.38 – 2.44 (2H, m), 2.6 – 2.68 (4H, m), 2.85 (2H, t), 3.07 – 3.17 (2H, m), 4.19 (2H, t), 5.29 (2H, s), 6.89 – 6.93 (2H, m), 7.04 (1H, dd), 7.17 – 7.23 (3H, m), 7.25 (1H, d), 7.41 (1H, d), 7.54 (1H, t), 8.61 (1H, s). | 547 |
| H22 | 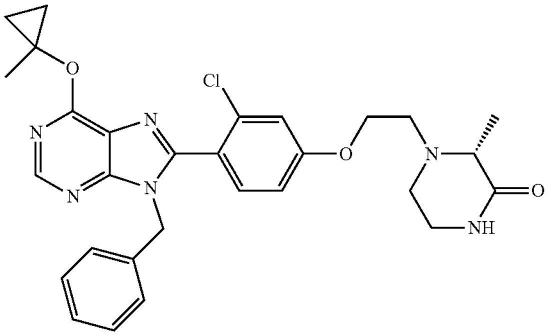 [SMILES: C[C@@H]1C(=O)NCCN1CCOc1ccc(-c2nc3c(OC4(C)CC4)ncnc3n2Cc2ccccc2)c(Cl)c1] | (R)-4-(2-(4-(9-benzyl-6-(1-methyl-cyclopropoxy)-9H-purin-8-yl)-3-chlorophenoxy)ethyl)-3-methylpiperazin-2-one | (400 MHz, DMSO-$d_6$): 0.84 (2H, t), 1.01 (2H, t), 1.24 (3H, d), 1.73 (3H, s), 2.57 – 2.67 (1H, m), 2.76 – 2.84 (1H, m), 2.93 – 3.03 (2H, m), 3.06 – 3.16 (3H, m), 4.17 – 4.23 (2H, m), 5.29 (2H, s), 6.87 – 6.92 (2H, m), 7.04 (1H, dd), 7.18 – 7.21 (3H, m), 7.26 (1H, d), 7.41 (1H, d), 7.67 (1H, s), 8.61 (1H, s) | 547 |

TABLE H-continued

| Ex # | Structure | Name | $^1H$ NMR | LCMS $[M + H]^+$ |
|---|---|---|---|---|
| H23 | 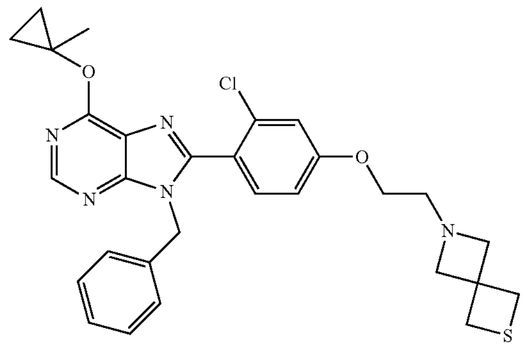 [SMILES: CC1(Oc2ncnc3c2nc(-c2ccc(OCCN4CC5(CSC5)C4)cc2Cl)n3Cc2ccccc2)CC1] | 6-(2-(4-(9-benzyl-6-(1-methyl-cyclopropoxy)-9H-purin-8-yl)-3-chlorophenoxy) ethyl)-2-thia-6-azaspiro[3.3]heptane | (400 MHz, DMSO-$d_6$): 0.85 (2H, t), 1.03 (2H, t), 1.73 (3H, s), 2.70 (2H, t), 3.23 – 3.29 (8H, m), 4.03 (2H, t), 5.29 (2H, s), 6.87-6.93 (2H, m), 6.98 – 7.03 (1H, m), 7.17 – 7.24 (4H, m), 7.37 – 7.44 (1H, m), 8.61 (1H, s) | 548 |

[H1] was prepared as follows:

2,6-Difluoro-4-(2-(4-methylpiperazin-1-yl)ethoxy)benzaldehyde (126 mg, 0.44 mmol) was added to N4-benzyl-6-(1-methylcyclopropoxy)pyrimidine-4,5-diamine (100 mg, 0.37 mmol, Example 4 Intermediate) in DMSO (1 mL). The resulting mixture was stirred at 120° C. for 2 days. The solvent was removed under reduced pressure. The crude product was purified by preparative HPLC; Column: XBridge Prep OBD C18 Column, 30*150 mm, 5 μm, using decreasingly polar mixtures of water (containing 10 mmol/L $NH_4HCO_3$ and 0.1% conc. aqueous ammonia) and MeCN. Fractions containing the desired compound were evaporated to dryness to afford 9-benzyl-8-(2,6-difluoro-4-(2-(4-methylpiperazin-1-yl)ethoxy)phenyl)-6-(1-methylcyclopropoxy)-9H-purine (27 mg, 14%) as a red solid.

2,6-Difluoro-4-(2-(4-methylpiperazin-1-yl)ethoxy)benzaldehyde used as starting material was made as follows:

Tert-butyl 4-(2-(3,5-difluoro-4-formylphenoxy)ethyl)piperazine-1-carboxylate was made from a similar procedure as tert-butyl 4-(2-(3-chloro-4-formylphenoxy)ethyl)piperazine-1-carboxylate (Example 4, intermediate), using 2,6-difluoro-4-hydroxybenzaldehyde and tert-butyl 4-(2-chloroethyl)piperazine-1-carboxylate as starting materials. $^1H$ NMR (400 MHz, DMSO-$d_6$): 1.40 (9H, s), 2.43 (4H, t), 2.73 (2H, t), 4.23 (2H, t), 6.91 (2H, d), 10.07 (1H, s). 4 protons not observed. m/z: ES+ [M+H]+ 371.

2,6-Difluoro-4-(2-(4-methylpiperazin-1-yl)ethoxy)benzaldehyde was made from a similar procedure as 2-chloro-4-(2-(4-methylpiperazin-1-yl)ethoxy)benzaldehyde (Example 4, intermediate), using tert-butyl 4-(2-(3,5-difluoro-4-formylphenoxy)ethyl)piperazine-1-carboxylate as starting material. $^1H$ NMR (300 MHz, DMSO-$d_6$): 2.12 (3H, s), 2.28 (4H, s), 2.43 (4H, s), 2.66 (2H, t), 4.19 (2H, t), 6.85-6.93 (2H, m), 10.05 (1H, s). m/z: ES+ [M+H]+ 285.

[H2] made from a similar procedure as 9-benzyl-8-(2,6-difluoro-4-(2-(4-methylpiperazin-1-yl)ethoxy)phenyl)-6-(1-methylcyclopropoxy)-9H-purine (Example H1), using N4-benzyl-6-(1-methylcyclopropoxy)pyrimidine-4,5-diamine (Example 4, intermediate) and 2-fluoro-4-(2-(4-methylpiperazin-1-yl)ethoxy)benzaldehyde as starting materials. 2-Fluoro-4-(2-(4-methylpiperazin-1-yl)ethoxy)benzaldehyde made from a similar procedure as 2-chloro-4-(2-(4-methylpiperazin-1-yl)ethoxy)benzaldehyde (Example 4, intermediate), using tert-butyl 4-(2-(3-fluoro-4-formylphenoxy)ethyl)piperazine-1-carboxylate as starting material. $^1H$ NMR (300 MHz, DMSO-$d_6$): 2.12 (3H, s), 2.29 (4H, s), 2.47 (4H, s), 2.68 (2H, t), 4.18 (2H, t), 6.93 (1H, m), 7.00 (1H, m), 7.75 (1H, t), 10.05 (1H, s). m/z: ES+ [M+H]+ 267.

Tert-butyl 4-(2-(3-fluoro-4-formylphenoxy)ethyl)piperazine-1-carboxylate was made from a similar procedure as tert-butyl 4-(2-(3-chloro-4-formylphenoxy)ethyl)piperazine-1-carboxylate (Example 4, intermediate), using 2-fluoro-4-hydroxybenzaldehyde and tert-butyl 4-(2-chloroethyl)piperazine-1-carboxylate as starting materials. $^1H$ NMR (400 MHz, DMSO-$d_6$): 1.40 (9H, s), 2.44 (4H, t), 2.74 (2H, t), 4.23 (2H, t), 6.96 (1H, m), 7.03 (1H, m), 7.78 (1H, t), 10.08 (1H, s). 4 protons not observed. m/z: ES+ [M+H]+ 353.

[H3] made from a similar procedure as 9-benzyl-8-(2,6-difluoro-4-(2-(4-methylpiperazin-1-yl)ethoxy)phenyl)-6-(1-methylcyclopropoxy)-9H-purine (Example H1) using N4-benzyl-6-(1-methylcyclopropoxy)pyrimidine-4,5-diamine (Example 4, intermediate) and 2-methoxy-4-(2-(4-methylpiperazin-1-yl)ethoxy)benzaldehyde as starting materials. 2-Methoxy-4-(2-(4-methylpiperazin-1-yl)ethoxy) benzaldehyde made from a similar procedure as 2,6-difluoro-4-(2-(4-methylpiperazin-1-yl)ethoxy)benzaldehyde (Example H1, intermediate), using tert-butyl 4-(2-(4-formyl-3-methoxyphenoxy)ethyl)piperazine-1-carboxylate as starting material. $^1H$ NMR (300 MHz, DMSO-$d_6$): 2.13 (3H, s), 2.30 (4H, s), 2.47 (4H, s), 2.68 (2H, t), 3.89 (3H, s), 4.18 (2H, t), 6.63 (1H, m), 6.68 (1H, d), 7.63 (1H, d), 10.16 (1H, s). m/z: ES+ [M+H]+ 279.

Tert-butyl 4-(2-(4-formyl-3-methoxyphenoxy)ethyl)piperazine-1-carboxylate was made from a similar procedure as tert-butyl 4-(2-(3,5-difluoro-4-formylphenoxy)ethyl)piperazine-1-carboxylate (Example H1, intermediate), using 4-hydroxy-2-methoxybenzaldehyde and tert-butyl 4-(2-chloroethyl)piperazine-1-carboxylate as starting materials. $^1H$ NMR (400 MHz, DMSO-$d_6$): 1.40 (9H, s), 2.45 (4H, t), 2.74 (2H, t), 3.91 (3H, s), 4.22 (2H, t), 6.64-6.68 (1H, m), 6.70 (1H, d), 7.65 (1H, d), 10.18 (1H, s). 4 protons not observed. m/z: ES+ [M+H]+ 365.

[H4] made from a similar procedure as 9-benzyl-8-(2,6-difluoro-4-(2-(4-methylpiperazin-1-yl)ethoxy)phenyl)-6-(1-methylcyclopropoxy)-9H-purine (Example H1) using N4-benzyl-6-(1-methylcyclopropoxy)pyrimidine-4,5-diamine (Example 4, intermediate) and 2,6-dimethyl-4-(2-(4-methylpiperazin-1-yl)ethoxy)benzaldehyde as starting materials. 2,6-Dimethyl-4-(2-(4-methylpiperazin-1-yl) ethoxy)benzaldehyde was made from a similar procedure as 2,6-difluoro-4-(2-(4-methylpiperazin-1-yl)ethoxy)benzaldehyde (Example H1, intermediate), using tert-butyl 4-(2-

(4-formyl-3,5-dimethylphenoxy)ethyl)piperazine-1-carboxylate as starting material. $^1$H NMR (300 MHz, DMSO-$d_6$): 2.12 (3H, s), 2.29 (4H, s), 2.44 (4H, s), 2.52 (6H, s), 2.66 (2H, t), 4.12 (2H, t), 6.72 (2H, s), 10.35 (1H, s). m/z: ES+ [M+H]+ 277.

Tert-butyl 4-(2-(4-formyl-3,5-dimethylphenoxy)ethyl) piperazine-1-carboxylate was made from a similar procedure as tert-butyl 4-(2-(3,5-difluoro-4-formylphenoxy) ethyl)piperazine-1-carboxylate (Example H1, intermediate), using 4-hydroxy-2,6-dimethylbenzaldehyde and tert-butyl 4-(2-chloroethyl)piperazine-1-carboxylate as starting materials. $^1$H NMR (400 MHz, DMSO-$d_6$): 1.40 (9H, s), 2.44 (4H, t), 2.55 (6H, s), 2.72 (2H, t), 4.17 (2H, t), 6.74 (2H, s), 10.38 (1H, s). 4 protons not observed. m/z: ES+ [M+H]+ 363.

[H5] made from a similar procedure as 9-benzyl-8-(2,6-difluoro-4-(2-(4-methylpiperazin-1-yl)ethoxy)phenyl)-6-(1-methylcyclopropoxy)-9H-purine (Example H1) using N4-benzyl-6-(1-methylcyclopropoxy)pyrimidine-4,5-diamine (Example 4, intermediate) and 2,3-difluoro-4-(2-(4-methylpiperazin-1-yl)ethoxy)benzaldehyde as starting materials. 2,3-Difluoro-4-(2-(4-methylpiperazin-1-yl) ethoxy)benzaldehyde made from a similar procedure as 2,6-difluoro-4-(2-(4-methylpiperazin-1-yl)ethoxy)benzaldehyde (Example H1, intermediate), using tert-butyl 4-(2-(2,3-difluoro-4-formylphenoxy)ethyl)piperazine-1-carboxylate as starting material. $^1$H NMR (300 MHz, DMSO-$d_6$): 2.14 (3H, s), 2.30 (4H, s), 2.50 (4H, s), 2.74 (2H, t), 4.32 (2H, t), 7.26 (1H, m), 7.67 (1H, m), 10.05 (1H, s). m/z: ES+ [M+H]+ 285.

Tert-butyl 4-(2-(2,3-difluoro-4-formylphenoxy)ethyl)piperazine-1-carboxylate was made from a similar procedure as tert-butyl 4-(2-(3,5-difluoro-4-formylphenoxy)ethyl)piperazine-1-carboxylate (Example H1, intermediate), using 2,3-difluoro-4-hydroxybenzaldehyde and tert-butyl 4-(2-chloroethyl)piperazine-1-carboxylate as starting materials. $^1$H NMR (400 MHz, DMSO-$d_6$): 1.39 (9H, s), 2.44 (4H, s), 2.78 (2H, m), 4.34 (2H, m), 7.26 (1H, t), 7.67 (1H, t), 10.04 (1H, s). 4 protons not observed. m/z: ES+ [M+H]+ 371.

[H6] made from a similar procedure as 9-benzyl-8-(2,6-difluoro-4-(2-(4-methylpiperazin-1-yl)ethoxy)phenyl)-6-(1-methylcyclopropoxy)-9H-purine (Example H1) using N4-benzyl-6-(1-methylcyclopropoxy)pyrimidine-4,5-diamine (Example 4, intermediate) and 2-bromo-4-(2-(4-methylpiperazin-1-yl)ethoxy)benzaldehyde as starting materials.

2-Bromo-4-(2-(4-methylpiperazin-1-yl)ethoxy)benzaldehyde made from a similar procedure as 2,6-difluoro-4-(2-(4-methylpiperazin-1-yl)ethoxy)benzaldehyde (Example H1, intermediate), using tert-butyl 4-(2-(3-bromo-4-formylphenoxy)ethyl)piperazine-1-carboxylate as starting material. $^1$H NMR (300 MHz, DMSO-$d_6$): 2.12 (3H, s), 2.29 (4H, s), 2.45 (4H, s), 2.67 (2H, t), 4.20 (2H, t), 7.11 (1H, m), 7.36 (1H, d), 7.79 (1H, d), 10.07 (1H, s). m/z: ES+ [M+H]+ 327.

Tert-butyl 4-(2-(3-bromo-4-formylphenoxy)ethyl)piperazine-1-carboxylate was made from a similar procedure as tert-butyl 4-(2-(3,5-difluoro-4-formylphenoxy)ethyl)piperazine-1-carboxylate (Example H1, intermediate), using 2-bromo-4-hydroxybenzaldehyde and tert-butyl 4-(2-chloroethyl)piperazine-1-carboxylate as starting materials $^1$H NMR (400 MHz, DMSO-$d_6$): 1.40 (9H, s), 2.44 (4H, t), 2.74 (2H, t), 4.24 (2H, t), 7.14 (1H, m), 7.38 (1H, d), 7.81 (1H, d), 10.09 (1H, m). 4 protons not observed. m/z: ES+ [M+H]+ 413.

[H7] was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example H1), using 6-(1-methylcyclopropoxy)-5-nitro-N-(pyridin-2-ylmethyl)pyrimidin-4-amine (Example E5, intermediate) and 2-chloro-4-(2-(4-methylpiperazin-1-yl)ethoxy)benzaldehyde (Example 4, intermediate) as starting materials.

[H8] was synthesized as follows:

Sodium triacetoxyborohydride (46.6 mg, 0.22 mmol) was added to 2-(9-benzyl-6-(1-methylcyclopropoxy)-9H-purin-8-yl)-5-(2-(piperazin-1-yl)ethoxy)benzonitrile, hydrochloride salt (30 mg, 0.05 mmol) in 37% aqueous formaldehyde solution (1 mL). The resulting mixture was stirred at room temperature for 1 hour. The solvent was removed under reduced pressure. The crude product was purified by preparative HPLC (XBridge Prep OBD C18 column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 2-(9-benzyl-6-(1-methylcyclopropoxy)-9H-purin-8-yl)-5-(2-(4-methylpiperazin-1-yl)ethoxy)benzonitrile (12.0 mg, 42%) as a light yellow solid.

2-(9-Benzyl-6-(1-methylcyclopropoxy)-9H-purin-8-yl)-5-(2-(piperazin-1-yl)ethoxy)benzonitrile, hydrochloride salt was made from a similar procedure as Example 16, using tert-butyl 4-(2-(4-(9-benzyl-6-(1-methylcyclopropoxy)-9H-purin-8-yl)-3-cyanophenoxy)ethyl)piperazine-1-carboxylate as starting material and EtOAc as solvent. The crude product was used in next step without further purification. m/z: ES+ [M+H]+ 510.

Tert-butyl 4-(2-(4-(9-benzyl-6-(1-methylcyclopropoxy)-9H-purin-8-yl)-3-cyanophenoxy)ethyl)piperazine-1-carboxylate was made from a similar procedure as Example H1 using N4-benzyl-6-(1-methylcyclopropoxy)pyrimidine-4,5-diamine (Example 4, intermediate) and tert-butyl 4-(2-(3-cyano-4-formylphenoxy)ethyl)piperazine-1-carboxylate as starting materials. $^1$H NMR (400 MHz, DMSO-$d_6$): 0.87 (2H, d), 1.04 (2H, d), 1.40 (9H, s), 1.75 (3H, s), 2.45 (4H, t), 2.75 (2H, t), 3.30 (4H, s), 4.24 (2H, t), 5.44 (2H, s), 6.89 (2H, dd), 7.17-7.25 (3H, m), 7.41 (1H, dd), 7.57-7.79 (2H, m), 8.66 (1H, s). m/z: ES+ [M+H]+ 610.

Tert-butyl 4-(2-(3-cyano-4-formylphenoxy)ethyl)piperazine-1-carboxylate was made from a similar procedure as tert-butyl 4-(2-(3,5-difluoro-4-formylphenoxy)ethyl)piperazine-1-carboxylate (Example H1, intermediate), using 2-formyl-5-hydroxybenzonitrile and tert-butyl 4-(2-chloroethyl)piperazine-1-carboxylate as starting materials $^1$H NMR (400 MHz, DMSO-$d_6$): 1.40 (9H, s), 2.45 (4H, d), 2.76 (2H, t), 3.31 (4H, s), 4.29 (2H, t), 7.48 (1H, dd), 7.66 (1H, d), 8.04 (1H, d), 10.01 (1H, s). m/z: ES+ [M+H]+ 360.

[H9] was synthesized as follows:

TBAF (353 μL, 0.35 mmol, 1M in THF) was added to 9-benzyl-6-(1-methylcyclopropoxy)-8-(4-(2-(4-methylpiperazin-1-yl)ethoxy)-2-((triisopropylsilyl)ethynyl)phenyl)-9H-purine (200 mg, 0.29 mmol) in THF (3 mL) at room temperature. The resulting mixture was stirred at room temperature for 1 hour. The reaction mixture was concentrated and the resulting crude product was purified by preparative HPLC (XBridge Prep OBD C18 column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 9-benzyl-8-(2-ethynyl-4-(2-(4-methylpiperazin-1-yl) ethoxy)phenyl)-6-(1-methylcyclopropoxy)-9H-purine (0.024 g, 15%) as a brown solid.

9-Benzyl-6-(1-methylcyclopropoxy)-8-(4-(2-(4-methylpiperazin-1-yl)ethoxy)-2-((triisopropylsilyl)ethynyl)phenyl)-9H-purine was made from a similar procedure as Example H1 using N4-benzyl-6-(1-methylcyclopropoxy) pyrimidine-4,5-diamine (Example 4, intermediate) and 4-(2-(4-methylpiperazin-1-yl)ethoxy)-2-((triisopropylsilyl)ethynyl)benzaldehyde as starting materials. m/z: ES+ [M+H]+ 679.

4-(2-(4-Methylpiperazin-1-yl)ethoxy)-2-((triisopropylsilyl)ethynyl)benzaldehyde was synthesized as follows:

Bis(triphenylphosphine) palladium(II) dichloride (644 mg, 0.92 mmol) was added to 2-bromo-4-(2-(4-methylpiperazin-1-yl)ethoxy)benzaldehyde (Example H6 intermediate, 300 mg, 0.92 mmol), cuprous iodide (175 mg, 0.92 mmol) and (triisopropylsilyl)acetylene (334 mg, 1.83 mmol) in TEA (4 mL) at room temperature. The resulting mixture was stirred at room temperature for 1 hour. The reaction mixture was evaporated to dryness and redissolved in EtOAc (50 mL), and washed sequentially with water (50 mL×3) and saturated brine (50 mL×1). The organic layer was dried over $Na_2SO_4$, filtered and evaporated to afford crude product. The crude product was purified by flash silica chromatography, elution gradient 0 to 50% EtOAc in petroleum ether. Pure fractions were evaporated to dryness to afford 4-(2-(4-methylpiperazin-1-yl)ethoxy)-2-((triisopropylsilyl)ethynyl)benzaldehyde (0.300 g, 76%) as a pale yellow oil. $^1$H NMR (400 MHz, DMSO-$d_6$): 1.11 (21H, s), 2.16 (3H, s), 2.34 (5H, s), 2.51 (3H, s), 2.69 (2H, s), 4.22 (2H, s), 7.14 (2H, s), 7.78 (1H, s), 10.31 (1H, s). m/z: ES+ [M+H]+ 429.

[H10] was synthesized as follows:

$LiAlH_4$ (2.4 M in THF, 0.037 mL, 0.09 mmol) was added to methyl 2-(9-benzyl-6-(1-methylcyclopropoxy)-9H-purin-8-yl)-5-(2-(4-methylpiperazin-1-yl)ethoxy)benzoate (0.1 g, 0.18 mmol) in THF (3 mL) at 0° C. The resulting mixture was stirred at room temperature for 1 hour. The reaction mixture was quenched with water (5 mL) and the solvent removed under reduced pressure. The crude product was purified by preparative HPLC (XBridge Prep OBD C18 column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford (2-(9-benzyl-6-(1-methylcyclopropoxy)-9H-purin-8-yl)-5-(2-(4-methylpiperazin-1-yl)ethoxy)phenyl)methanol (0.031 g, 32%) as a white solid.

Methyl 2-(9-benzyl-6-(1-methylcyclopropoxy)-9H-purin-8-yl)-5-(2-(4-methylpiperazin-1-yl)ethoxy)benzoate was synthesized as follows:

$CH_3OH$ (5.0 mL) was added to 2-(9-benzyl-6-(1-methylcyclopropoxy)-9H-purin-8-yl)-5-(2-(4-methylpiperazin-1-yl)ethoxy)benzoic acid (700 mg, 1.29 mmol), HATU (736 mg, 1.93 mmol) and DIEA (676 μL, 3.87 mmol) in DMA (5 mL) at room temperature. The resulting mixture was stirred at room temperature for 1 hour. The reaction mixture was evaporated, EtOAc (100 mL) was added, and the organic layer washed sequentially with water (100 mL×3) and saturated brine (100 mL×1). The organic layer was dried over $Na_2SO_4$, filtered and evaporated to afford crude product. The crude product was purified by flash silica chromatography, elution gradient 0 to 10% MeOH in DCM. Pure fractions were evaporated to dryness to afford methyl 2-(9-benzyl-6-(1-methylcyclopropoxy)-9H-purin-8-yl)-5-(2-(4-methylpiperazin-1-yl)ethoxy)benzoate (0.600 g, 84%) as a brown gum. m/z: ES+ [M+H]+ 557.

2-(9-Benzyl-6-(1-methylcyclopropoxy)-9H-purin-8-yl)-5-(2-(4-methylpiperazin-1-yl)ethoxy)benzoic acid was made from a similar procedure as Example H1 using N4-benzyl-6-(1-methylcyclopropoxy)pyrimidine-4,5-diamine (Example 4, intermediate) and methyl 2-formyl-5-(2-(4-methylpiperazin-1-yl)ethoxy)benzoate as starting materials. m/z: ES+ [M+H]+ 543. Methyl 2-formyl-5-(2-(4-methylpiperazin-1-yl)ethoxy)benzoate was synthesized as follows: $PdCl_2$(dppf) (335 mg, 0.46 mmol), 2-bromo-4-(2-(4-methylpiperazin-1-yl)ethoxy)benzaldehyde (300 mg, 0.92 mmol; Example H6, intermediate) and TEA (383 μL, 2.75 mmol) in $CH_3OH$ (5 mL) were stirred under an atmosphere of carbon monoxide at 10 atm and 100° C. for 16 hours. The reaction mixture was concentrated and diluted with EtOAc (50 mL), and washed sequentially with water (50 mL×3) and saturated brine (50 mL×1). The organic layer was dried over $Na_2SO_4$, filtered and evaporated to afford the crude product. The crude product was purified by flash silica chromatography, elution gradient 0 to 10% MeOH in DCM. Pure fractions were evaporated to dryness to afford methyl 2-formyl-5-(2-(4-methylpiperazin-1-yl)ethoxy)benzoate (0.200 g, 71%) as a brown gum. m/z: ES+ [M+H]+ 307.

[H11] was obtained from the cyclisation of 3-(3-chloro-4-formylphenoxy)propanoic acid and N4-benzyl-6-(1-methylcyclopropoxy)pyrimidine-4,5-diamine (Example 4, intermediate synthesis), following the procedure described for the synthesis of 9-benzyl-8-(2,6-difluoro-4-(2-(4-methylpiperazin-1-yl)ethoxy)phenyl)-6-(1-methylcyclopropoxy)-9H-purine (Example H1). 3-(3-Chloro-4-formylphenoxy)propanoic acid was made through a Williamson ether synthesis of 3-bromopropanoic acid and 2-chloro-4-hydroxybenzaldehyde as follows: 2-chloro-4-hydroxybenzaldehyde (1.0 g, 6.39 mmol), 3-bromopropanoic acid (1.47 g, 9.58 mmol) and $K_2CO_3$ (2.65 g, 19.2 mmol) in MeCN (10 mL) were stirred at 80° C. for 12 hours. The solvent was removed under reduced pressure. The crude product was purified by flash C18-flash chromatography, elution gradient 5 to 100% MeCN in water (0.05% formic acid). Pure fractions were evaporated to dryness to afford 3-(3-chloro-4-formylphenoxy)propanoic acid (0.40 g, 27%) as a yellow solid. $^1$H NMR (300 MHz, DMSO-$d_6$): 2.72 (2H, t), 4.30 (2H, t), 7.08 (1H, dd), 7.19 (1H, d), 7.81 (1H, d), 10.18 (1H, d), 12.44 (1H, s). m/z: ES− [M−H]− 227.

[H12] was obtained from the cyclisation of (2-(3-chloro-4-formylphenoxy)ethyl)-L-proline and N4-benzyl-6-(1-methylcyclopropoxy)pyrimidine-4,5-diamine (Example 4, intermediate) in a similar procedure to Example P2.

(2-(3-Chloro-4-formylphenoxy)ethyl)-L-proline was made from methyl (2-(3-chloro-4-formylphenoxy)ethyl)-L-prolinate through an ester hydrolysis reaction similar to the reaction used to make (E)-3-(4-(9-benzyl-6-(1-methylcyclopropoxy)-9H-purin-8-yl)-3-chlorophenyl)acrylic acid (Example M4). $^1$H NMR (400 MHz, DMSO-$d_6$): 1.5-1.79 (3H, m), 1.88-2.07 (1H, m), 2.5-2.64 (1H, m), 2.88-3.01 (1H, m), 3.04-3.2 (2H, m), 3.22-3.34 (1H, m), 4.16 (2H, t), 6.96 (1H, dd), 7.07 (1H, d), 7.72 (1H, d), 10.08 (1H, s). One proton not observed. m/z: ES+ [M+H]+ 298.

Methyl (2-(3-chloro-4-formylphenoxy)ethyl)-L-prolinate was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purine (Example R3), using methyl L-prolinate hydrochloride and 4-(2-bromoethoxy)-2-chlorobenzaldehyde (Example 18, intermediate) as starting material. $^1$H NMR (300 MHz, DMSO-$d_6$): 1.79-1.99 (1H, m), 1.99-2.1 (2H, m), 2.36-2.48 (1H, m), 3.23-3.5 (1H, m), 3.58-3.78 (7H, m), 4.46-4.54 (2H, m), 7.11 (1H, dd), 7.24 (1H, d), 7.89 (1H, d), 10.23 (1H, s). m/z: ES+ [M+H]+ 312.

[H13] was obtained from the cyclisation of (R)-2-chloro-4-(2-(3-hydroxypyrrolidin-1-yl)ethoxy)benzaldehyde and N4-benzyl-6-(1-methylcyclopropoxy)pyrimidine-4,5-diamine (Example 4, intermediate) in a similar procedure to Example P2.

(R)-2-Chloro-4-(2-(3-hydroxypyrrolidin-1-yl)ethoxy)benzaldehyde was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purine (Example R3), using (R)-pyrrolidin-3-ol and 4-(2-bromoethoxy)-2-chlorobenzaldehyde (Example 18, intermediate) as starting material. $^1$H NMR (400 MHz, DMSO-$d_6$): 1.49-1.57 (1H, m), 1.90-2.01 (1H, m), 2.38-2.42 (1H, m), 2.61-2.70 (1H, m), 2.74-2.84 (3H, m), 3.17 (1H, s), 4.14-4.24 (3H, m), 4.71 (1H, s), 7.09 (1H, dd), 7.19 (1H, d), 7.82 (1H, d), 10.19 (1H, s). m/z: ES+ [M+H]+ 270.

[H14] was obtained from the cyclisation of 2-chloro-4-(2-(3-hydroxyazetidin-1-yl)ethoxy)benzaldehyde and N4-benzyl-6-(1-methylcyclopropoxy)pyrimidine-4,5-diamine (Example 4, intermediate) in a similar procedure to Example P2.

2-Chloro-4-(2-(3-hydroxyazetidin-1-yl)ethoxy)benzaldehyde was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purine (Example R3), using azetidin-3-ol and 4-(2-bromoethoxy)-2-chlorobenzaldehyde (Example 18, intermediate) as starting material. $^1$H NMR (400 MHz, DMSO-$d_6$): 2.80-2.94 (4H, m), 3.61-3.65 (2H, m), 4.10 (2H, t), 4.16-4.20 (1H, m), 7.02-7.11 (1H, m), 7.17 (1H, d), 7.82 (1H, d), 10.19 (1H, s). One proton not observed. m/z: ES+ [M+H]+ 256.

[H15] was obtained from the cyclisation of 2-chloro-4-(2-(4-hydroxypiperidin-1-yl)ethoxy)benzaldehyde and N4-benzyl-6-(1-methylcyclopropoxy)pyrimidine-4,5-diamine (Example 4, intermediate) in a similar procedure to Example P2.

2-Chloro-4-(2-(4-hydroxypiperidin-1-yl)ethoxy)benzaldehyde was made by N-alkylation using a similar procedure used in the synthesis of (R)-1-(2-(3-Chloro-4-(9-((4-chloropyridin-2-yl)methyl)-6-(1-methylcyclopropoxy)-9H-purin-8-yl)phenoxy)ethyl)pyrrolidin-3-ol (Example R2), using piperidin-4-ol and 4-(2-bromoethoxy)-2-chlorobenzaldehyde (Example 18, intermediate) as starting material. $^1$H NMR (300 MHz, DMSO-$d_6$): 1.35-1.92 (4H, m), 2.02-2.14 (2H, m), 3.02-3.2 (2H, m), 3.5-3.7 (2H, m), 4.28-4.32 (2H, m), 7.11 (1H, d), 7.23 (1H, s), 7.83 (1H, d), 8.19 (1H, s), 10.19 (1H, s). One proton not observed. m/z: ES+ [M+H]+ 284.

[H16] was obtained from the cyclisation of 2-chloro-4-(2-(6-hydroxy-2-azaspiro[3.3]heptan-2-yl)ethoxy)benzaldehyde and N4-benzyl-6-(1-methylcyclopropoxy)pyrimidine-4,5-diamine (Example 4, intermediate) in a similar procedure to Example P2.

2-Chloro-4-(2-(6-hydroxy-2-azaspiro[3.3]heptan-2-yl)ethoxy)benzaldehyde was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purin (Example R3), using 2-azaspiro[3.3]heptan-6-ol and 4-(2-bromoethoxy)-2-chlorobenzaldehyde (Example 18, intermediate) as starting material. $^1$H NMR (400 MHz, DMSO-$d_6$): 1.80-1.93 (2H, m), 2.28-2.37 (2H, m), 2.78-2.82 (2H, m), 3.17-3.30 (4H, m), 3.88-3.96 (1H, m), 4.08 (2H, t), 4.95 (1H, d), 7.06-7.12 (1H, m), 7.14-7.20 (1H, m), 7.79-7.83 (1H, m), 10.19 (1H, s). m/z: ES+ [M+H]+ 296.

[H17] was obtained from the cyclisation of 2-chloro-4-(3-(3-hydroxyazetidin-1-yl)propoxy)benzaldehyde and N4-benzyl-6-(1-methylcyclopropoxy)pyrimidine-4,5-diamine (Example 4, intermediate) in a similar procedure to Example P2.

2-Chloro-4-(3-(3-hydroxyazetidin-1-yl)propoxy)benzaldehyde was made in a N-alkylation using a similar procedure use in the synthesis of (S)-9-benzyl-8-(2-chloro-4-(2-(3-methylpiperazin-1-yl)ethoxy)phenyl)-6-(1-methylcyclopropoxy)-9H-purine (Example R3), using azetidin-3-ol and 4-(3-bromopropoxy)-2-chlorobenzaldehyde as starting material. $^1$H NMR (400 MHz, DMSO-$d_6$): 1.68-1.81 (2H, m), 2.62 (2H, t), 2.77-2.99 (2H, m), 3.5-3.65 (2H, m), 3.99-4.28 (4H, m), 7.01-7.11 (1H, m), 7.14-7.23 (1H, m), 7.79-7.83 (1H, m), 10.19 (1H, s). m/z: ES+ [M+H]+ 270.

4-(3-Bromopropoxy)-2-chlorobenzaldehyde was formed in a similar manner to 4-(2-bromoethoxy)-2-chlorobenzaldehyde (Example 18, intermediate) using 1,3-dibromopropane and 2-chloro-4-hydroxybenzaldehyde as starting material. $^1$H NMR (400 MHz, DMSO-$d_6$): 2.18-2.33 (2H, m), 3.65 (2H, t), 4.20 (2H, t), 7.08 (1H, dd), 7.17 (1H, d), 7.81 (1H, d), 10.17 (1H, s). m/z: ES+ [M+H]+ 276.9.

[H18] was obtained from tert-butyl 6-(2-(3-chloro-4-formylphenoxy)ethyl)-1,6-diazaspiro[3.3]heptane-1-carboxylate via a BOC deprotection similar to the procedure described in Example $R^3$ in the synthesis of (S)-9-benzyl-8-(2-chloro-4-(2-(3-methylpiperazin-1-yl)ethoxy)phenyl)-6-(1-methylcyclopropoxy)-9H-purine.

Tert-butyl 6-(2-(4-(9-benzyl-6-(1-methylcyclopropoxy)-9H-purin-8-yl)-3-chlorophenoxy)ethyl)-1,6-diazaspiro[3.3]heptane-1-carboxylate was made by cyclisation of tert-butyl 6-(2-(3-chloro-4-formylphenoxy)ethyl)-1,6-diazaspiro[3.3]heptane-1-carboxylate and N4-benzyl-6-(1-methylcyclopropoxy)pyrimidine-4,5-diamine (Example 4, intermediate) in a similar procedure to Example P2. $^1$H NMR (400 MHz, DMSO-$d_6$): 0.78-0.86 (2H, m), 0.97-1.04 (2H, m), 1.41 (9H, s), 1.73 (3H, s), 2.36-2.4 (2H, m), 2.77-2.82 (2H, m), 3.42-3.45 (2H, m), 3.59-3.69 (4H, m), 4.02-4.08 (2H, m), 5.28 (2H, s), 6.82-6.94 (2H, m), 6.94-7.03 (1H, m), 7.17-7.24 (4H, m), 7.27-7.33 (1H, m), 8.61 (1H, s). m/z: ES+ [M+H]+ 631.

Tert-butyl 6-(2-(3-chloro-4-formylphenoxy)ethyl)-1,6-diazaspiro[3.3]heptane-1-carboxylate was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purine (Example R3), using tert-butyl 1,6-diazaspiro[3.3]heptane-1-carboxylate and 4-(2-bromoethoxy)-2-chlorobenzaldehyde (Example 18, intermediate) as starting material. $^1$H NMR (400 MHz, DMSO-$d_6$): 1.40 (9H, s), 2.31-2.39 (2H, m), 2.74-2.87 (2H, m), 3.41-3.5 (2H, m), 3.5-3.77 (4H, m), 4.04-4.16 (2H, m), 7.07 (1H, dd), 7.18 (1H, d), 7.82 (1H, d), 10.19 (1H, s). m/z: ES+ [M+H]+ 381.

[H19] was obtained from the cyclisation of (S)-2-chloro-4-(2-(2-methyl-3-oxopiperazin-1-yl)ethoxy)benzaldehyde and N4-benzyl-6-(1-methylcyclopropoxy)pyrimidine-4,5-diamine (Example 4, intermediate) in a similar procedure to Example P2.

(S)-2-chloro-4-(2-(2-methyl-3-oxopiperazin-1-yl)ethoxy)benzaldehyde was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purine (Example R3), using (S)-3-methylpiperazin-2-one and 4-(2-bromoethoxy)-2-chlorobenzaldehyde (Example 18, intermediate) as starting material. $^1$H NMR (300 MHz, DMSO-$d_6$): 1.22 (3H, d), 2.55-2.65 (1H, m), 2.72-2.84 (1H, m), 2.93-3.04 (2H, m), 3.13-3.18 (3H, m), 4.19-4.3 (2H, m), 7.07-7.13 (1H, m), 7.22 (1H, d), 7.67 (1H, s), 7.83 (1H, d), 10.20 (1H, d). m/z: ES+ [M+H]+ 297.

[H20] was obtained from the oxidation of 6-(2-(4-(9-benzyl-6-(1-methylcyclopropoxy)-9H-purin-8-yl)-3-chlorophenoxy)ethyl)-2-thia-6-azaspiro[3.3]heptane (Example H23) as follows: Hydrogen peroxide (30% aqueous, 807 mg, 23.72 mmol) was added portionwise to a solution of 6-(2-(4-(9-benzyl-6-(1-methylcyclopropoxy)-9H-purin-8-yl)-3-chlorophenoxy)ethyl)-2-thia-6-azaspiro[3.3]heptane (130 mg, 0.24 mmol, Example H23) in dry acetic acid (1.42 g, 23.72 mmol) at 0° C. for 3 hours. The reaction mixture was diluted with DCM (50 mL), and washed sequentially with saturated $NaHCO_3$ (100 mL), water (100 mL) and saturated brine (100 mL). The organic layer was dried over $Na_2SO_4$, filtered and evaporated to afford the crude product. The crude product was purified by preparative HPLC (YMC-Actus Triart C18 ExRS column, 30 mm×150 mm, 5 μm), using decreasingly polar mixtures of water (containing 10 mmol/L $NH_4HCO_3$ and 0.1% aqueous ammonia) and MeCN as eluents. The fractions containing the desired compound were evaporated to dryness to afford Example H20 (4.0 mg, 3%) as a white solid.

6-(2-(4-(9-Benzyl-6-(1-methylcyclopropoxy)-9H-purin-8-yl)-3-chlorophenoxy)ethyl)-2-thia-6-azaspiro[3.3]heptane (Example H23) was formed from the cyclisation of (E)-5-((4-(2-(2-thia-6-azaspiro[3.3]heptan-6-yl)ethoxy)-2-chlorobenzylidene)amino)-N-benzyl-6-(1-methylcyclopropoxy) pyrimidin-4-amine in a similar procedure to (E)-N-benzyl-5-((2-chloro-4-(2-(4-methylpiperazin-1-yl)ethoxy) benzylidene)amino)-6-(1-methylcyclopropoxy)pyrimidin-4-amine (Example 4, intermediate).

(E)-5-((4-(2-(2-thia-6-azaspiro[3.3]heptan-6-yl)ethoxy)-2-chlorobenzylidene)amino)-N-benzyl-6-(1-methylcyclopropoxy)pyrimidin-4-amine was made using a similar method to tert-butyl (E)-4-(2-(3-chloro-4-(((4-((3-chlorobenzyl)amino)-6-(1-methylcyclopropoxy)pyrimidin-5-yl) imino)methyl)phenoxy)ethyl)piperazine-1-carboxylate (Example J13, intermediate), using 4-(2-(2-thia-6-azaspiro[3.3] heptan-6-yl)ethoxy)-2-chlorobenzaldehyde and N4-benzyl-6-(1-methylcyclopropoxy)pyrimidine-4,5-diamine (Example 4, intermediate). m/z: ES+ [M+H]+ 550. 4-(2-(2-Thia-6-azaspiro[3.3]heptan-6-yl)ethoxy)-2-chlorobenzaldehyde was made by N-alkylation using a similar procedure use in the synthesis of (S)-9-benzyl-8-(2-chloro-4-(2-(3-methylpiperazin-1-yl)ethoxy)phenyl)-6-(1-methylcyclopropoxy)-9H-purine (Example R3), using 2-thia-6-azaspiro [3.3]heptane, hemioxalate salt and 4-(2-bromoethoxy)-2-chlorobenzaldehyde (Example 18, intermediate) as starting material. $^1H$ NMR (300 MHz, DMSO-$d_6$): 2.70 (2H, t), 3.23-3.27 (8H, m), 4.07 (2H, t), 7.06 (1H, dd), 7.17 (1H, d), 7.82 (1H, d), 10.19 (1H, s). m/z: ES+ [M+H]+ 298.

[H21] was obtained from the reaction of 2-chloro-4-(2-(5-oxo-1,4-diazepan-1-yl)ethoxy)benzaldehyde and N4-benzyl-6-(1-methylcyclopropoxy)pyrimidine-4,5-diamine (Example 4, intermediate) in a similar procedure to Example P2.

2-Chloro-4-(2-(5-oxo-1,4-diazepan-1-yl)ethoxy)benzaldehyde was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purine (Example R3), using 1,4-diazepan-5-one and 4-(2-bromoethoxy)-2-chlorobenzaldehyde (Example 18, intermediate) as starting material. $^1H$ NMR (300 MHz, DMSO-$d_6$): 2.39-2.46 (2H, m), 2.59-2.71 (4H, m), 2.84-2.92 (2H, m), 3.12 (2H, s), 4.24 (2H, t), 7.05-7.13 (1H, m), 7.22 (1H, d), 7.54 (1H, s), 7.83 (1H, d), 10.20 (1H, d). m/z: ES+ [M+H]+ 297.

[H22] was obtained from the cyclisation of (R)-2-chloro-4-(2-(2-methyl-3-oxopiperazin-1-yl)ethoxy)benzaldehyde and N4-benzyl-6-(1-methylcyclopropoxy)pyrimidine-4,5-diamine (Example 4, intermediate) in a similar procedure to Example P2.

(R)-2-Chloro-4-(2-(2-methyl-3-oxopiperazin-1-yl) ethoxy)benzaldehyde was made by N-alkylation using a similar procedure used in the synthesis of (S)-9-benzyl-8-(2-chloro-4-(2-(3-methylpiperazin-1-yl)ethoxy)phenyl)-6-(1-methylcyclopropoxy)-9H-purine (Example R3), using (R)-3-methylpiperazin-2-one and 4-(2-bromoethoxy)-2-chlorobenzaldehyde (Example 18, intermediate) as starting material. $^1H$ NMR (300 MHz, DMSO-$d_6$): 1.23 (3H, d), 2.56-2.66 (1H, m), 2.74-2.87 (1H, m), 2.92-3.04 (2H, m), 3.06-3.17 (3H, m), 4.21-4.29 (2H, m), 7.10 (1H, dd), 7.22 (1H, d), 7.66 (1H, s), 7.83 (1H, d), 10.20 (1H, s). m/z: ES+ [M+H]+ 297.

The following examples in Table J were synthesised as stated in the notes at the bottom of Table J.

TABLE J

| Ex # | Structure | Name | $^1H$ NMR | LCMS $[M + H]^+$ |
|---|---|---|---|---|
| J1 | 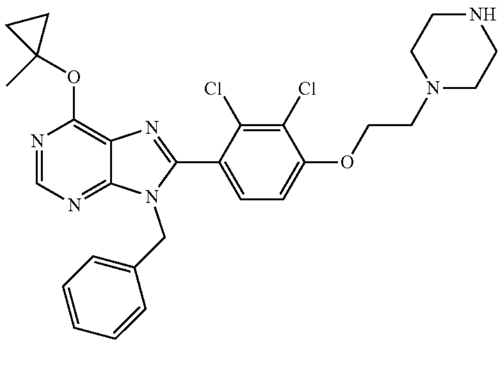 [SMILES: CC1(Oc2ncnc3c2nc(-c2ccc(OCCN4CCNCC4)c(Cl)c2Cl)n3Cc2ccccc2)CC1] | 9-benzyl-8-(2,3-dichloro-4-(2-(piperazin-1-yl)ethoxy) phenyl)-6-(1-methylcyclopropoxy)-9H-purine | (300 MHz, DMSO-$d_6$): 0.85 (2H, t), 1.04 (2H, t), 1.67 (3H, s), 1.94-2.30 (1H, m), 2.49-2.51 (4H, m), 2.65-2.74 (6H, m), 4.28 (2H, t), 5.28 (2H, s), 6.88-6.92 (2H, m), 7.19-7.28 (3H, m), 7.31 (1H, d), 7.45 (1H, d), 8.63 (1H, s). | 553 |

TABLE J-continued

| Ex # | Structure | Name | $^1$H NMR | LCMS [M + H]$^+$ |
|---|---|---|---|---|
| J2 | 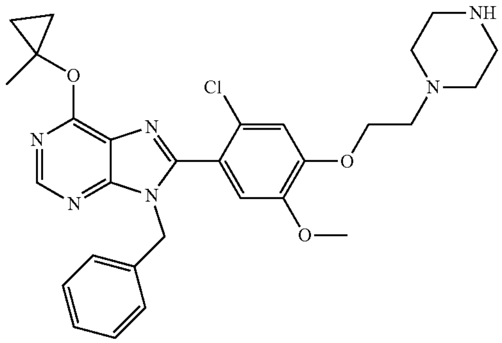 [SMILES: COc1cc(-c2nc3c(OC4(C)CC4)ncnc3n2Cc2ccccc2)c(Cl)cc1OCCN1CCNCC1] | 9-benzyl-8-(2-chloro-5-methoxy-4-(2-(piperazin-1-yl)ethoxy)phenyl)-6-(1-methylcyclopropoxy)-9H-purine | (300 MHz, DMSO-$d_6$): 0.86 (2H, t), 1.03 (2H, t), 1.74 (3H, s), 2.35 – 2.48 (4H, m), 2.64 – 2.72 (6H, m), 3.61 (3H, s), 4.17 (2H, t), 5.31 (2H, s), 6.9 – 6.96 (3H, m), 7.2 – 7.27 (4H, m), 8.63 (1H, s). One proton not seen. | 549 |
| J3 | 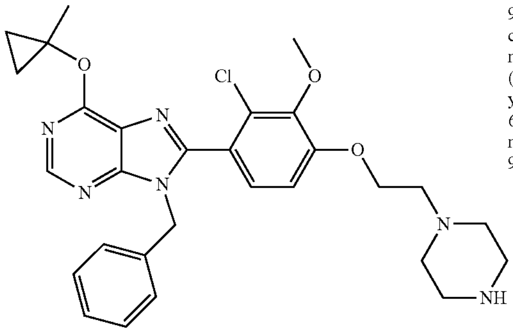 [SMILES: COc1c(OCCN2CCNCC2)ccc(-c2nc3c(OC4(C)CC4)ncnc3n2Cc2ccccc2)c1Cl] | 9-benzyl-8-(2-chloro-3-methoxy-4-(2-(piperazin-1-yl)ethoxy)phenyl)-6-(1-methylcyclopropoxy)-9H-purine | (300 MHz, DMSO-$d_6$): 0.65 – 0.94 (2H, m), 0.94 – 1.13 (2H, m), 1.72 (3H, s), 2.21 – 2.46 (4H, m), 2.58 – 2.86 (6H, m), 3.81 (3H, s), 4.21 (2H, t), 5.27 (2H, s), 6.71 – 7 (2H, m), 7 – 7.47 (5H, m), 8.61 (1H, s). One proton not seen. | 549 |
| J4 | 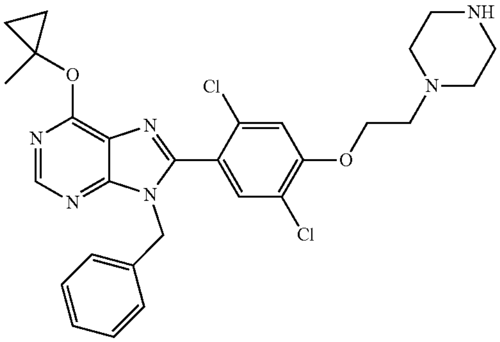 [SMILES: CC1(Oc2ncnc3c2nc(-c2cc(Cl)c(OCCN4CCNCC4)cc2Cl)n3Cc2ccccc2)CC1] | 9-benzyl-8-(2,5-dichloro-4-(2-(piperazin-1-yl)ethoxy)phenyl)-6-(1-methylcyclopropoxy)-9H-purine | (300 MHz, DMSO-$d_6$): 0.79 (2H, t), 1.00 (2H, t), 1.71 (3H, s), 2.39-2.45 (4H,m), 2.68 (6H, m), 4.27 (2H, t), 5.29 (2H, s), 6.91 (2H, m), 7.19 (3H, m), 7.48 (1H, s), 7.57 (1H, s), 8.62 (1H, s). One proton not seen. | 553 |
| J5 | 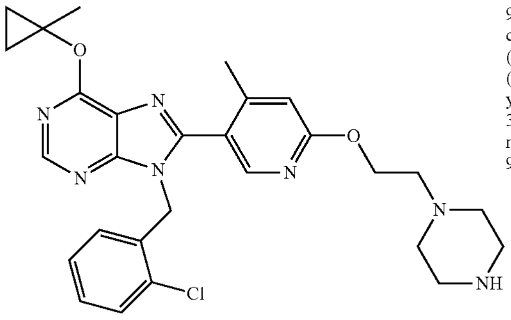 | 9-(2-chlorobenzyl)-8-(4-methyl-6-(2-(piperazin-1-yl)ethoxy)pyridin-3-yl)-6-(1-methylcyclopropoxy)-9H-purine | (400 MHz, DMSO-$d_6$): 0.86 (2H, t), 1.03 (2H, t), 1.74 (3H, s), 1.99 (3H, s), 2.36-2.40 (4H, m), 2.60-2.71 (6H, m), 4.38 (2H, t), 5.44 (2H, s), 6.73-6.81 (2H, m), 7.16 (1H, t), 7.27 (1H, td), 7.38 (1H, dd), 8.12 (1H, s), 8.62 (1H, s). 1H not observed. | 534 |

TABLE J-continued

| Ex # | Structure | Name | $^1$H NMR | LCMS [M + H]$^+$ |
|---|---|---|---|---|
| J6 | 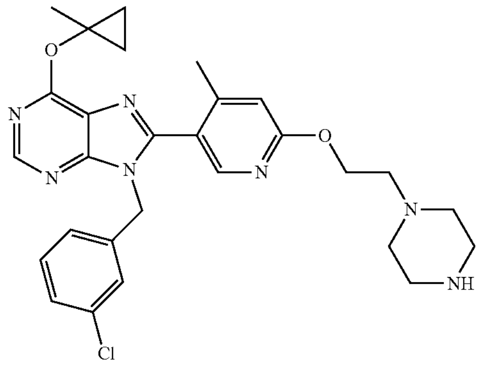 [SMILES: Cc1cc(OCCN2CCNCC2)ncc1-c1nc2c(OC3(C)CC3)ncnc2n1Cc1cccc(Cl)c1] | 9-(3-chlorobenzyl)-8-(4-methyl-6-(2-(piperazin-1-yl)ethoxy)pyridin-3-yl)-6-(1-methylcyclopropoxy)-9H-purine | (400 MHz, DMSO-$d_6$): 0.79 – 1.02 (4H, m), 1.73 (3H, s), 1.95 (3H, s), 2.31 – 2.40 (4H, m), 2.57 – 2.79 (6H, m), 4.30 – 4.51 (2H, m), 5.33 (2H, s), 6.73 – 7.05 (3H, m), 7.25 – 7.27 (2H, m), 8.10 (1H, s), 8.63 (1H, s). 1H not observed. | 534 |
| J7 | 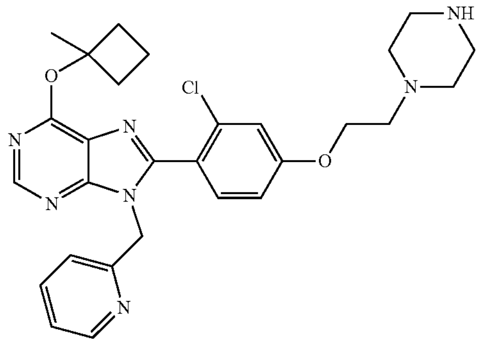 [SMILES: CC1(Oc2ncnc3c2nc(-c2ccc(OCCN4CCNCC4)cc2Cl)n3Cc2ccccn2)CCC1] | 8-(2-chloro-4-(2-(piperazin-1-yl)ethoxy)phenyl)-6-(1-methylcyclobutoxy)-9-(pyridin-2-ylmethyl)-9H-purine | (400 MHz, DMSO-$d_6$): 1.77 (5H, m), 2.28 – 2.43 (6H, m), 2.46-2.49 (2H, m), 2.66-2.71 (6H, m), 4.14 (2H, t), 5.38 (2H, s), 6.97 (1H, dd), 7.05 (1H, d), 7.21 (2H, m), 7.38 (1H, d), 7.60 – 7.70 (1H, m), 8.34 (1H, d), 8.45 (1H, s). 1H not observed. | 534 |
| J8 | 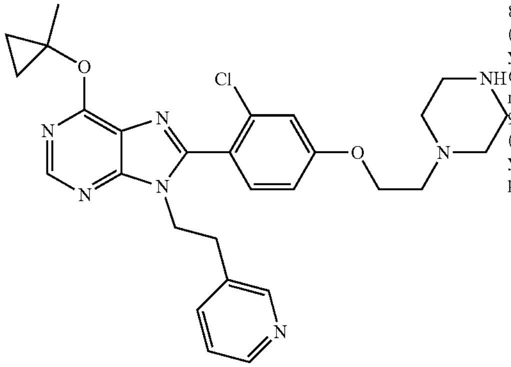 [SMILES: CC1(Oc2ncnc3c2nc(-c2ccc(OCCN4CCNCC4)cc2Cl)n3CCc2cccnc2)CC1] | 8-(2-chloro-4-(2-(piperazin-1-yl)ethoxy)phenyl)-6-(1-methylcyclopropoxy)-9-(2-(pyridin-3-yl)ethyl)-9H-purine | (300 MHz, $CDCl_3$): 0.71 (2H, t), 1.03 (2H, t), 1.68 (3H, s), 2.39 – 2.52 (4H, m), 2.71 (2H, t), 2.76 – 2.9 (4H, m), 3.16 (2H, t), 4.02 (2H, t), 4.43 (2H, t), 6.62 – 6.69 (2H, m), 6.79 (1H, d), 6.89 (1H, d), 6.92 – 6.99 (1H, m), 7.28 – 7.36 (1H, m), 8.23 (1H, d), 8.54 (1H, s). One proton not observed. | 534 |
| J9 | 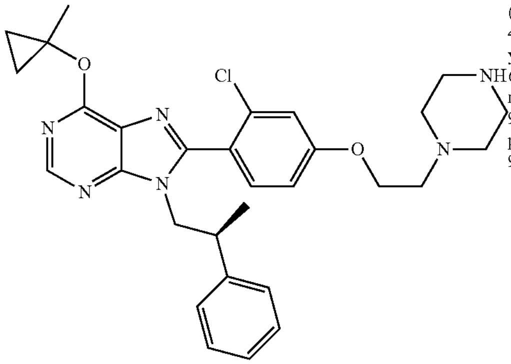 [SMILES: C[C@H](Cn1c(-c2ccc(OCCN3CCNCC3)cc2Cl)nc2c(OC3(C)CC3)ncnc21)c1ccccc1] | (S)-8-(2-chloro-4-(2-(piperazin-1-yl)ethoxy)phenyl)-6-(1-methylcyclopropoxy)-9-(2-phenylpropyl)-9H-purine | (400 MHz, $CDCl_3$): 0.83 (2H, t), 1.13 – 1.26 (5H, m), 1.82 (3H, s), 2.58 – 2.72 (4H, m), 2.87 (2H, t), 3.02 (4H, t), 3.4 – 3.49 (1H, m), 4.02 – 4.12 (1H, m), 4.17 (2H, t), 4.36 – 4.43 (1H, m), 6.61 – 6.92 (4H, m), 7.02 (1H, d), 7.11 – 7.18 (3H, m), 8.69 (1H, s). One proton not observed. | 547 |

TABLE J-continued

| Ex # | Structure | Name | $^1$H NMR | LCMS [M + H]$^+$ |
| --- | --- | --- | --- | --- |
| J10 | 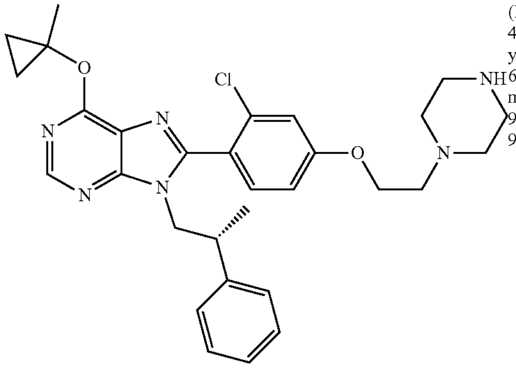 | (R)-8-(2-chloro-4-(2-(piperazin-1-yl)ethoxy)phenyl)-6-(1-methylcyclopropoxy)-9-(2-phenylpropyl)-9H-purine | (300 MHz, DMSO-$d_6$): 0.83 (2H, t), 0.99 (2H, t), 1.10 (3 H, d), 1.72 (3H, s), 2.39-2.47 (4H, m), 2.61 – 2.79 (6 H, m), 3.09 – 3.25 (2 H, m), 4.01 – 4.39 (4 H, m), 6.79 – 6.89 (2 H, m), 6.99-7.05 (2H, m), 7.09 – 7.20 (3 H, m), 7.26 – 7.29 (1 H, m), 8.62 (1H, s). | 547 |
| J11 | 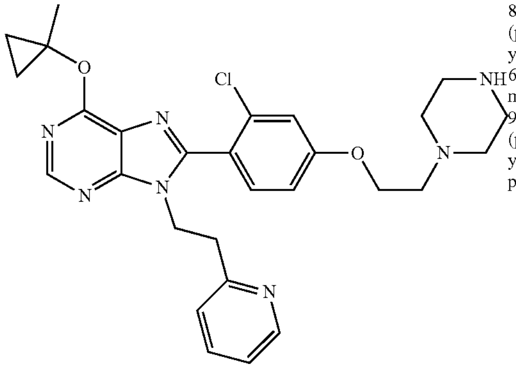 | 8-(2-chloro-4-(2-(piperazin-1-yl)ethoxy)phenyl)-6-(1-methylcyclopropoxy)-9-(2-(pyridin-2-yl)ethyl)-9H-purine | (400 MHz, DMSO-$d_6$): 0.84 (2H, t), 1.00 (2H, t), 1.72 (3H, s), 2.38-2.43 (4H, m), 2. 67-2.70 (6H, m), 3.15 (2H, t), 4.19 (2H, t), 4.42 (2H, t), 6.94-7.02 (2H, m), 7.13-7.18 (2H, m), 7.26 (1H, s), 7.55-7.59 (1H, m), 8.31 (1H, d), 8.60 (1H, s). One proton not observed. | 534 |
| J12 | 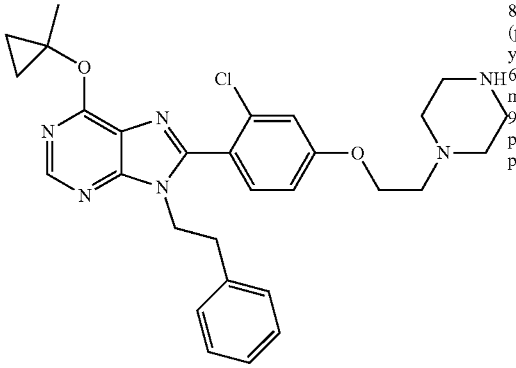 | 8-(2-chloro-4-(2-(piperazin-1-yl)ethoxy)phenyl)-6-(1-methylcyclopropoxy)-9-phenethyl-9H-purine | (400 MHz, DMSO-$d_6$): 0.84 (2H, t), 1.01 (2H, t), 1.73 (3H, s), 2.35 – 2.46 (4H, m), 2.60 – 2.75 (7H, m), 2.98 (2H, t), 4.14 – 4.31 (4H, m), 6.79 – 6.84 (2H, m), 6.93 – 7.02 (2H, m), 7.13 – 7.19 (3H, m), 7.27 (1H, s), 8.61 (1H, s). | 533 |
| J13 | 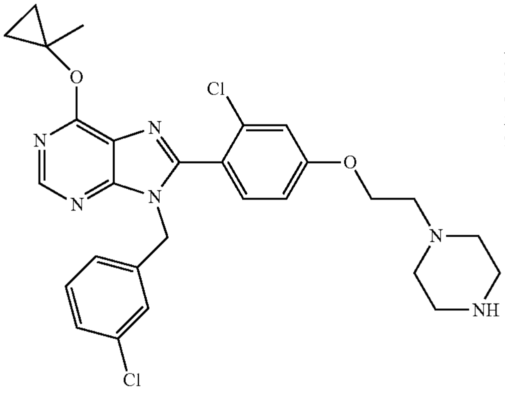 [SMILES: CC1(Oc2ncnc3c2nc(-c2ccc(OCCN4CCNCC4)cc2Cl)n3Cc2cccc(Cl)c2)CC1] | 8-(2-chloro-4-(2-(piperazin-1-yl)ethoxy)phenyl)-9-(3-chlorobenzyl)-6-(1-methylcyclopropoxy)-9H-purine | (400 MHz, DMSO-$d_6$): 0.85 (2H, t), 1.02 (2H, t), 1.73 (3H, s), 2.39 – 2.43 (4H, m), 2.64 – 2.73 (6H, m), 4.18 (2H, t), 5.29 (2H, s), 6.85 (1H, dt), 6.95 (1H, t), 7.05 (1H, dd), 7.19 – 7.32 (3H, m), 7.42 (1H, d), 8.63 (1H, s). One proton not observed. | 553 |

[J1] made from a similar procedure (BOC deprotection with TFA) as 9-benzyl-8-(2-chloro-4-(2-(piperazin-1-yl)ethoxy)phenyl)-6-((1,1,1-trifluoro-2-methylpropan-2-yl)oxy)-9H-purine (Example 11) using tert-butyl 4-(2-(4-(9- benzyl-6-(1-methylcyclopropoxy)-9H-purin-8-yl)-2,3-dichlorophenoxy)ethyl)piperazine-1-carboxylate as starting material.

Tert-butyl 4-(2-(4-(9-benzyl-6-(1-methylcyclopropoxy)-9H-purin-8-yl)-2,3-dichlorophenoxy)ethyl)piperazine-1-carboxylate was made from a similar procedure as 9-benzyl-8-(2-chloro-4-(2-(4-methylpiperazin-1-yl)ethoxy)phenyl)-6-(1-methylcyclopropoxy)-9H-purine (Example 4), using tert-butyl (E)-4-(2-(4-(((4-(benzylamino)-6-(1-methylcyclopropoxy)pyrimidin-5-yl)imino)methyl)-2,3-dichlorophenoxy)ethyl)piperazine-1-carboxylate as starting material. $^1H$ NMR (300 MHz, DMSO-$d_6$): 0.73 (2H, t), 0.90 (2H, t), 1.27 (9H, s), 1.61 (3H, s), 2.34-2.38 (4H, m), 2.69 (2H, t), 3.09-3.2 (4H, m), 4.17 (2H, t), 5.16 (2H, s), 6.67-6.89 (2H, m), 7.02-7.16 (3H, m), 7.17 (1H, d), 7.35 (1H, d), 8.51 (1H, s). m/z: ES+ [M+H]+ 653.

Tert-butyl (E)-4-(2-(4-(((4-(benzylamino)-6-(1-methylcyclopropoxy)pyrimidin-5-yl)imino)methyl)-2,3-dichlorophenoxy)ethyl)piperazine-1-carboxylate made from a similar procedure as (E)-N-benzyl-5-((2-chloro-4-(2-(4-methylpiperazin-1-yl)ethoxy)benzylidene)amino)-6-(1-methylcyclopropoxy)pyrimidin-4-amine (Example 4, intermediate), using tert-butyl 4-(2-(2,3-dichloro-4-formylphenoxy)ethyl)piperazine-1-carboxylate and N4-benzyl-6-(1-methylcyclopropoxy)pyrimidine-4,5-diamine (Example 4, intermediate) as starting materials. $^1H$ NMR (300 MHz, DMSO-$d_6$): 0.77 (2H, t), 0.94 (2H, t), 1.39 (9H, s), 1.65 (3H, s), 2.50 (4H, d), 2.78-2.87 (2H, m), 3.24-3.32 (4H, m), 4.11 (1H, s), 4.24-4.43 (2H, m), 4.67 (2H, d), 7.21-7.31 (4H, m), 7.71-7.85 (1H, m), 8.02-8.18 (1H, m), 8.3-8.56 (1H, m), 9.35 (1H, s), 12.00 (1H, m). m/z: ES+ [M+H]+ 655.

Tert-butyl 4-(2-(2,3-dichloro-4-formylphenoxy)ethyl)piperazine-1-carboxylate made from a similar procedure as tert-butyl 4-(2-(3-chloro-4-formylphenoxy)ethyl)piperazine-1-carboxylate (Example 4, intermediate), using 2,3-dichloro-4-hydroxybenzaldehyde and tert-butyl 4-(2-chloroethyl)piperazine-1-carboxylate as starting materials. $^1H$ NMR (300 MHz, DMSO-$d_6$): 1.27 (9H, s), 2.34-2.40 (4H, m), 2.68 (2H, t), 3.16-3.21 (4H, m), 4.22 (2H, t), 7.24 (1H, d), 7.72 (1H, d), 10.08 (1H, s). m/z: ES+ [M+H]+ 403.

[J2] made from a similar procedure as 9-benzyl-8-(2,3-dichloro-4-(2-(piperazin-1-yl)ethoxy)phenyl)-6-(1-methylcyclopropoxy)-9H-purine (Example J1) using tert-butyl 4-(2-(4-(9-benzyl-6-(1-methylcyclopropoxy)-9H-purin-8-yl)-5-chloro-2-methoxyphenoxy)ethyl)piperazine-1-carboxylate as starting material.

The intermediates in the synthesis were made following a similar procedure as Example J1: Tert-butyl 4-(2-(5-chloro-4-formyl-2-methoxyphenoxy)ethyl)piperazine-1-carboxylate made from 2-chloro-4-hydroxy-5-methoxybenzaldehyde and tert-butyl 4-(2-chloroethyl)piperazine-1-carboxylate as starting materials. $^1H$ NMR (300 MHz, DMSO-$d_6$): 1.27 (9H, s), 2.25-2.34 (4H, m), 2.61-2.65 (2H, m), 3.17-3.21 (4H, m), 3.70 (3H, s), 4.11 (2H, t), 7.06 (1H, s), 7.19 (1H, s), 10.06 (1H, s). m/z: ES+ [M+H]+ 399.

Tert-butyl (E)-4-(2-(4-(((4-(benzylamino)-6-(1-methylcyclopropoxy)pyrimidin-5-yl)imino)methyl)-5-chloro-2-methoxyphenoxy)ethyl)piperazine-1-carboxylate was made from tert-butyl 4-(2-(5-chloro-4-formyl-2-methoxyphenoxy)ethyl)piperazine-1-carboxylate and N4-benzyl-6-(1-methylcyclopropoxy)pyrimidine-4,5-diamine (Example 4, intermediate) as starting materials. $^1H$ NMR (300 MHz, DMSO-$d_6$): 0.74 (2H, d), 0.90 (2H, d), 1.38 (12H, s), 2.45 (4H, s), 2.80 (2H, d), 3.15 (4H, s), 3.85 (3H, s), 4.09 (2H, s), 4.19 (2H, q), 7.16 (1H, s), 7.17-7.32 (5H, m), 7.83 (1H, s), 9.24 (1H, s), 11.94 (2H, s). m/z: ES+ [M+H]+ 651.

Tert-butyl 4-(2-(4-(9-benzyl-6-(1-methylcyclopropoxy)-9H-purin-8-yl)-5-chloro-2-methoxyphenoxy)ethyl)piperazine-1-carboxylate made from tert-butyl (E)-4-(2-(4-(((4-(benzylamino)-6-(1-methylcyclopropoxy)pyrimidin-5-yl)imino)methyl)-5-chloro-2-methoxyphenoxy)ethyl)piperazine-1-carboxylate as starting material. $^1H$ NMR (300 MHz, DMSO-$d_6$): 0.85 (2H, t), 0.99 (2H, t), 1.39 (9H, s), 1.72 (3H, s), 2.33-2.49 (10H, m), 3.60 (3H, s), 4.1-4.35 (2H, m), 5.29 (2H, s), 6.73-7 (3H, m), 7.1-7.3 (4H, m), 8.61 (1H, s). m/z: ES+ [M+H]+ 649.

[J3] made from a similar procedure as 9-benzyl-8-(2,3-dichloro-4-(2-(piperazin-1-yl)ethoxy)phenyl)-6-(1-methylcyclopropoxy)-9H-purine (Example J1) using tert-butyl 4-(2-(4-(9-benzyl-6-(1-methylcyclopropoxy)-9H-purin-8-yl)-3-chloro-2-methoxyphenoxy)ethyl)piperazine-1-carboxylate as starting material.

Tert-butyl 4-(2-(4-(9-benzyl-6-(1-methylcyclopropoxy)-9H-purin-8-yl)-3-chloro-2-methoxyphenoxy)ethyl)piperazine-1-carboxylate made from a similar procedure as (E)-N-benzyl-5-((2-chloro-4-(2-(4-methylpiperazin-1-yl)ethoxy)benzylidene)amino)-6-(1-methylcyclopropoxy)pyrimidin-4-amine (Example 4, intermediate) followed by a similar procedure as 9-benzyl-8-(2-chloro-4-(2-(4-methylpiperazin-1-yl)ethoxy)phenyl)-6-(1-methylcyclopropoxy)-9H-purine (Example 4), using tert-butyl 4-(2-(3-chloro-4-formyl-2-methoxyphenoxy)ethyl)piperazine-1-carboxylate and N4-benzyl-6-(1-methylcyclopropoxy)pyrimidine-4,5-diamine (Example 4, intermediate) as starting materials. $^1H$ NMR (300 MHz, DMSO-$d_6$): 0.73 (2H, t), 0.89 (2H, t), 1.27 (9H, s), 1.61 (3H, s), 2.28-2.36 (4H, m), 2.67 (2H, t), 3.14-3.2 (4H, m), 3.69 (3H, s), 4.11 (2H, t), 5.16 (2H, s), 6.75-6.8 (2H, m), 7.04-7.13 (5H, m), 8.50 (1H, s). m/z: ES+ [M+H]+ 649.

Tert-butyl 4-(2-(3-chloro-4-formyl-2-methoxyphenoxy)ethyl)piperazine-1-carboxylate made from a similar procedure as tert-butyl 4-(2-(3-chloro-4-formylphenoxy)ethyl)piperazine-1-carboxylate (Example 4, intermediate), using 2-chloro-4-hydroxy-3-methoxybenzaldehyde and tert-butyl 4-(2-chloroethyl)piperazine-1-carboxylate as starting materials $^1H$ NMR (300 MHz, DMSO-$d_6$): 1.39 (9H, s), 2.46 (4H, t), 2.78 (2H, t), 3.30 (4H, t), 3.82 (3H, s), 4.27 (2H, t), 7.27 (1H, d), 7.66 (1H, d), 10.19 (1H, s). m/z: ES+ [M+H]+ 399.

[J4] made from a similar procedure as 9-benzyl-8-(2,3-dichloro-4-(2-(piperazin-1-yl)ethoxy)phenyl)-6-(1-methylcyclopropoxy)-9H-purine (Example J1) using tert-butyl 4-(2-(4-(9-benzyl-6-(1-methylcyclopropoxy)-9H-purin-8-yl)-2,5-dichlorophenoxy)ethyl)piperazine-1-carboxylate as starting material.

Tert-butyl 4-(2-(4-(9-benzyl-6-(1-methylcyclopropoxy)-9H-purin-8-yl)-2,5-dichlorophenoxy)ethyl)piperazine-1-carboxylate made from a similar procedure as 9-benzyl-8-(2-chloro-4-(2-(4-methylpiperazin-1-yl)ethoxy)phenyl)-6-(1-methylcyclopropoxy)-9H-purine (Example 4), using tert-butyl (E)-4-(2-(4-(((4-(benzylamino)-6-(1-methylcyclopropoxy)pyrimidin-5-yl)imino)methyl)-2,5-dichlorophenoxy)ethyl)piperazine-1-carboxylate as starting material. The product was used in next reaction without further purification. Tert-butyl (E)-4-(2-(4-(((4-(benzylamino)-6-(1-methylcyclopropoxy)pyrimidin-5-yl)imino)methyl)-2,5-dichlorophenoxy)ethyl)piperazine-1-carboxylate made from a similar procedure as (E)-N-benzyl-5-((2-chloro-4-(2-(4-methylpiperazin-1-yl)ethoxy)benzylidene)amino)-6-(1-methylcyclopropoxy)pyrimidin-4-amine (Example 4, intermediate), using tert-butyl 4-(2-(2,5-dichloro-4-formylphenoxy)ethyl)piperazine-1-carboxylate and N4-benzyl-6-(1-methylcyclopropoxy)pyrimidine-4,5- diamine (Example 4, intermediate) as starting materials. $^1H$ NMR (300 MHz, DMSO-$d_6$): 0.75 (2H, t), 0.91 (2H, t), 1.38 (9H, s), 1.63 (3H, s), 3.25-3.32 (6H, m) 3.13-3.18 (4H, m), 4.29 (2H, t), 4.66 (2H, d), 7.29 (5H, d), 7.38 (1H, s), 8.03 (1H, s), 8.54 (1H, s), 9.29 (1H, s), 11.94 (1H, s). m/z: ES+ [M+H]+ 655.

Tert-butyl 4-(2-(2,5-dichloro-4-formylphenoxy)ethyl) piperazine-1-carboxylate made from a similar procedure as tert-butyl 4-(2-(3-chloro-4-formylphenoxy)ethyl)piperazine-1-carboxylate (Example 4, intermediate), using 2,5-dichloro-4-hydroxybenzaldehyde and tert-butyl 4-(2-chloroethyl)piperazine-1-carboxylate as starting materials. $^1H$ NMR (300 MHz, DMSO-$d_6$): 1.27 (9H, s), 2.31-2.37 (4H, m), 2.67 (2H, t), 3.13-3.19 (4H, m), 4.23 (2H, t), 7.35 (1H, s), 7.73 (1H, s), 10.03 (1H, s). m/z: ES+ [M+H]+ 403.

[J5] 9-(2-Chlorobenzyl)-8-(4-methyl-6-(2-(piperazin-1-yl)ethoxy)pyridin-3-yl)-6-(1-methylcyclopropoxy)-9H-purine was made by the following multi-step sequence:

Iron (334 mg, 5.97 mmol) was added to ammonium chloride (32 mg, 0.60 mmol) and N-(2-chlorobenzyl)-6-(1-methylcyclopropoxy)-5-nitropyrimidin-4-amine (200 mg, 0.60 mmol, Example E1 intermediate) in ethanol:$H_2O$ (10:1; 0.40 mL) at 25° C. The resulting mixture was stirred at 60° C. for 1 hour. The reaction mixture was filtered, and the filtrate was concentrated under reduced pressure. The residue was added to a mixture of tert-butyl 4-(2-((5-formyl-4-methylpyridin-2-yl)oxy)ethyl)piperazine-1-carboxylate (251 mg, 0.72 mmol) in MeOH:acetic acid (20:1; 4 mL) and stirred at 25° C. for 16 hours. The solvent was removed under reduced pressure to afford crude tert-butyl (E)-4-(2-((5-(((4-((2-chlorobenzyl)amino)-6-(1-methylcyclopropoxy)pyrimidin-5-yl)imino)methyl)-4-methylpyridin-2-yl)oxy)ethyl)piperazine-1-carboxylate as a brown oil, which was used in the next step directly without further purification.

Tert-butyl 4-(2-((5-(9-(2-chlorobenzyl)-6-(1-methylcyclopropoxy)-9H-purin-8-yl)-4-methylpyridin-2-yl)oxy) ethyl)piperazine-1-carboxylate was obtained using a similar procedure as that described for 9-benzyl-8-(2-chloro-4-(2-(4-methylpiperazin-1-yl)ethoxy)phenyl)-6-(1-methylcyclopropoxy)-9H-purine (Example 4), using tert-butyl (E)-4-(2-((5-(((4-((2-chlorobenzyl)amino)-6-(1-methylcyclopropoxy)pyrimidin-5-yl)imino)methyl)-4-methylpyridin-2-yl)oxy)ethyl)piperazine-1-carboxylate (350 mg, 0.55 mmol) to afford tert-butyl 4-(2-((5-(9-(2-chlorobenzyl)-6-(1-methylcyclopropoxy)-9H-purin-8-yl)-4-methylpyridin-2-yl)oxy)ethyl)piperazine-1-carboxylate (100 mg, 29%) as a brown oil. $^1H$ NMR (400 MHz, DMSO-$d_6$): 0.87 (2H, t), 1.03 (2H, t), 1.40 (9H, s), 1.75 (3H, s), 1.99 (3H, s), 2.42 (4H, t), 2.70 (2H, t), 3.27-3.32 (4H, m), 4.40 (2H, t), 5.43 (2H, s), 6.74-6.81 (2H, m), 7.13-7.18 (1H, m), 7.24-7.28 (1H, m), 7.36-7.4 (1H, m), 8.12 (1H, s), 8.62 (1H, s). m/z: ES+ [M+H]+ 634.

Tert-butyl 4-(2-((5-(9-(2-chlorobenzyl)-6-(1-methylcyclopropoxy)-9H-purin-8-yl)-4-methylpyridin-2-yl)oxy) ethyl)piperazine-1-carboxylate underwent BOC deprotection as described for the synthesis of 8-(4-(2-(2,6-diazaspiro [3.3]heptan-2-yl)ethoxy)-2-chlorophenyl)-9-benzyl-6-(1-methylcyclopropoxy)-9H-purine (Example 18) to afford 9-(2-chlorobenzyl)-8-(4-methyl-6-(2-(piperazin-1-yl) ethoxy)pyridin-3-yl)-6-(1-methylcyclopropoxy)-9H-purine (28 mg, 33%) as a yellow solid.

Tert-butyl 4-(2-((5-formyl-4-methylpyridin-2-yl)oxy) ethyl)piperazine-1-carboxylate used as a starting material was obtained as described below:

Tert-butyl 4-(2-((5-bromo-4-methylpyridin-2-yl) oxy)ethyl)piperazine-1-carboxylate

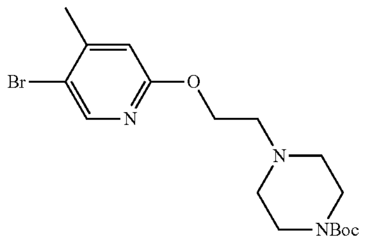 [SMILES: Cc1cc(OCCN2CCN(C(=O)OC(C)(C)C)CC2)ncc1Br]

Sodium hydride (144 mg, 3.60 mmol) was added portionwise to 5-bromo-2-fluoro-4-methylpyridine (570 mg, 3.00 mmol) and tert-butyl 4-(2-hydroxyethyl)piperazine-1-carboxylate (829 mg, 3.60 mmol) in THF (20 mL) at 0° C. over a period of 5 minutes under nitrogen. The resulting solution was stirred at 25° C. for 3 hours. The solvent was removed by distillation under vacuum. The reaction mixture was diluted with water (100 mL) and extracted with EtOAc (3×50 mL). The organic layer was dried over $Na_2SO_4$, filtered and evaporated to afford crude product. The crude product was purified by flash silica chromatography, elution gradient 0 to 30% EtOAc in petroleum ether. Pure fractions were evaporated to dryness to afford tert-butyl 4-(2-((5-bromo-4-methylpyridin-2-yl)oxy)ethyl)piperazine-1-carboxylate (1000 mg, 83%) as a colourless solid. $^1H$ NMR (300 MHz, $CDCl_3$): 1.48 (9H, s), 2.35 (3H, s), 2.56 (4H, t), 2.83 (2H, t), 3.49 (4H, t), 4.44 (2H, t), 6.68 (1H, s), 8.17 (1H, s). m/z: ES+ [M+H]+ 400.

Tert-butyl 4-(2-((5-formyl-4-methylpyridin-2-yl) oxy)ethyl)piperazine-1-carboxylate

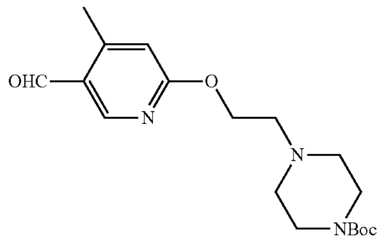 [SMILES: Cc1cc(OCCN2CCN(C(=O)OC(C)(C)C)CC2)ncc1C=O]

A solution of butyl lithium (0.96 mL, 2.40 mmol, 2.5 M) in hexane was added portionwise to a stirred solution of tert-butyl 4-(2-((5-bromo-4-methylpyridin-2-yl)oxy)ethyl) piperazine-1-carboxylate (800 mg, 2.00 mmol) in THF (20 mL) at −78° C. over a period of 2 minutes under nitrogen. The resulting solution was stirred at −78° C. for 18 minutes, followed by addition of N,N-dimethylformamide (438 mg, 6.00 mmol). The reaction mixture was diluted with water (20 mL) and extracted with EtOAc (3×15 mL). The organic layer was dried over $Na_2SO_4$, filtered and evaporated to afford crude product. The crude product was purified by flash silica chromatography, elution gradient 0 to 50% EtOAc in petroleum ether. Fractions containing the desired product were evaporated to dryness to afford crude tert-butyl 4-(2-((5-formyl-4-methylpyridin-2-yl)oxy)ethyl)piperazine-1-carboxylate (300 mg) as a colourless solid which was used directly with no further purification. m/z: ES+ [M+H]+ 350.

[J6] was obtained in a similar manner to that described for 9-(2-chlorobenzyl)-8-(4-methyl-6-(2-(piperazin-1-yl) ethoxy)pyridin-3-yl)-6-(1-methylcyclopropoxy)-9H-purine (Example J5) except that imine formation step was carried out directly between N4-(3-chlorobenzyl)-6-(1-methylcyclopropoxy)pyrimidine-4,5-diamine (200 mg, 0.66 mmol) and tert-butyl 4-(2-((5-formyl-4-methylpyridin-2-yl)oxy) ethyl)piperazine-1-carboxylate (275 mg, 0.79 mmol, Example J5 intermediate) in a similar manner to that described in the synthesis of 9-benzyl-8-(2-chloro-4-(2-(4-methylpiperazin-1-yl)ethoxy)phenyl)-6-(1-methylcyclopropoxy)-9H-purine (Example 4). N4-(3-Chlorobenzyl)-6-(1-methylcyclopropoxy)pyrimidine-4,5-diamine, used as a starting material, was made in a similar manner to N4-benzyl-6-(1-methylcyclopropoxy)pyrimidine-4,5-diamine (Example 4, intermediate) from (3-chlorophenyl)methanamine and 4,6-dichloro-5-nitropyrimidine, except that DIEA was used in place of TEA for the first step.

After three steps, this afforded N4-(3-chlorobenzyl)-6-(1-methylcyclopropoxy)pyrimidine-4,5-diamine as a brown oil. $^1$H NMR (300 MHz, DMSO-$d_6$): 0.68 (2H, t), 0.86 (2H, t), 1.60 (3H, s), 4.10 (2H, s), 4.59 (2H, d), 6.75 (1H, t), 7.24-7.38 (4H, m), 7.72 (1H, s). m/z: ES+ [M+H]+ 305.

[J7] To a stirred solution of 6-(1-methylcyclobutoxy)-N4-(pyridin-2-ylmethyl)pyrimidine-4,5-diamine (150 mg, 0.53 mmol), 2-chloro-4-(2-(piperazin-1-yl)ethoxy)benzaldehyde (160 mg, 0.60 mmol, Example 14 intermediate) in EtOH (3 mL) was added p-toluenesulfonic acid (136 mg, 0.79 mmol) at 60° C. for 2 h. The reaction mixture was diluted with DCM and saturated aq. $NaHCO_3$ was added. The reaction mixture was extracted with DCM (3×100 mL). The organic layer was dried over $Na_2SO_4$, filtered and evaporated to afford a white solid. The crude product was purified by preparative HPLC, column: YMC-Actus Triart C18, 30*150 mm, 5 μm; eluting with decreasingly polar mixtures of acetonitrile in water (containing 10 mmol/L $NH_4HCO_3$ and 0.1% aqueous ammonia). Fractions containing the desired compound were evaporated to dryness to afford 8-(2-chloro-4-(2-(piperazin-1-yl)ethoxy)phenyl)-6-(1-methylcyclobutoxy)-9-(pyridin-2-ylmethyl)-9H-purine (4 mg, 1%) as a white solid.

6-(1-Methylcyclobutoxy)-N4-(pyridin-2-ylmethyl)pyrimidine-4,5-diamine was obtained as follows:

Iron (531 mg, 9.51 mmol) was added to ammonium chloride (51 mg, 0.95 mmol) and 6-(1-methylcyclobutoxy)-5-nitro-N-(pyridin-2-ylmethyl)pyrimidin-4-amine (300 mg, 0.95 mmol) in ethanol/water (10:1; 10 mL) at 25° C. The resulting mixture was stirred at 60° C. for 1 hour. The solvent was removed under reduced pressure and the crude mixture was purified by flash silica chromatography, elution gradient 0 to 60% EtOAc in petroleum ether. Pure fractions were evaporated to dryness to afford 6-(1-methylcyclobutoxy)-N4-(pyridin-2-ylmethyl)pyrimidine-4,5-diamine (170 mg, 63%) as a white solid. $^1$H NMR (400 MHz, DMSO-$d_6$): 1.61 (3H, s), 1.58-1.82 (2H, m), 2.11-2.22 (2H, m), 2.31-2.39 (2H, m), 4.14 (2H, s), 4.65 (2H, d), 6.76-6.79 (1H, m), 7.19-7.31 (2H, m), 7.61 (1H, s), 7.69-7.73 (1H, m), 8.46-8.53 (1H, m). m/z: ES+ [M+H]+ 286.

6-(1-Methylcyclobutoxy)-5-nitro-N-(pyridin-2-ylmethyl) pyrimidin-4-amine was obtained as follows:

LHMDS (1M in THF, 9.4 mL, 9.4 mmol) was added dropwise to 6-chloro-5-nitro-N-(pyridin-2-ylmethyl)pyrimidin-4-amine (1 g, 3.76 mmol) and 1-methylcyclobutan-1-ol (0.648 g, 7.53 mmol) in THF (20 mL) at 0° C. under nitrogen. The resulting mixture was stirred at rt for 3 hours.

The reaction mixture was concentrated and diluted with EtOAc (100 mL), and washed sequentially with water (100 mL*3) and saturated brine (100 mL). The organic layer was dried over $Na_2SO_4$, filtered and evaporated to afford crude product. The crude product was purified by flash silica chromatography, elution gradient 0 to 80% EtOAc in petroleum ether. Pure fractions were evaporated to dryness to afford 6-(1-methylcyclobutoxy)-5-nitro-N-(pyridin-2-ylmethyl)pyrimidin-4-amine (300 mg, 25%) as a colourless gum. $^1$H NMR (400 MHz, DMSO-$d_6$): 1.63-1.84 (5H, m), 2.21-2.26 (2H, m), 2.32-2.39 (2H, m), 4.80 (2H, d), 7.23-7.37 (2H, m), 7.74-7.78 (1H, m), 8.22 (1H, s), 8.53 (1H, dd), 9.06 (1H, t). m/z: ES+ [M+H]+ 316.

6-Chloro-5-nitro-N-(pyridin-2-ylmethyl)pyrimidin-4-amine was made via a similar procedure to N-benzyl-6-chloro-5-nitropyrimidin-4-amine (Example 4 intermediate), starting from 4,6-dichloro-5-nitropyrimidine and pyridin-2-ylmethanamine. m/z: ES+ [M+H]+ 266.

[J8] Obtained via a similar procedure to 9-benzyl-8-(2-chloro-4-(2-(4-methylpiperazin-1-yl)ethoxy)phenyl)-6-(1-methylcyclopropoxy)-9H-purine (Example 4), using tert-butyl 4-(2-(3-chloro-4-formylphenoxy)ethyl)piperazine-1-carboxylate and 6-(1-methylcyclopropoxy)-N4-(2-(pyridin-3-yl)ethyl)pyrimidine-4,5-diamine, followed by BOC deprotection with t-butyldimethylsilyltrifluoromethanesulfonate (see Example 6 for such deprotection). 6-(1-Methylcyclopropoxy)-N4-(2-(pyridin-3-yl)ethyl)pyrimidine-4,5-diamine was made in a similar method as N4-benzyl-6-(1-methylcyclopropoxy)pyrimidine-4,5-diamine (see Example 4), starting from 4,6-dichloro-5-nitropyrimidine and 2-(pyridin-3-yl)ethan-1-amine.

$^1$H NMR (300 MHz, DMSO-$d_6$): 0.54 (2H, t), 0.72 (2H, t), 1.47 (3H, s), 2.87 (2H, t), 3.52-3.63 (2H, m), 3.88 (2H, s), 6.13 (1H, t), 7.06-7.17 (2H, m), 7.53-7.67 (2H, m), 8.38 (1H, d). m/z: ES+ [M+H]+ 286.

[J9] Obtained via a similar procedure as 8-(2-chloro-4-(2-(piperazin-1-yl)ethoxy)phenyl)-6-(1-methylcyclopropoxy)-9-(2-(pyridin-3-yl)ethyl)-9H-purine (Example J8), from tert-butyl 4-(2-(3-chloro-4-formylphenoxy)ethyl) piperazine-1-carboxylate and (S)-6-(1-methylcyclopropoxy)-N4-(2-phenylpropyl)pyrimidine-4,5-diamine.

(S)-6-(1-Methylcyclopropoxy)-N4-(2-phenylpropyl)pyrimidine-4,5-diamine was made in a similar method as N4-benzyl-6-(1-methylcyclopropoxy)pyrimidine-4,5-diamine (see Example 4), starting from 4,6-dichloro-5-nitropyrimidine and (2S)-2-phenyl-1-propanamine.

$^1$H NMR (300 MHz, DMSO-$d_6$): 0.54 (2H, t), 0.71 (2H, t), 1.09 (3H, d), 1.46 (3H, s), 2.88-2.99 (1H, m), 3.25-3.5 (2H, m), 3.92 (2H, s), 6.05 (1H, t), 7.02-7.23 (5H, m), 7.63 (1H, s). m/z: ES+ [M+H]+ 299.

[J10] Obtained via a similar procedure as 8-(2-chloro-4-(2-(piperazin-1-yl)ethoxy)phenyl)-6-(1-methylcyclopropoxy)-9-(2-(pyridin-3-yl)ethyl)-9H-purine (Example J8), from tert-butyl 4-(2-(3-chloro-4-formylphenoxy)ethyl) piperazine-1-carboxylate and (R)-6-(1-methylcyclopropoxy)-N4-(2-phenylpropyl)pyrimidine-4,5-diamine.

(R)-6-(1-Methylcyclopropoxy)-N4-(2-phenylpropyl)pyrimidine-4,5-diamine was made in a similar method as N4-benzyl-6-(1-methylcyclopropoxy)pyrimidine-4,5-diamine (see Example 4), starting from 4,6-dichloro-5-nitropyrimidine and (2R)-2-phenyl-1-propanamine.

$^1$H NMR (400 MHz, DMSO-$d_6$): 0.66 (2H, t), 0.84 (2H, t), 1.21 (3H, d), 1.58 (3H, s), 3.00-3.10 (1H, m), 3.39-3.47 (1H, m), 3.50-3.59 (1H, m), 4.02 (2H, s), 6.17 (1H, t), 7.16-7.21 (1H, m), 7.23-7.32 (4H, m), 7.74 (1H, s). m/z: ES+ [M+H]+ 299.

[J11] Obtained via a similar procedure as 8-(2-chloro-4-(2-(piperazin-1-yl)ethoxy)phenyl)-6-(1-methylcyclopropoxy)-9-(2-(pyridin-3-yl)ethyl)-9H-purine (Example J8), from tert-butyl 4-(2-(3-chloro-4-formylphenoxy)ethyl) piperazine-1-carboxylate and 6-(1-methylcyclopropoxy)-N4-(2-(pyridin-2-yl)ethyl)pyrimidine-4,5-diamine. 6-(1-Methylcyclopropoxy)-N4-(2-(pyridin-2-yl)ethyl) pyrimidine-4,5-diamine was made in a similar method as N4-benzyl-6-(1-methylcyclopropoxy)pyrimidine-4,5-diamine (see Example 4), starting from 4,6-dichloro-5-nitropyrimidine and 2-(pyridin-2-yl)ethan-1-amine.

$^1$H NMR (400 MHz, DMSO-$d_6$): 0.67 (2H, t), 0.83 (2H, t), 1.59 (3H, s), 2.95-3.10 (2H, m), 3.69-3.74 (2H, m), 3.90-3.99 (2H, m), 6.21-6.28 (1H, m), 7.13-7.34 (2H, m), 7.61-7.82 (2H, m), 8.50 (1H, s). m/z: ES+ [M+H]+ 286.

[J12] Obtained via a similar procedure as 8-(2-chloro-4-(2-(piperazin-1-yl)ethoxy)phenyl)-6-(1-methylcyclopropoxy)-9-(2-(pyridin-3-yl)ethyl)-9H-purine (Example J8), from 6-(1-methylcyclopropoxy)-N4-phenethylpyrimidine-4,5-diamine and tert-butyl 4-(2-(3-chloro-4-formylphenoxy)ethyl)piperazine-1-carboxylate.

6-(1-Methylcyclopropoxy)-N4-phenethylpyrimidine-4,5-diamine was made in a similar method as N4-Benzyl-6-(1-methylcyclopropoxy)pyrimidine-4,5-diamine (see Example 4), starting from 4,6-dichloro-5-nitropyrimidine and 2-phenylethan-1-amine. $^1$H NMR (300 MHz, DMSO-$d_6$): 0.53-0.74 (4H, m), 1.47 (3H, s), 2.72 (2H, t), 3.38-3.49 (2H, m), 3.81-4.00 (2H, m), 6.13 (1H, t), 7.07-7.21 (5H, m), 7.64 (1H, s).

[J13] was obtained via a similar procedure as 8-(2-chloro-4-(2-(piperazin-1-yl)ethoxy)phenyl)-6-(1-methylcyclopropoxy)-9-(2-(pyridin-3-yl)ethyl)-9H-purine (Example J8) from a cyclisation of tert-butyl (E)-4-(2-(3-chloro-4-(((4-((3-chlorobenzyl)amino)-6-(1-methylcyclopropoxy)pyrimidin-5-yl)imino)methyl)phenoxy)ethyl)piperazine-1-carboxylate, followed by a BOC deprotection of the resultant tert-butyl 4-(2-(3-chloro-4-(9-(3-chlorobenzyl)-6-(1-methylcyclopropoxy)-9H-purin-8-yl)phenoxy)ethyl)piperazine-1-carboxylate.

Tert-butyl 4-(2-(3-chloro-4-(9-(3-chlorobenzyl)-6-(1-methylcyclopropoxy)-9H-purin-8-yl)phenoxy)ethyl)piperazine-1-carboxylate. $^1$H NMR (400 MHz, DMSO-$d_6$): 0.85 (2H, t), 1.02 (2H, t), 1.40 (9H, s), 1.73 (3H, s), 2.45 (4H, t), 2.74 (2H, t), 3.16-3.19 (4H, m), 4.20 (2H, t), 5.30 (2H, s), 6.85 (1H, dt), 6.9-7 (1H, m), 7.06 (1H, dd), 7.18-7.34 (3H, m), 7.43 (1H, d), 8.63 (1H, s). m/z: ES+ [M+H]+ 653.

Tert-butyl (E)-4-(2-(3-chloro-4-(((4-((3-chlorobenzyl)amino)-6-(1-methylcyclopropoxy)pyrimidin-5-yl)imino)methyl)phenoxy)ethyl)piperazine-1-carboxylate was made as follows:

Tert-Butyl 4-(2-(3-chloro-4-formylphenoxy)ethyl)piperazine-1-carboxylate (Example 4, intermediate; 1017 mg, 2.76 mmol) was added to N4-(3-chlorobenzyl)-6-(1-methylcyclopropoxy)pyrimidine-4,5-diamine (Example J6 intermediate; 700 mg, 2.30 mmol) in MeOH:acetic acid (20:1; 15 mL) at rt. The resulting mixture was stirred at 25° C. for 2 hours. The solvent was removed under reduced pressure to afford yellow oil. The product was used in the next step directly without further purification. $^1$H NMR (400 MHz, DMSO-$d_6$): 0.76 (2H, t), 0.94 (2H, t), 1.40 (9H, s), 1.65 (3H, s), 2.41-2.47 (4H, m), 2.73 (2H, t), 3.32 (4H, t), 4.14-4.27 (2H, m), 4.65 (2H, d), 7.01-7.06 (1H, m), 7.16 (1H, d), 7.24-7.38 (4H, m), 8.06 (1H, s), 8.43 (1H, d), 9.33 (1H, s). One proton not observed. m/z: ES+ [M+H]+ 655.

The following examples in Table K were synthesised according to Example 23 unless stated otherwise in the notes at the bottom of Table K.

TABLE K

| Ex # | Structure | Name | $^1$H NMR | LCMS [M + H]$^+$ |
|---|---|---|---|---|
| K1 | 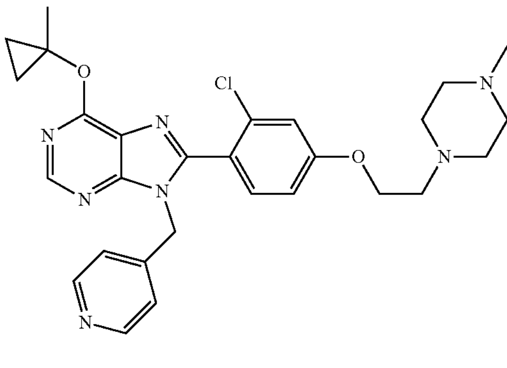 [SMILES: CN1CCN(CCOc2ccc(-c3nc4c(OC5(C)CC5)ncnc4n3Cc3ccncc3)c(Cl)c2)CC1] | 8-(2-chloro-4-(2-(4-methylpiperazin-1-yl)ethoxy)phenyl)-6-(1-methylcyclopropoxy)-9-(pyridin-4-ylmethyl)-9H-purine | (400 MHz, DMSO-$d_6$): 0.79 - 0.88 (2H, m), 1.02 (2H, d), 1.74 (3H, s), 2.14 (3H, s), 2.15-2.36 (4H, m), 2.36-2.50 (4H, m), 2.69 (2H, t), 4.16 (2H, t), 5.32 (2H, s), 6.85 - 6.98 (2H, m), 7.03 (1H, dd), 7.24 (1H, d), 7.45 (1H, d), 8.30 - 8.48 (2H, m), 8.60 (1H, s). | 534 |
| K2 | 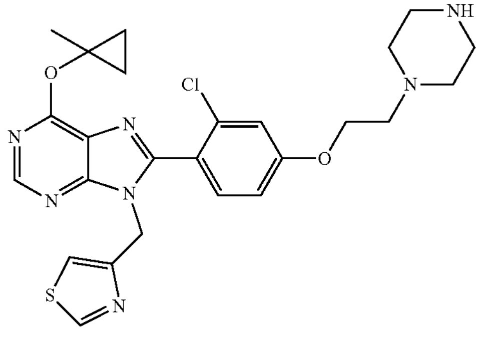 [SMILES: CC1(Oc2ncnc3c2nc(-c2ccc(OCCN4CCNCC4)cc2Cl)n3Cc2cscn2)CC1] | 4-((8-(2-chloro-4-(2-(piperazin-1-yl)ethoxy)phenyl)-6-(1-methylcyclopropoxy)-9H-purin-9-yl)methyl)thiazole | (400 MHz DMSO-$d_6$): 0.72 - 0.87 (2H, m), 1.01 (2H, d), 1.73 (3H, s), 2.40 (4H, s), 2.67 (6H, d), 4.16 (2H, t), 5.41 (2H, s), 6.99 - 7.04 (1H, m), 7.16 - 7.33 (2H, m), 7.40 (1H, d), 8.59 (1H, s), 8.91 (1H, d). One proton not observed. | 526 |

TABLE K-continued

| Ex # | Structure | Name | $^1$H NMR | LCMS $[M + H]^+$ |
|---|---|---|---|---|
| K3 | 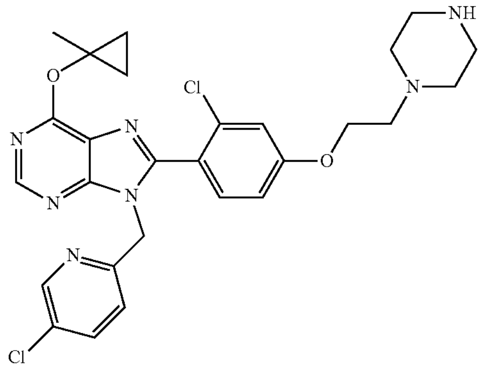 [SMILES: CC1(Oc2ncnc3c2nc(-c2ccc(OCCN4CCNCC4)cc2Cl)n3Cc2ccc(Cl)cn2)CC1] | 8-(2-chloro-4-(2-(piperazin-1-yl)ethoxy)phenyl)-9-((5-chloropyridin-2-yl)methyl)-6-(1-methylcyclopropoxy)-9H-purine | (400 MHz, DMSO-$d_6$): 0.85 (2H, t), 1.02 (2H, t), 1.73 (3H, s), 2.34-2.45 (4H, m), 2.62-2.78 (6H, m), 4.15 (2H, t), 5.39 (2H, s), 6.98 (1H, dd), 7.16 (2H, d), 7.37 (1H, d), 7.80 (1H, dd), 8.39 (1H, d), 8.56 (1H, s). One proton not observed. | 554 |
| K4 | 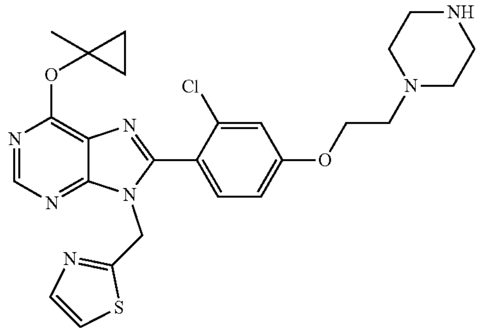 [SMILES: CC1(Oc2ncnc3c2nc(-c2ccc(OCCN4CCNCC4)cc2Cl)n3Cc2nccs2)CC1] | 2-((8-(2-chloro-4-(2-(piperazin-1-yl)ethoxy)phenyl)-6-(1-methylcyclopropoxy)-9H-purin-9-yl)methyl)thiazole | (400 MHz, DMSO-$d_6$): 0.85 (2H, t), 1.02 (2H, t), 1.73 (3H, s), 2.38-2.44 (4H, m), 2.66-2.72 (6H, m), 4.17 (2H, t), 5.61 (2H, s), 7.04 (1H, dd), 7.26 (1H, d), 7.43 (1H, d), 7.63 (2H, s), 8.62 (1H, s). One proton not observed. | 526 |
| K5 | 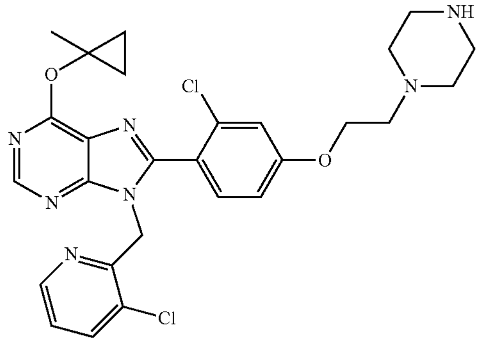 [SMILES: CC1(Oc2ncnc3c2nc(-c2ccc(OCCN4CCNCC4)cc2Cl)n3Cc2ncccc2Cl)CC1] | 8-(2-chloro-4-(2-(piperazin-1-yl)ethoxy)phenyl)-9-((3-chloropyridin-2-yl)methyl)-6-(1-methylcyclopropoxy)-9H-purine | (400 MHz, DMSO-$d_6$): 0.85 (2H, t), 1.03 (2H, t), 1.74 (3H, s), 2.34-2.42 (4H, m), 2.62-2.70 (6H, m), 4.13 (2H, t), 5.54 (2H, s), 6.92 (1H, dd), 7.20 (1H, d), 7.26 – 7.32 (2H, m), 7.86 (1H, dd), 8.25 (1H, dd), 8.54 (1H, s). One proton not observed. | 554 |
| K6 | 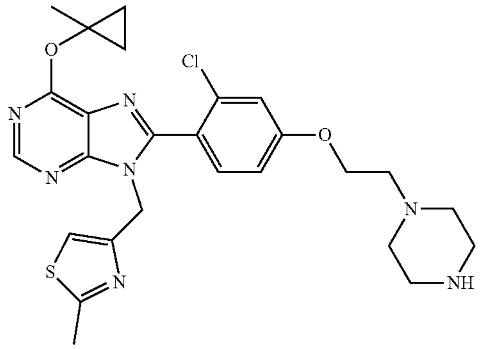 [SMILES: Cc1nc(Cn2c(-c3ccc(OCCN4CCNCC4)cc3Cl)nc3c(OC4(C)CC4)ncnc32)cs1] | 4-((8-(2-chloro-4-(2-(piperazin-1-yl)ethoxy)phenyl)-6-(1-methylcyclopropoxy)-9H-purin-9-yl)methyl)-2-methylthiazole | (500 MHz, $CDCl_3$): 0.79 – 0.84 (2H, m), 1.13 – 1.17 (2H, m), 1.79 (3H, s), 2.57 (7H, br s), 2.81 (2H, t), 2.93 (4H, t), 4.14 (2H, t), 5.41 (2H, s), 6.57 (1H, s), 6.85 (1H, dd), 7.03 (1H, d), 7.24 – 7.36 (1H, m), 8.65 (1H, s). One proton not observed. | 540 |

TABLE K-continued

| Ex # | Structure | Name | $^1H$ NMR | LCMS $[M + H]^+$ |
|---|---|---|---|---|
| K7 | 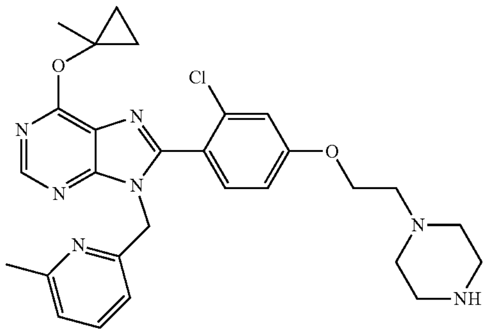 [SMILES: Cc1cccc(Cn2c(-c3ccc(OCCN4CCNCC4)cc3Cl)nc3c(OC4(C)CC4)ncnc32)n1] | 8-(2-chloro-4-(2-(piperazin-1-yl)ethoxy) phenyl)-6-(1-methylcyclopropoxy)-9-((6-methylpyridin-2-yl)methyl)-9H-purine | (500 MHz, $CDCl_3$): 0.81 - 0.85 (2H, m), 1.14 - 1.19 (2H, m), 1.80 (3H, s), 2.40 (3H, s), 2.55 (4H, s), 2.80 (2H, t), 2.92 (4H, t), 4.12 (2H, t), 5.42 (2H, s), 6.62 (1H, d), 6.80 (1H, dd), 6.95 (1H, d), 7.01 (1H, d), 7.27 - 7.33 (1H, m), 7.39 (1H, t), 8.62 (1H, s). One proton not observed. | 534 |
| K8 | 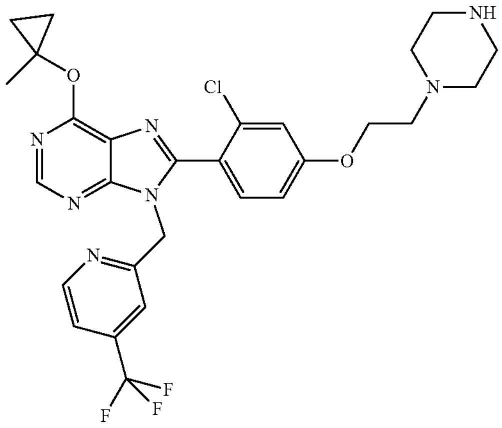 [SMILES: CC1(Oc2ncnc3c2nc(-c2ccc(OCCN4CCNCC4)cc2Cl)n3Cc2cc(C(F)(F)F)ccn2)CC1] | 8-(2-chloro-4-(2-(piperazin-1-yl)ethoxy)phenyl)-6-(1-methylcyclopropoxy)-9-((4-(trifluoromethyl) pyridin-2-yl)methyl)-9H-purine | (400 MHz, DMSO-$d_6$): 0.86 (2H, t), 1.04 (2H, t), 1.74 (3H, s), 2.38-2.44 (4H, m), 2.61-2.75 (6H, m), 4.05 - 4.24 (2H, m), 5.48 (2H, s), 6.91 - 7.00 (1H, m), 7.11-7.22 (1H, m), 7.28 - 7.35 (1H, m), 7.48-7.53 (1H, m), 7.61 (1H, s), 8.53 - 8.69 (2H, m). One proton not observed. | 588 |
| K9 | 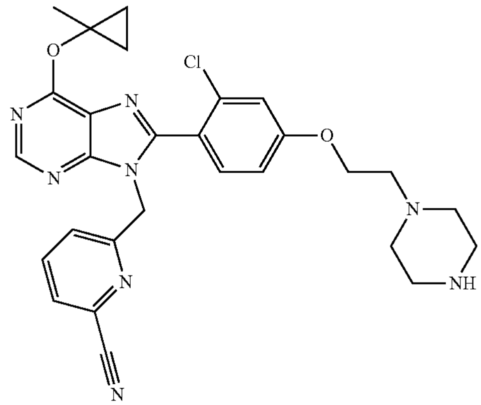 [SMILES: CC1(Oc2ncnc3c2nc(-c2ccc(OCCN4CCNCC4)cc2Cl)n3Cc2cccc(C#N)n2)CC1] | 6-((8-(2-chloro-4-(2-(piperazin-1-yl)ethoxy)phenyl)-6-(1-methylcyclopropoxy)-9H-purin-9-yl)methyl) picolinonitrile | (500 MHz, $CDCl_3$): 0.81 - 0.86 (2H, m), 1.13 - 1.2 (2H, m), 1.80 (3H, s), 2.56 (4H, br s), 2.81 (2H, t), 2.92 (4H, t), 4.14 (2H, t), 5.48 (2H, s), 6.87 (1H, dd), 7.03 (1H, d), 7.27 (1H, d), 7.35 (1H, d), 7.53 (1H, d), 7.72 (1H, t), 8.60 (1H, s). One proton not observed. | 545 |
| K10 | 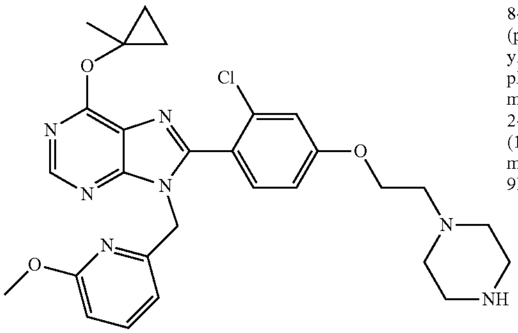 | 8-(2-chloro-4-(2-(piperazin-1-yl)ethoxy) phenyl)-9-((6-methoxypyridin-2-yl)methyl)-6-(1-methylcyclopropoxy)-9H-purine | (500 MHz, $CDCl_3$): 0.78 - 0.86 (2H, m), 1.12 -1.2 (2H, m), 1.80 (3H, s), 2.55 (4H, s), 2.80 (2H, t), 2.92 (4H, t), 3.63 (3H, s), 4.12 (2H, t), 5.35 (2H, s), 6.51 (2H, dd), 6.80 (1H, dd), 7.03 (1H, d), 7.32 (1H, d), 7.36 - 7.41 (1H, m), 8.62 (1H, s). One proton not observed. | 550 |

TABLE K-continued

| Ex # | Structure | Name | $^1$H NMR | LCMS [M + H]$^+$ |
|---|---|---|---|---|
| K11 | 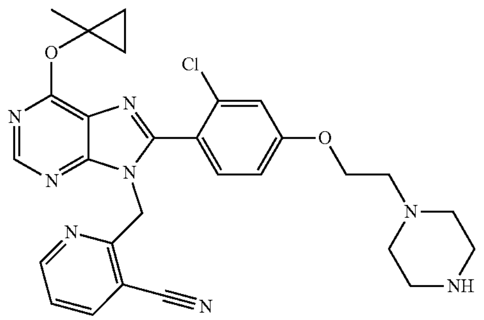 [SMILES: CC1(Oc2ncnc3c2nc(-c2ccc(OCCN4CCNCC4)cc2Cl)n3Cc2ncccc2C#N)CC1] | 2-((8-(2-chloro-4-(2-(piperazin-1-yl)ethoxy)phenyl)-6-(1-methylcyclopropoxy)-9H-purin-9-yl)methyl) nicotinonitrile | (500 MHz, $CDCl_3$): 0.8 – 0.86 (2H, m), 1.13 – 1.19 (2H, m), 1.80 (3H, s), 2.64 (4H, br s), 2.82 (2H, t), 2.96 – 3.05 (4H, m), 4.11 (2H, t), 5.69 (2H, s), 6.77 (1H, dd), 7.01 (1H, d), 7.23 – 7.26 (1H, m), 7.30 (1H, d), 7.86 (1H, dd), 8.53 (1H, dd), 8.59 (1H, s). One proton not observed. | 545 |
| K12 | 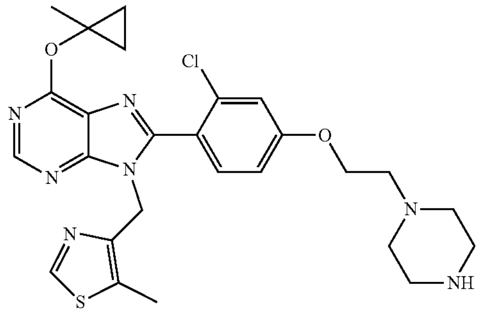 [SMILES: Cc1scnc1Cn1c(-c2ccc(OCCN3CCNCC3)cc2Cl)nc2c(OC3(C)CC3)ncnc21] | 4-((8-(2-chloro-4-(2-(piperazin-1-yl)ethoxy)phenyl)-6-(1-methylcyclopropoxy)-9H-purin-9-yl)methyl)-5-methylthiazole | (500 MHz, $CDCl_3$): 0.76- 0.85 (2H, m), 1.09 – 1.18 (2H, m), 1.78 (3H, s), 2.20 (3H, s), 2.68 (4H, br s), 2.84 (2H, t), 3.05 (4H, br s), 4.13 (2H, t), 5.41 (2H, s), 6.82 (1H, dd), 7.02 (1H, d), 7.24 (1H, d), 8.36 (1H, s), 8.66 (1H, s). One proton not observed. | 540 |

[K1] NaH (65 mg, 2.71 mmol) was added to 8-(2-chloro-4-(2-(4-methylpiperazin-1-yl)ethoxy)phenyl)-6-(1-methylcyclopropoxy)-7H-purine (600 mg, 1.35 mmol) in DMF (10 mL). The resulting mixture was stirred at RT for 10 minutes. Then 4-(chloromethyl)pyridine (259 mg, 2.03 mmol) was added. Finally triethylamine (283 µL, 2.03 mmol) was added. The resulting mixture was stirred at 50° C. for 30 minutes. The reaction mixture was concentrated and diluted with EtOAc (100 mL), and washed sequentially with water (100 mL×3) and saturated brine (100 mL). The organic layer was dried over $Na_2SO_4$, filtered and evaporated to afford crude product. The crude product was purified by preparative Column: XBridge Prep OBD C18 Column, 30*150 mm, 5 µm; using decreasingly polar mixtures of acetonitrile in water (containing 10 mmol/L $NH_4HCO_3$ and 0.1% aqueous ammonia). Fractions containing the desired compound were evaporated to afford 8-(2-chloro-4-(2-(4-methylpiperazin-1-yl)ethoxy)phenyl)-6-(1-methylcyclopropoxy)-9-(pyridin-4-ylmethyl)-9H-purine (7.9 mg, 11%) as a white solid.

8-(2-Chloro-4-(2-(4-methylpiperazin-1-yl)ethoxy)phenyl)-6-(1-methylcyclopropoxy)-7H-purine was made by a similar method as 4-((8-(2-chloro-4-(2-(4-methylpiperazin-1-yl)ethoxy)phenyl)-6-(1-methylcyclopropoxy)-9H-purin-9-yl)methyl)-2-methylthiazole (see Example 7), starting from 6-(1-methylcyclopropoxy)-5-nitropyrimidin-4-amine (see Example K5) and 2-chloro-4-(2-(4-methylpiperazin-1-yl)ethoxy)benzaldehyde (see Example 4). m/z: ES+ [M+H]+ 443

[K2] Obtained via a similar procedure as 9-benzyl-8-(2-chloro-4-(2-(piperazin-1-yl)ethoxy)phenyl)-6-(1-methylcyclobutoxy)-9H-purine (Example 12), using 4-((8-bromo-6-(1-methylcyclopropoxy)-9H-purin-9-yl)methyl)thiazole and tert-butyl 4-(2-(3-chloro-4-(4,4,5,5-tetramethyl-1,3,2-dioxaborolan-2-yl)phenoxy)ethyl)piperazine-1-carboxylate, followed by BOC deprotection using TFA.

4-((8-Bromo-6-(1-methylcyclopropoxy)-9H-purin-9-yl)methyl)thiazole was made as follows:

Cesium carbonate (726 mg, 2.23 mmol) was added dropwise to 4-(chloromethyl)thiazole hydrochloride (316 mg, 1.86 mmol) and 8-bromo-6-(1-methylcyclopropoxy)-9H-purine (500 mg, 1.86 mmol, obtained via free basing of the HBr salt, see Example 23) in DMF (10 mL) at 0° C. under nitrogen. The resulting mixture was stirred at rt for 16 hours. The reaction mixture was poured into water (500 mL) and extracted with EtOAc (3×500 mL). The organic layer was dried over $Na_2SO_4$, filtered and evaporated to afford a brown liquid. The crude product was purified by flash silica chromatography, elution gradient 50 to 100% EtOAc in petroleum ether. Pure fractions were evaporated to dryness to afford 4-((8-bromo-6-(1-methylcyclopropoxy)-9H-purin-9-yl)methyl)thiazole (90 mg, 13%). $^1$H NMR (300 MHz, DMSO-$d_6$): 0.71 (2H, t), 0.86 (2H, t), 1.58 (3H, s), 5.45 (2H, d), 7.49 (1H, d), 8.43 (1H, s), 8.91 (1H, d). m/z: ES+ [M+H]+ 366.

[K3] Obtained via a similar procedure as 8-(2-chloro-4-(2-(piperazin-1-yl)ethoxy)phenyl)-9-((6-chloropyridin-2-yl)methyl)-6-(1-methylcyclopropoxy)-9H-purine (Example 23), using tert-butyl 4-(2-(3-chloro-4-(6-(1-methylcyclopropoxy)-9H-purin-8-yl)phenoxy)ethyl)piperazine-1-carboxylate and 5-chloro-2-(chloromethyl)pyridine

[K4] Obtained via a similar procedure as 8-(2-chloro-4-(2-(piperazin-1-yl)ethoxy)phenyl)-9-((6-chloropyridin-2-yl)methyl)-6-(1-methylcyclopropoxy)-9H-purine (Example 23), using tert-butyl 4-(2-(3-chloro-4-(6-(1-methylcyclopropoxy)-9H-purin-8-yl)phenoxy)ethyl)piperazine-1-carboxylate and 2-(chloromethyl)thiazole

[K5] Obtained via a similar sequence as 2-(2-chloro-4-(2-(piperazin-1-yl)ethoxy)phenyl)-3-((4-chloropyridin-2-yl)methyl)-7-(1-methylcyclopropoxy)-3H-imidazo[4,5-b]pyridine (Example 14), starting from N-((3-chloropyridin-2-yl)methyl)-6-(1-methylcyclopropoxy)-5-nitropyrimidin-4-amine.

N-((3-Chloropyridin-2-yl)methyl)-6-(1-methylcyclopropoxy)-5-nitropyrimidin-4-amine used at the start of the sequence was made as follows:

N-(4-methoxybenzyl)-6-(1-methylcyclopropoxy)-5-nitropyrimidin-4-amine

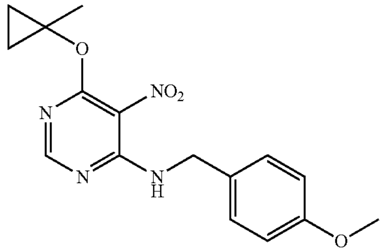 [SMILES: COc1ccc(CNc2ncnc(OC3(C)CC3)c2[N+](=O)[O-])cc1]

LHMDS (75 mL, 75 mmol) was added dropwise to 6-chloro-N-(4-methoxybenzyl)-5-nitropyrimidin-4-amine (10 g, 33.9 mmol; Bioorg. Med. Chem., 2010, 18, 3885-3897) and 1-methylcyclopropan-1-ol (3.67 g, 50.9 mmol) in THF (150 mL) at 0° C. under nitrogen. The resulting mixture was stirred at rt for 3 hours. The reaction mixture was then concentrated under reduced pressure and diluted with EtOAc (100 mL), and washed sequentially with water (100 mL*3) and saturated brine (100 mL). The organic layer was dried over $Na_2SO_4$, filtered and evaporated to afford crude product. The crude product was purified by flash silica chromatography, elution gradient 0 to 80% EtOAc in petroleum ether. Pure fractions were evaporated to dryness to afford N-(4-methoxybenzyl)-6-(1-methylcyclopropoxy)-5-nitropyrimidin-4-amine (9.0 g, 80%) as a colourless gum. $^1H$ NMR (400 MHz, DMSO-$d_6$): 0.70-0.80 (2H, t), 0.91 (2H, t), 1.61 (3H, s), 3.71 (3H, s), 4.61 (2H, d), 6.82-6.92 (2H, m), 7.19-7.31 (2H, m), 8.33 (1H, s), 8.78 (1H, t). m/z: ES+ [M+H]+ 331.

6-(1-methylcyclopropoxy)-5-nitropyrimidin-4-amine

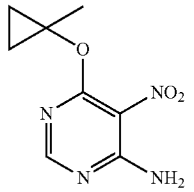

N-(4-methoxybenzyl)-6-(1-methylcyclopropoxy)-5-nitropyrimidin-4-amine (8.5 g, 25.7 mmol) was added into DCM (50 mL) and trifluoroacetic acid (50 mL). The resulting mixture was stirred at 80° C. for 3 hours. The reaction mixture was then cooled to RT and evaporated to afford crude product. The crude product was purified by flash C18-flash chromatography, elution gradient 0 to 100% MeCN in water (containing 0.05% TFA). Pure fractions were evaporated to dryness to afford 6-(1-methylcyclopropoxy)-5-nitropyrimidin-4-amine (4.25 g, 79%) as a yellow solid. $^1H$ NMR (300 MHz, DMSO-$d_6$): 0.76 (2H, t), 0.91 (2H, t), 1.62 (3H, s), 8.01 (2H, s), 8.25 (1H, s). m/z: ES+ [M+H]+ 211.

N-((3-chloropyridin-2-yl)methyl)-6-(1-methylcyclopropoxy)-5-nitropyrimidin-4-amine

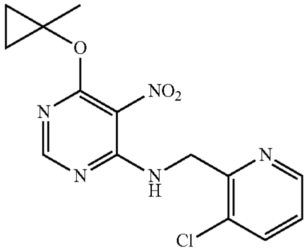 [SMILES: CC1(Oc2ncnc(NCc3ncccc3Cl)c2[N+](=O)[O-])CC1]

6-(1-methylcyclopropoxy)-5-nitropyrimidin-4-amine (300 mg, 1.43 mmol) and 3-chloro-2-(chloromethyl)pyridine (347 mg, 2.14 mmol) was added into DMF (6 mL) and $Cs_2CO_3$ (930 mg, 2.85 mmol). The resulting mixture was stirred at 100° C. for 1 hour. The reaction mixture was poured into aq. sat. $NaHCO_3$ (40 mL) and extracted with ethyl acetate (20 mL×3). The combined organic layers were washed with brine (20 mL×2), dried over $Na_2SO_4$, filtered and concentrated under reduced pressure to give the crude product. The crude product was purified by flash C18-flash chromatography, elution gradient 0 to 100% MeCN in water. Pure fractions were evaporated to dryness to afford N-((3-chloropyridin-2-yl)methyl)-6-(1-methylcyclopropoxy)-5-nitropyrimidin-4-amine (255 mg, 53%) as a pale yellow solid. m/z: ES+ [M+H]+ 336.

The following examples in Table L were synthesised according to Example L1 unless stated otherwise in the notes at the bottom of Table L.

TABLE L

| Ex# | Structure | Name | $^1H$ NMR | LCMS [M + H]+ |
|---|---|---|---|---|
| L1 | 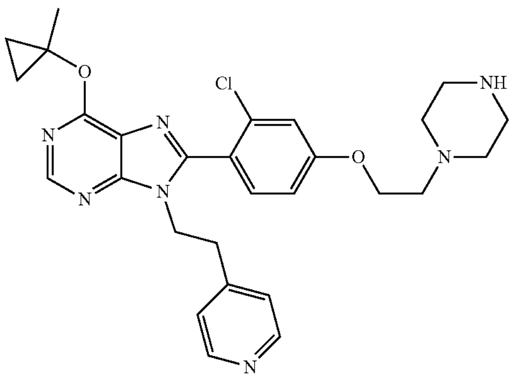 [SMILES: CC1(Oc2ncnc3c2nc(-c2ccc(OCCN4CCNCC4)cc2Cl)n3CCc2ccncc2)CC1] | 8-(2-chloro-4-(2-(piperazin-1-yl)ethoxy)phenyl)-6-(1-methyl-cyclopropoxy)-9-(2-(pyridin-4-yl)ethyl)-9H-purine | (400 MHz, $CD_3OD$): 0.87 (2H, t), 1.10 (2H, t), 1.80 (3H, s), 2.61-2.68 (4H, m), 2.87 (2H, t), 2.93 (4H, t), 3.14 (2H, t), 4.25 (2H, t), 4.48 (2H, t), 6.9-6.94 (2H, m), 6.98 (2H, d), 7.22 (1H, t), 8.27-8.3 (2H, m), 8.60 (1H, s). 1H not observed | 534 |

TABLE L-continued

| Ex# | Structure | Name | $^1$H NMR | LCMS [M + H]+ |
| --- | --- | --- | --- | --- |
| L2 | 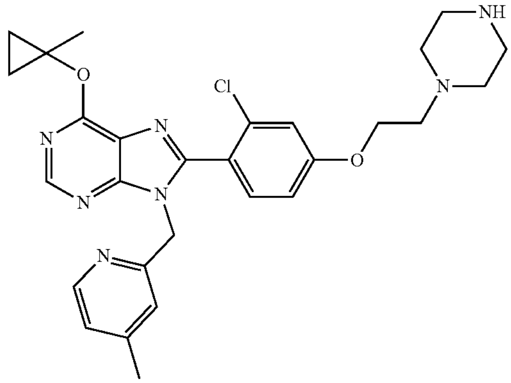 [SMILES: Cc1ccnc(Cn2c(-c3ccc(OCCN4CCNCC4)cc3Cl)nc3c(OC4(C)CC4)ncnc32)c1] | 8-(2-chloro-4-(2-(piperazin-1-yl)ethoxy)phenyl)-6-(1-methyl-cyclopropoxy)-9-((4-methylpyridin-2-yl)methyl)-9H-purine | (500 MHz, $CDCl_3$): 0.8-0.86 (2H, m), 1.13-1.2 (2H, m), 1.81 (3H, s), 2.21 (3H, s), 2.55 (4H, br s), 2.79 (2H, t), 2.86-2.97 (4H, m), 4.11 (2H, t), 5.43 (2H, s), 6.65 (1H, s), 6.77 (1H, dd), 6.91 (1H, d), 7.01 (1H, d), 7.24 (1H, d), 8.24 (1H, d), 8.64 (1H, s). 1H not observed | 534 |
| L3 | 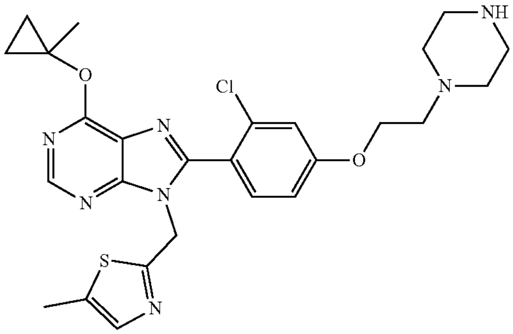 [SMILES: Cc1cnc(Cn2c(-c3ccc(OCCN4CCNCC4)cc3Cl)nc3c(OC4(C)CC4)ncnc32)s1] | 2-((8-(2-chloro-4-(2-(piperazin-1-yl)ethoxy)phenyl)-6-(1-methyl-cyclopropoxy)-9H-purin-9-yl)methyl)-5-methylthiazole | (500 MHz, $CDCl_3$): 0.79-0.85 (2H, m), 1.15 (2H, t), 1.79 (3H, s), 2.35 (3H, s), 2.56 (4H, s), 2.81 (2H, t), 2.93 (4H, t), 4.14 (2H, t), 5.55 (2H, s), 6.87 (1H, dd), 7.05 (1H, d), 7.24 (1H, s), 7.35 (1H, d), 8.67 (1H, s). 1H not observed | 540 |
| L4 | 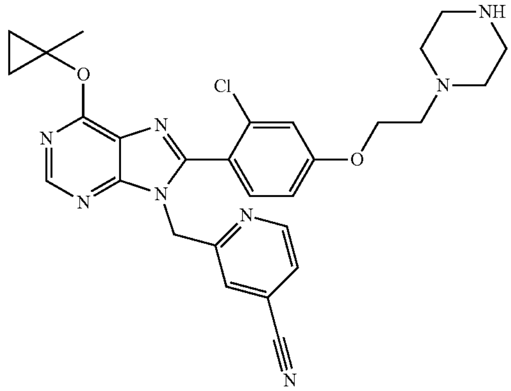 [SMILES: CC1(Oc2ncnc3c2nc(-c2ccc(OCCN4CCNCC4)cc2Cl)n3Cc2cc(C#N)ccn2)CC1] | 2-((8-(2-chloro-4-(2-(piperazin-1-yl)ethoxy)phenyl)-6-(1-methyl-cyclopropoxy)-9H-purin-9-yl)methyl)iso-nicotinonitrile | (500 MHz, $CDCl_3$): 0.8-0.87 (2H, m), 1.15-1.19 (2H, m), 1.81 (3H, s), 2.49-2.62 (4H, m), 2.81 (2H, t), 2.9-2.96 (4H, m), 4.12 (2H, t), 5.50 (2H, s), 6.82 (1H, dd), 7.02 (1H, d), 7.12-7.16 (1H, m), 7.27 (1H, d), 7.35 (1H, dd), 8.59 (1H, dd), 8.62 (1H, s). 1H not observed. | 545 |
| L5 | 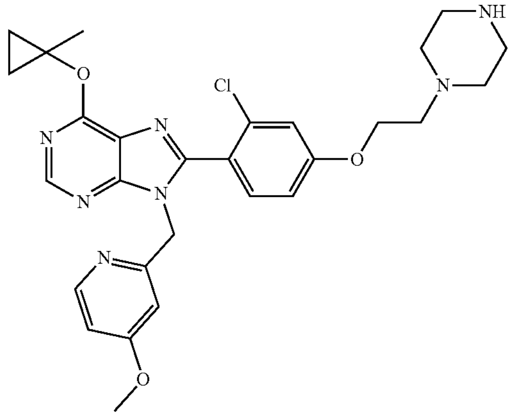 [SMILES: COc1ccnc(Cn2c(-c3ccc(OCCN4CCNCC4)cc3Cl)nc3c(OC4(C)CC4)ncnc32)c1] | 8-(2-chloro-4-(2-(piperazin-1-yl)ethoxy)phenyl)-9-((4-methoxypyridin-2-yl)methyl)-6-(1-methyl-cyclopropoxy)-9H-purine | (500 MHz, DMSO-$d_6$): 0.78-0.86 (2H, m), 1.14-1.19 (2H, m), 1.80 (3H, s), 2.51-2.58 (4H, m), 2.79 (2H, t), 2.9-2.93 (4H, m), 3.72 (3H, s), 4.11 (2H, t), 5.41 (2H, s), 6.36 (1H, d), 6.62 (1H, dd), 6.79 (1H, dd), 7.01 (1H, d), 7.26-7.28 (1H, m), 8.23 (1H, d), 8.64 (1H, s). 1H not observed. | 550 |

TABLE L-continued

| Ex# | Structure | Name | $^1H$ NMR | LCMS [M + H]+ |
|---|---|---|---|---|
| L6 | 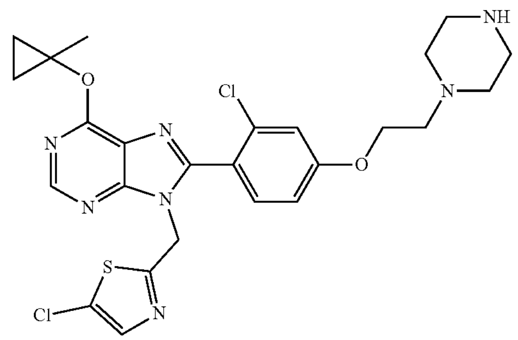 [SMILES: CC1(Oc2ncnc3c2nc(-c2ccc(OCCN4CCNCC4)cc2Cl)n3Cc2ncc(Cl)s2)CC1] | 5-chloro-2-((8-(2-chloro-4-(2-(piperazin-1-yl)ethoxy)phenyl)-6-(1-methyl-cyclopropoxy)-9H-purin-9-yl)methyl)thiazole | (500 MHz, DMSO-$d_6$): 0.81-0.87 (2H, m), 0.99-1.04 (2H, m), 1.72 (3H, s), 2.37-2.46 (4H, m), 2.68 (2H, t), 2.7-2.75 (4H, m), 4.18 (2H, t), 5.54 (2H, s), 7.06 (1H, dd), 7.25 (1H, d), 7.44 (1H, d), 7.64 (1H, s), 8.61 (1H, s). 1H not observed. | 560 |
| L7 | 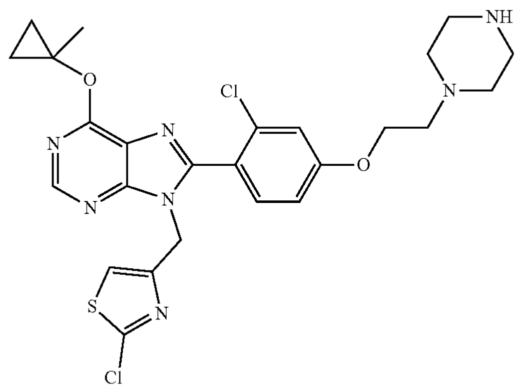 [SMILES: CC1(Oc2ncnc3c2nc(-c2ccc(OCCN4CCNCC4)cc2Cl)n3Cc2csc(Cl)n2)CC1] | 2-chloro-4-((8-(2-chloro-4-(2-(piperazin-1-yl)ethoxy)phenyl)-6-(1-methyl-cyclopropoxy)-9H-purin-9-yl)methyl)thiazole | (500 MHz, $CDCl_3$): 0.8-0.85 (2H, m), 1.13-1.18 (2H, m), 1.79 (3H, s), 2.59 (4H, s), 2.82 (2H, t), 2.95 (4H, t), 4.15 (2H, t), 5.38 (2H, s), 6.75 (1H, s), 6.88 (1H, dd), 7.04 (1H, d), 7.35 (1H, d), 8.64 (1H, s). 1H not observed. | 560 |
| L8 | 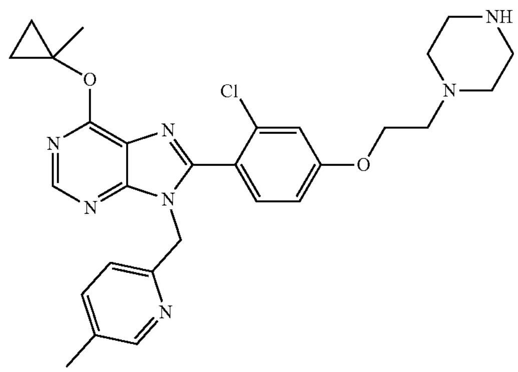 [SMILES: Cc1ccc(Cn2c(-c3ccc(OCCN4CCNCC4)cc3Cl)nc3c(OC4(C)CC4)ncnc32)nc1] | 8-(2-chloro-4-(2-(piperazin-1-yl)ethoxy)phenyl)-6-(1-methyl-cyclopropoxy)-9-((5-methylpyridin-2-yl)methyl)-9H-purine | (500 MHz, $CDCl_3$): 0.79-0.85 (2H, m), 1.14-1.18 (2H, m), 1.80 (3H, s), 2.24 (3H, s), 2.55 (4H, s), 2.80 (2H, t), 2.93 (4H, t), 4.11 (2H, t), 5.42 (2H, s), 6.75 (1H, d), 6.78 (1H, dd), 7.01 (1H, d), 7.25 (1H, s), 7.30 (1H, d), 8.23 (1H, s), 8.63 (1H, d). 1H not observed. | 534 |
| L9 | 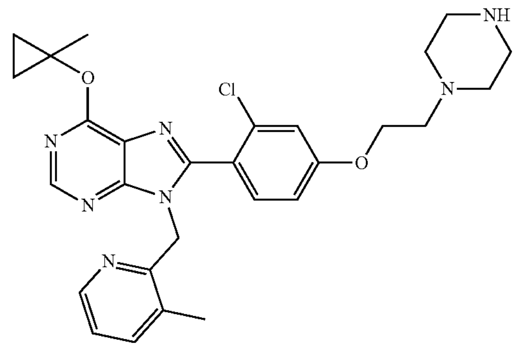 [SMILES: Cc1cccnc1Cn1c(-c2ccc(OCCN3CCNCC3)cc2Cl)nc2c(OC3(C)CC3)ncnc21] | 8-(2-chloro-4-(2-(piperazin-1-yl)ethoxy)phenyl)-6-(1-methyl-cyclopropoxy)-9-((3-methylpyridin-2-yl)methyl)-9H-purine | (500 MHz, DMSO-$d_6$): 0.87-0.92 (2H, m), 1.06-1.11 (2H, m), 1.78 (3H, s), 2.38-2.44 (4H, m), 2.60 (3H, s), 2.66 (2H, t), 2.68-2.73 (4H, m), 4.13 (2H, t), 5.84 (2H, s), 6.98 (1H, dd), 7.07 (1H, d), 7.22 (1H, dd), 7.67 (1H, d), 7.94 (1H, d), 8.22 (1H, d), 8.87 (1H, s). 1H not observed. | 534 |

TABLE L-continued

| Ex# | Structure | Name | $^1$H NMR | LCMS [M + H]+ |
|---|---|---|---|---|
| L10 | 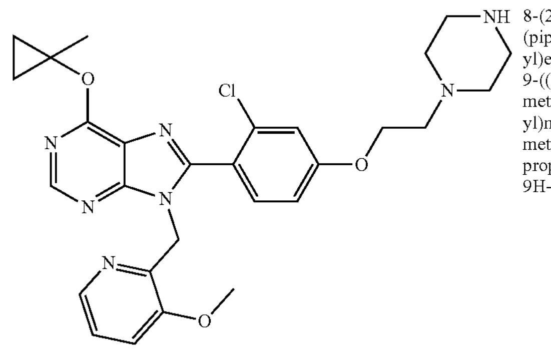 | 8-(2-chloro-4-(2-(piperazin-1-yl)ethoxy)phenyl)-9-((3-methoxypyridin-2-yl)methyl)-6-(1-methylcyclo-propoxy)-9H-purine | (500 MHz, $CDCl_3$): 0.78-0.85 (2H, m), 1.13-1.19 (2H, m), 1.80 (3H, s), 2.56 (4H, s), 2.79 (2H, t), 2.9-2.97 (4H, m), 3.72 (3H, s), 4.09 (2H, t), 5.50 (2H, s), 6.72 (1H, dd), 6.97 (1H, d), 7.00 (1H, dd), 7.06 (1H, dd), 7.28 (1H, d), 7.90 (1H, dd), 8.60 (1H, s). 1H not observed. | 550 |

[L1] 8-(2-Chloro-4-(2-(piperazin-1-yl)ethoxy)phenyl)-6-(1-methylcyclopropoxy)-9-(2-(pyridin-4-yl)ethyl)-9H-purine was made as follows:

Diisopropyl azodicarboxylate (DIAD) (344 mg, 1.70 mmol) was added dropwise to tert-butyl 4-(2-(3-chloro-4-(6-(1-methylcyclopropoxy)-9H-purin-8-yl)phenoxy)ethyl) piperazine-1-carboxylate (150 mg, 0.28 mmol), 2-(pyridin-4-yl)ethan-1-ol (52.4 mg, 0.43 mmol) and triphenylphosphine (223 mg, 0.85 mmol) in THF (3 mL) at 0° C. The resulting mixture was stirred at 0° C. for 1 hour. The reaction mixture was diluted with EtOAc (15 mL), and washed sequentially with water (15 mL×3). The organic layer was dried over $Na_2SO_4$, filtered and evaporated to afford crude product. The crude product was purified by flash silica chromatography, elution gradient 0 to 10% MeOH in DCM. Pure fractions were evaporated to dryness to afford tert-butyl 4-(2-(3-chloro-4-(6-(1-methylcyclopropoxy)-9-(2-(pyridin-4-yl)ethyl)-9H-purin-8-yl)phenoxy) ethyl)piperazine-1-carboxylate (90 mg, 50%) as a yellow oil. TFA (0.5 mL) was then added to tert-butyl 4-(2-(3-chloro-4-(6-(1-methylcyclopropoxy)-9-(2-(pyridin-4-yl) ethyl)-9H-purin-8-yl)phenoxy)ethyl)piperazine-1-carboxylate (70 mg, 0.11 mmol) in DCM (2 mL) at 25° C. The resulting mixture was stirred at 25° C. for 1 hour. The solvent was removed under reduced pressure. The crude product was purified by preparative HPLC (XBridge Prep C18 OBD column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford 8-(2-chloro-4-(2-(piperazin-1-yl)ethoxy) phenyl)-6-(1-methylcyclopropoxy)-9-(2-(pyridin-4-yl) ethyl)-9H-purine (21 mg, 36%) as a white solid.

[L2] Obtained from a similar procedure as 8-(2-chloro-4-(2-(piperazin-1-yl)ethoxy)phenyl)-6-(1-methylcyclopropoxy)-9-(2-(pyridin-4-yl)ethyl)-9H-purine (Example L1), using tert-butyl 4-(2-(3-chloro-4-(6-(1-methylcyclopropoxy)-9H-purin-8-yl)phenoxy)ethyl)piperazine-1-carboxylate and (4-methylpyridin-2-yl)methanol, except that the Mitsunobu reaction carried out at 60° C.

[L4] was made from a similar procedure as 8-(2-chloro-4-(2-(piperazin-1-yl)ethoxy)phenyl)-6-(1-methylcyclopropoxy)-9-(2-(pyridin-4-yl)ethyl)-9H-purine (Example L1), using tert-butyl 4-(2-(3-chloro-4-(6-(1-methylcyclopropoxy)-9H-purin-8-yl)phenoxy)ethyl)piperazine-1-carboxylate (157 mg, 0.30 mmol) and 2-(hydroxymethyl)isonicotinonitrile (80 mg, 0.59 mmol), except that the reagents were combined at ambient temperature and the reaction was stirred then at 60° C. for 2 hours. The crude product was purified by ion exchange chromatography, using an SCX column, and then preparative HPLC purification to afford the BOC protected product. BOC deprotection was carried out using HCl (1N in EtOAc) in EtOAc, followed by further addition of HCl (6N in IPA) and DCM, to afford 2-((8-(2-chloro-4-(2-(piperazin-1-yl)ethoxy)phenyl)-6-(1-methylcyclopropoxy)-9H-purin-9-yl)methyl)isonicotinonitrile (46 mg, 58%) as a solid.

[L5] was made from a similar procedure to 2-((8-(2-chloro-4-(2-(piperazin-1-yl)ethoxy)phenyl)-6-(1-methylcyclopropoxy)-9H-purin-9-yl)methyl)isonicotinonitrile (Example L4) using tert-butyl 4-(2-(3-chloro-4-(6-(1-methylcyclopropoxy)-9H-purin-8-yl)phenoxy)ethyl) piperazine-1-carboxylate (145 mg, 0.27 mmol) and (4-methoxypyridin-2-yl)methanol (76 mg, 0.55 mmol), except that BOC deprotection was carried out in DCM using 6N HCl in iPrOH.

[L6] was made from a similar procedure to 2-((8-(2-chloro-4-(2-(piperazin-1-yl)ethoxy)phenyl)-6-(1-methylcyclopropoxy)-9H-purin-9-yl)methyl)isonicotinonitrile (Example L4) using tert-butyl 4-(2-(3-chloro-4-(6-(1-methylcyclopropoxy)-9H-purin-8-yl)phenoxy)ethyl) piperazine-1-carboxylate (151 mg, 0.29 mmol) and (5-chlorothiazol-2-yl)methanol (85 mg, 0.57 mmol), except that BOC deprotection was carried out in DCM using 6N HCl in iPrOH.

[L9] was made from a similar procedure to 2-((8-(2-chloro-4-(2-(piperazin-1-yl)ethoxy)phenyl)-6-(1-methylcyclopropoxy)-9H-purin-9-yl)methyl)isonicotinonitrile (Example L4) using tert-butyl 4-(2-(3-chloro-4-(6-(1-methylcyclopropoxy)-9H-purin-8-yl)phenoxy)ethyl) piperazine-1-carboxylate (148 mg, 0.28 mmol) and (3-methylpyridin-2-yl)methanol (69 mg, 0.56 mmol), except that BOC deprotection was carried out in DCM using 6N HCl in iPrOH.

[L10] Obtained from a similar procedure as 8-(2-chloro-4-(2-(piperazin-1-yl)ethoxy)phenyl)-6-(1-methylcyclopropoxy)-9-(2-(pyridin-4-yl)ethyl)-9H-purine [Example L1], using tert-butyl 4-(2-(3-chloro-4-(6-(1-methylcyclopropoxy)-9H-purin-8-yl)phenoxy)ethyl)piperazine-1-carboxylate and (3-methoxypyridin-2-yl)methanol, except that the Mitsunobu reaction was carried out at 60° C.

The following examples in Table M were synthesised according the notes at the bottom of Table M.

TABLE M

| Ex# | Structure | Name | $^1$H NMR | LCMS [M + H]+ |
| --- | --- | --- | --- | --- |
| M1 | 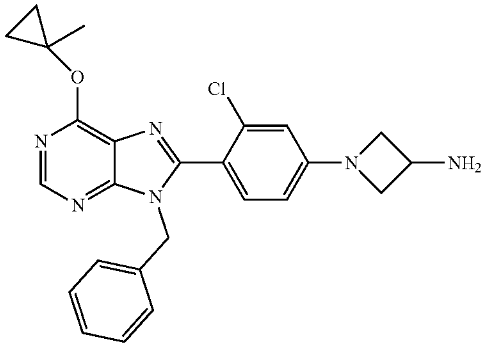 [SMILES: CC1(Oc2ncnc3c2nc(-c2ccc(N4CC(N)C4)cc2Cl)n3Cc2ccccc2)CC1] | 1-(4-(9-benzyl-6-(1-methyl-cyclopropoxy)-9H-purin-8-yl)-3-chlorophenyl) azetidin-3-amine | (400 MHz, DMSO-$d_6$): 0.80-0.87 (2H, m), 0.98-1.05 (2H, m), 1.72 (3H, s), 2.23 (2H, s), 3.49 (2H, dd), 3.82 (1H, p), 4.12 (2H, t), 5.28 (2H, s), 6.42 (1H, dd), 6.57 (1H, d), 6.90 (2H, dd), 7.16-7.27 (4H, m), 8.58 (1H, s). | 461 |
| M2 | 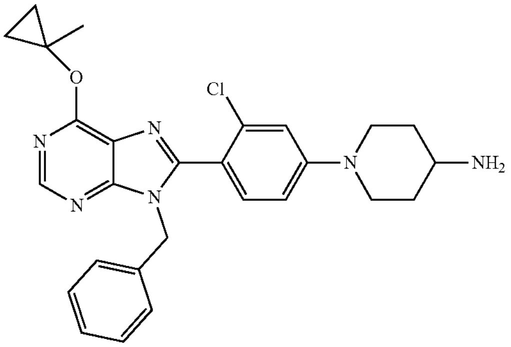 [SMILES: CC1(Oc2ncnc3c2nc(-c2ccc(N4CCC(N)CC4)cc2Cl)n3Cc2ccccc2)CC1] | 1-(4-(9-benzyl-6-(1-methyl-cyclopropoxy)-9H-purin-8-yl)-3-chlorophenyl) piperidin-4-amine | (400 MHz, DMSO-$d_6$): 0.79-0.88 (2H, m), 0.98-1.06 (2H, m), 1.23-1.37 (2H, m), 1.73 (3H, s), 1.75-1.85 (2H, m), 2.81-2.93 (3H, m), 3.80 (2H, dd), 5.30 (2H, s), 6.87-7.00 (3H, m), 7.09 (1H, d), 7.17-7.29 (4H, m), 8.59 (1H, s). Two protons not observed. | 489 |
| M3 | 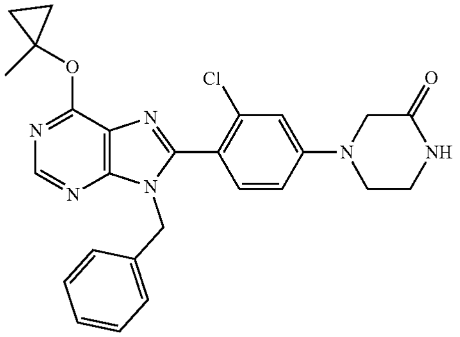 [SMILES: CC1(Oc2ncnc3c2nc(-c2ccc(N4CCNC(=O)C4)cc2Cl)n3Cc2ccccc2)CC1] | 4-(4-(9-benzyl-6-(1-methyl-cyclopropoxy)-9H-purin-8-yl)-3-chlorophenyl) piperazin-2-one | (500 MHz, $CDCl_3$): 0.8-0.85 (m, 2H), 1.13-1.18 (m, 2H), 1.80 (s, 3H), 3.57 (s, 4H), 3.98 (s, 2H), 5.35 (s, 2H), 6.70 (dd, 1H), 6.92 (d, 1H), 6.93-6.96 (m, 2H), 7.14-7.21 (m, 4H), 8.65 (s, 1H). One proton not observed. | 489 |
| M4 | 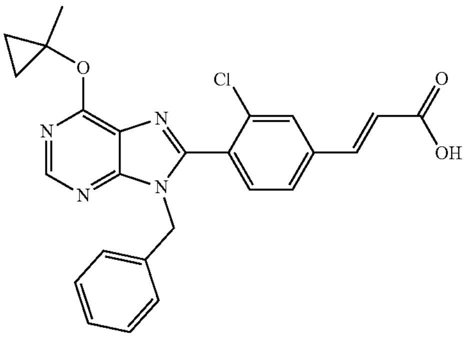 [SMILES: CC1(Oc2ncnc3c2nc(-c2ccc(/C=C/C(=O)O)cc2Cl)n3Cc2ccccc2)CC1] | (E)-3-(4-(9-benzyl-6-(1-methylcyclo-propoxy)-9H-purin-8-yl)-3-chlorophenyl) acrylic acid | (300 MHz, DMSO-$d_6$): 0.79-0.90 (2H, m), 1.02 (2H, d), 1.74 (3H, s), 5.33 (2H, s), 6.75 (1H, d), 6.90 (2H, dd), 7.12-7.26 (3H, m), 7.49-7.61 (2H, m), 7.76 (1H, dd), 7.99 (1H, d), 8.65 (1H, s). One proton not observed. | 461 |

TABLE M-continued

| Ex# | Structure | Name | $^1$H NMR | LCMS [M + H]+ |
|---|---|---|---|---|
| M5 | 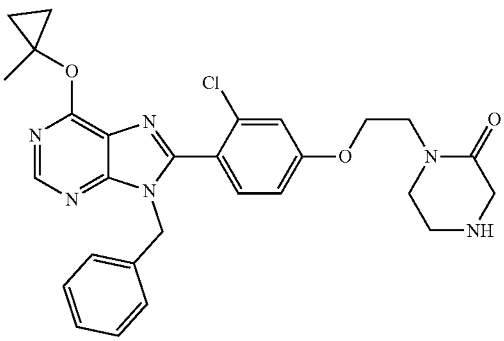 [SMILES: CC1(Oc2ncnc3c2nc(-c2ccc(OCCN4CCNCC4=O)cc2Cl)n3Cc2ccccc2)CC1] | 1-(2-(4-(9-benzyl-6-(1-methylcyclo-propoxy)-9H-purin-8-yl)-3-chlorophenoxy)ethyl)piperazin-2-one | (300 MHz, DMSO-$d_6$): 0.80-0.88 (2H, m), 0.99-1.05 (2H, m), 1.73 (3H, s), 2.85 (2H, t), 3.22 (2H, s), 3.39 (2H, t), 3.65 (2H, t), 4.23 (2H, t), 5.29 (2H, s), 6.90 (2H, dd), 7.05 (1H, dd), 7.16-7.23 (3H, m), 7.27 (1H, d), 7.42 (1H, d), 8.62 (1H, s). One proton not observed. | 533 |

[M1] was synthesised from tert-butyl (1-(4-(9-benzyl-6-(1-methylcyclopropoxy)-9H-purin-8-yl)-3-chlorophenyl)azetidin-3-yl)carbamate via a BOC deprotection using a similar procedure as used in the synthesis of 2-(2-chloro-4-(2-(piperazin-1-yl)ethoxy)phenyl)-1-((4-chloropyridin-2-yl)methyl)-4-(1-methylcyclopropoxy)-1H-benzo[d]imidazole (Example 2).

Tert-butyl (1-(4-(9-benzyl-6-(1-methylcyclopropoxy)-9H-purin-8-yl)-3-chlorophenyl)azetidin-3-yl)carbamate was made following a palladium catalysed cross coupling reaction, using 9-benzyl-8-(4-bromo-2-chlorophenyl)-6-(1-methylcyclopropoxy)-9H-purine and tert-butyl azetidin-3-ylcarbamate as starting materials, as follows:

9-Benzyl-8-(4-bromo-2-chlorophenyl)-6-(1-methylcyclopropoxy)-9H-purine (300 mg, 0.64 mmol), tert-butyl azetidin-3-ylcarbamate (165 mg, 0.96 mmol), $Cs_2CO_3$ (624 mg, 1.92 mmol) and rac-BINAP Pd G3 (127 mg, 0.13 mmol) in 1,4-dioxane (6 mL) were stirred under an atmosphere of nitrogen at 100° C. for 12 hours. The reaction mixture was concentrated and diluted with water (25 mL) and extracted with EtOAc (3×25 mL). The organic layer was dried over $Na_2SO_4$, filtered and evaporated to afford crude product. The crude product was purified by flash silica chromatography, elution gradient 0 to 40% EtOAc in pentane. Pure fractions were evaporated to dryness to afford tert-butyl (1-(4-(9-benzyl-6-(1-methylcyclopropoxy)-9H-purin-8-yl)-3-chlorophenyl)azetidin-3-yl)carbamate (0.220 g, 61%) as a yellow solid. $^1$H NMR (300 MHz, DMSO-$d_6$): 0.79-0.88 (2H, m), 1.01 (2H, d), 1.40 (9H, s), 1.72 (3H, s), 3.71 (2H, dd), 4.17 (2H, t), 4.43 (1H, t), 5.28 (2H, s), 6.43 (1H, dd), 6.60 (1H, d), 6.87-6.93 (2H, m), 7.17-7.24 (4H, m), 7.45-7.70 (1H, m), 8.58 (1H, s). m/z: ES+ [M+H]+ 561.

9-Benzyl-8-(4-bromo-2-chlorophenyl)-6-(1-methylcyclopropoxy)-9H-purine was made following a similar procedure to 4-((8-(2-chloro-4-(2-(4-methylpiperazin-1-yl)ethoxy)phenyl)-6-(1-methylcyclopropoxy)-9H-purin-9-yl)methyl)-2-methylthiazole (Example 7), using N-benzyl-6-(1-methylcyclopropoxy)-5-nitropyrimidin-4-amine (Example 4, intermediate). and 4-bromo-2-chlorobenzaldehyde as starting materials. $^1$H NMR (300 MHz, DMSO-$d_6$): 0.77-0.90 (2H, m), 0.90-1.12 (2H, m), 1.73 (3H, s), 5.32 (2H, s), 6.87-6.96 (2H, m), 7.15-7.26 (3H, m), 7.48 (1H, d), 7.70 (1H, dd), 7.96 (1H, d), 8.65 (1H, s). m/z: ES+ [M+H]+ 469.

[M2] was synthesised from tert-butyl (1-(4-(9-benzyl-6-(1-methylcyclopropoxy)-9H-purin-8-yl)-3-chlorophenyl)piperidin-4-yl)carbamate through a BOC deprotection similar to the procedure used in Example S1 to make 1-(3-(4-(9-benzyl-6-(1-methylcyclopropoxy)-9H-purin-8-yl)-3-chlorophenoxy)propyl)piperazin-2-one.

Tert-butyl (1-(4-(9-benzyl-6-(1-methylcyclopropoxy)-9H-purin-8-yl)-3-chlorophenyl)piperidin-4-yl)carbamate was synthesised from 9-benzyl-8-(4-bromo-2-chlorophenyl)-6-(1-methylcyclopropoxy)-9H-purine and tert-butyl piperidin-4-ylcarbamate by a palladium catalysed cross coupling similar to the synthesis of tert-butyl (1-(4-(9-benzyl-6-(1-methylcyclopropoxy)-9H-purin-8-yl)-3-chlorophenyl)azetidin-3-yl)carbamate (Example M1, intermediate). $^1$H NMR (300 MHz, DMSO-$d_6$): 0.78-0.89 (2H, m), 1.01 (2H, d), 1.39 (9H, s), 1.47 (2H, d), 1.73 (3H, s), 1.80 (2H, d), 2.91 (2H, t), 3.50 (1H, s), 3.82 (2H, d), 5.29 (2H, s), 6.92 (4H, ddt), 7.09 (1H, d), 7.18-7.27 (4H, m), 8.58 (1H, s). m/z: ES+ [M+H]+ 589.

[M3] was synthesised through a palladium catalysed cross coupling as follows: 9-Benzyl-8-(4-bromo-2-chlorophenyl)-6-(1-methylcyclopropoxy)-9H-purine (100 mg, 0.21 mmol), piperazin-2-one (32.0 mg, 0.32 mmol), cesium carbonate (208 mg, 0.64 mmol) and rac-BINAP-Pd-G3 (44 mg, 0.04 mmol) in 1,4-dioxane (2 mL) were stirred under an atmosphere of nitrogen at 100° C. for 12 hours. The reaction mixture was filtered through celite, and the solvents evaporated. The crude product was purified by preparative HPLC (Waters CSH C18 OBD column, 5μ silica, 30 mm diameter, 100 mm length), using decreasingly polar mixtures of water (containing 1% aqueous ammonia) and MeCN as eluents. Fractions containing the desired compound were evaporated to dryness to afford 4-(4-(9-benzyl-6-(1-methylcyclopropoxy)-9H-purin-8-yl)-3-chlorophenyl)piperazin-2-one (22.9 mg, 22%) as a pale yellow gum.

[M4] was synthesised using an ester hydrolysis from methyl (E)-3-(4-(9-benzyl-6-(1-methylcyclopropoxy)-9H-purin-8-yl)-3-chlorophenyl)acrylate as follows:

A solution of LiOH (65.5 mg, 2.74 mmol) in water (1 mL) was added to methyl (E)-3-(4-(9-benzyl-6-(1-methylcyclopropoxy)-9H-purin-8-yl)-3-chlorophenyl)acrylate (130 mg, 0.27 mmol) in EtOH (3 mL) at rt. The resulting mixture was stirred at rt for 1 hour. The reaction mixture was concentrated and adjusted to pH=3 with 3 M HCl and extracted with EtOAc (3×10 mL). The organic layer was dried over $Na_2SO_4$, filtered and evaporated. The crude product was purified by preparative HPLC; XBridge Shield RP18 OBD column, 30*150 mm, 5 μm; using decreasingly polar mixtures of water (containing 10 mmol/L $NH_4HCO_3$ and 0.1% aqueous ammonia) and MeCN as eluents. The fractions containing the desired compound were evaporated to dryness to afford (E)-3-(4-(9-benzyl-6-(1-methylcyclopropoxy)-9H-purin-8-yl)-3-chlorophenyl)acrylic acid (33 mg, 26%) as a white solid.

Methyl (E)-3-(4-(9-benzyl-6-(1-methylcyclopropoxy)-9H-purin-8-yl)-3-chlorophenyl)acrylate was made through a palladium catalysed cross coupling reaction as follows:

$PdCl_2$ $(PPh_3)_2$ (37.4 mg, 0.05 mmol) was added to tri (o-tolyl)phosphine (16.2 mg, 0.05 mmol), 9-benzyl-8-(4-bromo-2-chlorophenyl)-6-(1-methylcyclopropoxy)-9H-purine (250 mg, 0.53 mmol, Example M1), methyl acrylate (55.0 mg, 0.64 mmol) and $K_2CO_3$ (81 mg, 0.59 mmol) in DMF (3 mL) was stirred at 120° C. for 1 hour. The reaction mixture was diluted with EtOAc (20 mL), and washed sequentially with saturated brine (3× 75 mL). The organic layer was dried over $Na_2SO_4$, filtered and evaporated to afford crude product. The residue was purified by preparative TLC (petroleum ether:EtOAc=2:1), to afford methyl (E)-3-(4-(9-benzyl-6-(1-methylcyclopropoxy)-9H-purin-8-yl)-3-chlorophenyl)acrylate (0.14 g, 55%) as a colourless gum. $^1$H NMR (400 MHz, DMSO-$d_6$): 0.86 (2H, d), 1.02 (2H, d), 1.74 (3H, s), 3.76 (3H, s), 5.33 (2H, s), 5.76 (1H, s), 6.90 (2H, q), 7.15-7.24 (3H, m), 7.57 (1H, d), 7.73 (1H, d), 7.83 (1H, d), 8.09 (1H, s), 8.65 (1H, s). m/z: ES+ [M+H]+ 475.

[M5] was made from 9-benzyl-8-(4-bromo-2-chlorophenyl)-6-(1-methylcyclopropoxy)-9H-purine via a RockPhos coupling and subsequent BOC deprotection.

The RockPhos coupling to form tert-butyl 4-(2-(4-(9-benzyl-6-(1-methylcyclopropoxy)-9H-purin-8-yl)-3-chlorophenoxy)ethyl)-3-oxopiperazine-1-carboxylate from 9-benzyl-8-(4-bromo-2-chlorophenyl)-6-(1-methylcyclopropoxy)-9H-purine (Example M1 intermediate) and tert-butyl 4-(2-hydroxyethyl)-3-oxopiperazine-1-carboxylate followed a similar procedure to the synthesis of 4-methyl-6-(2-(4-methylpiperazin-1-yl)ethoxy) nicotinaldehyde (Example A5, intermediate). The product of this reaction was used directly in the deprotection without further purification. m/z: ES+ [M+H]+ 633.

The BOC deprotection of tert-butyl 4-(2-(4-(9-benzyl-6-(1-methylcyclopropoxy)-9H-purin-8-yl)-3-chlorophenoxy) ethyl)-3-oxopiperazine-1-carboxylate was done using similar conditions previously described in crude tert-butyl 4-(3-(4-(9-benzyl-6-(1-methylcyclopropoxy)-9H-purin-8-yl)-3-chlorophenoxy)propyl)-3-oxopiperazine-1-carboxylate (Example S1, intermediate).

The following examples in Table N were synthesised according the notes at the bottom of Table N.

TABLE N

| Ex# | Structure | Name | $^1$H NMR | LCMS [M + H]+ |
|---|---|---|---|---|
| N1 | 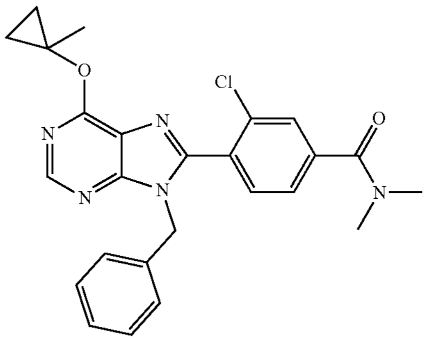 [SMILES: CN(C)C(=O)c1ccc(-c2nc3c(OC4(C)CC4)ncnc3n2Cc2ccccc2)c(Cl)c1] | 4-(9-benzyl-6-(1-methylcyclopropoxy)-9H-purin-8-yl)-3-chloro-N,N-dimethylbenzamide | (300 MHz, DMSO-$d_6$): 0.79-0.88 (2H, m), 1.02 (2H, d), 1.74 (3H, s), 2.93 (3H, s), 3.01 (3H, s), 5.34 (2H, s), 6.89 (2H, dd), 7.18 (3H, dd), 7.45 (1H, dd), 7.55 (1H, d), 7.66 (1H, d), 8.66 (1H, s) | 462 |
| N2 | 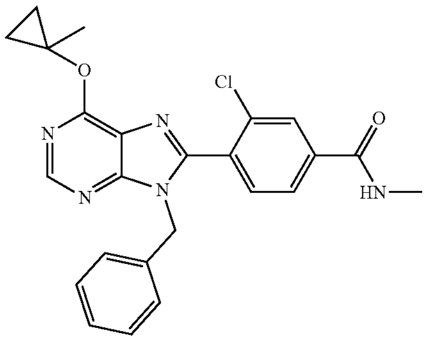 [SMILES: CNC(=O)c1ccc(-c2nc3c(OC4(C)CC4)ncnc3n2Cc2ccccc2)c(Cl)c1] | 4-(9-benzyl-6-(1-methylcyclopropoxy)-9H-purin-8-yl)-3-chloro-N-methylbenzamide | (400 MHz, DMSO-$d_6$): 0.86 (2H, d), 1.02 (2H, d), 1.74 (3H, s), 2.82 (3H, d), 5.32 (2H, s), 6.83-6.93 (2H, m), 7.19 (3H, m), 7.63 (1H, d), 7.88 (1H, dd), 8.04 (1H, d), 8.66 (1H, s), 8.73 (1H, d) | 448 |

TABLE N-continued

| Ex# | Structure | Name | ¹H NMR | LCMS [M + H]+ |
|---|---|---|---|---|
| N3 | 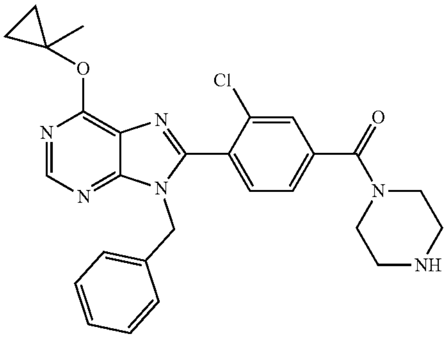 [SMILES: CC1(Oc2ncnc3c2nc(-c2ccc(C(=O)N4CCNCC4)cc2Cl)n3Cc2ccccc2)CC1] | (4-(9-benzyl-6-(1-methylcyclopropoxy)-9H-purin-8-yl)-3-chlorophenyl)(piperazin-1-yl)methanone | (400 MHz, DMSO-$d_6$): 0.80-0.87 (2H, m), 1.01 (2H, d), 1.73 (3H, s), 2.72 (4H, d), 3.24 (2H, s), 3.57 (2H, s), 5.33 (2H, s), 6.83-6.91 (2H, m), 7.11-7.22 (3H, m), 7.41 (1H, dd), 7.53 (1H, d), 7.61 (1H, d), 8.64 (1H, s). One proton not observed. | 503 |
| N4 | 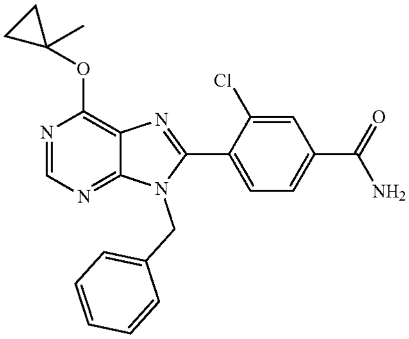 [SMILES: CC1(Oc2ncnc3c2nc(-c2ccc(C(N)=O)cc2Cl)n3Cc2ccccc2)CC1] | 4-(9-benzyl-6-(1-methylcyclopropoxy)-9H-purin-8-yl)-3-chlorobenzamide | (300 MHz, DMSO-$d_6$): 0.85 (2H, t), 1.03 (2H, t), 1.73 (3H, s), 5.32 (2H, s), 6.88-6.90 (2H, m), 7.18-7.21 (3H, m), 7.62 (1H, d), 7.72 (1H, s), 7.91-7.93 (1H, m), 8.09 (1H, d), 8.24 (1H, s), 8.66 (1H, s). | 434 |
| N5 | 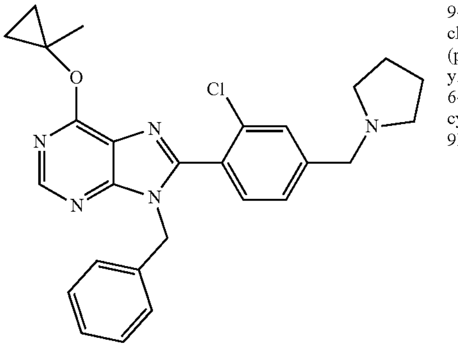 | 9-benzyl-8-(2-chloro-4-(pyrrolidin-1-ylmethyl)phenyl)-6-(1-methyl-cyclopropoxy)-9H-purine | (300 MHz, DMSO-$d_6$): 0.80-0.89 (2H, m), 1.02 (2H, d), 1.73 (7H, d), 2.46 (4H, d), 3.66 (2H, s), 5.30 (2H, s), 6.76-6.97 (2H, m), 7.12-7.25 (3H, m), 7.37 (1H, dd), 7.42 (1H, d), 7.55 (1H, d), 8.64 (1H, s) | 474 |
| N6 | 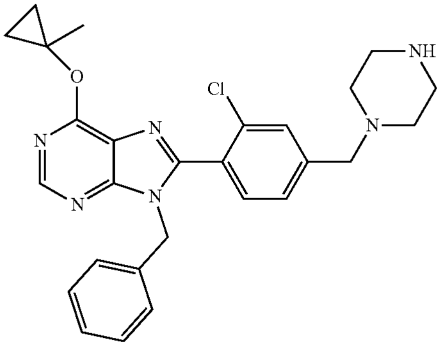 [SMILES: CC1(Oc2ncnc3c2nc(-c2ccc(CN4CCNCC4)cc2Cl)n3Cc2ccccc2)CC1] | 9-benzyl-8-(2-chloro-4-(piperazin-1-ylmethyl)phenyl)-6-(1-methyl-cyclopropoxy)-9H-purine | (300 MHz, DMSO-$d_6$): 0.80-0.88 (2H, m), 1.02 (2H, d), 1.73 (3H, s), 2.34 (4H, s), 2.75 (4H, t), 3.53 (2H, s), 5.30 (2H, s), 6.80-6.89 (2H, m), 7.13-7.22 (3H, m), 7.33-7.46 (2H, m), 7.54 (1H, d), 8.64 (1H, s). One proton not observed. | 489 |

TABLE N-continued

| Ex# | Structure | Name | $^1$H NMR | LCMS [M + H]+ |
|---|---|---|---|---|
| N7 | 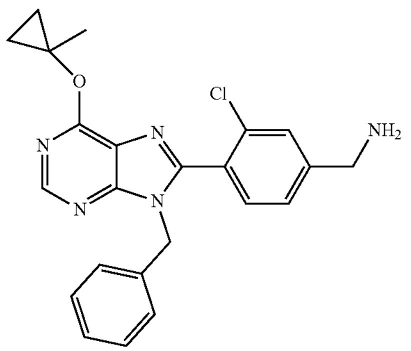 [SMILES: CC1(Oc2ncnc3c2nc(-c2ccc(CN)cc2Cl)n3Cc2ccccc2)CC1] | (4-(9-benzyl-6-(1-methylcyclopropoxy)-9H-purin-8-yl)-3-chlorophenyl) methanamine | (300 MHz, DMSO-$d_6$): 0.84 (2H, t), 1.02 (2H, t), 1.72 (3H, s), 3.96 (2H, s), 5.29 (2H, s), 6.89 (2H, t), 7.20 (3H, t), 7.47-7.54 (2H, m), 7.72 (1H, s), 8.63 (1H, s). Two protons not observed. | 420 |
| N8 | 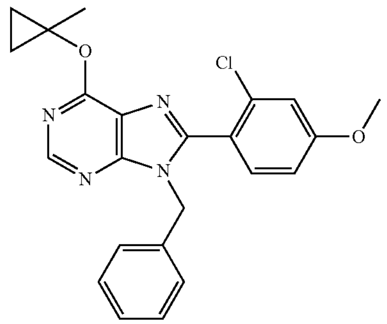 [SMILES: COc1ccc(-c2nc3c(OC4(C)CC4)ncnc3n2Cc2ccccc2)c(Cl)c1] | 9-benzyl-8-(2-chloro-4-methoxyphenyl)-6-(1-methyl-cyclopropoxy)-9H-purine | (500 MHz, DMSO-$d_6$): 0.81-0.87 (2H, m), 0.99-1.04 (2H, m), 1.73 (3H, s), 3.86 (3H, s), 5.29 (2H, s), 6.87-6.92 (2H, m), 7.03 (1H, dd), 7.18-7.22 (3H, m), 7.23 (1H, d), 7.42 (1H, d), 8.61 (1H, s). | 421 |
| N9 | 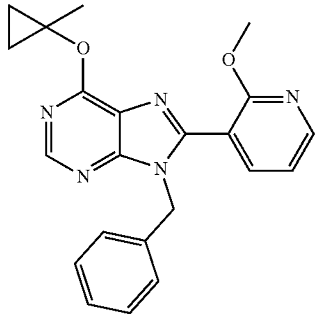 [SMILES: COc1ncccc1-c1nc2c(OC3(C)CC3)ncnc2n1Cc1ccccc1] | 9-benzyl-8-(2-methoxypyridin-3-yl)-6-(1-methylcyclopropoxy)-9H-purine | (500 MHz, $CDCl_3$): 0.79-0.86 (2H, m), 1.12-1.18 (2H, m), 1.79 (3H, s), 3.86 (3H, s), 5.39 (2H, s), 6.89-6.96 (3H, m), 7.16 (3H, dd), 7.66 (1H, dd), 8.30 (1H, dd), 8.66 (1H, s). | 388 |

[N1] was synthesised through amide coupling reaction from 4-(9-benzyl-6-(1-methylcyclopropoxy)-9H-purin-8-yl)-3-chlorobenzoic acid and dimethylamine through the following procedure:

T3P (658 mg, 1.03 mmol) was added to 4-(9-benzyl-6-(1-methylcyclopropoxy)-9H-purin-8-yl)-3-chlorobenzoic acid (150 mg, 0.34 mmol), dimethylamine (345 μL, 0.69 mmol, 2M in THF) and DIEA (181 μL, 1.03 mmol) in DMA (2 mL) at 0° C. for 15 minutes. The resulting mixture was stirred at rt for 1 hour. The solvent was removed under reduced pressure. The crude product was purified by preparative HPLC, XBridge Prep OBD C18 column, 30*150 mm, 5 μm; using decreasingly polar mixtures of water (containing 10 mmol/L $NH_4HCO_3$ and 0.1% aqueous ammonia) and MeCN as eluents. The fractions containing the desired compound were evaporated to dryness to afford 4-(9-benzyl-6-(1-methylcyclopropoxy)-9H-purin-8-yl)-3-chloro-N,N-dimethylbenzamide (0.042 g, 26%) as a white solid.

4-(9-Benzyl-6-(1-methylcyclopropoxy)-9H-purin-8-yl)-3-chlorobenzoic acid was made following a similar ester hydrolysis procedure to (E)-3-(4-(9-benzyl-6-(1-methylcyclopropoxy)-9H-purin-8-yl)-3-chlorophenyl)acrylic acid (Example M4), using methyl 4-(9-benzyl-6-(1-methylcyclopropoxy)-9H-purin-8-yl)-3-chlorobenzoate as starting material. $^1$H NMR (300 MHz, DMSO-$d_6$): 0.78-0.90 (2H, m), 1.03 (2H, d), 1.74 (3H, s), 5.33 (2H, s), 6.89 (2H, dd), 7.19 (3H, dd), 7.66 (1H, d), 7.96 (1H, dd), 8.07 (1H, d), 8.67 (1H, s). One proton not observed. m/z: ES+ [M+H]+ 435.

Methyl 4-(9-benzyl-6-(1-methylcyclopropoxy)-9H-purin-8-yl)-3-chlorobenzoate was made via a cyclisation reaction similar to a procedure previously described in the synthesis of 4-(1-benzyl-5-isopropoxy-1H-benzo[d]imidazol-2-yl)-3-chlorophenol (Example A1), using N-benzyl-6-(1-methylcyclopropoxy)-5-nitropyrimidin-4-amine (Example 4, intermediate) and methyl 3-chloro-4-formylbenzoate as starting materials. $^1$H NMR (300 MHz, DMSO-$d_6$): 0.78-0.92 (2H, m), 1.02 (2H, d), 1.74 (3H, s), 3.92 (3H, s), 5.34 (2H, s), 6.80-6.95 (2H, m), 7.19 (3H, m), 7.69 (1H, d), 7.99 (1H, dd), 8.09 (1H, d), 8.68 (1H, s). m/z: ES+ [M+H]+ 449.

[N2] was synthesised through amide coupling reaction similar to the previously described procedure for the synthesis of 4-(9-benzyl-6-(1-methylcyclopropoxy)-9H-purin- 8-yl)-3-chloro-N,N-dimethylbenzamide, using 4-(9-benzyl-6-(1-methylcyclopropoxy)-9H-purin-8-yl)-3-chlorobenzoic acid (Example N1, intermediate) and methanamine as starting materials.

[N3] was synthesised through amide coupling reaction similar to the previously described procedure for the synthesis of 4-(9-benzyl-6-(1-methylcyclopropoxy)-9H-purin-8-yl)-3-chloro-N,N-dimethylbenzamide, using 4-(9-benzyl-6-(1-methylcyclopropoxy)-9H-purin-8-yl)-3-chlorobenzoic acid (Example N1, intermediate) and piperazine as starting material.

[N4] was synthesised through amide coupling reaction similar to the previously described procedure for the synthesis of 4-(9-benzyl-6-(1-methylcyclopropoxy)-9H-purin-8-yl)-3-chloro-N,N-dimethylbenzamide, using 4-(9-benzyl-6-(1-methylcyclopropoxy)-9H-purin-8-yl)-3-chlorobenzoic acid (Example N1, intermediate) and ammonium chloride as starting material.

[N5] was made via a substitution reaction from 4-(9-benzyl-6-(1-methylcyclopropoxy)-9H-purin-8-yl)-3-chlorobenzyl methanesulfonate and pyrrolidine as follows:

Pyrrolidine (34.2 mg, 0.48 mmol) was added to 4-(9-benzyl-6-(1-methylcyclopropoxy)-9H-purin-8-yl)-3-chlorobenzyl methanesulfonate (120 mg, 0.24 mmol) and $K_2CO_3$ (100 mg, 0.72 mmol) in DMA (2 mL) at rt. The resulting mixture was stirred at 80° C. for 1 hour. The reaction mixture was diluted with water (25 mL), and washed sequentially with EtOAc (3×25 mL) and saturated brine (25 mL). The organic layer was dried over $Na_2SO_4$, filtered and evaporated to afford crude product. The crude product was purified by preparative HPLC, XBridge Prep OBD C18 column, 30*150 mm, 5 μm; using decreasingly polar mixtures of water (containing 10 mmol/L $NH_4HCO_3$ and 0.1% aqueous ammonia) and MeCN as eluents. The fractions containing the desired compound were evaporated to dryness to afford 9-benzyl-8-(2-chloro-4-(pyrrolidin-1-ylmethyl)phenyl)-6-(1-methylcyclopropoxy)-9H-purine (0.012 g, 10.88%) as a white solid.

4-(9-Benzyl-6-(1-methylcyclopropoxy)-9H-purin-8-yl)-3-chlorobenzyl methanesulfonate was made as follows:

$Ms_2O$ (149 mg, 0.86 mmol) in DCM (2 mL) was added dropwise into the solution of (4-(9-benzyl-6-(1-methylcyclopropoxy)-9H-purin-8-yl)-3-chlorophenyl)methanol (300 mg, 0.71 mmol) and TEA (216 mg, 2.14 mmol) in DCM (10 mL) at rt. The resulting mixture was stirred at rt for 2 hour. The reaction mixture was redissolved in DCM (50 mL), and washed sequentially with water (2×10 mL) and saturated brine (10 mL). The organic layer was dried over $Na_2SO_4$, filtered and evaporated to afford crude 4-(9-benzyl-6-(1-methylcyclopropoxy)-9H-purin-8-yl)-3-chlorobenzyl methanesulfonate (300 mg). The crude product was used to next directly without future purification.

(4-(9-Benzyl-6-(1-methylcyclopropoxy)-9H-purin-8-yl)-3-chlorophenyl)methanol was made through an ester reduction of methyl 4-(9-benzyl-6-(1-methylcyclopropoxy)-9H-purin-8-yl)-3-chlorobenzoate as follows:

A solution of $LiAlH_4$ (0.61 mL, 1.23 mmol, 2.4 M in THF) was added dropwise to methyl 4-(9-benzyl-6-(1-methylcyclopropoxy)-9H-purin-8-yl)-3-chlorobenzoate (Example N1, intermediate; 1.1 g, 2.45 mmol) in THF (10 mL) at 0° C. under nitrogen. The resulting mixture was stirred at rt for 1 hour. The reaction mixture was poured into water and 15% aq. NaOH. The organic layer was dried over $Na_2SO_4$, filtered and evaporated to afford (4-(9-benzyl-6-(1-methylcyclopropoxy)-9H-purin-8-yl)-3-chlorophenyl)methanol (0.90 g, 87%) as a yellow solid. The product was used in the next step directly without further purification. $^1$H NMR (300 MHz, DMSO-$d_6$): 0.78-0.90 (2H, m), 0.97-1.08 (2H, m), 1.74 (3H, s), 4.61 (2H, d), 5.30 (2H, s), 5.50 (1H, t), 6.90 (2H, dt), 7.20 (3H, ddt), 7.40 (1H, dd), 7.48 (1H, d), 7.58 (1H, d), 8.63 (1H, s). m/z: ES+ [M+H]+ 421.

[N6] was made via a reductive amination from 4-(9-benzyl-6-(1-methylcyclopropoxy)-9H-purin-8-yl)-3-chlorobenzaldehyde as follows:

Piperazine (103 mg, 1.19 mmol) was added to 4-(9-benzyl-6-(1-methylcyclopropoxy)-9H-purin-8-yl)-3-chlorobenzaldehyde (100 mg, 0.24 mmol) in DCM (4 mL) at rt. After 30 minutes, sodium triacetoxyborohydride (253 mg, 1.19 mmol) was added. The resulting mixture was stirred at rt for 1 hour. The reaction was quenched with MeOH (2 mL), concentrated under vacuum to afford a crude product. The crude product was purified by preparative HPLC, XBridge Prep OBD C18 column, 30*150 mm, 5 μm; using decreasingly polar mixtures of water (containing 10 mmol/L $NH_4HCO_3$ and 0.1% aqueous ammonia) and MeCN as eluents. Fractions containing the desired compound were evaporated to dryness to afford 9-benzyl-8-(2-chloro-4-(piperazin-1-ylmethyl)phenyl)-6-(1-methylcyclopropoxy)-9H-purine (10 mg, 9%) as a white solid. 4-(9-Benzyl-6-(1-methylcyclopropoxy)-9H-purin-8-yl)-3-chlorobenzaldehyde was formed through the oxidation of (4-(9-benzyl-6-(1-methylcyclopropoxy)-9H-purin-8-yl)-3-chlorophenyl)methanol (Example N5, intermediate) as follows:

Manganese(IV) oxide (640 mg, 4.28 mmol) was added to (4-(9-benzyl-6-(1-methylcyclopropoxy)-9H-purin-8-yl)-3-chlorophenyl)methanol (600 mg, 1.43 mmol) in EtOAc (15 mL) at rt. The resulting mixture was stirred at 80° C. for 16 hours. The reaction mixture was filtered through celite. The solvent was removed under reduced pressure. The crude product was purified by flash silica chromatography, elution gradient 0 to 50% EtOAc in pentane. Pure fractions were evaporated to dryness to afford 4-(9-benzyl-6-(1-methylcyclopropoxy)-9H-purin-8-yl)-3-chlorobenzaldehyde (0.450 g, 75%) as a yellow solid.

$^1$H NMR (300 MHz, DMSO-$d_6$): 0.81-0.89 (2H, m), 1.03 (2H, d), 1.74 (3H, s), 5.35 (2H, s), 6.85-6.93 (2H, m), 7.14-7.24 (3H, m), 7.77 (1H, d), 7.97 (1H, dd), 8.14 (1H, d), 8.68 (1H, s), 10.09 (1H, s). m/z: ES+ [M+H]+ 419.

[N7] was made via the reduction of (E)-4-(9-benzyl-6-(1-methylcyclopropoxy)-9H-purin-8-yl)-3-chlorobenzaldehyde oxime as follows:

Zinc (24.9 mg, 0.38 mmol) was added to (E)-4-(9-benzyl-6-(1-methylcyclopropoxy)-9H-purin-8-yl)-3-chlorobenzaldehyde oxime (55 mg, 0.13 mmol) in acetic acid (0.5 mL) at rt. The resulting mixture was stirred at rt for 1 hour. The solids were filtered off and the filtrate was concentrated under reduced pressure. The crude product was purified by preparative HPLC, Xselect CSH C18 OBD column; 30*150 mm, 5 μm; using decreasingly polar mixtures of water (containing 0.1% formic acid) and MeCN as eluents. The fractions containing the desired compound were evaporated to dryness to afford (4-(9-benzyl-6-(1-methylcyclopropoxy)-9H-purin-8-yl)-3-chlorophenyl)methanamine (14 mg, 26%) as a white solid.

(E)-4-(9-benzyl-6-(1-methylcyclopropoxy)-9H-purin-8-yl)-3-chlorobenzaldehyde oxime was made as follows:

$Na_2CO_3$ (29.6 mg, 0.28 mmol) was added to 4-(9-benzyl-6-(1-methylcyclopropoxy)-9H-purin-8-yl)-3-chlorobenzaldehyde (Example N6, intermediate) (65 mg, 0.16 mmol) and hydroxylammonium chloride solution (16.2 mg, 0.23 mmol) in water (1 mL)/MeOH (0.400 mL) at rt. The resulting mixture was stirred at rt for 3 hours. The solvent was removed under reduced pressure. The reaction mixture was diluted with EtOAc (10 mL), and washed sequentially with water (2×5 mL) and saturated brine (10 mL). The organic layer was dried over $Na_2SO_4$, filtered and evaporated to afford (E)-4-(9-benzyl-6-(1-methylcyclopropoxy)-9H-purin-8-yl)-3-chlorobenzaldehyde oxime (0.060 g, 89%) as yellow gum, which was used without any further purification. $^1$H NMR (300 MHz, DMSO-$d_6$): 0.85 (2H, t), 1.03 (2H, t), 1.74 (3H, s), 5.34 (2H, s), 6.85-6.96 (3H, m), 7.18-7.24 (3H, m), 7.9-8.3 (2H, m), 8.66 (1H, s), 10.09 (1H, s), 11.72 (1H, s). m/z: ES+ [M+H]+ 434.

[N8] 9-Benzyl-8-(2-chloro-4-methoxyphenyl)-6-(1-methylcyclopropoxy)-9H-purine was made as follows:

9-Benzyl-8-bromo-6-(1-methylcyclopropoxy)-9H-purine (123 mg, 0.34 mmol, see Example 5 intermediate), (2-chloro-4-methoxyphenyl)boronic acid (70 mg, 0.38 mmol), cesium carbonate (223 mg, 0.68 mmol) and tetrakis (triphenylphosphine) palladium (0) (19.8 mg, 0.02 mmol) were dissolved in 1,4-dioxane (1 mL) and water (0.2 mL) and sealed into a microwave tube. The reaction was heated to 110° C. for 2 hours in the microwave reactor and cooled to RT. The reaction mixture was diluted with EtOAc (50 mL), washed with water (50 mL), brine (50 mL), dried over $MgSO_4$, filtered and concentrated under reduced pressure. The crude sample was dissolved in DMSO, then purified by preparative HPLC (Waters CSH C18 OBD, 30×100 mm, 5 µm), using decreasingly polar mixtures of $H_2O$ (containing 0.3% ammonium hydroxide (aq)) and MeCN as eluents. After chromatography, fractions containing the desired compound were concentrated under reduced pressure to afford 9-benzyl-8-(2-chloro-4-methoxyphenyl)-6-(1-methylcyclopropoxy)-9H-purine (106 mg, 74%) as a colourless film. $^1$H NMR (500 MHz, DMSO-$d_6$): 0.81-0.87 (2H, m), 0.99-1.04 (2H, m), 1.73 (3H, s), 3.86 (3H, s), 5.29 (2H, s), 6.87-6.92 (2H, m), 7.03 (1H, dd), 7.18-7.22 (3H, m), 7.23 (1H, d), 7.42 (1H, d), 8.61 (1H, s). m/z: ES+ [M+H]+ 421.

[N9] 9-benzyl-8-(2-methoxypyridin-3-yl)-6-(1-methylcyclopropoxy)-9H-purine was made as follows:

To a stirred solution of 3-(9-benzyl-6-(1-methylcyclopropoxy)-9H-purin-8-yl)pyridin-2(1H)-one (38.7 mg, 0.10 mmol) and potassium carbonate (28.2 mg, 0.20 mmol) in DMF (0.5 mL), was added iodomethane (17.2 mg, 0.12 mmol). The reaction stirred at RT for 21 h. The reaction mixture then filtered and concentrated in vacuo. The crude product was purified by preparative HPLC (Waters CSH C18 OBD column, 5 µm silica, 30 mm diameter, 100 mm length), using decreasingly polar mixtures of water (containing 1% of aq. ammonia)) and MeCN as eluents. Fractions containing the desired compound were evaporated to dryness to yield 9-benzyl-8-(2-methoxypyridin-3-yl)-6-(1-methylcyclopropoxy)-9H-purine (1.2 mg, 3%).

3-(9-Benzyl-6-(1-methylcyclopropoxy)-9H-purin-8-yl) pyridin-2(1H)-one was made starting from 9-benzyl-8-bromo-6-(1-methylcyclopropoxy)-9H-purine (Example 5 intermediate) and (2-oxo-1,2-dihydropyridin-3-yl)boronic acid in a similar procedure as described for 4-(9-benzyl-6-(1-methylcyclopropoxy)-9H-purin-8-yl)-3-chlorophenol (see Example 5). $^1$H NMR (500 MHz, DMSO-$d_6$): 0.81-0.86 (2H, m), 0.98-1.03 (2H, m), 1.72 (3H, s), 5.54 (2H, s), 6.30 (1H, t), 6.9-6.96 (2H, m), 7.13-7.21 (3H, m), 7.64 (1H, dd), 7.72 (1H, dd), 8.58 (1H, s), 12.25 (1H, s). m/z: ES+ [M+H]+ 374

The following examples in Table P were synthesised according the notes at the bottom of Table P.

TABLE P

| Ex# | Structure | Name | $^1$H NMR | LCMS [M + H]+ |
|---|---|---|---|---|
| P1 | 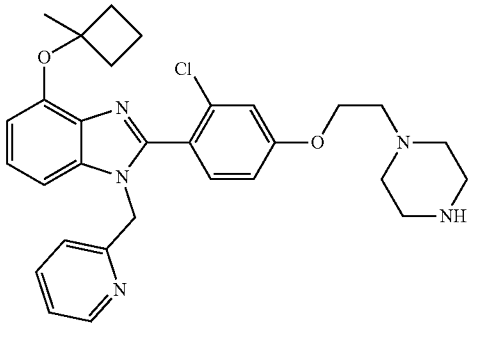 [SMILES: CC1(Oc2cccc3c2nc(-c2ccc(OCCN4CCNCC4)cc2Cl)n3Cc2ccccn2)CCC1] | 2-(2-chloro-4-(2-(piperazin-1-yl)ethoxy)phenyl)-4-(1-methylcyclobutoxy)-1-(pyridin-2-ylmethyl)-1H-benzo[d]imidazole | (300 MHz, DMSO-$d_6$): 1.60 (3H, s), 1.67-1.83 (2H, m), 2.17-2.29 (2H, m), 2.35-2.48 (6H, m), 2.63-2.71 (6H, m), 4.16 (2H, t), 5.32 (2H, s), 6.55 (1H, dd), 6.90-7.13 (4H, m), 7.19-7.29 (2H, m), 7.44 (1H, d), 7.68 (1H, td), 8.35-8.49 (1H, m). One proton not observed. | 532 |
| P2 | 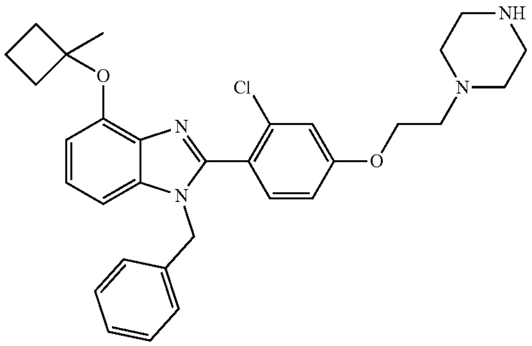 [SMILES: CC1(Oc2cccc3c2nc(-c2ccc(OCCN4CCNCC4)cc2Cl)n3Cc2ccccc2)CCC1] | 1-benzyl-2-(2-chloro-4-(2-(piperazin-1-yl)ethoxy)phenyl)-4-(1-methylcyclobutoxy)-1H-benzo[d]imidazole | (400 MHz, DMSO-$d_6$): 1.59 (3H, s), 1.7-1.79 (2H, m), 2.22 (2H, t), 2.36-2.47 (6H, m), 2.66-2.70 (6H, m), 4.18 (2H, t), 5.25 (2H, s), 6.55 (1H, d), 6.95-7.1 (5H, m), 7.18-7.28 (4H, m), 7.47 (1H, d). One proton not observed. | 531 |

TABLE P-continued

| Ex# | Structure | Name | $^1$H NMR | LCMS [M + H]+ |
| --- | --- | --- | --- | --- |
| P3 | 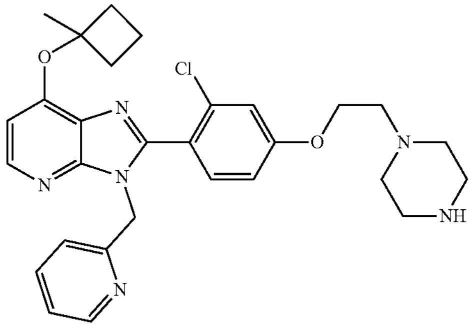 [SMILES: CC1(Oc2ccnc3c2nc(-c2ccc(OCCN4CCNCC4)cc2Cl)n3Cc2ccccn2)CCC1] | 2-(2-chloro-4-(2-(piperazin-1-yl)ethoxy)phenyl)-7-(1-methyl-cyclobutoxy)-3-(pyridin-2-ylmethyl)-3H-imidazo[4,5-b]pyridine | (400 MHz, $CDCl_3$) 1.75-1.85 (5H, m), 1.88-2(2H, m), 2.29-2.42 (2H, m), 2.62-2.81 (3H, m), 2.93-3.1 (4H, m), 3.2-3.39 (4H, m), 4.02-4.3 (2H, m), 5.52 (2H, s), 6.59 (1H, d), 6.80-6.86 (2H, m), 6.96-7.04 (1H, m), 7.07-7.16 (1H, m), 7.31 (1H, d), 7.45-7.58 (1H, m), 8.23 (1H, d), 8.43 (1H, d). | 533 |
| P4 | 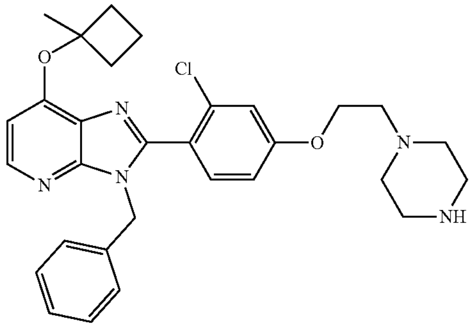 [SMILES: CC1(Oc2ccnc3c2nc(-c2ccc(OCCN4CCNCC4)cc2Cl)n3Cc2ccccc2)CCC1] | 3-benzyl-2-(2-chloro-4-(2-(piperazin-1-yl)ethoxy)phenyl)-7-(1-methyl-cyclobutoxy)-3H-imidazo[4,5-b]pyridine | (400 MHz, $CDCl_3$): 1.72 (5H, s), 1.83-1.95 (2H, m), 2.23-2.37 (3H, m), 2.55-2.74 (4H, m), 2.83-2.91 (2H, m), 3.04-3.14 (3H, m), 4.12 (2H, t), 5.36 (2H, s), 6.54 (1H, d), 6.77 (1H, dd), 6.86-6.96 (2H, m), 7.02 (1H, d), 7.11-7.17 (3H, m), 7.20 (1H, d), 8.22 (1H, d). One proton not observed. | 532 |

[P1] was made as follows:

p-Toluenesulfonic acid (58.3 mg, 0.34 mmol) was added to 3-(1-methylcyclobutoxy)-N1-(pyridin-2-ylmethyl)benzene-1,2-diamine (64.0 mg, 0.23 mmol) and 2-chloro-4-(2-(piperazin-1-yl)ethoxy)benzaldehyde (72.8 mg, 0.27 mmol, Example 14 intermediate) in EtOH (2 mL) at 20° C. The resulting mixture was stirred at 25° C. for 2 hours. The reaction mixture was adjusted to pH=8 with saturated $NaHCO_3$. The reaction mixture was concentrated and diluted with EtOAc (20 mL) and washed sequentially with water (3×5 mL), saturated brine (3×5 mL). The top layer was dried over $Na_2SO_4$, filtered and evaporated to afford crude product. The crude product was purified by preparative HPLC (Column: XBridge Prep Phenyl OBD Column, 19*250 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness and purified further by SFC (Column: YMC-Triart Diol-HILIC, 100*4.6 mm, 3 μm), eluting with 90% $scCO_2$, and MeOH (containing 1% 2M $NH_3$-MeOH). Fractions containing the desired compound were evaporated to dryness to afford 2-(2-chloro-4-(2-(piperazin-1-yl)ethoxy)phenyl)-4-(1-methylcyclobutoxy)-1-(pyridin-2-ylmethyl)-1H-benzo[d]imidazole (7.7 mg, 6.4%) as a white solid.

3-(1-Methylcyclobutoxy)-N1-(pyridin-2-ylmethyl)benzene-1,2-diamine was made following a similar procedure to N4-benzyl-2-isopropoxypyridine-3,4-diamine (Example 9, intermediate), using 3-(1-methylcyclobutoxy)-2-nitro-N-(pyridin-2-ylmethyl)aniline as the starting material. $^1$H NMR (400 MHz, $CDCl_3$): 1.28 (1H, d), 1.58 (3H, s), 1.63-1.87 (2H, m), 2.15 (2H, ddt), 2.4-2.54 (2H, m), 3.07 (4H, s), 6.33 (2H, d), 6.66 (1H, t), 7.24 (1H, d), 7.41 (1H, d), 7.72 (1H, td), 8.58-8.66 (1H, m). m/z: ES+ [M+H]+ 284.

3-(1-Methylcyclobutoxy)-2-nitro-N-(pyridin-2-ylmethyl)aniline was made as follows:

1-Fluoro-3-(1-methylcyclobutoxy)-2-nitrobenzene (300 mg, 1.33 mmol), pyridin-2-ylmethanamine (173 mg, 1.60 mmol) and potassium carbonate (552 mg, 4.00 mmol) was added in DMF (5 mL) at 20° C. The resulting mixture was stirred at 100° C. for 16 hours. The reaction mixture was concentrated and diluted with EtOAc (3×20 mL), and washed sequentially with water (75 mL), saturated brine (2×15 mL). The organic layer was dried over $Na_2SO_4$, filtered and evaporated to afford crude product. The residue was purified by preparative TLC (petroleum ether:EtOAc, 2:1), to afford 3-(1-methylcyclobutoxy)-2-nitro-N-(pyridin-2-ylmethyl)aniline (220 mg, 53%) as an orange oil. $^1$H NMR (400 MHz, DMSO-$d_6$): 1.50 (3H, s), 1.6-1.85 (2H, m), 2.07-2.21 (2H, m), 2.21-2.39 (2H, m), 4.45 (2H, d), 6.18 (1H, dd), 6.23-6.38 (1H, m), 6.79 (1H, t), 7.13 (1H, t), 7.24-7.3 (1H, m), 7.32 (1H, d), 7.77 (1H, td), 8.54 (1H, dt). m/z: ES+ [M+H]+ 314.

1-Fluoro-3-(1-methylcyclobutoxy)-2-nitrobenzene was made following a similar procedure to 9-benzyl-6-(1-methylcyclobutoxy)-9H-purine (Example 12, intermediate), using 1-methylcyclobutan-1-ol and 1,3-difluoro-2-nitrobenzene as starting materials. $^1$H NMR (300 MHz, $CDCl_3$): 1.21-1.34 (2H, m), 1.57 (3H, s), 2.12-2.23 (2H, m), 2.4-2.52 (2H, m), 6.65 (1H, ddd), 6.77 (1H, ddd), 7.29 (1H, ddd).

[P2] was made as follows:

Ferric chloride solution (43.1 mg, 0.27 mmol) was added to N1-benzyl-3-(1-methylcyclobutoxy)benzene-1,2-diamine (50 mg, 0.18 mmol) and 2-chloro-4-(2-(piperazin-1-yl)ethoxy)benzaldehyde (95 mg, 0.35 mmol, Example 14 intermediate) in 2-propanol (5 mL) at 25° C. The resulting mixture was stirred at 80° C. for 30 minutes. The reaction mixture was basified with saturated aq. $NaHCO_3$. The reaction mixture was concentrated and diluted with EtOAc (25 mL) and washed sequentially with water (2×10 mL) and saturated brine (2×10 mL). The organic layer was dried over $Na_2SO_4$, filtered and evaporated to afford crude product. The crude product was purified by flash C18-flash chromatography, elution gradient 0 to 80% AcOH in water. Fractions were evaporated to dryness to afford crude product. The crude product was purified by preparative HPLC (XBridge Prep C18 OBD column, 19*250 mm, 5 μm silica) using decreasingly polar mixtures of water (containing 10 mmol/L $NH_4HCO_3$ and 0.1% aq. ammonia) and MeCN as eluents. Fractions containing the desired compound were evaporated to dryness to afford 1-benzyl-2-(2-chloro-4-(2-(piperazin-1-yl)ethoxy)phenyl)-4-(1-methylcyclobutoxy)-1H-benzo[d]imidazole (5.7 mg, 6%) as a white solid.

N1-Benzyl-3-(1-methylcyclobutoxy)benzene-1,2-diamine was made following a similar procedure to 3-(1-methylcyclobutoxy)-N1-(pyridin-2-ylmethyl)benzene-1,2-diamine (Example P1, intermediate), using N-benzyl-3-(1-methylcyclobutoxy)-2-nitroaniline as the starting material. m/z: ES+ [M+H]+ 283.

N-Benzyl-3-(1-methylcyclobutoxy)-2-nitroaniline was made following a similar procedure to 3-(1-methylcyclobutoxy)-2-nitro-N-(pyridin-2-ylmethyl)aniline (Example P1, intermediate), using 1-fluoro-3-(1-methylcyclobutoxy)-2-nitrobenzene (Example P1, intermediate) and phenylmethanamine as starting materials. $^1$H NMR (400 MHz, DMSO-$d_6$): 1.48 (3H, s), 1.68-1.8 (2H, m), 2.05-2.18 (2H, m), 2.22-2.31 (2H, m), 4.36 (2H, d), 6.13 (1H, d), 6.24 (1H, d), 6.64 (1H, t), 7.06 (1H, t), 7.18-7.27 (1H, m), 7.3-7.34 (3H, m). One proton not observed. m/z: ES+ [M+H]+ 313.

[P3] was synthesised as follows:

4-Methylbenzoic acid (32 mg, 0.24 mmol) was added to 4-(1-methylcyclobutoxy)-N2-(pyridin-2-ylmethyl)pyridine-2,3-diamine (45 mg, 0.16 mmol) and 2-chloro-4-(2-(piperazin-1-yl)ethoxy)benzaldehyde (85 mg, 0.32 mmol) in EtOH (2 mL) 25° C. The resulting mixture was stirred at 80° C. for 4 hours. The reaction mixture was adjusted to pH=8 with saturated aq. $NaHCO_3$. The reaction mixture was concentrated and diluted with EtOAc (20 mL), and washed sequentially with water (3×10 mL), saturated brine (3×5 mL). The top layer was dried over $Na_2SO_4$, filtered and evaporated to afford crude product. The crude product was purified by preparative HPLC (XBridge Prep OBD column, 30*150 mm, 5 μm), using decreasingly polar mixtures of water (containing 10 mmol/L $NH_4HCO_3$ and 0.1% aq. ammonia) and MeCN as eluents. Fractions containing the desired compound were evaporated to dryness to afford 2-(2-chloro-4-(2-(piperazin-1-yl)ethoxy)phenyl)-7-(1-methylcyclobutoxy)-3-(pyridin-2-ylmethyl)-3H-imidazo[4,5-b]pyridine (13.5 mg, 16%) as a white solid.

4-(1-Methylcyclobutoxy)-N2-(pyridin-2-ylmethyl)pyridine-2,3-diamine was made following a similar procedure to N4-benzyl-2-isopropoxypyridine-3,4-diamine (Example 9, intermediate) using 4-(1-methylcyclobutoxy)-3-nitro-N-(pyridin-2-ylmethyl)pyridin-2-amine as the starting material. $^1$H NMR (300 MHz, DMSO-$d_6$): 1.50 (3H, s), 1.6-1.86 (2H, m), 2.06-2.23 (2H, m), 2.30-2.40 (2H, m), 4.15 (2H, s), 4.62 (2H, d), 6.02-6.24 (2H, m), 7.15-7.37 (3H, m), 7.64-7.77 (1H, m), 8.45-8.56 (1H, m). m/z: ES+ [M+H]+ 285.

4-(1-Methylcyclobutoxy)-3-nitro-N-(pyridin-2-ylmethyl)pyridin-2-amine was made following a similar procedure to 3-(1-methylcyclobutoxy)-2-nitro-N-(pyridin-2-ylmethyl)aniline (Example P1, intermediate) using 2-chloro-4-(1-methylcyclobutoxy)-3-nitropyridine and pyridin-2-ylmethanamine as starting materials. $^1$H NMR (300 MHz, DMSO-$d_6$, 43° C.): 1.57 (3H, s), 1.69-1.83 (2H, m), 2.17-2.4 (4H, m), 4.68 (2H, d), 6.27 (1H, d), 7.21-7.31 (2H, m), 7.68-7.87 (2H, m), 7.98 (1H, d), 8.51 (1H, dt). m/z: ES+ [M+H]+ 315.

2-Chloro-4-(1-methylcyclobutoxy)-3-nitropyridine was made following a similar procedure to 9-benzyl-6-(1-methylcyclobutoxy)-9H-purine (Example 12, intermediate), using 1-methylcyclobutan-1-ol and 2,4-dichloro-3-nitropyridine as starting materials. $^1$H NMR (400 MHz, DMSO-$d_6$): 1.58 (3H, s), 1.64-1.87 (2H, m), 2.21-2.38 (4H, m), 7.23 (1H, d), 8.40 (1H, d).

[P4] made from a similar procedure as 1-benzyl-2-(2-chloro-4-(2-(piperazin-1-yl)ethoxy)phenyl)-4-(1-methylcyclobutoxy)-1H-benzo[d]imidazole (Example P2), using N2-benzyl-4-(1-methylcyclobutoxy)pyridine-2,3-diamine (67.0 mg, 0.24 mmol) and 2-chloro-4-(2-(piperazin-1-yl)ethoxy)benzaldehyde (127 mg, 0.47 mmol).

N2-Benzyl-4-(1-methylcyclobutoxy)pyridine-2,3-diamine was made following a similar procedure to N4-benzyl-2-isopropoxypyridine-3,4-diamine (Example 9, intermediate) using N-benzyl-4-(1-methylcyclobutoxy)-3-nitropyridin-2-amine as the starting material. $^1$H NMR (400 MHz, DMSO-$d_6$): 1.49 (3H, s), 1.59-1.82 (2H, m), 1.98-2.23 (2H, m), 2.26-2.43 (2H, m), 4.14 (2H, s), 4.55 (2H, d), 5.98 (1H, t), 6.09 (1H, d), 7.16-7.23 (1H, m), 7.24-7.45 (5H, m). m/z: ES+ [M+H]+ 284.

N-Benzyl-4-(1-methylcyclobutoxy)-3-nitropyridin-2-amine was prepared from a similar procedure as 3-(1-methylcyclobutoxy)-2-nitro-N-(pyridin-2-ylmethyl)aniline (Example P1 intermediate), using 2-chloro-4-(1-methylcyclobutoxy)-3-nitropyridine (Example P3 intermediate) and phenylmethanamine, except that cesium carbonate was used instead of potassium carbonate. $^1$H NMR (400 MHz, DMSO-$d_6$): 1.55 (3H, s), 1.59-1.88 (2H, m), 2.16-2.26 (2H, m), 2.26-2.4 (2H, m), 4.59 (2H, d), 6.24 (1H, d), 7.12-7.25 (1H, m), 7.25-7.33 (4H, m), 7.64 (1H, t), 7.97 (1H, d). m/z: ES+ [M+H]+ 314.

The following examples in Table Q were synthesised as stated in the notes at the bottom of Table Q.

TABLE Q

| Ex# | Structure | Name | $^1$H NMR | LCMS [M + H]+ |
|---|---|---|---|---|
| Q1 | 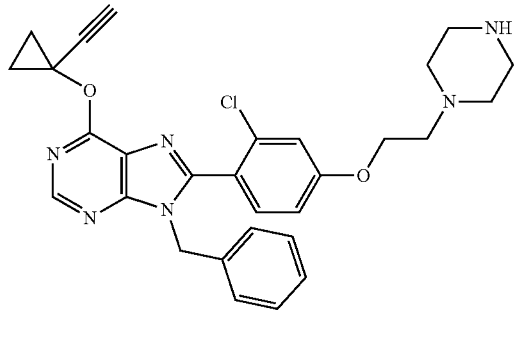 [SMILES: C#CC1(Oc2ncnc3c2nc(-c2ccc(OCCN4CCNCC4)cc2Cl)n3Cc2ccccc2)CC1] | 9-benzyl-8-(2-chloro-4-(2-(piperazin-1-yl)ethoxy)phenyl)-6-(1-ethynylcyclopropoxy)-9H-purine | (500 MHz, $CDCl_3$): 1.42-1.44 (2H, m), 1.44-1.46 (2H, m), 2.49 (1H, s), 2.59-2.66 (4H, m), 2.84 (2H, t), 2.96-3.01 (4H, m), 4.15 (2H, t), 5.35 (2H, s), 6.82 (1H, dd), 6.93 (2H, dd), 7.06 (1H, d), 7.17 (4H, dd), 8.76 (1H, s). 1H not observed. | 529 |

TABLE Q-continued

| Ex# | Structure | Name | $^1$H NMR | LCMS [M + H]+ |
|---|---|---|---|---|
| Q2 | 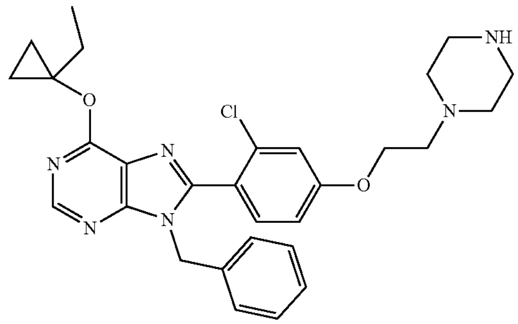 [SMILES: CCC1(Oc2ncnc3c2nc(-c2ccc(OCCN4CCNCC4)cc2Cl)n3Cc2ccccc2)CC1] | 9-benzyl-8-(2-chloro-4-(2-(piperazin-1-yl)ethoxy) phenyl)-6-(1-ethylcyclo-propoxy)-9H-purine | (500 MHz, $CDCl_3$): 0.82-0.85 (2H, m), 1.05 (3H, t), 1.09-1.13 (2H, m), 2.11 (2H, q), 2.56 (4H, s), 2.82 (2H, t), 2.93 (4H, t), 4.15 (2H, t), 5.34 (2H, s), 6.81 (1H, dd), 6.91-6.96 (2H, m), 7.05 (1H, d), 7.14-7.2 (4H, m), 8.64 (1H, s). 1H not observed. | 533 |
| Q3 | 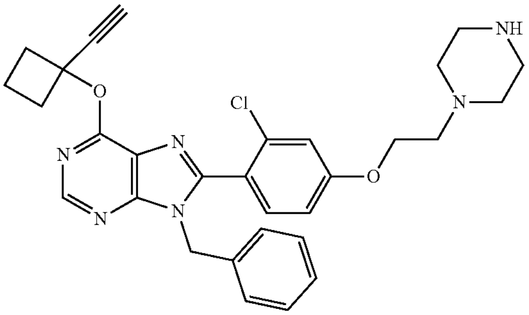 [SMILES: C#CC1(Oc2ncnc3c2nc(-c2ccc(OCCN4CCNCC4)cc2Cl)n3Cc2ccccc2)CCC1] | 9-benzyl-8-(2-chloro-4-(2-(piperazin-1-yl)ethoxy) phenyl)-6-(1-ethynylcyclo-butoxy)-9H-purine | (500 MHz, $CDCl_3$): 1.97-2.01 (1H, m), 2.04-2.09 (1H, m), 2.61 (1H, d), 2.69 (4H, s), 2.71-2.76 (2H, m), 2.8-2.87 (4H, m), 3.03 (4H, s), 4.15 (2H, t), 5.34 (2H, s), 6.81 (1H, d), 6.92 (2H, d), 7.05 (1H, s), 7.15-7.19 (4H, m), 8.64 (1H, s). 1H not observed. | 543 |
| Q4 | 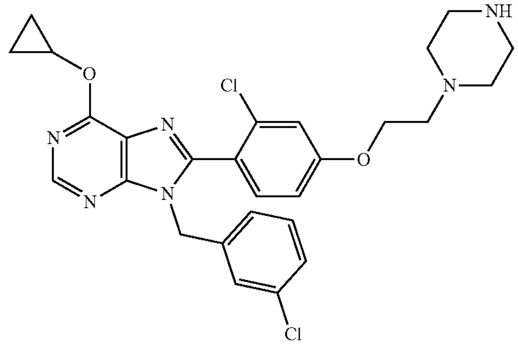 [SMILES: Clc1cccc(Cn2c(-c3ccc(OCCN4CCNCC4)cc3Cl)nc3c(OC4CC4)ncnc32)c1] | 8-(2-chloro-4-(2-(piperazin-1-yl)ethoxy) phenyl)-9-(3-chlorobenzyl)-6-cyclopropoxy-9H-purine | (500 MHz, $CDCl_3$): 0.86-0.92 (2H, m), 0.96-1.02 (2H, m), 2.61 (4H, s), 2.84 (2H, t), 2.94-3 (4H, m), 4.16 (2H, t), 4.61-4.71 (1H, m), 5.31 (2H, s), 6.81-6.87 (3H, m), 7.06 (1H, d), 7.11 (1H, t), 7.13-7.18 (2H, m), 8.66 (1H, s). 1H not observed. | 539 |
| Q5 | 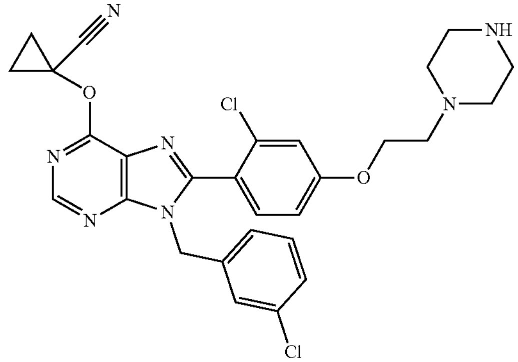 [SMILES: N#CC1(Oc2ncnc3c2nc(-c2ccc(OCCN4CCNCC4)cc2Cl)n3Cc2cccc(Cl)c2)CC1] | 1-((8-(2-chloro-4-(2-(piperazin-1-yl) ethoxy)phenyl)-9-(3-chlorobenzyl)-9H-purin-6-yl)oxy)cyclo-propane-1-carbonitrile | (500 MHz, $CDCl_3$): 1.57 (2H, t), 1.69 (2H, t), 2.65 (4H, s), 2.85 (2H, t), 3.01 (4H, s), 4.16 (2H, t), 5.33 (2H, s), 6.81-6.87 (3H, m), 7.08 (1H, d), 7.09-7.19 (3H, m), 8.75 (1H, s). 1H not observed. | 564 |

[Q1] was made from a similar procedure as 2-(2-chloro-4-(2-(piperazin-1-yl)ethoxy)phenyl)-1-((4-chloropyridin-2-yl)methyl)-4-(1-methylcyclopropoxy)-1H-imidazo[4,5-c] pyridine (Example 16), using tert-butyl 4-(2-(4-(9-benzyl-6-(1-ethynylcyclopropoxy)-9H-purin-8-yl)-3-chlorophenoxy)ethyl)piperazine-1-carboxylate as starting material and 1,4-dioxane as solvent. Tert-butyl 4-(2-(4-(9-benzyl-6-(1-ethynylcyclopropoxy)-9H-purin-8-yl)-3-chlorophenoxy)ethyl)piperazine-1-carboxylate was made from a similar procedure as tert-butyl 4-(2-(4-(9-benzyl-6-(1-methylcyclopropoxy)-9H-purin-8-yl)-3-chlorophenoxy)ethyl) piperazine-1-carboxylate (Example 6, intermediate), using tert-butyl 4-(2-(4-(9-benzyl-6-chloro-9H-purin-8-yl)-3-chlorophenoxy)ethyl)piperazine-1-carboxylate (Example 6, intermediate) and 1-ethynylcyclopropan-1-ol as starting materials. The crude product was used in next reaction without further purification. m/z: ES+ [M+H]+ 629.

[Q2] was made from a similar procedure as 2-(2-chloro-4-(2-(piperazin-1-yl)ethoxy)phenyl)-1-((4-chloropyridin-2-yl)methyl)-4-(1-methylcyclopropoxy)-1H-imidazo[4,5-c]pyridine (Example 16), using tert-butyl 4-(2-(4-(9-benzyl-6-(1-ethylcyclopropoxy)-9H-purin-8-yl)-3-chlorophenoxy)ethyl)piperazine-1-carboxylate as starting material and 1,4-dioxane as solvent. Tert-butyl 4-(2-(4-(9-benzyl-6-(1-ethylcyclopropoxy)-9H-purin-8-yl)-3-chlorophenoxy)ethyl)piperazine-1-carboxylate was made from a similar procedure as tert-butyl 4-(2-(4-(9-benzyl-6-(1-methylcyclopropoxy)-9H-purin-8-yl)-3-chlorophenoxy)ethyl)piperazine-1-carboxylate (Example 6, intermediate), using tert-butyl 4-(2-(4-(9-benzyl-6-chloro-9H-purin-8-yl)-3-chlorophenoxy)ethyl)piperazine-1-carboxylate (Example 6, intermediate) and 1-ethylcyclopropan-1-ol as starting materials. The crude product was used in next reaction without further purification. m/z: ES+ [M+H]+ 633.

[Q3] was made from a similar procedure as tert-butyl 4-(2-(4-(9-benzyl-6-(1-methylcyclopropoxy)-9H-purin-8-yl)-3-chlorophenoxy)ethyl)piperazine-1-carboxylate (Example 6, intermediate), using 4-(2-(4-(9-benzyl-6-chloro-9H-purin-8-yl)-3-chlorophenoxy)ethyl)piperazin-1-ium chloride and 1-ethynylcyclobutan-1-ol as starting materials, and DMF as solvent.

4-(2-(4-(9-Benzyl-6-chloro-9H-purin-8-yl)-3-chlorophenoxy)ethyl)piperazin-1-ium chloride was made from a similar procedure as 2-(2-chloro-4-(2-(piperazin-1-yl)ethoxy)phenyl)-1-((4-chloropyridin-2-yl)methyl)-4-(1-methylcyclopropoxy)-1H-imidazo[4,5-c]pyridine (Example 16), using tert-butyl 4-(2-(4-(9-benzyl-6-chloro-9H-purin-8-yl)-3-chlorophenoxy)ethyl)piperazine-1-carboxylate (Example 6, intermediate) as starting material and 1,4-dioxane as solvent. The crude product was used in next reaction without further purification. m/z: ES+ [M+H]+ 483.

[Q4] was made from a similar procedure as 2-(2-chloro-4-(2-(piperazin-1-yl)ethoxy)phenyl)-1-((4-chloropyridin-2-yl)methyl)-4-(1-methylcyclopropoxy)-1H-imidazo[4,5-c]pyridine (Example 16), using tert-butyl 4-(2-(3-chloro-4-(9-(3-chlorobenzyl)-6-cyclopropoxy-9H-purin-8-yl)phenoxy)ethyl)piperazine-1-carboxylate as starting material and 1,4-dioxane as solvent. Tert-butyl 4-(2-(3-chloro-4-(9-(3-chlorobenzyl)-6-cyclopropoxy-9H-purin-8-yl)phenoxy)ethyl)piperazine-1-carboxylate was made from a similar procedure as ter-butyl 4-(2-(4-(9-benzyl-6-(1-methylcyclopropoxy)-9H-purin-8-yl)-3-chlorophenoxy)ethyl)piperazine-1-carboxylate (Example 6, intermediate), using tert-butyl 4-(2-(3-chloro-4-(6-chloro-9-(3-chlorobenzyl)-9H-purin-8-yl)phenoxy)ethyl)piperazine-1-carboxylate and cyclopropanol as starting materials. The crude product was used in next reaction without further purification. m/z: ES+ [M+H]+ 639.

Tert-butyl 4-(2-(3-chloro-4-(6-chloro-9-(3-chlorobenzyl)-9H-purin-8-yl)phenoxy)ethyl)piperazine-1-carboxylate was made from a similar procedure as tert-butyl 4-(2-(3-chloro-4-(6-chloro-9-((4-chloropyridin-2-yl)methyl)-9H-purin-8-yl)phenoxy)ethyl)piperazine-1-carboxylate (Example 10, intermediate), using tert-butyl 4-(2-(3-chloro-4-(6-chloro-9H-purin-8-yl)phenoxy)ethyl)piperazine-1-carboxylate (Example 10, intermediate) and 1-chloro-3-(chloromethyl)benzene as starting materials. $^1$H NMR (500 MHz, $CDCl_3$): 1.47 (9H, s), 2.52-2.57 (4H, m), 2.86 (2H, t), 3.47 (4H, s), 4.18 (2H, t), 5.35 (2H, s), 6.82-6.9 (3H, m), 7.09-7.14 (2H, m), 7.19 (2H, d), 8.81 (1H, s). m/z: ES+ [M+H]+ 617.

[Q5] was made from a similar procedure as 2-(2-chloro-4-(2-(piperazin-1-yl)ethoxy)phenyl)-1-((4-chloropyridin-2-yl)methyl)-4-(1-methylcyclopropoxy)-1H-imidazo[4,5-c]pyridine (Example 16), using tert-butyl 4-(2-(3-chloro-4-(9-(3-chlorobenzyl)-6-(1-cyanocyclopropoxy)-9H-purin-8-yl)phenoxy)ethyl)piperazine-1-carboxylate as starting material and acetonitrile as solvent, except that the reaction mixture was kept at 0° C.

Tert-butyl 4-(2-(3-chloro-4-(9-(3-chlorobenzyl)-6-(1-cyanocyclopropoxy)-9H-purin-8-yl)phenoxy)ethyl)piperazine-1-carboxylate was made from a similar procedure as tert-butyl 4-(2-(4-(9-benzyl-6-(1-methylcyclopropoxy)-9H-purin-8-yl)-3-chlorophenoxy)ethyl)piperazine-1-carboxylate (Example 6, intermediate), using tert-butyl 4-(2-(3-chloro-4-(6-chloro-9-(3-chlorobenzyl)-9H-purin-8-yl)phenoxy)ethyl)piperazine-1-carboxylate (Example Q4, intermediate) and 1-hydroxycyclopropane-1-carbonitrile as starting materials. The crude product was used in next reaction without further purification. m/z: ES+ [M+H]+ 664.

The following examples in Table R were synthesised as stated in the notes at the bottom of Table R.

TABLE R

| Ex# | Structure | Name | $^1$H NMR | LCMS [M + H]+ |
|---|---|---|---|---|
| R1 | 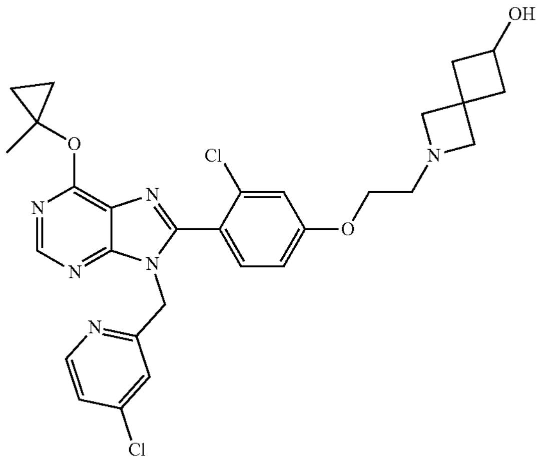 | 2-(2-(3-chloro-4-(9-((4-chloropyridin-2-yl)methyl)-6-(1-methylcyclopropoxy)-9H-purin-8-yl)phenoxy)ethyl)-2-azaspiro[3.3]heptan-6-ol | (400 MHz, DMSO-$d_6$): 0.85 (2H, t), 1.02 (2H, t), 1.73 (3H, s), 1.8-1.98 (2H, m), 2.21-2.4 (2H, m), 2.67 (2H, t), 3.12 (4H, d), 3.78-4.05 (3H, m), 4.94 (1H, d), 5.40 (2H, s), 6.93 (1H, dd), 7.15 (1H, d), 7.26 (1H, d), 7.3-7.44 (2H, m), 8.30 (1H, d), 8.57 (1H, s). | 581 |

TABLE R-continued

| Ex# | Structure | Name | $^1$H NMR | LCMS [M + H]+ |
|---|---|---|---|---|
| R2 | 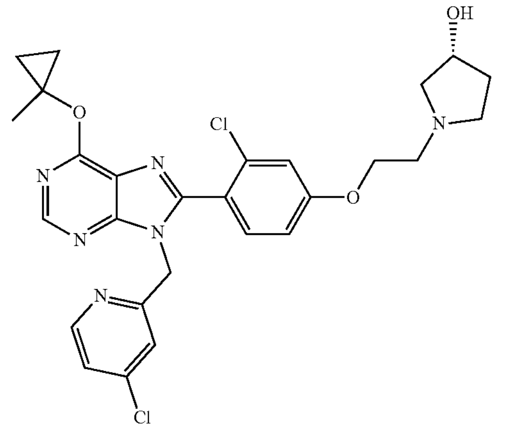 | (R)-1-(2-(3-chloro-4-(9-((4-chloropyridin-2-yl)methyl)-6-(1-methylcyclopropoxy)-9H-purin-8-yl)phenoxy)ethyl)pyrrolidin-3-ol | (300 MHz, DMSO-$d_6$): 0.84 (2H, t), 0.99 (2H, t), 1.46-1.58 (1H, m), 1.73 (3H, s), 1.88-2.04 (1H, m), 2.37-2.42 (1H, m), 2.59-2.69 (1H, m), 2.73-2.82 (3H, m), 4.10-4.38 (3H, m), 4.66-4.72 (1H, m), 5.40 (2H, s), 6.96-7.00 (1H, m), 7.11-7.21 (1H, m), 7.22-7.29 (1H, m), 7.34-7.41 (2H, m), 8.31 (1H, d), 8.57 (1H,s). One proton not observed. | 555 |
| R3 | 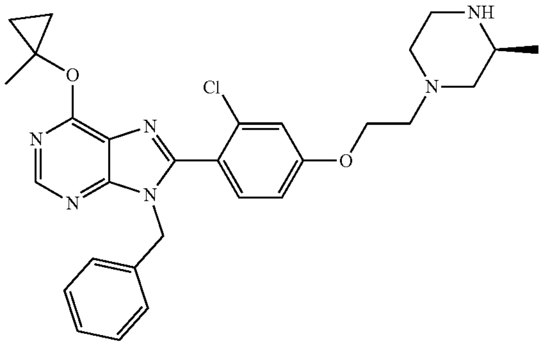 | (S)-9-benzyl-8-(2-chloro-4-(2-(3-methylpiperazin-1-yl)ethoxy)phenyl)-6-(1-methyl-cyclopropoxy)-9H-purine | (400 MHz, DMSO-$d_6$): 0.84 (2H, t), 0.91 (3H, d), 1.03 (2H, t), 1.63 (1H, t), 1.73 (3H, s), 1.9-2.03 (1H, m), 2.6-2.7 (4H, m), 2.72-2.83 (3H, m), 4.18 (2H, t), 5.29 (2H, s), 6.82-6.96 (2H, m), 7-7.07 (1H, m), 7.16-7.23 (3H, m), 7.25 (1H, d), 7.40 (1H, d), 8.61 (1H, s). One proton not observed. | 533 |
| R4 | 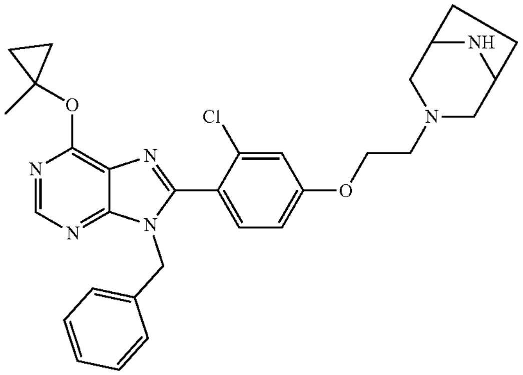 | 8-(4-(2-(3,8-diazabicyclo[3.2.1]octan-3-yl)ethoxy)-2-chlorophenyl)-9-benzyl-6-(1-methylcyclopropoxy)-9H-purine | (400 MHz, DMSO-$d_6$): 0.84 (2H, t), 1.02 (2H, t), 1.48-1.56 (2H, m), 1.63-1.71 (2H, m), 1.73 (3H, s), 2.22 (2H, d), 2.57-2.7 (4H, m), 3.19-3.35 (2H, m), 4.16 (2H, t), 5.29 (2H, s), 6.85-6.94 (2H, m), 6.99-7.06 (1H, m), 7.14-7.23 (3H, m), 7.25 (1H, d), 7.38 (1H, d), 8.61 (1H, s). One proton not observed. | 545 |
| R5 | 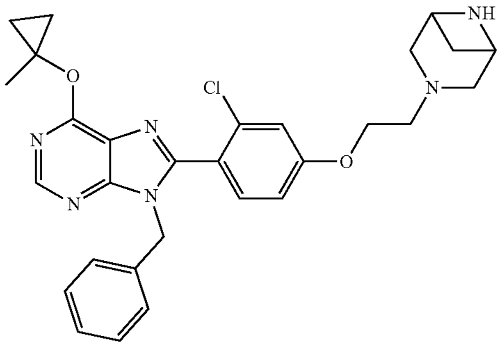 | 3-(2-(4-(9-benzyl-6-(1-methylcyclopropoxy)-9H-purin-8-yl)-3-chlorophenoxy)ethyl)-3,6-diazabicyclo[3.1.1]heptane | (400 MHz, DMSO-$d_6$): 0.84 (2H, t), 1.01 (2H, t), 1.73 (3H, s), 1.74-1.76 (1H, m), 2.17-2.26 (1H, m), 2.74 (2H, d), 2.94 (2H, t), 3.10 (2H, d), 3.43 (2H, d), 4.23 (2H, t), 5.29 (2H, s), 6.87-6.95 (2H, m), 7.02-7.08 (1H, m), 7.17-7.23 (3H, m), 7.27 (1H, d), 7.41 (1H, d), 8.61 (1H, s). One proton not observed. | 531 |

TABLE R-continued

| Ex# | Structure | Name | $^1H$ NMR | LCMS [M + H]+ |
|---|---|---|---|---|
| R6 | 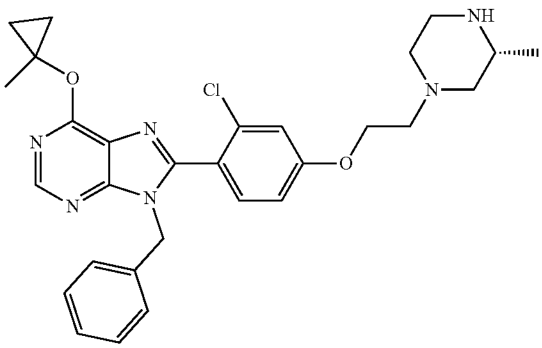 | (R)-9-benzyl-8-(2-chloro-4-(2-(3-methylpiperazin-1-yl) ethoxy)phenyl)-6-(1-methyl-cyclopropoxy)-9H-purine | (400 MHz, DMSO-$d_6$): 0.84 (2H, t), 0.91 (3H, d), 1.03 (2H, t), 1.63 (1H, t), 1.73 (3H, s), 1.9-2.03 (1H, m), 2.6-2.7 (4H, m), 2.72-2.83 (3H, m), 3.51 (1H, s), 4.18 (2H, t), 5.29 (2H, s), 6.82-6.96 (2H, m), 7-7.07 (1H, m), 7.16-7.23 (3H, m), 7.25 (1H, d), 7.40 (1H, d), 8.61 (1H, s). | 533 |
| R7 | 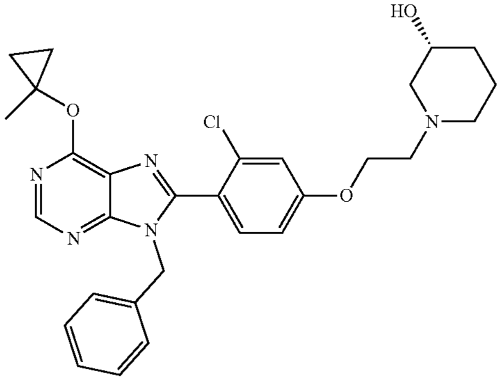 | (R)-1-(2-(4-(9-benzyl-6-(1-methylcyclo-propoxy)-9H-purin-8-yl)-3-chlorophenoxy) ethyl) piperidin-3-ol | (400 MHz, $CDCl_3$): 0.85 (2H, t), 1.16 (2H, t), 1.6-1.74 (3H, m), 1.81 (3H, s), 1.91-2.02 (1H, m), 2.66-3.07 (6H, m), 3.95-4 (1H, m), 4.25 (2H, t), 5.35 (2H, s), 6.79-6.87 (1H, m), 6.92-6.97 (2H, m), 7.07 (1H, d), 7.14-7.23 (4H, m), 8.68 (1H, s). One proton not observed. | 534 |
| R8 | 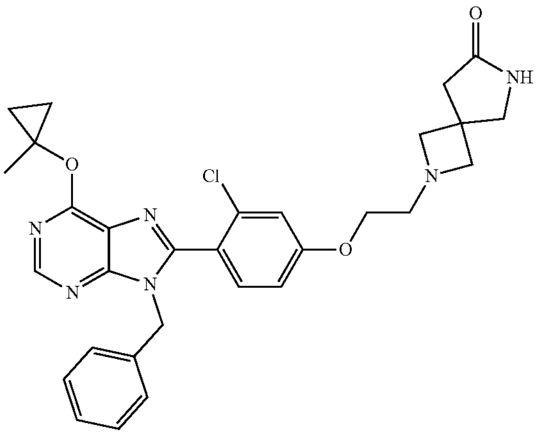 | 2-(2-(4-(9-benzyl-6-(1-methylcyclo-propoxy)-9H-purin-8-yl)-3-chlorophenoxy) ethyl)-2,6-diazaspiro[3.4] octan-7-one | (400 MHz, DMSO-$d_6$): 0.84 (2H, t), 1.01 (2H, t), 1.73 (3H, s), 2.34 (2H, s), 2.75 (2H, t), 3.21 (4H, t), 3.37 (2H, s), 4.05 (2H, t), 5.29 (2H, s), 6.87-6.93 (2H, m), 7.01 (1H, dd), 7.18-7.23 (4H, m), 7.40 (1H, d), 7.54 (1H, s), 8.61 (1H, s). | 559 |
| R9 | 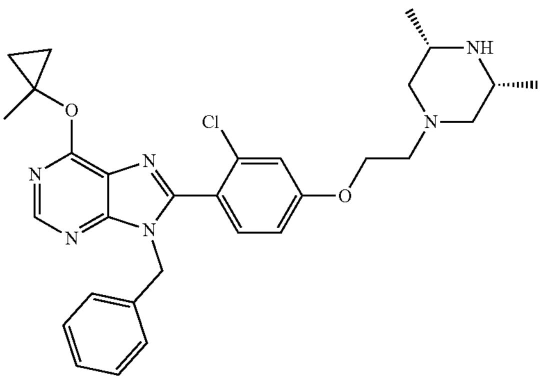 Relative stereochemistry | (cis)-9-benzyl-8-(2-chloro-4-(2-(3,5-dimethyl-piperazin-1-yl)ethoxy) phenyl)-6-(1-methylcyclo-propoxy)-9H-purine | (400 MHz, DMSO-$d_6$): 0.83 (2H, t), 0.93-1.06 (8H, m), 1.73 (3H, s), 2.15-2.28 (2H, m), 2.43-2.49 (2H, m), 2.66-2.74 (2H, m), 2.97 (2H, t), 3.54 (1H, s), 4.09 (2H, t), 5.29 (2H, s), 6.87-6.93 (2H, m), 6.99-7.04 (1H, m), 7.17-7.22 (3H, m), 7.24 (1H, d), 7.41 (1H, d), 8.61 (1H, s). | 547 |

TABLE R-continued

| Ex# | Structure | Name | $^1$H NMR | LCMS [M + H]+ |
|---|---|---|---|---|
| R10 | 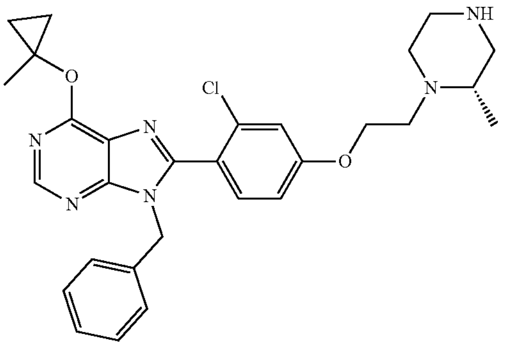 | (S)-9-benzyl-8-(2-chloro-4-(2-(2-methylpiperazin-1-yl) ethoxy)phenyl)-6-(1-methyl-cyclopropoxy)-9H-purine | (400 MHz, DMSO-$d_6$): 0.83 (2H, t), 0.96 (3H, d), 1.01 (2H, t), 1.73 (3H, s), 2.21-2.38 (3H, m), 2.55-2.65 (2H, m), 2.67-2.81 (3H, m), 2.96-3.06 (1H, m), 4.15 (2H, t), 5.29 (2H, s), 6.87-6.93 (2H, m), 7-7.05 (1H, m), 7.17-7.22 (3H, m), 7.25 (1H, d), 7.40 (1H, d), 8.61 (1H, s). One proton not observed. | 533 |
| R11 | 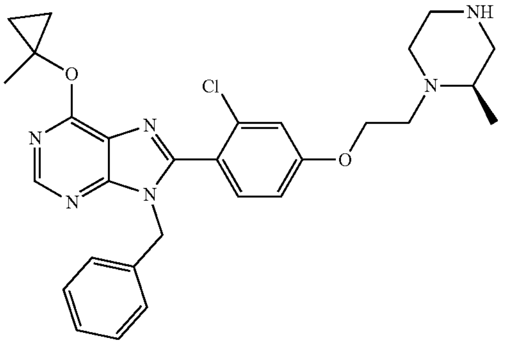 | (R)-9-benzyl-8-(2-chloro-4-(2-(2-methylpiperazin-1-yl) ethoxy)phenyl)-6-(1-methyl-cyclopropoxy)-9H-purine | (300 MHz, DMSO-$d_6$): 0.83 (2H, t), 0.96 (3H, d), 1.01 (2H, t), 1.73 (3H, s), 2.21-2.38 (3H, m), 2.55-2.65 (2H, m), 2.68-2.8 (3H, m), 2.98-3.06 (1H, m), 4.15 (2H, t), 5.29 (2H, s), 6.85-6.92 (2H, m), 7-7.05 (1H, m), 7.16-7.22 (3H, m), 7.25 (1H, d), 7.40 (1H, d), 8.61 (1H, s). One proton not observed. | 533 |
| R12 | 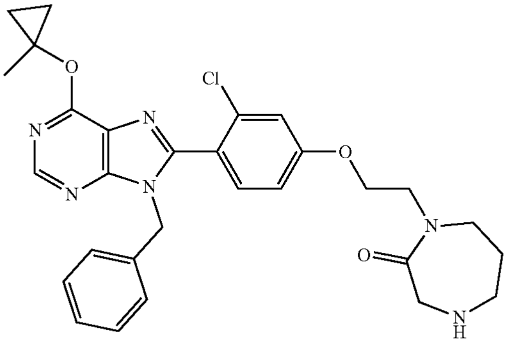 | 1-(2-(4-(9-benzyl-6-(1-methylcyclo-propoxy)-9H-purin-8-yl)-3-chlorophenoxy) ethyl)-1,4-diazepan-2-one | (400 MHz, DMSO-$d_6$): 0.85 (2H, t), 1.01 (2H, t), 1.52-1.65 (2H, m), 1.73 (3H, s), 2.79-2.89 (2H, m), 3.48-3.6 (2H, m), 3.63-3.75 (2H, m), 3.67 (2H, t), 4.15 (2H, t), 5.29 (2H, s), 6.85-6.94 (2H, m), 6.99-7.07 (1H, m), 7.15-7.22 (3H, m), 7.25 (1H, d), 7.41 (1H, d), 8.61 (1H, s). One proton not observed. | 547 |
| R13 | 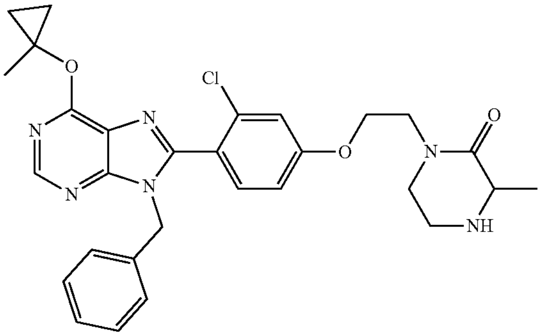 Isomer 1 | 1-(2-(4-(9-benzyl-6-(1-methylcyclo-propoxy)-9H-purin-8-yl)-3-chlorophenoxy) ethyl)-3-methylpiperazin-2-one (Isomer 1) | (400 MHz, DMSO-$d_6$): 0.84 (2H, t), 1.03 (2H, t), 1.18 (3H, d), 1.73 (3H, s), 2.66 (1H, s), 2.74-2.85 (1H, m), 2.93-3.01 (1H, m), 3.21-3.3 (1H, m), 3.33-3.36 (1H, m), 3.43-3.51 (1H, m), 3.59-3.68 (2H, m), 4.22 (2H, t), 5.29 (2H, s), 6.84-6.96 (2H, m), 7.02-7.07 (1H, m), 7.16-7.23 (3H, m), 7.26 (1H, d), 7.41 (1H, d), 8.61 (1H, s). | 547 |

TABLE R-continued

| Ex# | Structure | Name | $^1$H NMR | LCMS [M + H]+ |
|---|---|---|---|---|
| R14 | 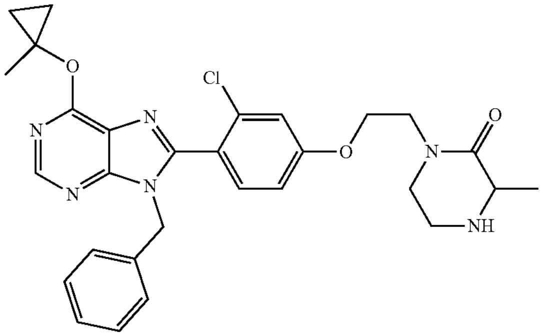 Isomer 2 | 1-(2-(4-(9-benzyl-6-(1-methylcyclo-propoxy)-9H-purin-8-yl)-3-chlorophenoxy) ethyl)-3-methylpiperazin-2-one (Isomer 2) | (400 MHz, DMSO-$d_6$): 0.84 (2H, t), 1.02 (2H, t), 1.18 (3H, d), 1.73 (3H, s), 2.63 (1H, s), 2.75-2.84 (1H, m), 2.93-3.01 (1H, m), 3.22-3.3 (1H, m), 3.33-3.36 (1H, m), 3.42-3.51 (1H, m), 3.57-3.69 (2H, m), 4.22 (2H, t), 5.29 (2H, s), 6.87-6.94 (2H, m), 7.02-7.08 (1H, m), 7.16-7.23 (3H, m), 7.26 (1H, d), 7.41 (1H, d), 8.61 (1H, s). | 547 |
| R15 | 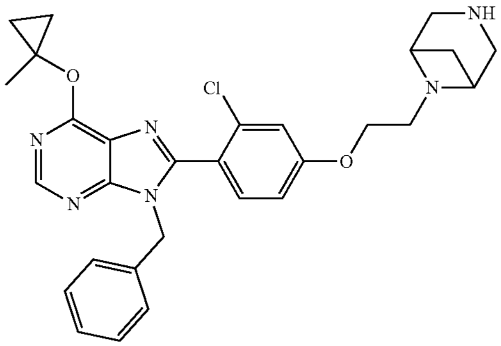 | 6-(2-(4-(9-benzyl-6-(1-methylcyclo-propoxy)-9H-purin-8-yl)-3-chlorophenoxy) ethyl)-3,6-diazabicyclo [3.1.1]heptane | (400 MHz, DMSO-$d_6$): 0.83 (2H, t), 1.02 (2H, t), 1.72-1.74 (4H, m), 2.33-2.41 (1H, m), 2.65-2.75 (1H, m), 2.84-2.9 (2H, m), 3.24-3.3 (2H, m), 3.38-3.46 (2H, m), 3.52-3.65 (2H, m), 4.10 (2H, t), 5.29 (2H, s), 6.88-6.93 (2H, m), 6.98-7.03 (1H, m), 7.17-7.22 (4H, m), 7.40 (1H, d), 8.61 (1H, s). | 531 |
| R16 | 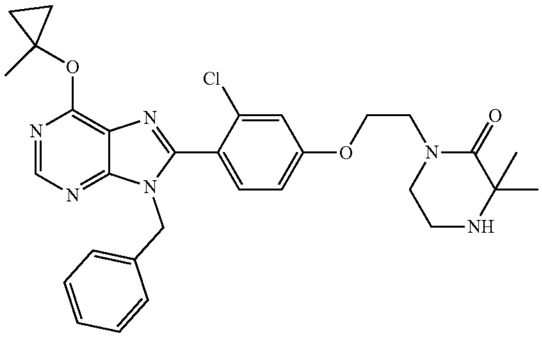 | 1-(2-(4-(9-benzyl-6-(1-methylcyclo-propoxy)-9H-purin-8-yl)-3-chlorophenoxy) ethyl)-3,3-dimethyl-piperazin-2-one | (400 MHz, DMSO-$d_6$): 0.83 (2H, t), 1.02 (2H, t), 1.18 (6H, s), 1.73 (3H, s), 2.38 (1H, s), 2.88 (2H, t), 3.40 (2H, t), 3.62 (2H, t), 4.21 (2H, t), 5.29 (2H, s), 6.87-6.94 (2H, m), 7.02-7.07 (1H, m), 7.17-7.22 (3H, m), 7.26 (1H, d), 7.41 (1H, d), 8.62 (1H, s). | 561 |
| R17 | 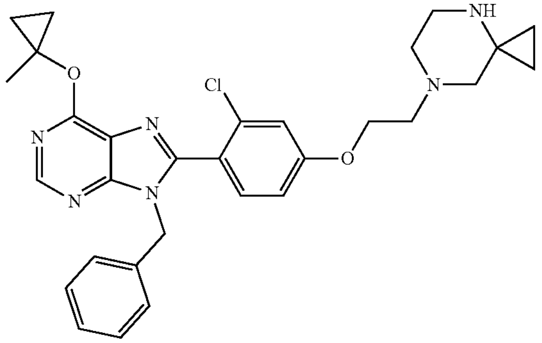 | 8-(4-(2-(4,7-diazaspiro [2.5]octan-7-yl)ethoxy)-2-chlorophenyl)-9-benzyl-6-(1-methylcyclo-propoxy)-9H-purine | (400 MHz DMSO-$d_6$): 0.28-0.45 (4H, m), 0.85 (2H, t), 1.01 (2H, t), 1.73 (3H, s), 2.01 (1H, s), 2.28 (2H, s), 2.37-2.46 (2H, m), 2.66 (2H, t), 2.73 (2H, t), 4.17 (2H, t), 5.28 (2H, s), 6.85-6.93 (2H, m), 7.03 (1H, dd), 7.16-7.22 (3H, m), 7.25 (1H, d), 7.40 (1H, d), 8.61 (1H, s). | 545 |

TABLE R-continued

| Ex# | Structure | Name | $^1$H NMR | LCMS [M + H]+ |
|---|---|---|---|---|
| R18 | 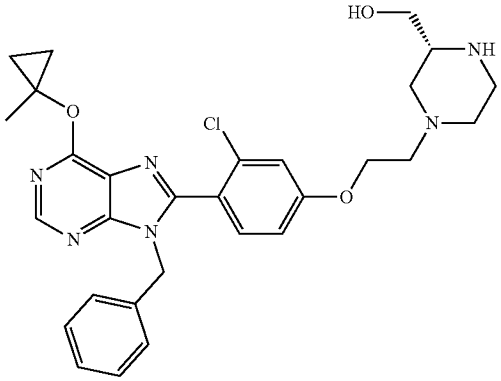 | (R)-(4-(2-(4-(9-benzyl-6-(1-methylcyclo-propoxy)-9H-purin-8-yl)-3-chlorophenoxy) ethyl)piperazin-2-yl)methanol | (400 MHz, DMSO-$d_6$): 0.85 (2H, t), 1.01 (2H, t), 1.66-1.75 (4H, m), 1.96-2.07 (2H, m), 2.6-2.71 (4H, m), 2.72-2.79 (1H, m), 2.8-2.86 (2H, m), 3.27 (2H, t), 4.18 (2H, t), 4.51 (1H, t), 5.29 (2H, s), 6.88-6.92 (2H, m), 7.01-7.05 (1H, m), 7.16-7.28 (4H, m), 7.40 (1H, d), 8.61 (1H, s). | 549 |
| R19 | 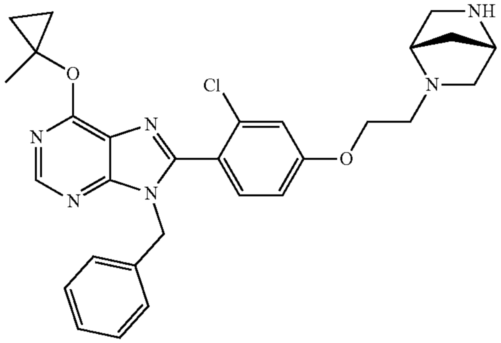 | 8-(4-(2-((1S,4S)-2,5-diazabicyclo [2.2.1]heptan-2-yl)ethoxy)-2-chlorophenyl)-9-benzyl-6-(1-methylcyclo-propoxy)-9H-purine | (400 MHz, DMSO-$d_6$): 0.85 (2H, t), 1.01 (2H, t), 1.40 (1H, d), 1.60 (1H, d), 1.73 (3H, s), 2.32-2.43 (1H, m), 2.57-2.68 (1H, m), 2.78-3.02 (4H, m), 3.34-3.52 (3H, m), 4.11 (2H, t), 5.29 (2H, s), 6.74-6.98 (2H, m), 6.99-7.05 (1H, m), 7.11-7.29 (4H, m), 7.40 (1H, d), 8.61 (1H, s). | 531 |
| R20 | 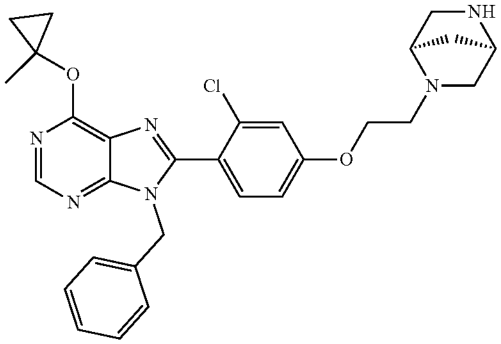 | 8-(4-(2-((1R,4R)-2,5-diazabicyclo [2.2.1]heptan-2-yl)ethoxy)-2-chlorophenyl)-9-benzyl-6-(1-methylcyclo-propoxy)-9H-purine | (400 MHz, DMSO-$d_6$): 0.84 (2H, t), 1.01 (2H, t), 1.41 (1H, d), 1.60 (1H, d), 1.73 (3H, s), 2.33-2.41 (1H, m), 2.6-2.69 (1H, m), 2.78-2.97 (4H, m), 3.28-3.4 (2H, m), 3.54 (1H, s), 4.10 (2H, t), 5.29 (2H, s), 6.85-6.96 (2H, m), 6.98-7.06 (1H, m), 7.16-7.3 (4H, m), 7.40 (1H, d), 8.61 (1H, s). | 531 |
| R21 | 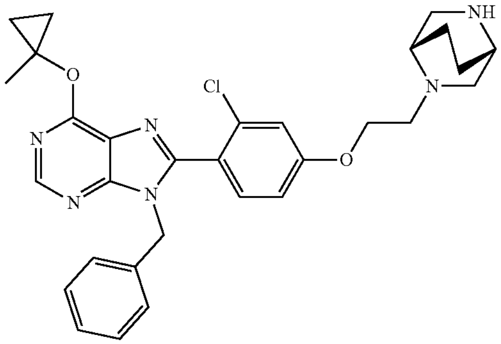 | (1S,4S)-2-(2-(4-(9-benzyl-6-(1-methylcyclo-propoxy)-9H-purin-8-yl)-3-chlorophenoxy) ethyl)-2,5-diazabicyclo [2.2.2]octane | (400 MHz, DMSO-$d_6$): 0.84 (2H, t), 1.01 (2H, t), 1.48-1.65 (2H, m), 1.63-1.81 (4H, m), 1.82-2.00 (1H, m), 2.57-2.73 (2H, m), 2.75-2.81 (1H, m), 2.84-2.96 (4H, m), 3.20 (1H, d), 3.86 (1H, s), 4.13 (2H, t), 5.29 (2H, s), 6.81-6.93 (2H, m), 6.98-7.11 (1H, m), 7.15-7.29 (4H, m), 7.40 (1H, d), 8.61 (1H, s). | 545 |

TABLE R-continued

| Ex# | Structure | Name | $^1H$ NMR | LCMS [M + H]+ |
|---|---|---|---|---|
| R22 | 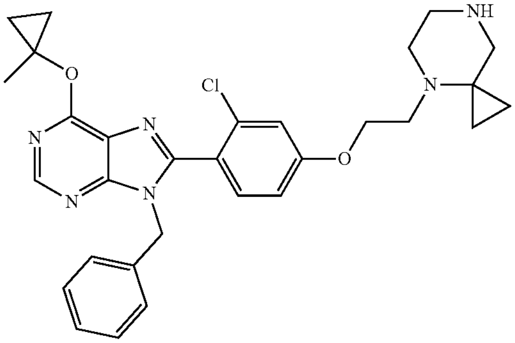 | 8-(4-(2-(4,7-diazaspiro[2.5]octan-4-yl)ethoxy)-2-chlorophenyl)-9-benzyl-6-(1-methylcyclopropoxy)-9H-purine | (400 MHz, DMSO-$d_6$): 0.39 (2H, t), 0.51 (2H, t), 0.85 (2H, t), 1.01 (2H, t), 1.73 (3H, s), 2.69 (2H, s), 2.83 (2H, t), 3.04 (2H, t), 3.22-3.44 (3H, m), 4.03 (2H, t), 5.28 (2H, s), 6.87-6.94 (2H, m), 6.97-7.02 (1H, m), 7.17-7.22 (4H, m), 7.38 (1H, d), 8.62 (1H, s). | 545 |
| R23 | 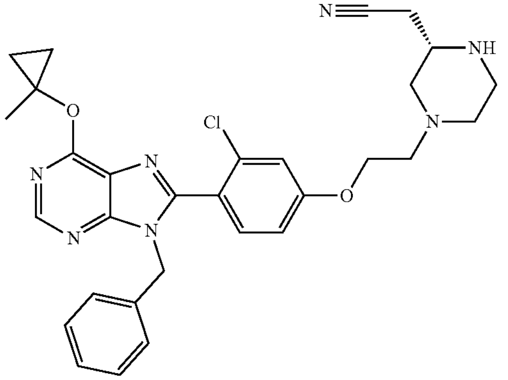 | (S)-2-(4-(2-(4-(9-benzyl-6-(1-methylcyclopropoxy)-9H-purin-8-yl)-3-chlorophenoxy)ethyl)piperazin-2-yl)acetonitrile | (400 MHz, DMSO-$d_6$): 0.84 (2H, t), 1.03 (2H, t), 1.72 (3H, s), 1.85-1.96 (1H, m), 2.01-2.12 (1H, m), 2.2-2.4 (1H, m), 2.55-2.6 (2H, m), 2.62-2.77 (4H, m), 2.79-2.91 (3H, m), 4.18 (2H, t), 5.29 (2H, s), 6.86-6.96 (2H, m), 7.00-7.08 (1H, m), 7.16-7.23 (3H, m), 7.25 (1H, d), 7.40 (1H, d), 8.61 (1H, s). | 558 |

[R1] was made by alkylation of 3-chloro-4-(9-((4-chloropyridin-2-yl)methyl)-6-(1-methylcyclopropoxy)-9H-purin-8-yl)phenol (Example 17 intermediate) with 2-(2-chloroethyl)-2-azaspiro[3.3]heptan-6-ol following a similar procedure as Example 17, except that the reaction was heated at 80° C.

2-(2-Chloroethyl)-2-azaspiro[3.3]heptan-6-ol was synthesised as follows:

1-Bromo-2-chloroethane (456 mg, 3.18 mmol) was added to 2-azaspiro[3.3]heptan-6-ol (300 mg, 2.65 mmol) and $K_2CO_3$ (733 mg, 5.30 mmol) in MeCN (5 mL). The resulting mixture was stirred at 80° C. for 2 hours. The solvent was removed under reduced pressure. The crude product was purified by flash silica chromatography, elution gradient 0 to 30% EtOAc in petroleum ether. Pure fractions were evaporated to dryness to afford 2-(2-chloroethyl)-2-azaspiro[3.3]heptan-6-ol (200 mg, 43%) as a yellow solid. $^1H$ NMR (300 MHz, $CDCl_3$): 2.00-2.06 (2H, m), 2.49-2.56 (2H, m), 2.73-2.77 (2H, m), 3.29 (4H, d), 3.43-3.47 (2H, m), 4.15-4.23 (1H, m). One proton not observed. m/z: ES+ [M+H]+ 176.

[R2] was synthesised as follows:

(R)-Pyrrolidin-3-ol (34.3 mg, 0.39 mmol) was added to 8-(4-(2-bromoethoxy)-2-chlorophenyl)-9-((4-chloropyridin-2-yl)methyl)-6-(1-methylcyclopropoxy)-9H-purine (180 mg, 0.33 mmol), sodium iodide (246 mg, 1.64 mmol) and DIEA (0.172 mL, 0.98 mmol) in DMF (5 mL). The resulting mixture was stirred at 35° C. for 12 hours. The resulting mixture was evaporated to dryness to afford crude product. The crude product was purified by preparative HPLC, XBridge Prep OBD C18 column, 30*150 mm, 5 μm; using decreasingly polar mixtures of water (containing 10 mmol/L $NH_4HCO_3$ and 0.1% aqueous ammonia) and MeCN as eluents. Fractions containing the desired compound were evaporated to dryness to afford (R)-1-(2-(3-chloro-4-(9-((4-chloropyridin-2-yl)methyl)-6-(1-methylcyclopropoxy)-9H-purin-8-yl)phenoxy)ethyl)pyrrolidin-3-ol (47 mg, 26%) as a white solid.

8-(4-(2-Bromoethoxy)-2-chlorophenyl)-9-((4-chloropyridin-2-yl)methyl)-6-(1-methylcyclopropoxy)-9H-purine was synthesised as follows:

3-Chloro-4-(9-((4-chloropyridin-2-yl)methyl)-6-(1-methylcyclopropoxy)-9H-purin-8-yl)phenol (800 mg, 1.81 mmol, Example 17 intermediate) was added to 1,2-dibromoethane (3.40 g, 18.1 mmol) and $K_2CO_3$ (875 mg, 6.33 mmol) in MeCN (30 mL) at 25° C. The resulting mixture was stirred at 60° C. for 16 hours. The reaction mixture was poured into water (300 mL) and extracted with EtOAc (3×300 mL). The organic layer was dried over $Na_2SO_4$, filtered and evaporated to afford crude product. The crude product was purified by flash silica chromatography, elution gradient 50 to 70% EtOAc in petroleum ether. Pure fractions were evaporated to dryness to afford 8-(4-(2-bromoethoxy)-2-chlorophenyl)-9-((4-chloropyridin-2-yl)methyl)-6-(1-methylcyclopropoxy)-9H-purine (700 mg, 70%) as a green oil. $^1H$ NMR (300 MHz, DMSO-$d_6$): 0.86 (2H, t), 1.03 (2H, t), 1.74 (3H, s), 3.83 (2H, t), 4.43 (2H, t), 5.41 (2H, s), 7.02 (1H, dd), 7.24 (1H, d), 7.28 (1H, d), 7.37-7.42 (2H, m), 8.31 (1H, d), 8.58 (1H, s). m/z: ES+ [M+H]+ 548.

[R3] was made by an N-alkylation reaction of 9-benzyl-8-(4-(2-bromoethoxy)-2-chlorophenyl)-6-(1-methylcyclopropoxy)-9H-purine with tert-butyl (S)-2-methylpiperazine-1-carboxylate using a similar procedure as Example R2, except that the reaction was run in DMF at 35° C. to give tert-butyl (S)-4-(2-(4-(9-benzyl-6-(1-methylcyclopropoxy)-

9H-purin-8-yl)-3-chlorophenoxy)ethyl)-2-methylpiperazine-1-carboxylate. $^1$H NMR (300 MHz, DMSO-$d_6$): 0.83 (2H, t), 1.00 (2H, t), 1.11 (3H, d), 1.38 (9H, s), 1.71 (3H, s), 1.92-2.04 (1H, m), 2.04-2.22 (1H, m), 2.59-2.8 (3H, m), 2.8-3.05 (2H, m), 3.54-3.72 (1H, m), 3.93-4.12 (1H, m), 4.19 (2H, t), 5.27 (2H, s), 6.83-6.96 (2H, m), 7.03 (1H, dd), 7.13-7.21 (3H, m), 7.25 (1H, d), 7.40 (1H, d), 8.60 (1H, s). m/z: ES+ [M+H]+ 633.

BOC deprotection of tert-butyl (S)-4-(2-(4-(9-benzyl-6-(1-methylcyclopropoxy)-9H-purin-8-yl)-3-chlorophenoxy) ethyl)-2-methylpiperazine-1-carboxylate using TFA in DCM provided Example R3.

9-Benzyl-8-(4-(2-bromoethoxy)-2-chlorophenyl)-6-(1-methylcyclopropoxy)-9H-purine was made through a Williamson ether synthesis reaction from 4-(9-benzyl-6-(1-methylcyclopropoxy)-9H-purin-8-yl)-3-chlorophenol (Example 5 intermediate) and 1,2-dibromoethane as follows:

1,2-Dibromoethane (11.5 g, 61.4 mmol) was added to 4-(9-benzyl-6-(1-methylcyclopropoxy)-9H-purin-8-yl)-3-chlorophenol (5.0 g, 12.3 mmol) and $K_2CO_3$ (2.55 g, 18.4 mmol) in MeCN (20 mL) at 25° C. The resulting mixture was stirred at 80° C. for 4 hours. The reaction mixture was diluted with EtOAc (50 mL), and washed sequentially with water (3×50 mL). The organic layer was dried over $Na_2SO_4$, filtered and evaporated to afford crude product. The crude product was purified by flash silica chromatography, elution gradient 0 to 100% EtOAc in petroleum ether. Pure fractions were evaporated to dryness to afford 9-benzyl-8-(4-(2-bromoethoxy)-2-chlorophenyl)-6-(1-methylcyclopropoxy)-9H-purine (3.00 g, 47%) as a white solid. $^1$H NMR (300 MHz, $CDCl_3$): 0.87 (2H, t), 1.17 (2H, t), 1.82 (3H, s), 3.69 (2H, t), 4.36 (2H, t), 5.37 (2H, s), 6.84 (1H, dd), 6.9-6.99 (2H, m), 7.09 (1H, d), 7.14-7.26 (4H, m), 8.70 (1H, s). m/z: ES+ [M+H]+ 515.

[R4] was made using a similar procedure described in Example R3 for the synthesis of (S)-9-benzyl-8-(2-chloro-4-(2-(3-methylpiperazin-1-yl)ethoxy)phenyl)-6-(1-methylcyclopropoxy)-9H-purine, by N-alkylation reaction of 9-benzyl-8-(4-(2-bromoethoxy)-2-chlorophenyl)-6-(1-methylcyclopropoxy)-9H-purine (Example R3, intermediate) with ter-butyl 3,8-diazabicyclo[3.2.1]octane-8-carboxylate and the BOC deprotection of the resultant tert-butyl (S)-4-(2-(4-(9-benzyl-6-(1-methylcyclopropoxy)-9H-purin-8-yl)-3-chlorophenoxy)ethyl)-2-methylpiperazine-1-carboxylate.

Tert-butyl (S)-4-(2-(4-(9-benzyl-6-(1-methylcyclopropoxy)-9H-purin-8-yl)-3-chlorophenoxy)ethyl)-2-methylpiperazine-1-carboxylate: $^1$H NMR (300 MHz, DMSO-$d_6$): 0.82 (2H, t), 1.00 (2H, t), 1.37 (9H, s), 1.6-1.79 (7H, m), 2.24 (2H, d), 2.62-2.72 (4H, m), 3.94-4.09 (2H, m), 4.18 (2H, t), 5.27 (2H, s), 6.79-6.93 (2H, m), 7.02 (1H, dd), 7.14-7.22 (3H, m), 7.24 (1H, d), 7.40 (1H, d), 8.60 (1H, s). m/z: ES+ [M+H]+ 645.

[R5] was made using a similar procedure described in Example R3 for the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl 3,6-diazabicyclo[3.1.1]heptane-6-carboxylate and the BOC deprotection of the resultant tert-butyl (1R,5S)-3-(2-(4-(9-benzyl-6-(1-methylcyclopropoxy)-9H-purin-8-yl)-3-chlorophenoxy)ethyl)-3,6-diazabicyclo[3.1.1]heptane-6-carboxylate.

Tert-butyl (1R,5S)-3-(2-(4-(9-benzyl-6-(1-methylcyclopropoxy)-9H-purin-8-yl)-3-chlorophenoxy)ethyl)-3,6-diazabicyclo[3.1.1]heptane-6-carboxylate. $^1$H NMR (300 MHz, DMSO-$d_6$): 0.84 (2H, t), 1.00 (2H, t), 1.33 (9H, s), 1.46-1.58 (1H, m), 1.72 (3H, s), 2.15-2.34 (1H, m), 2.75-2.87 (2H, m), 2.92 (2H, t), 3.01-3.25 (2H, m), 3.94 (2H, d), 4.19 (2H, t), 5.27 (2H, s), 6.8-6.95 (2H, m), 7.02 (1H, dd), 7.11-7.26 (4H, m), 7.41 (1H, d), 8.60 (1H, s). m/z: ES+ [M+H]+ 631.

[R6] was made using a similar procedure described in Example R3 for the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl (R)-2-methylpiperazine-1-carboxylate and the BOC deprotection of the resultant tert-butyl (R)-4-(2-(4-(9-benzyl-6-(1-methylcyclopropoxy)-9H-purin-8-yl)-3-chlorophenoxy)ethyl)-2-methylpiperazine-1-carboxylate.

Tert-butyl (R)-4-(2-(4-(9-benzyl-6-(1-methylcyclopropoxy)-9H-purin-8-yl)-3-chlorophenoxy)ethyl)-2-methylpiperazine-1-carboxylate. $^1$H NMR (300 MHz, DMSO-$d_6$): 0.83 (2H, t), 1.00 (2H, t), 1.11 (3H, d), 1.38 (9H, s), 1.71 (3H, s), 1.92-2.04 (1H, m), 2.04-2.22 (1H, m), 2.59-2.8 (3H, m), 2.8-3.05 (2H, m), 3.54-3.72 (1H, m), 3.93-4.12 (1H, m), 4.19 (2H, t), 5.27 (2H, s), 6.83-6.96 (2H, m), 7.03 (1H, dd), 7.13-7.21 (3H, m), 7.25 (1H, d), 7.40 (1H, d), 8.60 (1H, s). m/z: ES+ [M+H]+ 633.

[R7] was made by a similar procedure previously described in Example R3 in the synthesis of tert-butyl (S)-4-(2-(4-(9-benzyl-6-(1-methylcyclopropoxy)-9H-purin-8-yl)-3-chlorophenoxy)ethyl)-2-methylpiperazine-1-carboxylate, by N-alkylation using 9-benzyl-8-(4-(2-bromoethoxy)-2-chlorophenyl)-6-(1-methylcyclopropoxy)-9H-purine (Example R3, intermediate) and (R)-piperidin-3-ol as starting materials.

[R8] was made by a similar procedure previously described in Example R3 in the synthesis of tert-butyl (S)-4-(2-(4-(9-benzyl-6-(1-methylcyclopropoxy)-9H-purin-8-yl)-3-chlorophenoxy)ethyl)-2-methylpiperazine-1-carboxylate, by N-alkylation using 9-benzyl-8-(4-(2-bromoethoxy)-2-chlorophenyl)-6-(1-methylcyclopropoxy)-9H-purine (Example R3, intermediate) and 2,6-diazaspiro[3.4]octan-7-one as starting materials.

[R9] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl (cis)-2,6-dimethylpiperazine-1-carboxylate and the BOC deprotection of the resultant tert-butyl (cis)-4-(2-(4-(9-benzyl-6-(1-methylcyclopropoxy)-9H-purin-8-yl)-3-chlorophenoxy)ethyl)-2,6-dimethylpiperazine-1-carboxylate.

Tert-butyl (cis)-4-(2-(4-(9-benzyl-6-(1-methylcyclopropoxy)-9H-purin-8-yl)-3-chlorophenoxy)ethyl)-2,6-dimethylpiperazine-1-carboxylate. $^1$H NMR (300 MHz, DMSO-$d_6$): 0.85 (2H, t), 0.97-1.11 (8H, m), 1.39 (9H, s), 1.73 (3H, s), 2.50-2.62 (2H, m), 2.66-2.72 (2H, m), 3.00-3.08 (2H, m), 3.70-7.80 (2H, m), 4.11 (2H, t), 5.29 (2H, s), 6.90-6.93 (2H, m), 7.03 (1H, d), 7.16-7.28 (4H, m), 7.42 (1H, d), 8.62 (1H, s). m/z: ES+ [M+H]+ 647.

[R10] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate)) with tert-butyl (S)-3-methylpiperazine-1-carboxylate and the BOC deprotection of the resultant tert-butyl (S)-4-(2-(4-(9-benzyl-6-(1-methylcyclopropoxy)-9H-purin-8-yl)-3-chlorophenoxy)ethyl)-3-methylpiperazine-1-carboxylate.

Tert-butyl (S)-4-(2-(4-(9-benzyl-6-(1-methylcyclopropoxy)-9H-purin-8-yl)-3-chlorophenoxy)ethyl)-3-methylpiperazine-1-carboxylate. $^1$H NMR (300 MHz, DMSO-$d_6$): 0.86 (2H, t), 0.96-1.09 (5H, m), 1.40 (9H, s), 1.73 (3H, s), 2.21-2.47 (2H, m), 2.56-2.73 (2H, m), 2.78-2.87 (1H, m), 2.97-3.15 (2H, m), 3.49-3.7 (2H, m), 4.12-4.3 (2H, m), 5.29 (2H, s), 6.85-6.97 (2H, m), 6.99-7.08 (1H, m), 7.15-7.33 (4H, m), 7.42 (1H, d), 8.62 (1H, s). m/z: ES+ [M+H]+ 633.

[R11] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl (R)-3-methylpiperazine-1-carboxylate and the BOC deprotection of the resultant tert-butyl (R)-4-(2-(4-(9-benzyl-6-(1-methylcyclopropoxy)-9H-purin-8-yl)-3-chlorophenoxy)ethyl)-3-methylpiperazine-1-carboxylate.

Tert-butyl (R)-4-(2-(4-(9-benzyl-6-(1-methylcyclopropoxy)-9H-purin-8-yl)-3-chlorophenoxy)ethyl)-3-methylpiperazine-1-carboxylate. $^1$H NMR (300 MHz, DMSO-$d_6$): 0.85 (2H, t), 0.96-1.08 (5H, m), 1.40 (9H, s), 1.74 (3H, s), 2.21-2.43 (2H, m), 2.64-2.85 (3H, m), 2.94-3.1 (2H, m), 3.5-3.64 (2H, m), 4.18 (2H, t), 5.29 (2H, s), 6.87-6.93 (2H, m), 7-7.06 (1H, m), 7.18-7.22 (3H, m), 7.26 (1H, d), 7.41 (1H, d), 8.62 (1H, s). m/z: ES+ [M+H]+ 633.

[R12] The BOC deprotection of tert-butyl 4-(2-(4-(9-benzyl-6-(1-methylcyclopropoxy)-9H-purin-8-yl)-3-chlorophenoxy)ethyl)-3-oxo-1,4-diazepane-1-carboxylate followed a procedure previously described in Example R3 in the synthesis of (S)-9-benzyl-8-(2-chloro-4-(2-(3-methylpiperazin-1-yl)ethoxy)phenyl)-6-(1-methylcyclopropoxy)-9H-purine.

Tert-butyl 4-(2-(4-(9-benzyl-6-(1-methylcyclopropoxy)-9H-purin-8-yl)-3-chlorophenoxy)ethyl)-3-oxo-1,4-diazepane-1-carboxylate was made by reaction of 9-benzyl-8-(4-(2-bromoethoxy)-2-chlorophenyl)-6-(1-methylcyclopropoxy)-9H-purine (Example R3, intermediate) with tert-butyl 3-oxo-1,4-diazepane-1-carboxylate as follows:

Sodium hydride (8.56 mg, 0.21 mmol) was added to 9-benzyl-8-(4-(2-bromoethoxy)-2-chlorophenyl)-6-(1-methylcyclopropoxy)-9H-purine (100 mg, 0.19 mmol) and tert-butyl 3-oxo-1,4-diazepane-1-carboxylate (75 mg, 0.35 mmol) in DMF (3 mL) under nitrogen. The resulting mixture was stirred at 20° C. for 2 hours. The reaction mixture was concentrated and diluted with EtOAc (10 mL), and washed sequentially with water (3×15 mL). The organic layer was dried over $Na_2SO_4$, filtered and evaporated to afford crude product. The crude product was purified by flash silica chromatography, elution gradient 0 to 10% EtOH in DCM. Pure fractions were evaporated to dryness to afford tert-butyl 4-(2-(4-(9-benzyl-6-(1-methylcyclopropoxy)-9H-purin-8-yl)-3-chlorophenoxy)ethyl)-3-oxo-1,4-diazepane-1-carboxylate (70.0 mg, 56%) as a white solid. $^1$H NMR (300 MHz, DMSO-$d_6$): 0.83 (2H, t), 0.99 (2H, t), 1.28 (9H, s), 1.7-1.78 (5H, m), 3.09-3.13 (2H, m), 3.39-3.44 (2H, m), 3.51-3.63 (2H, m), 3.68 (2H, t), 4.10 (2H, t), 5.27 (2H, s), 6.7-6.96 (2H, m), 7.00 (1H, dd), 7.14-7.22 (4H, m), 7.35-7.43 (1H, m), 8.60 (1H, s). m/z: ES+ [M+H]+ 647.

[R13] Racemic 1-(2-(4-(9-benzyl-6-(1-methylcyclopropoxy)-9H-purin-8-yl)-3-chlorophenoxy)ethyl)-3-methylpiperazin-2-one was made using similar procedure described in Example R12 in the synthesis of 1-(2-(4-(9-benzyl-6-(1-methylcyclopropoxy)-9H-purin-8-yl)-3-chlorophenoxy)ethyl)-1,4-diazepan-2-one, by N-alkylation of 9-benzyl-8-(4-(2-bromoethoxy)-2-chlorophenyl)-6-(1-methylcyclopropoxy)-9H-purine (Example R12, intermediate) with ter-butyl (R)-2-methyl-3-oxopiperazine-1-carboxylate and the BOC deprotection of the resultant tert-butyl (R)-4-(2-(4-(9-benzyl-6-(1-methylcyclopropoxy)-9H-purin-8-yl)-3-chlorophenoxy)ethyl)-2-methyl-3-oxopiperazine-1-carboxylate.

Tert-butyl (R)-4-(2-(4-(9-benzyl-6-(1-methylcyclopropoxy)-9H-purin-8-yl)-3-chlorophenoxy)ethyl)-2-methyl-3-oxopiperazine-1-carboxylate. $^1$H NMR (300 MHz, DMSO-$d_6$): 0.85 (2H, t), 1.01 (2H, t), 1.29 (3H, d), 1.41 (9H, s), 1.73 (3H, s), 3.19-3.23 (1H, m), 3.37-3.45 (1H, m), 3.5-3.65 (2H, m), 3.72-3.82 (1H, m), 3.87 (1H, d), 4.23 (2H, t), 4.27-4.35 (1H, m), 5.28 (2H, s), 6.88-6.92 (2H, m), 7.04 (1H, dd), 7.16-7.22 (3H, m), 7.26 (1H, d), 7.41 (1H, d), 8.61 (1H, s). m/z: ES+ [M+H]+ 647.

The two enantiomers of racemic 1-(2-(4-(9-benzyl-6-(1-methylcyclopropoxy)-9H-purin-8-yl)-3-chlorophenoxy)ethyl)-3-methylpiperazin-2-one were purified by preparative chiral-HPLC on a CHIRALPAK IC-3 column, eluting isocratically with 25% DCM in hexane (modified with TEA) as eluent. The fractions containing the desired compound were evaporated to dryness to afford 1-(2-(4-(9-benzyl-6-(1-methylcyclopropoxy)-9H-purin-8-yl)-3-chlorophenoxy)ethyl)-3-methylpiperazin-2-one, isomer 2 (Example R14, 30.0 mg, 27%) as a white solid and 1-(2-(4-(9-benzyl-6-(1-methylcyclopropoxy)-9H-purin-8-yl)-3-chlorophenoxy)ethyl)-3-methylpiperazin-2-one, isomer 1 (Example R13 (30.0 mg, 27%).

[R15] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl 3,6-diazabicyclo[3.1.1]heptane-3-carboxylate and the BOC deprotection of the resultant tert-butyl 6-(2-(4-(9-benzyl-6-(1-methylcyclopropoxy)-9H-purin-8-yl)-3-chlorophenoxy)ethyl)-3,6-diazabicyclo[3.1.1]heptane-3-carboxylate.

Tert-butyl 6-(2-(4-(9-benzyl-6-(1-methylcyclopropoxy)-9H-purin-8-yl)-3-chlorophenoxy)ethyl)-3,6-diazabicyclo[3.1.1]heptane-3-carboxylate. $^1$H NMR (300 MHz, DMSO-$d_6$): 0.85 (2H, s), 1.03 (2H, s), 1.40 (1H, d), 1.44 (9H, s), 1.73 (3H, s), 2.35-2.46 (1H, m), 2.71 (2H, t), 3.27 (2H, s), 3.58 (4H, t), 4.10 (2H, t), 5.29 (2H, s), 6.91 (2H, dd), 7.01 (1H, dd), 7.21 (4H, dq), 7.41 (1H, d), 8.62 (1H, s). m/z: ES+ [M+H]+ 631.

[R16] was made using a similar procedure described in Example R12 in the synthesis of tert-butyl 4-(2-(4-(9-benzyl-6-(1-methylcyclopropoxy)-9H-purin-8-yl)-3-chlorophenoxy)ethyl)-3-oxo-1,4-diazepane-1-carboxylate (Example R12, intermediate), by N-alkylation of 9-benzyl-8-(4-(2-bromoethoxy)-2-chlorophenyl)-6-(1-methylcyclopropoxy)-9H-purine (Example R3, intermediate) with benzyl 2,2-dimethyl-3-oxopiperazine-1-carboxylate to afford benzyl 4-(2-(4-(9-benzyl-6-(1-methylcyclopropoxy)-9H-purin-8-yl)-3-chlorophenoxy)ethyl)-2,2-dimethyl-3-oxopiperazine-1-carboxylate. $^1$H NMR (300 MHz, DMSO-$d_6$): 0.86 (2H, t), 1.01 (2H, t), 1.56 (6H, d), 1.73 (3H, s), 3.47-3.55 (2H, m), 3.62-3.69 (2H, m), 3.73 (2H, t), 4.23 (2H, t), 5.09 (2H, s), 5.28 (2H, s), 6.83-6.93 (2H, m), 7.04 (1H, dd), 7.14-7.23 (3H, m), 7.27 (1H, d), 7.34-7.43 (6H, m), 8.62 (1H, s). m/z: ES+ [M+H]+ 695.

This step was followed by a Cbz deprotection of the resultant benzyl 4-(2-(4-(9-benzyl-6-(1-methylcyclopropoxy)-9H-purin-8-yl)-3-chlorophenoxy)ethyl)-2,2-dimethyl-3-oxopiperazine-1-carboxylate as follows:

Palladium on charcoal (10%) (18.37 mg, 0.17 mmol) was added to benzyl 4-(2-(4-(9-benzyl-6-(1-methylcyclopropoxy)-9H-purin-8-yl)-3-chlorophenoxy)ethyl)-2,2-dimethyl-3-oxopiperazine-1-carboxylate (120 mg, 0.17 mmol) in MeOH (3.0 mL) under hydrogen. The resulting mixture was stirred at 50° C. for 5 hours. The reaction mixture was filtered through filter paper. The solvent was removed under reduced pressure. The crude product was purified by preparative HPLC Column: XBridge Prep OBD C18 Column, 30*150 mm, 5 μm), using decreasingly polar mixtures of water (containing 10 mmol/L $NH_4HCO_3$+0.1% $NH_3 \cdot H_2O$) and MeCN as eluents. Fractions containing the desired compound were evaporated to dryness to afford 1-(2-(4-(9-benzyl-6-(1-methylcyclopropoxy)-9H-purin-8-yl)-3-chlorophenoxy)ethyl)-3,3-dimethylpiperazin-2-one (70 mg, 72%) as a white solid.

[R17] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl 4,7-diazaspiro[2.5]octane-4-carboxylate and the BOC deprotection of the resultant tert-butyl 7-(2-(4-(9-benzyl-6-(1-methylcyclopropoxy)-9H-purin-8-yl)-3-chlorophenoxy)ethyl)-4,7-diazaspiro[2.5]octane-4-carboxylate.

Tert-butyl 7-(2-(4-(9-benzyl-6-(1-methylcyclopropoxy)-9H-purin-8-yl)-3-chlorophenoxy)ethyl)-4,7-diazaspiro[2.5]octane-4-carboxylate. $^1H$ NMR (300 MHz, DMSO-$d_6$): 0.70 (2H, t), 0.8-0.88 (4H, m), 1.03 (2H, t), 1.40 (9H, s), 1.73 (3H, s), 2.29-2.35 (2H, m), 2.40-2.50 (2H, m), 2.66-2.72 (2H, m), 2.90 (2H, s), 4.18 (2H, t), 5.29 (2H, s), 6.87-6.94 (2H, m), 7.03 (1H, dd), 7.17-7.24 (3H, m), 7.26 (1H, d), 7.41 (1H, d), 8.62 (1H, s). m/z: ES+ [M+H]+ 645.

[R18] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl (R)-2-(hydroxymethyl)piperazine-1-carboxylate and the BOC deprotection of the resultant tert-butyl (R)-4-(2-(4-(9-benzyl-6-(1-methylcyclopropoxy)-9H-purin-8-yl)-3-chlorophenoxy)ethyl)-2-(hydroxymethyl)piperazine-1-carboxylate.

Tert-butyl (R)-4-(2-(4-(9-benzyl-6-(1-methylcyclopropoxy)-9H-purin-8-yl)-3-chlorophenoxy)ethyl)-2-(hydroxymethyl)piperazine-1-carboxylate. $^1H$ NMR (300 MHz, DMSO-$d_6$): 0.86 (2H, t), 1.02 (2H, t), 1.40 (9H, s), 1.74 (3H, s), 1.93-2.14 (2H, m), 2.72 (2H, t), 2.81-2.96 (2H, m), 3.01-3.12 (1H, m), 3.36-3.42 (1H, m), 3.55-3.76 (2H, m), 3.90 (1H, s), 4.20 (2H, t), 4.69 (1H, t), 5.30 (2H, s), 6.83-6.95 (2H, m), 7.02-7.1 (1H, m), 7.15-7.31 (4H, m), 7.41 (1H, d), 8.62 (1H, s). m/z: ES+ [M+H]+ 649.

[R19] was obtained using a similar method to(S)-9-benzyl-8-(2-chloro-4-(2-(3-methylpiperazin-1-yl)ethoxy)phenyl)-6-(1-methylcyclopropoxy)-9H-purine tert-butyl (1S,4S)-2,5-diazabicyclo[2.2.1]heptane-2-carboxylate (Example R3), starting from 9-benzyl-8-(4-(2-bromoethoxy)-2-chlorophenyl)-6-(1-methylcyclopropoxy)-9H-purine and tert-butyl (1S,4S)-2,5-diazabicyclo[2.2.1]heptane-2-carboxylate.

[R20] was obtained using a similar method to(S)-9-benzyl-8-(2-chloro-4-(2-(3-methylpiperazin-1-yl)ethoxy)phenyl)-6-(1-methylcyclopropoxy)-9H-purine tert-butyl (1R,4R)-2,5-diazabicyclo[2.2.1]heptane-2-carboxylate (Example R3), starting from 9-benzyl-8-(4-(2-bromoethoxy)-2-chlorophenyl)-6-(1-methylcyclopropoxy)-9H-purine and tert-butyl (1R,4R)-2,5-diazabicyclo[2.2.1]heptane-2-carboxylate.

[R21] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl (1S,4S)-2,5-diazabicyclo[2.2.2]octane-2-carboxylate and the BOC deprotection of tert-butyl (1S,4S)-5-(2-(4-(9-benzyl-6-(1-methylcyclopropoxy)-9H-purin-8-yl)-3-chlorophenoxy)ethyl)-2,5-diazabicyclo[2.2.2]octane-2-carboxylate.

Tert-butyl (1S,4S)-5-(2-(4-(9-benzyl-6-(1-methylcyclopropoxy)-9H-purin-8-yl)-3-chlorophenoxy)ethyl)-2,5-diazabicyclo[2.2.2]octane-2-carboxylate. $^1H$ NMR (300 MHz, DMSO-$d_6$): 0.85 (2H, t), 1.02 (2H, t), 1.32-1.5 (10H, m), 1.63-1.81 (5H, m), 1.86-1.99 (1H, m), 2.82-3.07 (5H, m), 3.13-3.27 (1H, m), 3.44-3.67 (1H, m), 3.75-3.95 (1H, m), 4.13 (2H, t), 5.29 (2H, s), 6.7-6.98 (2H, m), 6.98-7.14 (1H, m), 7.17-7.28 (4H, m), 7.41 (1H, d), 8.62 (1H, s). m/z: ES+ [M+H]+ 645.

[R22] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl 4,7-diazaspiro[2.5]octane-7-carboxylate and the BOC deprotection of tert-butyl 4-(2-(4-(9-benzyl-6-(1-methylcyclopropoxy)-9H-purin-8-yl)-3-chlorophenoxy)ethyl)-4,7-diazaspiro[2.5]octane-7-carboxylate.

Tert-butyl 4-(2-(4-(9-benzyl-6-(1-methylcyclopropoxy)-9H-purin-8-yl)-3-chlorophenoxy)ethyl)-4,7-diazaspiro[2.5]octane-7-carboxylate. $^1H$ NMR (300 MHz, DMSO-$d_6$): 0.50 (2H, t), 0.53-0.63 (2H, t), 0.85 (2H, t), 0.97-1.1 (2H, t), 1.40 (9H, s), 1.73 (3H, s), 2.86-2.94 (2H, m), 3.01-3.14 (2H, m), 3.14-3.23 (2H, m), 3.35-3.42 (2H, m), 4.07 (2H, t), 5.29 (2H, s), 6.83-6.94 (2H, m), 7.01 (1H, dd), 7.12-7.27 (4H, m), 7.40 (1H, d), 8.62 (1H, s). m/z: ES+ [M+H]+ 645.

[R23] was made using a similar procedure described in Example R3 in the synthesis of (S)-9-benzyl-8-(2-chloro-4-(2-(3-methylpiperazin-1-yl)ethoxy)phenyl)-6-(1-methylcyclopropoxy)-9H-purine, by N-alkylation of 9-benzyl-8-(4-(2-bromoethoxy)-2-chlorophenyl)-6-(1-methylcyclopropoxy)-9H-purine (Example R3, intermediate) with tert-butyl (S)-2-(cyanomethyl)piperazine-1-carboxylate and the BOC deprotection of tert-butyl (S)-4-(2-(4-(9-benzyl-6-(1-methylcyclopropoxy)-9H-purin-8-yl)-3-chlorophenoxy)ethyl)-2-(cyanomethyl)piperazine-1-carboxylate.

Tert-butyl (S)-4-(2-(4-(9-benzyl-6-(1-methylcyclopropoxy)-9H-purin-8-yl)-3-chlorophenoxy)ethyl)-2-(cyanomethyl)piperazine-1-carboxylate. $^1H$ NMR (300 MHz, DMSO-$d_6$): 0.86 (2H, t), 1.03 (2H, t), 1.42 (9H, s), 1.74 (3H, s), 2.15-2.36 (2H, m), 2.7-2.85 (4H, m), 2.83-3.01 (4H, m), 3.74-3.80 (1H, m), 4.20 (2H, t), 5.29 (2H, s), 6.88-6.93 (2H, m), 7.04 (1H, dd), 7.17-7.28 (4H, m), 7.42 (1H, d), 8.62 (1H, s). m/z: ES+ [M+H]+ 658.

The following examples in Table S were synthesised as stated in the notes at the bottom of Table S.

TABLE S

| Ex# | Structure | Name | $^1$H NMR | LCMS [M + H]+ |
|---|---|---|---|---|
| S1 | 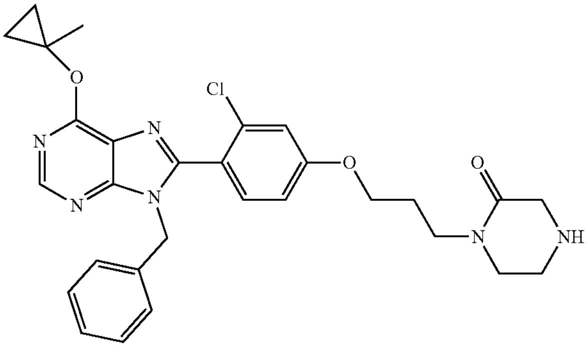 [SMILES: CC1(Oc2ncnc3c2nc(-c2ccc(OCCCN4CCNCC4=O)cc2Cl)n3Cc2ccccc2)CC1] | 1-(3-(4-(9-benzyl-6-(1-methyl-cyclopropoxy)-9H-purin-8-yl)-3-chlorophenoxy) propyl)piperazin-2-one | (400 MHz, DMSO-$d_6$): 0.80-0.88 (2H, m), 1.01 (2H, d), 1.72 (3H, s), 1.96 (2H, p), 2.87 (2H, t), 3.20 (2H, s), 3.25 (2H, t), 3.43 (2H, t), 4.08 (2H, t), 5.29 (2H, s), 6.89 (2H, dd), 7.02 (1H, dd), 7.20 (4H, dd), 7.41 (1H, d), 8.61 (1H, s). One proton not observed. | 547 |
| S2 | 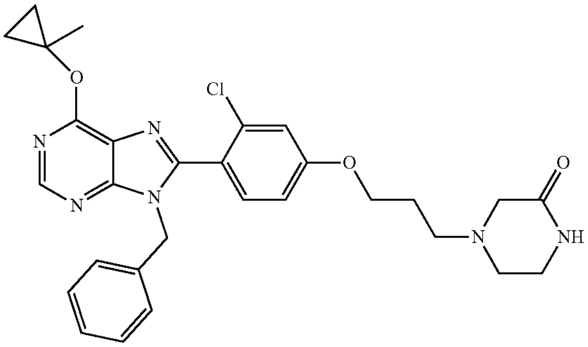 [SMILES: CC1(Oc2ncnc3c2nc(-c2ccc(OCCCN4CCNC(=O)C4)cc2Cl)n3Cc2ccccc2)CC1] | 4-(3-(4-(9-benzyl-6-(1-methyl-cyclopropoxy)-9H-purin-8-yl)-3-chlorophenoxy) propyl)piperazin-2-one | (300 MHz, DMSO-$d_6$): 0.85 (2H, d), 1.01 (2H, d), 1.73 (3H, s), 1.96 (2H, p), 2.87 (2H, t), 3.20 (2H, s), 3.25 (2H, d), 3.43 (2H, s), 4.09 (2H, t), 5.29 (2H, s), 6.89 (2H, dd), 7.02 (1H, dd), 7.14-7.29 (4H, m), 7.41 (1H, d), 8.61 (1H, s). One proton not observed. | 547 |
| S3 | 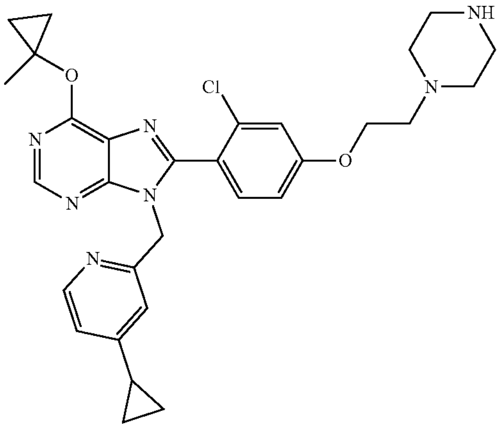 [SMILES: CC1(Oc2ncnc3c2nc(-c2ccc(OCCN4CCNCC4)cc2Cl)n3Cc2cc(C3CC3)ccn2)CC1] | 8-(2-chloro-4-(2-(piperazin-1-yl)ethoxy)phenyl)-9-((4-cyclo-propylpyridin-2-yl)methyl)-6-(1-methyl-cyclopropoxy)-9H-purine | (400 MHz, DMSO-$d_6$): 0.65 (2H, t), 0.85 (2H, t), 0.94-1.07 (4H, m), 1.73 (3H, s), 1.77-1.85 (1H, m), 2.34-2.39 (4H, m), 2.59-2.74 (6H, m), 4.14 (2H, t), 5.32 (2H, s), 6.74 (1H, s), 6.85-6.90 (1H, m), 6.92-6.98 (1H, m), 7.11-7.19 (1H, m), 7.28-7.34 (1H, m), 8.08-8.13 (1H, m), 8.56 (1H, s). One proton not observed. | 560 |
| S4 | 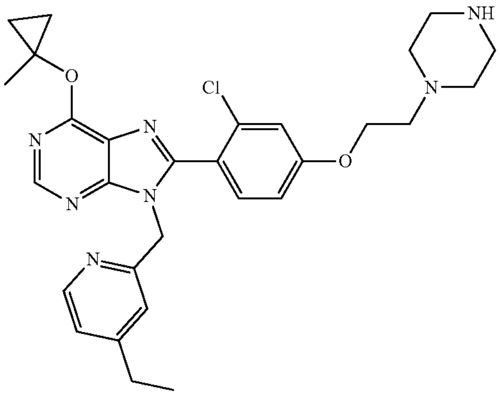 [SMILES: CCc1ccnc(Cn2c(-c3ccc(OCCN4CCNCC4)cc3Cl)nc3c(OC4(C)CC4)ncnc32)c1] | 8-(2-chloro-4-(2-(piperazin-1-yl)ethoxy)phenyl)-9-((4-ethylpyridin-2-yl)methyl)-6-(1-methylcyclo-propoxy)-9H-purine | (400 MHz, DMSO-$d_6$): 0.84 (2H, t), 1.00-1.03 (2H, m), 1.07 (3H, t), 1.74 (3H, s), 2.33-2.43 (4H, m), 2.44-2.49 (2H, m), 2.65 (2H, t), 2.69 (4H, t), 4.13 (2H, t), 5.36 (2H, s), 6.87 (1H, d), 6.94 (1H, dd), 7.05 (1H, d), 7.19 (1H, d), 7.32 (1H, d), 8.19 (1H, d), 8.57 (1H, s). One proton not observed. | 548 |

TABLE S-continued

| Ex# | Structure | Name | $^1$H NMR | LCMS [M + H]+ |
|---|---|---|---|---|
| S5 | 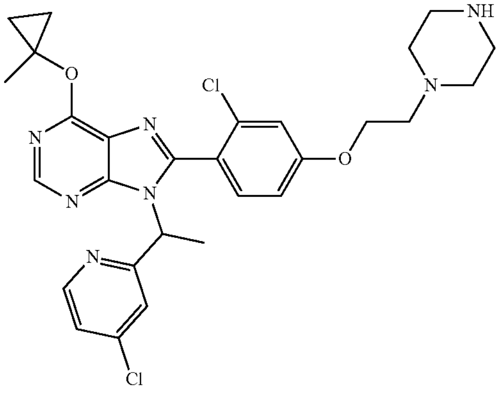 [SMILES: CC(c1cc(Cl)ccn1)n1c(-c2ccc(OCCN3CCNCC3)cc2Cl)nc2c(OC3(C)CC3)ncnc21] Isomer 2 | 8-(2-chloro-4-(2-(piperazin-1-yl)ethoxy)phenyl)-9-(1-(4-chloropyridin-2-yl)ethyl)-6-(1-methylcyclo-propoxy)-9H-purine (Isomer 2) | (400 MHz, DMSO-$d_6$): 0.84 (2H, t), 1.01 (2H, t), 1.71 (3H, s), 2.03 (3H, d), 2.36-2.43 (4H, m), 2.63-2.72 (6H, m), 4.17 (2H, t), 5.45-5.49 (1H, m), 7.04 (1H, dd), 7.26 (1H, d), 7.41-7.45 (3H, m), 8.38 (1H, d), 8.49 (1H, s). One proton not observed. | 568 |
| S6 | 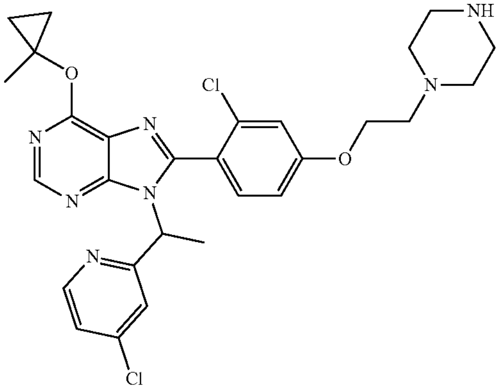 [SMILES: CC(c1cc(Cl)ccn1)n1c(-c2ccc(OCCN3CCNCC3)cc2Cl)nc2c(OC3(C)CC3)ncnc21] Isomer 1 | 8-(2-chloro-4-(2-(piperazin-1-yl)ethoxy)phenyl)-9-(1-(4-chloropyridin-2-yl)ethyl)-6-(1-methylcyclo-propoxy)-9H-purine (Isomer 1) | (400 MHz, DMSO-$d_6$): 0.84 (2H, t), 1.00 (2H, t), 1.71 (3H, s), 2.03 (3H, d), 2.36-2.43 (4H, m), 2.63-2.71 (6H, m), 4.17 (2H, t), 5.45-5.49 (1H, m), 7.04 (1H, dd), 7.26 (1H, d), 7.39-7.46 (3H, m), 8.38 (1H, d), 8.49 (1H, s). One proton not observed. | 568 |
| S7 | 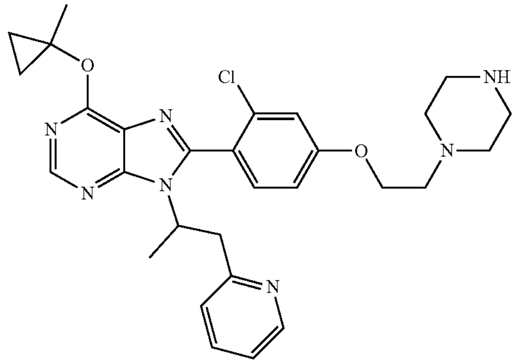 [SMILES: CC(Cc1ccccn1)n1c(-c2ccc(OCCN3CCNCC3)cc2Cl)nc2c(OC3(C)CC3)ncnc21] Isomer 2 | 8-(2-chloro-4-(2-(piperazin-1-yl)ethoxy)phenyl)-6-(1-methyl-cyclopropoxy)-9-(1-(pyridin-2-yl)propan-2-yl)-9H-purine (Isomer 2) | (400 MHz, DMSO-$d_6$, 80° C.): 0.77 (2H, t), 0.97 (2H, t), 1.73-1.88 (6H, m), 2.45-2.61 (4H, m), 2.65-2.71 (6H, m), 3.27-3.30 (1H, m), 3.68-3.71 (1H, m), 4.17 (2H, t), 4.48-4.6 (1H, m), 6.78-6.81 (2H, m), 6.92 (1H, d), 7.08-7.19 (2H, m), 7.46-7.53 (1H, m), 8.28 (1H, d), 8.58 (1H, s). One proton not observed. | 548 |

TABLE S-continued

| Ex# | Structure | Name | $^1$H NMR | LCMS [M + H]+ |
|---|---|---|---|---|
| S8 | 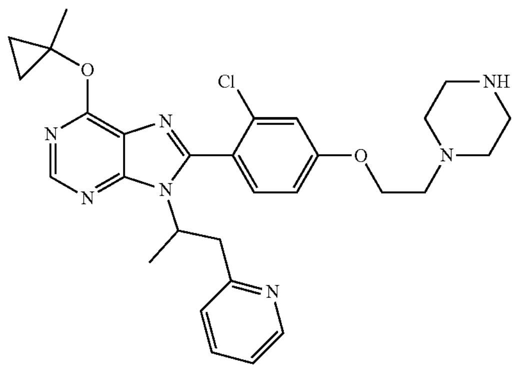 [SMILES: CC(Cc1ccccn1)n1c(-c2ccc(OCCN3CCNCC3)cc2Cl)nc2c(OC3(C)CC3)ncnc21] Isomer 1 | 8-(2-chloro-4-(2-(piperazin-1-yl)ethoxy)phenyl)-6-(1-methyl-cyclopropoxy)-9-(1-(pyridin-2-yl)propan-2-yl)-9H-purine (Isomer 1) | (400 MHz, DMSO-$d_6$, 80° C.): 0.80 (2H, t), 0.98 (2H, t), 1.68-1.72 (6H, m), 2.38-2.42 (4H, m), 2.65-2.72 (6H, m), 3.26 (1H, dd), 3.68 (1H, dd), 4.17 (2H, t), 4.48-4.59 (1H, m), 6.78 (2H, d), 6.92 (1H, dd), 7.09-7.14 (1H, m), 7.16 (1H, d), 7.46-7.52 (1H, m), 8.28 (1H, d), 8.58 (1H, s). One proton not observed. | 548 |

[S1] was obtained by nucleophilic displacement of 9-benzyl-8-(4-(3-bromopropoxy)-2-chlorophenyl)-6-(1-methylcyclopropoxy)-9H-purine with tert-butyl 3-oxopiperazine-1-carboxylate, followed by BOC deprotection as follows:

Sodium hydride (16 mg, 0.40 mmol) was added to tert-butyl 3-oxopiperazine-1-carboxylate (120 mg, 0.60 mmol) and KI (6.6 mg, 0.04 mmol) in DMF (1 mL) at 0° C. The resulting mixture was stirred at rt for 15 minutes. Then 9-benzyl-8-(4-(3-bromopropoxy)-2-chlorophenyl)-6-(1-methylcyclopropoxy)-9H-purine (105 mg, 0.20 mmol) in DMF (1 mL) was added to the mixture. The resulting mixture was stirred at rt for 1 hour. The reaction mixture was quenched with saturated aq. $NH_4Cl$ (15 mL) and extracted with EtOAc (3×20 mL). The organic layer was dried over $Na_2SO_4$, filtered and evaporated to afford crude tert-butyl 4-(3-(4-(9-benzyl-6-(1-methylcyclopropoxy)-9H-purin-8-yl)-3-chlorophenoxy)propyl)-3-oxopiperazine-1-carboxylate (0.2 g) as a yellow solid. The product was used in the next step directly without further purification.

HCl in dioxane (0.3 mL, 1.20 mmol, 4N) was added to tert-butyl 4-(3-(4-(9-benzyl-6-(1-methylcyclopropoxy)-9H-purin-8-yl)-3-chlorophenoxy)propyl)-3-oxopiperazine-1-carboxylate (180 mg, 0.28 mmol) in EtOAc (1 mL). The resulting mixture was stirred at rt for 2 hours. The solvent was removed under reduced pressure. The crude product was purified by preparative HPLC, Xselect CSH C18 OBD column, 30*150 mm, 5 μm, using decreasingly polar mixtures of water (0.1% formic acid) and MeCN as eluents. Fractions containing the desired compound were evaporated to dryness and purified again by preparative HPLC, YMC-Actus Triart C18 ExRS column, 30*150 mm, 5 μm, using decreasingly polar mixtures of water (containing 10 mmol/L $NH_4HCO_3$ and 0.1% aqueous ammonia) and MeCN as eluents. Fractions containing the desired compound were evaporated to dryness to afford 1-(3-(4-(9-benzyl-6-(1-methylcyclopropoxy)-9H-purin-8-yl)-3-chlorophenoxy)propyl)piperazin-2-one (13 mg, 8.5%) as a light yellow solid.

9-Benzyl-8-(4-(3-bromopropoxy)-2-chlorophenyl)-6-(1-methylcyclopropoxy)-9H-purine was synthesised as follows:

4-(9-Benzyl-6-(1-methylcyclopropoxy)-9H-purin-8-yl)-3-chlorophenol (300 mg, 0.74 mmol, Example 5), 1,3-dibromopropane (223 mg, 1.11 mmol) and $K_2CO_3$ (306 mg, 2.21 mmol) in MeCN (6 mL) were stirred at 80° C. for 3 hours. The reaction mixture was diluted with water (25 mL) and extracted with EtOAc (3×25 mL). The organic layer was dried over $Na_2SO_4$, filtered and evaporated to afford a yellow gum. The residue was purified by preparative silica chromatography (eluting with pentane:EtOAc=1:1), to afford 9-benzyl-8-(4-(3-bromopropoxy)-2-chlorophenyl)-6-(1-methylcyclopropoxy)-9H-purine (0.17 g, 44%) as a yellow solid. $^1$H NMR (300 MHz, DMSO-$d_6$): 0.84 (2H, t), 1.00 (2H, d), 1.72 (3H, s), 2.27 (2H, p), 3.67 (2H, t), 4.18 (2H, t), 5.28 (2H, s), 6.88 (2H, dt), 7.04 (1H, dt), 7.13-7.29 (4H, m), 7.41 (1H, dd), 8.61 (1H, s). m/z: ES+ [M+H]+ 527.

[S2] was obtained by nucleophilic displacement of 9-benzyl-8-(4-(3-bromopropoxy)-2-chlorophenyl)-6-(1-methylcyclopropoxy)-9H-purine with tert-butyl 2-oxopiperazine-1-carboxylate and BOC deprotection, using a similar procedure as Example S1, except that KI was omitted.

[S3] was obtained via BOC deprotection of tert-butyl 4-(2-(3-chloro-4-(9-((4-cyclopropylpyridin-2-yl)methyl)-6-(1-methylcyclopropoxy)-9H-purin-8-yl)phenoxy)ethyl)piperazine-1-carboxylate, using TFA.

The synthesis of tert-butyl 4-(2-(3-chloro-4-(9-((4-cyclopropylpyridin-2-yl)methyl)-6-(1-methylcyclopropoxy)-9H-purin-8-yl)phenoxy)ethyl)piperazine-1-carboxylate is described below: A solution of cyclopropylzinc bromide (1M, 1.4 mL, 1.4 mmol) was added to a solution of tert-butyl 4-(2-(3-chloro-4-(9-((4-chloropyridin-2-yl)methyl)-6-(1-methylcyclopropoxy)-9H-purin-8-yl)phenoxy)ethyl)piperazine-1-carboxylate (300 mg, 0.46 mmol, Example 10 intermediate) and tetrakis(triphenylphosphine)palladium (106 mg, 0.09 mmol) in THF (10 mL) at 0° C. over a period of 3 minutes under nitrogen. The resulting mixture was stirred at 60° C. for 16 hours. The reaction mixture was poured into saturated aq. $NH_4Cl$ (50 mL) and extracted with EtOAc (3×50 mL). The organic layers were dried over $Na_2SO_4$, filtered and evaporated to afford a brown solid. The crude product was purified by flash silica chromatography, elution gradient 0 to 100% EtOAc in petroleum ether. Pure fractions were evaporated to dryness to afford tert-butyl 4-(2-(3-chloro-4-(9-((4-cyclopropylpyridin-2-yl)methyl)-6-(1-methylcyclopropoxy)-9H-purin-8-yl)phenoxy)ethyl)piperazine-1-carboxylate (210 mg, 69%) as a brown solid. $^1$H NMR (400 MHz, DMSO-$d_6$): 0.66 (2H, t), 0.84 (2H, t), 0.95-1.05 (4H, m), 1.40 (9H, s), 1.74 (3H, s), 1.89-1.92 (1H, m), 2.38-2.46 (4H, m), 2.69-2.76 (2H, m), 3.33-3.45 (4H, m), 4.09-4.23 (2H, m), 5.26-5.42 (2H, m), 6.69-6.75 (1H, m), 6.84-6.91 (1H, m), 6.92-6.99 (1H, m), 7.24-7.33 (2H, m), 8.01-8.13 (1H, m), 8.57 (1H, s). m/z: ES+ [M+H]+ 660

[S4] obtained via a similar procedure to 8-(2-chloro-4-(2-(piperazin-1-yl)ethoxy)phenyl)-9-((4-cyclopropylpyridin-2-yl)methyl)-6-(1-methylcyclopropoxy)-9H-purine [Example S3], starting from tert-butyl 4-(2-(3-chloro-4-(9-((4-chloropyridin-2-yl)methyl)-6-(1-methylcyclopropoxy)-9H-purin-8-yl)phenoxy)ethyl)piperazine-1-carboxylate (300 mg, 0.46 mmol, Example 10 intermediate) and diethylzinc, followed by Boc deprotection with TFA.

[S5] Racemic 8-(2-chloro-4-(2-(piperazin-1-yl)ethoxy)phenyl)-9-(1-(4-chloropyridin-2-yl)ethyl)-6-(1-methylcyclopropoxy)-9H-purine was obtained via a similar procedure to 8-(2-chloro-4-(2-(piperazin-1-yl)ethoxy)phenyl)-6-(1-methylcyclopropoxy)-9-(2-(pyridin-4-yl)ethyl)-9H-purine [Example L1], starting from tert-butyl 4-(2-(3-chloro-4-(6-(1-methylcyclopropoxy)-9H-purin-8-yl)phenoxy)ethyl)piperazine-1-carboxylate and rac-1-(4-chloropyridin-2-yl)ethan-1-ol. Separation of enantiomers [Example S5] and [Example S6] was achieved by preparative chiral-HPLC on a CHIRALPAK IG-3, 4.6*50 mm, 3 μm column, eluting isocratically with 70% hexane in EtOH (modified with 0.1% DEA) as eluent.

[S7] Racemic 8-(2-chloro-4-(2-(piperazin-1-yl)ethoxy)phenyl)-6-(1-methylcyclopropoxy)-9-(1-(pyridin-2-yl)propan-2-yl)-9H-purine was obtained via a similar procedure to 9-benzyl-8-(2-chloro-4-(2-(4-methylpiperazin-1-yl)ethoxy)phenyl)-6-(1-methylcyclopropoxy)-9H-purine (Example 4), using tert-butyl 4-(2-(3-chloro-4-formylphenoxy)ethyl)piperazine-1-carboxylate and 6-(1-methylcyclopropoxy)-N4-(1-(pyridin-2-yl)propan-2-yl)pyrimidine-4,5-diamine, followed by BOC deprotection with HCl. Separation of enantiomers [Example S7] and [Example S8] was achieved by preparative HPLC (Column: CHIRALPAK IA-3, 4.6*50 mm, 3 μm), eluting isocratically with 80% hexane in EtOH (modified with 0.1% DEA) as eluent. 6-(1-Methylcyclopropoxy)-N4-(1-(pyridin-2-yl)propan-2-yl)pyrimidine-4,5-diamine was made in a similar method as N4-benzyl-6-(1-methylcyclopropoxy)pyrimidine-4,5-diamine (Example 4 intermediate), starting from 4,6-dichloro-5-nitropyrimidine and rac-1-(pyridin-2-yl)propan-2-amine. $^1$H NMR (300 MHz, DMSO-$d_6$): 0.64-0.69 (2H, m), 0.83 (2H, t), 1.11 (3H, d), 1.59 (3H, s), 2.80 (1H, dd), 3.08 (1H, dd), 4.05 (2H, s), 4.47-4.59 (1H, m), 6.01 (1H, d), 7.16-7.22 (1H, m), 7.27 (1H, d), 7.64-7.74 (2H, m), 8.46-8.5 (1H, m). m/z: ES+ [M+H]+ 300.

Example 28

Polθ Polymerase Domain Enzyme Inhibition

The following assay was used to identify compounds that inhibit Polθ polymerase domain. The ability of compounds to inhibit the isolated polymerase domain (I1780-V2590) of DNA polymerase theta (Polθ) was assessed in a PPiLight inorganic pyrophosphate assay (Lonza, product code LT07-610) with the luminescent end point detection of the formation of the product inorganic pyrophosphate (PPi). The PPiLight inorganic pyrophosphate assay provides a high-throughput screening method to monitoring polymerase activity by quantifying the amount of PPi released during the polymerisation reaction using luciferase.

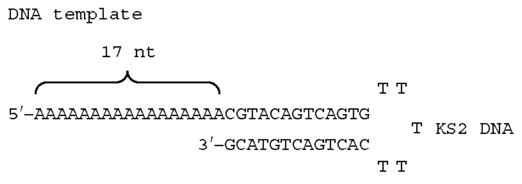

In the assay, Polθ interacts with the substrates (deoxy thymidine triphosphate (dTTP) (Sigma, product code T0251) and a DNA template with a 17-nucleotide overhang (Eurogentec, custom creates order), and PPi is formed due to the polymerase reaction. This free PPi interacts with AMP, to generate the ATP used in the luciferase reaction in the production of light. The test compound competitive binding inhibits the polymerase reaction, resulting in the loss of luminescence.

The assay was performed as follows with all reagent additions carried out using a CERTUS FLEX liquid dispenser workstation:

Test compound (15 nL) was acoustically dispensed into Greiner 1536 well white small volume medium bind assay plates.

1× assay screening buffer (50 mM Tris pH7.5, 5 mM $MgCl_2$, 0.01% v/v Pluronic F127, 2 mM DTT, 0.05 mg/ml BSA) is prepared dTTP/DNA (1.5 μL) was dispensed of into each of the wells followed by 1.5 μL of Polθ, the plates are covered and the reaction is allowed to progress for 20 minutes at room temperature.

To quench, TFA (0.5 μL) was dispensed into the wells, then 2.0 μL of PPiLight reagent was dispensed into each well and incubated at room temperature for 1 hour.

Plates were then read on an EnVision plate reader for luminescence 400-700 nm.

Compounds were dosed directly from a compound source plate containing serially diluted compounds (4 wells containing 10 mM, 0.1 mM, 1 μM and 10 nM respectively) to an assay microplate using a labcyte ECHO 550 liquid handler. The ECHO 550 using acoustic technology to transfer between microplates of DMSO compound solutions, with the system being able to be programmed to transfer small nL volumes of compounds from different source plate wells to give serial dilutions for the compounds to be tested and backfilled to normalise the DMSO concentration across the dilution range.

In total 15 nL of compound plus DMSO were added to each wells and compounds tested over 12 concentrations points. The final concentration range was 10, 3.33333, 1.66667, 0.3, 0.1, 0.025, 0.009, 0.003, 0.0015, 0.00027, 0.0001125 and 0.0000225 mM. The luminescence response measured on the EnVision for each compound was exported into Genedata to perform curve fitting analysis and expressed as an $IC_{50}$ value. This was determined by calculation of the compound required to give a 50% reduction in control compound binding to Polθ.

Results are shown in Tables 1A and 1B.

Example 29

Homologous Recombination Synthetic Lethal Inhibition of Proliferation.

This assay identifies anti-proliferative effects of POLQ compounds in the homologous recombination deficient colorectal cell line DLD-1 BRCA2−/− over 8-9 population doublings (7 days for DLD-1 and 12 days for DLD-1 BRCA2−/−). DLD1 BRCA2 wt are used as a control to detect cell toxic effects not specific to homologous recombination deficiency.

DLD-1 BRCA2−/− and DLD-1 cells were kept in continuous culture in Assay Medium (RPMI 1640 phenol red free (Sigma R7509) containing 1% GlutaMAX (Gibco 35050) and 10% Foetal Bovine Serum (Gibco 10270-106)). On the day of the assay cells in culture of ~80-90% confluent were used. Cell monolayers were washed with 10 mL PBS, then removed and added 2 mL TrypLE Express (Gibco 12604). The cells with TrypLE Express were incubated for 5 minutes in cell culture incubator and then the detached cells resuspend in 15 mL Assay Medium. Cells were counted using a ViCell and the cell images were monitored for clumps of cells, ideally they should be single or ≤3 cell clusters. The cells were diluted to 3,000 cells/mL of DLD-1 BRCA2−/− and 1,500 cells/mL of DLD-1 in Assay Medium and 100 μL added per well of transparent bottomed, black, tissue culture-treated 96-well plates (CoStar, No. 3904) Assay Ready Plates. The Assay Ready Plates contain a 10 point 10 μM to 0.51 nM dose range with three-fold dilutions in DMSO with a final volume of 100 nL. The plates were incubated at 37° C. with 5% $CO_2$ for 6 days. On day 6, 100 μL/well of Assay Medium was added to duplicate Assay Ready Plates. 90 μL of culture medium was removed from the cell plates and replenished with the Assay Media and compounds from the duplicate Assay Ready Plates using the Bravo. The plates were further incubated at 37° C. with 5% $CO_2$. On day 7 the plates containing DLD-1 and Cell Titre Glo 3D (Promega G9683) were equilibrated to room temperature, then 60 μL of Cell Titre Glo 3D was added per well and incubated on a shaking platform for 30 min. Plates were read on the Envision measuring luminescence for 1 second per well. On day 12 the plates containing DLD-1 BRCA2−/− cells and Cell Titre Glo 3D (Promega G9683) were equilibrated to room temperature, then 60 μL Cell Titre Glo 3D added per well and incubated on a shaking platform for 30 min. Plates were read on the Envision measuring luminescence for 1 second per well. The data was exported into a suitable software package (such as Genedata) to perform curve fitting analysis. Inhibition of cell proliferation was expressed as an $IC_{50}$ value and was determined by calculation of the concentration of compound that was required to give a 50% reduction of the average maximum Total Intensity signal.

Results are shown in Tables 1A and 1B.

TABLE 1A

| Assay Results | | | |
|---|---|---|---|
| Example # | POLQ Enz Lumin Primary CR GMean pIC50 | POLQ PD Prolif Lumin BRCA2 −/− mean pIC50 | POLQ PD Prolif Lumin DLD1 mean pIC50 |
| 1 | 8.6 | 6.2 | 5.2 |
| 10 | 8.2 | 6.7 | <5.0 |
| 11 | 8.6 | 6.6 | 6.1 |
| 12 | 8.4 | 6.9 | 5.7 |
| 13 | 8.5 | 6.6 | <5.0 |
| 14 | 8.6 | 6.6 | <5.0 |
| 15 | 8.7 | 6.6 | 5.2 |
| 16 | 8.6 | 6.4 | <5.0 |
| 17 | 8.2 | 7.1 | <5.0 |
| 18 | 8.5 | 6.4 | 5.3 |
| 19 | 8.5 | 6.3 | <5.0 |
| 2 | 8.7 | | |
| 20 | 8.3 | 6.4 | 5.1 |
| 21 | 8.5 | 6.4 | <5.0 |
| 22 | 8.1 | 6.2 | <5.0 |
| 23 | 7.9 | 6.2 | <5.0 |
| 24 | 8.3 | 6.8 | 5.4 |
| 25 | 8.2 | 7.0 | <5.0 |
| 26 | 8.4 | 6.3 | <5.0 |
| 3 | 8.7 | 6.0 | 5.8 |
| 4 | 8.5 | 7.2 | 5.4 |
| 5 | 8.7 | 7.3 | 5.5 |
| 6 | 8.5 | 6.8 | 5.4 |
| 7 | 8.4 | 6.1 | <5.0 |
| 8 | 8.1 | 6.0 | 5.5 |
| 9 | 8.1 | 6.2 | 5.6 |

TABLE 1A-continued

| Assay Results | | | |
|---|---|---|---|
| Example # | POLQ Enz Lumin Primary CR GMean pIC50 | POLQ PD Prolif Lumin BRCA2 −/− mean pIC50 | POLQ PD Prolif Lumin DLD1 mean pIC50 |
| A1 | 8.3 | | |
| A10 | 8.7 | 6.1 | 5.6 |
| A11 | 8.7 | 6.1 | 5.8 |
| A12 | 8.4 | 5.7 | <5.0 |
| A2 | 7.9 | | |
| A3 | 8.7 | 6.3 | 5.3 |
| A4 | 8.1 | | |
| A5 | 8.4 | | |
| A6 | 8.0 | | |
| A7 | 8.7 | 6.6 | 5.8 |
| A8 | 8.7 | 6.9 | 6.3 |
| A9 | 8.5 | 6.7 | 6.3 |
| B1 | 8.1 | 6.0 | 5.1 |
| B2 | 8.7 | 6.3 | 5.2 |
| B3 | 8.3 | | |
| B4 | 8.6 | 6.1 | <5.0 |
| B5 | 8.3 | | |
| C1 | 8.6 | 7.0 | 5.3 |
| C2 | 8.6 | 6.5 | <5.0 |
| C3 | 8.6 | 6.5 | 5.1 |
| C4 | 8.6 | 6.7 | 5.6 |
| C5 | 8.6 | 6.5 | <5.0 |
| C6 | 8.7 | 7.1 | <5.0 |
| C7 | 8.6 | 6.6 | 5.2 |
| C8 | 8.4 | 6.5 | 5.2 |
| C9 | 8.4 | 6.9 | <5.0 |
| D1 | 8.7 | 7.1 | 5.2 |
| D10 | 8.7 | 6.9 | 5.3 |
| D11 | 8.6 | 6.6 | 5.5 |
| D12 | 8.7 | 7.3 | 5.3 |
| D13 | 8.6 | 6.9 | 5.4 |
| D14 | 8.7 | 7.0 | 5.4 |
| D15 | 8.5 | 7.1 | <5.0 |
| D16 | 8.6 | 6.8 | 5.4 |
| D17 | 8.3 | 7.0 | 5.5 |
| D18 | 8.6 | 6.9 | 5.5 |
| D19 | 8.6 | 6.3 | 5.3 |
| D2 | 8.7 | 7.8 | 5.9 |
| D20 | 8.4 | 6.7 | <5.0 |
| D21 | 8.3 | 6.9 | <5.0 |
| D22 | 8.4 | 6.9 | <5.0 |
| D23 | 8.3 | 6.1 | 5.1 |
| D24 | 8.0 | <5.0 | <5.0 |
| D25 | 8.2 | 7.0 | 5.6 |
| D26 | 8.3 | 7.0 | |
| D27 | 8.1 | 7.0 | <5.0 |
| D28 | 8.4 | 7.1 | <5.0 |
| D29 | 8.0 | 5.3 | <5.0 |
| D3 | 8.2 | 7.2 | 5.7 |
| D30 | 8.4 | 5.9 | <5.0 |
| D31 | 8.1 | 6.7 | 5.1 |
| D32 | 8.6 | 6.9 | 5.2 |
| D33 | 8.6 | 7.2 | 5.5 |
| D34 | 8.6 | 6.7 | 5.4 |
| D35 | 8.4 | 6.3 | 5.4 |
| D4 | 8.3 | 7.3 | 6.2 |
| D5 | 8.7 | 7.2 | 5.6 |
| D6 | 8.5 | 6.2 | 5.3 |
| D7 | 8.6 | 6.9 | 5.2 |
| D8 | 8.7 | 7.3 | 5.2 |
| D9 | 8.6 | 6.8 | 5.7 |
| E1 | 8.6 | 7.5 | 5.6 |
| E2 | 8.6 | 7.6 | 5.5 |
| E3 | 8.6 | 7.3 | 5.4 |
| E4 | 8.3 | 6.7 | 5.1 |
| E5 | 8.4 | 6.3 | 5.1 |
| E6 | 7.9 | 5.8 | <5.0 |
| E7 | 8.3 | 5.9 | <5.0 |
| F1 | 8.4 | 6.4 | <5.0 |
| F2 | 8.6 | 6.5 | <5.0 |
| F3 | 8.6 | 6.6 | <5.0 |
| G1 | 8.6 | 6.3 | 5.2 |
| G10 | 8.3 | 6.2 | <5.0 |
| G11 | 8.4 | 5.9 | 5.2 |

TABLE 1A-continued

| Assay Results | | | |
|---|---|---|---|
| Example # | POLQ Enz Lumin Primary CR GMean pIC50 | POLQ PD Prolif Lumin BRCA2 −/− mean pIC50 | POLQ PD Prolif Lumin DLD1 mean pIC50 |
| G12 | 8.2 | 6.5 | <5.0 |
| G13 | 8.5 | 6.3 | <5.0 |
| G14 | 8.6 | 6.1 | 5.1 |
| G15 | 8.3 | 6.4 | <5.0 |
| G16 | 8.4 | 6.1 | <5.0 |
| G17 | 8.0 | | 5.1 |
| G2 | 8.5 | 6.0 | <5.0 |
| G3 | 8.7 | 6.0 | 5.2 |
| G4 | 8.7 | 5.9 | <5.0 |
| G5 | 8.6 | 6.4 | 5.1 |
| G6 | 8.6 | 6.3 | <5.0 |
| G7 | 8.5 | 6.4 | <5.0 |
| G8 | 8.6 | 5.7 | 5.1 |
| G9 | 8.4 | 6.1 | 5.8 |
| H1 | 8.6 | 6.7 | 5.4 |
| H10 | 8.4 | 6.1 | <5.0 |
| H11 | 8.3 | 6.0 | <5.0 |
| H12 | 8.2 | 6.0 | <5.0 |
| H13 | 8.6 | 7.0 | 5.5 |
| H14 | 8.6 | 6.9 | 5.2 |
| H15 | 8.6 | 7.1 | 5.8 |
| H16 | 8.6 | 7.3 | 5.3 |
| H17 | 8.7 | 7.2 | 5.7 |
| H18 | 8.6 | 6.5 | 5.5 |
| H19 | 8.6 | 7.2 | <5.0 |
| H2 | 8.7 | 6.9 | 5.5 |
| H20 | 8.6 | 7.0 | 5.4 |
| H21 | 8.6 | 7.2 | <5.0 |
| H22 | 8.7 | 6.9 | <5.0 |
| H23 | | 6.9 | 5.6 |
| H3 | 8.5 | 6.2 | 5.1 |
| H4 | 8.7 | 6.6 | <5.0 |
| H5 | 8.6 | 6.4 | 5.1 |
| H6 | 8.7 | 7.2 | 5.3 |
| H7 | 7.7 | 6.0 | 5.5 |
| H8 | 8.4 | 6.4 | <5.0 |
| H9 | 8.4 | 6.3 | 5.4 |
| J1 | 8.2 | 6.6 | 6.3 |
| J10 | 8.7 | 6.2 | 5.4 |
| J11 | 7.4 | | <5.0 |
| J12 | 8.7 | 6.3 | <5.0 |
| J13 | 8.5 | 7.3 | 5.5 |
| J2 | 8.1 | 6.1 | 5.4 |
| J3 | 8.2 | 6.3 | 5.5 |
| J4 | 8.3 | 7.3 | 5.4 |
| J5 | 8.2 | 6.0 | <5.0 |
| J6 | 8.7 | 6.2 | <5.0 |
| J7 | 8.3 | 6.5 | 5.1 |
| J8 | 7.0 | <5.0 | 5.1 |
| J9 | 8.0 | 5.6 | 5.3 |
| K1 | 7.3 | 6.0 | <5.0 |
| K10 | 8.1 | 5.8 | <5.0 |
| K11 | 7.7 | 5.7 | <5.0 |
| K12 | 7.2 | 5.8 | <5.0 |
| K2 | 7.9 | 5.7 | 5.2 |
| K3 | 8.3 | 5.9 | <5.0 |
| K4 | 8.2 | 5.4 | <5.0 |
| K5 | 7.7 | 5.6 | <5.0 |
| K6 | 7.9 | 5.4 | <5.0 |
| K7 | 8.1 | 5.9 | <5.0 |
| K8 | 8.7 | 6.4 | 5.1 |
| K9 | 8.4 | 5.8 | <5.0 |
| L1 | 7.6 | <5.0 | |
| L10 | 7.9 | 5.5 | <5.0 |
| L2 | 8.6 | 6.4 | <5.0 |
| L3 | 8.5 | 6.4 | <5.0 |
| L4 | 8.7 | 6.0 | <5.0 |
| L5 | 8.2 | 5.8 | <5.0 |
| L6 | 8.5 | 6.4 | <5.0 |
| L7 | 8.1 | 5.8 | <5.0 |
| L8 | 8.2 | 5.7 | <5.0 |
| L9 | 7.9 | 5.5 | <5.0 |

TABLE 1A-continued

| Assay Results | | | |
|---|---|---|---|
| Example # | POLQ Enz Lumin Primary CR GMean pIC50 | POLQ PD Prolif Lumin BRCA2 −/− mean pIC50 | POLQ PD Prolif Lumin DLD1 mean pIC50 |
| M1 | 8.2 | 6.3 | <5.0 |
| M2 | 8.4 | 6.5 | 5.3 |
| M3 | 8.2 | 6.3 | 5.1 |
| M4 | 8.3 | 6.2 | <5.0 |
| M5 | 8.4 | 7.0 | <5.0 |
| N1 | 7.7 | 6.7 | <5.0 |
| N2 | 8.3 | 6.6 | <5.0 |
| N3 | 7.5 | 6.1 | <5.0 |
| N4 | 8.5 | 6.7 | <5.0 |
| N5 | 7.8 | 7.0 | 5.4 |
| N6 | 8.2 | 7.0 | 5.4 |
| N7 | 8.4 | 6.2 | 5.2 |
| N8 | 8.5 | 6.6 | <5.0 |
| N9 | 8.0 | 5.9 | <5.0 |
| P1 | 8.5 | 5.9 | <5.0 |
| P2 | 8.2 | 6.1 | 5.6 |
| P3 | 8.2 | 5.7 | <5.0 |
| P4 | 8.2 | 6.5 | 5.9 |
| Q1 | 8.6 | 6.5 | <5.0 |
| Q2 | 8.6 | 6.4 | 5.7 |
| Q3 | 8.5 | 6.6 | 5.3 |
| Q4 | 8.7 | 6.7 | 5.7 |
| Q5 | 8.3 | 6.8 | 5.2 |
| R1 | 8.6 | 6.9 | <5.0 |
| R10 | 8.7 | 6.9 | 5.7 |
| R11 | 8.7 | 7.0 | 5.6 |
| R12 | 8.7 | 7.0 | 5.6 |
| R13 | 8.6 | 6.7 | |
| R14 | 8.7 | 6.8 | |
| R15 | 8.7 | 6.3 | 5.3 |
| R16 | 8.7 | 7.2 | |
| R17 | 8.7 | 7.0 | 6.0 |
| R18 | 8.7 | 6.9 | 5.2 |
| R19 | 8.7 | 6.7 | 5.4 |
| R2 | 8.5 | 6.9 | <5.0 |
| R20 | 8.7 | 6.7 | 5.6 |
| R21 | 8.7 | 6.5 | 5.8 |
| R22 | 8.6 | 6.6 | 5.5 |
| R23 | 8.6 | 7.2 | |
| R3 | 8.6 | 7.2 | 5.5 |
| R4 | 8.5 | 6.9 | 5.5 |
| R5 | 8.4 | 7.0 | 5.4 |
| R6 | 8.5 | 7.2 | 5.5 |
| R7 | 8.5 | 7.2 | 5.5 |
| R8 | 8.6 | 6.6 | 5.4 |
| R9 | 8.5 | 7.3 | 5.8 |
| S1 | 8.4 | 7.4 | <5.0 |
| S2 | 8.3 | 7.3 | 5.6 |
| S3 | 8.7 | 6.1 | <5.0 |
| S4 | 8.7 | 6.1 | <5.0 |
| S5 | 8.4 | 6.1 | <5.0 |
| S6 | 8.5 | 6.5 | <5.0 |
| S7 | 7.8 | 5.2 | |
| S8 | 6.5 | 5.0 | <5.0 |

Example 30

2-(3-Chloro-4-(6-(1-methylcyclopropoxy)-9-((4-methylpyridin-2-yl)methyl)-9H-purin-8-yl)phenyl)acetamide

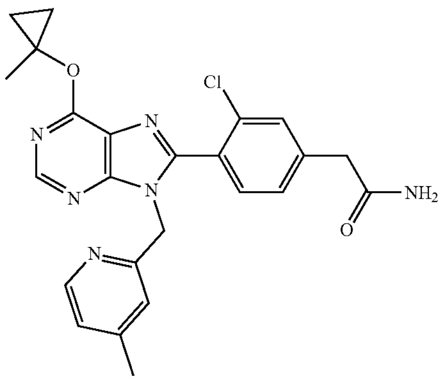 [SMILES: Cc1ccnc(Cn2c(-c3ccc(CC(N)=O)cc3Cl)nc3c(OC4(C)CC4)ncnc32)c1]

HATU (369 mg, 0.97 mmol) was added to 2-(3-chloro-4-(6-(1-methylcyclopropoxy)-9-((4-methylpyridin-2-yl)methyl)-9H-purin-8-yl)phenyl)acetic acid (150 mg, 0.32 mmol), ammonium chloride (86 mg, 1.62 mmol) and triethylamine (164 mg, 1.62 mmol) in DCM (15 mL) at room temperature. The resulting mixture was stirred at room temperature for 2 hours. The reaction mixture was diluted with DCM (100 mL), and washed sequentially with saturated brine (15 mL×3). The organic layer was dried over $Na_2SO_4$, filtered and evaporated to afford the crude product. The crude product was purified by preparative HPLC (Column: XBridge Prep OBD C18 Column, 30*150 mm, 5 μm) using decreasingly polar mixtures of water (containing 0.1% aq. $NH_3$ and 10 mmol/L $NH_4HCO_3$) and MeCN as eluents. Fractions containing the desired compound were evaporated to dryness to afford 2-(3-chloro-4-(6-(1-methylcyclopropoxy)-9-((4-methylpyridin-2-yl)methyl)-9H-purin-8-yl)phenyl)acetamide (35 mg, 24%) as a pale yellow solid. $^1H$ NMR (400 MHz, DMSO-$d_6$): 0.86 (2H, t), 1.04 (2H, t), 1.74 (3H, s), 2.19 (3H, s), 3.47 (2H, s), 5.35 (2H, s), 6.85 (1H, s), 7.03 (2H, d), 7.27 (1H, d), 7.42 (1H, d), 7.50 (1H, s), 7.56 (1H, s), 8.17 (1H, d), 8.58 (1H, s). m/z: ES+ [M+H]+ 463.

2-(3-Chloro-4-(6-(1-methylcyclopropoxy)-9-((4-methylpyridin-2-yl)methyl)-9H-purin-8-yl)phenyl)acetic acid used as a starting material was made as follows.

Ethyl 2-(3-chloro-4-(6-(1-methylcyclopropoxy)-9-((4-methylpyridin-2-yl)methyl)-9H-purin-8-yl)phenyl)acetate

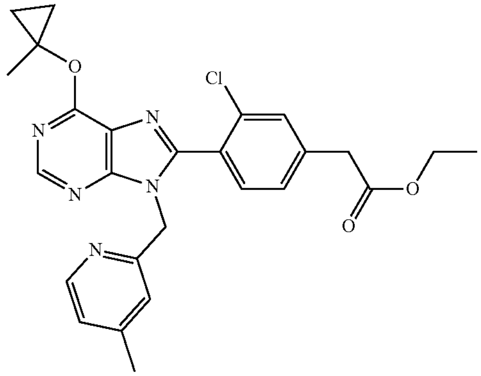 [SMILES: CCOC(=O)Cc1ccc(-c2nc3c(OC4(C)CC4)ncnc3n2Cc2cc(C)ccn2)c(Cl)c1]

$PdCl_2$(dppf) (0.842 g, 1.03 mmol) was added to 8-(4-bromo-2-chlorophenyl)-6-(1-methylcyclopropoxy)-9-((4-methylpyridin-2-yl)methyl)-9H-purine (5.00 g, 10.31 mmol, Example 25 intermediate), 4,4,4',4',5,5,5',5'-octamethyl-2,2'-bi(1,3,2-dioxaborolane) (3.93 g, 15.47 mmol) and potassium acetate (2.024 g, 20.63 mmol) in 1,4-dioxane (100 mL) at room temperature under nitrogen. The resulting solution was stirred at 100° C. for 2 hours. The reaction mixture was filtered through celite and evaporated to afford crude 8-(2-chloro-4-(4,4,5,5-tetramethyl-1,3,2-dioxaborolan-2-yl)phenyl)-6-(1-methylcyclopropoxy)-9-((4-methylpyridin-2-yl)methyl)-9H-purine. $Pd(PPh_3)_4$ (1.192 g, 1.03 mmol) was added to the above crude 8-(2-chloro-4-(4,4,5,5-tetramethyl-1,3,2-dioxaborolan-2-yl)phenyl)-6-(1-methylcyclopropoxy)-9-((4-methylpyridin-2-yl)methyl)-9H-purine, ethyl 2-bromoacetate (17.22 g, 103.14 mmol) and tripotassium phosphate (6.57 g, 30.94 mmol) in 1,4-dioxane:water (5:1, 120 mL) at room temperature under nitrogen. The resulting mixture was stirred at 100° C. for 4 hours. The reaction mixture was diluted with EtOAc (500 mL), and washed sequentially with saturated brine (100 mL×3). The organic layer was dried over $Na_2SO_4$, filtered and evaporated to afford the crude title product. The crude title product was purified by flash silica chromatography, elution gradient 40 to 100% EtOAc in petroleum ether and 0 to 20% MeOH in DCM. Pure fractions were evaporated to dryness to afford ethyl 2-(3-chloro-4-(6-(1-methylcyclopropoxy)-9-((4-methylpyridin-2-yl)methyl)-9H-purin-8-yl)phenyl)acetate (3.50 g, 69%) as a brown solid. $^1H$ NMR (400 MHz, DMSO-$d_6$): 0.85 (2H, t), 1.03 (2H, t), 1.21 (3H, t), 1.74 (3H, s), 2.18 (3H, s), 3.79 (2H, s), 4.05-4.17 (2H, m), 5.36 (2H, s), 6.85 (1H, s), 7.02 (1H, d), 7.30 (1H, dd), 7.44 (1H, d), 7.55 (1H, d), 8.17 (1H, d), 8.58 (1H, s). m/z: ES+ [M+H]+ 492.

2-(3-Chloro-4-(6-(1-methylcyclopropoxy)-9-((4-methylpyridin-2-yl)methyl)-9H-purin-8-yl)phenyl)acetic Acid

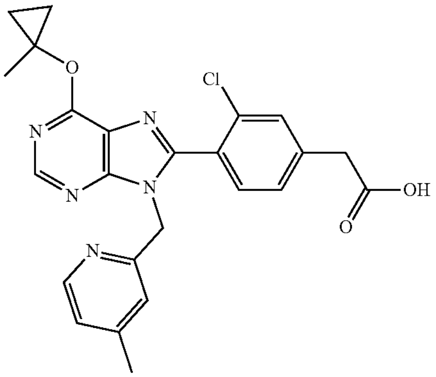 [SMILES: Cc1ccnc(Cn2c(-c3ccc(CC(=O)O)cc3Cl)nc3c(OC4(C)CC4)ncnc32)c1]

Sodium hydroxide (1.02 g, 25.4 mmol) in water was added to ethyl 2-(3-chloro-4-(6-(1-methylcyclopropoxy)-9-((4-methylpyridin-2-yl)methyl)-9H-purin-8-yl)phenyl)acetate (2.5 g, 5.08 mmol) in 1,4-dioxane (50 mL) and water (25 mL) at room temperature. The resulting solution was stirred at room temperature for 2 hours. The reaction mixture was acidified with 0.5M citric acid. The reaction mixture was diluted with EtOAc (200 mL), and washed sequentially with saturated brine (50 mL×3). The organic layer was dried over $Na_2SO_4$, filtered and evaporated to afford the crude product. The crude product was purified by flash silica chromatography, elution gradient 0 to 20% MeOH in DCM. Pure fractions were evaporated to dryness to afford 2-(3-chloro-4-(6-(1-methylcyclopropoxy)-9-((4-methylpyridin-2-yl)methyl)-9H-purin-8-yl)phenyl)acetic acid (2.20 g, 93%) as a pale yellow solid. $^1H$ NMR (300 MHz, DMSO-$d_6$): 0.83 (2H, t), 1.01 (2H, t), 1.73 (3H, s), 2.17 (3H, s), 3.68 (2H, s), 5.34 (2H, s), 6.82 (1H, s), 7.01 (1H, d), 7.28 (1H, dd), 7.41 (1H, d), 7.52 (1H, d), 8.15 (1H, d), 8.56 (1H, s), 12.53 (1H, s). m/z: ES+ [M+H]+ 464.

Example 31

(E)-3-(3-Chloro-4-(9-(3-chlorobenzyl)-6-(1-methylcyclopropoxy)-9H-purin-8-yl)phenyl)acrylic Acid

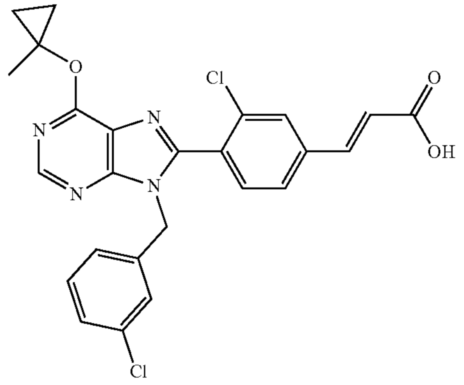 [SMILES: CC1(Oc2ncnc3c2nc(-c2ccc(/C=C/C(=O)O)cc2Cl)n3Cc2cccc(Cl)c2)CC1]

$Pd(PPh_3)_4$ (45.8 mg, 0.04 mmol) was added to 8-(4-bromo-2-chlorophenyl)-9-(3-chlorobenzyl)-6-(1-methylcyclopropoxy)-9H-purine (200 mg, 0.40 mmol), ethyl acrylate (79 mg, 0.79 mmol) and triethylamine (120 mg, 1.19 mmol) in DMF (3 mL) at 25° C. under nitrogen. The resulting mixture was stirred at 100° C. for 1 hour. The solvent was removed under reduced pressure. Sodium hydroxide (79 mg, 1.98 mmol) was added to the mixture in 1,4-dioxane (6 mL) and water (3 mL) at 25° C. under air. The resulting mixture was stirred at 25° C. for 1 hour. The reaction mixture was diluted with EtOAc (50 mL), and washed sequentially with water (15 mL×3). The organic layer was dried over $Na_2SO_4$, filtered and evaporated to afford the crude product. The crude product was purified by preparative HPLC (XBridge Prep C18 OBD column, 30*150 mm, 5 μm), using decreasingly polar mixtures of water (containing 0.1% aq. $NH_3$ and 10 mmol/L $NH_4HCO_3$) and MeCN as eluents. Fractions containing the desired compound were evaporated to dryness to afford (E)-3-(3-chloro-4-(9-(3-chlorobenzyl)-6-(1-methylcyclopropoxy)-9H-purin-8-yl)phenyl)acrylic acid (23 mg, 12%) as a white solid. $^1H$ NMR (400 MHz, DMSO-$d_6$): 0.85 (2H, t), 1.03 (2H, t), 1.73 (3H, s), 5.32 (2H, s), 6.67 (1H, d), 6.83 (1H, d), 6.93 (1H, s), 7.19-7.29 (2H, m), 7.43 (1H, d), 7.52 (1H, d), 7.71 (1H, d), 7.90 (1H, s), 8.64 (1H, s). One exchangeable proton not observed. m/z: ES+ [M+H]+ 495.

8-(4-Bromo-2-chlorophenyl)-9-(3-chlorobenzyl)-6-(1-methylcyclopropoxy)-9H-purine used as a starting material was made as follows.

8-(4-Bromo-2-chlorophenyl)-6-chloro-9-(3-chlorobenzyl)-9H-purine

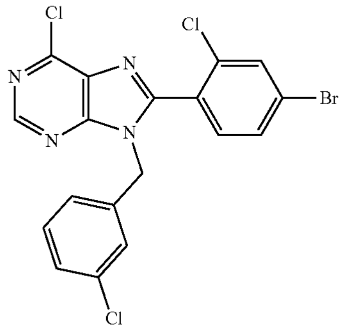 [SMILES: Clc1cccc(Cn2c(-c3ccc(Br)cc3Cl)nc3c(Cl)ncnc32)c1]

$Cs_2CO_3$ (19.89 g, 61.05 mmol) was added in one portion to 8-(4-bromo-2-chlorophenyl)-6-chloro-9H-purine (7 g, 20.35 mmol, Example 25 intermediate) and 1-chloro-3-(chloromethyl)benzene (4.92 g, 30.52 mmol) in DMF (140 mL) at room temperature. The resulting mixture was stirred at 80° C. for 3 hours. The reaction mixture was diluted with EtOAc (200 mL), and washed sequentially with water (75 mL×3). The organic layer was dried over $Na_2SO_4$, filtered and evaporated to afford crude product. The crude product was purified by flash silica chromatography, elution gradient 0 to 30% EtOAc in petroleum ether. Pure fractions were evaporated to dryness to afford 8-(4-bromo-2-chlorophenyl)-6-chloro-9-(3-chlorobenzyl)-9H-purine (5.00 g, 52%) as a yellow oil. $^1H$ NMR (300 MHz, DMSO-$d_6$): 5.40 (2H, s), 6.88-6.94 (1H, m), 7.02 (1H, t), 7.19-7.34 (2H, m), 7.59 (1H, d), 7.77 (1H, dd), 7.99 (1H, d), 8.91 (1H, s). m/z: ES+ [M+H]+ 469 ($^{35}Cl^{81}Br/^{37}Cl^{79}Br$ peak).

8-(4-Bromo-2-chlorophenyl)-9-(3-chlorobenzyl)-6-(1-methylcyclopropoxy)-9H-purine

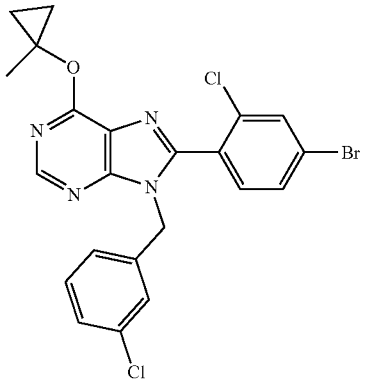 [SMILES: CC1(Oc2ncnc3c2nc(-c2ccc(Br)cc2Cl)n3Cc2cccc(Cl)c2)CC1]

NaH (0.768 g, 32.01 mmol) was added to 1-methylcyclopropan-1-ol (0.693 g, 9.60 mmol) and 8-(4-bromo-2-chlorophenyl)-6-chloro-9-(3-chlorobenzyl)-9H-purine (3 g, 6.40 mmol) in DMF (20 mL) at 0° C. under nitrogen for 10 minutes. The resulting mixture was stirred at room temperature for 50 minutes. The reaction mixture was poured into ice-water. The reaction mixture was diluted with EtOAc (75 mL), and washed sequentially with water (50 mL×3). The organic layer was dried over $Na_2SO_4$, filtered and evaporated to afford the crude product. The crude product was purified by flash silica chromatography, elution gradient 0 to 25% EtOAc in petroleum ether. Pure fractions were evaporated to dryness to afford 8-(4-bromo-2-chlorophenyl)-9-(3-chlorobenzyl)-6-(1-methylcyclopropoxy)-9H-purine (2.50 g, 77%) as a yellow solid. $^1$H NMR (300 MHz, DMSO-$d_6$): 0.86 (2H, t), 1.03 (2H, t), 1.74 (3H, s), 5.33 (2H, s), 6.84-6.89 (1H, m), 6.97 (1H, t), 7.22 (1H, d), 7.26-7.29 (1H, m), 7.52 (1H, d), 7.72 (1H, dd), 7.96 (1H, d), 8.66 (1H, s). m/z: ES+ [M+H]+ 505 ($^{35}$Cl$^{81}$Br/$^{37}$Cl$^{79}$Br peak).

Example 32

3-(3-Chloro-4-(9-(3-chlorobenzyl)-6-(1-methylcyclopropoxy)-9H-purin-8-yl)phenoxy)-2,2-dimethylpropanoic Acid

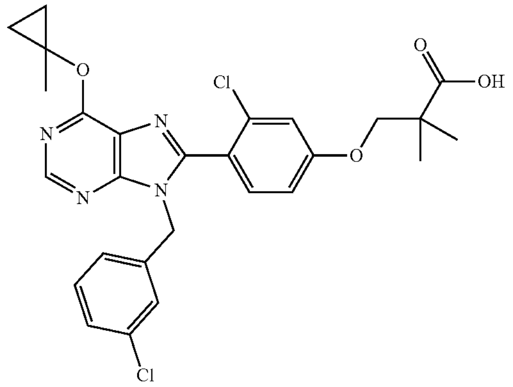 [SMILES: CC1(Oc2ncnc3c2nc(-c2ccc(OCC(C)(C)C(=O)O)cc2Cl)n3Cc2cccc(Cl)c2)CC1]

Sodium metaperiodate (487 mg, 2.28 mmol) was added slowly to 3-(3-chloro-4-(9-(3-chlorobenzyl)-6-(1-methylcyclopropoxy)-9H-purin-8-yl)phenoxy)-2,2-dimethylpropan-1-ol (120 mg, 0.23 mmol) and ruthenium(III) chloride (236 mg, 1.14 mmol) in MeCN/water/EtOAc (1:1.5:1, 3 mL) at 25° C. The resulting mixture was stirred at room temperature for 1 hour. The reaction mixture was diluted with EtOAc (50 mL), and washed sequentially with saturated $Na_2S_2O_3$ (10 mL×2), 0.1M aq. HCl (10 mL×2), and saturated brine (10 mL×2). The organic layer was dried over $Na_2SO_4$, filtered and evaporated to afford the crude product. The crude product was purified by flash C18-flash chromatography, elution: gradient 1 to 50% MeCN in water (containing 10 mmol/L $NH_4HCO_3$). Pure fractions were evaporated to dryness to afford 3-(3-chloro-4-(9-(3-chlorobenzyl)-6-(1-methylcyclopropoxy)-9H-purin-8-yl)phenoxy)-2,2-dimethylpropanoic acid (39.0 mg, 32%) as a white solid. $^1$H NMR (400 MHz, DMSO-$d_6$): 0.85 (2H, t), 1.02 (2H, t), 1.23 (6H, s), 1.73 (3H, s), 4.07 (2H, s), 5.30 (2H, s), 6.82-6.89 (1H, m), 6.97 (1H, t), 7.05 (1H, dd), 7.21-7.29 (3H, m), 7.43 (1H, d), 8.63 (1H, s). One exchangeable proton not observed. m/z: ES+ [M+H]+ 541.

3-(3-Chloro-4-(9-(3-chlorobenzyl)-6-(1-methylcyclopropoxy)-9H-purin-8-yl)phenoxy)-2,2-dimethylpropan-1-ol used as a starting material was made as follows.

3-Chloro-4-(9-(3-chlorobenzyl)-6-(1-methylcyclopropoxy)-9H-purin-8-yl)phenol

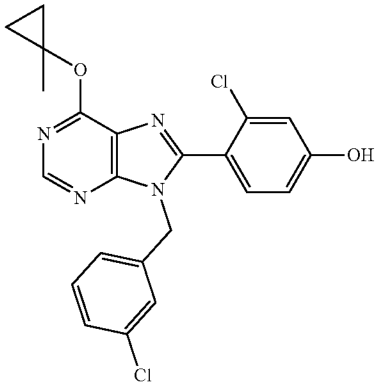 [SMILES: CC1(Oc2ncnc3c2nc(-c2ccc(O)cc2Cl)n3Cc2cccc(Cl)c2)CC1]

1,1'-Bis(diphenylphosphino)ferrocenedichloropalladium (II) dichloromethane adduct (0.437 g, 0.54 mmol) was added to 8-(4-bromo-2-chlorophenyl)-9-(3-chlorobenzyl)-6-(1-methylcyclopropoxy)-9H-purine (2.7 g, 5.35 mmol, Example 31 intermediate), 4,4,4',4',5,5,5',5'-octamethyl-2,2'-bi(1,3,2-dioxaborolane) (2.45 g, 9.64 mmol) and potassium acetate (1.58 g, 16.1 mmol) in 1,4-dioxane (30 mL) at room temperature under nitrogen. The resulting mixture was stirred at 100° C. for 1 hour. The solvent was removed under reduced pressure. The solid was diluted with THF/water (45 mL). Sodium perborate (2.19 g, 26.8 mmol) was added, and the mixture was stirred at room temperature for further 30 minutes. The reaction mixture was diluted with EtOAc (200 mL), and washed sequentially with water (75 mL×3). The organic layer was dried over $Na_2SO_4$, filtered and evaporated to afford the crude product. The crude product was purified by flash silica chromatography, elution gradient 0 to 30% EtOAc in petroleum ether. Pure fractions were evaporated to dryness to afford 3-chloro-4-(9-(3-chlorobenzyl)-6-(1-methylcyclopropoxy)-9H-purin-8-yl)phenol (1.30 g, 55%) as a white solid. $^1$H NMR (300 MHz, DMSO-$d_6$): 0.85 (2H, t), 1.02 (2H, t), 1.73 (3H, s), 5.29 (2H, s), 6.84 (1H, d), 6.87 (1H, d), 6.97 (1H, t), 6.99 (1H, d), 7.23 (1H, d), 7.27 (1H, dd), 7.32 (1H, d), 8.62 (1H, s), 10.51 (1H, s). m/z: ES+ [M+H]+ 441.

3-(3-Chloro-4-(9-(3-chlorobenzyl)-6-(1-methylcyclopropoxy)-9H-purin-8-yl)phenoxy)-2,2-dimethylpropan-1-ol

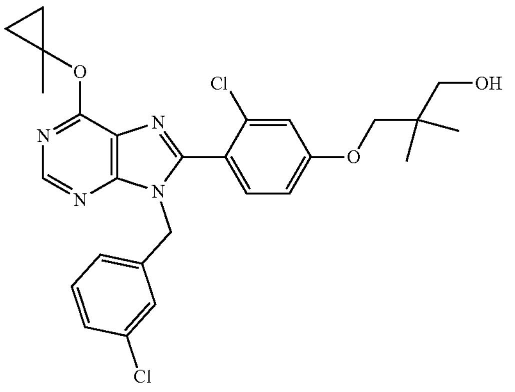 [SMILES: CC(C)(CO)COc1ccc(-c2nc3c(OC4(C)CC4)ncnc3n2Cc2cccc(Cl)c2)c(Cl)c1]

3-Bromo-2,2-dimethylpropan-1-ol (757 mg, 4.53 mmol) was added to 3-chloro-4-(9-(3-chlorobenzyl)-6-(1-methylcyclopropoxy)-9H-purin-8-yl)phenol (200 mg, 0.45 mmol) and $K_2CO_3$ (626 mg, 4.53 mmol) in MeCN (10 mL) at 0° C. The resulting mixture was stirred at 80° C. for 18 hours. The reaction mixture was diluted with EtOAc (100 mL), and washed sequentially with water (10 mL×3) and saturated brine (10 mL×3). The organic layer was dried over $Na_2SO_4$, filtered and evaporated to afford the crude product. The crude product was purified by flash silica chromatography, elution gradient 20 to 70% EtOAc in petroleum ether. Pure fractions were evaporated to dryness to afford 3-(3-chloro-4-(9-(3-chlorobenzyl)-6-(1-methylcyclopropoxy)-9H-purin-8-yl)phenoxy)-2,2-dimethylpropan-1-ol (132 mg, 55%) as a pale yellow solid. $^1$H NMR (300 MHz, DMSO-$d_6$): 0.84 (2H, t), 0.93 (6H, s), 1.00 (2H, t), 1.71 (3H, s), 3.79 (2H, s), 4.31 (2H, d), 4.62-4.67 (1H, m), 5.28 (2H, s), 6.84 (1H, d), 6.95 (1H, s), 7.02 (1H, dd), 7.18-7.3 (3H, m), 7.41 (1H, d), 8.61 (1H, s). m/z: ES+ [M+H]+ 527.

Example 33

2-(3-Chloro-4-(6-(1-methylcyclopropoxy)-9-((4-methylpyridin-2-yl)methyl)-9H-purin-8-yl)phenoxy)ethan-1-ol

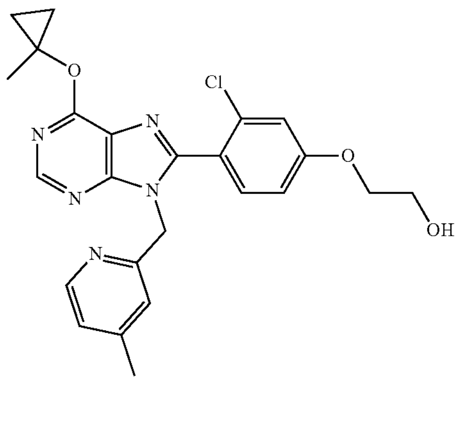

Tetrabutylammonium fluoride (270 mg, 1.03 mmol) was added dropwise to 8-(4-(2-((tert-butyldimethylsilyl)oxy)ethoxy)-2-chlorophenyl)-6-(1-methylcyclopropoxy)-9-((4-methylpyridin-2-yl)methyl)-9H-purine (120 mg, 0.21 mmol) in THF (3 mL) at room temperature over a period of 5 minutes under air. The resulting mixture was stirred at 60° C. for 3 hours. The solvent was removed under reduced pressure. The crude product was purified by preparative HPLC (XBridge Prep C18 OBD column, 30*150 mm, 5 μm), using decreasingly polar mixtures of water (containing 0.1% aq. $NH_3$ and 10 mmol/L $NH_4HCO_3$) and MeCN as eluents. Fractions containing the desired compound were evaporated to dryness to afford 2-(3-chloro-4-(6-(1-methylcyclopropoxy)-9-((4-methylpyridin-2-yl)methyl)-9H-purin-8-yl)phenoxy)ethan-1-ol (30.5 mg, 32%) as a white solid. $^1$H NMR (400 MHz, DMSO-$d_6$): 0.85 (2H, t), 1.02 (2H, t), 1.74 (3H, s), 2.19 (3H, s), 3.67-3.76 (2H, m), 4.07 (2H, t), 4.93 (1H, t), 5.35 (2H, s), 6.86 (1H, s), 6.96 (1H, dd), 7.04 (1H, d), 7.18 (1H, d), 7.37 (1H, d), 8.18 (1H, d), 8.57 (1H, s). m/z: ES+ [M+H]+ 466.

8-(4-(2-((Tert-butyldimethylsilyl)oxy) ethoxy)-2-chlorophenyl)-6-(1-methylcyclopropoxy)-9-((4-methylpyridin-2-yl)methyl)-9H-purine used as a starting material was made as follows.

8-(4-(2-((Tert-butyldimethylsilyl)oxy) ethoxy)-2-chlorophenyl)-6-(1-methylcyclopropoxy)-9-((4-methylpyridin-2-yl)methyl)-9H-purine

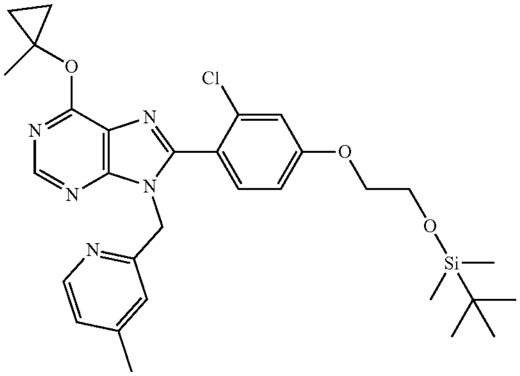 [SMILES: Cc1ccnc(Cn2c(-c3ccc(OCCO[Si](C)(C)C(C)(C)C)cc3Cl)nc3c(OC4(C)CC4)ncnc32)c1]

(2-Bromoethoxy)(tert-butyl)dimethylsilane (136 mg, 0.57 mmol) was added portionwise to $K_2CO_3$ (98 mg, 0.71 mmol) and 3-chloro-4-(6-(1-methylcyclopropoxy)-9-((4-methylpyridin-2-yl)methyl)-9H-purin-8-yl)phenol (200 mg, 0.47 mmol, Example 25 intermediate) in MeCN (5 mL) at room temperature over a period of 5 minutes under air. The resulting mixture was stirred at 60° C. for 8 hours. The reaction mixture was evaporated to dryness, redissolved in EtOAc (100 mL), and washed sequentially with water (125 mL×2) and saturated brine (100 mL×2). The organic layer was dried over $Na_2SO_4$, filtered and evaporated to afford the crude product. The crude product was purified by flash silica chromatography, elution gradient 0 to 10% MeOH in DCM. Pure fractions were evaporated to dryness to afford 8-(4-(2-((tert-butyldimethylsilyl)oxy) ethoxy)-2-chlorophenyl)-6-(1-methylcyclopropoxy)-9-((4-methylpyridin-2-yl)methyl)-9H-purine (150 mg, 54%) as a brown solid. $^1$H NMR (300 MHz, $CDCl_3$): 0.12 (6H, s), 0.85 (2H, t), 0.93 (9H, s), 1.18 (2H, t), 1.83 (3H, s), 2.25 (3H, s), 3.99 (2H, t), 4.08 (2H, t), 5.50 (2H, s), 6.70 (1H, s), 6.81 (1H, dd), 6.99 (1H, d), 7.03 (1H, d), 7.28 (1H, s), 8.29 (1H, d), 8.66 (1H, s). m/z: ES+ [M+H]+ 580.

Example 34

4-(3-Chloro-4-(9-(3-chlorobenzyl)-6-(1-methylcyclopropoxy)-9H-purin-8-yl)phenoxy)-2-methylbutanoic Acid (Isomer 1)

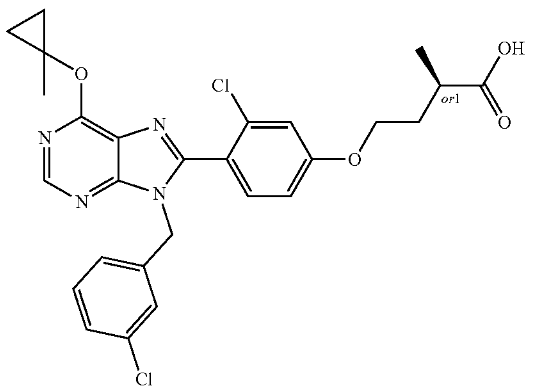 [SMILES: C[C@H](CCOc1ccc(-c2nc3c(OC4(C)CC4)ncnc3n2Cc2cccc(Cl)c2)c(Cl)c1)C(=O)O]

Isomer 1 (Unknown Absolute Stereochemistry)

The compound was obtained by separation of enantiomers from racemic 4-(3-chloro-4-(9-(3-chlorobenzyl)-6-(1-methylcyclopropoxy)-9H-purin-8-yl)phenoxy)-2-methylbutanoic acid by preparative chiral HPLC (CHIRALPAK AD-H column; Mobile Phase A: hexane (0.1% formic acid), Mobile Phase B: IPA; Flow rate: 20 mL/min; isocratic conditions: 20% B in A. The fractions containing the desired compound (eluting first, retention time=19.78 minutes) were evaporated to dryness to afford 4-(3-chloro-4-(9-(3-chlorobenzyl)-6-(1-methylcyclopropoxy)-9H-purin-8-yl)phenoxy)-2-methylbutanoic acid (Isomer 1) (26.0 mg) as a white solid. $^1$H NMR (400 MHz, DMSO-$d_6$): 0.86 (2H, t), 1.02 (2H, t), 1.16 (3H, d), 1.74 (3H, s), 1.82 (1H, d), 2.04-2.14 (1H, m), 2.54-2.61 (1H, m), 4.11 (2H, t), 5.29 (2H, s), 6.85 (1H, d), 6.94-6.96 (1H, m), 7.04 (1H, dd), 7.21-7.26 (2H, m), 7.27-7.3 (1H, m), 7.42 (1H, d), 8.63 (1H, s). One exchangable proton not observed. m/z: ES+ [M+H]+ 541. Chiral analysis was measured via chiral HPLC using a ChiralPak AD-H, 250×4.6 mm, 5 μm column, mobile phase: 40:60:0.1 heptane:IPA:formic acid (isocratic), flow rate: 1 mL/min, UV wavelength: 254 nm, run time: 16 minutes, retention time=8.7 minutes.

Racemic 4-(3-chloro-4-(9-(3-chlorobenzyl)-6-(1-methylcyclopropoxy)-9H-purin-8-yl)phenoxy)-2-methylbutanoic acid used as a starting material was made as follows.

Methyl 4-iodo-2-methylbutanoate

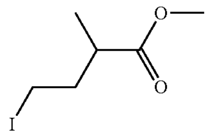

Sodium iodide (80 g, 531 mmol) was added to methyl 4-chloro-2-methylbutanoate (4 g, 26.6 mmol) in acetone (80 mL) at 25° C. The resulting mixture was stirred at 60° C. for 18 hours. The reaction mixture was diluted with EtOAc (100 mL), and washed sequentially with water (50 mL×3). The organic layer was dried over $Na_2SO_4$, filtered and evaporated to afford crude product. Pure fractions were evaporated to dryness to afford methyl 4-iodo-2-methylbutanoate (4.50 g, 70%) as a yellow liquid. $^1$H NMR (400 MHz, DMSO-$d_6$): 1.10 (3H, d), 1.8-1.91 (1H, m), 2.04-2.16 (1H, m), 2.53-2.58 (1H, m), 3.25 (2H, t), 3.62 (3H, s). m/z: ES+ [M+H]+ 243.

Methyl 4-(3-chloro-4-(9-(3-chlorobenzyl)-6-(1-methylcyclopropoxy)-9H-purin-8-yl)phenoxy)-2-methylbutanoate

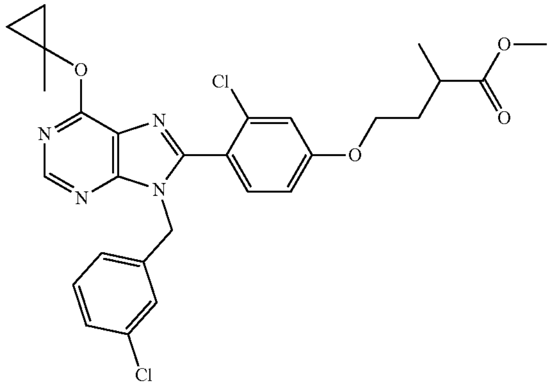 [SMILES: COC(=O)C(C)CCOc1ccc(-c2nc3c(OC4(C)CC4)ncnc3n2Cc2cccc(Cl)c2)c(Cl)c1]

Methyl 4-iodo-2-methylbutanoate (2.88 g, 11.9 mmol) was added to 3-chloro-4-(9-(3-chlorobenzyl)-6-(1-methylcyclopropoxy)-9H-purin-8-yl)phenol (350 mg, 0.79 mmol, Example 32 intermediate) and $K_2CO_3$ (1096 mg, 7.93 mmol) in MeCN (6 mL) at 25° C. under air. The resulting mixture was stirred at 60° C. for 45 hours. The reaction mixture was diluted with EtOAc (75 mL), and washed sequentially with water (25 mL×3). The organic layer was dried over $Na_2SO_4$, filtered and evaporated to afford the crude product. The crude product was purified by flash silica chromatography, elution gradient 0 to 40% EtOAc in petroleum ether. Pure fractions were evaporated to dryness to afford methyl 4-(3-chloro-4-(9-(3-chlorobenzyl)-6-(1-methylcyclopropoxy)-9H-purin-8-yl)phenoxy)-2-methylbutanoate (250 mg, 57%) as a white solid. $^1$H NMR (300 MHz, DMSO-$d_6$): 0.85 (2H, t), 1.01 (2H, t), 1.17 (3H, d), 1.73 (3H, s), 1.81-1.9 (1H, m), 2.03-2.14 (1H, m), 2.63-2.74 (1H, m), 3.62 (3H, s), 4.11 (2H, t), 5.29 (2H, s), 6.82-6.87 (1H, m), 6.92-6.96 (1H, m), 7.02 (1H, dd), 7.19-7.31 (3H, m), 7.42 (1H, d), 8.63 (1H, s). m/z: ES+ [M+H]+ 555.

4-(3-Chloro-4-(9-(3-chlorobenzyl)-6-(1-methylcyclopropoxy)-9H-purin-8-yl)phenoxy)-2-methylbutanoic Acid (Racemic)

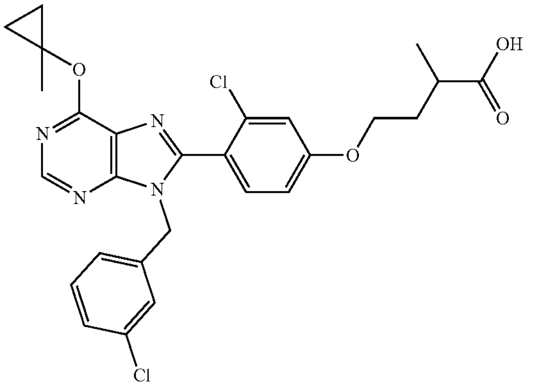 [SMILES: CC(CCOc1ccc(-c2nc3c(OC4(C)CC4)ncnc3n2Cc2cccc(Cl)c2)c(Cl)c1)C(=O)O]

NaOH (115 mg, 2.88 mmol) was added to methyl 4-(3-chloro-4-(9-(3-chlorobenzyl)-6-(1-methylcyclopropoxy)-9H-purin-8-yl)phenoxy)-2-methylbutanoate (80 mg, 0.14 mmol) in water (1 mL) and 1,4-dioxane (1 mL) at 25° C. The resulting mixture was stirred at 25° C. for 2 hours. The reaction mixture was diluted with EtOAc (20 mL), and washed sequentially with water (20 mL×3). The organic layer was dried over $Na_2SO_4$, filtered and evaporated to afford the crude product. The crude product was purified by preparative HPLC (XBridge Prep OBD C18 column, 30*150 mm, 5 μm), using decreasingly polar mixtures of water (containing 10 mmol/L $NH_4HCO_3$+0.1% $NH_3 \cdot H_2O$) and MeCN as eluents. Fractions containing the desired compound were evaporated to dryness to afford racemic 4-(3-chloro-4-(9-(3-chlorobenzyl)-6-(1-methylcyclopropoxy)-9H-purin-8-yl)phenoxy)-2-methylbutanoic acid (60.0 mg, 77%) as a white solid. $^1H$ NMR (400 MHz, DMSO-$d_6$): 0.85 (2H, t), 1.03 (2H, t), 1.15 (3H, d), 1.73 (3H, s), 1.77-1.84 (1H, m), 2.04-2.11 (1H, m), 2.54-2.6 (1H, m), 4.11 (2H, t), 5.29 (2H, s), 6.83-6.86 (1H, m), 6.94-6.96 (1H, m), 7.04 (1H, dd), 7.21-7.3 (3H, m), 7.42 (1H, d), 8.63 (1H, s). One exchangeable proton not observed. m/z: ES+ [M+H]+ 541.

Example 35

4-(3-Chloro-4-(9-(3-chlorobenzyl)-6-(1-methylcyclopropoxy)-9H-purin-8-yl)phenoxy)-2-methylbutanoic Acid (Isomer 2)

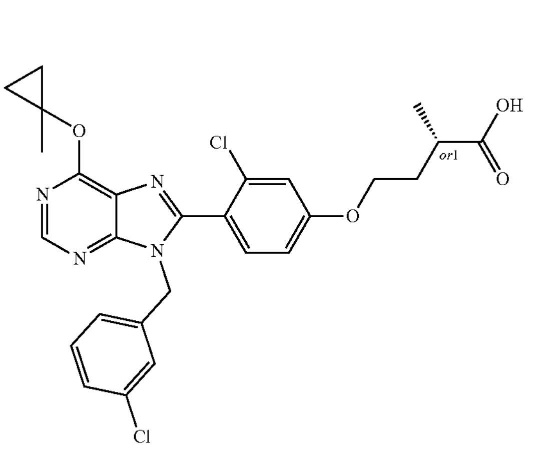 [SMILES: C[C@@H](CCOc1ccc(-c2nc3c(OC4(C)CC4)ncnc3n2Cc2cccc(Cl)c2)c(Cl)c1)C(=O)O]

Isomer 2 (Unknown Absolute Stereochemistry)

The compound was obtained by separation of enantiomers from racemic 4-(3-chloro-4-(9-(3-chlorobenzyl)-6-(1-methylcyclopropoxy)-9H-purin-8-yl)phenoxy)-2-methylbutanoic acid (see Example 34 for separation conditions). The fractions containing the desired compound (eluting second, retention time=23.69 minutes) were evaporated to dryness to afford 4-(3-chloro-4-(9-(3-chlorobenzyl)-6-(1-methylcyclopropoxy)-9H-purin-8-yl)phenoxy)-2-methylbutanoic acid (Isomer 2) (22 mg, 37%) as a white solid. $^1H$ NMR (400 MHz, DMSO-$d_6$): 0.86 (2H, t), 1.02 (2H, t), 1.15 (3H, d), 1.73 (3H, s), 1.78-1.84 (1H, m), 2.02-2.13 (1H, m), 2.54-2.61 (1H, m), 4.11 (2H, t), 5.29 (2H, s), 6.85 (1H, d), 6.95 (1H, t), 7.04 (1H, dd), 7.22-7.26 (2H, m), 7.27-7.3 (1H, m), 7.42 (1H, d), 8.63 (1H, s). One exchangeable proton not observed. m/z: ES+ [M+H]+ 541. Chiral analysis was measured via chiral HPLC using a ChiralPak AD-H, 250×4.6 mm, 5 um column, mobile phase: 40:60:0.1 heptane:IPA: formic acid (isocratic), flow rate: 1 mL/min, UV wavelength: 254 nm, run time: 16 minutes, retention time=11.8 minutes.

Example 36

(S)-1-(3-Chloro-4-(6-(1-methylcyclopropoxy)-9-((4-methylpyridin-2-yl)methyl)-9H-purin-8-yl)phenoxy) propan-2-ol

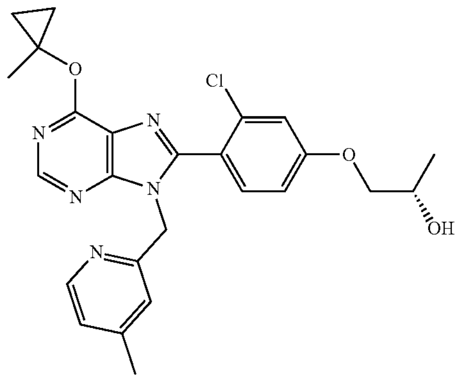 [SMILES: Cc1ccnc(Cn2c(-c3ccc(OC[C@H](C)O)cc3Cl)nc3c(OC4(C)CC4)ncnc32)c1]

Triethylamine (36.0 mg, 0.36 mmol) was added to 3-chloro-4-(6-(1-methylcyclopropoxy)-9-((4-methylpyridin-2-yl)methyl)-9H-purin-8-yl)phenol (50 mg, 0.12 mmol, Example 25 intermediate) and (S)-2-methyloxirane (68.8 mg, 1.19 mmol) in NMP (1.5 mL) at 25° C. under air. The resulting mixture was stirred at 120° C. for 2 hours. The solvent was removed under reduced pressure. The crude product was purified by preparative HPLC (XBridge Prep C18 OBD column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford(S)-1-(3-chloro-4-(6-(1-methylcyclopropoxy)-9-((4-methylpyridin-2-yl)methyl)-9H-purin-8-yl) phenoxy)propan-2-ol (9.6 mg, 17%) as a pink solid. $^1H$ NMR (400 MHz, DMSO-$d_6$): 0.86 (2H, t), 1.02 (2H, t), 1.1-1.27 (3H, m), 1.74 (3H, s), 2.19 (3H, s), 3.88 (2H, d), 3.91-4 (1H, m), 4.92 (1H, d), 5.34 (2H, s), 6.85 (1H, s), 6.95 (1H, dd), 7.03 (1H, d), 7.18 (1H, d), 7.36 (1H, d), 8.17 (1H, d), 8.56 (1H, s). m/z: ES+ [M+H]+ 480. Chiral analysis was measured via chiral SFC, using a YMC SA 3.0×150 mm 3.0

μm column, mobile phase: A=scCO2, B IPA+0.1% DEA. Isocratic 20% B, flow rate: 2.0 ml/min, BPR: 120 bar, Temperature: 40 deg C., Instrument: Waters UPC2 with MS/DAD detector, Sample Preparation: approx. 1 mg/ml in MeCN (100%), retention time=3.72 minutes.

Example 37

(R)-1-(3-Chloro-4-(6-(1-methylcyclopropoxy)-9-((4-methylpyridin-2-yl)methyl)-9H-purin-8-yl)phenoxy)propan-2-ol

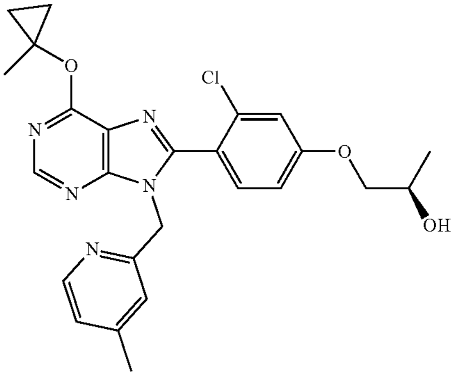 [SMILES: Cc1ccnc(Cn2c(-c3ccc(OC[C@@H](C)O)cc3Cl)nc3c(OC4(C)CC4)ncnc32)c1]

Triethylamine (36.0 mg, 0.36 mmol) was added to 3-chloro-4-(6-(1-methylcyclopropoxy)-9-((4-methylpyridin-2-yl)methyl)-9H-purin-8-yl)phenol (50 mg, 0.12 mmol, Example 25 intermediate) and (R)-2-methyloxirane (34.4 mg, 0.59 mmol) in NMP (2 mL) at 25° C. under air. The resulting mixture was stirred at 120° C. for 16 hours. The solvent was removed under reduced pressure. The crude product was purified by preparative HPLC (XBridge Prep C18 OBD column, 30*150 mm, 5 μm), using decreasingly polar mixtures of water (containing 10 mmol/L $NH_4HCO_3$ and 0.1% aqueous ammonia) and MeCN as eluents. Fractions containing the desired compound were evaporated to dryness to afford (R)-1-(3-chloro-4-(6-(1-methylcyclopropoxy)-9-((4-methylpyridin-2-yl)methyl)-9H-purin-8-yl)phenoxy)propan-2-ol (7.3 mg, 13%) as a pink solid. $^1$H NMR (400 MHz, DMSO-$d_6$): 0.86 (2H, t), 1.02 (2H, t), 1.1-1.26 (3H, m), 1.74 (3H, s), 2.19 (3H, s), 3.88 (2H, d), 3.92-4.02 (1H, m), 4.92 (1H, d), 5.34 (2H, s), 6.86 (1H, s), 6.95 (1H, dd), 7.03 (1H, d), 7.18 (1H, d), 7.35 (1H, t), 8.17 (1H, d), 8.56 (1H, s). m/z: ES+ [M+H]+ 480. Chiral analysis was measured using the same conditions as described in Example 36, retention time=4.09 minutes.

Example 38

2-(3-Chloro-4-(9-((4-chloropyridin-2-yl)methyl)-6-(1-methylcyclopropoxy)-9H-purin-8-yl)phenyl)acetamide

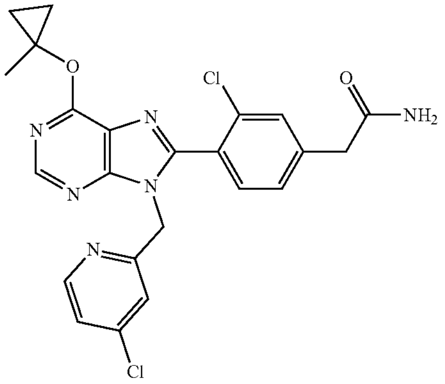 [SMILES: CC1(Oc2ncnc3c2nc(-c2ccc(CC(N)=O)cc2Cl)n3Cc2cc(Cl)ccn2)CC1]

To a solution of 2-(3-chloro-4-(6-(1-methylcyclopropoxy)-9H-purin-8-yl)phenyl)acetamide (22 mg, 0.06 mmol) and 4-chloro-2-(chloromethyl)pyridine hydrochloride (19 mg, 0.10 mmol) in DMF (0.620 mL) was added cesium carbonate (61.3 mg, 0.19 mmol). The reaction was stirred at 60° C. for 1 hour. The reaction mixture was filtered and concentrated under reduced pressure to give the crude product. The crude product was purified by preparative HPLC (Waters CSH C18 OBD column, 5μ silica, 30 mm diameter, 100 mm length), using decreasingly polar mixtures of water (containing 1% by volume of $NH_4OH$ (28-30% in $H_2O$)) and MeCN as eluents. Fractions containing the desired compound were evaporated to dryness to afford 2-(3-chloro-4-(9-((4-chloropyridin-2-yl)methyl)-6-(1-methylcyclopropoxy)-9H-purin-8-yl)phenyl)acetamide (8.7 mg, 29%) as a solid. $^1$H NMR (500 MHz, DMSO-$d_6$): 0.8-0.88 (2H, m), 1.01-1.06 (2H, m), 1.74 (3H, s), 3.47 (2H, s), 5.41 (2H, s), 6.99 (1H, s), 7.28 (1H, s), 7.30 (1H, s), 7.37 (1H, dd), 7.43 (1H, d), 7.51 (1H, d), 7.54 (1H, s), 8.30 (1H, d), 8.57 (1H, s). m/z: ES+ [M+H]+ 483.

2-(3-Chloro-4-(6-(1-methylcyclopropoxy)-9H-purin-8-yl)phenyl)acetamide used as a starting material was made as follows.

Methyl 2-(3-chloro-4-(6-(1-methylcyclopropoxy)-9H-purin-8-yl)phenyl)acetate

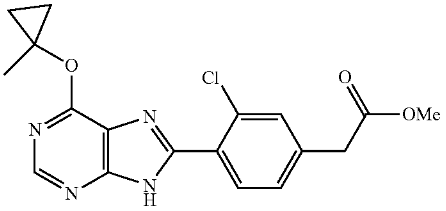 [SMILES: COC(=O)Cc1ccc(-c2nc3c(OC4(C)CC4)ncnc3[nH]2)c(Cl)c1]

8-Bromo-6-(1-methylcyclopropoxy)-9H-purine. HBr salt (443 mg, 1.65 mmol, Example 23 intermediate), methyl 2-(3-chloro-4-(4,4,5,5-tetramethyl-1,3,2-dioxaborolan-2-yl)phenyl)acetate (782 mg, 2.52 mmol), potassium phosphate (1.08 g, 5.09 mmol) and $PdCl_2$(dppf) (138 mg, 0.17 mmol)

were added to a microwave vial under nitrogen atmosphere. A degassed mixture of dioxane (9.6 mL) and water (1.4 mL) was added to the vial and the resulting mixture was heated to 110° C. for 4 hours. The reaction mixture was then heated to 110° C. in the microwave for a further 4 hours. The reaction mixture was then charged with additional $PdCl_2$ (dppf) (138 mg, 0.17 mmol) and heated to 110° C. in the microwave for a further hour. The crude product was purified by flash silica chromatography, elution gradient 0 to 50% 3:1 EtOAc/EtOH in heptane. Pure fractions were evaporated to dryness to afford methyl 2-(3-chloro-4-(6-(1-methylcyclopropoxy)-9H-purin-8-yl)phenyl)acetate (47 mg, 8%) as a yellow film. m/z: ES+ [M+H]+ 373.

2-(3-Chloro-4-(6-(1-methylcyclopropoxy)-9H-purin-8-yl)phenyl)acetamide

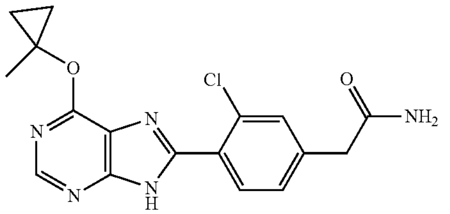 [SMILES: CC1(Oc2ncnc3[nH]c(-c4ccc(CC(N)=O)cc4Cl)nc23)CC1]

Methyl 2-(3-chloro-4-(6-(1-methylcyclopropoxy)-9H-purin-8-yl)phenyl)acetate (47 mg, 0.13 mmol) was stirred at room temperature in ammonia (7 M in MeOH, 0.5 mL, 3.50 mmol) for 70 hours. The reaction was then placed in the microwave for 16 hours at 100° C. The reaction mixture was evaporated to dryness in vacuo and was redissolved up in ammonium hydroxide (28%-33% aqueous, 0.5 mL, 0.13 mmol) and methanol (0.5 mL) and was stirred for 3 hours. The reaction mixture was evaporated to dryness to afford the crude product. The crude product was purified by preparative HPLC (Waters XSelect CSH C18 ODB column, 5μ silica, 30 mm diameter, 100 mm length), using decreasingly polar mixtures of water (containing 0.1% formic acid) and MeCN as eluents. Fractions containing the desired compound were evaporated to dryness to afford 2-(3-chloro-4-(6-(1-methylcyclopropoxy)-9H-purin-8-yl)phenyl)acetamide (22 mg, 50%) as a yellow dry film. m/z: ES+ [M+H]+ 358.

Example 39

1-(3-(3-Chloro-4-(6-(1-methylcyclopropoxy)-9-((4-methylpyridin-2-yl)methyl)-9H-purin-8-yl)phenoxy)azetidin-1-yl)-2-hydroxyethan-1-one

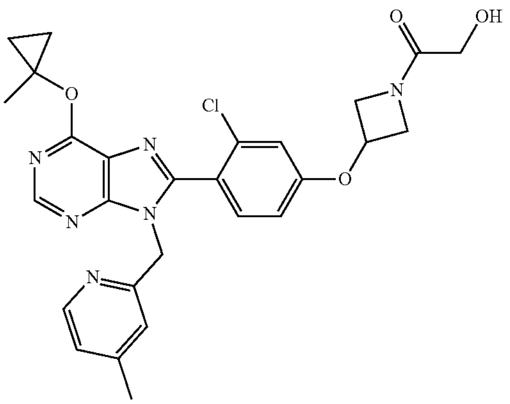 [SMILES: Cc1ccnc(Cn2c(-c3ccc(OC4CN(C(=O)CO)C4)cc3Cl)nc3c(OC4(C)CC4)ncnc32)c1]

Lithium hydroxide (9.96 mg, 0.42 mmol) was added to 2-(3-(3-chloro-4-(6-(1-methylcyclopropoxy)-9-((4-methylpyridin-2-yl)methyl)-9H-purin-8-yl)phenoxy)azetidin-1-yl)-2-oxoethyl acetate (80 mg, 0.14 mmol) in THF (2 mL) and water (2 mL) at room temperature. The resulting solution was stirred at room temperature for 1 hour. The organic solvent was removed under reduced pressure. The reaction mixture was adjusted to pH=7 with aq. 0.1M HCl. The reaction mixture was diluted with EtOAc (20 mL), and washed sequentially with water (20 mL×2). The organic layer was dried over $Na_2SO_4$, filtered and evaporated to afford the crude product. The crude product was purified by flash C18-flash chromatography, elution gradient 0 to 50% MeCN in water (containing 0.1% $NH_4HCO_3$). Pure fractions were evaporated to dryness to afford 1-(3-(3-chloro-4-(6-(1-methylcyclopropoxy)-9-((4-methylpyridin-2-yl)methyl)-9H-purin-8-yl)phenoxy)azetidin-1-yl)-2-hydroxyethan-1-one (20 mg, 27%) as a white solid. $^1$H NMR (400 MHz, DMSO-$d_6$): 0.86 (2H, t), 1.02 (2H, t), 1.74 (3H, s), 2.20 (3H, s), 3.84 (1H, dd), 3.95 (2H, s), 4.1-4.2 (1H, m), 4.37 (1H, dd), 4.66 (1H, dd), 4.97-5.22 (2H, m), 5.35 (2H, s), 6.85-6.93 (2H, m), 7.04 (1H, d), 7.11 (1H, d), 7.42 (1H, d), 8.18 (1H, d), 8.57 (1H, s). m/z: ES+ [M+H]+ 535.

2-(3-(3-Chloro-4-(6-(1-methylcyclopropoxy)-9-((4-methylpyridin-2-yl)methyl)-9H-purin-8-yl)phenoxy)azetidin-1-yl)-2-oxoethyl acetate used as starting material was made as follows.

Tert-butyl 3-(3-chloro-4-(6-(1-methylcyclopropoxy)-9-((4-methylpyridin-2-yl)methyl)-9H-purin-8-yl)phenoxy)azetidine-1-carboxylate

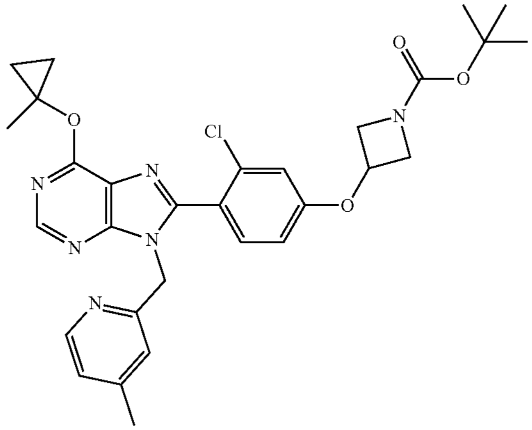 [SMILES: Cc1ccnc(Cn2c(-c3ccc(OC4CN(C(=O)OC(C)(C)C)C4)cc3Cl)nc3c(OC4(C)CC4)ncnc32)c1]

Tert-butyl 3-bromoazetidine-1-carboxylate (11.2 g, 47.4 mmol) was added to 3-chloro-4-(6-(1-methylcyclopropoxy)-9-((4-methylpyridin-2-yl)methyl)-9H-purin-8-yl)phenol (2.0 g, 4.74 mmol, Example 25 intermediate) and $K_2CO_3$ (9.83 g, 71.1 mmol) in MeCN (50 mL) at 25° C. The resulting mixture was stirred at 80° C. for 16 hours. The reaction mixture was diluted with EtOAc (15 mL), and washed sequentially with water (3×15 mL). The organic layer was dried over $Na_2SO_4$, filtered and evaporated to afford crude product. The crude product was purified by flash silica chromatography, elution gradient 0 to 100% EtOAc in pentane. Pure fractions were evaporated to dryness to afford tert-butyl 3-(3-chloro-4-(6-(1-methylcyclopropoxy)-9-((4-methylpyridin-2-yl)methyl)-9H-purin-8-yl)phenoxy)azetidine-1-carboxylate (2.20 g, 80%) as a yellow solid. $^1$H NMR (400 MHz, $CDCl_3$): 0.79-0.88 (2H, m), 1.1-1.21 (2H, m), 1.46 (9H, s), 1.80 (3H, s), 2.22 (3H, s), 3.89-4.05 (2H, m), 4.31 (2H, ddd), 4.87 (1H, dt), 5.30 (1H, s), 5.42 (2H, s), 6.54-6.72 (2H, m), 6.83 (1H, d), 6.88-6.95 (1H, m), 8.24 (1H, d), 8.64 (1H, s). m/z: ES+ [M+H]+ 577.

8-(4-(Azetidin-3-yloxy)-2-chlorophenyl)-6-(1-methylcyclopropoxy)-9-((4-methylpyridin-2-yl)methyl)-9H-purine

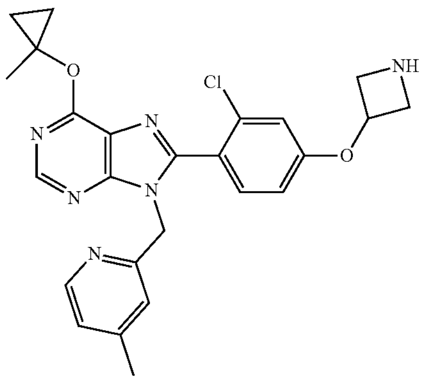 [SMILES: Cc1ccnc(Cn2c(-c3ccc(OC4CNC4)cc3Cl)nc3c(OC4(C)CC4)ncnc32)c1]

Tert-butyl 3-(3-chloro-4-(6-(1-methylcyclopropoxy)-9-((4-methylpyridin-2-yl)methyl)-9H-purin-8-yl)phenoxy) azetidine-1-carboxylate (2.2 g, 3.81 mmol) was dissolved in DCM (8 mL) at rt. After 5 minutes TFA (8 mL) was added and the resulting mixture was stirred at 25° C. for 2 hours. The solvent was removed under reduced pressure. This afforded 8-(4-(azetidin-3-yloxy)-2-chlorophenyl)-6-(1-methylcyclopropoxy)-9-((4-methylpyridin-2-yl)methyl)-9H-purine (1.80 g, 99%) as a yellow solid which was used in the next step directly without further purification. $^1$H NMR (400 MHz, $CDCl_3$): 0.85 (2H, d), 1.14 (2H, s), 1.28 (1H, t), 1.78 (3H, s), 2.06 (1H, s), 2.23 (3H, s), 3.85-4.24 (3H, m), 4.52 (2H, d), 6.55 (1H, dd), 6.77 (1H, s), 6.85 (1H, d), 6.94 (1H, d), 7.31 (2H, d), 8.22 (1H, d), 8.67 (1H, s). m/z: ES+ [M+H]+=477.

2-(3-(3-Chloro-4-(6-(1-methylcyclopropoxy)-9-((4-methylpyridin-2-yl)methyl)-9H-purin-8-yl)phenoxy) azetidin-1-yl)-2-oxoethyl Acetate

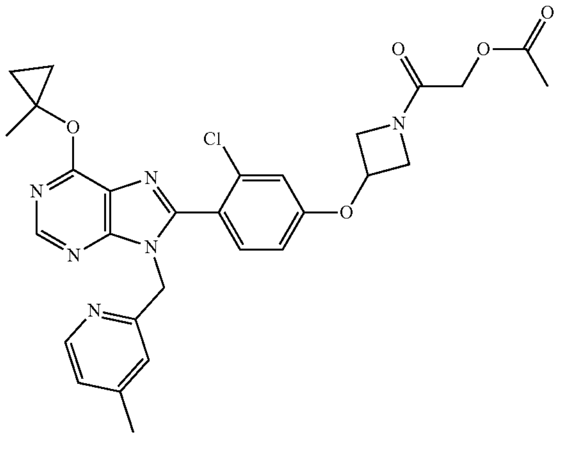 [SMILES: CC(=O)OCC(=O)N1CC(Oc2ccc(-c3nc4c(OC5(C)CC5)ncnc4n3Cc3cc(C)ccn3)c(Cl)c2)C1]

Triethylamine (0.070 mL, 0.50 mmol) was added to 8-(4-(azetidin-3-yloxy)-2-chlorophenyl)-6-(1-methylcyclopropoxy)-9-((4-methylpyridin-2-yl)methyl)-9H-purine (80 mg, 0.17 mmol) and 2-chloro-2-oxoethyl acetate (22.9 mg, 0.17 mmol) in DCM (0.5 mL) at rt. The resulting mixture was stirred at rt for 16 hours. The solvent was removed under reduced pressure. The crude product was purified by flash silica chromatography, elution gradient 0 to 20% MeOH in DCM. Pure fractions were evaporated to dryness to afford 2-(3-(3-chloro-4-(6-(1-methylcyclopropoxy)-9-((4-methylpyridin-2-yl)methyl)-9H-purin-8-yl)phenoxy) azetidin-1-yl)-2-oxoethyl acetate (50 mg, 52%) as a white solid. $^1$H NMR 0.84 (2H, t), 1.17 (2H, t), 1.82 (3H, s), 2.19 (3H, s), 2.24 (3H, s), 4.07-4.2 (1H, m), 4.24-4.32 (1H, m), 4.39-4.51 (1H, m), 4.53 (2H, s), 4.61-4.69 (1H, m), 4.96-5.1 (1H, m), 5.44 (2H, s), 6.65 (1H, dd), 6.73 (1H, s), 6.86 (1H, d), 6.95 (1H, d), 7.31 (1H, d), 8.26 (1H, d), 8.66 (1H, s). m/z: ES+ [M+H]+ 577.

Example 40

1-(3-(3-Chloro-4-(6-(1-methylcyclopropoxy)-9-((4-methylpyridin-2-yl)methyl)-9H-purin-8-yl)phenoxy) azetidin-1-yl)ethan-1-one

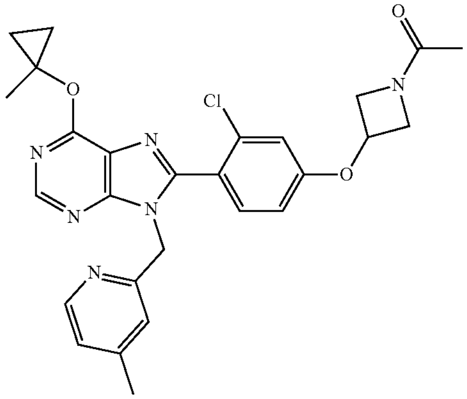 [SMILES: CC(=O)N1CC(Oc2ccc(-c3nc4c(OC5(C)CC5)ncnc4n3Cc3cc(C)ccn3)c(Cl)c2)C1]

Triethylamine (0.044 mL, 0.31 mmol) was added to 8-(4-(azetidin-3-yloxy)-2-chlorophenyl)-6-(1-methylcyclopropoxy)-9-((4-methylpyridin-2-yl)methyl)-9H-purine (50 mg, 0.10 mmol, Example 39 intermediate) and acetyl chloride (8.23 mg, 0.10 mmol) in DCM (0.5 mL) at rt. The resulting mixture was stirred at rt for 1 hour. The solvent was removed under reduced pressure. The crude product was purified by preparative HPLC (Column: XBridge Prep OBD C18 Column, 30*150 mm, 5 μm), using decreasingly polar mixtures of water (containing 10 mmol/L $NH_4HCO_3$ and 0.1% aq. ammonia) and MeCN as eluents. Fractions containing the desired compound were evaporated to dryness to afford 1-(3-(3-chloro-4-(6-(1-methylcyclopropoxy)-9-((4-methylpyridin-2-yl)methyl)-9H-purin-8-yl)phenoxy)azetidin-1-yl)ethan-1-one (19 mg, 35%) as a pale yellow solid. $^1$H NMR (400 MHz, DMSO-$d_6$): 0.86 (2H, t), 0.96-1.09 (2H, m), 1.74 (3H, s), 1.80 (3H, s), 2.20 (3H, s), 3.78 (1H, dd), 4.06-4.14 (1H, m), 4.30 (1H, dd), 4.54-4.62 (1H, m), 5.12 (1H, tt), 5.35 (2H, s), 6.85-6.94 (2H, m), 7.04 (1H, d), 7.11 (1H, d), 7.43 (1H, d), 8.15-8.21 (1H, m), 8.57 (1H, s). m/z: ES+ [M+H]+ 519.

Example 41

(S)-5-(3-Chloro-4-(6-(1-methylcyclopropoxy)-9-((4-methylpyridin-2-yl)methyl)-9H-purin-8-yl)phenoxy) piperidin-2-one

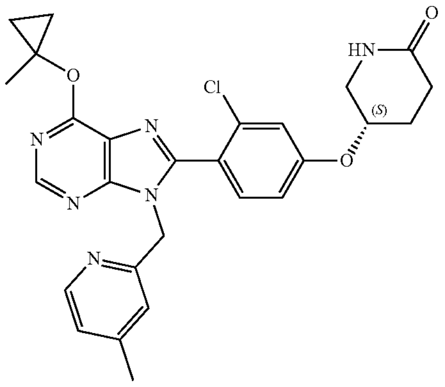

DIAD (0.12 mL, 0.59 mmol) was added slowly to 3-chloro-4-(6-(1-methylcyclopropoxy)-9-((4-methylpyridin-2-yl)methyl)-9H-purin-8-yl)phenol (50 mg, 0.12 mmol, Example 25 intermediate), (R)-5-hydroxypiperidin-2-one (68.2 mg, 0.59 mmol) and triphenylphosphine (155 mg, 0.59 mmol) in THF (1 mL) at 0° C. over a period of 2 hours under nitrogen. The resulting mixture was stirred at rt for 2 hours. The reaction mixture was then poured into water (10 mL), extracted with EtOAc (3×10 mL), the organic layer was dried over $Na_2SO_4$, filtered and the solvent was evaporated. The crude product was purified by preparative HPLC (Column: Xselect Peptide CSH C18 OBD Prep, 30*150 mm, 5 μm), using decreasingly polar mixtures of water (containing 10 mmol/L $NH_4HCO_3$ and 0.1% aq. ammonia) and MeCN as eluents. Fractions containing the desired compound were evaporated to dryness to afford(S)-5-(3-chloro-4-(6-(1-methylcyclopropoxy)-9-((4-methylpyridin-2-yl)methyl)-9H-purin-8-yl)phenoxy)piperidin-2-one (18 mg, 29%) as a white solid. $^1$H NMR (400 MHz, DMSO-$d_6$): 0.86 (2H, t), 1.03 (2H, t), 1.74 (3H, s), 1.96-2.08 (2H, m), 2.20 (3H, s), 2.21-2.31 (2H, m), 3.29 (1H, d), 3.46 (1H, d), 4.92 (1H, s), 5.35 (2H, s), 6.87 (1H, s), 6.99-7.07 (2H, m), 7.27 (1H, d), 7.38 (1H, d), 7.46 (1H, s), 8.18 (1H, d), 8.57 (1H, s). m/z: ES+ [M+H]+ 519.

Example 42

5-(3-Chloro-4-(6-(1-methylcyclopropoxy)-9-((4-methylpyridin-2-yl)methyl)-9H-purin-8-yl)phenoxy) tetrahydropyrimidin-2(1H)-one

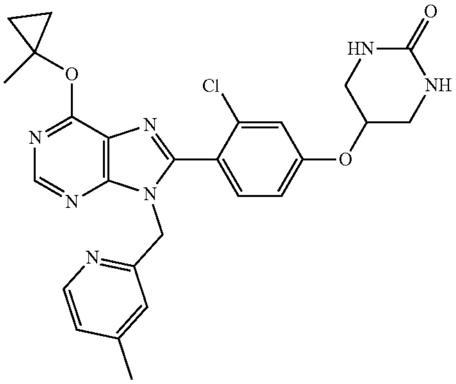 [SMILES: Cc1ccnc(Cn2c(-c3ccc(OC4CNC(=O)NC4)cc3Cl)nc3c(OC4(C)CC4)ncnc32)c1]

DIAD (121 mg, 0.59 mmol) was added slowly to 3-chloro-4-(6-(1-methylcyclopropoxy)-9-((4-methylpyridin-2-yl)methyl)-9H-purin-8-yl)phenol (50 mg, 0.12 mmol, Example 25 intermediate), 5-hydroxytetrahydropyrimidin-2(1H)-one (69 mg, 0.59 mmol) and triphenylphosphine (155 mg, 0.59 mmol) in THF (3 mL) at 0° C. over 1 hour under nitrogen. The resulting mixture was stirred at rt for 2 hours. The reaction mixture was poured into water (10 mL), extracted with EtOAc (3×10 mL), the organic layer was dried over $Na_2SO_4$, filtered and the solvent was evaporated off. The crude product was purified by preparative HPLC (Column: XBridge Prep OBD C18 Column, 30*150 mm, 5 μm), using decreasingly polar mixtures of water (containing 10 mmol/L $NH_4HCO_3$ and 0.1% aq. ammonia) and MeCN as eluents. Fractions containing the desired compound were evaporated to dryness to afford 5-(3-chloro-4-(6-(1-methylcyclopropoxy)-9-((4-methylpyridin-2-yl)methyl)-9H-purin-8-yl)phenoxy)tetrahydropyrimidin-2(1H)-one (6.5 mg, 11%) as a white solid. $^1$H NMR (400 MHz, DMSO-$d_6$): 0.86 (2H, t), 1.03 (2H, t), 1.74 (3H, s), 2.20 (3H, s), 3.28 (2H, t), 3.35-3.46 (2H, m), 4.88 (1H, s), 5.35 (2H, s), 6.13-6.18 (2H, m), 6.88 (1H, s), 6.99-7.07 (2H, m), 7.27 (1H, d), 7.40 (1H, d), 8.18 (1H, d), 8.57 (1H, s). m/z: ES+ [M+H]+ 520.

Example 43

5-(3-Chloro-4-(9-(3-chlorobenzyl)-6-(1-methylcyclopropoxy)-9H-purin-8-yl)phenoxy)pentanoic Acid

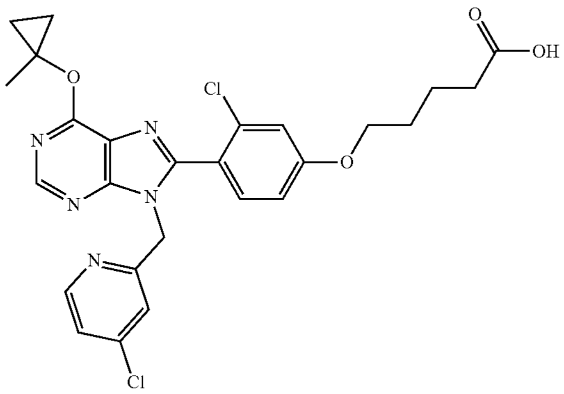 [SMILES: CC1(Oc2ncnc3c2nc(-c2ccc(OCCCCC(=O)O)cc2Cl)n3Cc2cc(Cl)ccn2)CC1]

$K_2CO_3$ (78 mg, 0.57 mmol) was added to 3-chloro-4-(9-(3-chlorobenzyl)-6-(1-methylcyclopropoxy)-9H-purin-8-yl) phenol (50 mg, 0.11 mmol, Example 32 intermediate) and methyl 5-bromopentanoate (110 mg, 0.57 mmol) in MeCN (2 mL) at 25° C. under air. The resulting mixture was stirred at 60° C. for 2 hours. The reaction mixture was evaporated to dryness and redissolved in DCM (20 mL), and washed sequentially with water (3×10 mL). The organic layer was dried over $Na_2SO_4$, filtered and evaporated. The crude product was redissolved in the mixed solvent of THF (3.0 mL) and water (0.6 mL), followed by addition of sodium hydroxide (91 mg, 2.27 mmol). The solution was stirred at 60° C. for 5 hours. The solvent was removed under reduced pressure to get the crude product. The crude product was purified by preparative HPLC (XBridge Prep C18 OBD column, 30*150 mm, 5 μm), using decreasingly polar mixtures of water (containing 10 mmol/L $NH_4HCO_3$ and 0.1% aq. ammonia) and MeCN as eluents. Fractions containing the desired compound were evaporated to dryness to afford 5-(3-chloro-4-(9-(3-chlorobenzyl)-6-(1-methylcyclopropoxy)-9H-purin-8-yl)phenoxy)pentanoic acid (6.5 mg, 11%) as a white solid. $^1$H NMR (400 MHz, DMSO-$d_6$): 0.85 (2H, t), 1.03 (2H, t), 1.62-1.7 (2H, m), 1.71-1.81 (5H, m), 2.28 (2H, t), 4.09 (2H, t), 5.29 (2H, s), 6.85 (1H, d), 6.96 (1H, s), 7-7.08 (1H, m), 7.21-7.32 (3H, m), 7.42 (1H, d), 8.63 (1H, s). One proton not observed. m/z: ES+ [M+H]+ 541.

Example 44

4-(3-Chloro-4-(9-(3-chlorobenzyl)-6-(1-methylcyclopropoxy)-9H-purin-8-yl)phenoxy)butanoic Acid

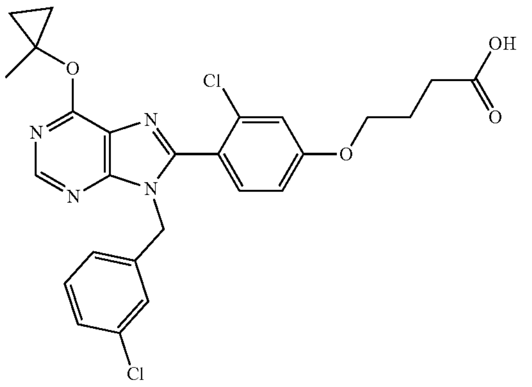 [SMILES: CC1(Oc2ncnc3c2nc(-c2ccc(OCCCC(=O)O)cc2Cl)n3Cc2cccc(Cl)c2)CC1]

$K_2CO_3$ (78 mg, 0.57 mmol) was added to 3-chloro-4-(9-(3-chlorobenzyl)-6-(1-methylcyclopropoxy)-9H-purin-8-yl) phenol (50 mg, 0.11 mmol, Example 32 intermediate) and methyl 4-bromobutanoate (103 mg, 0.57 mmol) in MeCN (2 mL) at 25° C. under air. The resulting mixture was stirred at 60° C. for 2 hours. The reaction mixture was evaporated to dryness and redissolved in DCM (20 mL), and washed sequentially with water (3×10 mL). The organic layer was dried over $Na_2SO_4$, filtered and evaporated to afford crude product. The crude product was redissolved in the mixed solvent of THF (3.0 mL) and water (2.0 mL), followed by addition of sodium hydroxide (45 mg, 1.13 mmol) and the solution was stirred at 60° C. for 5 hours. The solvent was removed under reduced pressure. The crude product was purified by preparative HPLC (Column: Xbridge Prep Shield RP18 OBD, 30*150 mm, 5 μm), using decreasingly polar mixtures of water (containing 10 mmol/L $NH_4HCO_3$ and 0.1% aq. ammonia) and MeCN as eluents. Fractions containing the desired compound were evaporated to dryness to afford 4-(3-chloro-4-(9-(3-chlorobenzyl)-6-(1-methylcyclopropoxy)-9H-purin-8-yl)phenoxy)butanoic acid (6.1 mg, 10%) as a white solid. $^1$H NMR (400 MHz, DMSO-$d_6$): 0.85 (2H, t), 1.02 (2H, t), 1.73 (3H, d), 1.96 (2H, s), 2.36 (2H, s), 4.10 (2H, s), 5.29 (2H, s), 6.84 (1H, d), 6.96 (1H, s), 7.04 (1H, d), 7.19-7.29 (3H, m), 7.42 (1H, dd), 8.63 (1H, d). One proton not observed. m/z: ES+ [M+H]+ 527.

Example 45

1-(3-Chloro-4-(6-(1-methylcyclopropoxy)-9-((4-methylpyridin-2-yl)methyl)-9H-purin-8-yl)phenoxy)-2-methylpropan-2-ol

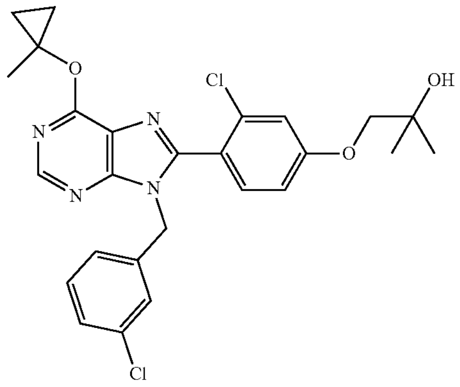 [SMILES: CC(C)(O)COc1ccc(-c2nc3c(OC4(C)CC4)ncnc3n2Cc2cccc(Cl)c2)c(Cl)c1]

RockPhos Pd G3 (4.3 mg, 5.2 μmol) was added to $Cs_2CO_3$ (50 mg, 0.15 mmol), 2-methylpropane-1,2-diol (9.3 mg, 0.10 mmol) and 8-(4-bromo-2-chlorophenyl)-6-(1-methylcyclopropoxy)-9-((4-methylpyridin-2-yl)methyl)-9H-purine (50 mg, 0.10 mmol, Example 25 intermediate) in toluene (0.5 mL) at rt over a period of 5 minutes. The resulting mixture was stirred at 100° C. for 2 hours under nitrogen. The solvent was removed under reduced pressure. The crude product was purified by preparative HPLC (Column: YMC-Actus Triant C18 ExRs, 30*150 mm, 5 μm), using decreasingly polar mixtures of water (containing 10 mmol/L $NH_4HCO_3$ and 0.05% aq. ammonia) and MeCN as eluents. Fractions containing the desired compound were evaporated to dryness to afford 1-(3-chloro-4-(6-(1-methylcyclopropoxy)-9-((4-methylpyridin-2-yl)methyl)-9H-purin-8-yl)phenoxy)-2-methylpropan-2-ol (17 mg, 34%) as a white solid. $^1$H NMR (400 MHz, DMSO-$d_6$): 0.86 (2H, t), 1.03 (2H, t), 1.20 (5H, s), 1.74 (3H, s), 2.19 (3H, s), 3.80 (2H, s), 4.68 (1H, s), 5.35 (2H, s), 6.86 (1H, s), 6.96 (1H, dd), 7.01-7.07 (1H, m), 7.18 (1H, d), 7.36 (1H, d), 8.18 (1H, d), 8.57 (1H, s). One proton not observed. m/z: ES+ [M+H]+ 494.

Example 46

2-(2-(3-Chloro-4-(9-(3-chlorobenzyl)-6-(1-methylcyclopropoxy)-9H-purin-8-yl)phenoxy)ethoxy)acetic Acid

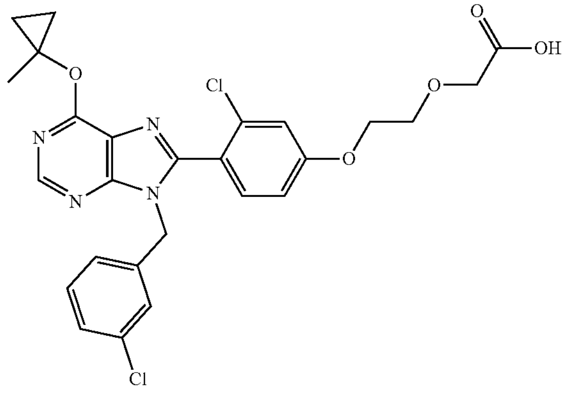 [SMILES: CC1(Oc2ncnc3c2nc(-c2ccc(OCCOCC(=O)O)cc2Cl)n3Cc2cccc(Cl)c2)CC1]

Sodium hydroxide (112 mg, 2.80 mmol) was added to ethyl 2-(2-(3-chloro-4-(9-(3-chlorobenzyl)-6-(1-methylcyclopropoxy)-9H-purin-8-yl)phenoxy)ethoxy)acetate (200 mg, 0.35 mmol) in THF (2.0 mL) and water (0.40 mL) at 25° C. The resulting mixture was stirred at 25° C. for 1 hour. The reaction mixture was filtered. The crude product was purified by preparative HPLC (XBridge Prep Phenyl OBD column, 19*150 mm, 5 μm), using decreasingly polar mixtures of water (containing 10 mmol/L $NH_4HCO_3$ and 0.1% aq. ammonia) and MeCN as eluents. Fractions containing the desired compound were evaporated to dryness to afford 2-(2-(3-chloro-4-(9-(3-chlorobenzyl)-6-(1-methylcyclopropoxy)-9H-purin-8-yl)phenoxy)ethoxy)acetic acid (27 mg, 14%) as a white solid. $^1H$ NMR (400 MHz, DMSO-$d_6$): 0.85 (2H, t), 1.02 (2H, t), 1.73 (3H, s), 3.83 (2H, t), 3.90 (2H, s), 4.22 (2H, t), 5.29 (2H, s), 6.84 (1H, d), 6.97 (1H, t), 7.06 (1H, dd), 7.2-7.31 (3H, m), 7.43 (1H, d), 8.63 (1H, s). One proton not observed. m/z: ES+ [M+H]+ 543.

Ethyl-2-(2-(3-chloro-4-(9-(3-chlorobenzyl)-6-(1-methylcyclopropoxy)-9H-purin-8-yl)phenoxy)ethoxy)acetate

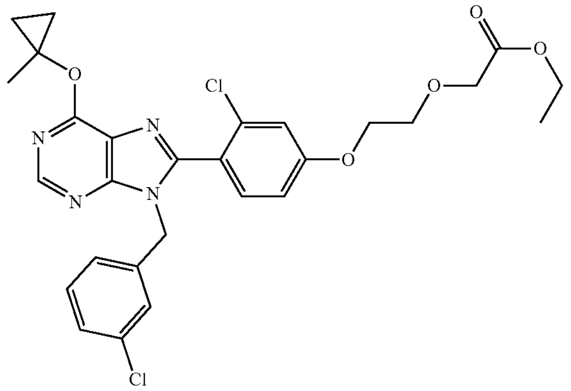 [SMILES: CCOC(=O)COCCOc1ccc(-c2nc3c(OC4(C)CC4)ncnc3n2Cc2cccc(Cl)c2)c(Cl)c1]

$Cs_2CO_3$ (1.11 g, 3.40 mmol) was added to 3-chloro-4-(9-(3-chlorobenzyl)-6-(1-methylcyclopropoxy)-9H-purin-8-yl)phenol (300 mg, 0.68 mmol, Example 32 intermediate) and ethyl 2-(2-chloroethoxy)acetate (566 mg, 3.40 mmol) in DMF (20 mL) at 25° C. The resulting mixture was stirred at 80° C. for 2 hours. The reaction mixture was diluted with EtOAc (75 mL), and washed with water (3x25 mL). The organic layer was dried over $Na_2SO_4$, filtered and evaporated to afford crude product. The crude product was purified by flash silica chromatography, elution gradient 0 to 25% EtOAc in petroleum ether. Pure fractions were evaporated to dryness to afford ethyl 2-(2-(3-chloro-4-(9-(3-chlorobenzyl)-6-(1-methylcyclopropoxy)-9H-purin-8-yl)phenoxy)ethoxy)acetate (210 mg, 54%) as a white solid. $^1H$ NMR (400 MHz, DMSO-$d_6$): 0.86 (2H, t), 1.02 (2H, t), 1.21 (3H, t), 1.74 (3H, s), 3.83-3.89 (2H, m), 4.08-4.14 (2H, m), 4.21 (2H, s), 4.23-4.27 (2H, m), 5.29 (2H, s), 6.82-6.9 (1H, m), 6.97 (1H, t), 7.06 (1H, dd), 7.19-7.34 (3H, m), 7.44 (1H, d), 8.64 (1H, s). m/z: ES+ [M+H]+ 571.

TABLE 1B

Assay Results for Examples 30-46

| Example # | POLQ Enz Lumin Primary CR GMean pIC50 | POLQ PD Prolif Lumin BRCA2 −/− Mean pIC50 | POLQ PD Prolif Lumin DLD1 Mean pIC50 |
|---|---|---|---|
| 30 | 8.1 | 6.2 | <5.0 |
| 31 | 8.5 | 6.4 | <5.0 |
| 32 | 8.3 | 6.2 | <5.0 |
| 33 | 8.2 | 6.9 | <5.0 |
| 34 | 8.3 | 6.7 | <5.0 |
| 35 | 8.4 | 6.9 | <5.0 |
| 36 | 8.2 | 6.6 | <5.0 |
| 37 | 8.2 | 6.9 | <5.0 |
| 38 | 8.0 | 6.4 | <5.0 |
| 39 | 8.3 | 6.8 | <5.0 |
| 40 | 8.0 | 6.8 | <5.0 |
| 41 | 8.1 | 6.1 | <5.0 |
| 42 | 8.0 | 5.2 | <5.0 |
| 43 | 8.3 | 7.1 | <5.0 |
| 44 | 8.2 | 6.8 | <5.0 |
| 45 | 8.2 | 6.7 | <5.0 |
| 46 | 8.3 | 5.9 | <5.0 |

Example 47

(R)-4-(3-chloro-4-(9-(5-chloro-2-methoxybenzyl)-6-(1-methylcyclopropoxy)-9H-purin-8-yl)phenoxy)-2-methylbutanoic Acid

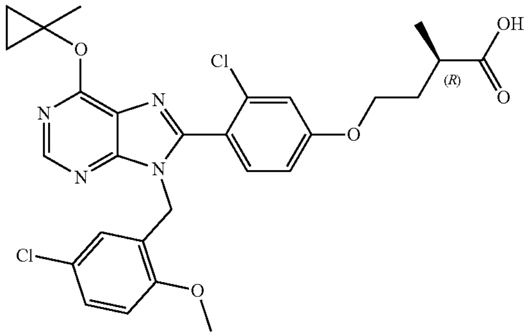

(R)-3-((R)-4-(3-chloro-4-(9-(5-chloro-2-methoxybenzyl)-6-(1-methylcyclopropoxy)-9H-purin-8-yl)phenoxy)-2-methylbutanoyl)-4-isopropyloxazolidin-2-one (2.1 g, 3.08 mmol) was dissolved in THF (21 mL) and cooled on ice. Hydrogen peroxide (1.05 mL, 30.8 mmol) was added dropwise, followed by the dropwise addition of lithium hydroxide hydrate (0.2M in water, 23.1 mL, 4.61 mmol) keeping the reaction mixture below 10° C. The reaction mixture was allowed to return to rt and stirred for one hour. Sodium hydrogen sulfite (1.60 g, 15.4 mmol), dissolved in water (15 mL), was added slowly, keeping the temperature below 20° C. The reaction mixture was partitioned between EtOAc (100 mL) and water (100 mL). The aqueous phase was re-extracted with EtOAc (50 mL). The organic phases were combined, washed with water (2x50 mL), brine (50 mL), passed through a phase separating filter paper and the solvent was removed in vacuo. The crude product was purified by reverse phase chromatography (C18), using decreasingly polar mixtures of water (containing by volume 1% concentrated ammonia (28-30% in water)) and MeCN as eluents. Fractions containing the desired compound were evaporated to remove MeCN, the aqueous phase neutralised with 0.2M HCl, and the aqueous extracted with EtOAc (2×100 mL). The combined organic phases were washed with water (100 mL) followed by brine (100 mL), then passed through a hydrophobic frit and concentrated in vacuo to give (R)-4-(3-chloro-4-(9-(5-chloro-2-methoxybenzyl)-6-(1-methylcyclopropoxy)-9H-purin-8-yl)phenoxy)-2-methylbutanoic acid (1.59 g, 90%) as a white foamy solid. $^1H$ NMR (500 MHz, DMSO-$d_6$): 0.82-0.87 (2H, m), 1.01-1.05 (2H, m), 1.16 (3H, d), 1.74 (3H, s), 1.80 (1H, dq), 2.07 (1H, dq), 2.57 (1H, p), 3.53 (3H, s), 4.11 (2H, t), 5.25 (2H, s), 6.76 (1H, d), 6.89 (1H, d), 7.01 (1H, dd), 7.18 (1H, d), 7.24 (1H, dd), 7.39 (1H, d), 8.62 (1H, s), 12.21 (1H, s). m/z: ES+ [M+H]+ 571. (571.4). Chiral analysis was measured via chiral HPLC using a ChiralPak IK, 150×3.0 mm, 3 um column, mobile phase: 20:80:0.1 ethyl acetate:heptane:TFA (isocratic), flow rate: 0.4 mL/min, UV wavelength: 254 nm, retention time=11.8 minutes (other enantiomer, retention time=13.1 minutes)

(R)-3-((R)-4-(3-chloro-4-(9-(5-chloro-2-methoxybenzyl)-6-(1-methylcyclopropoxy)-9H-purin-8-yl)phenoxy)-2-methylbutanoyl)-4-isopropyloxazolidin-2-one used as a starting material was prepared as follows.

(R)-3-((R)-4-(3-chloro-4-(9-(5-chloro-2-methoxybenzyl)-6-(1-methylcyclopropoxy)-9H-purin-8-yl)phenoxy)-2-methylbutanoyl)-4-isopropyloxazolidin-2-one

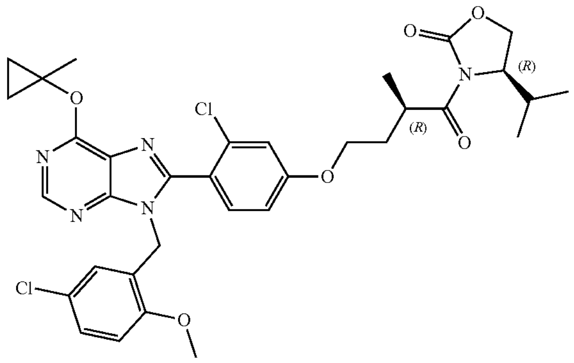

3-Chloro-4-(9-(5-chloro-2-methoxybenzyl)-6-(1-methylcyclopropoxy)-9H-purin-8-yl)phenol (1.45 g, 3.08 mmol), (R)-3-((R)-4-bromo-2-methylbutanoyl)-4-isopropyloxazolidin-2-one (1.25 g, 4.28 mmol) were dissolved in DMF (15 mL) and potassium carbonate (1.70 g, 12.3 mmol) was added. The reaction stirred at 45° C. for 3 h. The reaction mixture was then allowed to cool to rt, then EtOAc was added (50 mL) followed by water (50 mL). The phases were separated, then the organics were further washed with water (2×25 mL) and brine (25 mL). The organics were dried through a hydrophobic frit, concentrated in vacuo and the crude product was purified by flash silica gel chromatography, elution gradient 0 to 40% EtOAc in heptane. Pure fractions were evaporated to dryness to afford (R)-3-((R)-4-(3-chloro-4-(9-(5-chloro-2-methoxybenzyl)-6-(1-methylcyclopropoxy)-9H-purin-8-yl)phenoxy)-2-methylbutanoyl)-4-isopropyloxazolidin-2-one (2.10 g, 100%) as a foam. $^1H$ NMR (500 MHz, DMSO-$d_6$): 0.80 (3H, d), 0.83-0.87 (5H, m), 1-1.05 (2H, m), 1.20 (3H, d), 1.73 (3H, s), 1.79-1.86 (1H, m), 2.1-2.2 (2H, m), 3.53 (3H, s), 3.8-3.9 (1H, m), 4.06 (2H, dq), 4.25-4.32 (2H, m), 4.43 (1H, dt), 5.24 (2H, s), 6.75 (1H, d), 6.89 (1H, d), 6.98 (1H, dd), 7.15 (1H, d), 7.24 (1H, dd), 7.39 (1H, d), 8.61 (1H, s). m/z: ES+ [M+H]+ 682. (682.4)

3-Chloro-4-(9-(5-chloro-2-methoxybenzyl)-6-(1-methylcyclopropoxy)-9H-purin-8-yl)phenol used as starting materials was prepared as follows:

6-Chloro-N4-(5-chloro-2-methoxybenzyl)pyrimidine-4,5-diamine

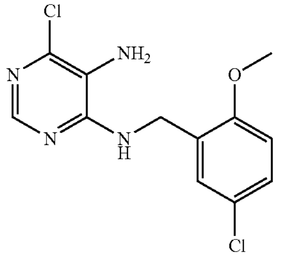 [SMILES: COc1ccc(Cl)cc1CNc1ncnc(Cl)c1N]

To (5-chloro-2-methoxyphenyl)methanamine hydrochloride (23.58 g, 113.3 mmol) and 4,6-dichloropyrimidin-5-amine (16.87 g, 102.9 mmol) in butan-1-ol (170 mL) was added N-ethyl-N-isopropylpropan-2-amine (54 mL, 310 mmol). The reaction mixture was stirred at 120° C. for 9 h. The reaction was then allowed to cool to RT and the reaction mixture was filtered, the cake washed with water followed by DCM and then dried to give 6-chloro-N4-(5-chloro-2-methoxybenzyl)pyrimidine-4,5-diamine (28.38 g, 92%) as a beige solid. The mother liquors were then washed with water and concentrated in vacuo. DCM was added, the solids were filtered and washed further with DCM. After drying, further 6-chloro-N4-(5-chloro-2-methoxybenzyl)pyrimidine-4,5-diamine (1.52 g, 4.9%) was obtained as a beige solid. $^1H$ NMR (500 MHz, DMSO-$d_6$): 3.83 (3H, s), 4.56 (2H, d), 5.12 (2H, s), 7.03 (1H, d), 7.15 (1H, d), 7.17 (1H, t), 7.29 (1H, dd), 7.72 (1H, s). m/z: ES+ [M+H]+ 299. (299.1)

8-(4-Bromo-2-chlorophenyl)-6-chloro-9-(5-chloro-2-methoxybenzyl)-9H-purine

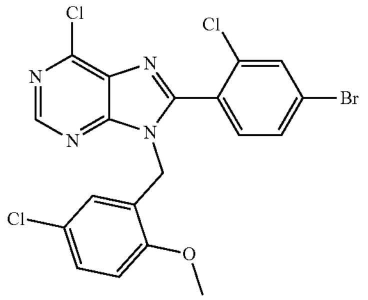 [SMILES: COc1ccc(Cl)cc1Cn1c(-c2ccc(Br)cc2Cl)nc2c(Cl)ncnc21]

To a flask were added 4-bromo-2-chlorobenzaldehyde (1.16 g, 5.26 mmol), iron(III) chloride (0.204 g, 1.26 mmol) and 6-chloro-N4-(5-chloro-2-methoxybenzyl)pyrimidine-4,5-diamine (1.51 g, 5.04 mmol). IPA (25 ml) was added and the reaction was stirred at 80° C. with a condenser attached open to air for 24 h. The reaction was cooled to RT, stirred open to air for a further 24 hours and then filtered. Evaporation of the solvent from the filtrate gave 8-(4-bromo-2- chlorophenyl)-6-chloro-9-(5-chloro-2-methoxybenzyl)-9H-purine as an orange solid, which was used in the next step without further purification.

A small sample was purified by preparative HPLC for NMR analysis (residual iron causing severe broadening). $^1$H NMR (500 MHz, DMSO-$d_6$): 3.46 (3H, s), 5.34 (2H, s), 45396.79-6.93 (2H, m), 7.26 (1H, dd), 7.55 (1H, d), 7.74 (1H, dd), 7.92 (1H, d), 8.90 (1H, s). m/z: ES+ [M+H]+ 499. (499.1)

8-(4-Bromo-2-chlorophenyl)-9-(5-chloro-2-methoxybenzyl)-6-(1-methylcyclopropoxy)-9H-purine

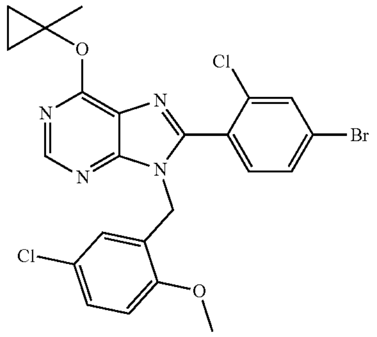 [SMILES: COc1ccc(Cl)cc1Cn1c(-c2ccc(Br)cc2Cl)nc2c(OC3(C)CC3)ncnc21]

To a flask was added 8-(4-bromo-2-chlorophenyl)-6-chloro-9-(5-chloro-2-methoxybenzyl)-9H-purine (1.89 g, 3.79 mmol), then a solution of 1-methylcyclopropan-1-ol (0.700 g, 9.71 mmol) in THF (19 mL) added. The mixture was cooled over ice and then sodium hydride (in paraffin oil, 742 mg, 18.5 mmol) added portionwise. The reaction stirred under nitrogen at rt for 5 hours. The reaction cooled over ice and quenched by addition of sat. $NH_4Cl$ (5 mL). Then EtOAc (50 mL) and water (50 mL) were added and the phases separated. The organic phase was passed through a filter. The aqueous layer was further extracted with EtOAc (2×25 mL). The combined organics were concentrated in vacuo and the crude product was purified by flash silica gel chromatography, elution gradient 0 to 50% EtOAc in heptane. Pure fractions were evaporated to dryness to afford 8-(4-bromo-2-chlorophenyl)-9-(5-chloro-2-methoxybenzyl)-6-(1-methylcyclopropoxy)-9H-purine (1.723 g, 85%) as a white foamy solid. $^1$H NMR (500 MHz, $CDCl_3$): 0.82-0.86 (2H, m), 1.14-1.2 (2H, m), 1.81 (3H, s), 3.55 (3H, s), 5.33 (2H, s), 6.62 (1H, d), 6.74 (1H, d), 7.09-7.14 (2H, m), 7.40 (1H, dd), 7.67 (1H, d), 8.68 (1H, s). m/z: ES+ [M+H]+ 533. (533.2)

3-Chloro-4-(9-(5-chloro-2-methoxybenzyl)-6-(1-methylcyclopropoxy)-9H-purin-8-yl)phenol

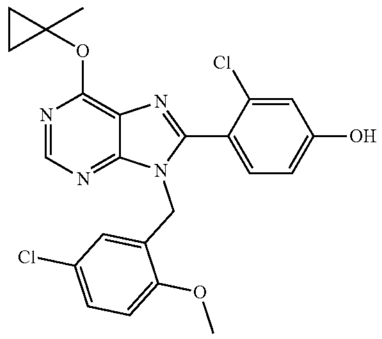 [SMILES: COc1ccc(Cl)cc1Cn1c(-c2ccc(O)cc2Cl)nc2c(OC3(C)CC3)ncnc21]

A solution of dioxane (110 ml) and water (110 ml) was added to a 3-neck flask containing 8-(4-bromo-2-chlorophenyl)-9-(5-chloro-2-methoxybenzyl)-6-(1-methylcyclopropoxy)-9H-purine (21.9 g, 41.0 mmol), $Pd_2(dba)_3$ (1.85 g, 2.02 mmol), potassium hydroxide (5.15 g, 91.8 mmol) and di-tert-butyl (2',4',6'-triisopropyl-[1,1'-biphenyl]-2-yl)phosphane (1.74 g, 4.10 mmol). The atmosphere was evacuated and refilled with nitrogen (×3). The reaction mixture was stirred under nitrogen for 50 minutes at 80° C., then allowed to cool to RT and diluted with water (250 mL) containing 2M HCl (50 mL). The aqueous layer was extracted with EtOAc (2×250 mL), the organics combined via hydrophobic frit and concentrated in vacuo. The crude product was purified by flash silica chromatography, elution gradient 0 to 50% EtOAc in heptane. Pure fractions were evaporated to dryness to afford 3-chloro-4-(9-(5-chloro-2-methoxybenzyl)-6-(1-methylcyclopropoxy)-9H-purin-8-yl)phenol (16.65 g, 86%) as a yellow solid. $^1$H NMR (500 MHz, DMSO-$d_6$): 0.8-0.86 (2H, m), 0.98-1.04 (2H, m), 1.73 (3H, s), 3.55 (3H, s), 5.24 (2H, s), 6.75 (1H, d), 6.83 (1H, dd), 6.90 (1H, d), 6.95 (1H, d), 7.24 (1H, dd), 7.29 (1H, d), 8.60 (1H, s), 10.41 (1H, s). m/z: ES+ [M+H]+ 471. (471.3)

(R)-3-((R)-4-bromo-2-methylbutanoyl)-4-isopropyloxazolidin-2-one was prepared as follows:

(R)-3-(4-(benzyloxy) butanoyl)-4-isopropyloxazolidin-2-one

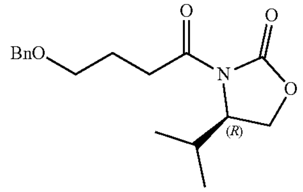

1,3-Diisopropylcarbodiimide (56.1 g, 444.41 mmol) was added in one portion to 4-(benzyloxy) butanoic acid (86 g, 444.41 mmol), (R)-4-isopropyloxazolidin-2-one (57.4 g, 444.41 mmol) and DMAP (54.3 g, 444.41 mmol) in DCM (50 mL) at rt. The resulting mixture was stirred at 25° C. for 5 hours. Another reaction was run using the same conditions, starting from 37.6 g of 4-(benzyloxy) butanoic acid. The two batches were combined and the mixture was poured to a mixture of ice and 1N HCl (aq., 700 mL). The aqueous phase was extracted with DCM (2×500 mL). The combined organic phase was washed with water (300 mL), sat. $NaHCO_3$ (aq., 300 mL), NaCl (aq., 300 mL), dried over $Na_2SO_4$, filtered and concentrated. The resulting crude material was loaded onto a silica gel pad (700 g, 15 cm diameter, 30 cm deep), elution gradient 0 to 16% EtOAc in petroleum ether then evaporated to give 170 g of product which was repurified by silica gel column chromatography to give (R)-3-(4-(benzyloxy) butanoyl)-4-isopropyloxazolidin-2-one (130 g, 58%) as a colorless oil. $^1H$ NMR (300 MHz, DMSO-$d_6$): 0.78 (3H, d), 0.84 (3H, d), 1.74-1.92 (2H, m), 2.17 (1H, m), 2.75-3.08 (2H, m), 3.47 (2H, t), 4.27 (2H, d), 4.34 (1H, ddd), 4.46 (2H, s), 7.12-7.51 (5H, m). m/z: ES+ [M+H]+ 306.

(R)-3-((R)-4-(benzyloxy)-2-methylbutanoyl)-4-isopropyloxazolidin-2-one

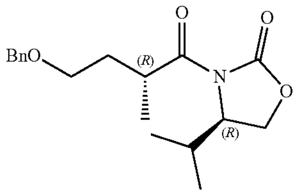

To a 2 L three-necked flask equipped with a 200 mL dropping funnel and a thermometer was charged with (R)-3-(4-(benzyloxy) butanoyl)-4-isopropyloxazolidin-2-one (40 g, 131 mmol) and THF (400 mL). The reaction mixture cooled to −75° C. under nitrogen and evacuated and back-filled with nitrogen three times. NaHMDS (131 mL, 262 mmol) was added dropwise via the 200 mL dropping funnel at −75° C. under nitrogen so that the temperature did not rise above-70° C. and stirred at −75° C. for 0.5 h. A 50 mL dropping funnel was then equipped into the above three-neck flask, and the system was evacuated and backfilled with nitrogen three times. Methyl iodide (41.0 mL, 655 mmol) was added dropwise via the 50 mL dropping funnel at −75° C. and the temperature did not rise above −70° C. then stirred at −70° C. for 2 hours. Then NaHMDS (32.7 mL, 65.5 mmol) was added dropwise via syringe to the above reaction mixture at −70° C. under nitrogen so that the temperature did not rise above −65° C. and stirred at −70° C. for 0.5 h. Methyl iodide (8.20 mL, 131 mmol) was added at −70° C. via syringe and the temperature did not rise above −65° C. then stirred at −70° C. for 2 hours. The mixture was poured into a mixture of ice and $NH_4Cl$ (aq., 400 mL) and water (400 mL). The aqueous phase was extracted with EtOAc (3×400 mL). The organic phase was washed with brine (400 mL), dried over $Na_2SO_4$, filtered and evaporated to give the crude product. The reaction was repeated 3 times on 40 g scale and once on 5 g scale. The crude products were combined (~240 g) and purified by silica gel chromatography, elution gradient 0 to 10% EtOAc in petroleum ether. Pure fractions were evaporated to dryness to afford (R)-3-((R)-4-(benzyloxy)-2-methylbutanoyl)-4-isopropyloxazolidin-2-one (125 g, 72%, dr 90:10) as a colourless oil. $^1H$ NMR (300 MHz, DMSO-$d_6$): 0.75 (3H, d), 0.81 (3H, d), 1.10 (3H, d), 1.53-1.66 (1H, m), 1.89-2.02 (1H, m), 2.04-2.17 (1H, m), 3.37-3.48 (2H, m), 3.72-3.86 (1H, m), 4.09 (1H, t), 4.30-4.31 (2H, m), 4.39 (2H, s), 7.21-7.40 (5H, m). m/z: ES+ [M+H]+ 320.

(R)-3-((R)-4-hydroxy-2-methylbutanoyl)-4-isopropyloxazolidin-2-one

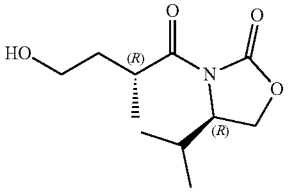

(R)-3-((R)-4-(benzyloxy)-2-methylbutanoyl)-4-isopropyloxazolidin-2-one (40 g, 125.2 mmol) was dissolved in ethanol (400 mL), and fresh Pd on charcoal (4.0 g, 0.09 mmol) was added under nitrogen. The 1 L flask was fitted with a balloon of hydrogen, evacuated and back-filled with hydrogen 3 times; then fitted with another balloon of hydrogen, evacuated and back-filled with hydrogen 1 times. The resulting suspension was stirred at 25° C. for 8 hours. The reaction was repeated three times on a 5 g, 40 g and 36 g scale. The reaction mixtures were combined, filtered through celite, and washed with DCM:EtOH (v/v=10:1, 1 L×3). The solvent was removed under reduced pressure to afford (R)-3-((R)-4-hydroxy-2-methylbutanoyl)-4-isopropyloxazolidin-2-one (84 g, 96%) as a colorless oil. The product was used in the next step directly without further purification. $^1H$ NMR (300 MHz, DMSO-$d_6$): 0.80 (3H, d), 0.86 (3H, d), 1.12 (3H, d), 1.40-1.55 (1H, m), 1.77-1.92 (1H, m), 2.08-2.24 (1H, m), 3.34-3.43 (2H, m), 3.66-3.83 (1H, m), 4.27-4.33 (2H, m), 4.34-4.44 (2H, m). m/z: ES+ [M+H]+ 230.

(R)-3-((R)-4-bromo-2-methylbutanoyl)-4-isopropyloxazolidin-2-one

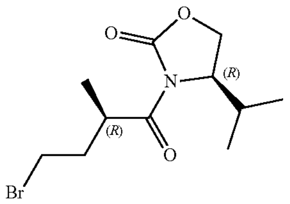

To a 1 L three-necked round bottle was added (R)-3-((R)-4-hydroxy-2-methylbutanoyl)-4-isopropyloxazolidin-2-one (10 g, 43.6 mmol) and THF (300 mL), then the mixture was cooled on ice-water bath to 5° C. $CBr_4$ (87 g, 261.69 mmol) was added followed by portionwise addition of triphenylphosphine (68.6 g, 261.7 mmol) so that the temperature did not rise above 15° C. The resulting mixture was stirred (mechanical stirring) at rt for 1 hour. The reaction mixture was filtered through celite, and washed with THF (200 mL×3). The solvent was removed under reduced pressure to afford the crude.

The reaction was repeated on a 10 g scale. The crude products were combined and purified by silica gel chromatography, elution gradient 0 to 10% EtOAc in petroleum ether. Pure fractions were evaporated to dryness to afford (R)-3-((R)-4-bromo-2-methylbutanoyl)-4-isopropyloxazolidin-2-one (20 g, dr 90:10) as a yellow solid.

The whole reaction was repeated starting from 40 g to provide additional (R)-3-((R)-4-bromo-2-methylbutanoyl)-4-isopropyloxazolidin-2-one.

All the batches (from the 10 g, 30 g and 40 g reaction) were combined, suspended in heptane (380 mL, 10 volumes), brought up to reflux to dissolve, allowed to cool and crystals formed. The solid was filtered off and dried to afford the desired product (26 g) as a white crystalline solid, which was re-purified again by crystallisation from pentane (260 mL, 10 volumes) and dried to afford (R)-3-((R)-4-bromo-2-methylbutanoyl)-4-isopropyloxazolidin-2-one (20 g, batch 1) as a white crystalline solid. The filtrate was combined and concentrated to give impure product (~18 g) and then re-purified by silica gel chromatography, elution gradient 0 to 10% EtOAc in petroleum ether. Pure fractions were evaporated to dryness to afford a solid (13 g) which was re-purified by crystallisation from pentane (100 mL×2, 5 volumes×2) twice and dried to afford (R)-3-((R)-4-bromo-2-methylbutanoyl)-4-isopropyloxazolidin-2-one (10 g) as a white crystalline solid (batch 2). The impure mother liquor were combined and concentrated to give a solid (~5 g) which was re-purified by silica gel chromatography, elution gradient 0 to 10% EtOAc in petroleum ether. Pure fractions were evaporated to dryness to afford a solid (3 g) which was re-purified by crystallisation from pentane (15 mL, 5 volumes) and dried to afford (R)-3-((R)-4-bromo-2-methylbutanoyl)-4-isopropyloxazolidin-2-one (2 g) as a white crystalline solid (batch 3). The three batches were combined to give (R)-3-((R)-4-bromo-2-methylbutanoyl)-4-isopropyloxazolidin-2-one (32.0 g, 31.4%) as a white crystalline solid (98:2 dr). $^1$H NMR (300 MHz, DMSO-$d_6$): 0.78 (3H, d), 0.85 (3H, d), 1.14 (3H, d), 1.79-1.94 (1H, m), 2.05-2.29 (2H, m), 3.42-3.56 (2H, m), 3.69-3.84 (1H, m), 4.26-4.35 (2H, m), 4.35-4.44 (1H, m). m/z: ES+ [M+H]+ 292.

Example 48

(S)-4-(3-chloro-4-(9-(5-chloro-2-methoxybenzyl)-6-(1-methylcyclopropoxy)-9H-purin-8-yl)phenoxy)-2-methylbutanoic Acid

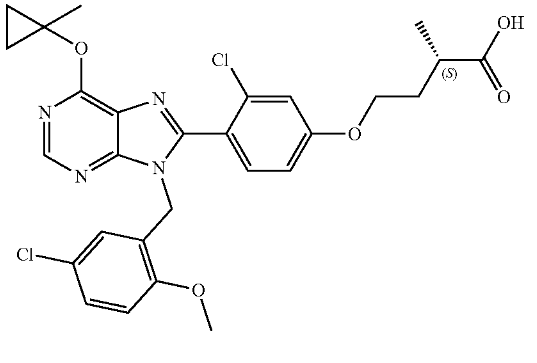

(S)-4-(3-Chloro-4-(9-(5-chloro-2-methoxybenzyl)-6-(1-methylcyclopropoxy)-9H-purin-8-yl)phenoxy)-2-methylbutanoic acid was prepared in a similar manner to Example 47, starting from (S)-3-((S)-4-(3-chloro-4-(9-(5-chloro-2-methoxybenzyl)-6-(1-methylcyclopropoxy)-9H-purin-8-yl)phenoxy)-2-methylbutanoyl)-4-isopropyloxazolidin-2-one (1.67 g, 2.45 mmol) to yield(S)-4-(3-chloro-4-(9-(5-chloro-2-methoxybenzyl)-6-(1-methylcyclopropoxy)-9H-purin-8-yl)phenoxy)-2-methylbutanoic acid (1.17 g, 83%) as a white foamy solid. $^1$H NMR (500 MHz, DMSO-$d_6$): 0.84-0.88 (2H, m), 1.01-1.05 (2H, m), 1.16 (3H, d), 1.74 (3H, s), 1.80 (1H, dq), 2.07 (1H, dq), 2.57 (1H, p), 3.53 (3H, s), 4.11 (2H, t), 5.25 (2H, s), 6.76 (1H, d), 6.89 (1H, d), 7.01 (1H, dd), 7.18 (1H, d), 7.24 (1H, dd), 7.39 (1H, d), 8.62 (1H, s), 12.22 (1H, s). m/z: ES+ [M+H]+ 571. (571.3) Chiral analysis was measured via chiral HPLC using a ChiralPak IK, 150×3.0 mm, 3 um column, mobile phase: 20:80:0.1 ethyl acetate:heptane:TFA (isocratic), flow rate: 0.4 mL/min, UV wavelength: 254 nm, retention time=13.1 minutes (other enantiomer, retention time=11.8 minutes)

(S)-4-(3-Chloro-4-(9-(5-chloro-2-methoxybenzyl)-6-(1-methylcyclopropoxy)-9H-purin-8-yl)phenoxy)-2-methylbutanoic acid used as a starting material was prepared as follows.

(S)-4-(3-chloro-4-(9-(5-chloro-2-methoxybenzyl)-6-(1-methylcyclopropoxy)-9H-purin-8-yl)phenoxy)-2-methylbutanoic Acid

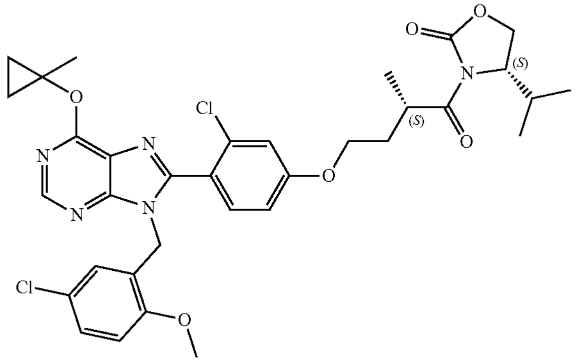

(S)-4-(3-Chloro-4-(9-(5-chloro-2-methoxybenzyl)-6-(1-methylcyclopropoxy)-9H-purin-8-yl)phenoxy)-2-methylbutanoic acid was prepared in a similar manner to Example 47, starting from 3-chloro-4-(9-(5-chloro-2-methoxybenzyl)-6-(1-methylcyclopropoxy)-9H-purin-8-yl)phenol (intermediate in Example 47) and (S)-3-((S)-4-bromo-2-methylbutanoyl)-4-isopropyloxazolidin-(S)-3-((S)-4-(3-chloro-4-(9-(5-chloro-2-methoxybenzyl)-6-(1-2-one to yield methylcyclopropoxy)-9H-purin-8-yl)phenoxy)-2-methylbutanoyl)-4-isopropyloxazolidin-2-one (1.67 g, 96%) as a foam. $^1$H NMR (500 MHz, DMSO-$d_6$): 0.80 (3H, d), 0.84-0.87 (5H, m), 1-1.04 (2H, m), 1.20 (3H, d), 1.73 (3H, s), 1.82 (1H, dq), 2.11-2.23 (2H, m), 3.53 (3H, s), 3.81-3.89 (1H, m), 4.05-4.11 (2H, m), 4.29 (2H, q), 4.43 (1H, dt), 5.24 (2H, s), 6.75 (1H, d), 6.89 (1H, d), 6.98 (1H, dd), 7.15 (1H, d), 7.24 (1H, dd), 7.38 (1H, d), 8.61 (1H, s). m/z: ES+ [M+H]+ 682. (682.3)

(S)-3-((S)-4-bromo-2-methylbutanoyl)-4-isopropyloxazolidin-2-one used as a starting material was prepared as follows.

(S)-3-((S)-4-bromo-2-methylbutanoyl)-4-isopropyloxazolidin-2-one

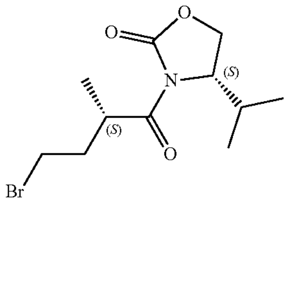

(S)-3-((S)-4-bromo-2-methylbutanoyl)-4-isopropyloxazolidin-2-one was prepared in a similar manner to Example 47, starting from(S)-4-isopropyloxazolidin-2-one instead. $^1$H NMR (500 MHz, DMSO-$d_6$) 0.79 (3H, d), 0.85 (3H, d), 1.14 (3H, d), 1.87 (1H, dq), 2.14 (1H, ddp), 2.21 (1H, dq), 3.44-3.53 (2H, m), 3.78 (1H, h), 4.26-4.36 (2H, m), 4.40 (1H, dt). m/z: ES+ [M+H]+ 294. (294.1)

Example 49

3-(2-Chloro-3-(9-(5-chloro-2-methoxybenzyl)-6-(1-methylcyclopropoxy)-9H-purin-8-yl)phenoxy)propanoic Acid

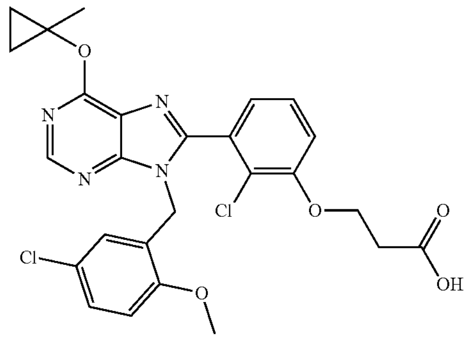 [SMILES: COc1ccc(Cl)cc1Cn1c(-c2cccc(OCCC(=O)O)c2Cl)nc2c(OC3(C)CC3)ncnc21]

Sodium chlorite (34.2 mg, 0.38 mmol) was added to sodium hypochlorite (0.06 mL, 0.97 mmol), TEMPO (2.66 mg, 0.02 mmol) and 3-(2-chloro-3-(9-(5-chloro-2-methoxybenzyl)-6-(1-methylcyclopropoxy)-9H-purin-8-yl)phenoxy) propan-1-ol (100 mg, 0.19 mmol) in MeCN (3 mL) and $Na_3PO_4$ aq. buffer (1 mL). The resulting mixture was stirred at 25° C. for 1 hour. The reaction mixture was adjusted to pH 6 with 2M HCl. The reaction mixture was poured into water (50 mL) and extracted with EtOAc (3×25 mL). The organic layer was dried over $Na_2SO_4$, filtered and evaporated to afford a yellow solid. The crude product was purified by preparative HPLC (Column: XBridge Prep OBD C18 Column, 30*150 mm, 5 μm) using decreasingly polar mixtures of water (containing 0.1% aq. $NH_3$ and 10 mmol/L $NH_4HCO_3$) and MeCN as eluents.

Fractions containing the desired compound were evaporated to dryness and lyophilized to afford 3-(2-chloro-3-(9-(5-chloro-2-methoxybenzyl)-6-(1-methylcyclopropoxy)-9H-purin-8-yl)phenoxy)propanoic acid (58.0 mg, 56%) as a white solid. $^1$H NMR (500 MHz, DMSO-$d_6$): 0.85 (2H, d), 1.03 (2H, d), 1.74 (3H, s), 2.72 (2H, s), 3.51 (3H, d), 4.26-4.35 (2H, m), 5.23 (2H, s), 6.81 (1H, d), 6.87 (1H, dd), 7.01-7.04 (1H, m), 7.24 (1H, dt), 7.35-7.44 (2H, m), 8.63 (1H, s). One proton not observed. m/z: ES+ [M+H]+ 543.

3-(2-Chloro-3-(9-(5-chloro-2-methoxybenzyl)-6-(1-methylcyclopropoxy)-9H-purin-8-yl)phenoxy)propan-1-ol used as a starting material was prepared as follows.

8-(3-Bromo-2-chlorophenyl)-6-chloro-9H-purine

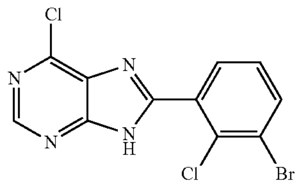 [SMILES: Clc1c(Br)cccc1-c1nc2c(Cl)ncnc2[nH]1]

Ferric chloride (50.5 g, 311 mmol) was added slowly to 6-chloropyrimidine-4,5-diamine (15 g, 104 mmol) and 3-bromo-2-chlorobenzaldehyde (22.77 g, 104 mmol) in IPA (300 mL). The resulting mixture was stirred at 75° C. for 12 hours. The solvent was removed under reduced pressure. The reaction mixture was washed with water (750 mL), filtered and the resulting solid was collected and poured into THF (1 L). The solution was filtered and the filtrate was collected. The solvent was removed under reduced pressure to afford 8-(3-bromo-2-chlorophenyl)-6-chloro-9H-purine (15.0 g, 42%) as a yellow solid used without further purification. $^1$H NMR (500 MHz, $CDCl_3$): 7.19 (1H, s), 7.47-7.64 (2H, m), 7.89 (1H, s), 8.98 (1H, d). m/z: ES+ [M+H]+ 343.

8-(3-Bromo-2-chlorophenyl)-6-chloro-9-(5-chloro-2-methoxybenzyl)-9H-purine

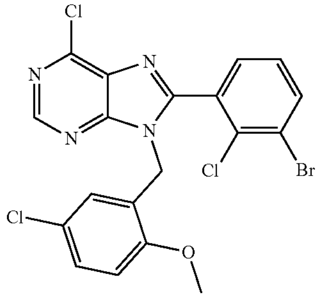 [SMILES: COc1ccc(Cl)cc1Cn1c(-c2cccc(Br)c2Cl)nc2c(Cl)ncnc21]

8-(3-Bromo-2-chlorophenyl)-6-chloro-9H-purine (8.0 g, 23.3 mmol) was added to 4-chloro-2-(chloromethyl)-1-methoxybenzene (4.44 g, 23.3 mmol) and DIPEA (12.2 mL, 69.8 mmol) in MeCN (200 mL). The resulting mixture was stirred at 80° C. for 3 hours. The reaction mixture was poured into water (500 mL) and extracted with EtOAc (3×400 mL). The organic layer was dried over $Na_2SO_4$, filtered and evaporated to afford the crude product, which was purified by flash silica chromatography, elution gradient 0 to 100% EtOAc in petroleum ether. Pure fractions were evaporated to dryness to afford 8-(3-bromo-2-chlorophenyl)-6-chloro-9-(5-chloro-2-methoxybenzyl)-9H-purine (9.00 g, 78%) as a yellow solid. $^1$H NMR (500 MHz, DMSO-$d_6$): 3.45 (3H, s), 5.34 (2H, s), 6.79-6.89 (2H, m), 7.24 (1H, dd), 7.44 (1H, t), 7.62 (1H, dd), 8.01 (1H, dd), 8.91 (1H, s). m/z: ES+ [M+H]+ 497.

8-(3-bromo-2-chlorophenyl)-9-(5-chloro-2-methoxy-benzyl)-6-(1-methylcyclopropoxy)-9H-purine

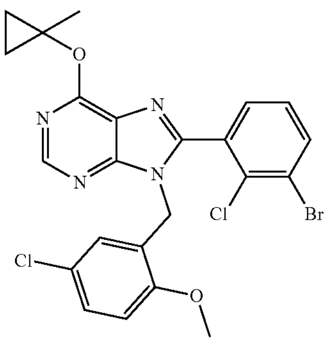 [SMILES: COc1ccc(Cl)cc1Cn1c(-c2cccc(Br)c2Cl)nc2c(OC3(C)CC3)ncnc21]

NaH (3.21 g, 80.23 mmol) was added to 15-crown-5 (0.353 g, 1.60 mmol), 1-methylcyclopropan-1-ol (2.314 g, 32.09 mmol) and 8-(3-bromo-2-chlorophenyl)-6-chloro-9-(5-chloro-2-methoxybenzyl)-9H-purine (8 g, 16.05 mmol) in THF (200 mL). The resulting mixture was stirred at rt for 2 hours. The reaction mixture was poured into water (500 mL) and extracted with EtOAc (3×400 mL). The organic layer was dried over $Na_2SO_4$, filtered and evaporated to afford the crude product, which was purified by flash silica chromatography, elution gradient 0 to 100% EtOAc in petroleum ether. Pure fractions were evaporated to dryness to afford 8-(3-bromo-2-chlorophenyl)-9-(5-chloro-2-methoxybenzyl)-6-(1-methylcyclopropoxy)-9H-purine (8.00 g, 93%) as a yellow solid. $^1$H NMR (500 MHz, DMSO-$d_6$): 0.81-0.85 (2H, m), 0.98-1.04 (2H, m), 1.73 (3H, s), 3.48 (3H, s), 5.27 (2H, s), 6.84-6.89 (2H, m), 7.22 (1H, dd), 7.40 (1H, t), 7.54 (1H, dd), 7.96 (1H, dd), 8.67 (1H, s). m/z: ES+ [M+H]+ 533.

2-Chloro-3-(9-(5-chloro-2-methoxybenzyl)-6-(1-methylcyclopropoxy)-9H-purin-8-yl)phenol

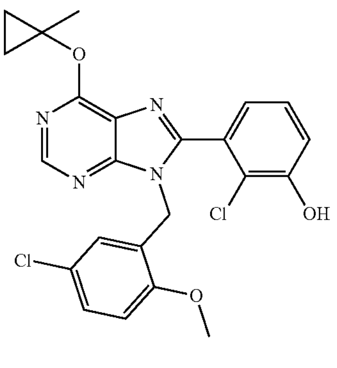 [SMILES: COc1ccc(Cl)cc1Cn1c(-c2cccc(O)c2Cl)nc2c(OC3(C)CC3)ncnc21]

8-(3-Bromo-2-chlorophenyl)-9-(5-chloro-2-methoxybenzyl)-6-(1-methylcyclopropoxy)-9H-purine (2 g, 3.74 mmol) was added to KOH (0.420 g, 7.49 mmol), $Pd_2(dba)_3$ (0.343 g, 0.37 mmol), 2-di-tert-butylphosphino-2',4',6'-triisopropyl-1,1'-biphenyl (0.159 g, 0.37 mmol) in 1,4-dioxane:water (1:1, 40 mL). The resulting mixture was stirred at 80° C. for 2 hours under nitrogen. The reaction mixture was poured into water (400 mL) and extracted with EtOAc (3×250 mL). The organic layer was dried over $Na_2SO_4$, filtered and evaporated to afford the crude product, which was purified by flash silica chromatography, elution gradient 0 to 100% EtOAc in petroleum ether. Pure fractions were evaporated to dryness to afford 2-chloro-3-(9-(5-chloro-2-methoxybenzyl)-6-(1-methylcyclopropoxy)-9H-purin-8-yl)phenol (1.50 g, 85%) as a yellow solid. $^1$H NMR (500 MHz, DMSO-$d_6$): 0.81-0.91 (2H, m), 1.03 (2H, d), 1.74 (3H, s), 3.54 (3H, s), 5.24 (2H, s), 6.77 (1H, d), 6.86-6.92 (2H, m), 7.15 (1H, dd), 7.21-7.28 (2H, m), 8.62 (1H, s), 10.57 (1H, s). m/z: ES+ [M+H]+ 471.

3-(2-Chloro-3-(9-(5-chloro-2-methoxybenzyl)-6-(1-methylcyclopropoxy)-9H-purin-8-yl)phenoxy)propan-1-ol

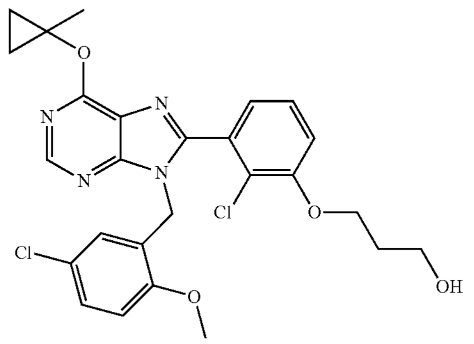 [SMILES: COc1ccc(Cl)cc1Cn1c(-c2cccc(OCCCO)c2Cl)nc2c(OC3(C)CC3)ncnc21]

2-Chloro-3-(9-(5-chloro-2-methoxybenzyl)-6-(1-methylcyclopropoxy)-9H-purin-8-yl)phenol (300 mg, 0.64 mmol) was added to 3-bromopropan-1-ol (88 mg, 0.64 mmol) and $K_2CO_3$ (88 mg, 0.64 mmol) in MeCN (5 mL). The resulting mixture was stirred at 80° C. for 2 hours. The reaction mixture was poured into water (25 mL) and extracted with EtOAc (3×15 mL). The organic layer was dried over $Na_2SO_4$, filtered and evaporated to afford a yellow solid, which was purified by flash silica chromatography, elution gradient 0 to 50% EtOAc in petroleum ether. Pure fractions were evaporated to dryness to afford 3-(2-chloro-3-(9-(5-chloro-2-methoxybenzyl)-6-(1-methylcyclopropoxy)-9H-purin-8-yl)phenoxy)propan-1-ol (250 mg, 74%) as a colourless oil which solidified on standing. $^1$H NMR (500 MHz, DMSO-$d_6$): 0.83-0.86 (2H, m), 1.03 (2H, d), 1.74 (3H, s), 1.9-1.94 (2H, m), 3.51 (3H, s), 3.61 (2H, q), 4.20 (2H, t), 4.59 (1H, t), 5.24 (2H, s), 6.78 (1H, d), 6.88 (1H, d), 7.03 (1H, dd), 7.24 (1H, dd), 7.34 (1H, dd), 7.38-7.42 (1H, m), 8.64 (1H, s). m/z: ES+ [M+H]+ 529.

Example 50

4-(2-Chloro-3-(9-(5-chloro-2-methoxybenzyl)-6-(1-methylcyclopropoxy)-9H-purin-8-yl)phenoxy)-3-methylbutanoic Acid (Isomer 1)

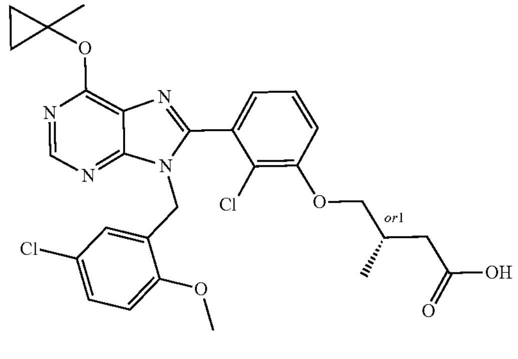

isomer 1

(unknown absolute stereochemistry)

LiOH (14.72 mg, 0.61 mmol) was added to 4-(2-chloro-3-(9-(5-chloro-2-methoxybenzyl)-6-(1-methylcyclopropoxy)-9H-purin-8-yl)phenoxy)-3-methylbutanoate (isomer 1) (120 mg, 0.20 mmol) in THF:water (1:1, 3 mL). The resulting mixture was stirred at rt for 2 hours. The reaction mixture was adjusted to pH 6 with HCl, poured into water (100 mL) and extracted with EtOAc (3x75 mL). The organic layer was dried over $Na_2SO_4$, filtered and evaporated to afford the crude product, which was purified by preparative HPLC (Column: Xselect CSH Prep C18 OBD, 30*150 mm, 5 μm) using decreasingly polar mixtures of water (containing 0.1% aq. $NH_3$ and 10 mmol/L $NH_4HCO_3$) and MeCN as eluents. Fractions containing the desired compound were evaporated to dryness and lyophilized to afford 4-(2-chloro-3-(9-(5-chloro-2-methoxybenzyl)-6-(1-methylcyclopropoxy)-9H-purin-8-yl)phenoxy)-3-methylbutanoic acid (isomer 1) (40.0 mg, 34%) as a white solid. $^1$H NMR (400 MHz, DMSO-d$_6$): 0.85 (2H, d), 0.93-1.08 (5H, m), 1.74 (3H, s), 2.19 (1H, dd), 2.35 (1H, dt), 2.42-2.48 (1H, m), 3.51 (3H, s), 3.94-4.21 (2H, m), 5.24 (2H, s), 6.78 (1H, d), 6.87 (1H, d), 7.03 (1H, dd), 7.22 (1H, dd), 7.33 (1H, d), 7.39 (1H, t), 8.64 (1H, s). One proton not observed. m/z: ES+ [M+H]+ 571.

4-(2-Chloro-3-(9-(5-chloro-2-methoxybenzyl)-6-(1-methylcyclopropoxy)-9H-purin-8-yl)phenoxy)-3-methylbutanoate (isomer 1) used as a starting material was prepared as follows.

4-(2-Chloro-3-(9-(5-chloro-2-methoxybenzyl)-6-(1-methylcyclopropoxy)-9H-purin-8-yl)phenoxy)-3-methylbutanoate (Isomer 1 and 2)

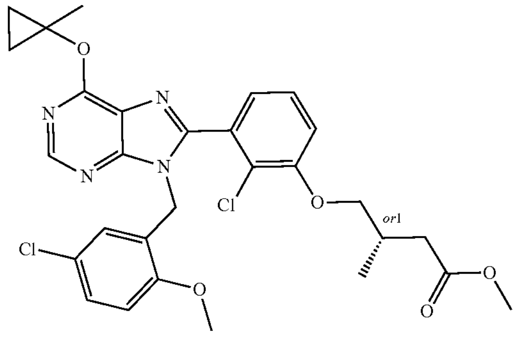

isomer 1

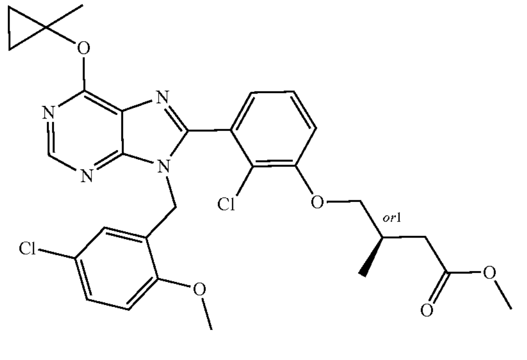

isomer 2

(unknown absolute stereochemistry)

$K_2CO_3$ (308 mg, 2.23 mmol) was added to 4-bromo-3-methylbutanoate (290 mg, 1.49 mmol, racemic), 2-chloro-3-(9-(5-chloro-2-methoxybenzyl)-6-(1-methylcyclopropoxy)-9H-purin-8-yl)phenol (350 mg, 0.74 mmol, Intermediate Example 49) in MeCN (10 mL). The resulting mixture was stirred at 80° C. for 2 hours. The reaction mixture was poured into water (200 mL) and extracted with EtOAc (3x200 mL). The organic layer was dried over $Na_2SO_4$, filtered and evaporated to afford the crude product, which was purified by flash silica chromatography, elution gradient 0 to 100% EtOAc in petroleum ether. Relevant fractions were evaporated to dryness to give 4-(2-chloro-3-(9-(5-chloro-2-methoxybenzyl)-6-(1-methylcyclopropoxy)-9H-purin-8-yl)phenoxy)-3-methylbutanoate (racemic mixture). The two enantiomers were separated by preparative chiral HPLC (CHIRALPAK IH-3 4.6x50 mm 3 μm), Mobile Phase: Hexane (0.1% DEA):EtOH (80:20) isocratic. The fractions containing the enantiomer eluting first were evaporated to dryness to afford 4-(2-chloro-3-(9-(5-chloro-2-methoxybenzyl)-6-(1-methylcyclopropoxy)-9H-purin-8-yl)phenoxy)-3-methylbutanoate (isomer 1) (130 mg, 30%) as a white solid. The fractions containing the enantiomer eluting second were evaporated to dryness to afford 4-(2-chloro-3-(9-(5-chloro-2-methoxybenzyl)-6-(1-methylcyclopropoxy)-9H-purin-8-yl)phenoxy)-3-methylbutanoate (100 mg, 23%) (isomer 2) as a white solid.

Isomer 1: $^1$H NMR (500 MHz, DMSO-d$_6$): 0.83 (2H, s), 1.05 (5H, q), 1.73 (3H, s), 2.37 (2H, ddd), 2.58 (1H, dd), 3.50 (3H, s), 3.61 (3H, s), 4.01 (2H, d), 5.25 (2H, s), 6.93 (2H, s), 7.04 (1H, d), 7.15-7.51 (3H, m), 8.64 (1H, s). m/z: ES+ [M+H]+ 585.

Isomer 2: $^1$H NMR (500 MHz, DMSO-$d_6$): 0.81-0.89 (2H, m), 1.01-1.08 (5H, m), 1.73 (3H, s), 2.38 (2H, ddt), 2.56-2.64 (1H, m), 3.50 (3H, s), 3.61 (3H, s), 3.96-4.05 (2H, m), 5.25 (2H, s), 6.77 (1H, d), 6.87 (1H, s), 7.04 (1H, dd), 7.21 (1H, dd), 7.33 (1H, d), 7.39 (1H, t), 8.64 (1H, s). m/z: ES+ [M+H]+=585.

Example 51

4-(2-Chloro-3-(9-(5-chloro-2-methoxybenzyl)-6-(1-methylcyclopropoxy)-9H-purin-8-yl)phenoxy)-3-methylbutanoic Acid (Isomer 2)

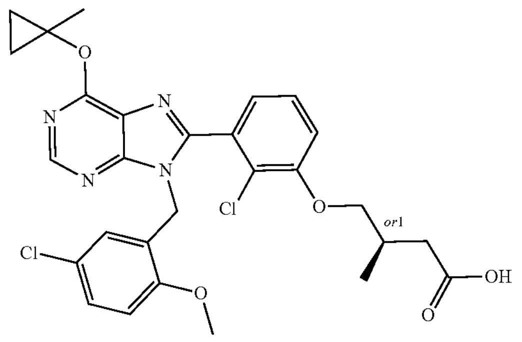

isomer 2

(unknown absolute stereochemistry)

Prepared in a similar manner to Example 50, using 4-(2-chloro-3-(9-(5-chloro-2-methoxybenzyl)-6-(1-methylcyclopropoxy)-9H-purin-8-yl)phenoxy)-3-methylbutanoate (isomer 2) (90 mg, see Example 50 intermediate) to yield 4-(2-Chloro-3-(9-(5-chloro-2-methoxybenzyl)-6-(1-methylcyclopropoxy)-9H-purin-8-yl)phenoxy)-3-methylbutanoic acid (isomer 2) as a white solid (30 mg, 34%).

$^1$H NMR (400 MHz, DMSO-$d_6$): 0.85 (2H, t), 0.95-1.08 (5H, m), 1.73 (3H, s), 2.18 (1H, dd), 2.36 (1H, dq), 2.45 (1H, dd), 3.49 (3H, s), 3.97 (1H, dd), 4.04 (1H, dd), 5.24 (2H, s), 6.78 (1H, d), 6.86 (1H, d), 7.02 (1H, dd), 7.22 (1H, dd), 7.33 (1H, dd), 7.38 (1H, t), 8.64 (1H, s). One proton not observed. m/z: ES+ [M+H]+ 571.

Example 52

(1s,3s)-3-(2-chloro-3-(9-(5-chloro-2-methoxybenzyl)-6-(1-methylcyclopropoxy)-9H-purin-8-yl)phenoxy)cyclobutane-1-carboxylic Acid

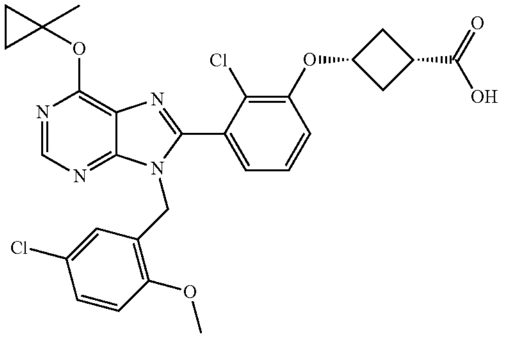 [SMILES: COc1ccc(Cl)cc1Cn1c(-c2cccc(O[C@H]3C[C@@H](C(=O)O)C3)c2Cl)nc2c(OC3(C)CC3)ncnc21]

LiOH (13.54 mg, 0.57 mmol) was added to methyl (1s,3s)-3-(2-chloro-3-(9-(5-chloro-2-methoxybenzyl)-6-(1-methylcyclopropoxy)-9H-purin-8-yl)phenoxy)cyclobutane-1-carboxylate (110 mg, 0.19 mmol) in THF:$H_2O$ (1:1, 5 mL). The resulting mixture was stirred at 60° C. for 2 hours, then cooled and adjusted to pH 5 with 2M HCl. The reaction mixture was poured into water (50 mL) and extracted with EtOAc (3×25 mL). The organic layer was dried over $Na_2SO_4$, filtered and evaporated to afford a white solid, which was purified by preparative HPLC (Column: Xbridge Prep C18 OBD, 30*150 mm, 5 μm) using decreasingly polar mixtures of water (containing 0.1% aq. $NH_3$ and 10 mmol/L $NH_4HCO_3$) and MeCN as eluents. Fractions containing the desired compound were evaporated to dryness to afford (1s,3s)-3-(2-chloro-3-(9-(5-chloro-2-methoxybenzyl)-6-(1-methylcyclopropoxy)-9H-purin-8-yl)phenoxy)cyclobutane-1-carboxylic acid (57.0 mg, 53%) as a white solid. $^1$H NMR (400 MHz, DMSO-$d_6$): 0.81-0.86 (2H, m), 1.02 (2H, d), 1.74 (3H, s), 2.24 (2H, dd), 2.72 (3H, s), 3.49 (3H, s), 4.75 (1H, d), 5.24 (2H, s), 6.77 (1H, d), 6.88 (1H, d), 6.99-7.03 (1H, m), 7.18 (1H, d), 7.23 (1H, dd), 7.36 (1H, t), 8.64 (1H, s) One proton not observed. m/z: ES+ [M+H]+ 569.

Methyl (1s,3s)-3-(2-chloro-3-(9-(5-chloro-2-methoxybenzyl)-6-(1-methylcyclopropoxy)-9H-purin-8-yl)phenoxy) cyclobutane-1-carboxylate used as a starting material was prepared as follows.

Methyl (1s,3s)-3-(2-chloro-3-(9-(5-chloro-2-methoxybenzyl)-6-(1-methylcyclopropoxy)-9H-purin-8-yl)phenoxy)cyclobutane-1-carboxylate

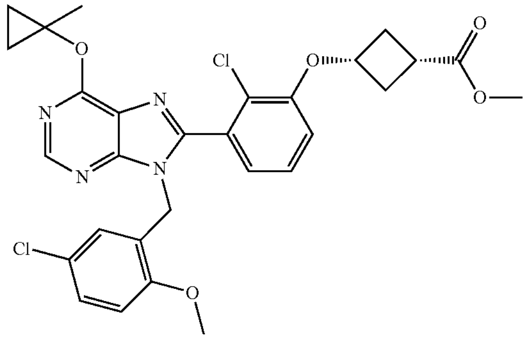 [SMILES: COc1ccc(Cl)cc1Cn1c(-c2cccc(O[C@H]3C[C@@H](C(=O)OC)C3)c2Cl)nc2c(OC3(C)CC3)ncnc21]

2-Chloro-3-(9-(5-chloro-2-methoxybenzyl)-6-(1-methylcyclopropoxy)-9H-purin-8-yl)phenol (140 mg, 0.30 mmol, Intermediate Example 49) was added to methyl (1r,3r)-3-hydroxycyclobutane-1-carboxylate (77 mg, 0.59 mmol), diisopropyl (E)-diazene-1,2-dicarboxylate (0.28 mL, 1.49 mmol) and triphenylphosphine (390 mg, 1.49 mmol) in THF (5 mL) under nitrogen. The resulting mixture was stirred at 40° C. for 1 hour. The reaction mixture was poured into water (50 mL) and extracted with EtOAc (3×25 mL). The organic layer was dried over $Na_2SO_4$, filtered and evaporated to afford the crude product, which was purified by flash silica chromatography, elution gradient 0 to 100% EtOAc in petroleum ether. Pure fractions were evaporated to dryness to afford methyl (1s,3s)-3-(2-chloro-3-(9-(5-chloro-2-methoxybenzyl)-6-(1-methylcyclopropoxy)-9H-purin-8-yl) phenoxy)cyclobutane-1-carboxylate (140 mg, 81%) as a white solid. $^1$H NMR (400 MHz, DMSO-$d_6$): 0.78-0.85 (2H, m), 1.00 (2H, d), 1.72 (3H, s), 2.26 (2H, dt), 2.74-2.84 (2H, m), 2.86-2.96 (1H, m), 3.48 (3H, s), 3.62 (3H, s), 4.78 (1H, q), 5.22 (2H, s), 6.75 (1H, d), 6.86 (1H, d), 6.99-7.03 (1H, m), 7.16 (1H, dd), 7.21 (1H, dd), 7.35 (1H, t), 8.62 (1H, s). m/z: ES+ [M+H]+ 583.

Example 53

(R)-4-(2-Chloro-3-(9-(5-chloro-2-cyanobenzyl)-6-(1-methylcyclopropoxy)-9H-purin-8-yl)phenoxy)-2-methylbutanoic Acid

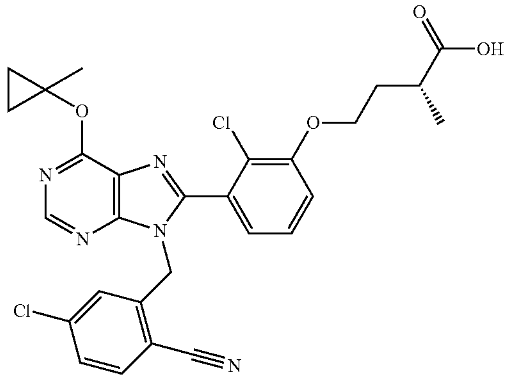 [SMILES: C[C@H](CCOc1cccc(-c2nc3c(OC4(C)CC4)ncnc3n2Cc2cc(Cl)ccc2C#N)c1Cl)C(=O)O]

LiOH (30.0 mg, 1.25 mmol) was added to 4-chloro-2-((8-(2-chloro-3-((R)-4-((R)-4-isopropyl-2-oxooxazolidin-3-yl)-3-methyl-4-oxobutoxy)phenyl)-6-(1-methylcyclopropoxy)-9H-purin-9-yl)methyl)benzonitrile (170 mg, 0.25 mmol) in water (1 mL) and THF (3 mL) at 25° C. The resulting mixture was stirred at 25° C. for 2 hours. The reaction mixture was diluted with EtOAc (20 mL), and washed sequentially with water (20 mL×3). The organic layer was dried over $Na_2SO_4$, filtered and evaporated to afford the crude product. The crude product was purified by preparative HPLC (Column: Xbridge Prep C18 OBD, 30*150 mm, 5 μm) using decreasingly polar mixtures of water (containing 0.1% aq. $NH_3$ and 10 mmol/L $NH_4HCO_3$) and MeCN as eluents. Fractions containing the desired compound were evaporated to dryness to afford (R)-4-(2-chloro-3-(9-(5-chloro-2-cyanobenzyl)-6-(1-methylcyclopropoxy)-9H-purin-8-yl)phenoxy)-2-methylbutanoic acid (38.0 mg, 26.7%) as a white solid. $^1H$ NMR (400 MHz, DMSO-$d_6$): 0.86 (2H, t), 1.03 (2H, t), 1.15 (3H, d), 1.75 (3H, s), 1.76-1.81 (1H, m), 2.03-2.13 (1H, m), 2.54-2.58 (1H, m), 4.13 (2H, t), 5.50 (2H, s), 7.06 (1H, dd), 7.10 (1H, d), 7.3-7.38 (2H, m), 7.50 (1H, dd), 7.75 (1H, d), 8.66 (1H, s); one H not seen. m/z: (ES+) [M+H]+ 566

4-Chloro-2-((8-(2-chloro-3-((R)-4-((R)-4-isopropyl-2-oxooxazolidin-3-yl)-3-methyl-4-oxobutoxy)phenyl)-6-(1-methylcyclopropoxy)-9H-purin-9-yl)methyl)benzonitrile used as starting material was prepared as follows:

2-((8-(3-Bromo-2-chlorophenyl)-6-chloro-9H-purin-9-yl)methyl)-4-chlorobenzonitrile

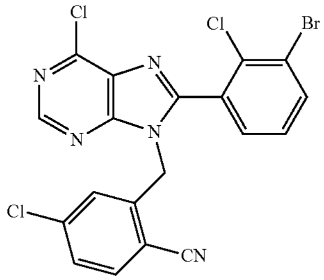 [SMILES: N#Cc1ccc(Cl)cc1Cn1c(-c2cccc(Br)c2Cl)nc2c(Cl)ncnc21]

2-(Bromomethyl)-4-chlorobenzonitrile (5.03 g, 21.80 mmol) was added to 8-(3-bromo-2-chlorophenyl)-6-chloro-9H-purine (5 g, 14.54 mmol, see Intermediate Example 49) and $K_2CO_3$ (6.03 g, 43.61 mmol) in MeCN (20 mL) at 25° C. The resulting mixture was stirred at 80° C. for 2 hours. The reaction mixture was diluted with EtOAc (25 mL) and washed sequentially with water (25 mL×3). The organic layer was dried over $Na_2SO_4$, filtered and evaporated to afford the crude product. The crude product was purified by flash silica chromatography, elution gradient 0 to 100% EtOAc in petroleum ether. Pure fractions were evaporated to dryness to afford 2-((8-(3-bromo-2-chlorophenyl)-6-chloro-9H-purin-9-yl)methyl)-4-chlorobenzonitrile (4.20 g, 58%) as a yellow solid. $^1H$ NMR (300 MHz, DMSO-$d_6$): 5.62 (2H, s), 7.23 (1H, d), 7.43 (1H, t), 7.54 (1H, dd), 7.67 (1H, dd), 7.78 (1H, d), 7.99 (1H, dd), 8.94 (1H, s); m/z: (ES+) [M+H]+ 494 {$^{37}Cl$, 2 $^{35}Cl$ and $^{79}Br$ isotopes}

2-((8-(3-Bromo-2-chlorophenyl)-6-(1-methylcyclopropoxy)-9H-purin-9-yl)methyl)-4-chlorobenzonitrile

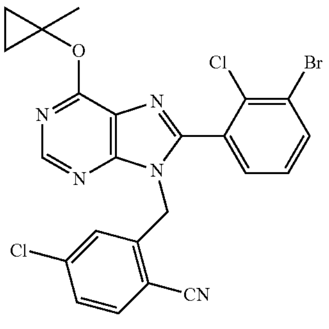 [SMILES: CC1(Oc2ncnc3c2nc(-c2cccc(Br)c2Cl)n3Cc2cc(Cl)ccc2C#N)CC1]

NaH (0.583 g, 24.31 mmol) was added to 2-((8-(3-bromo-2-chlorophenyl)-6-chloro-9H-purin-9-yl)methyl)-4-chlorobenzonitrile (4.0 g, 8.10 mmol), 1-methylcyclopropan-1-ol (1.17 g, 16.21 mmol) and 15-crown-5 (0.268 g, 1.22 mmol) in THF (80 mL) cooled to 0° C. under nitrogen. The resulting mixture was stirred at 0° C. for 1 hour. The reaction mixture was diluted with EtOAc (50 mL), and washed sequentially with water (50 mL×3). The organic layer was dried over $Na_2SO_4$, filtered and evaporated to afford the crude product. The crude product was purified by flash silica chromatography, elution gradient 0 to 100% EtOAc in petroleum ether. Pure fractions were evaporated to dryness to afford 2-((8-(3-bromo-2-chlorophenyl)-6-(1-methylcyclopropoxy)-9H-purin-9-yl)methyl)-4-chlorobenzonitrile (4.00 g, 93%) as a yellow solid. $^{1}H$ NMR (300 MHz, DMSO-$d_6$): 0.87 (2H, d), 1.03 (2H, t), 1.75 (3H, s), 5.53 (2H, s), 7.17 (1H, d), 7.39 (1H, t), 7.53 (1H, dd), 7.59 (1H, dd), 7.77 (1H, d), 7.96 (1H, dd), 8.69 (1H, s). m/z: (ES+) [M+H]+ 530 {$^{37}Cl$, $^{35}Cl$ and $^{79}Br$ isotopes}.

4-Chloro-2-((8-(2-chloro-3-hydroxyphenyl)-6-(1-methylcyclopropoxy)-9H-purin-9-yl)methyl)benzonitrile

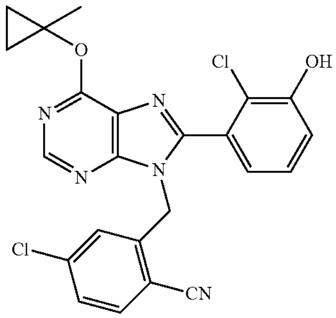 [SMILES: CC1(Oc2ncnc3c2nc(-c2cccc(O)c2Cl)n3Cc2cc(Cl)ccc2C#N)CC1]

4,4,4',4',5,5,5',5'-Octamethyl-2,2'-bi(1,3,2-dioxaborolane) (9.36 g, 36.85 mmol) was added to 2-((8-(3-bromo-2-chlorophenyl)-6-(1-methylcyclopropoxy)-9H-purin-9-yl)methyl)-4-chlorobenzonitrile (3.9 g, 7.37 mmol), potassium acetate (2.17 g, 22.11 mmol) and [1,1'-bis(diphenylphosphino)ferrocene]dichloropalladium(II) (0.541 g, 0.74 mmol) in 1,4-dioxane (80 mL) under nitrogen. The resulting mixture was stirred at 80° C. for 1 hour. Sodium perborate (6.03 g, 73.69 mmol) in water (20 mL) at 25° C. was then added. The resulting mixture was stirred at 25° C. for 2 hours. The reaction mixture was diluted with EtOAc (50 mL), and washed sequentially with water (50 mL×3). The organic layer was dried over $Na_2SO_4$, filtered and evaporated to afford the crude product. The crude product was purified by flash silica chromatography, elution gradient 0 to 100% EtOAc in petroleum ether. Pure fractions were evaporated to dryness to afford 4-chloro-2-((8-(2-chloro-3-hydroxyphenyl)-6-(1-methylcyclopropoxy)-9H-purin-9-yl)methyl)benzonitrile (2.00 g, 58.2%) as a yellow solid. $^{1}H$ NMR (300 MHz, DMSO-$d_6$): 0.87 (2H, t), 1.01-1.06 (2H, m), 1.75 (3H, s), 5.50 (2H, s), 6.91 (1H, dd), 7.08-7.11 (1H, m), 7.13 (1H, d), 7.22 (1H, dd), 7.52 (1H, dd), 7.77 (1H, d), 8.65 (1H, s), 10.56 (1H, s). m/z: (ES+) [M+H]+ 466.

4-Chloro-2-((8-(2-chloro-3-((R)-4-((R)-4-isopropyl-2-oxooxazolidin-3-yl)-3-methyl-4-oxobutoxy)phenyl)-6-(1-methylcyclopropoxy)-9H-purin-9-yl)methyl)benzonitrile

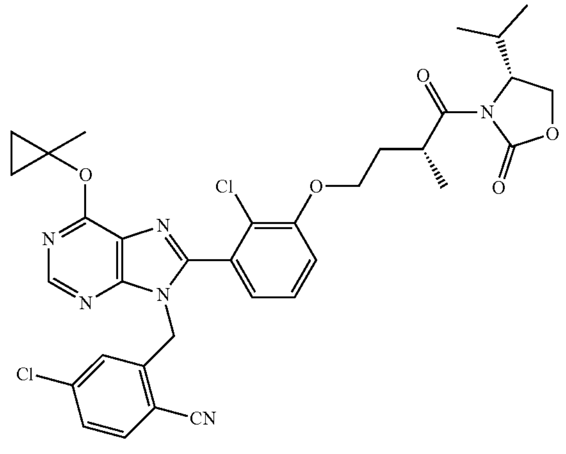 [SMILES: CC(C)[C@@H]1COC(=O)N1C(=O)[C@H](C)CCOc1cccc(-c2nc3c(OC4(C)CC4)ncnc3n2Cc2cc(Cl)ccc2C#N)c1Cl]

$K_2CO_3$ (225 mg, 1.63 mmol) was added to 4-chloro-2-((8-(2-chloro-3-hydroxyphenyl)-6-(1-methylcyclopropoxy)-9H-purin-9-yl)methyl)benzonitrile (190 mg, 0.41 mmol) and (R)-3-((R)-4-bromo-2-methylbutanoyl)-4-isopropyloxazolidin-2-one (143 mg, 0.49 mmol, see Intermediate Example 47) in MeCN (5 mL) at 25° C. The resulting mixture was stirred at 45° C. for 2 hours. The reaction mixture was diluted with EtOAc (20 mL), and washed sequentially with water (20 mL×3). The organic layer was dried over $Na_2SO_4$, filtered and evaporated to afford the crude product. The crude product was purified by flash silica chromatography, elution gradient 0 to 100% EtOAc in petroleum ether. Pure fractions were evaporated to dryness to afford 4-chloro-2-((8-(2-chloro-3-((R)-4-((R)-4-isopropyl-2-oxooxazolidin-3-yl)-3-methyl-4-oxobutoxy)phenyl)-6-(1-methylcyclopropoxy)-9H-purin-9-yl)methyl)benzonitrile (207 mg, 75%) as a yellow gum. $^{1}H$ NMR (300 MHz, DMSO-$d_6$): 0.76-0.77 (2H, m), 0.79-0.81 (2H, m), 1.06 (6H, s), 1.20 (3H, d), 1.73 (3H, s), 2.07-2.23 (4H, m), 3.92-4.00 (1H, m), 4.05-4.14 (2H, m), 4.36-4.42 (2H, m), 5.47 (2H, s), 7.02 (1H, dd), 7.08 (1H, d), 7.27-7.37 (2H, m), 7.49 (1H, dd), 7.74 (1H, d), 8.64 (1H, s). m/z: (ES+) [M+H]+ 677.

Example 54

(S)-4-(2-Chloro-3-(9-(5-chloro-2-cyanobenzyl)-6-(1-methylcyclopropoxy)-9H-purin-8-yl)phenoxy)-2-methylbutanoic Acid

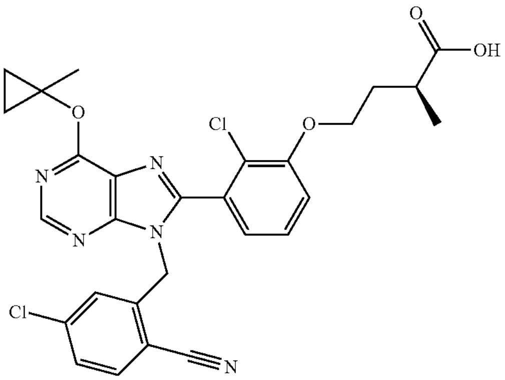 [SMILES: C[C@@H](CCOc1cccc(-c2nc3c(OC4(C)CC4)ncnc3n2Cc2cc(Cl)ccc2C#N)c1Cl)C(=O)O]

LiOH (31.8 mg, 1.33 mmol) was added to 4-chloro-2-((8-(2-chloro-3-((S)-4-((S)-4-isopropyl-2-oxooxazolidin-3-yl)-3-methyl-4-oxobutoxy)phenyl)-6-(1-methylcyclopropoxy)-9H-purin-9-yl)methyl)benzonitrile (180 mg, 0.27 mmol) in water (0.1 mL) and THF (0.3 mL) at 25° C. The resulting mixture was stirred at 25° C. for 2 hours. The reaction mixture was diluted with EtOAc (20 mL), and washed sequentially with water (20 mL×3). The organic layer was dried over $Na_2SO_4$, filtered and evaporated to afford the crude product. The crude product was purified by preparative HPLC (Column: YMC-Actus Triant C18 Column, 30*75 mm, 3 μm) using decreasingly polar mixtures of water (containing 0.1% aq. $NH_3$ and 10 mmol/L $NH_4HCO_3$) and MeCN as eluents. Fractions containing the desired compound were evaporated to dryness to afford (S)-4-(2-chloro-3-(9-(5-chloro-2-cyanobenzyl)-6-(1-methylcyclopropoxy)-9H-purin-8-yl)phenoxy)-2-methylbutanoic acid (40.0 mg, 27%) as a white solid. $^{1}H$ NMR (300 MHz, DMSO-$d_6$): 0.86 (2H, t), 1.03 (2H, t), 1.15 (3H, d), 1.75 (3H, s), 1.76-1.82 (1H, m), 2.03-2.14 (1H, m), 2.54-2.59 (1H, m), 4.13 (2H, t), 5.50 (2H, s), 7.06 (1H, dd), 7.10 (1H, d), 7.3-7.39 (2H, m), 7.50 (1H, dd), 7.75 (1H, d), 8.66 (1H, s). One H not seen. m/z: (ES+) [M+H]+ 566.

4-Chloro-2-((8-(2-chloro-3-((S)-4-((S)-4-isopropyl-2-oxooxazolidin-3-yl)-3-methyl-4-oxobutoxy)phenyl)-6-(1-methylcyclopropoxy)-9H-purin-9-yl)methyl)benzonitrile used as starting material was prepared as follows.

4-Chloro-2-((8-(2-chloro-3-((S)-4-((S)-4-isopropyl-2-oxooxazolidin-3-yl)-3-methyl-4-oxobutoxy)phenyl)-6-(1-methylcyclopropoxy)-9H-purin-9-yl)methyl)benzonitrile

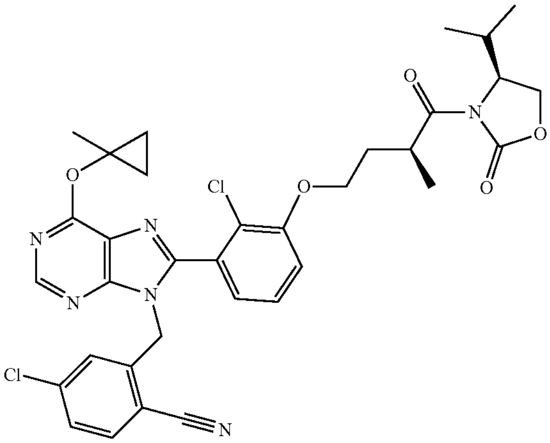 [SMILES: CC(C)[C@H]1COC(=O)N1C(=O)[C@@H](C)CCOc1cccc(-c2nc3c(OC4(C)CC4)ncnc3n2Cc2cc(Cl)ccc2C#N)c1Cl]

$K_2CO_3$ (225 mg, 1.63 mmol) was added to 4-chloro-2-((8-(2-chloro-3-hydroxyphenyl)-6-(1-methylcyclopropoxy)-9H-purin-9-yl)methyl)benzonitrile (190 mg, 0.41 mmol, Intermediate Example 53) and (S)-3-((S)-4-bromo-2-methylbutanoyl)-4-isopropyloxazolidin-2-one (143 mg, 0.49 mmol, Intermediate Example 48) in MeCN (2 mL) at 25° C. The resulting mixture was stirred at 45° C. for 2 hours. The reaction mixture was diluted with EtOAc (20 mL), and washed sequentially with water (20 mL×3). The organic layer was dried over $Na_2SO_4$, filtered and evaporated to afford the crude product. The crude product was purified by flash silica chromatography, elution gradient 0 to 100% EtOAc in petroleum ether. Pure fractions were evaporated to dryness to afford 4-chloro-2-((8-(2-chloro-3-((S)-4-((S)-4-isopropyl-2-oxooxazolidin-3-yl)-3-methyl-4-oxobutoxy)phenyl)-6-(1-methylcyclopropoxy)-9H-purin-9-yl)methyl)benzonitrile (196 mg, 71%) as a yellow gum. $^1H$ NMR (300 MHz, DMSO-$d_6$): 0.76-0.77 (2H, m), 0.79-0.81 (2H, m), 1.06 (6H, s), 1.20 (3H, d), 1.73 (3H, s), 2.07-2.23 (4H, m), 3.92-4 (1H, m), 4.05-4.14 (2H, m), 4.36-4.42 (2H, m), 5.47 (2H, s), 7.02 (1H, dd), 7.08 (1H, d), 7.27-7.37 (2H, m), 7.49 (1H, dd), 7.74 (1H, d), 8.64 (1H, s). m/z: (ES+) [M+H]+ 677.

TABLE 1C

Assay Results for Examples 47-52

| Example # | POLQ Enz Lumin Primary CR GMean pIC50 | POLQ PD Prolif Lumin BRCA2 −/− mean pIC50 | POLQ PD Prolif Lumin DLD1 mean pIC50 |
|---|---|---|---|
| 47 | 8.2 | 7.6 | <5.1 |
| 48 | 8.3 | 7.4 | <5.0 |
| 49 | 8.1 | 7.8 | <5.0 |
| 50 | 8.2 | 8.2 | <5.0 |
| 51 | 8.2 | 8.1 | <5.0 |
| 52 | 8.4 | 7.9 | <5.0 |

Example 53: Further Examples

The following examples in Tables T and U were synthesised using similar methods previously exemplified in Examples 1-27, 30-46 and 47-54 and assayed as described in Examples 28 and 29.

TABLE T

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T1 | 2-(3-chloro-4-(9-((5-methyl-1,3,4-thiadiazol-2-yl)methyl)-6-(1-methylcyclopropoxy)-9H-purin-8-yl)phenyl)acetamide | 470 | C21 H20 Cl N7 O2 S | 6.1 | <5.0 | |
| T2 | 2-(3-chloro-4-(9-((5-methyl-1,3,4-oxadiazol-2-yl)methyl)-6-(1-methylcyclopropoxy)-9H-purin-8-yl)phenyl)acetamide | 454 | C21 H20 Cl N7 O3 | 5.2 | <5.0 | |
| T3 | 3-chloro-4-(6-(1-methylcyclopropoxy)-9-((4-methylpyridin-2-yl)methyl)-9H-purin-8-yl)aniline | 421 | C22 H21 Cl N6 O | 8.1 | 6.7 | |
| T4 | 2-(3-chloro-4-(6-(1-methylcyclopropoxy)-9-((5-methylthiazol-2-yl)methyl)-9H-purin-8-yl)phenyl)acetamide | 469 | C22 H21 Cl N6 O2 S | 7.8 | 5.9 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T5 | 2-(3-chloro-4-(6-(1-methylcyclopropoxy)-9-((2-methylthiazol-5-yl)methyl)-9H-purin-8-yl)phenyl)acetamide | 469 | C22 H21 Cl N6 O2 S | 7.4 | <5.1 | |
| T6 | 2-(3-chloro-4-(6-(1-methylcyclopropoxy)-9-((2-methylthiazol-4-yl)methyl)-9H-purin-8-yl)phenyl)acetamide | 469 | C22 H21 Cl N6 O2 S | 7.2 | 5.1 | |
| T7 | 2-(3-chloro-4-(6-(1-methylcyclopropoxy)-9-(2-(thiazol-2-yl)ethyl)-9H-purin-8-yl)phenyl)acetamide | 469 | C22 H21 Cl N6 O2 S | 6.2 | <5.0 | |
| T8 | 2-(3-chloro-4-(6-(1-methylcyclopropoxy)-9-(thiazol-5-ylmethyl)-9H-purin-8-yl)phenoxy)-N-methylacetamide | 485 | C22 H21 Cl N6 O3 S | 7.1 | 5.3 | |
| T9 | 3-chloro-4-(6-(1-methylcyclopropoxy)-9-((4-methylpyridin-2-yl)methyl)-9H-purin-8-yl)benzenesulfonamide | 485 | C22 H21 Cl N6 O3 S | 8 | 6.3 | <5.0 |
| T10 | 2-(3-chloro-4-(9-((5-ethyl-1,3,4-oxadiazol-2-yl)methyl)-6-(1-methylcyclopropoxy)-9H-purin-8-yl)phenyl)acetamide | 468 | C22 H22 Cl N7 O3 | 5.7 | | |
| T11 | 3-chloro-4-(9-(3-chlorobenzyl)-6-(1-methylcyclopropoxy)-9H-purin-8-yl)benzoic acid | 469 | C23 H18 Cl2 N4 O3 | 8.1 | 6.1 | |
| T12 | 2-chloro-3-(9-(3-chlorobenzyl)-6-(1-methylcyclopropoxy)-9H-purin-8-yl)benzoic acid | 469 | C23 H18 Cl2 N4 O3 | 8 | <5.0 | <5.0 |
| T13 | 3-chloro-4-(6-(1-methylcyclopropoxy)-9-((4-methylpyridin-2-yl)methyl)-9H-purin-8-yl)benzoic acid | 450 | C23 H20 Cl N5 O3 | 8.2 | <5.0 | <5.0 |
| T14 | 3-chloro-4-(6-(1-methylcyclopropoxy)-9-((4-methylpyridin-2-yl)methyl)-9H-purin-8-yl)benzamide | 449 | C23 H21 Cl N6 O2 | 8.2 | 6.3 | <5.0 |
| T15 | 2-(3-chloro-4-(9-((4-chloropyridin-2-yl)methyl)-6-(1-methylcyclopropoxy)-9H-purin-8-yl)phenoxy)ethan-1-ol | 486 | C23 H21 Cl2 N5 O3 | 8 | 7 | <5.0 |
| T16 | 8-(2-chloro-4-(methylsulfonyl)phenyl)-6-(1-methylcyclopropoxy)-9-((4-methylpyridin-2-yl)methyl)-9H-purine | 484 | C23 H22 Cl N5 O3 S | 7.9 | 6.1 | <5.0 |
| T17 | 2-(3-chloro-4-(6-(1-methylcyclopropoxy)-9-((3-methylpyridazin-4-yl)methyl)-9H-purin-8-yl)phenyl)acetamide | 464 | C23 H22 Cl N7 O2 | 5 | <5.0 | |
| T18 | 2-(3-chloro-4-(6-(1-methylcyclopropoxy)-9-((5-methylpyridazin-3-yl)methyl)-9H-purin-8-yl)phenyl)acetamide | 464 | C23 H22 Cl N7 O2 | 6.7 | <5.0 | |
| T19 | 2-(3-chloro-4-(6-(1-methylcyclopropoxy)-9-((6-methylpyrimidin-4-yl)methyl)-9H-purin-8-yl)phenyl)acetamide | 464 | C23 H22 Cl N7 O2 | 6.2 | <5.0 | |
| T20 | 2-(3-chloro-4-(9-((5-cyclopropyl-1,3,4-thiadiazol-2-yl)methyl)-6-(1-methylcyclopropoxy)-9H-purin-8-yl)phenyl)acetamide | 496 | C23 H22 Cl N7 O2 S | 7.6 | 5.6 | |
| T21 | 2-(3-chloro-4-(9-((5-cyclopropyl-1,3,4-oxadiazol-2-yl)methyl)-6-(1-methylcyclopropoxy)-9H-purin-8-yl)phenyl)acetamide | 480 | C23 H22 Cl N7 O3 | 6.3 | <5.0 | |
| T22 | 2-(3-chloro-4-(9-((5-methoxypyridazin-3-yl)methyl)-6-(1-methylcyclopropoxy)-9H-purin-8-yl)phenyl)acetamide | 480 | C23 H22 Cl N7 O3 | 6.2 | 5.4 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T23 | 2-(3-chloro-4-(9-((3-cyclopropyl-1,2,4-oxadiazol-5-yl)methyl)-6-(1-methylcyclopropoxy)-9H-purin-8-yl)phenyl)acetamide | 480 | C23 H22 Cl N7 O3 | 7.1 | 5.9 | |
| T24 | 2-(3-chloro-4-(9-((4,5-dimethylthiazol-2-yl)methyl)-6-(1-methylcyclopropoxy)-9H-purin-8-yl)phenyl)acetamide | 483 | C23 H23 Cl N6 O2 S | 7.9 | 6.1 | |
| T25 | 2-(3-chloro-4-(9-((2,4-dimethylthiazol-5-yl)methyl)-6-(1-methylcyclopropoxy)-9H-purin-8-yl)phenyl)acetamide | 483 | C23 H23 Cl N6 O2 S | 7.1 | 6 | |
| T26 | 2-(3-chloro-4-(6-(1-methylcyclopropoxy)-9-(2-(4-methylthiazol-5-yl)ethyl)-9H-purin-8-yl)phenyl)acetamide | 483 | C23 H23 Cl N6 O2 S | 5.3 | 6.5 | |
| T27 | 2-(3-chloro-4-(9-((3,5-dimethylisoxazol-4-yl)methyl)-6-(1-methylcyclopropoxy)-9H-purin-8-yl)phenyl)acetamide | 467 | C23 H23 Cl N6 O3 | 5.2 | <5.0 | |
| T28 | 2-(3-chloro-4-(6-(1-methylcyclopropoxy)-9-((5-methylthiazol-2-yl)methyl)-9H-purin-8-yl)phenoxy)-N-methylacetamide | 499 | C23 H23 Cl N6 O3 S | 8.0 | 6.2 | |
| T29 | N-(3-chloro-4-(6-(1-methylcyclopropoxy)-9-((4-methylpyridin-2-yl)methyl)-9H-purin-8-yl)phenyl)methanesulfonamide | 499 | C23 H23 Cl N6 O3 S | 8 | 5.9 | <5.0 |
| T30 | 3-chloro-N-methyl-4-(6-(1-methylcyclopropoxy)-9-((4-methylpyridin-2-yl)methyl)-9H-purin-8-yl)benzenesulfonamide | 499 | C23 H23 Cl N6 O3 S | 7.8 | 6.2 | |
| T31 | 2-(3-chloro-4-(9-((1,4-dimethyl-1H-pyrazol-5-yl)methyl)-6-(1-methylcyclopropoxy)-9H-purin-8-yl)phenyl)acetamide | 466 | C23 H24 Cl N7 O2 | 6.1 | <5.0 | |
| T32 | 2-(3-chloro-4-(9-((1,3-dimethyl-1H-pyrazol-5-yl)methyl)-6-(1-methylcyclopropoxy)-9H-purin-8-yl)phenyl)acetamide | 466 | C23 H24 Cl N7 O2 | 6.2 | 5.7 | |
| T33 | 2-(3-chloro-4-(9-((1,3-dimethyl-1H-pyrazol-4-yl)methyl)-6-(1-methylcyclopropoxy)-9H-purin-8-yl)phenyl)acetamide | 466 | C23 H24 Cl N7 O2 | 6.3 | <5.0 | |
| T34 | 2-(3-chloro-4-(6-(1-methylcyclopropoxy)-9-((5-methylthiazol-2-yl)methyl)-9H-purin-8-yl)phenoxy)-N-methylethan-1-amine | 485 | C23 H25 Cl N6 O2 S | 7.9 | 6.3 | <5.0 |
| T35 | 2-(3-chloro-4-(6-(1-methylcyclopropoxy)-9-((2-(trifluoromethyl)pyridin-4-yl)methyl)-9H-purin-8-yl)phenyl)acetamide | 517 | C24 H20 Cl F3 N6 O2 | 7.4 | 5.6 | |
| T36 | 2-(3-chloro-4-(6-(1-methylcyclopropoxy)-9-((4-(trifluoromethyl)pyridin-2-yl)methyl)-9H-purin-8-yl)phenyl)acetamide | 517 | C24 H20 Cl F3 N6 O2 | 8.1 | 6.3 | |
| T37 | 2-(3-chloro-4-(6-(1-methylcyclopropoxy)-9-((2-(trifluoromethyl)pyridin-3-yl)methyl)-9H-purin-8-yl)phenyl)acetamide | 517 | C24 H20 Cl F3 N6 O2 | 6.6 | <5.0 | |
| T38 | 2-(3-chloro-4-(6-(1-methylcyclopropoxy)-9-((6-(trifluoromethyl)pyridin-3-yl)methyl)-9H-purin-8-yl)phenyl)acetamide | 517 | C24 H20 Cl F3 N6 O2 | 6.9 | 5.2 | |
| T39 | 2-(3-chloro-4-(9-((5-cyanopyridin-3-yl)methyl)-6-(1-methylcyclopropoxy)-9H-purin-8-yl)phenyl)acetamide | 474 | C24 H20 Cl N7 O2 | 7.3 | 5.2 | |
| T40 | 2-(3-chloro-4-(9-((2-cyanopyridin-4-yl)methyl)-6-(1-methylcyclopropoxy)-9H-purin-8-yl)phenyl)acetamide | 474 | C24 H20 Cl N7 O2 | 7.1 | 5.3 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T41 | 2-(2-chloro-3-(9-(3-chlorobenzyl)-6-(1-methylcyclopropoxy)-9H-purin-8-yl)phenoxy)acetic acid | 499 | C24 H20 Cl2 N4 O4 | 8.2 | <5.1 | <5.0 |
| T42 | 2-(3-chloro-4-(9-(3-fluorobenzyl)-6-(1-methylcyclopropoxy)-9H-purin-8-yl)phenyl)acetamide | 466 | C24 H21 Cl F N5 O2 | 8.1 | 6.8 | |
| T43 | 2-(3-chloro-4-(9-(4-fluorobenzyl)-6-(1-methylcyclopropoxy)-9H-purin-8-yl)phenyl)acetamide | 466 | C24 H21 Cl F N5 O2 | 8.1 | 6.2 | |
| T44 | 2-(3-chloro-4-(6-(1-methylcyclopropoxy)-9-((4-(trifluoromethyl)pyridin-2-yl)methyl)-9H-purin-8-yl)phenoxy)ethan-1-ol | 520 | C24 H21 Cl F3 N5 O3 | 8.3 | 6.6 | |
| T45 | 2-(3-chloro-4-(9-(3-chlorobenzyl)-6-(1-methylcyclopropoxy)-9H-purin-8-yl)phenyl)acetamide | 482 | C24 H21 Cl2 N5 O2 | 8.3 | 7.3 | |
| T46 | 2-(4-(9-(2-(6-bromopyridin-2-yl)ethyl)-6-(1-methylcyclopropoxy)-9H-purin-8-yl)-3-chlorophenyl)acetamide | 541 | C24 H22 Br Cl N6 O2 | 5.8 | <5.0 | |
| T47 | 8-(2-chloro-4-(2,2-difluoroethoxy)phenyl)-6-(1-methylcyclopropoxy)-9-((4-methylpyridin-2-yl)methyl)-9H-purine | 486 | C24 H22 Cl F2 N5 O2 | 8.3 | 6.7 | |
| T48 | 2-(4-(9-benzyl-6-(1-methylcyclopropoxy)-9H-purin-8-yl)-3-chlorophenyl)acetamide | 448 | C24 H22 Cl N5 O2 | 8.2 | 6.7 | |
| T49 | 2-(3-chloro-4-(6-(1-methylcyclopropoxy)-9-((4-methylpyridin-2-yl)methyl)-9H-purin-8-yl)phenyl)acetic acid | 464 | C24 H22 Cl N5 O3 | 8.1 | <5.0 | <5.0 |
| T50 | 8-(4-(azetidin-3-yloxy)-2-chlorophenyl)-9-((4-chloropyridin-2-yl)methyl)-6-(1-methylcyclopropoxy)-9H-purine | 497 | C24 H22 Cl2 N6 O2 | 8.6 | 6.6 | 5.3 |
| T51 | 2-(3-chloro-4-(9-((4-chloropyridin-2-yl)methyl)-6-(1-methylcyclopropoxy)-9H-purin-8-yl)phenoxy)-N-methylacetamide | 513 | C24 H22 Cl2 N6 O3 | 8.3 | 6.8 | |
| T52 | 3-chloro-N-methyl-4-(6-(1-methylcyclopropoxy)-9-((4-methylpyridin-2-yl)methyl)-9H-purin-8-yl)benzamide | 463 | C24 H23 Cl N6 O2 | 8.6 | 6.3 | <5.0 |
| T53 | N-(3-chloro-4-(6-(1-methylcyclopropoxy)-9-((4-methylpyridin-2-yl)methyl)-9H-purin-8-yl)phenyl)acetamide | 463 | C24 H23 Cl N6 O2 | 8.2 | 6.5 | <5.0 |
| T54 | 4-chloro-N-methyl-3-(6-(1-methylcyclopropoxy)-9-((4-methylpyridin-2-yl)methyl)-9H-purin-8-yl)benzamide | 463 | C24 H23 Cl N6 O2 | 6.4 | <5.0 | |
| T55 | 2-chloro-N-methyl-3-(6-(1-methylcyclopropoxy)-9-((4-methylpyridin-2-yl)methyl)-9H-purin-8-yl)benzamide | 463 | C24 H23 Cl N6 O2 | 7.7 | 6.2 | |
| T56 | 2-(2-chloro-3-(6-(1-methylcyclopropoxy)-9-((4-methylpyridin-2-yl)methyl)-9H-purin-8-yl)phenyl)acetamide | 463 | C24 H23 Cl N6 O2 | 7.7 | 6.1 | <5.0 |
| T57 | 2-(4-chloro-3-(6-(1-methylcyclopropoxy)-9-((4-methylpyridin-2-yl)methyl)-9H-purin-8-yl)phenyl)acetamide | 463 | C24 H23 Cl N6 O2 | 6.9 | <5.0 | |
| T58 | 2-(3-chloro-4-(6-(1-methylcyclopropoxy)-9-((2-methylpyridin-4-yl)methyl)-9H-purin-8-yl)phenyl)acetamide | 463 | C24 H23 Cl N6 O2 | 6.8 | <5.0 | |
| T59 | 2-(3-chloro-4-(6-(1-methylcyclopropoxy)-9-((6-methylpyridin-2-yl)methyl)-9H-purin-8-yl)phenyl)acetamide | 463 | C24 H23 Cl N6 O2 | 7.6 | 5.6 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T60 | 2-(3-chloro-4-(6-(1-methylcyclopropoxy)-9-((2-methylpyridin-3-yl)methyl)-9H-purin-8-yl)phenyl)acetamide | 463 | C24 H23 Cl N6 O2 | 6.4 | 5 | |
| T61 | 2-(3-chloro-4-(6-(1-methylcyclopropoxy)-9-((4-methylpyridin-2-yl)methyl)-9H-purin-8-yl)phenoxy)acetamide | 479 | C24 H23 Cl N6 O3 | 8.2 | 6.6 | |
| T62 | methyl (3-chloro-4-(6-(1-methylcyclopropoxy)-9-((4-methylpyridin-2-yl)methyl)-9H-purin-8-yl)phenyl)carbamate | 479 | C24 H23 Cl N6 O3 | 8.4 | 6.6 | |
| T63 | 2-(3-chloro-4-(9-((4-methoxypyridin-2-yl)methyl)-6-(1-methylcyclopropoxy)-9H-purin-8-yl)phenyl)acetamide | 479 | C24 H23 Cl N6 O3 | 7.6 | 6 | |
| T64 | 3-(3-chloro-4-(9-((4-chloropyridin-2-yl)methyl)-6-(1-methylcyclopropoxy)-9H-purin-8-yl)phenoxy)propan-1-ol | 500 | C24 H23 Cl2 N5 O3 | 8.2 | 6.8 | <5.0 |
| T65 | 2-(3-chloro-4-(6-(1-methylcyclopropoxy)-9-((4-methylpyridin-2-yl)methyl)-9H-purin-8-yl)phenyl)ethan-1-ol | 450 | C24 H24 Cl N5 O2 | 8.1 | 6.6 | |
| T66 | 1-(3-chloro-4-(6-(1-methylcyclopropoxy)-9-((4-methylpyridin-2-yl)methyl)-9H-purin-8-yl)phenyl)-3-methylurea | 478 | C24 H24 Cl N7 O2 | 8.4 | 6.4 | |
| T67 | 2-(3-chloro-4-(9-((4-chloropyridin-2-yl)methyl)-6-(1-methylcyclopropoxy)-9H-purin-8-yl)phenoxy)-N-methylethan-1-amine | 499 | C24 H24 Cl2 N6 O2 | 8 | 6.9 | <5.0 |
| T68 | 1-(3-chloro-4-(6-(1-methylcyclopropoxy)-9-((4-methylpyridin-2-yl)methyl)-9H-purin-8-yl)phenyl)-N-methylmethanamine | 449 | C24 H25 Cl N6 O | 7.8 | 6 | <5.0 |
| T69 | 2-(3-chloro-4-(6-(1-methylcyclopropoxy)-9-((4-methylpyridin-2-yl)methyl)-9H-purin-8-yl)phenoxy)ethan-1-amine | 465 | C24 H25 Cl N6 O2 | 8 | 6.7 | <5.0 |
| T70 | (S)-2-((8-(2-chloro-4-(pyrrolidin-3-yloxy)phenyl)-6-(1-methylcyclopropoxy)-9H-purin-9-yl)methyl)-5-methylthiazole | 497 | C24 H25 Cl N6 O2 S | 8.2 | 6.2 | <5.0 |
| T71 | 2-(4-(9-((5-(tert-butyl)-1,2,4-oxadiazol-3-yl)methyl)-6-(1-methylcyclopropoxy)-9H-purin-8-yl)-3-chlorophenyl)acetamide | 496 | C24 H26 Cl N7 O3 | 7 | 5.1 | |
| T72 | 2-(3-chloro-4-(6-(1-methylcyclopropoxy)-9-((5-methylthiazol-2-yl)methyl)-9H-purin-8-yl)phenoxy)-N,N-dimethylethan-1-amine | 499 | C24 H27 Cl N6 O2 S | 8.1 | 6.7 | <5.0 |
| T73 | 2-(2-chloro-3-(6-(1-methylcyclopropoxy)-9-((5-methylthiazol-2-yl)methyl)-9H-purin-8-yl)phenoxy)-N,N-dimethylethan-1-amine | 499 | C24 H27 Cl N6 O2 S | 8 | 6.2 | <5.0 |
| T74 | 3-(3-chloro-4-(6-(1-methylcyclopropoxy)-9-((5-methylthiazol-2-yl)methyl)-9H-purin-8-yl)phenoxy)-N-methylpropan-1-amine | 499 | C24 H27 Cl N6 O2 S | 8.3 | 6.3 | <5.0 |
| T75 | 2-((8-(2-chloro-4-(2-(piperazin-1-yl)ethoxy)phenyl)-6-(1-methylcyclopropoxy)-9H-purin-9-yl)methyl)-1,3,4-thiadiazole | 527 | C24 H27 Cl N8 O2 S | 6.4 | <5.0 | <5.0 |
| T76 | 2-((8-(2-chloro-4-(2-(piperazin-1-yl)ethoxy)phenyl)-6-(1-methylcyclopropoxy)-9H-purin-9-yl)methyl)-1,3,4-oxadiazole | 511 | C24 H27 Cl N8 O3 | 6 | <5.0 | <5.5 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T77 | 2-(3-chloro-4-(9-(5-cyano-2-fluorobenzyl)-6-(1-methylcyclopropoxy)-9H-purin-8-yl)phenyl)acetamide | 491 | C25 H20 Cl F N6 O2 | 8.1 | 6.8 | |
| T78 | 2-(3-chloro-4-(9-(2-cyano-4-fluorobenzyl)-6-(1-methylcyclopropoxy)-9H-purin-8-yl)phenyl)acetamide | 491 | C25 H20 Cl F N6 O2 | 6.8 | 5.3 | |
| T79 | 2-(3-chloro-4-(9-(2-cyano-5-fluorobenzyl)-6-(1-methylcyclopropoxy)-9H-purin-8-yl)phenyl)acetamide | 491 | C25 H20 Cl F N6 O2 | 8 | 6.8 | |
| T80 | (E)-3-(2-chloro-3-(9-(3-chlorobenzyl)-6-(1-methylcyclopropoxy)-9H-purin-8-yl)phenyl)acrylic acid | 495 | C25 H20 Cl2 N4 O3 | 8.1 | 7 | <5.0 |
| T81 | 2-(3-chloro-4-(9-(3-cyanobenzyl)-6-(1-methylcyclopropoxy)-9H-purin-8-yl)phenyl)acetamide | 473 | C25 H21 Cl N6 O2 | 8.2 | 6.7 | |
| T82 | 2-(3-chloro-4-(9-(2-cyanobenzyl)-6-(1-methylcyclopropoxy)-9H-purin-8-yl)phenyl)acetamide | 473 | C25 H21 Cl N6 O2 | 7.8 | 6.5 | |
| T83 | 2-(3-chloro-4-(9-(4-cyanobenzyl)-6-(1-methylcyclopropoxy)-9H-purin-8-yl)phenyl)acetamide | 473 | C25 H21 Cl N6 O2 | 7.3 | 5.1 | |
| T84 | 3-(3-chloro-4-(9-(3,4-dichlorobenzyl)-6-(1-methylcyclopropoxy)-9H-purin-8-yl)phenoxy)propanoic acid | 547 (35Cl, 35Cl, 37Cl) | C25 H21 Cl3 N4 O4 | 8 | 5.7 | |
| T85 | 3-(3-chloro-4-(9-(2,3-dichlorobenzyl)-6-(1-methylcyclopropoxy)-9H-purin-8-yl)phenoxy)propanoic acid | 547 (35Cl, 35Cl, 37Cl) | C25 H21 Cl3 N4 O4 | 8.1 | 6.1 | <5.0 |
| T86 | 3-chloro-4-(6-(1-methylcyclopropoxy)-9-((4-methylpyridin-2-yl)methyl)-9H-purin-8-yl)-N-(2,2,2-trifluoroethyl)benzamide | 531 | C25 H22 Cl F3 N6 O2 | 7.8 | 6.3 | |
| T87 | 3-(3-chloro-4-(9-(3-chlorobenzyl)-6-(1-methylcyclopropoxy)-9H-purin-8-yl)phenoxy)propanoic acid | 513 | C25 H22 Cl2 N4 O4 | 8.3 | 6.4 | <5.0 |
| T88 | 3-(3-chloro-4-(9-(2-chlorobenzyl)-6-(1-methylcyclopropoxy)-9H-purin-8-yl)phenoxy)propanoic acid | 513 | C25 H22 Cl2 N4 O4 | 8 | 6.1 | |
| T89 | 3-(2-chloro-3-(9-(3-chlorobenzyl)-6-(1-methylcyclopropoxy)-9H-purin-8-yl)phenoxy)propanoic acid | 513 | C25 H22 Cl2 N4 O4 | 8.2 | 7.4 | <5.0 |
| T90 | (S)-2-(2-chloro-3-(9-(3-chlorobenzyl)-6-(1-methylcyclopropoxy)-9H-purin-8-yl)phenoxy)propanoic acid | 513 | C25 H22 Cl2 N4 O4 | 8.2 | 5.7 | |
| T91 | (R)-2-(2-chloro-3-(9-(3-chlorobenzyl)-6-(1-methylcyclopropoxy)-9H-purin-8-yl)phenoxy)propanoic acid | 513 | C25 H22 Cl2 N4 O4 | 8 | <5.0 | <5.0 |
| T92 | 8-(4-(2-(2H-tetrazol-5-yl)ethoxy)-2-chlorophenyl)-9-(3-chlorobenzyl)-6-(1-methylcyclopropoxy)-9H-purine | 537 | C25 H22 Cl2 N8 O2 | 8.1 | 5.7 | <5.0 |
| T93 | 3-chloro-N-(2,2-difluoroethyl)-4-(6-(1-methylcyclopropoxy)-9-((4-methylpyridin-2-yl)methyl)-9H-purin-8-yl)benzamide | 513 | C25 H23 Cl F2 N6 O2 | 7.8 | 6.5 | |
| T94 | 3-(3-chloro-4-(6-(1-methylcyclopropoxy)-9-((4-(trifluoromethyl)pyridin-2-yl)methyl)-9H-purin-8-yl)phenoxy)propan-1-ol | 534 | C25 H23 Cl F3 N5 O3 | 8.3 | 6.7 | |
| T95 | 1-(3-chloro-4-(6-(1-methylcyclopropoxy)-9-((4-methylpyridin-2-yl)methyl)-9H-purin-8-yl)phenyl)azetidin-2-one | 475 | C25 H23 Cl N6 O2 | 8.1 | 6.7 | |
| T96 | 3-(3-chloro-4-(6-(1-methylcyclopropoxy)-9-((4-methylpyridin-2-yl)methyl)-9H-purin-8-yl)phenyl)oxazolidin-2-one | 491 | C25 H23 Cl N6 O3 | 8.1 | 7 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T97 | 3-((3-chloro-4-(9-(3-chlorobenzyl)-6-(1-methylcyclopropoxy)-9H-purin-8-yl)phenyl)amino)propanoic acid | 512 | C25 H23 Cl2 N5 O3 | 8.3 | 5.9 | |
| T98 | 3-(3-chloro-4-(6-(1-methylcyclopropoxy)-9-((4-methylpyridin-2-yl)methyl)-9H-purin-8-yl)phenoxy)-2,2-difluoropropan-1-ol | 516 | C25 H24 Cl F2 N5 O3 | 8.2 | 7 | |
| T99 | 2-(3-chloro-4-(9-(3-methylbenzyl)-6-(1-methylcyclopropoxy)-9H-purin-8-yl)phenyl)acetamide | 462 | C25 H24 Cl N5 O2 | 8.3 | 7.1 | |
| T100 | 2-(3-chloro-4-(9-(4-methylbenzyl)-6-(1-methylcyclopropoxy)-9H-purin-8-yl)phenyl)acetamide | 462 | C25 H24 Cl N5 O2 | 8 | 6.1 | |
| T101 | 2-(3-chloro-4-(9-(2-methylbenzyl)-6-(1-methylcyclopropoxy)-9H-purin-8-yl)phenyl)acetamide | 462 | C25 H24 Cl N5 O2 | 8.1 | 6.3 | |
| T102 | 2-(3-chloro-4-(6-(1-methylcyclopropoxy)-9-phenethyl-9H-purin-8-yl)phenyl)acetamide | 462 | C25 H24 Cl N5 O2 | 7.8 | 5.8 | |
| T103 | 8-(2-chloro-4-(oxetan-3-yloxy)phenyl)-6-(1-methylcyclopropoxy)-9-((4-methylpyridin-2-yl)methyl)-9H-purine | 478 | C25 H24 Cl N5 O3 | 8.2 | 6.8 | |
| T104 | 1-(3-chloro-4-(6-(1-methylcyclopropoxy)-9-((4-methylpyridin-2-yl)methyl)-9H-purin-8-yl)phenoxy)propan-2-one | 478 | C25 H24 Cl N5 O3 | 8.2 | 6.7 | <5.0 |
| T105 | 2-(3-chloro-4-(9-(3-methoxybenzyl)-6-(1-methylcyclopropoxy)-9H-purin-8-yl)phenyl)acetamide | 478 | C25 H24 Cl N5 O3 | 8.1 | 6.2 | |
| T106 | 2-(3-chloro-4-(9-(4-methoxybenzyl)-6-(1-methylcyclopropoxy)-9H-purin-8-yl)phenyl)acetamide | 478 | C25 H24 Cl N5 O3 | 7.8 | 6.2 | |
| T107 | 1-(3-chloro-4-(6-(1-methylcyclopropoxy)-9-((4-methylpyridin-2-yl)methyl)-9H-purin-8-yl)phenyl)imidazolidin-2-one | 490 | C25 H24 Cl N7 O2 | 8.2 | 6.4 | <5.0 |
| T108 | 8-(2-chloro-4-(3-fluoropropoxy)phenyl)-6-(1-methylcyclopropoxy)-9-((4-methylpyridin-2-yl)methyl)-9H-purine | 482 | C25 H25 Cl F N5 O2 | 8.3 | 6.9 | |
| T109 | 3-(3-chloro-4-(6-(1-methylcyclopropoxy)-9-((4-methylpyridin-2-yl)methyl)-9H-purin-8-yl)phenoxy)-2-fluoropropan-1-ol (Isomer 1) | 498 | C25 H25 Cl F N5 O3 | 8.2 | 6.8 | |
| T110 | 3-(3-chloro-4-(6-(1-methylcyclopropoxy)-9-((4-methylpyridin-2-yl)methyl)-9H-purin-8-yl)phenoxy)-2-fluoropropan-1-ol (Isomer 2) | 498 | C25 H25 Cl F N5 O3 | 8.3 | 7 | |
| T111 | 8-(4-(azetidin-3-yloxy)-2-chlorophenyl)-6-(1-methylcyclopropoxy)-9-((4-methylpyridin-2-yl)methyl)-9H-purine | 477 | C25 H25 Cl N6 O2 | 8.2 | 6.5 | <5.0 |
| T112 | 3-chloro-N,N-dimethyl-4-(6-(1-methylcyclopropoxy)-9-((4-methylpyridin-2-yl)methyl)-9H-purin-8-yl)benzamide | 477 | C25 H25 Cl N6 O2 | 8 | 5.8 | <5.0 |
| T113 | 2-(3-chloro-4-(6-(1-methylcyclopropoxy)-9-((4-methylpyridin-2-yl)methyl)-9H-purin-8-yl)phenyl)-N-methylacetamide | 477 | C25 H25 Cl N6 O2 | 8.1 | 6.5 | |
| T114 | 3-chloro-N-ethyl-4-(6-(1-methylcyclopropoxy)-9-((4-methylpyridin-2-yl)methyl)-9H-purin-8-yl)benzamide | 477 | C25 H25 Cl N6 O2 | 7.8 | 6.5 | |
| T115 | 1-(3-chloro-4-(6-(1-methylcyclopropoxy)-9-((4-methylpyridin-2-yl)methyl)-9H-purin-8-yl)phenyl)azetidin-3-ol | 477 | C25 H25 Cl N6 O2 | 8.2 | 6.7 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T116 | 3-(3-chloro-4-(6-(1-methylcyclopropoxy)-9-((4-methylpyridin-2-yl)methyl)-9H-purin-8-yl)phenyl)propanamide | 477 | C25 H25 Cl N6 O2 | 8.1 | 6.2 | <5.0 |
| T117 | 2-(3-chloro-4-(6-(1-methylcyclopropoxy)-9-(2-(3-methylpyridin-2-yl)ethyl)-9H-purin-8-yl)phenyl)acetamide | 477 | C25 H25 Cl N6 O2 | 5.9 | | |
| T118 | 2-(3-chloro-4-(6-(1-methylcyclopropoxy)-9-((4-methylpyridin-2-yl)methyl)-9H-purin-8-yl)phenoxy)-N-methylacetamide | 493 | C25 H25 Cl N6 O3 | 8.3 | 6.6 | |
| T119 | 3-chloro-N-(2-hydroxyethyl)-4-(6-(1-methylcyclopropoxy)-9-((4-methylpyridin-2-yl)methyl)-9H-purin-8-yl)benzamide | 493 | C25 H25 Cl N6 O3 | 7.9 | 6.1 | <5.0 |
| T120 | 2-(2-chloro-3-(6-(1-methylcyclopropoxy)-9-((4-methylpyridin-2-yl)methyl)-9H-purin-8-yl)phenoxy)-N-methylacetamide | 493 | C25 H25 Cl N6 O3 | 8.2 | 6.8 | <5.2 |
| T121 | (R)-N-(3-chloro-4-(6-(1-methylcyclopropoxy)-9-((4-methylpyridin-2-yl)methyl)-9H-purin-8-yl)phenyl)-2-hydroxypropanamide | 493 | C25 H25 Cl N6 O3 | 8.3 | 6.5 | <5.0 |
| T122 | 2-(4-chloro-3-(6-(1-methylcyclopropoxy)-9-((4-methylpyridin-2-yl)methyl)-9H-purin-8-yl)phenoxy)-N-methylacetamide | 493 | C25 H25 Cl N6 O3 | 6.8 | 5.2 | |
| T123 | 2-hydroxyethyl (3-chloro-4-(6-(1-methylcyclopropoxy)-9-((4-methylpyridin-2-yl)methyl)-9H-purin-8-yl)phenyl)carbamate | 509 | C25 H25 Cl N6 O4 | 8.2 | 6.7 | <5.0 |
| T124 | 3-(3-chloro-4-(6-(1-methylcyclopropoxy)-9-((4-methylpyridin-2-yl)methyl)-9H-purin-8-yl)phenoxy)propan-1-ol | 480 | C25 H26 Cl N5 O3 | 8.2 | 7.1 | |
| T125 | 8-(2-chloro-4-(2-methoxyethoxy)phenyl)-6-(1-methylcyclopropoxy)-9-((4-methylpyridin-2-yl)methyl)-9H-purine | 480 | C25 H26 Cl N5 O3 | 8.1 | 7 | |
| T126 | 2-(3-chloro-4-(6-(1-methylcyclopropoxy)-9-((4-methylpyridin-2-yl)methyl)-9H-purin-8-yl)phenoxy)propan-1-ol (Isomer 2) | 480 | C25 H26 Cl N5 O3 | 8.5 | | |
| T127 | 2-(3-chloro-4-(6-(1-methylcyclopropoxy)-9-((4-methylpyridin-2-yl)methyl)-9H-purin-8-yl)phenoxy)propan-1-ol (Isomer 1) | 480 | C25 H26 Cl N5 O3 | 8.4 | 6.6 | |
| T129 | 8-(2-chloro-4-(2-(methylsulfonyl)ethoxy)phenyl)-6-(1-methylcyclopropoxy)-9-((4-methylpyridin-2-yl)methyl)-9H-purine | 528 | C25 H26 Cl N5 O4 S | 8.2 | 6.8 | <5.0 |
| T130 | 3-(3-chloro-4-(6-(1-methylcyclopropoxy)-9-((4-methylpyridin-2-yl)methyl)-9H-purin-8-yl)phenyl)-1,1-dimethylurea | 492 | C25 H26 Cl N7 O2 | 8.3 | 6.3 | |
| T131 | 2-((3-chloro-4-(6-(1-methylcyclopropoxy)-9-((4-methylpyridin-2-yl)methyl)-9H-purin-8-yl)phenyl)amino)-N-methylacetamide | 492 | C25 H26 Cl N7 O2 | 8.2 | 6.1 | |
| T132 | 1-(3-chloro-4-(6-(1-methylcyclopropoxy)-9-((4-methylpyridin-2-yl)methyl)-9H-purin-8-yl)phenyl)-3-(2-hydroxyethyl)urea | 508 | C25 H26 Cl N7 O3 | 8.3 | 5.7 | <5.0 |
| T133 | 1-(2-(3-chloro-4-(6-(1-methylcyclopropoxy)-9-((4-methylpyridin-2-yl)methyl)-9H-purin-8-yl)phenoxy)ethyl)urea | 508 | C25 H26 Cl N7 O3 | 8.6 | 6.6 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T134 | 3-(3-chloro-4-(9-((4-chloropyridin-2-yl)methyl)-6-(1-methylcyclopropoxy)-9H-purin-8-yl)phenoxy)-N-methylpropan-1-amine | 513 | C25 H26 Cl2 N6 O2 | 8.1 | 6.9 | <5.0 |
| T135 | 2-(3-chloro-4-(9-((4-chloropyridin-2-yl)methyl)-6-(1-methylcyclopropoxy)-9H-purin-8-yl)phenoxy)-N,N-dimethylethan-1-amine | 513 | C25 H26 Cl2 N6 O2 | 8.1 | 7.3 | <5.0 |
| T136 | 1-(3-chloro-4-(6-(1-methylcyclopropoxy)-9-((4-methylpyridin-2-yl)methyl)-9H-purin-8-yl)phenyl)-N,N-dimethylmethanamine | 463 | C25 H27 Cl N6 O | 8.2 | 6.3 | <5.0 |
| T137 | 2-(3-chloro-4-(6-(1-methylcyclopropoxy)-9-((4-methylpyridin-2-yl)methyl)-9H-purin-8-yl)phenoxy)-N-methylethan-1-amine | 479 | C25 H27 Cl N6 O2 | 8.1 | 6.7 | <5.0 |
| T138 | 2-((8-(2-chloro-4-(piperidin-4-yloxy)phenyl)-6-(1-methylcyclopropoxy)-9H-purin-9-yl)methyl)-5-methylthiazole | 511 | C25 H27 Cl N6 O2 S | 8.1 | 6.3 | <5.0 |
| T139 | (R)-2-((8-(2-chloro-4-(pyrrolidin-2-ylmethoxy)phenyl)-6-(1-methylcyclopropoxy)-9H-purin-9-yl)methyl)-5-methylthiazole | 511 | C25 H27 Cl N6 O2 S | 8 | 6.4 | <5.0 |
| T140 | (S)-2-((8-(2-chloro-4-((1-methylpyrrolidin-3-yl)oxy)phenyl)-6-(1-methylcyclopropoxy)-9H-purin-9-yl)methyl)-5-methylthiazole | 511 | C25 H27 Cl N6 O2 S | 8.4 | 6.6 | <5.0 |
| T141 | 1-(2-(3-chloro-4-(6-(1-methylcyclopropoxy)-9-((5-methylthiazol-2-yl)methyl)-9H-purin-8-yl)phenoxy)ethyl)azetidin-3-ol | 527 | C25 H27 Cl N6 O3 S | 8.1 | 6.3 | |
| T142 | 1-(2-(2-chloro-3-(6-(1-methylcyclopropoxy)-9-((5-methylthiazol-2-yl)methyl)-9H-purin-8-yl)phenoxy)ethyl)azetidin-3-ol | 527 | C25 H27 Cl N6 O3 S | 7.8 | 6 | <5.0 |
| T143 | N-(3-chloro-4-(6-(1-methylcyclopropoxy)-9-((4-methylpyridin-2-yl)methyl)-9H-purin-8-yl)phenethyl)methanesulfonamide | 527 | C25 H27 Cl N6 O3 S | 8.1 | 6.4 | |
| T144 | N-(2-(3-chloro-4-(6-(1-methylcyclopropoxy)-9-((4-methylpyridin-2-yl)methyl)-9H-purin-8-yl)phenoxy)ethyl)methanesulfonamide | 543 | C25 H27 Cl N6 O4 S | 8.2 | 6.8 | |
| T145 | 5-chloro-4-((8-(2-chloro-4-(2-(piperazin-1-yl)ethoxy)phenyl)-6-(1-methylcyclopropoxy)-9H-purin-9-yl)methyl)thiazole | 560 | C25 H27 Cl2 N7 O2 S | 7.4 | 5.7 | <5.0 |
| T146 | 2-chloro-5-((8-(2-chloro-4-(2-(piperazin-1-yl)ethoxy)phenyl)-6-(1-methylcyclopropoxy)-9H-purin-9-yl)methyl)thiazole | 560 | C25 H27 Cl2 N7 O2 S | 8.2 | 5.9 | <5.0 |
| T147 | 2-(3-chloro-4-(6-(1-methylcyclopropoxy)-9-(2-(1,3,5-trimethyl-1H-pyrazol-4-yl)ethyl)-9H-purin-8-yl)phenyl)acetamide | 494 | C25 H28 Cl N7 O2 | 5 | <5.0 | |
| T148 | 3-(3-chloro-4-(6-(1-methylcyclopropoxy)-9-((5-methylthiazol-2-yl)methyl)-9H-purin-8-yl)phenoxy)-N,N-dimethylpropan-1-amine | 513 | C25 H29 Cl N6 O2 S | 7.9 | 6.5 | <5.1 |
| T149 | 3-(2-chloro-3-(6-(1-methylcyclopropoxy)-9-((5-methylthiazol-2-yl)methyl)-9H-purin-8-yl)phenoxy)-N,N-dimethylpropan-1-amine | 513 | C25 H29 Cl N6 O2 S | 8.3 | 6.5 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T150 | 8-(2-chloro-4-(2-(piperazin-1-yl)ethoxy)phenyl)-9-((4-methyl-4H-1,2,4-triazol-3-yl)methyl)-6-(1-methylcyclopropoxy)-9H-purine | 524 | C25 H30 Cl N9 O2 | 5 | <5.0 | <5.0 |
| T151 | 3-(3-chloro-4-(6-(1-methylcyclopropoxy)-9-(3-(trifluoromethyl)benzyl)-9H-purin-8-yl)phenoxy)propanoic acid | 547 | C26 H22 Cl F3 N4 O4 | 8.1 | 6.4 | <5.0 |
| T152 | 3-chloro-4-(6-(1-methylcyclopropoxy)-9-((4-methylpyridin-2-yl)methyl)-9H-purin-8-yl)-N-(prop-2-yn-1-yl)benzamide | 487 | C26 H23 Cl N6 O2 | 8.1 | 6.4 | |
| T153 | (3-chloro-4-(6-(1-methylcyclopropoxy)-9-((4-methylpyridin-2-yl)methyl)-9H-purin-8-yl)phenyl)(3-fluoroazetidin-1-yl)methanone | 507 | C26 H24 Cl F N6 O2 | 7.7 | 6.3 | |
| T154 | 2-(3-chloro-4-(6-(1-methylcyclopropoxy)-9-((4-methylpyridin-2-yl)methyl)-9H-purin-8-yl)phenoxy)-N-(2,2,2-trifluoroethyl)acetamide | 561 | C26 H24 Cl F3 N6 O3 | 8.2 | 6.7 | |
| T155 | 4-(3-chloro-4-(9-(3-chlorobenzyl)-6-(1-methylcyclopropoxy)-9H-purin-8-yl)phenyl)butanoic acid | 511 | C26 H24 Cl2 N4 O3 | 8.3 | 6.2 | |
| T156 | methyl 3-(3-chloro-4-(9-(3-chlorobenzyl)-6-(1-methylcyclopropoxy)-9H-purin-8-yl)phenoxy)propanoate | 527 | C26 H24 Cl2 N4 O4 | 8.4 | 6.7 | |
| T157 | 4-(2-chloro-3-(9-(3-chlorobenzyl)-6-(1-methylcyclopropoxy)-9H-purin-8-yl)phenoxy)butanoic acid | 527 | C26 H24 Cl2 N4 O4 | 8.3 | 7.5 | <5.0 |
| T158 | 2-(2-chloro-3-(9-(3-chlorobenzyl)-6-(1-methylcyclopropoxy)-9H-purin-8-yl)phenoxy)-2-methylpropanoic acid | 527 | C26 H24 Cl2 N4 O4 | 8 | <5.0 | <5.0 |
| T159 | (R)-3-(2-chloro-3-(9-(3-chlorobenzyl)-6-(1-methylcyclopropoxy)-9H-purin-8-yl)phenoxy)-2-methylpropanoic acid | 527 | C26 H24 Cl2 N4 O4 | 8.2 | 6.9 | |
| T160 | (S)-3-(2-chloro-3-(9-(3-chlorobenzyl)-6-(1-methylcyclopropoxy)-9H-purin-8-yl)phenoxy)-2-methylpropanoic acid | 527 | C26 H24 Cl2 N4 O4 | 8.2 | 6.7 | |
| T162 | 2-(2-(2-chloro-3-(9-(3-chlorobenzyl)-6-(1-methylcyclopropoxy)-9H-purin-8-yl)phenoxy)ethoxy)acetic acid | 543 | C26 H24 Cl2 N4 O5 | 8.2 | 6.9 | |
| T163 | 8-(3-(3-(2H-tetrazol-5-yl)propoxy)-2-chlorophenyl)-9-(3-chlorobenzyl)-6-(1-methylcyclopropoxy)-9H-purine | 551 | C26 H24 Cl2 N8 O2 | 8.2 | 6.6 | |
| T164 | 8-(4-(3-(1H-tetrazol-5-yl)propoxy)-2-chlorophenyl)-9-(3-chlorobenzyl)-6-(1-methylcyclopropoxy)-9H-purine | 551 | C26 H24 Cl2 N8 O2 | 8.2 | 6.1 | |
| T165 | 2-(3-chloro-4-(6-(1-methylcyclopropoxy)-9-((4-methylpyridin-2-yl)methyl)-9H-purin-8-yl)phenyl)-N-(2,2-difluoroethyl)acetamide | 527 | C26 H25 Cl F2 N6 O2 | 8.3 | 7 | |
| T166 | 2-(3-chloro-4-(6-(1-methylcyclopropoxy)-9-((4-methylpyridin-2-yl)methyl)-9H-purin-8-yl)phenoxy)-N-(2,2-difluoroethyl)acetamide | 543 | C26 H25 Cl F2 N6 O3 | 8.1 | 6.5 | |
| T167 | 3-(3-chloro-4-(9-(3-methylbenzyl)-6-(1-methylcyclopropoxy)-9H-purin-8-yl)phenoxy)propanoic acid | 493 | C26 H25 Cl N4 O4 | 8.1 | 6.1 | |
| T168 | 3-(3-chloro-4-(9-(2-methylbenzyl)-6-(1-methylcyclopropoxy)-9H-purin-8-yl)phenoxy)propanoic acid | 493 | C26 H25 Cl N4 O4 | 7.9 | 5.9 | |
| T169 | azetidin-1-yl(3-chloro-4-(6-(1-methylcyclopropoxy)-9-((4-methylpyridin-2-yl)methyl)-9H-purin-8-yl)phenyl)methanone | 489 | C26 H25 Cl N6 O2 | 8.2 | 6.2 | 5 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T170 | 3-chloro-N-cyclopropyl-4-(6-(1-methylcyclopropoxy)-9-((4-methylpyridin-2-yl)methyl)-9H-purin-8-yl)benzamide | 489 | C26 H25 Cl N6 O2 | 7.8 | 6.2 | |
| T171 | 1-(3-chloro-4-(6-(1-methylcyclopropoxy)-9-((4-methylpyridin-2-yl)methyl)-9H-purin-8-yl)phenyl)pyrrolidin-2-one | 489 | C26 H25 Cl N6 O2 | 8.2 | 6.8 | <5.0 |
| T172 | 5-(3-chloro-4-(6-(1-methylcyclopropoxy)-9-((4-methylpyridin-2-yl)methyl)-9H-purin-8-yl)phenyl)pyrrolidin-2-one (Isomer 1) | 489 | C26 H25 Cl N6 O2 | 8.1 | 6.4 | |
| T173 | 5-(3-chloro-4-(6-(1-methylcyclopropoxy)-9-((4-methylpyridin-2-yl)methyl)-9H-purin-8-yl)phenyl)pyrrolidin-2-one (Isomer 2) | 489 | C26 H25 Cl N6 O2 | 7.8 | 6.1 | <5.0 |
| T174 | 4-(3-chloro-4-(6-(1-methylcyclopropoxy)-9-((4-methylpyridin-2-yl)methyl)-9H-purin-8-yl)phenyl)pyrrolidin-2-one (Isomer 1) | 489 | C26 H25 Cl N6 O2 | 8 | 6.3 | |
| T175 | 4-(3-chloro-4-(6-(1-methylcyclopropoxy)-9-((4-methylpyridin-2-yl)methyl)-9H-purin-8-yl)phenyl)pyrrolidin-2-one (Isomer 2) | 489 | C26 H25 Cl N6 O2 | 8.1 | 6.1 | |
| T176 | 3-(3-chloro-4-(6-(1-methylcyclopropoxy)-9-((4-methylpyridin-2-yl)methyl)-9H-purin-8-yl)phenyl)pyrrolidin-2-one (racemic) | 489 | C26 H25 Cl N6 O2 | 7.9 | 6.1 | |
| T177 | 3-chloro-4-(6-(1-methylcyclopropoxy)-9-((4-methylpyridin-2-yl)methyl)-9H-purin-8-yl)-N-(oxetan-3-yl)benzamide | 505 | C26 H25 Cl N6 O3 | 7.6 | 6 | |
| T178 | 3-(3-chloro-4-(6-(1-methylcyclopropoxy)-9-((4-methylpyridin-2-yl)methyl)-9H-purin-8-yl)phenoxy)pyrrolidin-2-one (racemic) | 505 | C26 H25 Cl N6 O3 | 8 | 6.3 | |
| T179 | 4-(3-chloro-4-(6-(1-methylcyclopropoxy)-9-((4-methylpyridin-2-yl)methyl)-9H-purin-8-yl)phenoxy)pyrrolidin-2-one (racemic) | 505 | C26 H25 Cl N6 O3 | 8.2 | 6.5 | <5.0 |
| T180 | (3-chloro-4-(6-(1-methylcyclopropoxy)-9-((4-methylpyridin-2-yl)methyl)-9H-purin-8-yl)phenyl)(3-hydroxyazetidin-1-yl)methanone | 505 | C26 H25 Cl N6 O3 | 8.1 | 6 | |
| T181 | (R)-1-(3-chloro-4-(6-(1-methylcyclopropoxy)-9-((4-methylpyridin-2-yl)methyl)-9H-purin-8-yl)phenyl)-3-hydroxypyrrolidin-2-one | 505 | C26 H25 Cl N6 O3 | 8.2 | 6.5 | <5.0 |
| T182 | 4-(3-chloro-4-(6-(1-methylcyclopropoxy)-9-((4-methylpyridin-2-yl)methyl)-9H-purin-8-yl)phenyl)morpholin-3-one | 505 | C26 H25 Cl N6 O3 | 7.8 | 6.2 | |
| T183 | (R)-4-(3-chloro-4-(6-(1-methylcyclopropoxy)-9-((4-methylpyridin-2-yl)methyl)-9H-purin-8-yl)phenoxy)pyrrolidin-2-one | 505 | C26 H25 Cl N6 O3 | 8.5 | 6.4 | |
| T184 | (S)-4-(3-chloro-4-(6-(1-methylcyclopropoxy)-9-((4-methylpyridin-2-yl)methyl)-9H-purin-8-yl)phenoxy)pyrrolidin-2-one | 505 | C26 H25 Cl N6 O3 | 8.5 | 6.6 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T185 | (S)-3-(3-chloro-4-(6-(1-methylcyclopropoxy)-9-((4-methylpyridin-2-yl)methyl)-9H-purin-8-yl)phenoxy)pyrrolidin-2-one | 505 | C26 H25 Cl N6 O3 | 8.3 | 6.3 | <5.0 |
| T186 | (R)-3-(3-chloro-4-(6-(1-methylcyclopropoxy)-9-((4-methylpyridin-2-yl)methyl)-9H-purin-8-yl)phenoxy)pyrrolidin-2-one | 505 | C26 H25 Cl N6 O3 | 8.4 | 6.6 | <5.0 |
| T187 | 5-(3-chloro-4-(6-(1-methylcyclopropoxy)-9-((4-methylpyridin-2-yl)methyl)-9H-purin-8-yl)phenoxy)-1,3-oxazinan-2-one (racemic) | 521 | C26 H25 Cl N6 O4 | 7.8 | 6 | <5.0 |
| T188 | (R)-5-((3-chloro-4-(6-(1-methylcyclopropoxy)-9-((4-methylpyridin-2-yl)methyl)-9H-purin-8-yl)phenoxy)methyl)oxazolidin-2-one | 521 | C26 H25 Cl N6 O4 | 8.4 | 6.3 | |
| T189 | 3-(3-chloro-4-(9-(3-chlorobenzyl)-6-(1-methylcyclopropoxy)-9H-purin-8-yl)phenoxy)-N-(methylsulfonyl)propanamide | 590 | C26 H25 Cl2 N5 O5 S | 8.1 | 5.4 | |
| T190 | (S)-3-chloro-N-(2-fluoropropyl)-4-(6-(1-methylcyclopropoxy)-9-((4-methylpyridin-2-yl)methyl)-9H-purin-8-yl)benzamide | 509 | C26 H26 Cl F N6 O2 | 7.9 | 6.4 | |
| T191 | 3-chloro-N-(3-fluoropropyl)-4-(6-(1-methylcyclopropoxy)-9-((4-methylpyridin-2-yl)methyl)-9H-purin-8-yl)benzamide | 509 | C26 H26 Cl F N6 O2 | 7.9 | 6.4 | |
| T192 | 1-(4-(2-(4-(9-((1,3,4-oxadiazol-2-yl)methyl)-6-(1-methylcyclopropoxy)-9H-purin-8-yl)-3-chlorophenoxy)ethyl)piperazin-1-yl)-2,2,2-trifluoroethan-1-one | 607 | C26 H26 Cl F3 N8 O4 | 6.1 | | |
| T193 | 8-(2-chloro-4-(oxetan-3-ylmethoxy)phenyl)-6-(1-methylcyclopropoxy)-9-((4-methylpyridin-2-yl)methyl)-9H-purine | 492 | C26 H26 Cl N5 O3 | 7.6 | 6.6 | |
| T194 | (R)-8-(2-chloro-4-(oxetan-2-ylmethoxy)phenyl)-6-(1-methylcyclopropoxy)-9-((4-methylpyridin-2-yl)methyl)-9H-purine | 492 | C26 H26 Cl N5 O3 | 8.1 | 6.6 | |
| T195 | 2-(3-chloro-4-(6-(1-methylcyclopropoxy)-9-phenethyl-9H-purin-8-yl)phenoxy)-N-methylacetamide | 492 | C26 H26 Cl N5 O3 | 8.2 | 5.9 | |
| T196 | (S)-8-(2-chloro-4-((tetrahydrofuran-3-yl)oxy)phenyl)-6-(1-methylcyclopropoxy)-9-((4-methylpyridin-2-yl)methyl)-9H-purine | 492 | C26 H26 Cl N5 O3 | 8.4 | 7 | |
| T197 | 1-((3-chloro-4-(6-(1-methylcyclopropoxy)-9-((4-methylpyridin-2-yl)methyl)-9H-purin-8-yl)phenoxy)methyl)cyclopropan-1-ol | 492 | C26 H26 Cl N5 O3 | 8.2 | 6.6 | <5.0 |
| T198 | (1s,3s)-3-(3-chloro-4-(6-(1-methylcyclopropoxy)-9-((4-methylpyridin-2-yl)methyl)-9H-purin-8-yl)phenoxy)cyclobutan-1-ol | 492 | C26 H26 Cl N5 O3 | 8.2 | 6.6 | |
| T199 | (1r,3r)-3-(3-chloro-4-(6-(1-methylcyclopropoxy)-9-((4-methylpyridin-2-yl)methyl)-9H-purin-8-yl)phenoxy)cyclobutan-1-ol | 492 | C26 H26 Cl N5 O3 | 8.4 | 7 | |
| T200 | 3-((3-chloro-4-(6-(1-methylcyclopropoxy)-9-((4-methylpyridin-2-yl)methyl)-9H-purin-8-yl)phenoxy)methyl)oxetan-3-ol | 508 | C26 H26 Cl N5 O4 | 8.1 | 6.5 | |
| T201 | 4-(3-chloro-4-(6-(1-methylcyclopropoxy)-9-((4-methylpyridin-2-yl)methyl)-9H-purin-8-yl)phenyl)piperazin-2-one | 504 | C26 H26 Cl N7 O2 | 8.2 | 6.3 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T202 | 1-(3-chloro-4-(6-(1-methylcyclopropoxy)-9-((4-methylpyridin-2-yl)methyl)-9H-purin-8-yl)phenyl)piperazin-2-one | 504 | C26 H26 Cl N7 O2 | 7.4 | 5.6 | |
| T203 | 1-((8-(2-chloro-4-(2-(dimethylamino)ethoxy)phenyl)-9-((4-methylpyridin-2-yl)methyl)-9H-purin-6-yl)oxy)cyclopropane-1-carbonitrile | 504 | C26 H26 Cl N7 O2 | 8.2 | 6.4 | <5.0 |
| T204 | 1-(3-chloro-4-(6-(1-methylcyclopropoxy)-9-((4-methylpyridin-2-yl)methyl)-9H-purin-8-yl)phenyl)azetidine-3-carboxamide | 504 | C26 H26 Cl N7 O2 | 8.1 | 6.2 | <5.0 |
| T205 | 3-(3-chloro-4-(6-(1-methylcyclopropoxy)-9-((4-methylpyridin-2-yl)methyl)-9H-purin-8-yl)phenoxy)azetidine-1-carboxamide | 520 | C26 H26 Cl N7 O3 | 8.2 | 6.4 | <5.0 |
| T206 | 1-(2-(3-chloro-4-(9-((4-chloropyridin-2-yl)methyl)-6-(1-methylcyclopropoxy)-9H-purin-8-yl)phenoxy)ethyl)azetidin-3-ol | 541 | C26 H26 Cl2 N6 O3 | 8 | 6.9 | <5.0 |
| T207 | 2-((8-(2-chloro-4-(2-(piperazin-1-yl)ethoxy)phenyl)-6-(1-methylcyclopropoxy)-9H-purin-9-yl)methyl)-5-(trifluoromethyl)thiazole | 594 | C26 H27 Cl F3 N7 O2 S | 8.1 | 6.1 | 5 |
| T208 | (S)-8-(2-chloro-4-(pyrrolidin-3-yloxy)phenyl)-6-(1-methylcyclopropoxy)-9-((4-methylpyridin-2-yl)methyl)-9H-purine | 491 | C26 H27 Cl N6 O2 | 8.6 | 6.3 | <5.0 |
| T209 | 1-(3-chloro-4-(6-(1-methylcyclopropoxy)-9-((4-methylpyridin-2-yl)methyl)-9H-purin-8-yl)benzyl)azetidin-3-ol | 491 | C26 H27 Cl N6 O2 | 8.3 | 6.2 | <5.0 |
| T210 | 2-(3-chloro-4-(6-(1-methylcyclopropoxy)-9-((4-methylpyridin-2-yl)methyl)-9H-purin-8-yl)phenyl)-N,N-dimethylacetamide | 491 | C26 H27 Cl N6 O2 | 8.5 | 6.5 | <5.0 |
| T211 | 3-chloro-N-isopropyl-4-(6-(1-methylcyclopropoxy)-9-((4-methylpyridin-2-yl)methyl)-9H-purin-8-yl)benzamide | 491 | C26 H27 Cl N6 O2 | 7.7 | 6.3 | |
| T212 | N-(3-chloro-4-(6-(1-methylcyclopropoxy)-9-((4-methylpyridin-2-yl)methyl)-9H-purin-8-yl)phenethyl)acetamide | 491 | C26 H27 Cl N6 O2 | 8.2 | 6.4 | |
| T213 | 2-(3-chloro-4-(6-(1-methylcyclopropoxy)-9-((4-methylpyridin-2-yl)methyl)-9H-purin-8-yl)phenyl)-N-ethylacetamide | 491 | C26 H27 Cl N6 O2 | 8.2 | 6.6 | |
| T214 | 3-(3-chloro-4-(6-(1-methylcyclopropoxy)-9-((4-methylpyridin-2-yl)methyl)-9H-purin-8-yl)phenyl)-N-methylpropanamide | 491 | C26 H27 Cl N6 O2 | 8.2 | 6.5 | |
| T215 | 2-((8-(4-((2-azaspiro[3.3 ]heptan-6-yl)oxy)-2-chlorophenyl)-6-(1-methylcyclopropoxy)-9H-purin-9-yl)methyl)-5-methylthiazole | 523 | C26 H27 Cl N6 O2 S | 8.1 | 6 | <5.0 |
| T216 | 2-(3-chloro-4-(6-(1-methylcyclopropoxy)-9-((4-methylpyridin-2-yl)methyl)-9H-purin-8-yl)phenoxy)-N,N-dimethylacetamide | 507 | C26 H27 Cl N6 O3 | 8.1 | 6.5 | |
| T217 | 3-chloro-N-(3-hydroxypropyl)-4-(6-(1-methylcyclopropoxy)-9-((4-methylpyridin-2-yl)methyl)-9H-purin-8-yl)benzamide | 507 | C26 H27 Cl N6 O3 | 7.8 | 6 | |
| T218 | (S)-3-chloro-N-(2-hydroxypropyl)-4-(6-(1-methylcyclopropoxy)-9-((4-methylpyridin-2-yl)methyl)-9H-purin-8-yl)benzamide | 507 | C26 H27 Cl N6 O3 | 8.1 | 6.2 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T219 | N-(2-(3-chloro-4-(6-(1-methylcyclopropoxy)-9-((4-methylpyridin-2-yl)methyl)-9H-purin-8-yl)phenoxy)ethyl)acetamide | 507 | C26 H27 Cl N6 O3 | 8 | 6.6 | |
| T220 | 3-chloro-N-(2-hydroxyethyl)-N-methyl-4-(6-(1-methylcyclopropoxy)-9-((4-methylpyridin-2-yl)methyl)-9H-purin-8-yl)benzamide | 507 | C26 H27 Cl N6 O3 | 7.6 | 5.5 | |
| T221 | 2-(3-chloro-4-(6-(1-methylcyclopropoxy)-9-((4-methylpyridin-2-yl)methyl)-9H-purin-8-yl)phenoxy)-N-ethylacetamide | 507 | C26 H27 Cl N6 O3 | 8.1 | 6.5 | |
| T222 | methyl (3-chloro-4-(6-(1-methylcyclopropoxy)-9-((4-methylpyridin-2-yl)methyl)-9H-purin-8-yl)phenethyl)carbamate | 507 | C26 H27 Cl N6 O3 | 8.5 | 6.7 | |
| T223 | N-(3-chloro-4-(6-(1-methylcyclopropoxy)-9-((4-methylpyridin-2-yl)methyl)-9H-purin-8-yl)phenethyl)-2-hydroxyacetamide | 507 | C26 H27 Cl N6 O3 | 8.2 | 6.3 | |
| T224 | 2-(3-chloro-4-(6-(1-methylcyclopropoxy)-9-((4-methylpyridin-2-yl)methyl)-9H-purin-8-yl)phenyl)-N-(2-hydroxyethyl)acetamide | 507 | C26 H27 Cl N6 O3 | 8.2 | 6 | |
| T225 | 4-(3-chloro-4-(6-(1-methylcyclopropoxy)-9-((4-methylpyridin-2-yl)methyl)-9H-purin-8-yl)phenyl)thiomorpholine 1,1-dioxide | 539 | C26 H27 Cl N6 O3 S | 8.1 | 6.2 | <5.0 |
| T226 | 2-(3-chloro-4-(6-(1-methylcyclopropoxy)-9-((4-methylpyridin-2-yl)methyl)-9H-purin-8-yl)phenoxy)-N-(2-hydroxyethyl)acetamide | 523 | C26 H27 Cl N6 O4 | 8 | 6.8 | |
| T227 | N-(2-(3-chloro-4-(6-(1-methylcyclopropoxy)-9-((4-methylpyridin-2-yl)methyl)-9H-purin-8-yl)phenoxy)ethyl)-2-hydroxyacetamide | 523 | C26 H27 Cl N6 O4 | 8.3 | 6.5 | |
| T228 | methyl (2-(3-chloro-4-(6-(1-methylcyclopropoxy)-9-((4-methylpyridin-2-yl)methyl)-9H-purin-8-yl)phenoxy)ethyl)carbamate | 523 | C26 H27 Cl N6 O4 | 8.5 | 6.9 | |
| T230 | 1-(3-chloro-4-(9-((4-chloropyridin-2-yl)methyl)-6-(1-methylcyclopropoxy)-9H-purin-8-yl)phenyl)piperidin-4-amine | 524 | C26 H27 Cl2 N7 O | 8.3 | 6.4 | <5.0 |
| T231 | 3-(4-(9-((4-chloropyridin-2-yl)methyl)-6-(1-methylcyclopropoxy)-9H-purin-8-yl)-3-fluorophenoxy)-N,N-dimethylpropan-1-amine | 511 | C26 H28 Cl F N6 O2 | 8.5 | 6.6 | <5.0 |
| T232 | 8-(4-(sec-butyl)-2-chlorophenyl)-6-(1-methylcyclopropoxy)-9-((4-methylpyridin-2-yl)methyl)-9H-purine (racemic) | 462 | C26 H28 Cl N5 O | 7.9 | <5.8 | |
| T233 | 2-(2-(3-chloro-4-(6-(1-methylcyclopropoxy)-9-((4-methylpyridin-2-yl)methyl)-9H-purin-8-yl)phenoxy)ethoxy)ethan-1-ol | 510 | C26 H28 Cl N5 O4 | 8.4 | 6.8 | |
| T234 | 8-(2-chloro-4-(3-(methylsulfonyl)propoxy)phenyl)-6-(1-methylcyclopropoxy)-9-((4-methylpyridin-2-yl)methyl)-9H-purine | 542 | C26 H28 Cl N5 O4 S | 8.3 | 6.7 | <5.0 |
| T235 | 8-(2-chloro-4-(piperazin-1-yl)phenyl)-6-(1-methylcyclopropoxy)-9-((4-methylpyridin-2-yl)methyl)-9H-purine | 490 | C26 H28 Cl N7 O | 8.2 | 6.4 | |
| T236 | 2-(3-chloro-4-(6-(1-methylcyclopropoxy)-9-((4-methylpyridin-2-yl)methyl)-9H-purin-8-yl)phenyl)-N,N-dimethylethan-1-amine | 477 | C26 H29 Cl N6 O | 8.3 | 6.6 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T237 | 2-(2-chloro-3-(6-(1-methylcyclopropoxy)-9-((4-methylpyridin-2-yl)methyl)-9H-purin-8-yl)phenoxy)-N,N-dimethylethan-1-amine | 493 | C26 H29 Cl N6 O2 | 8 | 7.3 | <5.0 |
| T238 | 3-(3-chloro-4-(6-(1-methylcyclopropoxy)-9-((4-methylpyridin-2-yl)methyl)-9H-purin-8-yl)phenoxy)-N-methylpropan-1-amine | 493 | C26 H29 Cl N6 O2 | 8.6 | 6.3 | <5.0 |
| T239 | 2-((8-(2-chloro-4-(2-(pyrrolidin-1-yl)ethoxy)phenyl)-6-(1-methylcyclopropoxy)-9H-purin-9-yl)methyl)-5-methylthiazole | 525 | C26 H29 Cl N6 O2 S | 8.2 | 6.6 | <5.0 |
| T240 | (R)-2-((8-(2-chloro-4-((1-methylpyrrolidin-2-yl)methoxy)phenyl)-6-(1-methylcyclopropoxy)-9H-purin-9-yl)methyl)-5-methylthiazole | 525 | C26 H29 Cl N6 O2 S | 8.3 | 6.5 | <5.0 |
| T241 | 2-((8-(2-chloro-4-((1-methylpiperidin-4-yl)oxy)phenyl)-6-(1-methylcyclopropoxy)-9H-purin-9-yl)methyl)-5-methylthiazole | 525 | C26 H29 Cl N6 O2 S | 8.4 | 6.5 | <5.0 |
| T242 | 2-((8-(4-(azepan-4-yloxy)-2-chlorophenyl)-6-(1-methylcyclopropoxy)-9H-purin-9-yl)methyl)-5-methylthiazole (isomer 2) | 525 | C26 H29 Cl N6 O2 S | 8.3 | 6.1 | <5.0 |
| T243 | 2-((8-(4-(azepan-4-yloxy)-2-chlorophenyl)-6-(1-methylcyclopropoxy)-9H-purin-9-yl)methyl)-5-methylthiazole (isomer 1) | 525 | C26 H29 Cl N6 O2 S | 7.8 | 6.3 | <5.0 |
| T244 | 1-(3-(3-chloro-4-(6-(1-methylcyclopropoxy)-9-((5-methylthiazol-2-yl)methyl)-9H-purin-8-yl)phenoxy)propyl)azetidin-3-ol | 541 | C26 H29 Cl N6 O3 S | 8.3 | 6.3 | <5.1 |
| T245 | (R)-1-(2-(3-chloro-4-(6-(1-methylcyclopropoxy)-9-((5-methylthiazol-2-yl)methyl)-9H-purin-8-yl)phenoxy)ethyl)pyrrolidin-3-ol | 541 | C26 H29 Cl N6 O3 S | 8.2 | 6.2 | |
| T246 | 1-(3-(2-chloro-3-(6-(1-methylcyclopropoxy)-9-((5-methylthiazol-2-yl)methyl)-9H-purin-8-yl)phenoxy)propyl)azetidin-3-ol | 541 | C26 H29 Cl N6 O3 S | 8 | 6.1 | <5.0 |
| T247 | N1-(3-chloro-4-(6-(1-methylcyclopropoxy)-9-((4-methylpyridin-2-yl)methyl)-9H-purin-8-yl)phenyl)-N2,N2-dimethylethane-1,2-diamine | 492 | C26 H30 Cl N7 O | 8.2 | 6.3 | |
| T248 | 2-((8-(2-chloro-4-(2-(piperazin-1-yl)ethoxy)phenyl)-6-(1-methylcyclopropoxy)-9H-purin-9-yl)methyl)-4-methylthiazole | 540 | C26 H30 Cl N7 O2 S | 8.4 | 5.7 | <5.0 |
| T249 | 5-((8-(2-chloro-4-(2-(piperazin-1-yl)ethoxy)phenyl)-6-(1-methylcyclopropoxy)-9H-purin-9-yl)methyl)-2-methylthiazole | 540 | C26 H30 Cl N7 O2 S | 7.7 | 5.4 | <5.0 |
| T250 | 2-((3-chloro-4-(9-(3-chlorobenzyl)-6-(1-methylcyclopropoxy)-9H-purin-8-yl)phenoxy)methyl)thiazole-4-carboxylic acid | 582 | C27 H21 Cl2 N5 O4 S | 8.4 | 5.5 | <5.0 |
| T251 | 4-(3-chloro-4-(6-(1-methylcyclopropoxy)-9-((perfluorophenyl)methyl)-9H-purin-8-yl)phenoxy)-2-methylbutanoic acid (racemic) | 597 | C27 H22 Cl F5 N4 O4 | 7.4 | 5.7 | <5.0 |
| T252 | 4-(3-chloro-4-(9-(3-chlorobenzyl)-6-(1-cyanocyclopropoxy)-9H-purin-8-yl)phenoxy)-2-methylbutanoic acid (racemic) | 552 | C27 H23 Cl2 N5 O4 | 8 | 6.4 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T253 | (1r,3r)-3-(3-chloro-4-(9-(3-chlorobenzyl)-6-(1-methylcyclopropoxy)-9H-purin-8-yl)phenoxy)cyclobutane-1-carboxylic acid | 539 | C27 H24 Cl2 N4 O4 | 8.5 | 6.5 | <5.0 |
| T254 | (1s,3s)-3-(3-chloro-4-(9-(3-chlorobenzyl)-6-(1-methylcyclopropoxy)-9H-purin-8-yl)phenoxy)cyclobutane-1-carboxylic acid | 539 | C27 H24 Cl2 N4 O4 | 8.3 | 6.8 | <5.0 |
| T255 | (E)-4-(3-chloro-4-(9-(3-chlorobenzyl)-6-(1-methylcyclopropoxy)-9H-purin-8-yl)phenoxy)-2-methylbut-2-enoic acid | 539 | C27 H24 Cl2 N4 O4 | 8.5 | 6.5 | |
| T256 | (1r,3r)-3-(2-chloro-3-(9-(3-chlorobenzyl)-6-(1-methylcyclopropoxy)-9H-purin-8-yl)phenoxy)cyclobutane-1-carboxylic acid | 539 | C27 H24 Cl2 N4 O4 | 8.5 | 6.9 | |
| T257 | (1s,3s)-3-(2-chloro-3-(9-(3-chlorobenzyl)-6-(1-methylcyclopropoxy)-9H-purin-8-yl)phenoxy)cyclobutane-1-carboxylic acid | 539 | C27 H24 Cl2 N4 O4 | 8.5 | 7 | |
| T258 | 4-(4-(9-(5-bromo-2-fluorobenzyl)-6-(1-methylcyclopropoxy)-9H-purin-8-yl)-3-chlorophenoxy)-2-methylbutanoic acid (racemic) | 603 | C27 H25 Br Cl F N4 O4 | 8.4 | 7.1 | <5.0 |
| T259 | 4-(4-(9-(2-bromo-6-chlorobenzyl)-6-(1-methylcyclopropoxy)-9H-purin-8-yl)-3-chlorophenoxy)-2-methylbutanoic acid (racemic) | 619 | C27 H25 Br Cl2 N4 O4 | 7.9 | 5.5 | <5.0 |
| T260 | 4-(3-chloro-4-(9-(3,5-difluorobenzyl)-6-(1-methylcyclopropoxy)-9H-purin-8-yl)phenoxy)-2-methylbutanoic acid (racemic) | 543 | C27 H25 Cl F2 N4 O4 | 8.2 | 6.6 | <5.0 |
| T261 | 4-(3-chloro-4-(9-(2,3-difluorobenzyl)-6-(1-methylcyclopropoxy)-9H-purin-8-yl)phenoxy)-2-methylbutanoic acid (Isomer 1) | 543 | C27 H25 Cl F2 N4 O4 | 8 | 6.2 | |
| T262 | 4-(3-chloro-4-(9-(2,3-difluorobenzyl)-6-(1-methylcyclopropoxy)-9H-purin-8-yl)phenoxy)-2-methylbutanoic acid (Isomer 2) | 543 | C27 H25 Cl F2 N4 O4 | 8.4 | 6.3 | |
| T263 | 4-(3-chloro-4-(9-(2,6-difluorobenzyl)-6-(1-methylcyclopropoxy)-9H-purin-8-yl)phenoxy)-2-methylbutanoic acid (isomer 1) | 543 | C27 H25 Cl F2 N4 O4 | 8.2 | 6.1 | |
| T264 | 4-(3-chloro-4-(9-(2,6-difluorobenzyl)-6-(1-methylcyclopropoxy)-9H-purin-8-yl)phenoxy)-2-methylbutanoic acid (isomer 2) | 543 | C27 H25 Cl F2 N4 O4 | 8.2 | 6.1 | |
| T266 | 2-(3-chloro-4-(6-(1-methylcyclopropoxy)-9-((4-methylpyridin-2-yl)methyl)-9H-purin-8-yl)phenoxy)-N-(prop-2-yn-1-yl)acetamide | 517 | C27 H25 Cl N6 O3 | 8.2 | 6.8 | |
| T267 | 4-(3-chloro-4-(9-(3-chloro-2-fluorobenzyl)-6-(1-methylcyclopropoxy)-9H-purin-8-yl)phenoxy)-2-methylbutanoic acid (racemic) | 559 | C27 H25 Cl2 F N4 O4 | 8.2 | 6.4 | |
| T268 | 4-(3-chloro-4-(9-(5-chloro-2-fluorobenzyl)-6-(1-methylcyclopropoxy)-9H-purin-8-yl)phenoxy)-2-methylbutanoic acid (racemic) | 559 | C27 H25 Cl2 F N4 O4 | 8.2 | 7.2 | <5.0 |
| T269 | 4-(3-chloro-4-(9-(3-chloro-4-fluorobenzyl)-6-(1-methylcyclopropoxy)-9H-purin-8-yl)phenoxy)-2-methylbutanoic acid (racemic) | 559 | C27 H25 Cl2 F N4 O4 | 8.1 | 5.9 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T270 | 4-(3-chloro-4-(9-(3-chloro-2-fluorobenzyl)-6-(1-methylcyclopropoxy)-9H-purin-8-yl)phenoxy)-2-methylbutanoic acid (Isomer 1) | 559 | C27 H25 Cl2 F N4 O4 | 8.2 | 6.3 | |
| T271 | 4-(3-chloro-4-(9-(3-chloro-2-fluorobenzyl)-6-(1-methylcyclopropoxy)-9H-purin-8-yl)phenoxy)-2-methylbutanoic acid (Isomer 2) | 559 | C27 H25 Cl2 F N4 O4 | 8.2 | 6.4 | |
| T272 | 4-(3-chloro-4-(9-(3-chloro-5-fluorobenzyl)-6-(1-methylcyclopropoxy)-9H-purin-8-yl)phenoxy)-2-methylbutanoic acid (isomer 1) | 559 | C27 H25 Cl2 F N4 O4 | 8.4 | 6.7 | |
| T273 | 4-(3-chloro-4-(9-(3-chloro-5-fluorobenzyl)-6-(1-methylcyclopropoxy)-9H-purin-8-yl)phenoxy)-2-methylbutanoic acid (isomer 2) | 559 | C27 H25 Cl2 F N4 O4 | 8.5 | 6.8 | |
| T274 | 4-(3-chloro-4-(9-(3-chlorobenzyl)-6-((1,1,1-trifluoro-2-methylpropan-2-yl)oxy)-9H-purin-8-yl)phenoxy)-2-methylbutanoic acid (racemic) | 597 | C27 H25 Cl2 F3 N4 O4 | 8.4 | 6.5 | <5.0 |
| T275 | 4-(3-chloro-4-(9-(3,5-dichlorobenzyl)-6-(1-methylcyclopropoxy)-9H-purin-8-yl)phenoxy)-2-methylbutanoic acid (racemic) | 575 | C27 H25 Cl3 N4 O4 | 8.2 | 6.9 | <5.0 |
| T276 | 4-(3-chloro-4-(9-(2,5-dichlorobenzyl)-6-(1-methylcyclopropoxy)-9H-purin-8-yl)phenoxy)-2-methylbutanoic acid (racemic) | 575 | C27 H25 Cl3 N4 O4 | 8.3 | 7.2 | <5.0 |
| T277 | 4-(3-chloro-4-(9-(2,6-dichlorobenzyl)-6-(1-methylcyclopropoxy)-9H-purin-8-yl)phenoxy)-2-methylbutanoic acid (racemic) | 575 | C27 H25 Cl3 N4 O4 | 8.1 | 5.7 | <5.0 |
| T278 | 4-(4-(9-(2-bromobenzyl)-6-(1-methylcyclopropoxy)-9H-purin-8-yl)-3-chlorophenoxy)-2-methylbutanoic acid (racemic) | 585 | C27 H26 Br Cl N4 O4 | 8 | 6.5 | <5.0 |
| T279 | 4-(4-(9-(3-bromobenzyl)-6-(1-methylcyclopropoxy)-9H-purin-8-yl)-3-chlorophenoxy)-2-methylbutanoic acid (racemic) | 585 | C27 H26 Br Cl N4 O4 | 8.1 | 6.7 | <5.0 |
| T280 | 3-chloro-N-(3-fluorocyclobutyl)-4-(6-(1-methylcyclopropoxy)-9-((4-methylpyridin-2-yl)methyl)-9H-purin-8-yl)benzamide | 521 | C27 H26 Cl F N6 O2 | 7.8 | 6.1 | |
| T281 | (S)-(3-chloro-4-(6-(1-methylcyclopropoxy)-9-((4-methylpyridin-2-yl)methyl)-9H-purin-8-yl)phenyl)(3-fluoropyrrolidin-1-yl)methanone | 521 | C27 H26 Cl F N6 O2 | 7.7 | 6.1 | |
| T282 | (3-chloro-4-(6-(1-methylcyclopropoxy)-9-((4-methylpyridin-2-yl)methyl)-9H-purin-8-yl)phenyl)((3R,4R)-3-fluoro-4-hydroxypyrrolidin-1-yl)methanone | 537 | C27 H26 Cl F N6 O3 | 7.4 | 5.6 | |
| T283 | 2-(3-chloro-4-(6-(1-methylcyclopropoxy)-9-((4-methylpyridin-2-yl)methyl)-9H-purin-8-yl)phenoxy)-1-(3-fluoroazetidin-1-yl)ethan-1-one | 537 | C27 H26 Cl F N6 O3 | 8.3 | 6.8 | |
| T284 | 1-(2-(3-chloro-4-(6-(1-methylcyclopropoxy)-9-((4-(trifluoromethyl)pyridin-2-yl)methyl)-9H-purin-8-yl)phenoxy)ethyl)azetidin-3-ol | 575 | C27 H26 Cl F3 N6 O3 | 8.5 | 6.3 | <5.0 |
| T285 | 4-(3-chloro-4-(9-(3-iodobenzyl)-6-(1-methylcyclopropoxy)-9H-purin-8-yl)phenoxy)-2-methylbutanoic acid (racemic) | 633 | C27 H26 Cl I N4 O4 | 8.1 | 6.6 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T286 | 3-chloro-N-(2-cyanoethyl)-N-methyl-4-(6-(1-methylcyclopropoxy)-9-((4-methylpyridin-2-yl)methyl)-9H-purin-8-yl)benzamide | 516 | C27 H26 Cl N7 O2 | 7.2 | 5.9 | |
| T287 | 4-(3-chloro-4-(6-(1-methylcyclopropoxy)-9-((4-methylpyridin-2-yl)methyl)-9H-purin-8-yl)benzoyl)piperazin-2-one | 532 | C27 H26 Cl N7 O3 | 7.3 | <5.1 | |
| T288 | 3-(4-(4-(tert-butoxy)-1-(3-chlorobenzyl)-1H-benzo[d]imidazol-2-yl)-3-chlorophenoxy)propanoic acid | 513 | C27 H26 Cl2 N2 O4 | 7.8 | 5.7 | <5.0 |
| T289 | 5-(3-chloro-4-(9-(3-chlorobenzyl)-6-(1-methylcyclopropoxy)-9H-purin-8-yl)phenyl)pentanoic acid | 525 | C27 H26 Cl2 N4 O3 | 8.3 | 6.9 | |
| T290 | 4-(3-chloro-4-(9-(3-chlorobenzyl)-6-(1-methylcyclopropoxy)-9H-purin-8-yl)phenyl)-2-methylbutanoic acid (racemic) | 525 | C27 H26 Cl2 N4 O3 | 8.2 | 6.6 | |
| T291 | 4-(3-chloro-4-(9-(3-chlorobenzyl)-6-(1-methylcyclopropoxy)-9H-purin-8-yl)phenoxy)-2-methylbutanoic acid (racemic) | 541 | C27 H26 Cl2 N4 O4 | 8.2 | 6.8 | |
| T292 | 5-(2-chloro-3-(9-(3-chlorobenzyl)-6-(1-methylcyclopropoxy)-9H-purin-8-yl)phenoxy)pentanoic acid | 541 | C27 H26 Cl2 N4 O4 | 8.3 | 7.5 | <5.0 |
| T293 | 4-(2-chloro-3-(9-(3-chlorobenzyl)-6-(1-methylcyclopropoxy)-9H-purin-8-yl)phenoxy)-2-methylbutanoic acid (racemic) | 541 | C27 H26 Cl2 N4 O4 | 8.3 | 7.5 | <5.5 |
| T294 | 4-(3-chloro-4-(9-(3-chlorobenzyl)-6-(1-methylcyclopropoxy)-9H-purin-8-yl)phenoxy)-3-methylbutanoic acid (Isomer 1) | 541 | C27 H26 Cl2 N4 O4 | 8.2 | 6.8 | <5.0 |
| T295 | 4-(3-chloro-4-(9-(3-chlorobenzyl)-6-(1-methylcyclopropoxy)-9H-purin-8-yl)phenoxy)-3-methylbutanoic acid (Isomer 2) | 541 | C27 H26 Cl2 N4 O4 | 8.3 | 6.9 | <5.0 |
| T296 | (S)-4-(2-chloro-3-(9-(3-chlorobenzyl)-6-(1-methylcyclopropoxy)-9H-purin-8-yl)phenoxy)-2-methylbutanoic acid | 541 | C27 H26 Cl2 N4 O4 | 8.3 | 7.6 | <5.0 |
| T297 | (R)-4-(2-chloro-3-(9-(3-chlorobenzyl)-6-(1-methylcyclopropoxy)-9H-purin-8-yl)phenoxy)-2-methylbutanoic acid | 541 | C27 H26 Cl2 N4 O4 | 8.2 | 7.2 | |
| T298 | 3-(2-chloro-3-(9-(3-chlorobenzyl)-6-(1-methylcyclopropoxy)-9H-purin-8-yl)phenoxy)-2,2-dimethylpropanoic acid | 541 | C27 H26 Cl2 N4 O4 | 8.5 | 6.2 | |
| T299 | 4-(2-chloro-3-(9-(3-chlorobenzyl)-6-(1-methylcyclopropoxy)-9H-purin-8-yl)phenoxy)-3-methylbutanoic acid (Isomer 2) | 541 | C27 H26 Cl2 N4 O4 | 8.1 | 7.1 | <5.0 |
| T300 | 4-(2-chloro-3-(9-(3-chlorobenzyl)-6-(1-methylcyclopropoxy)-9H-purin-8-yl)phenoxy)-3-methylbutanoic acid (Isomer 1) | 541 | C27 H26 Cl2 N4 O4 | 8.4 | 7.2 | <5.0 |
| T301 | (R)-4-(3-chloro-4-(9-(3-chlorobenzyl)-6-(1-methylcyclopropoxy)-9H-purin-8-yl)phenoxy)-2-hydroxy-2-methylbutanoic acid | 557 | C27 H26 Cl2 N4 O5 | 8.2 | 5.6 | |
| T302 | 2-(3-(3-chloro-4-(9-(3-chlorobenzyl)-6-(1-methylcyclopropoxy)-9H-purin-8-yl)phenoxy)propoxy)acetic acid | 557 | C27 H26 Cl2 N4 O5 | 8.3 | 6.5 | <5.0 |
| T303 | 3-(2-(3-chloro-4-(9-(3-chlorobenzyl)-6-(1-methylcyclopropoxy)-9H-purin-8-yl)phenoxy)ethoxy)propanoic acid | 557 | C27 H26 Cl2 N4 O5 | 8.1 | 6.9 | |
| T304 | 2-(3-(2-chloro-3-(9-(3-chlorobenzyl)-6-(1-methylcyclopropoxy)-9H-purin-8-yl)phenoxy)propoxy)acetic acid | 557 | C27 H26 Cl2 N4 O5 | 8.2 | 7 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T305 | rac-(R)-2-(2-(3-chloro-4-(9-(3-chlorobenzyl)-6-(1-methylcyclopropoxy)-9H-purin-8-yl)phenoxy)ethoxy)propanoic acid | 557 | C27 H26 Cl2 N4 O5 | 8.4 | 6.1 | <5.0 |
| T306 | (R)-2-(2-(3-chloro-4-(9-(3-chlorobenzyl)-6-(1-methylcyclopropoxy)-9H-purin-8-yl)phenoxy)ethoxy)propanoic acid | 557 | C27 H26 Cl2 N4 O5 | 8.5 | 6.1 | |
| T307 | 1-(2-(3-chloro-4-(9-((4-(difluoromethyl)pyridin-2-yl)methyl)-6-(1-methylcyclopropoxy)-9H-purin-8-yl)phenoxy)ethyl)azetidin-3-ol | 557 | C27 H27 Cl F2 N6 O3 | 8.3 | 5.8 | <5.0 |
| T308 | 1-(azetidin-1-yl)-2-(3-chloro-4-(6-(1-methylcyclopropoxy)-9-((4-methylpyridin-2-yl)methyl)-9H-purin-8-yl)phenyl)ethan-1-one | 503 | C27 H27 Cl N6 O2 | 8.2 | 6.5 | <5.0 |
| T309 | (3-chloro-4-(6-(1-methylcyclopropoxy)-9-((4-methylpyridin-2-yl)methyl)-9H-purin-8-yl)phenyl)(pyrrolidin-1-yl)methanone | 503 | C27 H27 Cl N6 O2 | 8 | 6.2 | |
| T310 | 2-(3-chloro-4-(6-(1-methylcyclopropoxy)-9-((4-methylpyridin-2-yl)methyl)-9H-purin-8-yl)phenyl)-N-cyclopropylacetamide | 503 | C27 H27 Cl N6 O2 | 8.1 | 6.4 | <5.0 |
| T311 | (R)-(3-chloro-4-(6-(1-methylcyclopropoxy)-9-((4-methylpyridin-2-yl)methyl)-9H-purin-8-yl)phenyl)(3-hydroxypyrrolidin-1-yl)methanone | 519 | C27 H27 Cl N6 O3 | 8.1 | 5.4 | <5.0 |
| T312 | 1-(azetidin-1-yl)-2-(3-chloro-4-(6-(1-methylcyclopropoxy)-9-((4-methylpyridin-2-yl)methyl)-9H-purin-8-yl)phenoxy)ethan-1-one | 519 | C27 H27 Cl N6 O3 | 8.2 | 6.7 | |
| T313 | 1-(2-(3-chloro-4-(6-(1-methylcyclopropoxy)-9-((4-methylpyridin-2-yl)methyl)-9H-purin-8-yl)phenoxy)ethyl)azetidin-2-one | 519 | C27 H27 Cl N6 O3 | 8.3 | 6.7 | |
| T314 | (3-chloro-4-(6-(1-methylcyclopropoxy)-9-((4-methylpyridin-2-yl)methyl)-9H-purin-8-yl)phenyl)(3-hydroxy-3-methylazetidin-1-yl)methanone | 519 | C27 H27 Cl N6 O3 | 7.8 | 5.9 | |
| T315 | (3-chloro-4-(6-(1-methylcyclopropoxy)-9-((4-methylpyridin-2-yl)methyl)-9H-purin-8-yl)phenyl)(morpholino)methanone | 519 | C27 H27 Cl N6 O3 | 7.1 | 5.8 | |
| T316 | (R)-3-chloro-4-(6-(1-methylcyclopropoxy)-9-((4-methylpyridin-2-yl)methyl)-9H-purin-8-yl)-N-(tetrahydrofuran-3-yl)benzamide | 519 | C27 H27 Cl N6 O3 | 7.9 | 6.2 | |
| T317 | 3-chloro-4-(6-(1-methylcyclopropoxy)-9-((4-methylpyridin-2-yl)methyl)-9H-purin-8-yl)-N-(3-methyloxetan-3-yl)benzamide | 519 | C27 H27 Cl N6 O3 | 7.7 | 6 | |
| T318 | 2-(3-chloro-4-(6-(1-methylcyclopropoxy)-9-((4-methylpyridin-2-yl)methyl)-9H-purin-8-yl)phenoxy)-N-cyclopropylacetamide | 519 | C27 H27 Cl N6 O3 | 8 | 6.4 | |
| T319 | 3-chloro-N-(3-hydroxycyclobutyl)-4-(6-(1-methylcyclopropoxy)-9-((4-methylpyridin-2-yl)methyl)-9H-purin-8-yl)benzamide | 519 | C27 H27 Cl N6 O3 | 8.1 | 5.6 | |
| T320 | 3-chloro-N-methyl-4-(6-(1-methylcyclopropoxy)-9-((4-methylpyridin-2-yl)methyl)-9H-purin-8-yl)-N-(oxetan-3-yl)benzamide | 519 | C27 H27 Cl N6 O3 | 7.6 | 5.5 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T321 | 1-(3-chloro-4-(6-(1-methylcyclopropoxy)-9-((4-methylpyridin-2-yl)methyl)-9H-purin-8-yl)phenyl)-4-hydroxypiperidin-2-one (racemic) | 519 | C27 H27 Cl N6 O3 | 7.8 | 5.4 | |
| T322 | 2-(3-chloro-4-(6-(1-methylcyclopropoxy)-9-((4-methylpyridin-2-yl)methyl)-9H-purin-8-yl)phenoxy)-1-(3-hydroxyazetidin-1-yl)ethan-1-one | 535 | C27 H27 Cl N6 O4 | 8.1 | 6.2 | |
| T323 | 2-(3-chloro-4-(6-(1-methylcyclopropoxy)-9-((4-methylpyridin-2-yl)methyl)-9H-purin-8-yl)phenoxy)-N-(oxetan-3-yl)acetamide | 535 | C27 H27 Cl N6 O4 | 8.1 | 6.7 | |
| T324 | (S)-6-((3-chloro-4-(6-(1-methylcyclopropoxy)-9-((4-methylpyridin-2-yl)methyl)-9H-purin-8-yl)phenoxy)methyl)morpholin-3-one | 535 | C27 H27 Cl N6 O4 | 8.4 | 6.4 | |
| T325 | 4-(2-chloro-3-(9-(3-chlorobenzyl)-6-(1-methylcyclopropoxy)-9H-purin-8-yl)phenoxy)-N-(methylsulfonyl)butanamide | 604 | C27 H27 Cl2 N5 O5 S | 8.3 | 6.5 | |
| T326 | 4-(3-chloro-4-(9-(3-chlorobenzyl)-6-(1-methylcyclopropoxy)-9H-purin-8-yl)phenoxy)-N-(methylsulfonyl)butanamide | 604 | C27 H27 Cl2 N5 O5 S | 8.5 | 6.2 | <5.0 |
| T327 | (S)-2-(3-chloro-4-(6-(1-methylcyclopropoxy)-9-((4-methylpyridin-2-yl)methyl)-9H-purin-8-yl)phenoxy)-N-(2-fluoropropyl)acetamide | 539 | C27 H28 Cl F N6 O3 | 8 | 6.7 | |
| T328 | 2-(3-chloro-4-(6-(1-methylcyclopropoxy)-9-((4-methylpyridin-2-yl)methyl)-9H-purin-8-yl)phenoxy)-N-(3-fluoropropyl)acetamide | 539 | C27 H28 Cl F N6 O3 | 8 | 6.4 | |
| T329 | 3-(3-chloro-4-(6-(1-methylcyclopropoxy)-9-((4-(trifluoromethyl)pyridin-2-yl)methyl)-9H-purin-8-yl)phenoxy)-N,N-dimethylpropan-1-amine | 561 | C27 H28 Cl F3 N6 O2 | 8.6 | 6.9 | 5 |
| T330 | rel-(1R,3R)-3-(3-chloro-4-(6-(1-methylcyclopropoxy)-9-((4-methylpyridin-2-yl)methyl)-9H-purin-8-yl)phenoxy)cyclopentan-1-ol (Isomer 1) | 506 | C27 H28 Cl N5 O3 | 8.2 | 6.7 | |
| T333 | 8-(2-chloro-4-((3-methoxyoxetan-3-yl)methoxy)phenyl)-6-(1-methylcyclopropoxy)-9-((4-methylpyridin-2-yl)methyl)-9H-purine | 522 | C27 H28 Cl N5 O4 | 8 | 6.6 | |
| T334 | 3-(2-(3-chloro-4-(6-(1-methylcyclopropoxy)-9-((4-methylpyridin-2-yl)methyl)-9H-purin-8-yl)phenoxy)ethyl)oxetan-3-ol | 522 | C27 H28 Cl N5 O4 | 8.2 | 6.6 | |
| T335 | 4-(3-chloro-4-(6-(1-methylcyclopropoxy)-9-((4-methylpyridin-2-yl)methyl)-9H-purin-8-yl)phenoxy)tetrahydro-2H-thiopyran 1,1-dioxide | 554 | C27 H28 Cl N5 O4 S | 8.2 | 6.6 | <5.0 |
| T336 | 8-(4-((1R,4R)-2,5-diazabicyclo[2.2.1 ]heptan-2-yl)-2-chlorophenyl)-6-(1-methylcyclopropoxy)-9-((4-methylpyridin-2-yl)methyl)-9H-purine | 502 | C27 H28 Cl N7 0 | 8.1 | 5.8 | <5.0 |
| T337 | (3-chloro-4-(6-(1-methylcyclopropoxy)-9-((4-methylpyridin-2-yl)methyl)-9H-purin-8-yl)phenyl)(piperazin-1-yl)methanone | 518 | C27 H28 Cl N7 O2 | 7.8 | 5.3 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T338 | 4-(3-chloro-4-(6-(1-methylcyclopropoxy)-9-((4-methylpyridin-2-yl)methyl)-9H-purin-8-yl)phenyl)-1,4-diazepan-5-one | 518 | C27 H28 Cl N7 O2 | 7.5 | 5.7 | |
| T339 | 1-(3-chloro-4-(6-(1-methylcyclopropoxy)-9-((4-methylpyridin-2-yl)methyl)-9H-purin-8-yl)phenyl)-1,4-diazepan-5-one | 518 | C27 H28 Cl N7 O2 | 8.2 | 6.3 | |
| T340 | (S)-1-(3-chloro-4-(6-(1-methylcyclopropoxy)-9-((4-methylpyridin-2-yl)methyl)-9H-purin-8-yl)phenyl)pyrrolidine-3-carboxamide | 518 | C27 H28 Cl N7 O2 | 8.1 | 5.9 | |
| T341 | 1-(3-chloro-4-(6-(1-methylcyclopropoxy)-9-((4-methylpyridin-2-yl)methyl)-9H-purin-8-yl)phenyl)-N-methylazetidine-3-carboxamide | 518 | C27 H28 Cl N7 O2 | 8.2 | 6.5 | |
| T342 | (R)-N-(3-chloro-4-(6-(1-methylcyclopropoxy)-9-((4-methylpyridin-2-yl)methyl)-9H-purin-8-yl)phenyl)-3-hydroxypyrrolidine-1-carboxamide | 534 | C27 H28 Cl N7 O3 | 8.1 | <5.4 | <5.0 |
| T343 | 3-(3-chloro-4-(6-(1-methylcyclopropoxy)-9-((4-methylpyridin-2-yl)methyl)-9H-purin-8-yl)phenoxy)-N-methylazetidine-1-carboxamide | 534 | C27 H28 Cl N7 O3 | 8.1 | 6.4 | |
| T344 | (R)-3-(3-chloro-4-(6-(1-methylcyclopropoxy)-9-((4-methylpyridin-2-yl)methyl)-9H-purin-8-yl)phenoxy)pyrrolidine-1-carboxamide | 534 | C27 H28 Cl N7 O3 | 7.9 | 5.7 | |
| T345 | 9-((4-chloro-3-fluoropyridin-2-yl)methyl)-8-(2-chloro-4-(2-(piperazin-1-yl)ethoxy)phenyl)-6-(1-methylcyclopropoxy)-9H-purine | 572 | C27 H28 Cl2 F N7 O2 | 7.9 | 6.1 | 5 |
| T346 | 8-(2-chloro-4-(2-(piperazin-1-yl)ethoxy)phenyl)-9-((4-chloro-5-fluoropyridin-2-yl)methyl)-6-(1-methylcyclopropoxy)-9H-purine | 572 | C27 H28 Cl2 F N7 O2 | 8.2 | 5.8 | <5.0 |
| T347 | 1-(3-(3-chloro-4-(9-((4-chloropyridin-2-yl)methyl)-6-(1-methylcyclopropoxy)-9H-purin-8-yl)phenoxy)propyl)azetidin-3-ol | 555 | C27 H28 Cl2 N6 O3 | 8.6 | 6.8 | <5.1 |
| T348 | 8-(2-bromo-4-(2-(piperazin-1-yl)ethoxy)phenyl)-9-((4-chloropyridin-2-yl)methyl)-6-(1-methylcyclopropoxy)-9H-purine | 598 | C27 H29 Br Cl N7 O2 | 8.3 | 6.9 | <5.0 |
| T349 | 9-((4-chloropyridin-2-yl)methyl)-8-(2-fluoro-4-(2-(piperazin-1-yl)ethoxy)phenyl)-6-(1-methylcyclopropoxy)-9H-purine | 538 | C27 H29 Cl F N7 O2 | 7.9 | 6.2 | <5.0 |
| T350 | 8-(2-chloro-4-(2-(piperazin-1-yl)ethoxy)phenyl)-9-((5-fluoropyridin-2-yl)methyl)-6-(1-methylcyclopropoxy)-9H-purine | 540 (37Cl) | C27 H29 Cl F N7 O2 | 7.8 | 5.6 | |
| T351 | 8-(2-chloro-4-(2-(piperazin-1-yl)ethoxy)phenyl)-9-((3-fluoropyridin-2-yl)methyl)-6-(1-methylcyclopropoxy)-9H-purine | 538 | C27 H29 Cl F N7 O2 | 7.7 | 5.5 | |
| T352 | 3-(3-chloro-4-(9-((4-(difluoromethyl)pyridin-2-yl)methyl)-6-(1-methylcyclopropoxy)-9H-purin-8-yl)phenoxy)-N,N-dimethylpropan-1-amine | 543 | C27 H29 Cl F2 N6 O2 | 8.2 | 6.8 | <5.0 |
| T353 | (R)-1-(3-chloro-4-(6-(1-methylcyclopropoxy)-9-((4-methylpyridin-2-yl)methyl)-9H-purin-8-yl)benzyl)pyrrolidin-3-ol | 505 | C27 H29 Cl N6 O2 | 8.3 | 6.5 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T354 | 8-(2-chloro-4-(piperidin-4-yloxy)phenyl)-6-(1-methylcyclopropoxy)-9-((4-methylpyridin-2-yl)methyl)-9H-purine | 505 | C27 H29 Cl N6 O2 | 8.3 | 6.3 | <5.0 |
| T355 | 1-(3-chloro-4-(6-(1-methylcyclopropoxy)-9-((4-methylpyridin-2-yl)methyl)-9H-purin-8-yl)phenethyl)azetidin-3-ol | 505 | C27 H29 Cl N6 O2 | 8.2 | 6.2 | <5.0 |
| T356 | (R)-8-(2-chloro-4-(pyrrolidin-2-ylmethoxy)phenyl)-6-(1-methylcyclopropoxy)-9-((4-methylpyridin-2-yl)methyl)-9H-purine | 505 | C27 H29 Cl N6 O2 | 8.4 | 6.7 | <5.0 |
| T357 | 2-(3-chloro-4-(6-(1-methylcyclopropoxy)-9-((4-methylpyridin-2-yl)methyl)-9H-purin-8-yl)phenyl)-N-isopropylacetamide | 505 | C27 H29 Cl N6 O2 | 8.1 | 6.4 | <5.0 |
| T358 | 3-(3-chloro-4-(6-(1-methylcyclopropoxy)-9-((4-methylpyridin-2-yl)methyl)-9H-purin-8-yl)phenyl)-N,N-dimethylpropanamide | 505 | C27 H29 Cl N6 O2 | 8.2 | 6.6 | |
| T359 | 2-((8-(2-chloro-4-((2-methyl-2-azaspiro[3.3 ]heptan-6-yl)oxy)phenyl)-6-(1-methylcyclopropoxy)-9H-purin-9-yl)methyl)-5-methylthiazole | 537 | C27 H29 Cl N6 O2 S | 8.5 | 6.3 | <5.0 |
| T360 | 1-(2-(2-chloro-3-(6-(1-methylcyclopropoxy)-9-((4-methylpyridin-2-yl)methyl)-9H-purin-8-yl)phenoxy)ethyl)azetidin-3-ol | 521 | C27 H29 Cl N6 O3 | 8.1 | 6.1 | <5.0 |
| T361 | (R)-3-chloro-N-(1-hydroxybutan-2-yl)-4-(6-(1-methylcyclopropoxy)-9-((4-methylpyridin-2-yl)methyl)-9H-purin-8-yl)benzamide | 521 | C27 H29 Cl N6 O3 | 7.9 | 6.2 | |
| T362 | 3-chloro-N-(1-hydroxy-2-methylpropan-2-yl)-4-(6-(1-methylcyclopropoxy)-9-((4-methylpyridin-2-yl)methyl)-9H-purin-8-yl)benzamide | 521 | C27 H29 Cl N6 O3 | 7.9 | 6.2 | |
| T363 | 3-chloro-N-(2-hydroxy-2-methylpropyl)-4-(6-(1-methylcyclopropoxy)-9-((4-methylpyridin-2-yl)methyl)-9H-purin-8-yl)benzamide | 521 | C27 H29 Cl N6 O3 | 7.9 | 6.1 | <5.0 |
| T364 | (R)-3-chloro-N-(4-hydroxybutan-2-yl)-4-(6-(1-methylcyclopropoxy)-9-((4-methylpyridin-2-yl)methyl)-9H-purin-8-yl)benzamide | 521 | C27 H29 Cl N6 O3 | 7.8 | 6.1 | |
| T365 | (R)-3-chloro-N-(2-hydroxybutyl)-4-(6-(1-methylcyclopropoxy)-9-((4-methylpyridin-2-yl)methyl)-9H-purin-8-yl)benzamide | 521 | C27 H29 Cl N6 O3 | 8 | 6.1 | |
| T366 | 2-(3-chloro-4-(6-(1-methylcyclopropoxy)-9-((4-methylpyridin-2-yl)methyl)-9H-purin-8-yl)phenoxy)-N-isopropylacetamide | 521 | C27 H29 Cl N6 O3 | 8.1 | 6.7 | |
| T367 | N-(3-(3-chloro-4-(6-(1-methylcyclopropoxy)-9-((4-methylpyridin-2-yl)methyl)-9H-purin-8-yl)phenoxy)propyl)acetamide | 521 | C27 H29 Cl N6 O3 | 8.3 | 6.5 | |
| T368 | (R)-N-(3-chloro-4-(6-(1-methylcyclopropoxy)-9-((4-methylpyridin-2-yl)methyl)-9H-purin-8-yl)phenethyl)-2-hydroxypropanamide | 521 | C27 H29 Cl N6 O3 | 8.3 | 6.2 | |
| T369 | 2-(3-chloro-4-(6-(1-methylcyclopropoxy)-9-((4-methylpyridin-2-yl)methyl)-9H-purin-8-yl)phenyl)-N-(2-hydroxyethyl)-N-methylacetamide | 521 | C27 H29 Cl N6 O3 | 8.1 | 6 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T370 | 2-(3-chloro-4-(6-(1-methylcyclopropoxy)-9-((4-methylpyridin-2-yl)methyl)-9H-purin-8-yl)phenyl)-N-(3-hydroxypropyl)acetamide | 521 | C27 H29 Cl N6 O3 | 8.1 | 6 | |
| T371 | (S)-2-(3-chloro-4-(6-(1-methylcyclopropoxy)-9-((4-methylpyridin-2-yl)methyl)-9H-purin-8-yl)phenyl)-N-(2-hydroxypropyl)acetamide | 521 | C27 H29 Cl N6 O3 | 8 | 6 | <5.0 |
| T372 | (S)-2-(3-chloro-4-(6-(1-methylcyclopropoxy)-9-((4-methylpyridin-2-yl)methyl)-9H-purin-8-yl)phenoxy)-N-(2-hydroxypropyl)acetamide | 537 | C27 H29 Cl N6 O4 | 8.2 | 6.4 | |
| T373 | 2-(3-chloro-4-(6-(1-methylcyclopropoxy)-9-((4-methylpyridin-2-yl)methyl)-9H-purin-8-yl)phenoxy)-N-(3-hydroxypropyl)acetamide | 537 | C27 H29 Cl N6 O4 | 8.1 | 6.5 | |
| T374 | 2-(3-chloro-4-(6-(1-methylcyclopropoxy)-9-((4-methylpyridin-2-yl)methyl)-9H-purin-8-yl)phenoxy)-N-(2-hydroxyethyl)-N-methylacetamide | 537 | C27 H29 Cl N6 O4 | 8.1 | 5.9 | |
| T375 | (R)-N-(2-(3-chloro-4-(6-(1-methylcyclopropoxy)-9-((4-methylpyridin-2-yl)methyl)-9H-purin-8-yl)phenoxy)ethyl)-2-hydroxypropanamide | 537 | C27 H29 Cl N6 O4 | 8.3 | 6.6 | |
| T377 | 3-(3-chloro-4-(1-((4-chloropyridin-2-yl)methyl)-4-(1-methylcyclopropoxy)-1H-imidazo[4,5-c]pyridin-2-yl)phenoxy)-N,N-dimethylpropan-1-amine | 526 | C27 H29 Cl2 N5 O2 | 8.2 | 6.8 | <5.1 |
| T378 | 8-(2-chloro-4-(2-(piperazin-1-yl)ethoxy)phenyl)-9-((2-chloropyridin-4-yl)methyl)-6-(1-methylcyclopropoxy)-9H-purine | 554 | C27 H29 Cl2 N7 O2 | 8 | 5.8 | <5.0 |
| T379 | 8-(2-chloro-4-(2-(piperazin-1-yl)ethoxy)phenyl)-9-((5-chloropyridin-3-yl)methyl)-6-(1-methylcyclopropoxy)-9H-purine | 554 | C27 H29 Cl2 N7 O2 | 7.7 | 6.6 | <5.0 |
| T380 | 4-(2-(3-chloro-4-(9-((4-chloropyridin-2-yl)methyl)-6-(1-methylcyclopropoxy)-9H-purin-8-yl)phenoxy)ethyl)piperazine-1-sulfonic acid | 634 | C27 H29 Cl2 N7 O5 S | 7.6 | 5.1 | <5.0 |
| T381 | 2-(3-chloro-4-(4-(1-methylcyclopropoxy)-1-((4-methylpyridin-2-yl)methyl)-1H-imidazo[4,5-c]pyridin-2-yl)phenoxy)-N,N-dimethylethan-1-amine | 492 | C27 H30 Cl N5 O2 | 8 | 6.6 | |
| T382 | 4-(3-chloro-4-(6-(1-methylcyclopropoxy)-9-((4-methylpyridin-2-yl)methyl)-9H-purin-8-yl)phenoxy)-2-methylbutan-2-ol | 508 | C27 H30 Cl N5 O3 | 8.3 | 7 | <5.0 |
| T383 | 3-(3-chloro-4-(6-(1-methylcyclopropoxy)-9-((4-methylpyridin-2-yl)methyl)-9H-purin-8-yl)phenoxy)-2,2-dimethylpropan-1-ol | 508 | C27 H30 Cl N5 O3 | 8.2 | 6.9 | |
| T384 | 8-(2-chloro-4-(1,4-diazepan-1-yl)phenyl)-6-(1-methylcyclopropoxy)-9-((4-methylpyridin-2-yl)methyl)-9H-purine | 504 | C27 H30 Cl N7 O | 8.2 | 6.4 | |
| T385 | 3-(3-chloro-4-(6-(1-methylcyclopropoxy)-9-((4-methylpyridin-2-yl)methyl)-9H-purin-8-yl)phenoxy)-N,N-dimethylpropan-1-amine | 507 | C27 H31 Cl N6 O2 | 8.2 | 7.1 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T386 | 3-(2-chloro-3-(6-(1-methylcyclopropoxy)-9-((4-methylpyridin-2-yl)methyl)-9H-purin-8-yl)phenoxy)-N,N-dimethylpropan-1-amine | 507 | C27 H31 Cl N6 O2 | 8.2 | 7 | <5.0 |
| T387 | 3-(4-(9-((4-chloropyridin-2-yl)methyl)-6-(1-methylcyclopropoxy)-9H-purin-8-yl)-3-methylphenoxy)-N,N-dimethylpropan-1-amine | 507 | C27 H31 Cl N6 O2 | 8.1 | 6.8 | |
| T388 | 2-((8-(2-chloro-4-(3-(pyrrolidin-1-yl)propoxy)phenyl)-6-(1-methylcyclopropoxy)-9H-purin-9-yl)methyl)-5-methylthiazole | 539 | C27 H31 Cl N6 O2 S | 8.3 | 6.6 | <5.0 |
| T389 | 2-((8-(2-chloro-4-((1-methylazepan-4-yl)oxy)phenyl)-6-(1-methylcyclopropoxy)-9H-purin-9-yl)methyl)-5-methylthiazole (isomer 1) | 539 | C27 H31 Cl N6 O2 S | 8.3 | 6.5 | <5.0 |
| T390 | 2-((8-(2-chloro-4-((1-methylazepan-4-yl)oxy)phenyl)-6-(1-methylcyclopropoxy)-9H-purin-9-yl)methyl)-5-methylthiazole (isomer 2) | 539 | C27 H31 Cl N6 O2 S | 8.4 | 6.5 | <5.0 |
| T391 | (R)-1-(3-(3-chloro-4-(6-(1-methylcyclopropoxy)-9-((5-methylthiazol-2-yl)methyl)-9H-purin-8-yl)phenoxy)propyl)pyrrolidin-3-ol | 555 | C27 H31 Cl N6 O3 S | 8.3 | 6.3 | <5.0 |
| T392 | (R)-1-(3-(2-chloro-3-(6-(1-methylcyclopropoxy)-9-((5-methylthiazol-2-yl)methyl)-9H-purin-8-yl)phenoxy)propyl)pyrrolidin-3-ol | 555 | C27 H31 Cl N6 O3 S | 8.1 | 6.1 | 6.1 |
| T393 | (S)-2-((8-(2-chloro-4-(2-(2-methylpiperazin-1-yl)ethoxy)phenyl)-6-(1-methylcyclopropoxy)-9H-purin-9-yl)methyl)-5-methylthiazole | 554 | C27 H32 Cl N7 O2 S | 8.3 | 6.1 | <5.0 |
| T394 | 3-((3-chloro-4-(9-(3-chlorobenzyl)-6-(1-methylcyclopropoxy)-9H-purin-8-yl)phenoxy)methyl)-1-methyl-1H-pyrazole-5-carboxylic acid | 579 | C28 H24 Cl2 N6 O4 | 8.5 | 5.5 | |
| T395 | 4-(3-chloro-4-(9-(2-fluoro-5-(trifluoromethyl)benzyl)-6-(1-methylcyclopropoxy)-9H-purin-8-yl)phenoxy)-2-methylbutanoic acid (racemic) | 593 | C28 H25 Cl F4 N4 O4 | 8.6 | 7 | <5.0 |
| T396 | 4-(3-chloro-4-(6-(1-methylcyclopropoxy)-9-(3-(trifluoromethyl)benzyl)-9H-purin-8-yl)phenoxy)-2-methylbutanoic acid (Isomer 1) | 575 | C28 H26 Cl F3 N4 O4 | 8.1 | 6.6 | |
| T397 | 4-(3-chloro-4-(6-(1-methylcyclopropoxy)-9-(3-(trifluoromethyl)benzyl)-9H-purin-8-yl)phenoxy)-2-methylbutanoic acid (Isomer 2) | 575 | C28 H26 Cl F3 N4 O4 | 8.2 | 6.4 | |
| T399 | 4-(3-chloro-4-(9-(3-cyanobenzyl)-6-(1-methylcyclopropoxy)-9H-purin-8-yl)phenoxy)-2-methylbutanoic acid (racemic) | 532 | C28 H26 Cl N5 O4 | 8.5 | 6.5 | <5.0 |
| T400 | 4-(3-chloro-4-(9-(2-cyanobenzyl)-6-(1-methylcyclopropoxy)-9H-purin-8-yl)phenoxy)-2-methylbutanoic acid (racemic) | 532 | C28 H26 Cl N5 O4 | 8.2 | 6.6 | <5.0 |
| T401 | (R)-4-(3-chloro-4-(9-(3-cyanobenzyl)-6-(1-methylcyclopropoxy)-9H-purin-8-yl)phenoxy)-2-methylbutanoic acid | 532 | C28 H26 Cl N5 O4 | 8.4 | 6.4 | <5.0 |
| T402 | (R)-4-(3-chloro-4-(9-(2-cyanobenzyl)-6-(1-methylcyclopropoxy)-9H-purin-8-yl)phenoxy)-2-methylbutanoic acid | 532 | C28 H26 Cl N5 O4 | 8.0 | 6.4 | <5.0 |
| T403 | (S)-4-(3-chloro-4-(9-(2-cyanobenzyl)-6-(1-methylcyclopropoxy)-9H-purin-8-yl)phenoxy)-2-methylbutanoic acid | 532 | C28 H26 Cl N5 O4 | 8.0 | 6.4 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T404 | (S)-1-(3-chloro-4-(6-(1-methylcyclopropoxy)-9-((4-methylpyridin-2-yl)methyl)-9H-purin-8-yl)benzoyl)pyrrolidine-2-carbonitrile | 528 | C28 H26 Cl N7 O2 | 7.4 | 5.9 | |
| T405 | (R)-1-(3-chloro-4-(6-(1-methylcyclopropoxy)-9-((4-methylpyridin-2-yl)methyl)-9H-purin-8-yl)benzoyl)pyrrolidine-3-carbonitrile | 528 | C28 H26 Cl N7 O2 | 7.6 | 5.9 | |
| T406 | 3-(3-chloro-4-(1-(3-chlorobenzyl)-4-(1-methylcyclobutoxy)-1H-benzo[d]imidazol-2-yl)phenoxy)propanoic acid | 525 | C28 H26 Cl2 N2 O4 | 8 | 5.7 | <5.0 |
| T407 | 1-(2-(3-chloro-4-(9-(3-chlorobenzyl)-6-(1-methylcyclopropoxy)-9H-purin-8-yl)phenoxy)ethyl)cyclopropane-1-carboxylic acid | 553 | C28 H26 Cl2 N4 O4 | 8 | 6.5 | <5.0 |
| T409 | (1s,3s)-3-((3-chloro-4-(9-(3-chlorobenzyl)-6-(1-methylcyclopropoxy)-9H-purin-8-yl)phenoxy)methyl)cyclobutane-1-carboxylic acid | 553 | C28 H26 Cl2 N4 O4 | 8.2 | 6.8 | |
| T410 | (1r,3r)-3-((3-chloro-4-(9-(3-chlorobenzyl)-6-(1-methylcyclopropoxy)-9H-purin-8-yl)phenoxy)methyl)cyclobutane-1-carboxylic acid | 553 | C28 H26 Cl2 N4 O4 | 8.1 | 7.1 | |
| T412 | 4-(3-chloro-4-(9-(3-(difluoromethyl)benzyl)-6-(1-methylcyclopropoxy)-9H-purin-8-yl)phenoxy)-2-methylbutanoic acid (Isomer 1) | 557 | C28 H27 Cl F2 N4 O4 | 8.3 | 6.6 | |
| T413 | 4-(3-chloro-4-(9-(3-(difluoromethyl)benzyl)-6-(1-methylcyclopropoxy)-9H-purin-8-yl)phenoxy)-2-methylbutanoic acid (Isomer 2) | 557 | C28 H27 Cl F2 N4 O4 | 8.1 | 6.6 | |
| T414 | 4-(3-chloro-4-(9-(2-(difluoromethyl)benzyl)-6-(1-methylcyclopropoxy)-9H-purin-8-yl)phenoxy)-2-methylbutanoic acid (Isomer 1) | 557 | C28 H27 Cl F2 N4 O4 | 8.1 | 5.8 | |
| T415 | 4-(3-chloro-4-(9-(2-(difluoromethyl)benzyl)-6-(1-methylcyclopropoxy)-9H-purin-8-yl)phenoxy)-2-methylbutanoic acid (Isomer 2) | 557 | C28 H27 Cl F2 N4 O4 | 8.1 | 6 | |
| T416 | ((1S,4S)-2-oxa-5-azabicyclo[2.2.1]heptan-5-yl)(3-chloro-4-(6-(1-methylcyclopropoxy)-9-((4-methylpyridin-2-yl)methyl)-9H-purin-8-yl)phenyl)methanone | 531 | C28 H27 Cl N6 O3 | 7.3 | 5.8 | |
| T417 | 4-(3-chloro-4-(9-(2-fluoro-5-methylbenzyl)-6-(1-methylcyclopropoxy)-9H-purin-8-yl)phenoxy)-2-methylbutanoic acid (racemic) | 539 | C28 H28 Cl F N4 O4 | 8.5 | 7.3 | <5.0 |
| T418 | (S)-(3-chloro-4-(6-(1-methylcyclopropoxy)-9-((4-methylpyridin-2-yl)methyl)-9H-purin-8-yl)phenyl)(3-fluoropiperidin-1-yl)methanone | 535 | C28 H28 Cl F N6 O2 | 7.3 | 6.2 | |
| T419 | (3-chloro-4-(6-(1-methylcyclopropoxy)-9-((4-methylpyridin-2-yl)methyl)-9H-purin-8-yl)phenyl)(4-fluoropiperidin-1-yl)methanone | 535 | C28 H28 Cl F N6 O2 | 7.3 | 6 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T420 | (S)-2-(3-chloro-4-(6-(1-methylcyclopropoxy)-9-((4-methylpyridin-2-yl)methyl)-9H-purin-8-yl)phenoxy)-1-(3-fluoropyrrolidin-1-yl)ethan-1-one | 551 | C28 H28 Cl F N6 O3 | 8.1 | 6.6 | |
| T421 | 2-(3-chloro-4-(6-(1-methylcyclopropoxy)-9-((4-methylpyridin-2-yl)methyl)-9H-purin-8-yl)phenoxy)-N-(3-fluorocyclobutyl)acetamide | 551 | C28 H28 Cl F N6 O3 | 8.1 | 6.6 | |
| T422 | 2-(3-chloro-4-(6-(1-methylcyclopropoxy)-9-((4-methylpyridin-2-yl)methyl)-9H-purin-8-yl)phenyl)-1-((3R,4R)-3-fluoro-4-hydroxypyrrolidin-1-yl)ethan-1-one | 551 | C28 H28 Cl F N6 O3 | 8 | 6 | <5.0 |
| T423 | 2-(3-chloro-4-(6-(1-methylcyclopropoxy)-9-((4-methylpyridin-2-yl)methyl)-9H-purin-8-yl)phenoxy)-1-((3R,4R)-3-fluoro-4-hydroxypyrrolidin-1-yl)ethan-1-one | 567 | C28 H28 Cl F N6 O4 | 8.2 | 6 | |
| T424 | 9-benzyl-8-(2-chloro-4-(2-(piperazin-1-yl)ethoxy)phenyl)-6-((3-(trifluoromethyl)oxetan-3-yl)oxy)-9H-purine | 589 | C28 H28 Cl F3 N6 O3 | 7.4 | 5.7 | 5 |
| T425 | 1-(3-(3-chloro-4-(6-(1-methylcyclopropoxy)-9-((4-(trifluoromethyl)pyridin-2-yl)methyl)-9H-purin-8-yl)phenoxy)propyl)azetidin-3-ol | 589 | C28 H28 Cl F3 N6 O3 | 8.3 | 6.3 | <5.0 |
| T426 | 8-(4-((2-oxaspiro[3.3]heptan-6-yl)oxy)-2-chlorophenyl)-6-(1-methylcyclopropoxy)-9-((4-methylpyridin-2-yl)methyl)-9H-purine | 518 | C28 H28 Cl N5 O3 | 8.1 | 7 | |
| T427 | (3,6-diazabicyclo[3.1.1]heptan-3-yl)(3-chloro-4-(6-(1-methylcyclopropoxy)-9-((4-methylpyridin-2-yl)methyl)-9H-purin-8-yl)phenyl)methanone | 530 | C28 H28 Cl N7 O2 | 7.6 | 5.1 | <5.0 |
| T428 | (3-chloro-4-(6-(1-methylcyclopropoxy)-9-((4-methylpyridin-2-yl)methyl)-9H-purin-8-yl)phenyl)(2,6-diazaspiro[3.3] heptan-2-yl)methanone | 530 | C28 H28 Cl N7 O2 | 8.6 | <5.0 | <5.0 |
| T429 | (3-chloro-4-(6-(1-methylcyclopropoxy)-9-((4-methylpyridin-2-yl)methyl)-9H-purin-8-yl)phenyl)(1,6-diazaspiro[3.3] heptan-6-yl)methanone | 530 | C28 H28 Cl N7 O2 | 8.4 | 5.9 | <5.0 |
| T430 | 2-(3-chloro-4-(6-(1-methylcyclopropoxy)-9-((4-methylpyridin-2-yl)methyl)-9H-purin-8-yl)phenoxy)-N-(2-cyanoethyl)-N-methylacetamide | 546 | C28 H28 Cl N7 O3 | 7.8 | 6.3 | |
| T431 | 4-(2-(3-chloro-4-(6-(1-methylcyclopropoxy)-9-((4-methylpyridin-2-yl)methyl)-9H-purin-8-yl)phenyl)acetyl)piperazin-2-one | 546 | C28 H28 Cl N7 O3 | 7.8 | 5.6 | <5.0 |
| T432 | 4-(2-(3-chloro-4-(6-(1-methylcyclopropoxy)-9-((4-methylpyridin-2-yl)methyl)-9H-purin-8-yl)phenoxy)acetyl)piperazin-2-one | 562 | C28 H28 Cl N7 O4 | 7.9 | <5.2 | |
| T433 | 3-((3-chloro-4-(6-(1-methylcyclopropoxy)-9-((4-methylpyridin-2-yl)methyl)-9H-purin-8-yl)phenoxy)methyl)-5,6,7,8-tetrahydro-[1,2,4]triazolo[4,3-alpyrazine | 558 | C28 H28 Cl N9 O2 | 8.4 | 5.5 | |
| T434 | 5-(3-chloro-4-(9-(3-chlorobenzyl)-6-(1-methylcyclopropoxy)-9H-purin-8-yl)phenyl)-2-methylpentanoic acid (racemic) | 539 | C28 H28 Cl2 N4 O3 | 8.1 | 6.8 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T435 | 4-(3-chloro-4-(9-(3-chlorobenzyl)-6-(1-methylcyclopropoxy)-9H-purin-8-yl)phenoxy)-2,2-dimethylbutanoic acid | 555 | C28 H28 Cl2 N4 O4 | 8.2 | 6.7 | <5.0 |
| T436 | 4-(3-chloro-4-(9-(3-chlorobenzyl)-6-(1-methylcyclopropoxy)-9H-purin-8-yl)phenoxy)-3,3-dimethylbutanoic acid | 555 | C28 H28 Cl2 N4 O4 | 8.1 | 6.7 | |
| T437 | 6-(3-chloro-4-(9-(3-chlorobenzyl)-6-(1-methylcyclopropoxy)-9H-purin-8-yl)phenoxy)hexanoic acid | 555 | C28 H28 Cl2 N4 O4 | 8.4 | 7.2 | <5.0 |
| T438 | 5-(3-chloro-4-(9-(3-chlorobenzyl)-6-(1-methylcyclopropoxy)-9H-purin-8-yl)phenoxy)-2-methylpentanoic acid (isomer 2) | 555 | C28 H28 Cl2 N4 O4 | 8.5 | 6.9 | |
| T439 | 5-(3-chloro-4-(9-(3-chlorobenzyl)-6-(1-methylcyclopropoxy)-9H-purin-8-yl)phenoxy)-2-methylpentanoic acid (isomer 1) | 555 | C28 H28 Cl2 N4 O4 | 8.5 | 6.9 | |
| T440 | 6-(2-chloro-3-(9-(3-chlorobenzyl)-6-(1-methylcyclopropoxy)-9H-purin-8-yl)phenoxy)hexanoic acid | 555 | C28 H28 Cl2 N4 O4 | 8.2 | 7.6 | <5.0 |
| T441 | 4-(3-chloro-4-(9-(3-chlorobenzyl)-6-(1-methylcyclopropoxy)-9H-purin-8-yl)phenoxy)-2-ethylbutanoic acid (racemic) | 555 | C28 H28 Cl2 N4 O4 | 8.1 | 6.8 | |
| T442 | 4-(2-chloro-3-(9-(3-chlorobenzyl)-6-(1-methylcyclopropoxy)-9H-purin-8-yl)phenoxy)-2,2-dimethylbutanoic acid | 555 | C28 H28 Cl2 N4 O4 | 8.5 | 7.1 | |
| T443 | 5-(2-chloro-3-(9-(3-chlorobenzyl)-6-(1-methylcyclopropoxy)-9H-purin-8-yl)phenoxy)-2-methylpentanoic acid (Isomer 1) | 555 | C28 H28 Cl2 N4 O4 | 8.2 | 7.1 | |
| T444 | 5-(2-chloro-3-(9-(3-chlorobenzyl)-6-(1-methylcyclopropoxy)-9H-purin-8-yl)phenoxy)-2-methylpentanoic acid (Isomer 2) | 555 | C28 H28 Cl2 N4 O4 | 8.3 | 6.8 | |
| T445 | 2-(4-(3-chloro-4-(9-(3-chlorobenzyl)-6-(1-methylcyclopropoxy)-9H-purin-8-yl)phenoxy)butoxy)acetic acid | 571 | C28 H28 Cl2 N4 O5 | 8.3 | 6.6 | <5.0 |
| T446 | 4-(3-chloro-4-(9-(3-chloro-5-methoxybenzyl)-6-(1-methylcyclopropoxy)-9H-purin-8-yl)phenoxy)-2-methylbutanoic acid (Isomer 1) | 571 | C28 H28 Cl2 N4 O5 | 8.2 | 6.5 | |
| T447 | 4-(3-chloro-4-(9-(3-chloro-5-methoxybenzyl)-6-(1-methylcyclopropoxy)-9H-purin-8-yl)phenoxy)-2-methylbutanoic acid (Isomer 2) | 571 | C28 H28 Cl2 N4 O5 | 8.5 | 6.3 | |
| T448 | 2-(4-(2-chloro-3-(9-(3-chlorobenzyl)-6-(1-methylcyclopropoxy)-9H-purin-8-yl)phenoxy)butoxy)acetic acid | 571 | C28 H28 Cl2 N4 O5 | 8.1 | 7.1 | <5.0 |
| T449 | 3-(3-(3-chloro-4-(9-(3-chlorobenzyl)-6-(1-methylcyclopropoxy)-9H-purin-8-yl)phenoxy)propoxy)propanoic acid | 571 | C28 H28 Cl2 N4 O5 | 8.5 | 7.3 | <5.0 |
| T450 | 2-(2-(3-chloro-4-(9-(3-chlorobenzyl)-6-(1-methylcyclopropoxy)-9H-purin-8-yl)phenoxy)ethoxy)-2-methylpropanoic acid | 571 | C28 H28 Cl2 N4 O5 | 8.6 | 6.7 | <5.0 |
| T451 | 2-(2-(2-(3-chloro-4-(9-(3-chlorobenzyl)-6-(1-methylcyclopropoxy)-9H-purin-8-yl)phenoxy)ethoxy)ethoxy)acetic acid | 587 | C28 H28 Cl2 N4 O6 | 8.4 | 6.3 | <5.0 |
| T452 | 1-(3-(3-chloro-4-(9-((4-(difluoromethyl)pyridin-2-yl)methyl)-6-(1-methylcyclopropoxy)-9H-purin-8-yl)phenoxy)propyl)azetidin-3-ol | 571 | C28 H29 Cl F2 N6 O3 | 8.1 | 6.1 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T453 | 9-((4-chloropyridin-2-yl)methyl)-6-(1-methylcyclopropoxy)-8-(4-(2-(piperazin-1-yl)ethoxy)-2-(trifluoromethyl)phenyl)-9H-purine | 588 | C28 H29 Cl F3 N7 O2 | 8 | 6.6 | <5.0 |
| T454 | 4-(3-chloro-4-(9-(3-methoxybenzyl)-6-(1-methylcyclopropoxy)-9H-purin-8-yl)phenoxy)-2-methylbutanoic acid (racemic) | 537 | C28 H29 Cl N4 O5 | 8.4 | 6.1 | |
| T455 | 4-(3-chloro-4-(9-(3-methoxybenzyl)-6-(1-methylcyclopropoxy)-9H-purin-8-yl)phenoxy)-2-methylbutanoic acid (Isomer 1) | 537 | C28 H29 Cl N4 O5 | 8.2 | 5.8 | |
| T456 | 4-(3-chloro-4-(9-(3-methoxybenzyl)-6-(1-methylcyclopropoxy)-9H-purin-8-yl)phenoxy)-2-methylbutanoic acid (Isomer 2) | 537 | C28 H29 Cl N4 O5 | 8.2 | 6.1 | |
| T457 | 8-(4-((2-azaspiro[3.3]heptan-6-yl)oxy)-2-chlorophenyl)-6-(1-methylcyclopropoxy)-9-((4-methylpyridin-2-yl)methyl)-9H-purine | 517 | C28 H29 Cl N6 O2 | 8.4 | 6.5 | <5.0 |
| T458 | (R)-2-(3-chloro-4-(6-(1-methylcyclopropoxy)-9-((4-methylpyridin-2-yl)methyl)-9H-purin-8-yl)phenyl)-1-(3-hydroxypyrrolidin-1-yl)ethan-1-one | 533 | C28 H29 Cl N6 O3 | 8 | 6.2 | |
| T459 | (R)-(3-chloro-4-(6-(1-methylcyclopropoxy)-9-((4-methylpyridin-2-yl)methyl)-9H-purin-8-yl)phenyl)(2-(hydroxymethyl)pyrrolidin-1-yl)methanone | 533 | C28 H29 Cl N6 O3 | 7.6 | 5.9 | |
| T460 | (3-chloro-4-(6-(1-methylcyclopropoxy)-9-((4-methylpyridin-2-yl)methyl)-9H-purin-8-yl)phenyl)(4-hydroxypiperidin-1-yl)methanone | 533 | C28 H29 Cl N6 O3 | 7.2 | 5.5 | <5.0 |
| T461 | (S)-(3-chloro-4-(6-(1-methylcyclopropoxy)-9-((4-methylpyridin-2-yl)methyl)-9H-purin-8-yl)phenyl)(3-hydroxypiperidin-1-yl)methanone | 533 | C28 H29 Cl N6 O3 | 7.2 | 5.9 | |
| T462 | 3-chloro-N-((1-hydroxycyclopropyl)methyl)-N-methyl-4-(6-(1-methylcyclopropoxy)-9-((4-methylpyridin-2-yl)methyl)-9H-purin-8-yl)benzamide | 533 | C28 H29 Cl N6 O3 | 7.2 | 5.8 | |
| T463 | (R)-(3-chloro-4-(6-(1-methylcyclopropoxy)-9-((4-methylpyridin-2-yl)methyl)-9H-purin-8-yl)phenyl)(3-hydroxy-3-methylpyrrolidin-1-yl)methanone | 533 | C28 H29 Cl N6 O3 | 7.5 | 5.8 | |
| T464 | (R)-(3-chloro-4-(6-(1-methylcyclopropoxy)-9-((4-methylpyridin-2-yl)methyl)-9H-purin-8-yl)phenyl)(3-(hydroxymethyl)pyrrolidin-1-yl)methanone | 533 | C28 H29 Cl N6 O3 | 7.8 | 5.8 | |
| T465 | (S)-(3-chloro-4-(6-(1-methylcyclopropoxy)-9-((4-methylpyridin-2-yl)methyl)-9H-purin-8-yl)phenyl)(3-methoxypyrrolidin-1-yl)methanone | 533 | C28 H29 Cl N6 O3 | 7.8 | 6.2 | |
| T466 | (S)-(3-chloro-4-(6-(1-methylcyclopropoxy)-9-((4-methylpyridin-2-yl)methyl)-9H-purin-8-yl)phenyl)(2-(hydroxymethyl)pyrrolidin-1-yl)methanone | 533 | C28 H29 Cl N6 O3 | 7.4 | 6 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T467 | 2-(3-chloro-4-(6-(1-methylcyclopropoxy)-9-((4-methylpyridin-2-yl)methyl)-9H-purin-8-yl)phenoxy)-1-(pyrrolidin-1-yl)ethan-1-one | 533 | C28 H29 Cl N6 O3 | 8 | 6.5 | |
| T468 | 3-chloro-N-((1s,3s)-3-hydroxycyclobutyl)-N-methyl-4-(6-(1-methylcyclopropoxy)-9-((4-methylpyridin-2-yl)methyl)-9H-purin-8-yl)benzamide | 533 | C28 H29 Cl N6 O3 | 7.3 | 5.9 | |
| T469 | 1-(2-(3-chloro-4-(6-(1-methylcyclopropoxy)-9-((4-methylpyridin-2-yl)methyl)-9H-purin-8-yl)phenoxy)ethyl)pyrrolidin-2-one | 533 | C28 H29 Cl N6 O3 | 8.3 | 6.8 | |
| T470 | 2-(3-chloro-4-(6-(1-methylcyclopropoxy)-9-((4-methylpyridin-2-yl)methyl)-9H-purin-8-yl)phenyl)-1-(3-hydroxy-3-methylazetidin-1-yl)ethan-1-one | 533 | C28 H29 Cl N6 O3 | 8.2 | 6 | <5.0 |
| T471 | 1-(3-(3-chloro-4-(6-(1-methylcyclopropoxy)-9-((4-methylpyridin-2-yl)methyl)-9H-purin-8-yl)phenoxy)azetidin-1-yl)propan-1-one | 533 | C28 H29 Cl N6 O3 | 8.3 | 6.8 | |
| T472 | (R)-1-(3-(3-chloro-4-(6-(1-methylcyclopropoxy)-9-((4-methylpyridin-2-yl)methyl)-9H-purin-8-yl)phenoxy)pyrrolidin-1-yl)ethan-1-one | 533 | C28 H29 Cl N6 O3 | 8.1 | 6.7 | |
| T473 | (R)-2-(3-chloro-4-(6-(1-methylcyclopropoxy)-9-((4-methylpyridin-2-yl)methyl)-9H-purin-8-yl)phenoxy)-1-(3-hydroxypyrrolidin-1-yl)ethan-1-one | 549 | C28 H29 Cl N6 O4 | 8.2 | 6 | |
| T474 | (R)-1-(2-(3-chloro-4-(6-(1-methylcyclopropoxy)-9-((4-methylpyridin-2-yl)methyl)-9H-purin-8-yl)phenoxy)ethyl)-3-hydroxypyrrolidin-2-one | 549 | C28 H29 Cl N6 O4 | 8.1 | 6.6 | |
| T475 | 2-(3-chloro-4-(6-(1-methylcyclopropoxy)-9-((4-methylpyridin-2-yl)methyl)-9H-purin-8-yl)phenoxy)-1-morpholinoethan-1-one | 549 | C28 H29 Cl N6 O4 | 8 | 6.6 | |
| T476 | 2-(3-chloro-4-(6-(1-methylcyclopropoxy)-9-((4-methylpyridin-2-yl)methyl)-9H-purin-8-yl)phenoxy)-N-(3-methyloxetan-3-yl)acetamide | 549 | C28 H29 Cl N6 O4 | 8.1 | 6.6 | |
| T477 | 2-(3-chloro-4-(6-(1-methylcyclopropoxy)-9-((4-methylpyridin-2-yl)methyl)-9H-purin-8-yl)phenoxy)-1-(3-hydroxy-3-methylazetidin-1-yl)ethan-1-one | 549 | C28 H29 Cl N6 O4 | 8 | 5.9 | |
| T478 | (R)-2-(3-chloro-4-(6-(1-methylcyclopropoxy)-9-((4-methylpyridin-2-yl)methyl)-9H-purin-8-yl)phenoxy)-N-(tetrahydrofuran-3-yl)acetamide | 549 | C28 H29 Cl N6 O4 | 8.1 | 6.3 | |
| T479 | 2-(3-chloro-4-(6-(1-methylcyclopropoxy)-9-((4-methylpyridin-2-yl)methyl)-9H-purin-8-yl)phenoxy)-N-(3-hydroxycyclobutyl)acetamide | 549 | C28 H29 Cl N6 O4 | 8.1 | 6.4 | |
| T480 | 2-(3-chloro-4-(6-(1-methylcyclopropoxy)-9-((4-methylpyridin-2-yl)methyl)-9H-purin-8-yl)phenoxy)-N-methyl-N-(oxetan-3-yl)acetamide | 549 | C28 H29 Cl N6 O4 | 8 | 6.3 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T481 | 4-(2-(3-chloro-4-(6-(1-methylcyclopropoxy)-9-((4-methylpyridin-2-yl)methyl)-9H-purin-8-yl)phenoxy)ethyl)morpholin-3-one | 549 | C28 H29 Cl N6 O4 | 8.2 | 6.5 | |
| T482 | (R)-1-(3-(3-chloro-4-(6-(1-methylcyclopropoxy)-9-((4-methylpyridin-2-yl)methyl)-9H-purin-8-yl)phenoxy)azetidin-1-yl)-2-hydroxypropan-1-one | 549 | C28 H29 Cl N6 O4 | 8.3 | 6.5 | <5.0 |
| T483 | (S)-1-(3-(3-chloro-4-(6-(1-methylcyclopropoxy)-9-((4-methylpyridin-2-yl)methyl)-9H-purin-8-yl)phenoxy)pyrrolidin-1-yl)-2-hydroxyethan-1-one | 549 | C28 H29 Cl N6 O4 | 8.1 | 6.2 | |
| T484 | 6-((8-(2-chloro-4-(2-(piperazin-1-yl)ethoxy)phenyl)-6-(1-methylcyclopropoxy)-9H-purin-9-yl)methyl)nicotinonitrile | 545 | C28 H29 Cl N8 O2 | 7 | <5.1 | <5.0 |
| T485 | 8-(4-(2-((1R,4R)-2,5-diazabicyclo[2.2.1] heptan-2-yl)ethoxy)-2-chlorophenyl)-9-((4-chloropyridin-2-yl)methyl)-6-(1-methylcyclopropoxy)-9H-purine | 566 | C28 H29 Cl2 N7 O2 | 8.3 | 6.3 | |
| T486 | 8-(4-(2-(1,6-diazaspiro[3.3 ]heptan-6-yl)ethoxy)-2-chlorophenyl)-9-((4-chloropyridin-2-yl)methyl)-6-(1-methylcyclopropoxy)-9H-purine | 566 | C28 H29 Cl2 N7 O2 | 8.2 | 6.3 | |
| T487 | 8-(4-(2-((1S,4S)-2,5-diazabicyclo[2.2.1] heptan-2-yl)ethoxy)-2-chlorophenyl)-9-((4-chloropyridin-2-yl)methyl)-6-(1-methylcyclopropoxy)-9H-purine | 566 | C28 H29 Cl2 N7 O2 | 8.2 | 6.4 | |
| T488 | 8-(2-chloro-4-(2-(piperazin-1-yl)ethoxy)phenyl)-9-((4-(difluoromethyl)pyridin-2-yl)methyl)-6-(1-methylcyclopropoxy)-9H-purine | 570 | C28 H30 Cl F2 N7 O2 | 8 | 6 | <5.0 |
| T489 | 8-(4-((1,6-diazaspiro[3.3]heptan-6-yl)methyl)-2-chlorophenyl)-6-(1-methylcyclopropoxy)-9-((4-methylpyridin-2-yl)methyl)-9H-purine | 516 | C28 H30 Cl N7 O | 8.2 | 6.1 | 5.3 |
| T490 | 8-(2-chloro-4-(2,6-diazaspiro[3.4] octan-6-yl)phenyl)-6-(1-methylcyclopropoxy)-9-((4-methylpyridin-2-yl)methyl)-9H-purine | 516 | C28 H30 Cl N7 O | 8.1 | 5.7 | |
| T491 | 8-(4-(2,6-diazabicyclo[3.2.1 ]octan-6-yl)-2-chlorophenyl)-6-(1-methylcyclopropoxy)-9-((4-methylpyridin-2-yl)methyl)-9H-purine (racemic) | 516 | C28 H30 Cl N7 O | 8.2 | 6.3 | |
| T492 | 8-(2-chloro-4-(hexahydropyrrolo[3,2-b]pyrrol-1(2H)-yl)phenyl)-6-(1-methylcyclopropoxy)-9-((4-methylpyridin-2-yl)methyl)-9H-purine (unknown absolute stereochemistry) | 516 | C28 H30 Cl N7 0 | 8.2 | 6.4 | |
| T493 | 8-(4-(1,4-diazabicyclo[3.2.1]octan-4-yl)-2-chlorophenyl)-6-(1-methylcyclopropoxy)-9-((4-methylpyridin-2-yl)methyl)-9H-purine (racemic) | 516 | C28 H30 Cl N7 O | 8.3 | 6.6 | |
| T494 | 8-(2-chloro-4-((3aR,6aR)-hexahydropyrrolo[3,4-b]pyrrol-5(1H)-yl)phenyl)-6-(1-methylcyclopropoxy)-9-((4-methylpyridin-2-yl)methyl)-9H-purine | 516 | C28 H30 Cl N7 O | 8.3 | 6.5 | |
| T495 | 2-(3-chloro-4-(6-(1-methylcyclopropoxy)-9-((4-methylpyridin-2-yl)methyl)-9H-purin-8-yl)phenyl)-1-(piperazin-1-yl)ethan-1-one | 532 | C28 H30 Cl N7 O2 | 8.6 | 6.1 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T496 | (3-chloro-4-(6-(1-methylcyclopropoxy)-9-((4-methylpyridin-2-yl)methyl)-9H-purin-8-yl)phenyl)(1,4-diazepan-1-yl)methanone | 532 | C28 H30 Cl N7 O2 | 7.9 | <5.0 | <5.0 |
| T497 | (S)-1-(3-chloro-4-(6-(1-methylcyclopropoxy)-9-((4-methylpyridin-2-yl)methyl)-9H-purin-8-yl)phenyl)-N-methylpyrrolidine-3-carboxamide | 532 | C28 H30 Cl N7 O2 | 8.2 | 6.3 | |
| T498 | 1-(2-(3-chloro-4-(6-(1-methylcyclopropoxy)-9-((4-methylpyridin-2-yl)methyl)-9H-purin-8-yl)phenoxy)ethyl)piperazin-2-one | 548 | C28 H30 Cl N7 O3 | 8.2 | 6.5 | |
| T499 | 4-(2-(3-chloro-4-(6-(1-methylcyclopropoxy)-9-((4-methylpyridin-2-yl)methyl)-9H-purin-8-yl)phenoxy)ethyl)piperazin-2-one | 548 | C28 H30 Cl N7 O3 | 8.2 | 6.5 | |
| T500 | 3-(3-chloro-4-(6-(1-methylcyclopropoxy)-9-((4-methylpyridin-2-yl)methyl)-9H-purin-8-yl)phenoxy)-N,N-dimethylazetidine-1-carboxamide | 548 | C28 H30 Cl N7 O3 | 7.7 | 6.8 | <5.0 |
| T501 | (R)-3-(3-chloro-4-(6-(1-methylcyclopropoxy)-9-((4-methylpyridin-2-yl)methyl)-9H-purin-8-yl)phenoxy)-N-methylpyrrolidine-1-carboxamide | 548 | C28 H30 Cl N7 O3 | 8.1 | 6.1 | |
| T502 | (R)-1-(3-(3-chloro-4-(9-((4-chloropyridin-2-yl)methyl)-6-(1-methylcyclopropoxy)-9H-purin-8-yl)phenoxy)propyl)pyrrolidin-3-ol | 569 | C28 H30 Cl2 N6 O3 | 8.5 | 6.9 | <5.1 |
| T503 | (S)-1-(3-(3-chloro-4-(9-((4-chloropyridin-2-yl)methyl)-6-(1-methylcyclopropoxy)-9H-purin-8-yl)phenoxy)propyl)pyrrolidin-3-ol | 569 | C28 H30 Cl2 N6 O3 | 8.3 | 7 | <5.1 |
| T504 | 8-(2-chloro-4-(2-(piperazin-1-yl)ethoxy)phenyl)-9-((3-fluoro-4-methylpyridin-2-yl)methyl)-6-(1-methylcyclopropoxy)-9H-purine | 552 | C28 H31 Cl F N7 O2 | 8.3 | 5.7 | <5.0 |
| T505 | 8-(2-chloro-4-(2-(pyrrolidin-1-yl)ethyl)phenyl)-6-(1-methylcyclopropoxy)-9-((4-methylpyridin-2-yl)methyl)-9H-purine | 503 | C28 H31 Cl N6 O | 8.3 | 6.8 | <5.0 |
| T506 | 9-benzyl-8-(2-chloro-4-(2-(piperazin-1-yl)ethoxy)phenyl)-6-cyclobutoxy-9H-purine | 519 | C28 H31 Cl N6 O2 | 7.9 | 6.3 | 5.7 |
| T507 | 8-(2-chloro-4-(2-(pyrrolidin-1-yl)ethoxy)phenyl)-6-(1-methylcyclopropoxy)-9-((4-methylpyridin-2-yl)methyl)-9H-purine | 519 | C28 H31 Cl N6 O2 | 8.2 | 7 | <5.0 |
| T508 | 1-(3-chloro-4-(6-(1-methylcyclopropoxy)-9-((4-methylpyridin-2-yl)methyl)-9H-purin-8-yl)benzyl)piperidin-4-ol | 519 | C28 H31 Cl N6 O2 | 8.4 | 6.5 | <5.0 |
| T509 | 8-(4-(azepan-4-yloxy)-2-chlorophenyl)-6-(1-methylcyclopropoxy)-9-((4-methylpyridin-2-yl)methyl)-9H-purine (isomer 2) | 519 | C28 H31 Cl N6 O2 | 8.4 | 6.4 | <5.0 |
| T510 | 8-(4-(azepan-4-yloxy)-2-chlorophenyl)-6-(1-methylcyclopropoxy)-9-((4-methylpyridin-2-yl)methyl)-9H-purine (isomer 1) | 519 | C28 H31 Cl N6 O2 | 8.3 | 6 | <5.0 |
| T511 | (R)-1-(3-chloro-4-(6-(1-methylcyclopropoxy)-9-((4-methylpyridin-2-yl)methyl)-9H-purin-8-yl)phenethyl)pyrrolidin-3-ol | 519 | C28 H31 Cl N6 O2 | 8.4 | 6.5 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T512 | (R)-1-(2-(3-chloro-4-(6-(1-methylcyclopropoxy)-9-((4-methylpyridin-2-yl)methyl)-9H-purin-8-yl)phenoxy)ethyl)pyrrolidin-3-ol | 535 | C28 H31 Cl N6 O3 | 8.3 | 6.7 | <5.0 |
| T513 | 1-(3-(3-chloro-4-(6-(1-methylcyclopropoxy)-9-((4-methylpyridin-2-yl)methyl)-9H-purin-8-yl)phenoxy)propyl)azetidin-3-ol | 535 | C28 H31 Cl N6 O3 | 8.3 | 6.5 | <5.0 |
| T514 | 1-(3-(2-chloro-3-(6-(1-methylcyclopropoxy)-9-((4-methylpyridin-2-yl)methyl)-9H-purin-8-yl)phenoxy)propyl)azetidin-3-ol | 535 | C28 H31 Cl N6 O3 | 8.1 | 6.4 | <5.0 |
| T515 | 2-(3-chloro-4-(6-(1-methylcyclopropoxy)-9-((4-methylpyridin-2-yl)methyl)-9H-purin-8-yl)phenyl)-N-(2-hydroxy-2-methylpropyl)acetamide | 535 | C28 H31 Cl N6 O3 | 8.1 | 6.2 | |
| T516 | (R)-2-(3-chloro-4-(6-(1-methylcyclopropoxy)-9-((4-methylpyridin-2-yl)methyl)-9H-purin-8-yl)phenoxy)-N-(4-hydroxybutan-2-yl)acetamide | 551 | C28 H31 Cl N6 O4 | 8 | 6.7 | |
| T517 | 2-(3-chloro-4-(6-(1-methylcyclopropoxy)-9-((4-methylpyridin-2-yl)methyl)-9H-purin-8-yl)phenoxy)-N-(2-hydroxy-2-methylpropyl)acetamide | 551 | C28 H31 Cl N6 O4 | 8.1 | 6.4 | |
| T518 | (R)-2-(3-chloro-4-(6-(1-methylcyclopropoxy)-9-((4-methylpyridin-2-yl)methyl)-9H-purin-8-yl)phenoxy)-N-(1-hydroxybutan-2-yl)acetamide | 551 | C28 H31 Cl N6 O4 | 8 | 6.4 | |
| T519 | 2-(3-chloro-4-(6-(1-methylcyclopropoxy)-9-((4-methylpyridin-2-yl)methyl)-9H-purin-8-yl)phenoxy)-N-(1-hydroxy-2-methylpropan-2-yl)acetamide | 551 | C28 H31 Cl N6 O4 | 8.1 | 6.5 | |
| T520 | (R)-2-(3-chloro-4-(6-(1-methylcyclopropoxy)-9-((4-methylpyridin-2-yl)methyl)-9H-purin-8-yl)phenoxy)-N-(2-hydroxybutyl)acetamide | 551 | C28 H31 Cl N6 O4 | 8.3 | 6.4 | |
| T522 | (R)-8-(2-chloro-4-(2-(2-methylpiperazin-1-yl)ethoxy)phenyl)-9-((4-chloropyridin-2-yl)methyl)-6-(1-methylcyclopropoxy)-9H-purine | 568 | C28 H31 Cl2 N7 O2 | 8.2 | 6.6 | |
| T523 | (S)-8-(2-chloro-4-(2-(2-methylpiperazin-1-yl)ethoxy)phenyl)-9-((4-chloropyridin-2-yl)methyl)-6-(1-methylcyclopropoxy)-9H-purine | 568 | C28 H31 Cl2 N7 O2 | 8.4 | 6.7 | <5.0 |
| T524 | 8-(2-chloro-4-(2-(piperazin-1-yl)ethoxy)phenyl)-9-((6-chloro-4-methylpyridin-2-yl)methyl)-6-(1-methylcyclopropoxy)-9H-purine | 568 | C28 H31 Cl2 N7 O2 | 8.4 | 6.3 | <5.0 |
| T525 | 9-((4-chloro-3-methylpyridin-2-yl)methyl)-8-(2-chloro-4-(2-(piperazin-1-yl)ethoxy)phenyl)-6-(1-methylcyclopropoxy)-9H-purine | 568 | C28 H31 Cl2 N7 O2 | 7.9 | 5.9 | <5.0 |
| T526 | 8-(2-chloro-4-(2-(piperazin-1-yl)ethoxy)phenyl)-9-((4-chloro-5-methylpyridin-2-yl)methyl)-6-(1-methylcyclopropoxy)-9H-purine | 568 | C28 H31 Cl2 N7 O2 | 8.4 | 6.2 | <5.0 |
| T527 | 8-(2-chloro-4-(2-(piperazin-1-yl)ethoxy)phenyl)-9-((4-chloro-6-methylpyridin-2-yl)methyl)-6-(1-methylcyclopropoxy)-9H-purine | 568 | C28 H31 Cl2 N7 O2 | 8.3 | 6.4 | <5.2 |
| T528 | 8-(2-chloro-4-(2-(piperazin-1-yl)ethyl)phenyl)-6-(1-methylcyclopropoxy)-9-((4-methylpyridin-2-yl)methyl)-9H-purine | 518 | C28 H32 Cl N7 O | 8.4 | 6.4 | 5.1 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T529 | 9-((4-chloropyridin-2-yl)methyl)-8-(2-methyl-4-(2-(piperazin-1-yl)ethoxy)phenyl)-6-(1-methylcyclopropoxy)-9H-purine | 534 | C28 H32 Cl N7 O2 | 8.1 | 6.2 | <5.0 |
| T530 | 8-(2-chloro-4-(2-(piperazin-1-yl)ethoxy)phenyl)-6-(1-methylcyclopropoxy)-9-((5-methylpyridin-3-yl)methyl)-9H-purine | 534 | C28 H32 Cl N7 O2 | 7.9 | 6 | <5.0 |
| T531 | 8-(2-chloro-4-(2-(piperazin-1-yl)ethoxy)phenyl)-6-(1-methylcyclopropoxy)-9-((2-methylpyridin-4-yl)methyl)-9H-purine | 534 | C28 H32 Cl N7 O2 | 6.9 | 5.2 | <5.0 |
| T532 | 8-(2-chloro-4-(2-(piperazin-1-yl)ethoxy)phenyl)-9-((5-methoxypyridin-2-yl)methyl)-6-(1-methylcyclopropoxy)-9H-purine | 550 | C28 H32 Cl N7 O3 | 7.4 | 5.2 | <5.0 |
| T533 | 4-(4-(9-(3,5-bis(trifluoromethyl)benzyl)-6-(1-methylcyclopropoxy)-9H-purin-8-yl)-3-chlorophenoxy)-2-methylbutanoic acid (racemic) | 643 | C29 H25 Cl F6 N4 O4 | 8.1 | 6.4 | <5.5 |
| T534 | 4-(3-chloro-4-(9-(2-methyl-3-(trifluoromethyl)benzyl)-6-(1-methylcyclopropoxy)-9H-purin-8-yl)phenoxy)-2-methylbutanoic acid (isomer 1) | 589 | C29 H28 Cl F3 N4 O4 | 8 | 5.5 | |
| T535 | 4-(3-chloro-4-(9-(2-methyl-3-(trifluoromethyl)benzyl)-6-(1-methylcyclopropoxy)-9H-purin-8-yl)phenoxy)-2-methylbutanoic acid (isomer 2) | 589 | C29 H28 Cl F3 N4 O4 | 8 | 5.6 | |
| T536 | 8-(2-chloro-4-((5,6,7,8-tetrahydroimidazo[1,2-a]pyridin-6-yl)oxy)phenyl)-6-(1-methylcyclopropoxy)-9-((4-methylpyridin-2-yl)methyl)-9H-purine (Isomer 2) | 542 | C29 H28 Cl N7 O2 | 8.3 | 6.3 | |
| T537 | 8-(2-chloro-4-((5,6,7,8-tetrahydroimidazo[1,2-a]pyridin-6-yl)oxy)phenyl)-6-(1-methylcyclopropoxy)-9-((4-methylpyridin-2-yl)methyl)-9H-purine (Isomer 1) | 542 | C29 H28 Cl N7 O2 | 8.3 | 6.5 | |
| T538 | (R)-1-(2-(3-chloro-4-(6-(1-methylcyclopropoxy)-9-((4-methylpyridin-2-yl)methyl)-9H-purin-8-yl)phenoxy)acetyl)pyrrolidine-3-carbonitrile | 558 | C29 H28 Cl N7 O3 | 8 | 6.3 | |
| T539 | (S)-1-(2-(3-chloro-4-(6-(1-methylcyclopropoxy)-9-((4-methylpyridin-2-yl)methyl)-9H-purin-8-yl)phenoxy)acetyl)pyrrolidine-2-carbonitrile | 558 | C29 H28 Cl N7 O3 | 8 | 6.5 | |
| T540 | (1r,4r)-4-(3-chloro-4-(9-(3-chlorobenzyl)-6-(1-methylcyclopropoxy)-9H-purin-8-yl)phenoxy)cyclohexane-1-carboxylic acid | 567 | C29 H28 Cl2 N4 O4 | 8.4 | 7.1 | <5.0 |
| T541 | (1s,4s)-4-(3-chloro-4-(9-(3-chlorobenzyl)-6-(1-methylcyclopropoxy)-9H-purin-8-yl)phenoxy)cyclohexane-1-carboxylic acid | 567 | C29 H28 Cl2 N4 O4 | 8.2 | 6.8 | <5.0 |
| T542 | (1r,4r)-4-(2-chloro-3-(9-(3-chlorobenzyl)-6-(1-methylcyclopropoxy)-9H-purin-8-yl)phenoxy)cyclohexane-1-carboxylic acid | 567 | C29 H28 Cl2 N4 O4 | 8.5 | 7.4 | <5.0 |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T543 | (1s,4s)-4-(2-chloro-3-(9-(3-chlorobenzyl)-6-(1-methylcyclopropoxy)-9H-purin-8-yl)phenoxy)cyclohexane-1-carboxylic acid | 567 | C29 H28 Cl2 N4 O4 | 8.4 | 6.7 | |
| T544 | 4-(3-chloro-4-(9-(3-(1,1-difluoroethyl)benzyl)-6-(1-methylcyclopropoxy)-9H-purin-8-yl)phenoxy)-2-methylbutanoic acid (racemic) | 571 | C29 H29 Cl F2 N4 O4 | 8.6 | 6.3 | <5.0 |
| T545 | 4-(3-chloro-4-(9-(3-(1,1-difluoroethyl)benzyl)-6-(1-methylcyclopropoxy)-9H-purin-8-yl)phenoxy)-2-methylbutanoic acid (Isomer 1) | 571 | C29 H29 Cl F2 N4 O4 | 8.2 | 6 | |
| T546 | 4-(3-chloro-4-(9-(3-(1,1-difluoroethyl)benzyl)-6-(1-methylcyclopropoxy)-9H-purin-8-yl)phenoxy)-2-methylbutanoic acid (Isomer 2) | 571 | C29 H29 Cl F2 N4 O4 | 8.3 | 6.1 | |
| T547 | rel-1-((1R,5S)-6-oxa-3-azabicyclo [3.1.1]heptan-3-yl)-2-(3-chloro-4-(6-(1-methylcyclopropoxy)-9-((4-methylpyridin-2-yl)methyl)-9H-purin-8-yl)phenyl)ethan-1-one (racemic) | 545 | C29 H29 Cl N6 O3 | 8.1 | 6.3 | <5.0 |
| T549 | 1-((1S,4S)-2-oxa-5-azabicyclo[2.2.1 heptan-5-yl)-2-(3-chloro-4-(6-(1-methylcyclopropoxy)-9-((4-methylpyridin-2-yl)methyl)-9H-purin-8-yl)phenoxy)ethan-1-one | 561 | C29 H29 Cl N6 O4 | 8 | 6.6 | |
| T550 | rel-1-((1R,5S)-6-oxa-3-azabicyclo [3.1.1]heptan-3-yl)-2-(3-chloro-4-(6-(1-methylcyclopropoxy)-9-((4-methylpyridin-2-yl)methyl)-9H-purin-8-yl)phenoxy)ethan-1-one (racemic) | 561 | C29 H29 Cl N6 O4 | 8 | 6.5 | |
| T551 | (2-(3-chloro-4-(9-(3-chlorobenzyl)-6-(1-methylcyclopropoxy)-9H-purin-8-yl)phenoxy)ethyl)-L-proline | 582 | C29 H29 Cl2 N5 O4 | 8.2 | 6.5 | <5.0 |
| T552 | (S)-2-(3-chloro-4-(6-(1-methylcyclopropoxy)-9-((4-methylpyridin-2-yl)methyl)-9H-purin-8-yl)phenoxy)-1-(3-fluoropiperidin-1-yl)ethan-1-one | 565 | C29 H30 Cl F N6 O3 | 8.1 | 6.8 | |
| T553 | 2-(3-chloro-4-(6-(1-methylcyclopropoxy)-9-((4-methylpyridin-2-yl)methyl)-9H-purin-8-yl)phenoxy)-1-(4-fluoropiperidin-1-yl)ethan-1-one | 565 | C29 H30 Cl F N6 O3 | 8.3 | 6.7 | |
| T554 | (R)-1-(3-(3-chloro-4-(6-(1-methylcyclopropoxy)-9-((4-(trifluoromethyl)pyridin-2-yl)methyl)-9H-purin-8-yl)phenoxy)propyl)pyrrolidin-3-ol | 603 | C29 H30 Cl F3 N6 O3 | 8.1 | 6.5 | <5.0 |
| T555 | 1-(3,6-diazabicyclo[3.1.1]heptan-3-yl)-2-(3-chloro-4-(6-(1-methylcyclopropoxy)-9-((4-methylpyridin-2-yl)methyl)-9H-purin-8-yl)phenyl)ethan-1-one | 544 | C29 H30 Cl N7 O2 | 8.5 | <5.1 | <5.0 |
| T556 | 2-(3-chloro-4-(6-(1-methylcyclopropoxy)-9-((4-methylpyridin-2-yl)methyl)-9H-purin-8-yl)phenyl)-1-(1,6-diazaspiro[3.3] heptan-6-yl)ethan-1-one | 544 | C29 H30 Cl N7 O2 | 8.4 | 5.2 | |
| T557 | 1-(3,6-diazabicyclo[3.1.1 ]heptan-6-yl)-2-(3-chloro-4-(6-(1-methylcyclopropoxy)-9-((4-methylpyridin-2-yl)methyl)-9H-purin-8-yl)phenyl)ethan-1-one | 544 | C29 H30 Cl N7 O2 | 8.5 | 5.2 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T558 | 2-(3-chloro-4-(6-(1-methylcyclopropoxy)-9-((4-methylpyridin-2-yl)methyl)-9H-purin-8-yl)phenyl)-1-(2,6-diazaspiro[3.3]heptan-2-yl)ethan-1-one | 544 | C29 H30 Cl N7 O2 | 8.5 | <5.0 | |
| T559 | 1-((1S,4S)-2,5-diazabicyclo[2.2.1]heptan-2-yl)-2-(3-chloro-4-(6-(1-methylcyclopropoxy)-9-((4-methylpyridin-2-yl)methyl)-9H-purin-8-yl)phenyl)ethan-1-one | 544 | C29 H30 Cl N7 O2 | 8.1 | <5.2 | <5.0 |
| T560 | 7-(2-(3-chloro-4-(6-(1-methylcyclopropoxy)-9-((4-methylpyridin-2-yl)methyl)-9H-purin-8-yl)phenoxy)ethyl)-5,6,7,8-tetrahydro-[1,2,4]triazolo[4,3-alpyrazine | 572 | C29 H30 ClN9 O2 | 8.5 | 5.9 | |
| T561 | 7-(3-chloro-4-(9-(3-chlorobenzyl)-6-(1-methylcyclopropoxy)-9H-purin-8-yl)phenoxy)heptanoic acid | 569 | C29 H30 Cl2 N4 O4 | 8.2 | 7.4 | <5.0 |
| T562 | 5-(3-chloro-4-(9-(3-chlorobenzyl)-6-(1-methylcyclopropoxy)-9H-purin-8-yl)phenoxy)-3,3-dimethylpentanoic acid | 569 | C29 H30 Cl2 N4 O4 | 8.3 | 6.9 | |
| T563 | 5-(3-chloro-4-(9-(3-chlorobenzyl)-6-(1-methylcyclopropoxy)-9H-purin-8-yl)phenoxy)-2,2-dimethylpentanoic acid | 569 | C29 H30 Cl2 N4 O4 | 8.5 | 6.7 | 5 |
| T564 | 7-(2-chloro-3-(9-(3-chlorobenzyl)-6-(1-methylcyclopropoxy)-9H-purin-8-yl)phenoxy)heptanoic acid | 569 | C29 H30 Cl2 N4 O4 | 8.1 | 7.5 | |
| T565 | 5-(2-chloro-3-(9-(3-chlorobenzyl)-6-(1-methylcyclopropoxy)-9H-purin-8-yl)phenoxy)-2,2-dimethylpentanoic acid | 569 | C29 H30 Cl2 N4 O4 | 8.1 | 7 | |
| T566 | 4-(3-chloro-4-(9-(3-chlorobenzyl)-6-(1-methylcyclopropoxy)-9H-purin-8-yl)phenoxy)-2-isopropylbutanoic acid (racemic) | 569 | C29 H30 Cl2 N4 O4 | 8.4 | 6.8 | <5.0 |
| T567 | 9-benzyl-8-(2-chloro-4-(2-(2-(difluoromethyl)piperazin-1-yl)ethoxy)phenyl)-6-(1-methylcyclopropoxy)-9H-purine | 569 | C29 H31 Cl F2 N6 O2 | 8 | 6.8 | |
| T568 | (R)-1-(3-(3-chloro-4-(9-((4-(difluoromethyl)pyridin-2-yl)methyl)-6-(1-methylcyclopropoxy)-9H-purin-8-yl)phenoxy)propyl)pyrrolidin-3-ol | 585 | C29 H31 Cl F2 N6 O3 | 8.2 | 6.1 | <5.0 |
| T569 | 4-(3-chloro-4-(9-(2,5-dimethylbenzyl)-6-(1-methylcyclopropoxy)-9H-purin-8-yl)phenoxy)-2-methylbutanoic acid (racemic) | 535 | C29 H31 Cl N4 O4 | 8.3 | 6.2 | |
| T570 | 4-(3-chloro-4-(9-(2,3-dimethylbenzyl)-6-(1-methylcyclopropoxy)-9H-purin-8-yl)phenoxy)-2-methylbutanoic acid (racemic) | 535 | C29 H31 Cl N4 O4 | 8.3 | 6.4 | |
| T571 | 4-(3-chloro-4-(9-(2,6-dimethylbenzyl)-6-(1-methylcyclopropoxy)-9H-purin-8-yl)phenoxy)-2-methylbutanoic acid (racemic) | 535 | C29 H31 Cl N4 O4 | 8.1 | 5.9 | <5.0 |
| T572 | 4-(3-chloro-4-(9-(2,5-dimethylbenzyl)-6-(1-methylcyclopropoxy)-9H-purin-8-yl)phenoxy)-2-methylbutanoic acid (Isomer 1) | 535 | C29 H31 Cl N4 O4 | 8.3 | 6.2 | |
| T573 | 4-(3-chloro-4-(9-(2,5-dimethylbenzyl)-6-(1-methylcyclopropoxy)-9H-purin-8-yl)phenoxy)-2-methylbutanoic acid (Isomer 2) | 535 | C29 H31 Cl N4 O4 | 8.3 | 6.3 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T574 | 2-(3-chloro-4-(6-(1-methylcyclopropoxy)-9-((4-methylpyridin-2-yl)methyl)-9H-purin-8-yl)phenyl)-1-(4-hydroxypiperidin-1-yl)ethan-1-one | 547 | C29 H31 Cl N6 O3 | 8.1 | 6 | <5.0 |
| T575 | (S)-2-(3-chloro-4-(6-(1-methylcyclopropoxy)-9-((4-methylpyridin-2-yl)methyl)-9H-purin-8-yl)phenyl)-1-(3-hydroxy-3-methylpyrrolidin-1-yl)ethan-1-one | 547 | C29 H31 Cl N6 O3 | 8.2 | 6.5 | |
| T576 | (S)-2-(3-chloro-4-(6-(1-methylcyclopropoxy)-9-((4-methylpyridin-2-yl)methyl)-9H-purin-8-yl)phenoxy)-1-(2-(hydroxymethyl)pyrrolidin-1-yl)ethan-1-one | 563 | C29 H31 Cl N6 O4 | 8 | 6.3 | |
| T577 | (S)-2-(3-chloro-4-(6-(1-methylcyclopropoxy)-9-((4-methylpyridin-2-yl)methyl)-9H-purin-8-yl)phenoxy)-1-(3-methoxypyrrolidin-1-yl)ethan-1-one | 563 | C29 H31 Cl N6 O4 | 8.1 | 6.4 | |
| T578 | (R)-2-(3-chloro-4-(6-(1-methylcyclopropoxy)-9-((4-methylpyridin-2-yl)methyl)-9H-purin-8-yl)phenoxy)-1-(3-(hydroxymethyl)pyrrolidin-1-yl)ethan-1-one | 563 | C29 H31 Cl N6 O4 | 8 | 6.2 | |
| T579 | (R)-2-(3-chloro-4-(6-(1-methylcyclopropoxy)-9-((4-methylpyridin-2-yl)methyl)-9H-purin-8-yl)phenoxy)-1-(2-(hydroxymethyl)pyrrolidin-1-yl)ethan-1-one | 563 | C29 H31 Cl N6 O4 | 8 | 6.3 | |
| T580 | 2-(3-chloro-4-(6-(1-methylcyclopropoxy)-9-((4-methylpyridin-2-yl)methyl)-9H-purin-8-yl)phenoxy)-1-(4-hydroxypiperidin-1-yl)ethan-1-one | 563 | C29 H31 Cl N6 O4 | 8 | 6.3 | |
| T581 | (R)-2-(3-chloro-4-(6-(1-methylcyclopropoxy)-9-((4-methylpyridin-2-yl)methyl)-9H-purin-8-yl)phenoxy)-1-(3-hydroxy-3-methylpyrrolidin-1-yl)ethan-1-one | 563 | C29 H31 Cl N6 O4 | 8 | 6.3 | |
| T582 | 2-(3-chloro-4-(6-(1-methylcyclopropoxy)-9-((4-methylpyridin-2-yl)methyl)-9H-purin-8-yl)phenoxy)-N-((1s,3s)-3-hydroxycyclobutyl)-N-methylacetamide | 563 | C29 H31 Cl N6 O4 | 8 | 6.2 | |
| T583 | 2-(3-chloro-4-(6-(1-methylcyclopropoxy)-9-((4-methylpyridin-2-yl)methyl)-9H-purin-8-yl)phenoxy)-N-((1-hydroxycyclopropyl)methyl)-N-methylacetamide | 563 | C29 H31 Cl N6 O4 | 8 | 5.7 | |
| T584 | (R)-1-((S)-3-(3-chloro-4-(6-(1-methylcyclopropoxy)-9-((4-methylpyridin-2-yl)methyl)-9H-purin-8-yl)phenoxy)pyrrolidin-1-yl)-2-hydroxypropan-1-one | 563 | C29 H31 Cl N6 O4 | 8.1 | 6.1 | |
| T585 | (S)-8-(2-chloro-4-(hexahydropyrrolo[1,2-a]pyrazin-2(1H)-yl)phenyl)-6-(1-methylcyclopropoxy)-9-((4-methylpyridin-2-yl)methyl)-9H-purine | 530 | C29 H32 Cl N7 O | 8.2 | 6.7 | |
| T586 | 8-(2-chloro-4-(1,7-diazaspiro[3.5]nonan-7-yl)phenyl)-6-(1-methylcyclopropoxy)-9-((4-methylpyridin-2-yl)methyl)-9H-purine | 530 | C29 H32 Cl N7 O | 8.1 | 5.8 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T587 | 8-(4-(2-(1,6-diazaspiro[3.3 ]heptan-6-yl)ethoxy)-2-chlorophenyl)-6-(1-methylcyclopropoxy)-9-((4-methylpyridin-2-yl)methyl)-9H-purine | 546 | C29 H32 Cl N7 O2 | 8.3 | 6 | <5.0 |
| T588 | (S)-(3-chloro-4-(6-(1-methylcyclopropoxy)-9-((4-methylpyridin-2-yl)methyl)-9H-purin-8-yl)phenyl)(3-(dimethylamino)pyrrolidin-1-yl)methanone | 546 | C29 H32 Cl N7 O2 | 8.3 | 5.9 | <5.0 |
| T589 | 2-(3-chloro-4-(6-(1-methylcyclopropoxy)-9-((4-methylpyridin-2-yl)methyl)-9H-purin-8-yl)phenyl)-1-(1,4-diazepan-1-yl)ethan-1-one | 546 | C29 H32 Cl N7 O2 | 8.4 | 5.8 | <5.0 |
| T590 | 8-(2-chloro-4-(3-(pyrrolidin-1-yl)propoxy)phenyl)-6-(1-methylcyclopropoxy)-9-((4-methylpyridin-2-yl)methyl)-9H-purine | 533 | C29 H33 Cl N6 O2 | 8.1 | 6.6 | <5.0 |
| T591 | 1-(3-chloro-4-(6-(1-methylcyclopropoxy)-9-((4-methylpyridin-2-yl)methyl)-9H-purin-8-yl)phenethyl)piperidin-4-ol | 533 | C29 H33 Cl N6 O2 | 8.3 | 6.5 | <5.0 |
| T592 | (R)-1-(3-(3-chloro-4-(6-(1-methylcyclopropoxy)-9-((4-methylpyridin-2-yl)methyl)-9H-purin-8-yl)phenoxy)propyl)pyrrolidin-3-ol | 549 | C29 H33 Cl N6 O3 | 8.3 | 6.7 | <5.0 |
| T593 | (R)-1-(3-(2-chloro-3-(6-(1-methylcyclopropoxy)-9-((4-methylpyridin-2-yl)methyl)-9H-purin-8-yl)phenoxy)propyl)pyrrolidin-3-ol | 549 | C29 H33 Cl N6 O3 | 8.2 | 6.6 | <5.0 |
| T594 | (S)-8-(2-chloro-4-(2-(2-methylpiperazin-1-yl)ethoxy)phenyl)-6-(1-methylcyclopropoxy)-9-((4-methylpyridin-2-yl)methyl)-9H-purine | 548 | C29 H34 Cl N7 O2 | 8.2 | 6.3 | 5.6 |
| T595 | 8-(2-chloro-4-(2-(piperazin-1-yl)ethoxy)phenyl)-9-((4,6-dimethylpyridin-2-yl)methyl)-6-(1-methylcyclopropoxy)-9H-purine | 548 | C29 H34 Cl N7 O2 | 8.3 | 5.9 | <5.0 |
| T596 | 8-(2-chloro-4-(2-(piperazin-1-yl)ethoxy)phenyl)-9-((4,5-dimethylpyridin-2-yl)methyl)-6-(1-methylcyclopropoxy)-9H-purine | 548 | C29 H34 Cl N7 O2 | 8.2 | 5.3 | <5.0 |
| T597 | 8-(2-chloro-4-(2-(piperazin-1-yl)ethoxy)phenyl)-9-((3,4-dimethylpyridin-2-yl)methyl)-6-(1-methylcyclopropoxy)-9H-purine | 548 | C29 H34 Cl N7 O2 | 7.7 | 5.6 | 5.2 |
| T598 | 4-(3-chloro-4-(9-(2-cyclopropylbenzyl)-6-(1-methylcyclopropoxy)-9H-purin-8-yl)phenoxy)-2-methylbutanoic acid (racemic) | 547 | C30 H31 Cl N4 O4 | 8.2 | 6.2 | <5.0 |
| T599 | 4-(3-chloro-4-(9-(2-cyclopropylbenzyl)-6-(1-methylcyclopropoxy)-9H-purin-8-yl)phenoxy)-2-methylbutanoic acid (Isomer 1) | 547 | C30 H31 Cl N4 O4 | 8.2 | 6.2 | |
| T600 | 4-(3-chloro-4-(9-(2-cyclopropylbenzyl)-6-(1-methylcyclopropoxy)-9H-purin-8-yl)phenoxy)-2-methylbutanoic acid (Isomer 2) | 547 | C30 H31 Cl N4 O4 | 8.2 | 6.3 | |
| T601 | 4-(3-chloro-4-(9-(3-cyclopropylbenzyl)-6-(1-methylcyclopropoxy)-9H-purin-8-yl)phenoxy)-2-methylbutanoic acid (racemic) | 547 | C30 H31 Cl N4 O4 | 8.4 | 6.1 | |
| T602 | (3-chloro-4-(6-(1-methylcyclopropoxy)-9-((4-methylpyridin-2-yl)methyl)-9H-purin-8-yl)phenyl)(3-(pyrrolidin-1-yl)azetidin-1-yl)methanone | 558 | C30 H32 Cl N7 O2 | 8.6 | 5.9 | |

TABLE T-continued

| Ex# | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean PIC50 |
|---|---|---|---|---|---|---|
| T603 | 1-([1,3'-biazetidin]-1'-yl)-2-(3-chloro-4-(6-(1-methylcyclopropoxy)-9-((4-methylpyridin-2-yl)methyl)-9H-purin-8-yl)phenyl)ethan-1-one | 558 | C30 H32 Cl N7 O2 | 8.3 | 6.1 | |
| T604 | rel-(1R,4R)-2-(2-(4-(9-benzyl-6-(1-methylcyclopropoxy)-9H-purin-8-yl)-3-chlorophenoxy)ethyl)-2,5-diazabicyclo[2.2.2]octane (unknown absolute stereochemistry) | 545 | C30 H33 Cl N6 O2 | 8.5 | 6.6 | |
| T605 | 8-(4-(2-(3,8-diazabicyclo[3.2.1]octan-8-yl)ethoxy)-2-chlorophenyl)-9-benzyl-6-(1-methylcyclopropoxy)-9H-purine | 545 | C30 H33 Cl N6 O2 | 8.3 | 6.8 | |
| T606 | 2-(3-chloro-4-(6-(1-methylcyclopropoxy)-9-((4-methylpyridin-2-yl)methyl)-9H-purin-8-yl)phenyl)-1-((3R,5S)-3,5-dimethylpiperazin-1-yl)ethan-1-one | 560 | C30 H34 Cl N7 O2 | 8.2 | 6.1 | <5.0 |
| T607 | 1-(4-(2-(3-chloro-4-(6-(1-methylcyclopropoxy)-9-((4-methylpyridin-2-yl)methyl)-9H-purin-8-yl)phenoxy)ethyl)piperazin-1-yl)ethan-1-one | 576 | C30 H34 Cl N7 O3 | 8.1 | 6.9 | |
| T608 | 4-(tert-butoxy)-2-(2-chloro-4-(2-(piperazin-1-yl)ethoxy)phenyl)-1-(3-chlorobenzyl)-1H-benzo[d]imidazole | 553 | C30 H34 Cl2 N4 O2 | 7.9 | 6.3 | |
| T609 | 4-(tert-butoxy)-2-(2-chloro-4-(2-(piperazin-1-yl)ethoxy)phenyl)-1-((4-methylpyridin-2-yl)methyl)-1H-benzo[d]imidazole | 534 | C30 H36 Cl N5 O2 | 8.4 | 5.8 | <5.0 |
| T610 | 4-(tert-butoxy)-2-(2-chloro-4-(2-(4-methylpiperazin-1-yl)ethoxy)phenyl)-1-((4-methylpyridin-2-yl)methyl)-1H-imidazo[4,5-c]pyridine | 549 | C30 H37 Cl N6 O2 | 6.7 | <5.1 | |
| T611 | 2-(2-chloro-4-(2-(piperazin-1-yl)ethoxy)phenyl)-1-(3-chlorobenzyl)-4-(1-methylcyclobutoxy)-1H-benzo[d]imidazole | 565 | C31 H34 Cl2 N4 O2 | 7.8 | 6.5 | |
| T612 | 9-benzyl-8-(2-(methoxymethyl)-4-(2-(4-methylpiperazin-1-yl)ethoxy)phenyl)-6-(1-methylcyclopropoxy)-9H-purine | 543 | C31 H38 N6 O3 | 7.6 | 6 | <5.0 |

TABLE U

| Ex # | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean pIC50 |
|---|---|---|---|---|---|---|
| U1 | 4-(3-chloro-4-(9-(2-methoxy-5-methylbenzyl)-6-(1-methylcyclopropoxy)-9H-purin-8-yl)phenoxy)-2-methylbutanoic acid (racemic) | 551 | C29 H31 Cl N4 O5 | 8.3 | 7.3 | <5.0 |
| U2 | 4-(3-chloro-4-(9-(5-fluoro-2-methoxybenzyl)-6-(1-methylcyclopropoxy)-9H-purin-8-yl)phenoxy)-2-methylbutanoic acid (racemic) | 555 | C28 H28 Cl F N4 O5 | 8.3 | 7.2 | <5.0 |
| U3 | 4-(3-chloro-4-(9-(3-chloro-2-methoxybenzyl)-6-(1-methylcyclopropoxy)-9H-purin-8-yl)phenoxy)-2-methylbutanoic acid (racemic) | 571 | C28 H28 Cl2 N4 O5 | 7.9 | 5.4 | |
| U4 | 4-(3-chloro-4-(9-(2-methoxybenzyl)-6-(1-methylcyclopropoxy)-9H-purin-8-yl)phenoxy)-2-methylbutanoic acid (racemic) | 537 | C28 H29 Cl N4 O5 | 8.2 | 6.6 | |

TABLE U-continued

| Ex # | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean pIC50 |
|---|---|---|---|---|---|---|
| U5 | 4-(3-chloro-4-(9-(2-fluorobenzyl)-6-(1-methylcyclopropoxy)-9H-purin-8-yl)phenoxy)-2-methylbutanoic acid (racemic) | 525 | C27 H26 Cl F N4 O4 | 8.2 | 6.5 | |
| U6 | 4-(3-chloro-4-(9-(3-fluorobenzyl)-6-(1-methylcyclopropoxy)-9H-purin-8-yl)phenoxy)-2-methylbutanoic acid (racemic) | 525 | C27 H26 Cl F N4 O4 | 8.2 | 6.6 | |
| U7 | 4-(3-chloro-4-(9-(4-cyanobenzyl)-6-(1-methylcyclopropoxy)-9H-purin-8-yl)phenoxy)-2-methylbutanoic acid (racemic) | 532 | C28 H26 Cl N5 O4 | 8.1 | 5.6 | |
| U8 | (S)-4-(3-chloro-4-(9-(3-cyanobenzyl)-6-(1-methylcyclopropoxy)-9H-purin-8-yl)phenoxy)-2-methylbutanoic acid | 532 | C28 H26 Cl N5 O4 | 8.3 | 6.4 | <5.2 |
| U9 | 4-(3-chloro-4-(9-(5-chloro-2-cyanobenzyl)-6-(1-methylcyclopropoxy)-9H-purin-8-yl)phenoxy)-2-methylbutanoic acid (racemic) | 566 | C28 H25 Cl2 N5 O4 | 8.3 | 7.1 | <5.0 |
| U10 | (R)-4-(3-chloro-4-(9-(5-chloro-2-fluorobenzyl)-6-(1-methylcyclopropoxy)-9H-purin-8-yl)phenoxy)-2-methylbutanoic acid | 559 | C27 H25 Cl2 F N4 O4 | 8.4 | 7.2 | <5.0 |
| U11 | (S)-4-(3-chloro-4-(9-(5-chloro-2-fluorobenzyl)-6-(1-methylcyclopropoxy)-9H-purin-8-yl)phenoxy)-2-methylbutanoic acid | 559 | C27 H25 Cl2 F N4 O4 | 8.3 | 7.3 | <5.2 |
| U12 | 5-(3-chloro-4-(9-(2-cyanobenzyl)-6-(1-methylcyclopropoxy)-9H-purin-8-yl)phenyl)-2-methylpentanoic acid (racemic) | 530 | C29 H28 Cl N5 O3 | 8.1 | 6.4 | |
| U13 | 4-(3-chloro-4-(9-(2-cyano-6-fluorobenzyl)-6-(1-methylcyclopropoxy)-9H-purin-8-yl)phenoxy)-2-methylbutanoic acid (racemic) | 550 | C28 H25 Cl F N5 O4 | 7.7 | 5.5 | <5.0 |
| U14 | 4-(3-chloro-4-(9-(5-cyano-2-methoxybenzyl)-6-(1-methylcyclopropoxy)-9H-purin-8-yl)phenoxy)-2-methylbutanoic acid (racemic) | 562 | C29 H28 Cl N5 O5 | 8.3 | 6.4 | <5.0 |
| U15 | 2-(1-((3-chloro-4-(9-(2-cyanobenzyl)-6-(1-methylcyclopropoxy)-9H-purin-8-yl)phenoxy)methyl)cyclopropyl)acetic acid | 544 | C29 H26 Cl N5 O4 | 8 | 6.1 | |
| U16 | (1s,4s)-4-(3-chloro-4-(9-(2-cyanobenzyl)-6-(1-methylcyclopropoxy)-9H-purin-8-yl)phenoxy)cyclohexane-1-carboxylic acid | 558 | C30 H28 Cl N5 O4 | 8.2 | 6.4 | |
| U17 | 4-(3-chloro-4-(9-(2-cyanobenzyl)-6-(1-methylcyclopropoxy)-9H-purin-8-yl)phenoxy)-2,2-dimethylbutanoic acid | 546 | C29 H28 Cl N5 O4 | 8.2 | 6.6 | |
| U18 | 4-(3-chloro-4-(9-(5-cyano-2-fluorobenzyl)-6-(1-methylcyclopropoxy)-9H-purin-8-yl)phenoxy)-2-methylbutanoic acid (racemic) | 550 | C28 H25 Cl F N5 O4 | 8.2 | 6.4 | |
| U19 | (1r,4r)-4-(3-chloro-4-(9-(2-cyanobenzyl)-6-(1-methylcyclopropoxy)-9H-purin-8-yl)phenoxy)cyclohexane-1-carboxylic acid | 558 | C30 H28 Cl N5 O4 | 8.3 | 6.6 | |
| U20 | 5-(3-chloro-4-(9-(2-cyanobenzyl)-6-(1-methylcyclopropoxy)-9H-purin-8-yl)phenyl)pentanoic acid | 516 | C28 H26 Cl N5 O3 | 8.2 | 6.6 | |
| U21 | 5-(3-chloro-4-(9-(2-cyanobenzyl)-6-(1-methylcyclopropoxy)-9H-purin-8-yl)phenoxy)-2,2-dimethylpentanoic acid | 560 | C30 H30 Cl N5 O4 | 8.3 | 6.8 | |

TABLE U-continued

| Ex # | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean pIC50 |
|---|---|---|---|---|---|---|
| U22 | 2-(2-(2-chloro-3-(9-(5-chloro-2-fluorobenzyl)-6-(1-methylcyclopropoxy)-9H-purin-8-yl)phenoxy)ethoxy)acetic acid | 561 | C26 H23 Cl2 F N4 O5 | 8.3 | 7.3 | <5.0 |
| U24 | (S)-4-(2-chloro-3-(9-(5-chloro-2-fluorobenzyl)-6-(1-methylcyclopropoxy)-9H-purin-8-yl)phenoxy)-2-methylbutanoic acid | 559 | C27 H25 Cl2 F N4 O4 | 8.2 | 7.9 | <5.0 |
| U25 | 4-(3-chloro-4-(9-(2-cyanobenzyl)-6-(1-methylcyclopropoxy)-9H-purin-8-yl)phenoxy)-3-methylbutanoic acid (racemic) | 532 | C28 H26 Cl N5 O4 | 8 | 6.4 | |
| U26 | (R)-4-(2-chloro-3-(9-(5-chloro-2-fluorobenzyl)-6-(1-methylcyclopropoxy)-9H-purin-8-yl)phenoxy)-2-methylbutanoic acid | 559 | C27 H25 Cl2 F N4 O4 | 8.1 | 7.6 | <5.0 |
| U27 | (1r,3r)-3-((3-chloro-4-(9-(2-cyanobenzyl)-6-(1-methylcyclopropoxy)-9H-purin-8-yl)phenoxy)methyl)cyclobutane-1-carboxylic acid | 544 | C29 H26 Cl N5 O4 | 7.9 | 6.7 | |
| U28 | 5-(2-chloro-3-(9-(3-chlorobenzyl)-6-(1-methylcyclopropoxy)-9H-purin-8-yl)phenoxy)-3,3-dimethylpentanoic acid | 569 | C29 H30 Cl2 N4 O4 | 8.1 | 7.1 | <5.0 |
| U30 | 2-(3-(2-chloro-3-(9-(5-chloro-2-methoxybenzyl)-6-(1-methylcyclopropoxy)-9H-purin-8-yl)phenoxy)propoxy)acetic acid | 587 | C28 H28 Cl2 N4 O6 | 8.1 | 7.7 | <5.0 |
| U31 | 4-(3-chloro-4-(9-(5-chloro-2-methoxybenzyl)-6-(1-methylcyclopropoxy)-9H-purin-8-yl)phenoxy)-2,2-dimethylbutanoic acid | 585 | C29 H30 Cl2 N4 O5 | 8.1 | 7.3 | <5.1 |
| U32 | 3-(2-chloro-3-(9-(5-chloro-2-fluorobenzyl)-6-(1-methylcyclopropoxy)-9H-purin-8-yl)phenoxy)propanoic acid | 531 | C25 H21 Cl2 F N4 O4 | 8.1 | 7.4 | |
| U33 | 4-(2-chloro-3-(9-(5-chloro-2-fluorobenzyl)-6-(1-methylcyclopropoxy)-9H-purin-8-yl)phenoxy)-3-methylbutanoic acid (isomer 1) | 559 | C27 H25 Cl2 F N4 O4 | 8.1 | 7.8 | |
| U34 | 4-(2-chloro-3-(9-(5-chloro-2-fluorobenzyl)-6-(1-methylcyclopropoxy)-9H-purin-8-yl)phenoxy)-3-methylbutanoic acid (isomer 2) | 559 | C27 H25 Cl2 F N4 O4 | 8.1 | 7.5 | |
| U35 | 4-(3-chloro-4-(9-(3-chloro-2-fluoro-5-(trifluoromethyl)benzyl)-6-(1-methylcyclopropoxy)-9H-purin-8-yl)phenoxy)-2-methylbutanoic acid (racemic) | 627 | C28 H24 Cl2 F4 N4 O4 | 8 | 6.8 | |
| U36 | 4-(3-chloro-4-(9-(5-chloro-2-methylbenzyl)-6-(1-methylcyclopropoxy)-9H-purin-8-yl)phenoxy)-2-methylbutanoic acid (racemic) | 555 | C28 H28 Cl2 N4 O4 | 8.2 | 6.5 | |
| U37 | 4-(3-chloro-4-(9-(3-chloro-2-cyanobenzyl)-6-(1-methylcyclopropoxy)-9H-purin-8-yl)phenoxy)-2-methylbutanoic acid (racemic) | 566 | C28 H25 Cl2 N5 O4 | 7.7 | 5.7 | |
| U38 | (1r,4r)-4-(2-chloro-3-(9-(5-chloro-2-methoxybenzyl)-6-(1-methylcyclopropoxy)-9H-purin-8-yl)phenoxy)cyclohexane-1-carboxylic acid | 597 | C30 H30 Cl2 N4 O5 | 8.3 | 7.5 | 5.1 |
| U39 | 3-(2-chloro-3-(9-(3-chlorobenzyl)-6-(1-methylcyclopropoxy)-9H-purin-8-yl)-5-fluorophenoxy)propanoic acid | 531 | C25 H21 Cl2 F N4 O4 | 8.4 | 7.9 | <5.0 |

TABLE U-continued

| Ex # | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean pIC50 |
|---|---|---|---|---|---|---|
| U40 | (1s,4s)-4-(3-chloro-4-(9-(5-chloro-2-methoxybenzyl)-6-(1-methylcyclopropoxy)-9H-purin-8-yl)phenoxy)cyclohexane-1-carboxylic acid | 597 | C30 H30 Cl2 N4 O5 | 8 | 7 | <5.1 |
| U42 | 4-(3-chloro-4-(9-(5-chloro-2-methoxybenzyl)-6-(1-methylcyclopropoxy)-9H-purin-8-yl)phenoxy)-3-methylbutanoic acid (racemic) | 571 | C28 H28 Cl2 N4 O5 | 8.1 | 7.4 | <5.0 |
| U43 | (1r,4r)-4-(3-chloro-4-(9-(5-chloro-2-methoxybenzyl)-6-(1-methylcyclopropoxy)-9H-purin-8-yl)phenoxy)cyclohexane-1-carboxylic acid | 597 | C30 H30 Cl2 N4 O5 | 8.1 | 7.2 | <5.0 |
| U44 | (1s,4s)-4-(3-chloro-4-(9-(5-chloro-2-fluorobenzyl)-6-(1-methylcyclopropoxy)-9H-purin-8-yl)phenoxy)cyclohexane-1-carboxylic acid | 585 | C29 H27 Cl2 F N4 O4 | 8.3 | 7.2 | |
| U45 | 4-(3-chloro-4-(9-(5-chloro-2-fluorobenzyl)-6-(1-methylcyclopropoxy)-9H-purin-8-yl)phenoxy)-3-methylbutanoic acid (racemic) | 559 | C27 H25 Cl2 F N4 O4 | 8.3 | 7.1 | |
| U46 | 4-(3-chloro-4-(9-(5-chloro-2-fluorobenzyl)-6-(1-methylcyclopropoxy)-9H-purin-8-yl)phenoxy)-2,2-dimethylbutanoic acid | 573 | C28 H27 Cl2 F N4 O4 | 8.1 | 7.5 | |
| U47 | 5-(3-chloro-4-(9-(5-chloro-2-methoxybenzyl)-6-(1-methylcyclopropoxy)-9H-purin-8-yl)phenoxy)-2,2-dimethylpentanoic acid | 599 | C30 H32 Cl2 N4 O5 | 8.1 | 7.5 | 5.2 |
| U48 | 2-(2-(3-chloro-4-(9-(5-chloro-2-methoxybenzyl)-6-(1-methylcyclopropoxy)-9H-purin-8-yl)phenoxy)ethoxy)acetic acid | 573 | C27 H26 Cl2 N4 O6 | 8.2 | 6.2 | <5.0 |
| U49 | (1r,4r)-4-(3-chloro-4-(9-(5-chloro-2-fluorobenzyl)-6-(1-methylcyclopropoxy)-9H-purin-8-yl)phenoxy)cyclohexane-1-carboxylic acid | 585 | C29 H27 Cl2 F N4 O4 | 8 | 7.3 | |
| U50 | (1s,4s)-4-(2-chloro-3-(9-(5-chloro-2-methoxybenzyl)-6-(1-methylcyclopropoxy)-9H-purin-8-yl)phenoxy)cyclohexane-1-carboxylic acid | 597 | C30 H30 Cl2 N4 O5 | 8.1 | 7.6 | <5.0 |
| U51 | (1r,3r)-3-(2-chloro-3-(9-(5-chloro-2-methoxybenzyl)-6-(1-methylcyclopropoxy)-9H-purin-8-yl)phenoxy)cyclobutane-1-carboxylic acid | 569 | C28 H26 Cl2 N4 O5 | 8.2 | 7.2 | <5.0 |
| U52 | 2-(2-(2-chloro-3-(9-(5-chloro-2-methoxybenzyl)-6-(1-methylcyclopropoxy)-9H-purin-8-yl)phenoxy)ethoxy)acetic acid | 573 | C27 H26 Cl2 N4 O6 | 8.1 | 7.3 | <5.0 |
| U53 | 4-(3-chloro-4-(9-((5-chloro-2-methoxypyridin-3-yl)methyl)-6-(1-methylcyclopropoxy)-9H-purin-8-yl)phenoxy)-2-methylbutanoic acid (racemic) | 572 | C27 H27 Cl2 N5 O5 | 7.7 | 6.5 | |
| U54 | 2-(2-(3-chloro-4-(9-(5-chloro-2-methoxybenzyl)-6-(1-methylcyclopropoxy)-9H-purin-8-yl)phenoxy)ethoxy)-2-methylpropanoic acid | 601 | C29 H30 Cl2 N4 O6 | 8 | 6.9 | <5.0 |
| U55 | 5-(2-chloro-3-(9-(5-chloro-2-methoxybenzyl)-6-(1-methylcyclopropoxy)-9H-purin-8-yl)phenyl)-2-methylpentanoic acid (racemic) | 569 | C29 H30 Cl2 N4 O4 | 8.2 | 6.9 | <5.0 |

TABLE U-continued

| Ex # | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean pIC50 |
|---|---|---|---|---|---|---|
| U56 | 5-(3-chloro-4-(9-(5-chloro-2-methoxybenzyl)-6-(1-methylcyclopropoxy)-9H-purin-8-yl)phenyl)-2-methylpentanoic acid (racemic) | 569 | C29 H30 Cl2 N4 O4 | 8.2 | 6.9 | <5.0 |
| U57 | 4-(3-chloro-4-(9-(3-chloro-2-fluoro-6-methoxybenzyl)-6-(1-methylcyclopropoxy)-9H-purin-8-yl)phenoxy)-2-methylbutanoic acid (racemic) | 589 | C28 H27 Cl2 F N4 O5 | 8.5 | 6.9 | <5.0 |
| U59 | 4-(3-chloro-4-(9-(5-chloro-2-ethoxybenzyl)-6-(1-methylcyclopropoxy)-9H-purin-8-yl)phenoxy)-2-methylbutanoic acid (racemic) | 585 | C29 H30 Cl2 N4 O5 | 8.2 | 7.2 | |
| U60 | 4-(3-chloro-4-(9-(5-chloro-2-(difluoromethoxy)benzyl)-6-(1-methylcyclopropoxy)-9H-purin-8-yl)phenoxy)-2-methylbutanoic acid (racemic) | 607 | C28 H26 Cl2 F2 N4 O5 | 8 | 6.9 | |
| U61 | 4-(3-chloro-4-(9-(5-chloro-3-fluoro-2-methoxybenzyl)-6-(1-methylcyclopropoxy)-9H-purin-8-yl)phenoxy)-2-methylbutanoic acid (racemic) | 589 | C28 H27 Cl2 F N4 O5 | 8.2 | 6.8 | |
| U62 | 4-(2-chloro-3-(9-(5-chloro-2-methoxybenzyl)-6-(1-methylcyclopropoxy)-9H-purin-8-yl)phenyl)butanoic acid | 541 | C27 H26 Cl2 N4 O4 | 8.4 | 7.3 | <5.0 |
| U63 | 4-(2-chloro-3-(9-(3-chlorobenzyl)-6-(1-methylcyclopropoxy)-9H-purin-8-yl)phenoxy)-3,3-difluorobutanoic acid | 563 | C26 H22 Cl2 F2 N4 O4 | 8.5 | 6.3 | |
| U64 | 3-(2-chloro-3-(9-(5-chloro-2-methoxybenzyl)-6-(1-methylcyclopropoxy)-9H-purin-8-yl)phenyl)propanoic acid | 527 | C26 H24 Cl2 N4 O4 | 8.3 | 7 | <5.0 |
| U65 | 3-(2-chloro-3-(9-(3-chlorobenzyl)-6-(1-methylcyclopropoxy)-9H-purin-8-yl)-6-fluorophenoxy)propanoic acid | 531 | C25 H21 Cl2 F N4 O4 | 8.6 | 6.6 | <5.0 |
| U66 | 3-(2-chloro-3-(9-(3-chlorobenzyl)-6-(1-methylcyclopropoxy)-9H-purin-8-yl)-4-fluorophenoxy)propanoic acid | 531 | C25 H21 Cl2 F N4 O4 | >8.7 | 6.7 | |
| U67 | (R)-4-(3-chloro-4-(9-(5-fluoro-2-methoxybenzyl)-6-(1-methylcyclopropoxy)-9H-purin-8-yl)phenoxy)-2-methylbutanoic acid | 555 | C28 H28 Cl F N4 O5 | 8.7 | 7.3 | <5.0 |
| U68 | (S)-4-(3-chloro-4-(9-(5-fluoro-2-methoxybenzyl)-6-(1-methylcyclopropoxy)-9H-purin-8-yl)phenoxy)-2-methylbutanoic acid | 555 | C28 H28 Cl F N4 O5 | 8.6 | 7.4 | <5.0 |
| U69 | (1r,4r)-4-(2-chloro-3-(9-(5-fluoro-2-methoxybenzyl)-6-(1-methylcyclopropoxy)-9H-purin-8-yl)phenoxy)cyclohexane-1-carboxylic acid | 581 | C30 H30 Cl F N4 O5 | 8.5 | 7.4 | <5.0 |
| U71 | 2-(3-(2-chloro-3-(9-(5-fluoro-2-methoxybenzyl)-6-(1-methylcyclopropoxy)-9H-purin-8-yl)phenoxy)propoxy)acetic acid | 571 | C28 H28 Cl F N4 O6 | | | <5.0 |
| U72 | (S)-4-(2-chloro-3-(9-(5-fluoro-2-methoxybenzyl)-6-(1-methylcyclopropoxy)-9H-purin-8-yl)phenoxy)-2-methylbutanoic acid | 555 | C28 H28 Cl F N4 O5 | | 8.8 | |
| U73 | (S)-4-(2-chloro-3-(9-(5-chloro-2-methoxybenzyl)-6-(1-methylcyclopropoxy)-9H-purin-8-yl)phenoxy)-2-methylbutanoic acid | 571 | C28 H28 Cl2 N4 O5 | 8.5 | 8.7 | <5.0 |
| U74 | (1s,3s)-3-(2-chloro-3-(9-(5-fluoro-2-methoxybenzyl)-6-(1-methylcyclopropoxy)-9H-purin-8-yl)phenoxy)cyclobutane-1-carboxylic acid | 553 | C28 H26 Cl F N4 O5 | 8.4 | 7.2 | <5.0 |

TABLE U-continued

| Ex # | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean pIC50 |
|---|---|---|---|---|---|---|
| U75 | (R)-4-(2-chloro-3-(9-(5-chloro-2-methoxybenzyl)-6-(1-methylcyclopropoxy)-9H-purin-8-yl)phenoxy)-2-methylbutanoic acid | 571 | C28 H28 Cl2 N4 O5 | 8.5 | 8.7 | <5.0 |
| U76 | (S)-4-(3-chloro-4-(9-(2-methoxy-5-(trifluoromethyl)benzyl)-6-(1-methylcyclopropoxy)-9H-purin-8-yl)phenoxy)-2-methylbutanoic acid | 605 | C29 H28 Cl F3 N4 O5 | 8.4 | 6.7 | <5.0 |
| U77 | 4-(2-chloro-3-(9-(5-fluoro-2-methoxybenzyl)-6-(1-methylcyclopropoxy)-9H-purin-8-yl)phenoxy)-3-methylbutanoic acid (Isomer1) | 555 | C28 H28 Cl F N4 O5 | 8.5 | 8.1 | <5.0 |
| U78 | (R)-4-(2-chloro-3-(9-(5-fluoro-2-methoxybenzyl)-6-(1-methylcyclopropoxy)-9H-purin-8-yl)phenoxy)-2-methylbutanoic acid | 555 | C28 H28 Cl F N4 O5 | 8.7 | | <5.0 |
| U79 | (R)-4-(3-chloro-4-(9-(2-methoxy-5-(trifluoromethyl)benzyl)-6-(1-methylcyclopropoxy)-9H-purin-8-yl)phenoxy)-2-methylbutanoic acid | 605 | C29 H28 Cl F3 N4 O5 | 8.4 | | |
| U80 | 4-(2-chloro-3-(9-(5-fluoro-2-methoxybenzyl)-6-(1-methylcyclopropoxy)-9H-purin-8-yl)phenoxy)-3-methylbutanoic acid (Isomer 2) | 555 | C28 H28 Cl F N4 O5 | 8.5 | 8 | |
| U81 | (R)-4-(3-chloro-4-(9-(5-chloro-2-cyanobenzyl)-6-(1-methylcyclopropoxy)-9H-purin-8-yl)phenoxy)-2-methylbutanoic acid | 566 | C28 H25 Cl2 N5 O4 | 8.4 | 7.7 | <5.0 |
| U82 | (S)-4-(3-chloro-4-(9-(5-chloro-2-cyanobenzyl)-6-(1-methylcyclopropoxy)-9H-purin-8-yl)phenoxy)-2-methylbutanoic acid | 566 | C28 H25 Cl2 N5 O4 | 8.6 | 7.3 | <5.0 |
| U83 | 3-(2-chloro-3-(9-(5-fluoro-2-methoxybenzyl)-6-(1-methylcyclopropoxy)-9H-purin-8-yl)phenoxy)propanoic acid | 527 | C26 H24 Cl F N4 O5 | 8.4 | 7.3 | <5.0 |
| U84 | (1s,3s)-3-(2-chloro-3-(9-(5-chloro-2-cyanobenzyl)-6-(1-methylcyclopropoxy)-9H-purin-8-yl)phenoxy)cyclobutane-1-carboxylic acid | 564 | C28 H23 Cl2 N5 O4 | 8.4 | 7.3 | <5.0 |
| U85 | (1r,4r)-4-(2-chloro-3-(9-(5-chloro-2-cyanobenzyl)-6-(1-methylcyclopropoxy)-9H-purin-8-yl)phenoxy)cyclohexane-1-carboxylic acid | 592 | C30 H27 Cl2 N5 O4 | 8.4 | | <5.0 |
| U86 | (S)-(4-(3-chloro-4-(9-(3-chlorobenzyl)-6-(1-methylcyclopropoxy)-9H-purin-8-yl)phenoxy)-2-methylbutanoyl)glycine | 598 | C29 H29 Cl2 N5 O5 | 8.5 | 5.6 | <5.0 |
| U87 Example 54 | (S)-4-(2-chloro-3-(9-(5-chloro-2-cyanobenzyl)-6-(1-methylcyclopropoxy)-9H-purin-8-yl)phenoxy)-2-methylbutanoic acid | 566 | C28 H25 Cl2 N5 O4 | 8.4 | 7.8 | <5.0 |
| U89 | 3-(2-chloro-3-(9-(2-methoxy-5-methylbenzyl)-6-(1-methylcyclopropoxy)-9H-purin-8-yl)phenoxy)propanoic acid | 523 | C27 H27 Cl N4 O5 | 8.3 | 7.8 | 5.1 |
| U90 | 2-(3-(2-chloro-3-(9-(5-chloro-2-methoxybenzyl)-6-(1-methylcyclopropoxy)-9H-purin-8-yl)phenoxy)propoxy)-2-methylpropanoic acid | 615 | C30 H32 Cl2 N4 O6 | 8.3 | 8.3 | <5.0 |
| U91 | (1r,4r)-4-(2-chloro-3-(9-(2-methoxy-5-methylbenzyl)-6-(1-methylcyclopropoxy)-9H-purin-8-yl)phenoxy)cyclohexane-1-carboxylic acid | 577 | C31 H33 Cl N4 O5 | 8.4 | 7.8 | <5.0 |
| U92 | 2-(3-(3-chloro-4-(9-(5-chloro-2-methoxybenzyl)-6-(1-methylcyclopropoxy)-9H-purin-8-yl)phenoxy)propoxy)-2-methylpropanoic acid | 615 | C30 H32 Cl2 N4 O6 | 8.3 | | <5.0 |

TABLE U-continued

| Ex # | Name | ES (MH+) | Formula | POLQ Enz Lumin Primary CR GMean pIC50 | POLQ PD Prolif Lumin BRCA2 −/− mean pIC50 | POLQ PD Prolif Lumin DLD1 mean pIC50 |
|---|---|---|---|---|---|---|
| U93 | 2-(3-(2-chloro-3-(9-(2-methoxy-5-methylbenzyl)-6-(1-methylcyclopropoxy)-9H-purin-8-yl)phenoxy)propoxy)acetic acid | 567 | C29 H31 Cl N4 O6 | 8.2 | 7.9 | <5.0 |
| U94 | (S)-4-(3-chloro-4-(9-(2-methoxy-5-methylbenzyl)-6-(1-methylcyclopropoxy)-9H-purin-8-yl)phenoxy)-2-methylbutanoic acid | 551 | C29 H31 Cl N4 O5 | 8.3 | 7.3 | <5.0 |
| U95 Example 53 | (R)-4-(2-chloro-3-(9-(5-chloro-2-cyanobenzyl)-6-(1-methylcyclopropoxy)-9H-purin-8-yl)phenoxy)-2-methylbutanoic acid | 566 | C28 H25 Cl2 N5 O4 | 8.4 | 8.7 | <5.0 |
| U96 | 3-(2-chloro-3-(9-(5-chloro-2-cyanobenzyl)-6-(1-methylcyclopropoxy)-9H-purin-8-yl)phenoxy)propanoic acid | 538 | C26 H21 Cl2 N5 O4 | 8.4 | 8 | <5.0 |
| U98 | 2-(3-(2-chloro-3-(9-(5-chloro-2-cyanobenzyl)-6-(1-methylcyclopropoxy)-9H-purin-8-yl)phenoxy)propoxy)acetic acid | 581 | C28 H25 Cl2 N5 O5 | | 7.5 | <5.0 |
| U99 | 4-(2-chloro-3-(9-(2-methoxy-5-methylbenzyl)-6-(1-methylcyclopropoxy)-9H-purin-8-yl)phenoxy)-3-methylbutanoic acid (isomer 2) | 550 | C29 H31 Cl N4 O5 | | | |
| U100 | 4-(2-chloro-3-(9-(2-methoxy-5-methylbenzyl)-6-(1-methylcyclopropoxy)-9H-purin-8-yl)phenoxy)-3-methylbutanoic acid (Isomer 1) | 550 | C29 H31 Cl N4 O5 | | | |
| U101 | (1s,3s)-3-(2-chloro-3-(9-(2-methoxy-5-methylbenzyl)-6-(1-methylcyclopropoxy)-9H-purin-8-yl)phenoxy)cyclobutane-1-carboxylic acid | 548 | C29 H29 Cl N4 O5 | | | |
| U102 | (S)-4-(2-chloro-3-(9-(2-methoxy-5-methylbenzyl)-6-(1-methylcyclopropoxy)-9H-purin-8-yl)phenoxy)-2-methylbutanoic acid | 550 | C29 H31 Cl N4 O5 | | | |
| U103 | 4-(2-chloro-3-(9-(5-chloro-2-cyanobenzyl)-6-(1-methylcyclopropoxy)-9H-purin-8-yl)phenoxy)-3-methylbutanoic acid (Isomer 1) | 565 | C28 H25 Cl2 N5 O4 | | | |
| U104 | 4-(2-chloro-3-(9-(5-chloro-2-cyanobenzyl)-6-(1-methylcyclopropoxy)-9H-purin-8-yl)phenoxy)-3-methylbutanoic acid (Isomer 2) | 565 | C28 H25 Cl2 N5 O4 | | | |
| U105 | (R)-4-(2-chloro-3-(9-(2-methoxy-5-methylbenzyl)-6-(1-methylcyclopropoxy)-9H-purin-8-yl)phenoxy)-2-methylbutanoic acid | 550 | C29 H31 Cl N4 O5 | | | |

All references cited herein, including patents, patent applications, papers, text books, and the like, and the references cited therein, to the extent that they are not already, are hereby incorporated herein by reference in their entirety for all purposes.

REFERENCES

Alexandrov, L. B., Kim, J., Haradhvala, N. J., Huang, M. N., Tian Ng, A. W., Wu, Y., Boot, A., Covington, K. R., Gordenin, D. A., Bergstrom, E. N., et al. (2020). The repertoire of mutational signatures in human cancer. Nature 578, 94-101.

Ceccaldi, R., Liu, J. C., Amunugama, R., Hajdu, I., Primack, B., Petalcorin, M. I., O'Connor, K. W., Konstantinopoulos, P. A., Elledge, S. J., Boulton, S. J., et al. (2015). Homologous-recombination-deficient tumours are dependent on Poltheta-mediated repair. Nature 518, 258-262.

Ciccia, A., and Elledge, S. J. (2010). The DNA damage response: making it safe to play with knives. Mol Cell 40, 179-204.

Higgins, G. S., and Boulton, S. J. (2018). Beyond PARP—POLθ as an anticancer target. Science 359, 1217-1218.

Higgins, G. S., Prevo, R., Lee, Y. F., Helleday, T., Muschel, R. J., Taylor, S., Yoshimura, M., Hickson, I. D., Bernhard, E. J., and McKenna, W. G. (2010). A small interfering RNA screen of genes involved in DNA repair identifies tumor-specific radiosensitization by POLQ knockdown. Cancer Res 70, 2984-2993.

Loeb, L. A., and Monnat, R. J., Jr. (2008). DNA polymerases and human disease. Nat Rev Genet 9, 594-604.

Mateos-Gomez, P. A., Gong, F., Nair, N., Miller, K. M., Lazzerini-Denchi, E., and Sfeir, A. (2015). Mammalian polymerase theta promotes alternative NHEJ and suppresses recombination. Nature 518, 254-257.
Mateos-Gomez, P. A., Kent, T., Deng, S. K., McDevitt, S., Kashkina, E., Hoang, T. M., Pomerantz, R. T., and Sfeir, A. (2017). The helicase domain of Pol[theta] counteracts RPA to promote alt-NHEJ. Nat Struct Mol Biol advance online publication.
Nik-Zainal, S., Davies, H., Staaf, J., Ramakrishna, M., Glodzik, D., Zou, X., Martincorena, I., Alexandrov, L. B., Martin, S., Wedge, D. C., et al. (2016). Landscape of somatic mutations in 560 breast cancer whole-genome sequences. Nature 534, 47-54.
Pellegrino, B., Mateo, J., Serra, V., and Balmaña, J. (2019). Controversies in oncology: are genomic tests quantifying homologous recombination repair deficiency (HRD) useful for treatment decision making? ESMO Open 4.
Pettitt, S. J., Frankum, J. R., Punta, M., Lise, S., Alexander, J., Chen, Y., Yap, T. A., Haider, S., Tutt, A. N. J., and Lord, C. J. (2020). Clinical BRCA1/2 Reversion Analysis Identifies Hotspot Mutations and Predicted Neoantigens Associated with Therapy Resistance. Cancer Discov.
Ramsden, D. A., Carvajal-Garcia, J., and Gupta, G. P. (2022). Mechanism, cellular functions and cancer roles of polymerase-theta-mediated DNA end joining. Nature Reviews Molecular Cell Biology 23, 125-140.
Shima, N., Munroe, R. J., and Schimenti, J. C. (2004). The mouse genomic instability mutation chaos1 is an allele of Polq that exhibits genetic interaction with Atm. Mol Cell Biol 24, 10381-10389.
Tobalina, L., Armenia, J., Irving, E., O'Connor, M. J., and Forment, J. V. (2021). A meta-analysis of reversion mutations in BRCA genes identifies signatures of DNA end-joining repair mechanisms driving therapy resistance. Annals of Oncology 32, 103-112.
Wyatt, D. W., Feng, W., Conlin, M. P., Yousefzadeh, M. J., Roberts, S. A., Mieczkowski, P., Wood, R. D., Gupta, G. P., and Ramsden, D. A. (2016). Essential Roles for Polymerase theta-Mediated End Joining in the Repair of Chromosome Breaks. Mol Cell 63, 662-673.
Yoon, J.-H., McArthur, M. J., Park, J., Basu, D., Wakamiya, M., Prakash, L., and Prakash, S. (2019). Error-Prone Replication through UV Lesions by DNA Polymerase θ Protects against Skin Cancers. Cell 176, 1295-1309. e1215.
Yousefzadeh, M. J., Wyatt, D. W., Takata, K., Mu, Y., Hensley, S. C., Tomida, J., Bylund, G. O., Doublie, S., Johansson, E., Ramsden, D. A., et al. (2014). Mechanism of suppression of chromosomal instability by DNA polymerase POLQ. PLoS Genet 10, e1004654.
Zatreanu, D., Robinson, H. M. R., Alkhatib, O., Boursier, M., Finch, H., Geo, L., Grande, D., Grinkevich, V., Heald, R. A., Langdon, S., et al. (2021). Polθ inhibitors elicit BRCA-gene synthetic lethality and target PARP inhibitor resistance. Nature Communications 12, 3636.
Zhou, J., Gelot, C., Pantelidou, C., Li, A., Yücel, H., Davis, R. E., Färkkilä, A., Kochupurakkal, B., Syed, A., Shapiro, G. I., et al. (2021). A first-in-class polymerase theta inhibitor selectively targets homologous-recombination-deficient tumors. Nature Cancer 2, 598-610.

The invention claimed is:

1. A compound which is 2-(3-chloro-4-(6-(1-methylcyclopropoxy)-9-((4-methylpyridin-2-yl)methyl)-9H-purin-8-yl)phenoxy)-N,N-dimethylethan-1-amine:

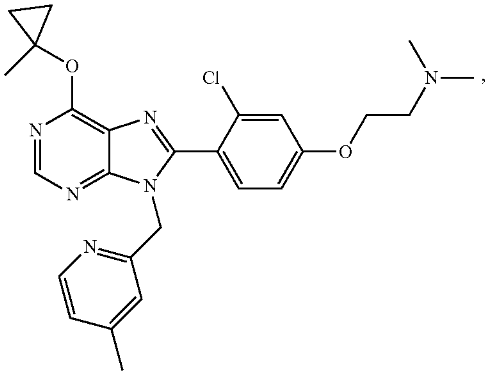

or a pharmaceutically acceptable salt thereof.

2. The compound of claim 1 which is 2-(3-chloro-4-(6-(1-methylcyclopropoxy)-9-((4-methylpyridin-2-yl)methyl)-9H-purin-8-yl)phenoxy)-N,N-dimethylethan-1-amine:

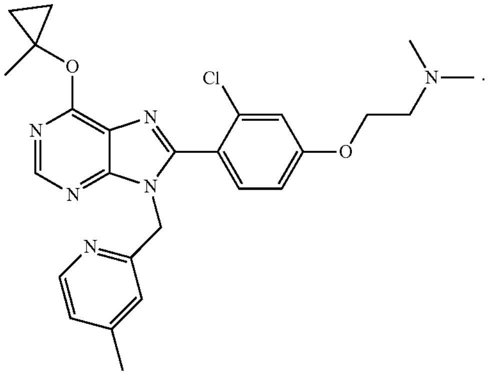

3. The pharmaceutically acceptable salt of claim 1, which is a pharmaceutically acceptable salt of 2-(3-chloro-4-(6-(1-methylcyclopropoxy)-9-((4-methylpyridin-2-yl)methyl)-9H-purin-8-yl)phenoxy)-N,N-dimethylethan-1-amine:

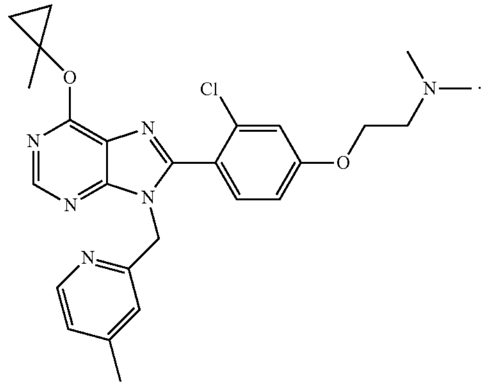 [SMILES: Cc1ccnc(Cn2c(-c3ccc(OCCN(C)C)cc3Cl)nc3c(OC4(C)CC4)ncnc32)c1]

4. A pharmaceutical composition comprising the compound or pharmaceutically acceptable salt thereof according to claim 1.

5. A compound selected from (R)-4-(3-chloro-4-(9-(3-chlorobenzyl)-6-(1-methylcyclopropoxy)-9H-purin-8-yl)phenoxy)-2-methylbutanoic acid and (S)-4-(3-chloro-4-(9-(3-chlorobenzyl)-6-(1-methylcyclopropoxy)-9H-purin-8-yl)phenoxy)-2-methylbutanoic acid:

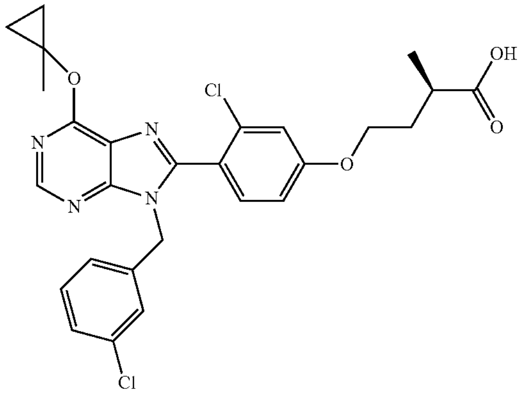

and

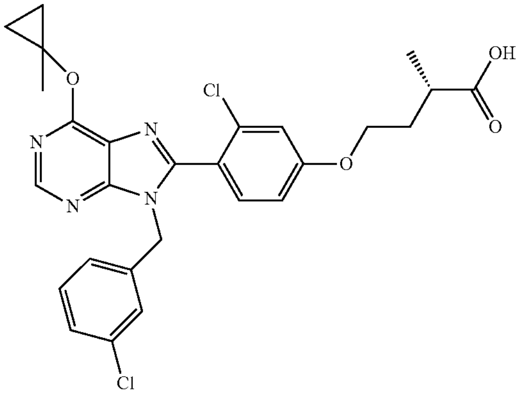 [SMILES: C[C@@H](CCOc1ccc(-c2nc3c(OC4(C)CC4)ncnc3n2Cc2cccc(Cl)c2)c(Cl)c1)C(=O)O]

or a pharmaceutically acceptable salt thereof.

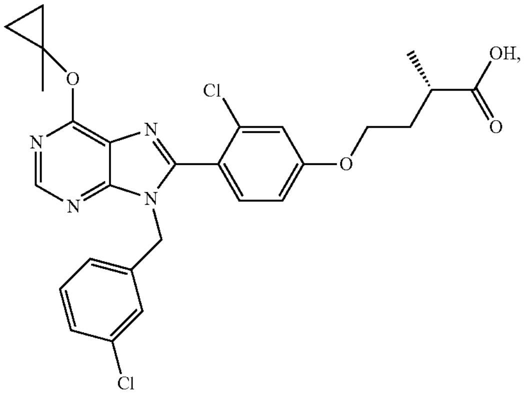

or a pharmaceutically acceptable salt thereof.

6. The compound of claim 5 which is (R)-4-(3-chloro-4-(9-(3-chlorobenzyl)-6-(1-methylcyclopropoxy)-9H-purin-8-yl)phenoxy)-2-methylbutanoic acid:

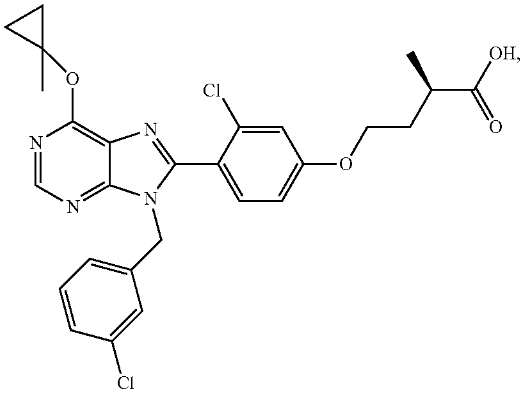

or a pharmaceutically acceptable salt thereof.

7. The compound of claim 5 which is (S)-4-(3-chloro-4-(9-(3-chlorobenzyl)-6-(1-methylcyclopropoxy)-9H-purin-8-yl)phenoxy)-2-methylbutanoic acid:

8. The compound of claim 6 which is (R)-4-(3-chloro-4-(9-(3-chlorobenzyl)-6-(1-methylcyclopropoxy)-9H-purin-8-yl)phenoxy)-2-methylbutanoic acid:

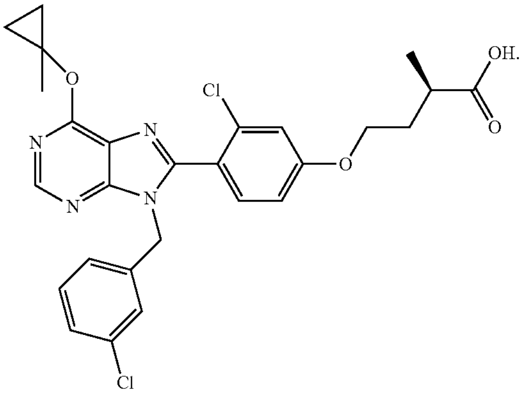 [SMILES: C[C@H](CCOc1ccc(-c2nc3c(OC4(C)CC4)ncnc3n2Cc2cccc(Cl)c2)c(Cl)c1)C(=O)O]

9. The compound of claim 7 which is (S)-4-(3-chloro-4-(9-(3-chlorobenzyl)-6-(1-methylcyclopropoxy)-9H-purin-8-yl)phenoxy)-2-methylbutanoic acid:

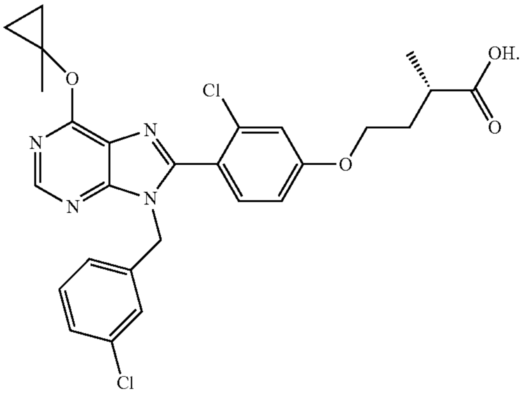 [SMILES: C[C@@H](CCOc1ccc(-c2nc3c(OC4(C)CC4)ncnc3n2Cc2cccc(Cl)c2)c(Cl)c1)C(=O)O]

10. The pharmaceutically acceptable salt of claim 6, which is a pharmaceutically acceptable salt of (R)-4-(3-chloro-4-(9-(3-chlorobenzyl)-6-(1-methylcyclopropoxy)-9H-purin-8-yl)phenoxy)-2-methylbutanoic acid:

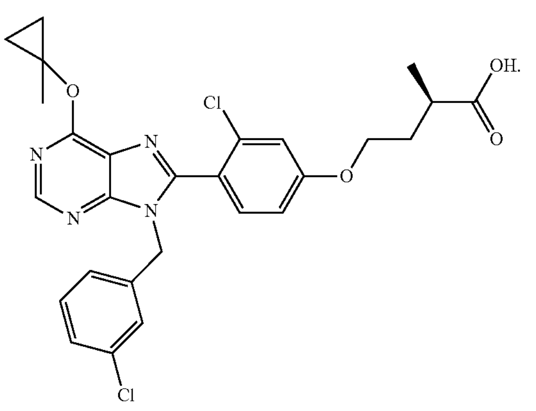 [SMILES: C[C@H](CCOc1ccc(-c2nc3c(OC4(C)CC4)ncnc3n2Cc2cccc(Cl)c2)c(Cl)c1)C(=O)O]

11. The pharmaceutically acceptable salt of claim 7, which is a pharmaceutically acceptable salt of (S)-4-(3-chloro-4-(9-(3-chlorobenzyl)-6-(1-methylcyclopropoxy)-9H-purin-8-yl)phenoxy)-2-methylbutanoic acid:

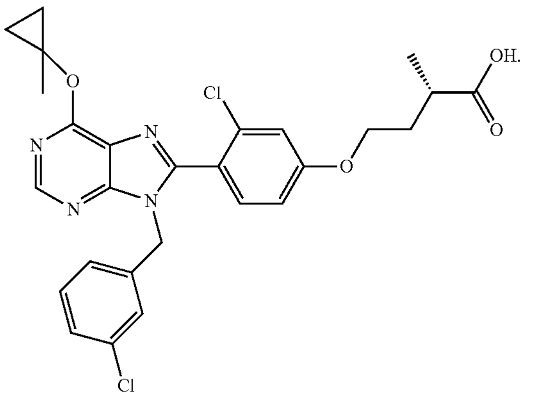 [SMILES: C[C@@H](CCOc1ccc(-c2nc3c(OC4(C)CC4)ncnc3n2Cc2cccc(Cl)c2)c(Cl)c1)C(=O)O]

12. A pharmaceutical composition comprising the compound or pharmaceutically acceptable salt thereof according to claim 5.

13. A pharmaceutical composition comprising the compound or pharmaceutically acceptable salt thereof according to claim 6.

14. A pharmaceutical composition comprising the compound or pharmaceutically acceptable salt thereof according to claim 7.

15. A compound selected from (R)-1-(3-chloro-4-(6-(1-methylcyclopropoxy)-9-((4-methylpyridin-2-yl)methyl)-9H-purin-8-yl)phenoxy)propan-2-ol and (S)-1-(3-chloro-4-(6-(1-methylcyclopropoxy)-9-((4-methylpyridin-2-yl) methyl)-9H-purin-8-yl)phenoxy)propan-2-ol:

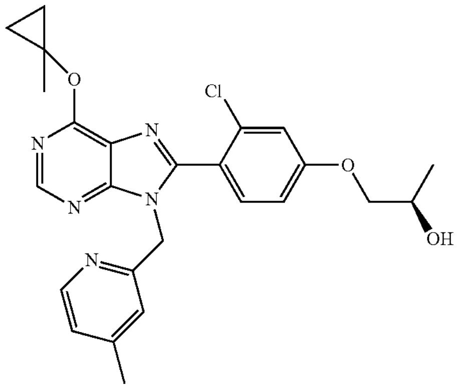 [SMILES: Cc1ccnc(Cn2c(-c3ccc(OC[C@@H](C)O)cc3Cl)nc3c(OC4(C)CC4)ncnc32)c1]
and

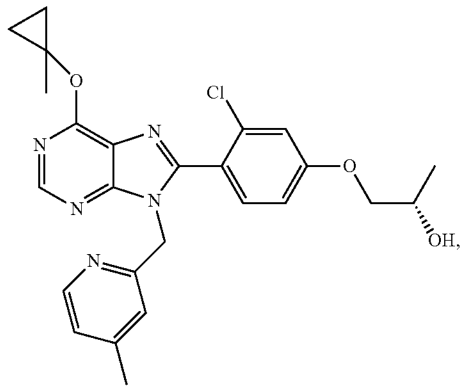 [SMILES: Cc1ccnc(Cn2c(-c3ccc(OC[C@H](C)O)cc3Cl)nc3c(OC4(C)CC4)ncnc32)c1]

or a pharmaceutically acceptable salt.

16. The compound of claim 15, which is (R)-1-(3-chloro-4-(6-(1-methylcyclopropoxy)-9-((4-methylpyridin-2-yl) methyl)-9H-purin-8-yl)phenoxy)propan-2-ol:

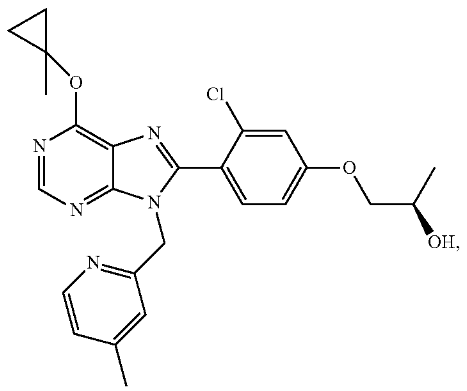 [SMILES: Cc1ccnc(Cn2c(-c3ccc(OC[C@@H](C)O)cc3Cl)nc3c(OC4(C)CC4)ncnc32)c1]

or a pharmaceutically acceptable salt.

17. The compound of claim 15, which is (S)-1-(3-chloro-4-(6-(1-methylcyclopropoxy)-9-((4-methylpyridin-2-yl) methyl)-9H-purin-8-yl)phenoxy)propan-2-ol:

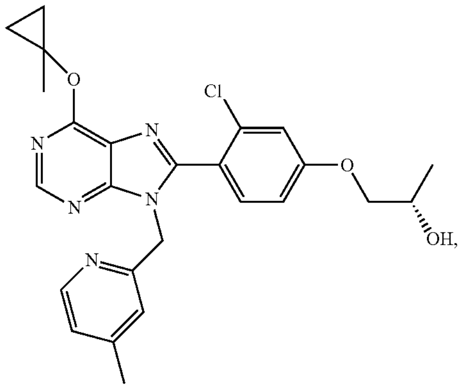 [SMILES: Cc1ccnc(Cn2c(-c3ccc(OC[C@H](C)O)cc3Cl)nc3c(OC4(C)CC4)ncnc32)c1]

or a pharmaceutically acceptable salt.

18. The compound of claim 16, which is (R)-1-(3-chloro-4-(6-(1-methylcyclopropoxy)-9-((4-methylpyridin-2-yl)methyl)-9H-purin-8-yl)phenoxy)propan-2-ol:

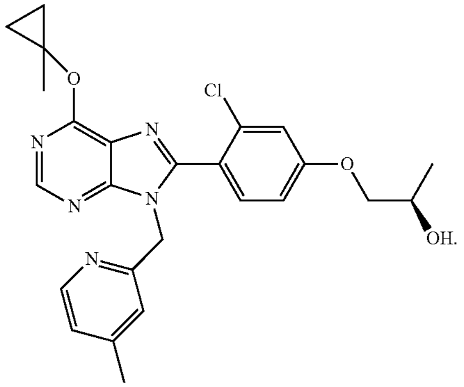

19. The compound of claim 17, which is (S)-1-(3-chloro-4-(6-(1-methylcyclopropoxy)-9-((4-methylpyridin-2-yl)methyl)-9H-purin-8-yl)phenoxy)propan-2-ol:

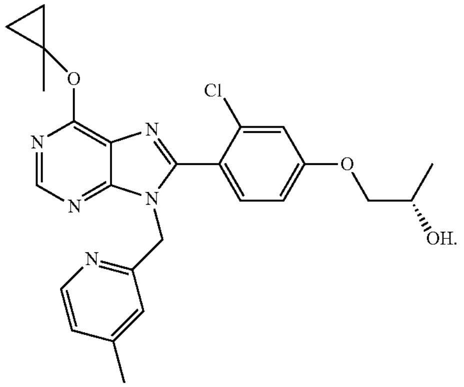

20. The pharmaceutically acceptable salt of claim 16, which is a pharmaceutically acceptable salt of (R)-1-(3-chloro-4-(6-(1-methylcyclopropoxy)-9-((4-methylpyridin-2-yl)methyl)-9H-purin-8-yl)phenoxy)propan-2-ol:

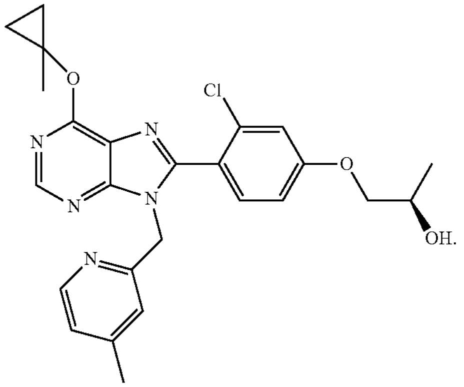 [SMILES: Cc1ccnc(Cn2c(-c3ccc(OC[C@@H](C)O)cc3Cl)nc3c(OC4(C)CC4)ncnc32)c1]

21. The pharmaceutically acceptable salt of claim 17, which is a pharmaceutically acceptable salt of (S)-1-(3-chloro-4-(6-(1-methylcyclopropoxy)-9-((4-methylpyridin-2-yl)methyl)-9H-purin-8-yl)phenoxy)propan-2-ol:

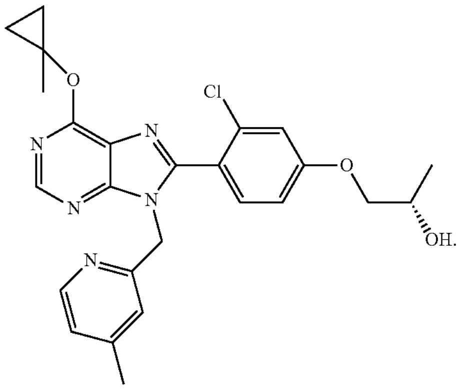 [SMILES: Cc1ccnc(Cn2c(-c3ccc(OC[C@H](C)O)cc3Cl)nc3c(OC4(C)CC4)ncnc32)c1]

22. A pharmaceutical composition comprising the compound or pharmaceutically acceptable salt thereof according to claim 15.

23. A pharmaceutical composition comprising the compound or pharmaceutically acceptable salt thereof according to claim 16.

24. A pharmaceutical composition comprising the compound or pharmaceutically acceptable salt thereof according to claim 17.

* * * * *